(12) United States Patent
Schwarz et al.

(10) Patent No.: US 9,422,276 B2
(45) Date of Patent: Aug. 23, 2016

(54) USE OF ARYL AND HETARYL CARBOXAMIDES AS ENDOPARASITICIDES

(71) Applicant: BAYER INTELLECTUAL PROPERTY GMBH, Monheim (DE)

(72) Inventors: Hans-Georg Schwarz, Dorsten (DE); Axel Trautwein, Düsseldorf (DE); Lothar Willms, Hofheim (DE); Maike Hink, Markgröningen (DE); Peter Lümmen, Idstein (DE); Ulrich Görgens, Ratingen (DE); Pierre-Yves Coqueron, Lyons (FR); Achim Harder, Köln (DE); Claudia Welz, Düsseldorf (DE); Joerg Nico Greul, Leverkusen (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 14/360,332

(22) PCT Filed: Nov. 23, 2012

(86) PCT No.: PCT/EP2012/073431
§ 371 (c)(1),
(2) Date: May 23, 2014

(87) PCT Pub. No.: WO2013/076230
PCT Pub. Date: May 30, 2013

(65) Prior Publication Data
US 2014/0323736 A1    Oct. 30, 2014

(30) Foreign Application Priority Data
Nov. 25, 2011 (EP) .................... 11190735

(51) Int. Cl.
| | | |
|---|---|---|
| C07D 211/72 | (2006.01) |
| C07D 417/12 | (2006.01) |
| A61K 31/166 | (2006.01) |
| A61K 31/18 | (2006.01) |
| A61K 31/341 | (2006.01) |
| A61K 31/381 | (2006.01) |
| A61K 31/425 | (2006.01) |
| A61K 31/4402 | (2006.01) |
| A61K 31/4406 | (2006.01) |
| A61K 31/443 | (2006.01) |
| A61K 31/4436 | (2006.01) |
| A61K 31/4439 | (2006.01) |
| C07C 233/73 | (2006.01) |
| C07D 213/82 | (2006.01) |
| C07D 275/03 | (2006.01) |
| C07D 307/68 | (2006.01) |
| C07D 333/24 | (2006.01) |
| C07D 333/38 | (2006.01) |
| C07D 409/12 | (2006.01) |

(52) U.S. Cl.
CPC .......... *C07D 417/12* (2013.01); *A61K 31/166* (2013.01); *A61K 31/18* (2013.01); *A61K 31/341* (2013.01); *A61K 31/381* (2013.01); *A61K 31/425* (2013.01); *A61K 31/4402* (2013.01); *A61K 31/443* (2013.01); *A61K 31/4406* (2013.01); *A61K 31/4436* (2013.01); *A61K 31/4439* (2013.01); *C07C 233/73* (2013.01); *C07D 213/82* (2013.01); *C07D 275/03* (2013.01); *C07D 307/68* (2013.01); *C07D 333/24* (2013.01); *C07D 333/38* (2013.01); *C07D 409/12* (2013.01)

(58) Field of Classification Search
None
See application file for complete search history.

(56) References Cited

U.S. PATENT DOCUMENTS

| | | |
|---|---|---|
| 7,560,567 B2 | 7/2009 | Coqueron et al. |
| 7,572,818 B2 | 8/2009 | Mansfield et al. |
| 7,723,363 B2 | 5/2010 | Mansfield et al. |
| 7,723,364 B2 | 5/2010 | Mansfield et al. |
| 7,754,741 B2 | 7/2010 | Mansfield et al. |
| 7,825,068 B2 | 11/2010 | Mansfield et al. |

(Continued)

FOREIGN PATENT DOCUMENTS

| | | |
|---|---|---|
| EP | 0152131 A2 | 8/1985 |
| EP | 0 480 258 A2 | 4/1992 |

(Continued)

OTHER PUBLICATIONS

Silverman, R. "The Organic Chemistry of Drug Design and Drug Action," 2004, Elsevier, pp. 29-32.*

(Continued)

*Primary Examiner* — Heidi Reese
(74) *Attorney, Agent, or Firm* — McBee Moore Woodward Vanik IP, LLC

(57) ABSTRACT

The present application relates to known and novel aryl- and hetarylcarboxamides of the formula (I)

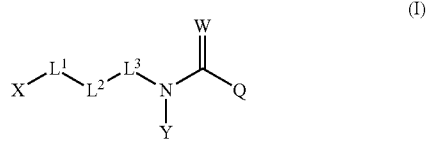

and to their use as medicaments for controlling endoparasites in animals or humans, and also to parasiticidal compositions, in particular endoparasites, comprising aryl- and hetarylcyclylcarboxamides.

16 Claims, No Drawings

(56) References Cited

U.S. PATENT DOCUMENTS

| | | |
|---|---|---|
| 7,888,289 B2 | 2/2011 | Mansfield et al. |
| 7,951,973 B2 | 5/2011 | Mansfield et al. |
| 8,071,627 B2 | 12/2011 | Coqueron et al. |
| 8,148,419 B2 | 4/2012 | Coqueron et al. |
| 8,283,349 B2 | 10/2012 | Coqueron et al. |
| 8,314,269 B2 | 11/2012 | Mansfield et al. |
| 8,318,777 B2 | 11/2012 | Coqueron et al. |
| 2004/0082624 A1* | 4/2004 | Ducray et al. ............ 514/357 |
| 2005/0234110 A1 | 10/2005 | Mansfield et al. |
| 2006/0052366 A1 | 3/2006 | Mansfield et al. |
| 2006/0173022 A1 | 8/2006 | Schaper |
| 2006/0246102 A1 | 11/2006 | Mansfield et al. |
| 2006/0276515 A1 | 12/2006 | Cywin et al. |
| 2007/0099965 A1 | 5/2007 | Coqueron et al. |
| 2007/0117845 A1 | 5/2007 | Coqueron et al. |
| 2007/0167491 A1 | 7/2007 | Mansfield et al. |
| 2009/0054492 A1 | 2/2009 | Mansfield et al. |
| 2009/0088456 A1 | 4/2009 | Coqueron et al. |
| 2009/0156651 A1 | 6/2009 | Mansfield et al. |
| 2009/0170924 A1 | 7/2009 | Mansfield et al. |
| 2009/0258912 A1 | 10/2009 | Coqueron et al. |
| 2010/0087494 A1 | 4/2010 | Coqueron et al. |
| 2011/0237678 A1 | 9/2011 | Mansfield et al. |
| 2012/0071517 A1 | 3/2012 | Coqueron et al. |
| 2013/0261158 A1 | 10/2013 | Bennabi et al. |

FOREIGN PATENT DOCUMENTS

| | | |
|---|---|---|
| EP | 1256569 A1 | 11/2002 |
| EP | 1792901 A1 | 6/2007 |
| EP | 1997800 A1 | 12/2008 |
| EP | 2132987 A1 | 12/2009 |
| GB | 2129798 A | 5/1984 |
| JP | S-59-176259 A | 10/1984 |
| JP | S61-50969 A | 3/1986 |
| JP | S-61-229864 A | 10/1986 |
| JP | H-0532631 A | 2/1993 |
| JP | H09-249648 A | 9/1997 |
| JP | 2001-316366 A | 11/2001 |
| JP | 2003515608 A | 5/2003 |
| JP | 2006518721 | 8/2006 |
| JP | 2008-536831 | 9/2008 |
| JP | 2009-516721 A | 4/2009 |
| JP | 2009-516722 A | 4/2009 |
| JP | 2010-519277 | 6/2010 |
| JP | 2011507910 A | 3/2011 |
| WO | 9924413 A | 5/1999 |
| WO | 0140223 A2 | 6/2001 |
| WO | 0160783 A | 8/2001 |
| WO | 02095361 A2 | 11/2002 |
| WO | 03080577 A2 | 10/2003 |
| WO | 2004016088 A2 | 2/2004 |
| WO | 2004074280 A | 9/2004 |
| WO | 2004076421 A1 | 9/2004 |
| WO | 2005014545 A | 2/2005 |
| WO | 2005058828 A1 | 6/2005 |
| WO | 2005058833 A | 6/2005 |
| WO | 2005085238 A | 9/2005 |
| WO | 2006/108791 | 10/2006 |
| WO | 2006108791 A | 10/2006 |
| WO | 2006108792 A | 10/2006 |
| WO | 2007060166 A1 | 3/2007 |
| WO | 2007062308 A2 | 3/2007 |
| WO | 2007060162 A | 5/2007 |
| WO | 2007060164 A1 | 5/2007 |
| WO | 2007060166 A1 | 5/2007 |
| WO | 2007108483 A | 9/2007 |
| WO | 2007108483 A1 | 9/2007 |
| WO | 2008/101976 | 8/2008 |
| WO | 2008101976 A1 | 8/2008 |
| WO | 2008/126922 A | 10/2008 |
| WO | 2008148570 A | 12/2008 |
| WO | 2009086303 A2 | 7/2009 |
| WO | 2010012795 A1 | 2/2010 |
| WO | 2010063700 A | 6/2010 |
| WO | 2010149760 A2 | 12/2010 |
| WO | 2011128989 A | 10/2011 |
| WO | 2013/064520 A1 | 5/2013 |

OTHER PUBLICATIONS

International Search Report received in PCT/EP2012/073431 mailed Jan. 28, 2013.

Fritzson et. al. "Fritzson, Ingela et al., N-Substituted salicylamides as selective malaria parasite dihydroorotate dehydrogenase inhibitors", MedChemComm, Sep. 2, 2011,(9), pp. 895-898.

Nicola et al. "Discovery of Novel Inhibitors Targeting Enoyl-Acyl Carrier Protein Reductase in Plasmodium falciparum by Structure-Based Virtual Screening, Biochemical and Biophysical Research Communications", 2007, 358(3), pp. 686-691, Supplementary Material.

Suter et al. "Various aryloxy-2-aminopropanes. II", Justus Liebings Annalen der Chemie, 1952, 576, pp. 223-231.

* cited by examiner

USE OF ARYL AND HETARYL CARBOXAMIDES AS ENDOPARASITICIDES

CROSS REFERENCE TO RELATED APPLICATIONS

This application is a §371 National Stage Application of PCT/EP2012/073431, filed Nov. 23, 2012, which claims priority to EP 11190735.8, filed Nov. 25, 2011.

BACKGROUND

1. Field of the Invention

The present application relates to known and novel aryl- and hetarylcarboxamides and their use as parasiticides for endoparasites in animals or humans, and also to parasiticides, in particular endoparasitices, comprising the aryl- and hetarylcarboxamides.

2. Description of Related Art

In the field of veterinary medicine, the occurrence of resistances against all commercially available anthelmintics is an increasing problem which requires endoparasiticides having novel molecular mechanisms of action. Such compounds should exhibit excellent efficacy against a broad spectrum of helminths and nematodes and at the same time not cause any toxic effects in the animals treated. Endoparasiticidal compositions are medicaments used for controlling endoparasites in humans and animals.

WO-A 2001/060783 claims certain phenacylbenzamides for oral use as anthelmintics in veterinary medicine.

Isothiazolecarboxamides are known from WO-A 1999/24413, heterocyclylethylcarboxamide derivatives from WO-A 2006/108791, heterocyclylethylbenzamide derivatives from WO-A 2006/108792, N-(1-methyl-2-phenylethyl)benzamides from WO-A 2007/060162, N-(1-methyl-2-phenylethyl)carboxamides from WO-A 2007060164, N-phenethylcarboxamide derivatives from WO-A 2007/060166, N-(3-phenylpropyl)carboxamides from WO-A 2008/101976, pyrazolecarboxamides from WO-A 2008/148570 and WO-A 2010/063700, pyrazinylcarboxamides from WO-A 2011/128989, and also various 2-pyridylethylcarboxamide derivatives from WO-A 2004/016088, WO-A 2004/074280, WO-A 2005/014545, WO-A 2005/058828, WO-A 2005/058833 and WO-A 2005/085238 as agrochemical fungicides. Furthermore, WO-A 2007/108483 describes N-2-(hetero)arylethylcarboxamide derivatives as fungicides and nematicides. WO-A 2008/126922 explicitly claims the use of 2-pyridylethylcarboxamide derivatives for use against nematodes in crop cultivation.

The use of these (het)arylethyl- or (het)arylpropylcarboxamides as endoparasiticides in veterinary medicine has hitherto not been described.

SUMMARY

It has now been found that compounds of the formula (I)

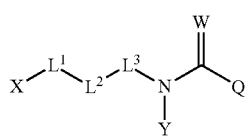

(I)

in which

X represents mono- or poly-$M^1$-substituted phenyl, thienyl or furanyl;

Q represents mono- or poly-$M^1$-substituted phenyl, pyridyl, thienyl, furanyl or isothiazolyl;

Y represents hydrogen or represents optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_1-C_{10})$-alkoxy, $(C_2-C_{10})$-alkenyloxy, $(C_3-C_{10})$-alkynyloxy, $(C_3-C_{14})$-cycloalkyl-$(C_1-C_{10})$-alkyl or represents an optionally mono- or poly-$M^2$-substituted 3- to 14-membered cyclic group;

W represents oxygen or sulfur;

$L^1$ represents —C($R^{11}$, $R^{12}$)—, oxygen, sulfur or —N($R^1$)—;

$L^2$ represents —C($R^{21}$, $R^{22}$)—;

$L^3$ represents —C($R^{31}$, $R^{32}$)— or a direct bond;

$M^1$ represents hydrogen, halogen, cyano, nitro, OH, $(C_1-C_{10})$-alkyl, $(C_1-C_{10})$-haloalkyl, $(C_1-C_{10})$-alkoxy, $(C_1-C_{10})$-haloalkoxy, $(C_1-C_{10})$-alkylthio, $(C_1-C_{10})$-haloalkylthio, $(C_1-C_{10})$-alkylsulfonyl, $(C_1-C_{10})$-haloalkylsulfonyl, $(C_1-C_{10})$-alkylsulfanyl, $(C_1-C_{10})$-haloalkylsulfanyl, (3- to 14-membered cyclic group)-O—;

$R^1$ represent hydrogen or optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_3-C_{10})$-cycloalkyl-$(C_1-C_{10})$-alkyl or represents an optionally mono- or poly-$M^2$-substituted 3- to 14-membered cyclic group;

$R^{11}$, $R^{12}$ each independently of one another represent hydrogen, halogen or optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_1-C_{10})$-alkoxy, $(C_2-C_{10})$-alkenyloxy, $(C_3-C_{10})$-alkynyloxy, $(C_3-C_{14})$-cycloalkyl-$(C_1-C_{10})$-alkyl or represents an optionally mono- or poly-$M^2$-substituted 3- to 14-membered cyclic group;

$R^{11}$, $R^{12}$ together represent an optionally mono- or poly-$M^2$-substituted spiro-attached 3- to 14-membered carbo- or 3- to 10-membered heterocyclic group;

$R^{21}$, $R^{22}$ each independently of one another represent hydrogen, halogen or optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_1-C_{10})$-alkoxy, $(C_1-C_{10})$-haloalkoxy, $(C_2-C_{10})$-alkenyloxy, $(C_3-C_{10})$-alkynyloxy, $(C_3-C_{14})$-cycloalkyl-$(C_1-C_{10})$-alkyl or represent an optionally mono- or poly-$M^2$-substituted 3- to 14-membered cyclic group;

$R^{21}$, $R^{22}$ together represent an optionally mono- or poly-$M^2$-substituted spiro-attached 3- to 14-membered carbo- or 3- to 10-membered heterocyclic group;

$R^{31}$, $R^{32}$ each independently of one another represent hydrogen or optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_3-C_{14})$-cycloalkyl-$(C_1-C_{10})$-alkyl or represent an optionally mono- or poly-$M^2$-substituted 3- to 14-membered cyclic group;

$R^{31}$, $R^{32}$ together represent an optionally mono- or poly-$M^2$-substituted spiro-attached 3- to 14-membered carbo- or 3- to 10-membered heterocyclic group;

$M^2$ each independently of one another represent halogen, formyl, cyano, nitro, $(C_1-C_{10})$-alkyl, $(C_1-C_{10})$-haloalkyl, $(C_2-C_{10})$-alkenyl, $(C_2-C_{10})$-haloalkenyl, $(C_2-C_{10})$-alkynyl, $(C_2-C_{10})$-haloalkynyl, $(C_1-C_{10})$-alkoxy, $(C_1-C_{10})$-haloalkoxy, $(C_2-C_{10})$-alkenyloxy, $(C_2-C_{10})$-haloalkenyloxy, $(C_3-C_{10})$-alkynyloxy, $(C_3-C_{10})$-haloalkynyloxy, $(C_1-C_{10})$-alkylthio, $(C_1-C_{10})$-haloalkylthio, $(C_2-C_{10})$-alkenylthio, $(C_2-C_{10})$-haloalkenylthio, $(C_3-C_{10})$-alkynylthio, $(C_3-C_{10})$-haloalkynylthio, $(C_1-C_{10})$-alkylsulfonyl, $(C_1-C_{10})$-haloalkylsulfonyl, $(C_2-C_{10})$-alkenylsulfonyl, $(C_2-C_{10})$-haloalkenylsulfonyl, $(C_3-C_{10})$-alkynylsulfonyl, $(C_3-C_{10})$-haloalkynylsulfonyl, $(C_1-C_{10})$-alkylsulfanyl, $(C_1-C_{10})$-haloalkylsulfanyl, $(C_2-C_{10})$-alkenylsulfanyl, $(C_2-C_{10})$-haloalkenylsulfanyl, $(C_3-C_{10})$-alkynylsulfanyl, $(C_3-C_{10})$-haloalkynylsulfanyl, $(C_1-C_{10})$-alkylcarbonyl, $(C_1-C_{10})$-haloalkylcarbonyl, $(C_2-C_{10})$-alkenylcarbonyl, $(C_2-C_{10})$-haloalkenylcarbonyl, $(C_2-C_{10})$-alkynylcarbonyl, $(C_2-C_{10})$-haloalkynylcarbonyl, $(C_1-C_{10})$-alkoxycarbonyl, $(C_1-C_{10})$-haloalkoxycarbonyl, $(C_2-C_{10})$-alkenyloxycarbonyl, $(C_2-C_{10})$-haloalkenyloxycarbonyl, $(C_3-C_{10})$-alkynyloxycarbonyl, $(C_3-C_{10})$-haloalkynyloxycarbonyl, $(C_1-C_{10})$-alkylcarbonyloxy, $(C_1-C_{10})$-haloalkylcarbonyloxy, $(C_2-C_{10})$-alkenylcarbonyloxy, $(C_2-C_{10})$-haloalkenylcarbonyloxy, $(C_2-C_{10})$-alkynylcarbonyloxy, $(C_2-C_{10})$-haloalkynylcarbonyloxy, a 3- to 14-membered cyclic group;
and salts, N-oxides and tautomeric forms of the compounds of the formula (I);
are used as medicaments in animals or humans, in particular for endoparasites.

DETAILED DESCRIPTION OF A PREFERRED EMBODIMENT

The compounds of the formula (I) may, where appropriate, depending on the nature of the substituents, be in the form of geometric and/or optically active isomers or corresponding isomer mixtures of varying composition. The invention relates both to the pure isomers and to the isomer mixtures.

The compounds according to the invention can also be present as metal complexes.

DEFINITIONS

The term animals does not include humans.

The term "mono- or poly-" means preferably mono- to hexa-, particularly preferably mono- to tetra-, very particularly preferably mono- to tri- and especially preferably mono- or di-.

The person skilled in the art is aware that the expressions "a" or "an" as used in the present application may, depending on the situation, mean "one (1)", "one (1) or more" or "at least one (1)".

For all ring systems hitherto described, adjacent atoms must not be —O—O— or —O—S—.

For the sake of simplicity, structures having a variable number of possible carbon atoms (C atoms) are referred to as $C_1-C_{10}$-structures $(C_1-C_{10})$ in the present application. Example: an alkyl group of 1 to 10 carbon atoms corresponds to $(C_1-C_{10})$-alkyl. Ring structures of carbon atoms and heteroatoms are referred to as "3- to 14-membered" structures.

If a collective term for a substituent, for example $(C_1-C_{10})$-alkyl, is at the end of a composite substituent such as, for example, $(C_3-C_{14})$-cycloalkyl-$(C_1-C_{10})$-alkyl, the component at the end of the composite substituent, for example the $(C_1-C_{10})$-alkyl, may be mono- or polysubstituted by identical or different substituents and independently of the substituent at the beginning, for example $(C_3-C_{14})$-cycloalkyl.

Unless defined differently, the definition for collective terms also applies to these collective terms in composite substituents. Example: The definition of $(C_1-C_{10})$-alkyl also applies to $(C_1-C_{10})$-alkyl as component of a composite substituent such as, for example, $(C_3-C_{14})$-cycloalkyl-$(C_1-C_{10})$-alkyl.

It is obvious to the person skilled in the art that the examples given in the present application are not to be considered as limiting, but rather describe some embodiments in more detail.

In the definitions of the symbols given in the formulae above, collective terms were used which are generally representative of the following substituents:

Collective Terms

Halogen, unless defined otherwise: elements of the 7th main group; preference is given to fluorine, chlorine, bromine and iodine.

$(C_1-C_{10})$-Alkyl, unless defined differently elsewhere: saturated straight-chain or branched hydrocarbon radicals having preferably $(C_1-C_6)$—, particularly preferably $(C_1-C_4)$-carbon atoms. Examples: methyl, ethyl, isopropyl, n-propyl, 1-methylethyl, butyl, tert-butyl, etc.

$(C_2-C_{10})$-Alkenyl, unless defined differently elsewhere: unsaturated straight-chain or branched hydrocarbon radicals having a double bond. Preference is given to $(C_2-C_6)$- or $(C_2-C_4)$-alkenyl. Examples: ethenyl, 1-propenyl, 3-butenyl, etc.

$(C_2-C_{10})$-Alkynyl, unless defined differently elsewhere: unsaturated straight-chain or branched hydrocarbon radicals having a triple bond. Preference is given to $(C_2-C_6)$- or $(C_2-C_4)$-alkynyl. Examples: ethynyl, 1-propynyl, etc.

$(C_1-C_{10})$-Alkoxy (alkyl radical-O—), unless defined differently elsewhere: an alkyl radical which is attached to the skeleton via an oxygen atom (—O—). Preference is given to $(C_1-C_6)$- or $(C_1-C_4)$-alkoxy. Examples: methoxy, ethoxy, propoxy, 1-methylethoxy, etc.

Analogously, $(C_2-C_{10})$-alkenyloxy and $(C_3-C_{10})$-alkynyloxy, unless defined differently elsewhere, are alkenyl radicals and alkynyl radicals, respectively, which are attached to the skeleton via —O—. Preference is given to $(C_2-C_6)$- or $(C_2-C_4)$-alkenyloxy. Preference is given to $(C_3-C_6)$- or $(C_3-C_4)$-alkynyloxy.

$(C_1-C_{10})$-Alkylcarbonyl (alkyl radical-C(=O)—), unless defined differently elsewhere: preference is given to $(C_1-C_6)$- or $(C_1-C_4)$-alkylcarbonyl. Here, the number of the carbon atoms refers to the alkyl radical in the alkylcarbonyl group.

Analogously, $(C_2-C_{10})$-alkenylcarbonyl and $(C_2-C_{10})$-alkynylcarbonyl, unless defined differently elsewhere, are: alkenyl radicals and alkynyl radicals, respectively, which are attached to the skeleton via —C(=O)—. Preference is given to $(C_2-C_6)$- or $(C_2-C_4)$-alkenylcarbonyl. Preference is given to $(C_2-C_6)$- or $(C_2-C_4)$-alkynylcarbonyl.

$(C_1-C_{10})$-Alkoxycarbonyl (alkyl radical-O—C(=O)—), unless defined differently elsewhere: preference is given to $(C_1-C_6)$- or $(C_1-C_4)$-alkoxycarbonyl. Here, the number of the carbon atoms refers to the alkyl radical in the alkoxycarbonyl group.

Analogously, $(C_2-C_{10})$-alkenyloxycarbonyl and $(C_3-C_{10})$-alkynyloxycarbonyl, unless defined differently elsewhere, are: alkenyl radicals and alkynyl radicals, respectively, which are attached to the skeleton via —O—C(=O)—. Preference is given to $(C_2-C_6)$- or $(C_2-C_4)$-alkenyloxycarbonyl. Preference is given to $(C_3-C_6)$- or $(C_3-C_4)$-alkynyloxycarbonyl.

$(C_1-C_{10})$-Alkylcarbonyloxy (alkyl radical-C(=O)—O—), unless defined differently elsewhere: an alkyl radical which is attached to the skeleton via a carbonyloxy group (—C(=O)—O—) with the oxygen. Preference is given to $(C_1-C_6)$- or $(C_1-C_4)$-alkylcarbonyloxy.

Analogously, $(C_2-C_{10})$-alkenylcarbonyloxy and $(C_2-C_{10})$-alkynylcarbonyloxy, unless defined differently elsewhere, are: alkenyl radicals and alkynyl radicals, respectively, which are attached to the skeleton via (—C(=O)—O—). Preference is given to $(C_2-C_6)$- or $(C_2-C_4)$-alkenylcarbonyloxy. Preference is given to $(C_2-C_6)$- or $(C_2-C_4)$-alkynylcarbonyloxy.

$(C_1-C_{10})$-Alkylthio, unless defined differently elsewhere: an alkyl radical which is attached to the skeleton via —S—. Preference is given to $(C_1-C_6)$- or $(C_1-C_4)$-alkylthio.

Analogously, $(C_2-C_{10})$-alkenylthio and $(C_3-C_{10})$-alkynylthio, unless defined differently elsewhere, are: alkenyl radicals and alkynyl radicals, respectively, which are attached to the skeleton via —S—. Preference is given to $(C_2-C_6)$- or $(C_2-C_4)$-alkenylthio. Preference is given to $(C_3-C_6)$- or $(C_3-C_4)$-alkynylthio.

$(C_1-C_{10})$-Alkylsulfinyl, unless defined differently elsewhere: an alkyl radical which is attached to the skeleton via —S(=O)—. Preference is given to $(C_1-C_6)$- or $(C_1-C_4)$-alkylsulfinyl.

Analogously, $(C_2-C_{10})$-alkenylsulfinyl and $(C_3-C_{10})$-alkynylsulfinyl, unless defined differently elsewhere, are: alkenyl radicals and alkynyl radicals, respectively, which are attached to the skeleton via —S(=O)—. Preference is given to $(C_2-C_6)$- or $(C_2-C_4)$-alkenylsulfinyl. Preference is given to $(C_3-C_6)$- or $(C_3-C_4)$-alkynylsulfinyl.

$(C_1-C_{10})$-Alkylsulfonyl, unless defined differently elsewhere: an alkyl radical which is attached to the skeleton via —S(=O)$_2$—. Preference is given to $(C_1-C_6)$- or $(C_1-C_4)$-alkylsulfonyl.

Analogously, $(C_2-C_{10})$-alkenylsulfonyl and $(C_3-C_{10})$-alkynylsulfonyl, unless defined differently elsewhere, are: alkenyl radicals and alkynyl radicals, respectively, which are attached to the skeleton via —S(=O)$_2$—. Preference is given to $(C_2-C_6)$- or $(C_2-C_4)$-alkenylsulfonyl. Preference is given to $(C_3-C_6)$- or $(C_3-C_4)$-alkynylsulfonyl.

$(C_1-C_{10})$-Haloalkyl, $(C_2-C_{10})$-haloalkenyl, $(C_2-C_{10})$-haloalkynyl, $(C_1-C_{10})$-haloalkoxy, $(C_2-C_{10})$-haloalkenyloxy, $(C_3-C_{10})$-haloalkynyloxy, $(C_1-C_{10})$-haloalkylcarbonyl, $(C_2-C_{10})$-haloalkenylcarbonyl, $(C_2-C_{10})$-haloalkynylcarbonyl, $(C_1-C_{10})$-haloalkoxycarbonyl, $(C_2-C_{10})$-haloalkenyloxycarbonyl, $(C_3-C_{10})$-haloalkynyloxycarbonyl, $(C_2-C_{10})$-haloalkylcarbonyloxy, $(C_2-C_{10})$-haloalkenylcarbonyloxy, $(C_2-C_{10})$-haloalkynylcarbonyloxy, $(C_1-C_{10})$-haloalkylthio, $(C_2-C_{10})$-haloalkenylthio, $(C_3-C_{10})$-haloalkynylthio, $(C_1-C_{10})$-haloalkylsulfinyl, $(C_2-C_{10})$-haloalkenylsulfinyl, $(C_3-C_{10})$-haloalkynylsulfinyl, $(C_1-C_{10})$-haloalkylsulfonyl, $(C_2-C_{10})$-haloalkenylsulfonyl, $(C_3-C_{10})$-haloalkynylsulfonyl are, unless defined differently, defined analogously to $(C_1-C_{10})$-alkyl, $(C_2-C_{10})$-alkenyl, $(C_2-C_{10})$-alkynyl, $(C_1-C_{10})$-alkoxy, $(C_2-C_{10})$-alkenyloxy, $(C_3-C_{10})$-alkynyloxy, $(C_1-C_{10})$-alkylcarbonyl, $(C_2-C_{10})$-alkenylcarbonyl, $(C_2-C_{10})$-alkynylcarbonyl, $(C_1-C_{10})$-alkoxycarbonyl, $(C_2-C_{10})$-alkenyloxycarbonyl, $(C_3-C_{10})$-alkynyloxycarbonyl, $(C_1-C_{10})$-alkylcarbonyloxy, $(C_2-C_{10})$-alkenylcarbonyloxyl, $(C_2-C_{10})$-alkynylcarbonyloxy, $(C_1-C_{10})$-alkylthio, $(C_2-C_{10})$-alkenylthio, $(C_3-C_{10})$-alkynylthio, $(C_1-C_{10})$-alkylsulfinyl, $(C_2-C_{10})$-alkenylsulfinyl, $(C_3-C_{10})$-alkynylsulfinyl, $(C_1-C_{10})$-alkylsulfonyl, $(C_3-C_{10})$-alkenylsulfonyl, $(C_3-C_{10})$-alkynylsulfonyl, where at least one hydrogen atom is replaced by a halogen atom as defined above. In one embodiment, all hydrogen atoms are replaced by halogen. Examples of halogenated structures are, for example, chloromethyl, trichloromethyl, fluoromethyl, chlorodifluoromethyl, dichlorofluoromethyl, trifluoromethyl, 2,2-difluoroethyl, difluoromethyl, difluoromethoxy, trifluoromethoxy, difluoromethylthio, trifluoromethylthio.

Cyclic Groups 3- to 14-membered cyclic group, unless defined differently elsewhere: $(C_3-C_{14})$-carbocyclic group, 3- to 10-membered heterocyclic group, halogenated $(C_3-C_{14})$-carbocyclic group, halogenated 3- to 10-membered heterocyclic group.

$(C_3-C_{14})$-Carbocyclic group, unless defined differently elsewhere: $(C_3-C_{14})$-cycloalkyl, $(C_3-C_{14})$-cycloalkenyl, $(C_6-C_{14})$-aryl, halogenated $(C_3-C_{14})$-cycloalkyl, halogenated $(C_3-C_{14})$-cycloalkenyl, halogenated $(C_6-C_{14})$-aryl.

$(C_3-C_{14})$-Cycloalkyl, unless defined differently elsewhere: mono-, bi- or tricyclic saturated hydrocarbon groups preferably having $(C_3-C_{14})$—, $(C_3-C_8)$- or $(C_3-C_6)$-ring atoms. Cycloalkyl may also be a spirocyclic group. Examples: cyclopropyl, -butyl, -pentyl, -hexyl, -heptyl, bicyclo[2.2.1]heptyl or adamantyl. "Cycloalkyl" preferably represents monocyclic groups of 3, 4, 5, 6 or 7 ring atoms.

Analogously, $(C_3-C_{14})$-cycloalkenyl, unless defined differently elsewhere, is: a mono-, bi- or tricyclic, but partially unsaturated hydrocarbon group having at least one double bond, preferably having $(C_3-C_8)$- or $(C_3-C_6)$-ring atoms. Examples: cyclopropenyl, cyclobutenyl, cyclopentenyl and cyclohexenyl.

$(C_6-C_{14})$-Aryl, unless defined differently elsewhere: mono-, bi- or tricyclic ring system group where at least one cycle is aromatic, preferably having $(C_6-C_8)$- or $(C_6)$-ring atoms. Preferably, aryl is an aromatic $C_6$-monocyclic ring system group; a bicyclic $(C_8-C_{14})$-ring system group; or a tricyclic $(C_{10}-C_{14})$-ring system group. Examples: phenyl, naphthyl, anthryl, phenanthryl, tetrahydronaphthyl, indenyl, indanyl, fluorenyl.

Halogenated $(C_3-C_{14})$-carbocyclic group, halogenated $(C_3-C_{14})$-cycloalkyl, halogenated $(C_3-C_{14})$-cycloalkenyl, halogenated $(C_6-C_{14})$-aryl are in each case, unless defined differently, defined analogously to $(C_3-C_{14})$-carbocyclic group, $(C_3-C_{14})$-cycloalkyl, $(C_3-C_{14})$-cycloalkenyl, $(C_6-C_{14})$-aryl, where at least one hydrogen atom is replaced by a halogen atom as mentioned above. In one embodiment, all hydrogen atoms are replaced by halogen. Examples of halogenated structures are 3-chlorophenyl, 2-bromocyclopentyl.

Heteroatom: for example N, O, S, P, B, Si.

3- to 10-membered heterocyclic group, unless defined differently elsewhere: 3- to 9-membered heterocyclyl group or 5- to 10-membered heteroaryl group, halogenated 3- to 9-membered heterocyclyl group or halogenated 5- to 10-membered heteroaryl group.

3- to 9-membered heterocyclyl, unless defined differently elsewhere: 3- to 9-membered saturated or partially unsaturated mono-, bi- or tricyclic ring system group of carbon atoms and at least one heteroatom preferably selected from the group consisting of N, O and S. The ring system is preferably a 3- to 6-membered ring system. Preferably, the ring system contains 1, 2, 3 or 4 heteroatoms, particularly preferably 1 or 2 heteroatoms. Preference is also given to a monocyclic ring system. In a further preferred embodiment, a monocyclic ring system is a partially unsaturated monocyclic ring system having a double bond. Heterocyclyl may be a spirocyclic system. Examples: piperazinyl, dihydropyridyl, morpholinyl, etc. This definition also applies to heterocyclyl as component of a composite substituent such as, for example, 3- to 9-membered heterocyclyl-$(C_1-C_{10})$-alkyl, unless defined differently elsewhere.

5- to 10-membered heteroaryl, unless defined differently elsewhere: mono-, bi- or tricyclic 5- to 10-membered heterocyclic group of carbon atoms and at least one heteroatom, preferably selected from the group consisting of N, O and S, where at least one cycle is aromatic. The ring system is preferably a 5- to 6-membered ring system. In one embodiment, heteroaryl is an aromatic monocyclic ring system of 5 or 6 ring atoms. Preferably, heteroaryl is an aromatic monocyclic ring system containing 1 to 4 heteroatoms from the group consisting of O, N and S. Furthermore, heteroaryl may be a bicyclic ring system consisting of 8 to 14 ring atoms or a tricyclic ring system consisting of 13 or 14 ring atoms. Examples: furyl, thienyl, pyrazolyl, imidazolyl, triazolyl, thiazolyl, indolyl, benzimidazolyl, indazolyl, benzofuranyl, benzothiophenyl, benzothiazolyl, benzoxazolyl, quinolinyl, isoquinolinyl. This definition also applies to heteroaryl as component of a composite substituent such as, for example, 5- to 10-membered heteroaryl-($C_5$-$C_{10}$)-alkyl, unless defined differently elsewhere. 5- and 6-membered heteroaryl groups are described in more detail below:

5-membered heteroaryl, unless defined differently elsewhere: heteroaryl group containing one to three or one to four nitrogen, oxygen and/or sulfur atom(s) as ring atoms. Examples: furanyl, thienyl, oxazolyl, thiazolyl. In one embodiment, a 5-membered heteroaryl group contains, in addition to carbon atoms, one to four nitrogen atoms or one to three nitrogen atoms as ring members. Examples: pyrrolyl, pyrazolyl, triazolyl, imidazolyl. In a further embodiment, a 5-membered heteroaryl contains one to three nitrogen atoms or one nitrogen atom and one oxygen or sulfur atom. Examples: thiazolyl, oxazolyl, oxadiazolyl.

6-membered heteroaryl, unless defined differently elsewhere: heteroaryl group containing one to three or one to four nitrogen atom(s) as ring atoms. In one embodiment, a 6-membered heteroaryl group contains one to three nitrogen atoms. Examples: pyridyl, pyridazinyl, pyrimidinyl, pyrazinyl, triazinyl, tetrazinyl.

Halogenated 3- to 9-membered heterocyclyl group or halogenated 5- to 10-membered heteroaryl group, in each case unless defined differently, are defined analogously to 3- to 9-membered heterocyclyl group or 5- to 10-membered heteroaryl group, where at least one hydrogen atom is replaced by a halogen atom as mentioned above. In one embodiment, all hydrogen atoms are replaced by halogen. Example of halogenated heterocyclic structures: 3-chlorotetrahydrothiopyran-2-yl, 4-chloropyridin-2-yl.

Not included are combinations which are against natural laws and which the person skilled in the art would therefore exclude based on his/her expert knowledge. Ring structures having three or more adjacent oxygen atoms, for example, are excluded.

Embodiments of the Compounds According to the Invention

It is obvious to the person skilled in the art that all embodiments can be present on their own or in combination.

The compounds of the formula (I) may, where appropriate, depending on the nature of the substituents, be in the form of salts, tautomers, geometric and/or optically active isomers or corresponding isomer mixtures in different compositions.

If appropriate, the compounds according to the invention may be present in various polymorphic forms or as a mixture of different polymorphic forms. Both the pure polymorphs and the polymorph mixtures are provided by the invention and can be used according to the invention.

Embodiments of the compounds of the formula (I) are described in more detail below:

X particularly preferably represents mono- or poly-$M^1$-substituted phenyl, 2-thienyl, 3-thienyl, 2-furanyl or 3-furanyl;

X particularly preferably represents mono- or tri-$M^1$-substituted phenyl or 2-thienyl, 3-thienyl, 2-furanyl, 3-furanyl;

X particularly preferably represents mono-$M^1$-substituted phenyl;

X particularly preferably represents mono-$M^1$-substituted thienyl;

X particularly preferably represents mono-$M^1$-substituted furanyl;

X particularly preferably represents di-$M^1$-substituted phenyl;

X particularly preferably represents di-$M^1$-substituted thienyl;

X particularly preferably represents di-$M^1$-substituted furanyl;

Q represents mono- or poly-$M^1$-substituted pyridyl, thienyl, furanyl or isothiazolyl;

Q preferably represents the structural elements below, where n for each Q is in each case as defined below:

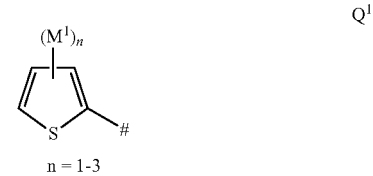

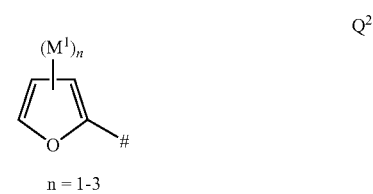

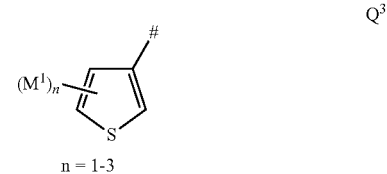

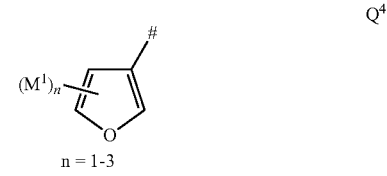

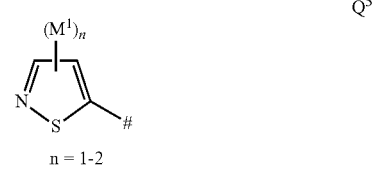

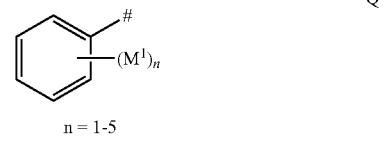

Q preferably represents the structural elements below, where n for each Q is in each case as defined below:

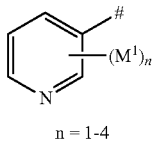

Q¹ n = 1-3

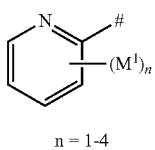

Q² n = 1-3


Q³ n = 1-3

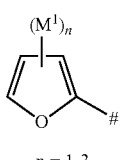

Q⁴ n = 1-3

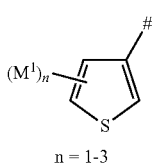

Q⁵ n = 1-2

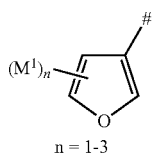

Q⁷ n = 1-4

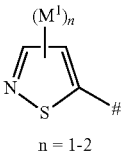

Q⁷ n = 1-4

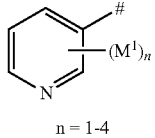

Q⁸ n = 1-4

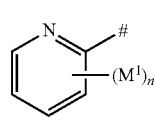

Q⁸ n = 1-4

Q particularly preferably represents mono- or poly-M¹-substituted 2-thienyl, 3-thienyl, 2-furanyl, 5-isothiazolyl, phenyl, 3-pyridyl or 2-pyridyl;

Q particularly preferably represents mono- or di-M¹-substituted 2-thienyl, 3-thienyl, 2-furanyl, 5-isothiazolyl, phenyl, 3-pyridyl or 2-pyridyl;

Q very particularly preferably represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 4-chloro-5-isothiazolyl, 3,4-dichloro-5-isothiazolyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-chloro-3-pyridyl, 3-chloro-2-pyridyl or 2-(trifluoromethyl)-3-pyridyl;

Q in particular very particularly preferably represents 3-chloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 2-chloro-3-thienyl, 2-bromo-3-thienyl, 2-iodo-3-thienyl, 2-methyl-3-thienyl, 3-bromo-2-furanyl, 3-methyl-2-furanyl, 2-chloro-3-furanyl, 2-bromo-3-furanyl, 2-iodo-3-furanyl, 2-methyl-3-furanyl, 3,4-dichloro-5-isothiazolyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-chloro-3-pyridyl, 3-chloro-2-pyridyl or 2-(trifluoromethyl)-3-pyridyl;

Q particularly preferably represents mono- or poly-M¹-substituted 2-thienyl, 3-thienyl, 2-furanyl, 5-isothiazolyl, 3-pyridyl or 2-pyridyl;

Q particularly preferably represents mono- or di-M¹-substituted 2-thienyl, 3-thienyl, 2-furanyl, 5-isothiazolyl, 3-pyridyl or 2-pyridyl;

Q very particularly preferably represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 4-chloro-5-isothiazolyl, 3,4-dichloro-5-isothiazolyl, 2-chloro-3-pyridyl, 3-chloro-2-pyridyl or 2-(trifluoromethyl)-3-pyridyl.

Q in particular very particularly preferably represents 3-chloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 2-chloro-3-thienyl, 2-bromo-3-thienyl, 2-iodo-3-thienyl, 2-methyl-3-thienyl, 3-bromo-2-furanyl, 3-methyl-2-furanyl, 2-chloro-3-furanyl, 2-bromo-3-furanyl, 2-iodo-3-furanyl, 2-methyl-3-furanyl, 3,4-dichloro-5-isothiazolyl, 2-chloro-3-pyridyl, 3-chloro-2-pyridyl or 2-(trifluoromethyl)-3-pyridyl;

Y preferably represents hydrogen or represents optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_1-C_{10})$-alkoxy, $(C_2-C_{10})$-alkenyloxy, $(C_3-C_{10})$-alkynyloxy, $(C_3-C_{14})$-cycloalkyl-$(C_1-C_{10})$-alkyl or represents an optionally mono- or poly-$M^2$-substituted 3- to 14-membered cyclic group;

Y preferably represents hydrogen or represents optionally mono- or poly-$M^2$-substituted $(C_1-C_4)$-alkyl, $(C_2-C_4)$-alkenyl, $(C_3-C_4)$-alkynyl, $(C_1-C_4)$-haloalkyl, $(C_2-C_4)$-haloalkenyl, $(C_3-C_4)$-haloalkynyl, $(C_1-C_4)$-alkoxy, $(C_2-C_4)$-alkenyloxy, $(C_3-C_4)$-alkynyloxy, $(C_3-C_6)$-cycloalkyl-$(C_1-C_4)$-alkyl or represents an optionally mono- or poly-$M^2$-substituted $C_3$- to $C_6$-membered carbocyclic group;

Y particularly preferably represents hydrogen, methyl, ethyl, n-propyl, isopropyl, n-butyl, sec-butyl, isobutyl, tert-butyl, cyanomethyl, 2,2-difluoroethyl, 2,2,2-trifluoroethyl, allyl, butenyl, propargyl, butynyl, 3,3-dichloroprop-2-enyl, methoxy, ethoxy, cyclopropylmethyl, cyclopropyl, cyclobutyl, cyclopentyl or cyclohexyl;

Y very particularly preferably represents hydrogen, methyl, ethyl, n-propyl, isopropyl, n-butyl, sec-butyl, isobutyl, tert-butyl, methoxy, ethoxy, cyclopropylmethyl, cyclopropyl, cyclobutyl;

Y very particularly preferably represents hydrogen, cyclopropyl;

W preferably represents oxygen;
W preferably represents sulfur;
$L^1$ preferably represents —C($R^{11}$, $R^{12}$)—, oxygen or —N($R^1$)—;
$L^1$ very particularly preferably represents —C($R^{11}$, $R^{12}$)— or —N($R^1$)—;
$L^1$ particularly preferably represents —C($R^{11}$, $R^{12}$)—;
$L^1$ particularly preferably represents oxygen;
$L^1$ particularly preferably represents —N($R^1$)—;
$L^3$ preferably represents a direct bond;
$L^3$ preferably represents —C($R^{31}$, $R^{32}$)—;
$M^1$ preferably represents hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulfonyl, $(C_1-C_6)$-haloalkylsulfonyl, $(C_1-C_6)$-alkylsulfanyl, $(C_1-C_6)$-haloalkylsulfanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—;
$M^1$ preferably represents hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulfonyl, $(C_1-C_4)$-haloalkylsulfonyl, $(C_1-C_4)$-alkylsulfanyl, $(C_1-C_6)$-haloalkylsulfanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—;

$M^1$ very particularly preferably represents hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulfonyl, $(C_1-C_4)$-haloalkylsulfonyl, $(C_1-C_4)$-alkylsulfanyl, $(C_1-C_6)$-haloalkylsulfanyl, $(C_6-C_{14})$-aryl-O—, halogenated $(C_6-C_{14})$-aryl)-O—;

$M^1$ very particularly preferably represents hydrogen, fluorine, bromine, chlorine, iodine, cyano, nitro, OH, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulfonyl, ethylsulfonyl, trifluoromethylsulfonyl, 2,2,2-trifluoroethylsulfonyl, methylsulfanyl, ethylsulfanyl, trifluoromethylsulfanyl, 2,2,2-trifluoroethylsulfanyl or phenoxy;

$M^1$ in particular very particularly preferably represents hydrogen, fluorine, bromine, chlorine, iodine, cyano, methyl, trifluoromethyl, difluoromethyl, methoxy, ethoxy, isopropoxy or phenoxy;

$R^1$ preferably represents hydrogen or optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_3-C_6)$—cycloalkyl-$(C_1-C_6)$-alkyl or represents an optionally mono- or poly-$M^2$-substituted $(C_3-C_{14})$-carbocyclic group;

$R^1$ preferably represents hydrogen or optionally mono- or poly-$M^2$-substituted $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_3-C_4)$-cycloalkyl-$(C_1-C_{10})$-alkyl or represents optionally mono- or poly-$M^2$-substituted $(C_3-C_8)$-cycloalkyl or halogenated $(C_3-C_8)$-cycloalkyl;

$R^1$ particularly preferably represents hydrogen or methyl, ethyl, n-propyl, isopropyl, allyl, propargyl, cyclopropylmethyl or cyclopropyl;

$R^1$ very particularly preferably represents hydrogen or $(C_1-C_4)$-alkyl;

$R^1$ particularly preferably represents hydrogen or methyl, ethyl, n-propyl, isopropyl;

$R^{11}$, $R^{12}$ preferably each independently of one another represent hydrogen, fluorine or optionally mono- or poly-$M^2$-substituted $(C_1-C_{10})$-alkyl, $(C_1-C_{10})$-haloalkyl, $(C_1-C_{10})$-alkoxy, $(C_3-C_{14})$-cycloalkyl-$(C_1-C_{10})$-alkyl or represent an optionally mono- or poly-$M^2$-substituted $(C_3-C_{14})$-carbocyclic group;

$R^{11}$, $R^{12}$ particularly preferably each independently of one another represent hydrogen, fluorine or optionally mono- or poly-$M^2$-substituted $(C_1-C_6)$-alkyl, $(C_1-C_6)$-haloalkyl, $(C_1-C_6)$-alkoxy, $(C_3-C_6)$-cycloalkyl-$(C_1-C_6)$-alkyl, $(C_3-C_8)$-cycloalkyl or halogenated $(C_3-C_8)$-cycloalkyl;

$R^{11}$, $R^{12}$ very particularly preferably each independently of one another represent hydrogen, fluorine or $(C_1-C_6)$-alkyl, $(C_1-C_6)$-haloalkyl, $(C_1-C_6)$-alkoxy, $(C_3-C_6)$-cycloalkyl-$(C_1-C_6)$-alkyl, $(C_3-C_6)$-cycloalkyl;

$R^{11}$, $R^{12}$ very particularly preferably each independently of one another represent hydrogen, fluorine, methyl, ethyl, n-propyl, isopropyl, trifluoromethyl, allyl, propargyl, methoxy, ethoxy, allyloxy, propargyloxy, cyclopropylmethyl, cyclopropyl;

$R^{11}$, $R^{12}$ very particularly preferably each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl;

$R^{11}$, $R^{12}$ very particularly preferably each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl;

$R^{11}$, $R^{12}$ very particularly preferably each independently of one another represent hydrogen, fluorine, methyl, ethyl, n-propyl, isopropyl, methoxy, ethoxy or $R^{11}$, $R^{12}$ very particularly preferably represent $C(R^{11}, R^{12})$ as spiro-$C(CH_2-CH_2)$;

$R^{11}$, $R^{12}$ in particular very particularly preferably each independently of one another represent hydrogen, $(C_1-C_6)$-alkoxy or $(C_1-C_6)$-alkyl;

$R^{11}$, $R^{12}$ in particular very particularly preferably independently of one another represent hydrogen, halogen, $(C_1-C_6)$-haloalkyl, $(C_1-C_6)$-alkoxy or $(C_1-C_6)$-alkyl; $R^{11}$, $R^{12}$ especially very particularly preferably independently of one another represent hydrogen, methoxy, methyl, ethyl;

$R^{11}$, $R^{12}$ in particular very particularly preferably independently of one another represent hydrogen, methoxy, methyl, ethyl, trifluoromethyl, fluorine;

$R^{21}$, $R^{22}$ preferably each independently of one another represent hydrogen, fluorine or optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_1-C_6)$-haloalkoxy, $(C_2-C_6)$-alkenyloxy, $(C_3-C_6)$-alkynyloxy, $(C_3-C_6)$-cycloalkyl-$(C_1-C_6)$-alkyl or represent an optionally mono- or poly-$M^2$-substituted $(C_3-C_{14})$-carbocyclic group;

$R^{21}$, $R^{22}$ preferably each independently of one another represent hydrogen, fluorine or optionally mono- or poly-$M^2$-substituted $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_1-C_6)$-alkoxy, $(C_1-C_4)$-haloalkoxy, $(C_2-C_4)$-alkenyloxy, $(C_3-C_4)$-alkynyloxy, $(C_3-C_4)$-cycloalkyl-$(C_1-C_4)$-alkyl, $(C_3-C_8)$-cycloalkyl or halogenated $(C_3-C_8)$-cycloalkyl;

$R^{21}$, $R^{22}$ particularly preferably each independently of one another represent hydrogen, fluorine or optionally mono- or poly-$M^2$-substituted $(C_1-C_4)$-alkyl, $(C_2-C_4)$-alkenyl, $(C_2-C_4)$-alkynyl, $(C_1-C_4)$-haloalkyl, $(C_1-C_6)$-alkoxy, $(C_2-C_4)$-alkenyloxy, $(C_3-C_4)$-alkynyloxy, $(C_3-C_4)$-cycloalkyl-$(C_1-C_4)$-alkyl, $(C_3-C_6)$-cycloalkyl;

$R^{21}$, $R^{22}$ preferably each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl;

$R^{21}$, $R^{22}$ very particularly preferably each independently of one another represent hydrogen, fluorine or $(C_1-C_4)$-alkyl, $(C_1-C_4)$-haloalkyl;

$R^{21}$, $R^{22}$ in particular very particularly preferably each independently of one another represent hydrogen, fluorine or methyl, ethyl;

$R^{21}$, $R^{22}$ very particularly preferably represent $C(R^{21}, R^{22})$ as spiro-$C(CH_2-CH_2)$;

$R^{31}$, $R^{32}$ preferably each independently of one another represent hydrogen or optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_1-C_6)$-haloalkoxy, $(C_2-C_6)$-alkenyloxy, $(C_3-C_6)$-alkynyloxy, $(C_3-C_6)$-cycloalkyl-$(C_1-C_6)$-alkyl or represent an optionally mono- or poly-$M^2$-substituted $(C_3-C_{14})$-carbocyclic group;

$R^{31}$, $R^{32}$ preferably each independently of one another represent hydrogen or optionally mono- or poly-$M^2$-substituted $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_1-C_6)$-alkoxy, $(C_1-C_4)$-haloalkoxy, $(C_2-C_4)$-alkenyloxy, $(C_3-C_4)$-alkynyloxy, $(C_3-C_4)$-cycloalkyl-$(C_1-C_4)$-alkyl or represent an optionally mono- or poly-$M^2$-substituted $(C_3-C_8)$-cycloalkyl or halogenated $(C_3-C_8)$-cycloalkyl;

$R^{31}$, $R^{32}$ particularly preferably each independently of one another represent hydrogen or optionally mono- or poly-$M^2$-substituted $(C_1-C_4)$-alkyl, $(C_1-C_4)$-haloalkyl, $(C_2-C_4)$-haloalkenyl, $(C_2-C_4)$-alkenyl, $(C_2-C_4)$-alkynyl, $(C_1-C_6)$-alkoxy, $(C_2-C_4)$-alkenyloxy, $(C_3-C_4)$-alkynyloxy, $(C_3-C_4)$-cycloalkyl-$(C_1-C_4)$-alkyl, $(C_3-C_6)$-cycloalkyl;

$R^{31}$, $R^{32}$ particularly preferably each independently of one another represent hydrogen, methyl, ethyl, n-propyl, isopropyl, tert-butyl, allyl, propargyl, methoxy, ethoxy, allyloxy, propargyloxy, cyclopropylmethyl, cyclopropyl;

$R^{31}$, $R^{32}$ very particularly preferably each independently of one another represent hydrogen or $(C_1-C_4)$-alkyl;

$R^{31}$, $R^{32}$ in particular very particularly preferably each independently of one another represent hydrogen, methyl, ethyl, n-propyl, isopropyl or tert-butyl;

$R^{31}$, $R^{32}$ very particularly preferably represent $C(R^{31}, R^{32})$ as spiro-$C(CH_2-CH_2)$;

$M^2$ preferably each independently of one another represent halogen, formyl, cyano, nitro, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_1-C_6)$-haloalkoxy, $(C_{uG}-C_{oG})$-alkenyloxy, $(C_2-C_6)$-haloalkenyloxy, $(C_3-C_6)$-alkynyloxy, $(C_3-C_6)$-haloalkynyloxy, $(C_1-C_6)$-alkylthio, $(C_1-C_6)$-haloalkylthio, $(C_2-C_6)$-alkenylthio, $(C_2-C_6)$-haloalkenylthio, $(C_3-C_6)$-alkynylthio, $(C_3-C_6)$-haloalkynylthio, $(C_1-C_6)$-alkylsulfonyl, $(C_1-C_6)$-haloalkylsulfonyl, $(C_2-C_6)$-alkenylsulfonyl, $(C_2-C_6)$-haloalkenylsulfonyl, $(C_3-C_6)$-alkynylsulfonyl, $(C_3-C_6)$-haloalkynylsulfonyl, $(C_1-C_6)$-alkylsulfanyl, $(C_1-C_6)$-haloalkylsulfanyl, $(C_2-C_6)$-alkenylsulfanyl, $(C_2-C_6)$-haloalkenylsulfanyl, $(C_3-C_6)$-alkynylsulfanyl, $(C_3-C_6)$-haloalkynylsulfanyl, formyl, $(C_1-C_6)$-alkylcarbonyl, $(C_1-C_6)$-haloalkylcarbonyl, $(C_2-C_6)$-alkenylcarbonyl, $(C_2-C_6)$-haloalkenylcarbonyl, $(C_2-C_6)$-alkynylcarbonyl, $(C_2-C_6)$-haloalkynylcarbonyl, $(C_1-C_6)$-alkoxycarbonyl, $(C_1-C_6)$-haloalkoxycarbonyl, $(C_2-C_6)$-alkenyloxycarbonyl, $(C_2-C_6)$-haloalkenyloxycarbonyl, $(C_3-C_6)$-alkynyloxycarbonyl, $(C_3-C_6)$-haloalkynyloxycarbonyl, $(C_1-C_6)$-alkylcarbonyloxy, $(C_1-C_6)$-haloalkylcarbonyloxy, $(C_2-C_6)$-alkenylcarbonyloxy, $(C_2-C_6)$-haloalkenylcarbonyloxy, $(C_2-C_6)$-alkynylcarbonyloxy, $(C_2-C_6)$-haloalkynylcarbonyloxy or $(C_3-C_{14})$-cycloalkyl.

$M^2$ particularly preferably each independently of one another represent halogen, formyl, cyano, nitro, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-haloalkoxy, $(C_2-C_4)$-alkenyloxy, $(C_2-C_4)$-haloalkenyloxy, $(C_3-C_4)$-alkynyloxy, $(C_3-C_4)$-haloalkynyloxy, $(C_1-C_4)$-alkylthio, $(C_1-C_4)$-haloalkylthio, $(C_2-C_4)$-alkenylthio, $(C_2-C_4)$-haloalkenylthio, $(C_3-C_4)$-alkynylthio, $(C_3-C_4)$-haloalkynylthio, $(C_1-C_4)$-alkylsulfonyl, $(C_1-C_4)$-haloalkylsulfonyl, $(C_2-C_4)$-alkenylsulfonyl, $(C_2-C_4)$-haloalkenylsulfonyl, $(C_3-C_4)$-alkynylsulfonyl, $(C_3-C_4)$-haloalkynylsulfonyl, $(C_1-C_4)$-alkylsulfanyl, $(C_1-C_4)$-haloalkylsulfanyl, $(C_2-C_4)$-alkenylsulfanyl, $(C_2-C_4)$-haloalkenylsulfanyl, $(C_3-C_4)$-alkynylsulfanyl, $(C_3-C_4)$-haloalkynylsulfanyl, $(C_1-C_4)$- alkylcarbonyl, (C₁-C₄)-haloalkylcarbonyl, (C₂-C₄)-alkenylcarbonyl, (C₂-C₄)-haloalkenylcarbonyl, (C₂-C₄)-alkynylcarbonyl, (C₂-C₄)-haloalkynylcarbonyl, (C₁-C₄)-alkoxycarbonyl, (C₁-C₄)-haloalkoxycarbonyl, (C₂-C₄)-alkenyloxycarbonyl, (C₂-C₄)-haloalkenyloxycarbonyl, (C₃-C₄)-alkynyloxycarbonyl, (C₃-C₄)-haloalkynyloxycarbonyl, (C₁-C₄)-alkylcarbonyloxy, (C₁-C₄)-haloalkylcarbonyloxy, (C₂-C₄)-alkenylcarbonyloxy, (C₂-C₄)-haloalkenylcarbonyloxy, (C₂-C₄)-alkynylcarbonyloxy, (C₂-C₄)-haloalkynylcarbonyloxy or (C₃-C₆)-cycloalkyl.

$M^2$ very particularly preferably each independently of one another represent chlorine, fluorine, formyl, cyano, nitro, (C₁-C₄)-alkyl, (C₁-C₄)-haloalkyl, (C₁-C₄)-alkoxy, (C₁-C₄)-haloalkoxy, (C₁-C₄)-alkylthio, (C₁-C₄)-haloalkylthio, (C₁-C₄)-alkylsulfonyl, (C₁-C₄)-haloalkylsulfonyl, (C₁-C₄)-alkylsulfanyl, (C₁-C₄)-haloalkylsulfanyl, (C₁-C₄)-alkylcarbonyl, (C₁-C₄)-haloalkylcarbonyl or (C₃-C₆)-cycloalkyl.

$M^2$ very particularly preferably each independently of one another represent fluorine, bromine, chlorine, iodine, cyano, nitro, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulfonyl, ethylsulfonyl, trifluoromethylsulfonyl, 2,2,2-trifluoroethylsulfonyl, methylsulfanyl, ethylsulfanyl, trifluoromethylsulfanyl, 2,2,2-trifluoroethylsulfanyl, cyclopropyl, cyclobutyl or cyclopentyl.

However, the general or preferred radical definitions or explanations given above can also be combined with one another as desired, i.e. including combinations between the respective ranges and preferred ranges. They apply both to the end products and, correspondingly, to precursors and intermediates.

The definitions mentioned can be combined with one another as desired. Moreover, individual definitions may not apply.

Preference, particular preference and very particular preference is given to compounds of the formula (I) which carry the substituents mentioned under preferred, particularly preferred, very particularly preferred or in particular very particularly preferred in each case.

In one embodiment, compounds of the formula (I) are compounds

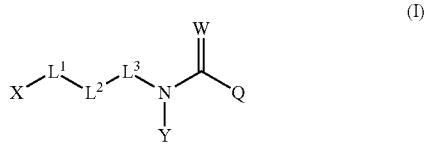

(I)

in which $L^1$, $L^2$, $L^3$, Q, W and Y are as defined above and
X represents phenyl, preferably mono- or polysubstituted by $M^1$ selected from the group consisting of hydrogen, halogen, cyano, nitro, OH, (C₁-C₄)-alkyl, (C₁-C₃)-haloalkyl, (C₁-C₄)-alkoxy, (C₁-C₃)-haloalkoxy, (C₁-C₄)-alkylthio, (C₁-C₃)-haloalkylthio, (C₁-C₄)-alkylsulfonyl, (C₁-C₃)-haloalkylsulfonyl, (C₁-C₄)-alkylsulfanyl, (C₁-C₃)-haloalkylsulfanyl and phenoxy;
X represents phenyl, particularly preferably mono- or polysubstituted by $M^1$ selected from the group consisting of hydrogen, fluorine, bromine, chlorine, iodine, cyano, nitro, OH, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulfonyl, ethylsulfonyl, trifluoromethylsulfonyl, 2,2,2-trifluoroethylsulfonyl, methylsulfanyl, ethylsulfanyl, trifluoromethylsulfanyl, 2,2,2-trifluoroethylsulfanyl and phenoxy;
X represents 2-thienyl, preferably mono- or polysubstituted by $M^1$ selected from the group consisting of hydrogen, halogen, cyano, nitro, OH, optionally substituted (C₁-C₄)-alkyl, (C₁-C₃)-haloalkyl, (C₁-C₄)-alkoxy and (C₁-C₃)-haloalkoxy;
X represents 2-thienyl, particularly preferably mono- or polysubstituted by $M^1$ selected from the group consisting of hydrogen, fluorine, chlorine, bromine, iodine, methyl and trifluoromethyl;
X represents 3-thienyl, preferably mono- or polysubstituted by $M^1$ selected from the group consisting of hydrogen, halogen, cyano, nitro, OH, optionally substituted (C₁-C₄)-alkyl, (C₁-C₃)-haloalkyl, (C₁-C₄)-alkoxy and (C₁-C₃)-haloalkoxy;
X represents 3-thienyl, particularly preferably mono- or polysubstituted by $M^1$ selected from the group consisting of hydrogen, fluorine, chlorine, bromine, iodine, methyl and trifluoromethyl;
X represents 2-furanyl, preferably mono- or polysubstituted by $M^1$ selected from the group consisting of hydrogen, halogen, cyano, nitro, OH, optionally substituted (C₁-C₄)-alkyl, (C₁-C₃)-haloalkyl, (C₁-C₄)-alkoxy and (C₁-C₃)-haloalkoxy;
X represents 2-furanyl, particularly preferably mono- or polysubstituted by $M^1$ selected from the group consisting of hydrogen, fluorine, chlorine, bromine, iodine, methyl and trifluoromethyl.
X represents 3-furanyl, preferably mono- or polysubstituted by $M^1$ selected from the group consisting of hydrogen, halogen, cyano, nitro, OH, optionally substituted (C₁-C₄)-alkyl, (C₁-C₃)-haloalkyl, (C₁-C₄)-alkoxy and (C₁-C₃)-haloalkoxy;
X represents 3-furanyl, particularly preferably mono- or polysubstituted by $M^1$ selected from the group consisting of hydrogen, fluorine, chlorine, bromine, iodine, methyl and trifluoromethyl.

In a further embodiment, compounds of the formula (I) are compounds

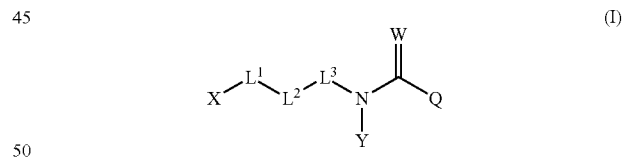

(I)

in which $L^1$, $L^2$, $L^3$, W, X and Y are as defined above and
Q preferably represents the following structural elements which may be mono- or polysubstituted by $M^1$ selected from the group consisting of hydrogen, halogen, cyano, optionally substituted (C₁-C₄)-alkyl, (C₁-C₃)-haloalkyl or (C₁-C₄)-alkoxy:

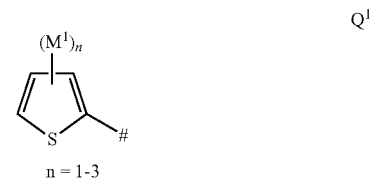

n = 1-3

-continued

Q²
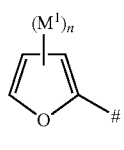
n = 1-3

Q³
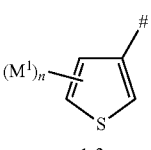
n = 1-3

Q⁴
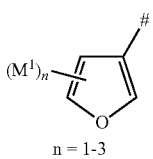
n = 1-3

Q⁵
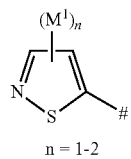
n = 1-2

Q⁶
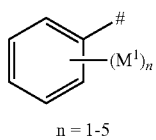
n = 1-5

Q⁷
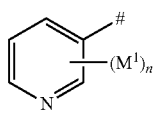
n = 1-4

Q⁸
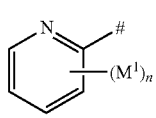
n = 1-4

Q particularly preferably represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 4-chloro-5-isothiazolyl, 3,4-dichloro-5-isothiazolyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-chloro-3-pyridyl, 3-chloro-2-pyridyl or 2-(trifluoromethyl)-3-pyridyl.

Q preferably represents the following structural elements which may be mono- or polysubstituted by M¹ selected from the group consisting of hydrogen, halogen, cyano, optionally substituted (C₁-C₄)-alkyl, (C₁-C₃)-haloalkyl or (C₁-C₄)-alkoxy:

Q¹
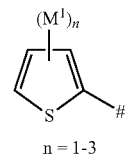
n = 1-3

Q²
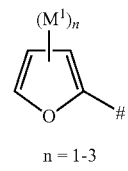
n = 1-3

Q³
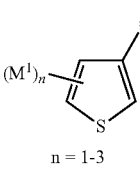
n = 1-3

Q⁴
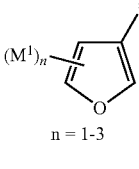
n = 1-3

Q⁵
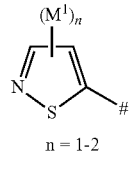
n = 1-2

Q⁷
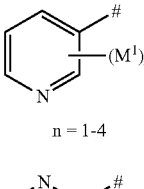
n = 1-4

Q⁸
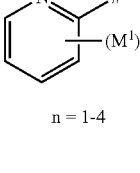
n = 1-4

Q particularly preferably represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 4-chloro-5-isothiazolyl, 3,4-dichloro-5-isothiazolyl, 2-chloro-3-pyridyl, 3-chloro-2-pyridyl or 2-(trifluoromethyl)-3-pyridyl;

and salts, N-oxides and tautomeric forms of the compounds of the formula (I).

In a further embodiment, compounds of the formula (I) are compounds

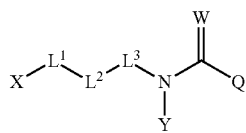

(I)

in which $L^1$, $L^2$, $L^3$, Q, W and X are as defined above and
Y preferably represents hydrogen or represents optionally mono- or poly-$M^2$-substituted $(C_1-C_4)$-alkyl, $(C_2-C_4)$-alkenyl, $(C_3-C_4)$-alkynyl, $(C_1-C_4)$-haloalkyl, $(C_2-C_4)$-haloalkenyl, $(C_3-C_4)$-haloalkynyl, $(C_1-C_4)$-alkoxy, $(C_2-C_4)$-alkenyloxy, $(C_3-C_4)$-alkynyloxy, $(C_3-C_6)$-cycloalkyl-$(C_1-C_4)$-alkyl or represents an optionally substituted $C_3$- to $C_6$-membered carbocyclic group;

Y particularly preferably represents hydrogen, methyl, ethyl, n-propyl, isopropyl, n-butyl, sec-butyl, isobutyl, tert-butyl, cyanomethyl, 2,2-difluoroethyl, 2,2,2-trifluoroethyl, allyl, butenyl, propargyl, butynyl, 3,3-dichloroprop-2-enyl, methoxy, ethoxy, cyclopropylmethyl, cyclopropyl, cyclobutyl, cyclopentyl or cyclohexyl;

and salts, N-oxides and tautomeric forms of the compounds of the formula (I).

In a further embodiment, compounds of the formula (I) are compounds

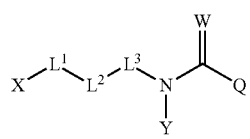

(I)

in which $L^1$, $L^2$, $L^3$, Q, X and Y are as defined above and
W preferably represents oxygen;
and salts, N-oxides and tautomeric forms of the compounds of the formula (I).

In a further embodiment, compounds of the formula (I) are compounds

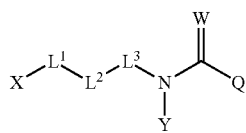

(I)

in which $L^2$, $L^3$, Q, W, X and Y are as defined above and
$L^1$ preferably represents $C(R^{11}, R^{12})$, where $R^{11}$ and $R^{12}$ each independently of one another represent hydrogen, fluorine or optionally mono- or poly-$M^2$-substituted $(C_1-C_4)$-alkyl, $(C_3-C_4)$-alkenyl, $(C_3-C_4)$-alkynyl, $(C_1-C_4)$-haloalkyl, $(C_3-C_4)$-haloalkenyl, $(C_3-C_4)$-haloalkynyl, $(C_1-C_4)$-alkoxy, $(C_3-C_4)$-alkenyloxy, $(C_3-C_4)$-alkynyloxy, $(C_3-C_6)$-cycloalkyl-$(C_1-C_4)$-alkyl or represents an optionally substituted $C_3$- to $C_6$-membered carbocyclic group, or where $R^{11}$ and $R^{12}$ together represent an optionally substituted spiro-linked 3- to 6-membered cyclic group;

$L^1$ preferably represents oxygen or sulfur;
$L^1$ preferably represents —$N(R^1)$ where $R^2$ represents hydrogen or optionally mono- or poly-$M^2$-substituted $(C_1-C_4)$-alkyl, $(C_3-C_4)$-alkenyl, $(C_3-C_4)$-alkynyl, $(C_1-C_4)$-haloalkyl, $(C_3-C_4)$-haloalkenyl, $(C_3-C_4)$-haloalkynyl, $(C_3-C_6)$-cycloalkyl-$(C_1-C_4)$-alkyl or represent an optionally substituted $C_3$- to $C_6$-membered carbocyclic group;

$L^1$ particularly preferably represents $C(R^{11}, R^{12})$ where $R^{11}$ and $R^{12}$ each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl, or where $C(R^{11}, R^{12})$ represents spiro-$C(CH_2$—$CH_2)$;

$L^1$ particularly preferably represents oxygen;
and salts, N-oxides and tautomeric forms of the compounds of the formula (I).

In a further embodiment, compounds of the formula (I) are compounds

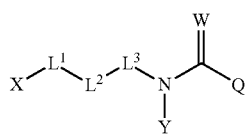

(I)

in which $L^2$, $L^3$, W, X and Y are as defined above and
Q preferably represents a mono- or poly-$M^1$-substituted phenyl, pyridyl, thienyl, furanyl or isothiazolyl;
Q preferably represents a mono- or poly-$M^1$-substituted pyridyl, thienyl, furanyl or isothiazolyl;
Q particularly preferably represents a mono- or poly-$M^1$-substituted phenyl;
$L^1$ preferably represents oxygen or sulfur;
$L^1$ preferably represents —$N(R^1)$ where $R^1$ represents hydrogen or optionally mono- or poly-$M^2$-substituted $(C_1-C_4)$-alkyl, $(C_3-C_4)$-alkenyl, $(C_3-C_4)$-alkynyl, $(C_1-C_4)$-haloalkyl, $(C_3-C_4)$-haloalkenyl, $(C_3-C_4)$-haloalkynyl, $(C_3-C_6)$-cycloalkyl-$(C_1-C_4)$-alkyl or represent an optionally substituted $C_3$- to $C_6$-membered carbocyclic group;
$L^1$ particularly preferably represents sulfur; $L^1$ particularly preferably represents —$N(R^1)$ where $R^1$ represents hydrogen, methyl, ethyl, n-propyl, isopropyl, allyl, propargyl, cyclopropylmethyl or cyclopropyl;
$L^1$ preferably represents —$C(R^{11}, R^{12})$— where $R^{11}$, $R^{12}$ each independently of one another represent halogen, $(C_1-C_6)$-haloalkyl or $(C_1-C_6)$-alkoxy;
$L^1$ particularly preferably represents —$C(R^{11}, R^{12})$— where $R^{11}$, $R^{12}$ independently of one another represent fluorine, trifluoromethyl, methoxy;
and salts, N-oxides and tautomeric forms of the compounds of the formula (I).

In a further embodiment, compounds of the formula (I) are compounds

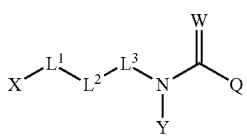

(I)

in which $L^1$, $L^3$, Q, W, X and Y are as defined above and
$L^2$ preferably represents $C(R^{21}, R^{22})$, where $R^{21}$ and $R^{22}$ each independently of one another represent hydrogen, fluorine or optionally mono- or poly-$M^2$-substituted ($C_1$-$C_4$)-alkyl, ($C_3$-$C_4$)-alkenyl, ($C_3$-$C_4$)-alkynyl, ($C_1$-$C_4$)-haloalkyl, ($C_3$-$C_4$)-haloalkenyl, ($C_3$-$C_4$)-haloalkynyl, ($C_1$-$C_4$)-alkoxy, ($C_3$-$C_4$)-alkenyloxy, ($C_3$-$C_4$)-alkynyloxy, ($C_3$-$C_6$)-cycloalkyl-($C_1$-$C_4$)-alkyl or represents an optionally substituted $C_3$- to $C_6$-membered carbocyclic group, or where $R^{21}$ and $R^{22}$ together represent an optionally substituted spiro-linked 3- to 6-membered cyclic group;

$L^2$ particularly preferably represents $C(R^{21}, R^{22})$ where $R^{21}$ and $R^{22}$ each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl, or where $C(R^{21}, R^{22})$ represents spiro-$C(CH_2$—$CH_2)$;

and salts, N-oxides and tautomeric forms of the compounds of the formula (I).

In a further embodiment, compounds of the formula (I) are compounds

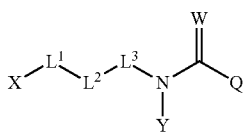

(I)

in which $L^1$, $L^2$, Q, W, X and Y are as defined above and
$L^3$ preferably represents $C(R^{31}, R^{32})$, where $R^{31}$ and $R^{32}$ each independently of one another represent hydrogen or optionally mono- or poly-$M^2$-substituted ($C_1$-$C_4$)-alkyl, ($C_3$-$C_4$)-alkenyl, ($C_3$-$C_4$)-alkynyl, ($C_1$-$C_4$)-haloalkyl, ($C_3$-$C_4$)-haloalkenyl, ($C_3$-$C_4$)-haloalkynyl, ($C_1$-$C_4$)-alkoxy, ($C_3$-$C_4$)-alkenyloxy, ($C_3$-$C_4$)-alkynyloxy, ($C_3$-$C_6$)-cycloalkyl-($C_1$-$C_4$)-alkyl or represents an optionally substituted $C_3$- to $C_6$-membered carbocyclic group, or where $R^{31}$ and $R^{32}$ together represent an optionally substituted spiro-linked 3- to 6-membered cyclic group;

$L^3$ particularly preferably represents $C(R^{31}, R^{32})$ where $R^{31}$ and $R^{32}$ each independently of one another represent hydrogen, methyl, ethyl, n-propyl, isopropyl, allyl, propargyl, methoxy, ethoxy, allyloxy, propargyloxy, cyclopropylmethyl, cyclopropyl, or where $C(R^{31}, R^{32})$ represents spiro-$C(CH_2$—$CH_2)$;

$L^3$ preferably and particularly preferably represents a direct bond between $L^2$ and N—Y;

and salts, N-oxides and tautomeric forms of the compounds of the formula (I).

In a further embodiment, compounds of the formula (I) are compounds

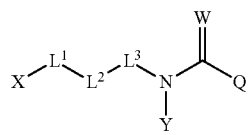

(I)

in which $L^1$, $L^2$, W, X and Y are as defined above and
Q preferably represents mono- or poly-$M^1$-substituted phenyl, pyridyl, thienyl, furanyl or isothiazolyl;

Q particularly preferably represents mono- or poly-$M^1$-substituted phenyl;

Q very particularly preferably represents mono- or poly-$M^1$-substituted phenyl where the phenyl may not be substituted by trifluoromethyl in the 2-position;

$L^3$ preferably represents $C(R^{31}, R^{32})$, where $R^{31}$ and $R^{32}$ each independently of one another represent hydrogen or optionally mono- or poly-$M^2$-substituted ($C_1$-$C_4$)-alkyl, ($C_3$-$C_4$)-alkenyl, ($C_3$-$C_4$)-alkynyl, ($C_1$-$C_4$)-haloalkyl, ($C_3$-$C_4$)-haloalkenyl, ($C_3$-$C_4$)-haloalkynyl, ($C_1$-$C_4$)-alkoxy, ($C_3$-$C_4$)-alkenyloxy, ($C_3$-$C_4$)-alkynyloxy, ($C_3$-$C_6$)-cycloalkyl-($C_1$-$C_4$)-alkyl or represents an optionally substituted $C_3$- to $C_6$-membered carbocyclic group, or where $R^{31}$ and $R^{32}$ together represent an optionally substituted spiro-linked 3- to 6-membered cyclic group;

$L^3$ particularly preferably represents $C(R^{31}, R^{32})$ where $R^{31}$ and $R^{32}$ each independently of one another represent hydrogen, methyl, ethyl, n-propyl, isopropyl, allyl, propargyl, methoxy, ethoxy, allyloxy, propargyloxy, cyclopropylmethyl, cyclopropyl;

$L^3$ particularly preferably represents $C(R^{31}, R^{32})$ where $R^{31}$ and $R^{32}$ each independently of one another represent methyl, ethyl, n-propyl, isopropyl, allyl, propargyl, methoxy, ethoxy, allyloxy, propargyloxy, cyclopropylmethyl, cyclopropyl;

and salts, N-oxides and tautomeric forms of the compounds of the formula (I).

In a very particularly preferred further embodiment, compounds of the formula (I) are compounds

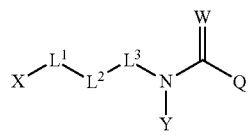

(I)

in which
X mono- or poly-$M^1$-substituted phenyl where $M^1$ is selected from the group consisting of hydrogen, fluorine, bromine, chlorine, iodine, cyano, nitro, OH, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulfonyl, ethylsulfonyl, trifluoromethylsulfonyl, 2,2,2-trifluoroethylsulfonyl, methylsulfanyl, ethylsulfanyl, trifluoromethylsulfanyl, 2,2,2-trifluoroethylsulfanyl and phenoxy;

X represents 2-thienyl which is mono- or polysubstituted by $M^1$ selected from the group consisting of hydrogen, fluorine, chlorine, bromine, iodine, methyl and trifluoromethyl;

X represents 3-thienyl which is mono- or polysubstituted by $M^1$ selected from the group consisting of hydrogen, fluorine, chlorine, bromine, iodine, methyl and trifluoromethyl;

X represents 2-furanyl which is mono- or polysubstituted by $M^1$ selected from the group consisting of hydrogen, fluorine, chlorine, bromine, iodine, methyl and trifluoromethyl;

X represents 3-furanyl which is mono- or polysubstituted by $M^1$ selected from the group consisting of hydrogen, fluorine, chlorine, bromine, iodine, methyl and trifluoromethyl;

Q represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 4-chloro-5-isothiazolyl, 3,4-dichloro-5-isothiazolyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-chloro-3-pyridyl, 3-chloro-2-pyridyl or 2-(trifluoromethyl)-3-pyridyl;

Y represents hydrogen, methyl, ethyl, n-propyl, isopropyl, n-butyl, sec-butyl, isobutyl, tert-butyl, cyanomethyl, 2,2-difluoroethyl, 2,2,2-trifluoroethyl, allyl, butenyl, propargyl, butynyl, 3,3-dichloroprop-2-enyl, methoxy, ethoxy, cyclopropylmethyl, cyclopropyl, cyclobutyl, cyclopentyl or cyclohexyl;

W represents oxygen;

$L^1$ represents —N($R^1$) where $R^2$ represents hydrogen, methyl, ethyl, n-propyl, isopropyl, allyl, propargyl, cyclopropylmethyl or cyclopropyl;

$L^2$ represents C($R^{21}$, $R^{22}$) where $R^{21}$ and $R^{22}$ each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl, or where C($R^{21}$, $R^{22}$) represents spiro-C(CH$_2$—CH$_2$);

$L^3$ represents a direct bond between $L^2$ and N—Y.

In a very particularly preferred further embodiment, compounds of the formula (I-b) are compounds

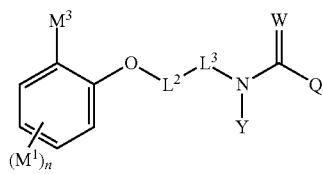

in which $L^2$, $L^3$, Q, W and Y are as defined above and $M^1$ and $M^3$ independently of one another represent halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulfonyl, ($C_1$-$C_{10}$)-haloalkylsulfonyl, ($C_1$-$C_{10}$)-alkylsulfanyl, ($C_1$-$C_{10}$)-haloalkylsulfanyl, (3- to 14-membered cyclic group)-O—.

Novel are the compounds of the formula (I-a)

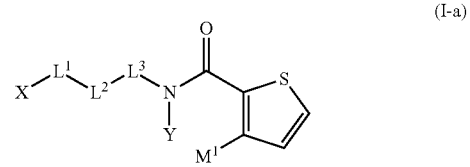

in which $M^1$ represents chlorine, bromine or iodine and $L^1$, $L^2$, $L^3$, X and Y are as defined above.

Novel are the compounds of the formula I-2

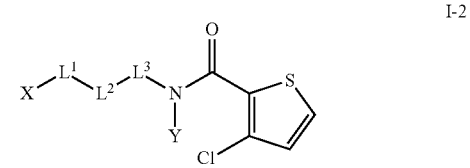

in which $L^1$, $L^2$, $L^3$, X and Y are as defined above.

Novel are the compounds of the formula I-3

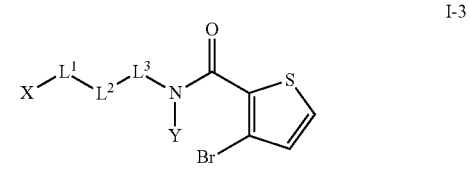

in which $L^1$, $L^2$, $L^3$, X and Y are as defined above.

Novel are the compounds of the formula I-4

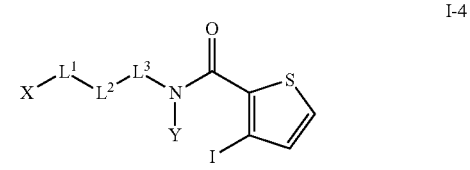

in which $L^1$, $L^2$, $L^3$, X and Y are as defined above.

Preparation Process A

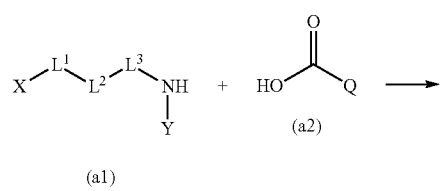

-continued

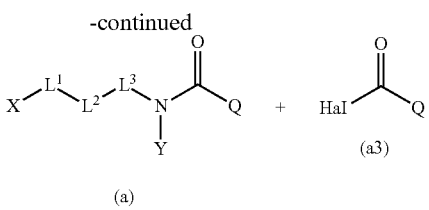

The radicals X, Y, L¹, L², L³ and Q have the meanings described above. W in this case represents oxygen.

Compounds of the general formula (a) according to the invention can be prepared from amines of the formula (a1) and carboxylic acids of the formula (a2) or halides thereof of the formula (a3) by generally known processes as described, for example, in WO-A 2007/060166. The amines of the formula (a1) and carboxylic acids of the formula (a2) and their halides of the formula (a3) are commercially available.

Preparation Process A-1

The compounds of the formula (I-a)

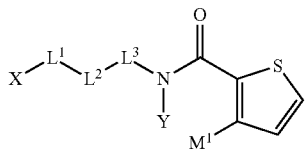
(I-a)

in which $M^1$ represents chlorine, bromine or iodine and $L^1$, $L^2$, $L^3$, X and Y are as defined above are prepared by reacting amines of the formula (a1)

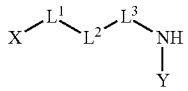
(a1)

where X, Y, $L^1$, $L^2$, $L^3$ have the meanings described above with carboxylic acids of the formula (a2-1)

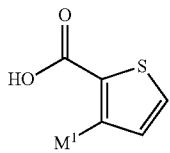
(a2-1)

where $M^1$ represents chlorine, bromine or iodine, or their acid halides of the formula (a3-1)

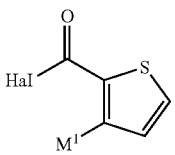
(a3-1)

where $M^1$ represents chlorine, bromine or iodine and Hal represents fluorine, chlorine or bromine, to give the compounds of the formula (I-a).

The amines of the formula (a1) and carboxylic acids of the formula (a2-1) and their halides of the formula (a3-1) are commercially available. Alternatively, the halides of the formula (a3-1) can be prepared by generally known methods from carboxylic acids of the formula (a2-1) using appropriate halogenating agents, for example phosphoryl chloride, phosphoryl bromide, thionyl chloride, oxalyl chloride or phosgene.

When using carbonyl halides of the general structure (a3-1), the compounds of the general formula (I-a) according to the invention are advantageously carried out in the presence of a reaction auxiliary. Suitable reaction auxiliaries are all customary inorganic or organic bases. These include, for example, alkaline earth metal or alkali metal hydrides, hydroxides, amides, alcoholates, acetates, carbonates or hydrogencarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogencarbonate or ammonium carbonate, and also tertiary amines, such as, for example, trimethylamine, triethylamine, diisopropylethylamine, tributylamine, N,N-dimethylaniline, pyridine, N-methylpiperidine, 4-(N,N-dimethylamino)pyridine, diazabicyclooctane (DABCO), diazabicyclononene (DBN) or diazabicycloundecene (DBU), in particular triethylamine.

When using carboxylic acids of the general structure (a2-1), the compounds of the general formula (I-a) according to the invention are advantageously carried out in the presence of a condensing agent. The carboxylic acids are commercially available. Suitable condensing agents are especially dehydrating chemicals. These preferably include acid anhydrides and acid halides, such as, for example, acetic anhydride, propionic anhydride, phosphorus(V) oxide, phosphoryl chloride, phosphoryl bromide, phosphorus trichloride, phosphorus tribromide, thionyl chloride, oxalyl chloride, phosgene, diphosgene, methyl formate, ethyl formate, and also carbodiimides such as, for example, N,N'-dicyclohexylcarbodiimide (DCC) or 1-ethyl-3-(3-dimethylaminopropyl)carbodiimide hydrochloride (EDC-HCl). Other known condensing agents are triphenylphosphine/carbon tetrachloride, 4-(4,6-dimethoxy[1.3.5]triazin-2-yl)-4-methylmorpholinium chloride hydrate or hydroxybenzotriazole (HOBt). Particular mention may be made here of the combination of 1-ethyl-3-(3-dimethylaminopropyl)carbodiimide hydrochloride (EDC-HCl) and hydroxybenzotriazole (HOBt).

The compounds of the general formula (I-a) according to the invention are optionally prepared using one or more diluents. Suitable diluents are especially inert organic solvents. These include in particular aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride, tetrahydrofuran, dioxane, acetonitrile or dimethylformamide.

When carrying out process A-1, the reaction temperatures can be varied within a relatively wide range. In general, the process is carried out at temperatures between 0° C. and 150° C., preferably between 10° C. and 120° C.

Process A-1 is generally carried out under atmospheric pressure. However, it is also possible to carry out process A-1 under elevated or reduced pressure—generally between 0.1 bar and 10 bar.

Preparation Process B

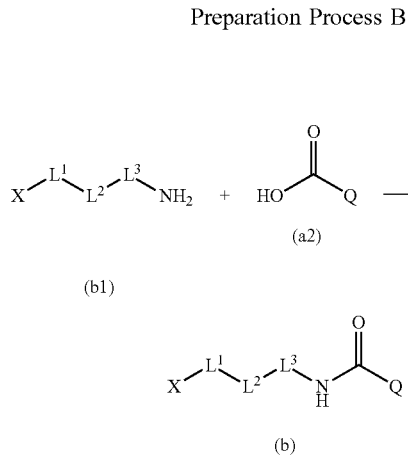

(b1)

(b)

The radicals X, L$^1$, L$^2$, L$^3$, and Q have the meanings described above. In this case, W represents oxygen, Y represents hydrogen.

Compounds of the general structure (I) or their embodiment (b) according to the invention can be prepared from amines of the formula (b1) and carboxylic acids of the formula (a2) or halides thereof of the formula (a3) by generally known processes as described, for example, in EP2007060166. The amines of the formula (b1) and carboxylic acids of the formula (a2) and their halides of the formula (a3) are commercially available.

Preparation Process C

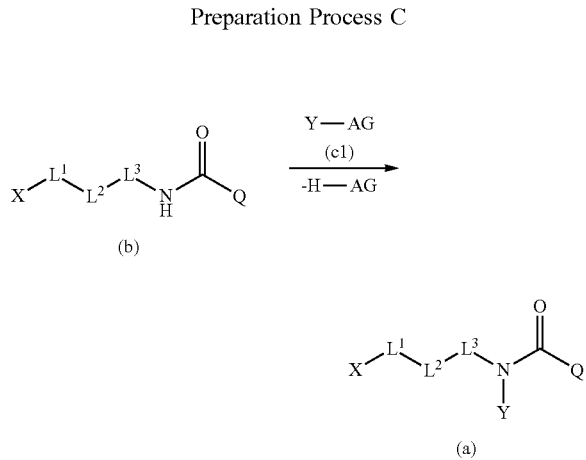

The radicals X, Y, L$^1$, L$^2$, L$^3$ and Q have the meanings described above. In this case, W represents oxygen, AG represents a leaving group, for example halogens or alkyl- or arylsulfonates.

Compounds of the general formula (I) according to the invention and their embodiment (a) can be prepared from amines of the formula (b) and alkylating agents of the formula (c1) by generally known processes as described, for example, in EP2007060166.

Preparation Process D

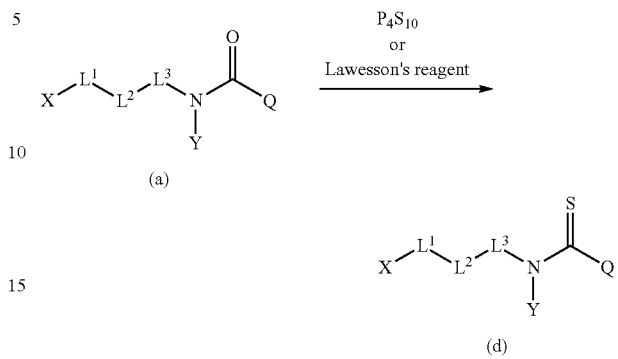

The radicals X, Y, L$^1$, L$^2$, L$^3$ and Q have the meanings described above. W=oxygen is transformed directly into W=sulfur.

Compounds of the general formula (I) according to the invention and their embodiment (d) can be prepared from compounds of the formula (a) and appropriate sulfurizing agents, for example tetraphosphorus decasulfide ("phosphorus pentasulfide") or 2,4-bis[4-methoxyphenyl]-2,4-dithiono-1,2,3,4-dithiadiphosphetane ("Lawesson's reagent"), by generally known processes. Process examples are known inter alia from Houben-Weyl, Methoden der Organischen Chemie [Methods of Organic Chemistry], E5, 1255 (Thieme Verlag, Stuttgart, 1985).

A further aspect of the present invention is a method for controlling endoparasitic pests, which method is characterized in that a compound of the formula (I) or (I-a) according to the invention or a salt, N-oxide or tautomeric form thereof is allowed to act on the pests and/or their habitat.

Field of Anthelmintic Use

The compositions according to the invention, having favorable homeotherm toxicity, are suitable for controlling pathogenic endoparasites which occur in humans and in animal keeping and animal breeding in the case of agricultural animals, breeding animals, zoo animals, laboratory animals, experimental animals and pets. They may be employed against all or individual stages of development of the pests and against resistant and normally sensitive endoparasite isolates. By controlling the pathogenic endoparasites, it is intended to reduce disease, mortality and decreasing performance (for example in the production of meat, milk, wool, hides, eggs, honey, etc.), so that more economical, simpler and healthier animal husbandry is possible by using the active compounds. The pathogenic endoparasites include helminths such as Platyhelmintha (in particular Monogenea, cestodes and trematodes), nematodes, Pentastoma and Acanthocephala. Examples which may be mentioned are:

Monogenea: for example: *Gyrodactylus* spp., *Dactylogyrus* spp., *Polystoma* spp.

Cestodes: From the order of the Pseudophyllidea, for example: *Diphyllobothrium* spp., *Spirometra* spp., *Schistocephalus* spp., *Ligula* spp., *Bothridium* spp., *Diphlogonoporus* spp.

From the order of the Cyclophyllidea, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echi*- nolepis spp., *Echinocotyle* spp., *Diochis* spp., *Dipylidium* spp., *Joyeuxiella* spp., *Diplopylidium* spp.

Trematodes: From the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp-, *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.

Nematodes: From the order of the Trichinellida, for example: *Trichuris* spp., *Capillaria* spp., *Trichomosoides* spp., *Trichinella* spp.

From the order of the Tylenchida, for example: *Micronema* spp., *Strongyloides* spp.

From the order of the Rhabditina, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acantocephala: From the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.

From the order of the Echinorhynchida, for example, *Acanthocephalus* spp., *Echinorhynchus* spp., *Leptorhynchoides* spp.

Pentastoma: From the order of the Porocephalida, for example, *Linguatula* spp.

According to a preferred embodiment, the compounds of the formula (I) are used for controlling nematodes. The following nematodes may be mentioned with particular preference: Trichinellida, Tylenchida, Rhabditina or the following from the order of the Spirurida: *Gnathostoma* spp., *Physaloptera* spp., *Thelazia* spp., *Gongylonema* spp., *Habronema* spp., *Parabronema* spp., *Draschia* spp., *Dracunculus* spp.

A further particularly preferred embodiment provides the use for controlling Strongylida, in particular *Haemonchus* spp. (e.g. *Haemonchus contortus*), *Trichostrongylus* spp. (e.g. *Trichostrongylus colubriformis*), *Cooperia* spp., and *Ostertagia* spp. or *Teladorsagia* spp.

A further particularly preferred embodiment provides the use for controlling Ascaridida such as, for example, *Parascaris* spp.

Animals can be fish, reptiles, birds or in particular mammals.

The agricultural and breeding livestock include mammals such as, for example, cattle, horses, sheep, pigs, goats, camels, water buffalo, donkeys, rabbits, fallow deer, reindeer, fur-bearing animals such as, for example, mink, chinchilla, raccoon, birds such as, for example, chicken, geese, turkeys, ducks, ostriches, fish such as trout, salmon, carp, perches, pikes, eels.

Laboratory and experimental animals include mice, rats, guinea pigs, golden hamsters, dogs and cats.

Pets include dogs and cats.

According to the invention, the use for animals is preferred; however, in principle, the use for humans is also possible. In humans, *Ascaris* spp., *Ancylostoma* spp, *Necator* spp., *Trichuris* spp., *Strongyloides* spp. and *Enterobius* spp. are controlled with preference.

According to one embodiment, from among the mammals, herbivores, that is animals living mainly off plants, are preferred for the use according to the invention. Particular preference is given to the treatment of ruminants (such as, for example, sheep, goats, cattle).

A preferred example of a non-ruminating mammalian herbivore are horses. Here, the above-mentioned combinations can preferably be employed, for example, for controlling Strongylida or in particular Ascaridida such as *Parascaris equorum*.

In the case of the ruminants, preference is given to controlling Strongylida, in particular *Haemonchus* spp., *Trichostrongylus* spp., *Cooperia* spp. and *Ostertagia* spp.

According to the invention, particular preference is given to treating sheep.

According to the invention, particular preference is likewise given to treating cattle.

The active compounds according to the invention are employed in the veterinary sector and in animal husbandry in a manner known per se directly or in the form of suitable preparations. Administration can be effected prophylactically as well as therapeutically.

The compounds of the general formula (I) or (I-a) can be employed on their own or in combination with other active compounds, for example with other parasiticides.

The examples below illustrate the invention without limiting it.

PREPARATION EXAMPLES

Example 14-11

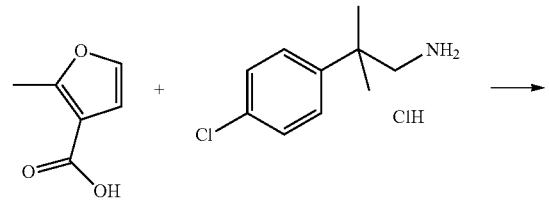

-continued

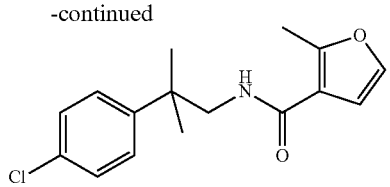

94.6 mg (0.75 mmol) of 2-methylfuran-3-carboxylic acid, 198 mg (0.90 mmol) of 2-(4-chlorophenyl)-2-methylpropane-1-amine, 50.6 mg (0.37 mmol) of 1-hydroxybenzotriazole (HOBt), 46 mg (0.37 mmol) of DMAP, 172.5 mg (0.90 mmol) of EDC hydrochloride and 116 mg (0.90 mmol) of diisopropylethylamine are dissolved in 10 ml of dichloromethane, and the solution is stirred at room temperature for 16 h. After the reaction has ended, 10 ml of water are added, the organic phase is separated off and the aqueous phase is re-extracted with 5 ml of dichloromethane. The dichloromethane phases are filtered through a sodium sulfate/silica gel cartridge, the solvent is evaporated and the residue is separated by preparative HPLC.

Yield: 139.3 mg (63.6% of theory), colorless solid.

$^1$H-NMR (d6-DMSO): δ [ppm], 7.73 (t, 1H, NH), 7.48 (d, 1H), 7.42 (d, 2H), 7.35 (d, 2H), 6.80 (d, 1H), 3.37 (d, 2H), 2.43 (s, 3H), 1.26 (s, 6H).

Example 20-238

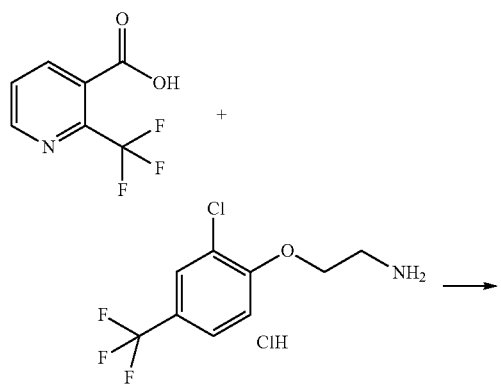

-continued

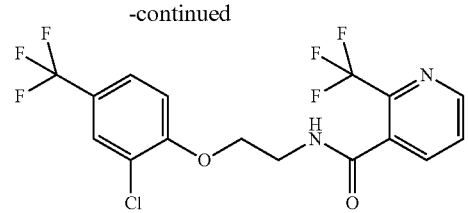

114 mg (0.6 mmol) of 2-(2-chloro-4-(trifluoromethyl)phenoxy)-1-ethylamine, 163 mg (0.72 mmol) of 2-(trifluoromethyl)nicotinoyl chloride, 40.5 mg (0.3 mmol) of 1-hydroxybenzotriazole (HOBt), 36.6 mg (0.3 mmol) of DMAP, 115 mg (0.6 mmol) of EDC hydrochloride and 77.5 mg (0.6 mmol) of diisopropylethylamine are dissolved in 10 ml of dichloromethane, and the solution is stirred at room temperature for 16 h. After the reaction has ended, 10 ml of water are added, the organic phase is separated off and the aqueous phase is re-extracted with 5 ml of dichloromethane. The dichloromethane phases are filtered through a sodium sulfate/silica gel cartridge, the solvent is evaporated and the residue is separated by preparative HPLC.

Yield: 146 mg (59.9% of theory), colourless solid.

$^1$H-NMR (d6-DMSO): δ [ppm], 8.95 (t, 1H, NH), 8.80-8.79 (d, 1H), 7.99-7.97 (d, 1H), 7.84 (s, 1H), 7.80-7.77 (dd, 1H), 7.72-7.69 (d, 1H), 7.40-7.38 (d, 1H), 4.30 (t, 2H), 3.70-3.67 (quart, 2H).

The examples listed in the table below can be prepared in the same manner.

$^1$H NMR Data

The $^1$H NMR data were determined with a Bruker Avance 400 equipped with a flow probe head (volume 60 μl), with tetramethylsilane as a reference (0.0) and the solvents $CD_3CN$, $CDCl_3$, $D_6$-DMSO.

The NMR data for selected examples are listed either in conventional form (δ values, multiplet splitting, number of hydrogen atoms) or as NMR peak lists.

NMR peak list method: When the $^1$H NMR data for selected examples are noted in the form of $^1$H NMR peak lists, first the δ value in ppm and then the signal intensity is listed for each signal peak, separated by a space. The δ value—signal intensity number pairs for different signal peaks are listed with separation from one another by semicolons. The peak list for one example therefore takes the form of: $δ_1$ (intensity$_1$); $δ_2$ (intensity$_2$); . . . ; $δ_i$ (intensity$_i$); . . . ; $δ_n$ (intensity$_n$) The solvent in which the NMR spectrum was recorded is listed in square brackets before the NMR peak list or the conventional NMR interpretation list.

TABLE 1

Compounds of the formula I-1

I-1

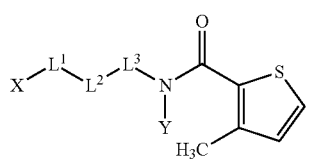

| Ex. No. | X | L$^1$ | L$^2$ | L$^3$ | Y | Physical data: $^1$H-NMR, δ [ppm] or CAS or patent No. |
|---|---|---|---|---|---|---|
| 1-1 | 3-methyl-2-thienyl | CH$_2$ | CH$_2$ | — | H | WO-A 2006/108791 |
| 1-2 | 2,4-dichlorophenyl | CH$_2$ | CH$_2$ | CH$_2$ | H | WO-A 2008/101976 |
| 1-3 | 4-chlorophenyl | CH$_2$ | CH$_2$ | — | H | CAS: 1043286-26-5 |
| 1-4 | 4-chlorophenyl | CH(OCH$_3$) | CH(CH$_3$) | — | H | |

TABLE 1-continued

Compounds of the formula I-1

I-1

| Ex. No. | X | L¹ | L² | L³ | Y | Physical data: ¹H-NMR, δ [ppm] or CAS or patent No. |
|---|---|---|---|---|---|---|
| 1-5 | 2,4-dichlorophenyl | CH(OCH3) | CH(CH3) | — | H | [DMSO], spectrometer: 399.95 MHz 7.7469 (1.12); 7.7252 (1.15); 7.7057 (0.94); 7.6841 (0.94); 7.6179 (1.95); 7.6129 (2.08); 7.5900 (2.33); 7.5853 (2.53); 7.5290 (3.02); 7.5166 (3.14); 7.4844 (0.67); 7.4796 (0.55); 7.4634 (2.97); 7.4586 (3.00); 7.4477 (3.91); 7.4430 (2.06); 7.4377 (1.80); 7.4267 (1.08); 7.4179 (2.89); 7.3969 (1.08); 6.9234 (2.11); 6.9114 (4.42); 6.8992 (2.53); 4.7378 (1.61); 4.7244 (1.71); 4.6260 (2.08); 4.6102 (2.30); 4.3387 (0.65); 4.3221 (1.13); 4.3180 (1.07); 4.3049 (0.95); 4.3009 (1.21); 4.2840 (0.75); 3.3237 (7.87); 3.1838 (16.00); 3.1784 (13.52); 2.5115 (4.24); 2.5072 (8.58); 2.5027 (11.54); 2.4982 (8.53); 2.4939 (4.20); 2.3293 (10.23); 2.2726 (13.26); 1.3965 (4.48); 1.1408 (5.91); 1.1234 (7.31); 1.1033 (4.64); 0.0080 (0.42); −0.0002 (11.36); -0.0084 (0.44) |
| 1-6 | 4-chlorophenyl | CH(CH3) | CH2 | — | H | spectrometer: 399.95 MHz 7.9424 (0.59); 7.9286 (1.15); 7.9146 (0.61); 7.5253 (2.91); 7.5129 (3.03); 7.3730 (0.33); 7.3668 (3.29); 7.3619 (1.23); 7.3506 (1.51); 7.3455 (6.10); 7.3396 (0.97); 7.2968 (0.78); 7.2911 (5.46); 7.2862 (1.62); 7.2744 (1.17); 7.2699 (3.14); 6.9182 (3.00); 6.9058 (2.92); 3.9077 (13.77); 3.5200 (0.43); 3.3909 (365.99); 3.3564 (4.91); 3.3378 (3.29); 3.3241 (2.05); 3.3086 (0.84); 3.3055 (0.88); 3.2918 (0.59); 3.1730 (0.70); 3.0889 (0.58); 3.0712 (1.07); 3.0532 (1.03); 3.0349 (0.52); 2.6786 (0.40); 2.5486 (0.35); 2.5318 (1.35); 2.5184 (23.02); 2.5140 (45.87); 2.5094 (60.62); 2.5049 (45.57); 2.5005 (23.03); 2.3362 (0.40); 2.2661 (16.00); 1.2158 (6.84); 1.1983 (6.73) |
| 1-7 | 2,4-dichlorophenyl | CH(CH3) | CH2 | — | H | spectrometer: 399.95 MHz 8.0105 (0.50); 7.9962 (0.98); 7.9821 (0.49); 7.5641 (2.66); 7.5588 (2.84); 7.5264 (2.39); 7.5140 (2.48); 7.4725 (1.36); 7.4514 (3.22); 7.4255 (1.99); 7.4202 (1.82); 7.4045 (0.81); 7.3991 (0.80); 6.9178 (2.43); 6.9054 (2.33); 3.9098 (16.00); 3.5797 (0.40); 3.5615 (0.77); 3.5439 (0.88); 3.5266 (0.58); 3.4821 (0.34); 3.4668 (0.44); 3.4493 (1.23); 3.4350 (1.79); 3.4225 (1.79); 3.4184 (2.08); 3.4030 (2.01); 3.3667 (243.69); 3.1736 (0.54); 2.6785 (0.37); 2.5487 (0.60); 2.5317 (1.37); 2.5183 (22.50); 2.5139 (44.62); 2.5093 (58.74); 2.5048 (44.01); 2.5003 (22.23); 2.3361 (0.37); 2.2755 (13.20); 1.2055 (5.51); 1.1882 (5.42) |
| 1-8 | 4-chlorophenyl | CH2 | CH(CH3) | — | H | compound No. 1-8, solvent: spectrometer: 399.95 MHz 7.8223 (1.2); 7.8015 (1.24); 7.5241 (3.11); 7.5117 (3.23); 7.3417 (3.49); 7.3369 (1.32); 7.3255 (1.69); 7.3205 (6.55); 7.3148 (1.04); 7.268 (5.53); 7.2469 (3.16); 6.9166 (3.19); 6.9042 (3.11); 4.1649 (0.58); 4.1488 (0.86); 4.1325 (0.65); 3.9091 (16); 3.3749 (344.32); 3.2939 (0.38); 3.1799 (0.46); 3.1673 (0.47); 2.8526 (0.66); 2.8318 (0.66); 2.819 (1.42); 2.7983 (1.41); 2.7712 (1.42); 2.756 (1.48); 2.7375 (0.68); 2.7223 (0.62); 2.6831 (0.33); 2.6785 (0.44); 2.6742 (0.32); 2.5486 (0.34); 2.5318 (1.47); 2.5184 (25.95); 2.514 (50.99); 2.5094 (66.77); 2.5049 (49.84); 2.5004 (24.96); 2.3407 (0.33); 2.3362 (0.44); |

TABLE 1-continued

Compounds of the formula I-1

I-1

$$X-L^1-L^2-L^3-N(Y)-C(=O)-\text{(3-methylthiophen-2-yl)}$$

| Ex. No. | X | L¹ | L² | L³ | Y | Physical data: ¹H-NMR, δ [ppm] or CAS or patent No. |
|---|---|---|---|---|---|---|
| | | | | | | 2.3315 (0.32); 2.2708 (15.79); 1.1618 (7.33); 1.1453 (7.28) |
| 1-9 | 2,4-dichlorophenyl | CH2 | CH(CH3) | — | H | |
| 1-10 | 4-chlorophenyl | C(CH3)2 | CH2 | — | H | spectrometer: 399.95 MHz<br>7.7190 (0.39); 7.7039 (0.75); 7.6887 (0.39); 7.5281 (2.00); 7.5157 (2.07); 7.4368 (2.17); 7.4316 (0.84); 7.4202 (1.10); 7.4149 (4.11); 7.4085 (0.64); 7.3725 (0.60); 7.3662 (4.25); 7.3608 (1.10); 7.3494 (0.82); 7.3443 (2.21); 6.9111 (2.05); 6.8987 (1.99); 3.9041 (11.04); 3.4232 (3.25); 3.4074 (3.61); 3.3650 (195.16); 3.1685 (0.56); 2.5265 (0.87); 2.5130 (17.60); 2.5087 (34.78); 2.5041 (45.86); 2.4996 (34.77); 2.4953 (18.07); 2.2374 (10.99); 1.2850 (16.00) |
| 1-11 | 2,4-dichlorophenyl | C(CH3)2 | CH2 | — | H | spectrometer: 399.95 MHz<br>7.7467 (0.44); 7.7315 (0.87); 7.7159 (0.43); 7.5311 (2.32); 7.5252 (2.49); 7.5174 (2.15); 7.5050 (2.15); 7.4758 (1.49); 7.4541 (2.25); 7.3769 (1.47); 7.3711 (1.40); 7.3554 (0.99); 7.3496 (0.94); 6.8988 (2.14); 6.8864 (2.07); 3.9046 (10.59); 3.7588 (2.77); 3.7430 (2.74); 3.3880 (1.35); 3.3535 (185.47); 3.1680 (0.59); 2.6726 (0.33); 2.5428 (0.63); 2.5257 (1.15); 2.5122 (20.13); 2.5080 (39.32); 2.5035 (51.69); 2.4990 (39.41); 2.4950 (20.61); 2.3302 (0.33); 2.3111 (0.33); 2.2063 (11.23): 1.4394 (16.00; −0.0002 (4.70) |
| 1-12 | 2-chlorophenyl | CH2 | CH2 | — | H | spectrometer: 399.95 MHz<br>8.0508 (0.61); 8.0368 (1.15); 8.0228 (0.60); 7.5422 (2.97); 7.5298 (3.08); 7.4403 (1.40); 7.4361 (1.12); 7.4223 (1.81); 7.4174 (1.79); 7.3536 (0.96); 7.3480 (1.18); 7.3353 (1.44); 7.3303 (1.95); 7.3045 (0.60); 7.3002 (0.80); 7.2862 (1.91); 7.2819 (1.78); 7.2732 (1.80); 7.2672 (2.05); 7.2546 (1.53); 7.2493 (1.28); 7.2362 (0.47); 7.2311 (0.37); 6.9380 (3.04); 6.9255 (2.93); 3.9044 (12.08); 3.4851 (1.15); 3.4681 (2.37); 3.4523 (2.36); 3.4349 (1.53); 3.3627 (281.12); 3.1686 (0.45); 2.9729 (2.05); 2.9547 (3.44); 2.9371 (1.82); 2.6731 (0.39); 2.5260 (1.29); 2.5125 (23.55); 2.5084 (45.80); 2.5040 (60.06); 2.4995 (45.39); 2.4954 (23.36); 2.3111 (0.33); 2.2063 (11.23); 1.4394 (16.00); −0.0002 (4.70)2.3422 (16.00); −0.0002 (0.79) |
| 1-13 | 3,4-dichlorophenyl | CH2 | CH2 | — | H | spectrometer: 399.95 MHz<br>8.0102 (0.60); 7.9967 (1.14); 7.9831 (0.59); 7.5613 (3.22); 7.5468 (3.04); 7.5407 (3.90); 7.5345 (3.17); 7.5192 (2.81); 7.5143 (2.91); 7.3199 (0.42); 7.3151 (0.40); 7.2519 (1.61); 7.2468 (1.59); 7.2313 (1.42); 7.2263 (1.39); 6.9403 (3.14); 6.9279 (3.02); 3.9089 (11.33); 3.4723 (1.28); 3.4551 (2.84); 3.4405 (3.05); 3.4235 (2.16); 3.3770 (275.74); 3.1735 (0.54); 2.8541 (1.81); 2.8369 (3.59); 2.8196 (1.60); 2.6786 (0.34); 2.5318 (1.11); 2.5184 (19.55); 2.5140 (39.18); 2.5094 (51.97); 2.5049 (39.10); 2.5004 (19.77); 2.3362 (0.43); 2.3311 (0.44); 2.3198 (16.00) |
| 1-14 | 3,5-dichlorophenyl | CH2 | CH2 | — | H | compound No. 1-14, solvent: spectrometer: 399.95 MHz<br>8.0159 (0.55); 8.0022 (1.11); 7.9887 (0.61); 7.5485 (2.74); 7.536 (2.91); 7.4478 (1.39); 7.4431 (2.85); 7.4383 (1.7); 7.3187 (6.2); 7.314 (6.04); 6.9405 (2.88); 6.9281 (2.85); 3.9076 (13.02); |

TABLE 1-continued

Compounds of the formula I-1

I-1

X—L¹—L²—L³—N(Y)—C(=O)—[3-methylthiophen-2-yl]

| Ex. No. | X | L¹ | L² | L³ | Y | Physical data: ¹H-NMR, δ [ppm] or CAS or patent No. |
|---|---|---|---|---|---|---|
| | | | | | | 3.5201 (0.46); 3.4809 (1.61); 3.464 (3.39); 3.4494 (4.07); 3.4321 (4.33); 3.3912 (389.41); 3.1791 (0.47); 3.1663 (0.46); 2.8652 (1.72); 2.8483 (3.49); 2.8313 (1.59); 2.6831 (0.34); 2.6785 (0.45); 2.6742 (0.35); 2.5317 (1.51); 2.5184 (24.67); 2.514 (49.01); 2.5094 (64.75); 2.5048 (48.68); 2.5005 (24.91); 2.3407 (0.36); 2.3362 (0.47); 2.3316 (0.39); 2.3145 (16) |
| 1-15 | 3-chlorophenyl | CH2 | CH2 | — | H | CAS: 1325308-79-9 |
| 1-16 | 2-fluorophenyl | CH2 | CH2 | — | H | CAS: 1240811-68-0 |
| 1-17 | 2,6-difluorophenyl | CH2 | CH2 | — | H | spectrometer: 399.95 MHz 7.7467 (0.44); 7.7315 (0.87); 7.7159 (0.43); 7.5311 (2.32); 7.5252 (2.49); 7.5174 (2.15); 7.5050 (2.15); 7.4758 (1.49); 7.4541 (2.25); 7.3769 (1.47); 7.3711 (1.40); 7.3554 (0.99); 7.3496 (0.94); 6.8988 (2.14); 6.8864 (2.07); 3.9046 (10.59); 3.7588 (2.77); 3.7430 (2.74); 3.3880 (1.35); 3.3535 (185.47); 3.1680 (0.59); 2.6726 (0.33); 2.5428 (0.63); 2.5257 (1.15); 2.5122 (20.13); 2.5080 (39.32); 2.5035 (51.69); 2.4990 (39.41); 2.4950 (20.61); 2.3302 (0.33); 2.3111 (0.33); 2.2063 (11.23); 1.4394 (16.00); −0.0002 (4.70) |
| 1-18 | 2,6-dichlorophenyl | CH2 | CH2 | — | H | spectrometer: 399.95 MHz 8.1088 (0.60); 8.0946 (1.16); 8.0802 (0.61); 7.5393 (2.88); 7.5269 (3.00); 7.4613 (4.88); 7.4411 (6.73); 7.2999 (2.24); 7.2807 (2.27); 7.2789 (2.11); 7.2596 (1.45); 6.9373 (2.97); 6.9249 (2.89); 3.9046 (15.92); 3.4731 (0.91); 3.4564 (2.21); 3.4389 (2.16); 3.4231 (1.15); 3.3464 (188.35); 3.1666 (2.10); 3.1485 (3.24); 3.1314 (1.60); 2.6723 (0.43); 2.5425 (0.50); 2.5254 (1.38); 2.5121 (25.86); 2.5077 (51.09); 2.5032 (67.50); 2.4986 (51.02); 2.4943 (26.32); 2.3579 (16.00); 2.3346 (0.41); 2.3299 (0.49); 2.3255 (0.35); −0.0002 (7.67); −0.0085 (0.33) |
| 1-19 | 3-(trifluoromethyl)phenyl | CH2 | CH2 | — | H | compound No. 1-19, solvent: spectrometer: 399.95 MHz 8.0151 (0.61); 8.0015 (1.13); 7.9878 (0.59); 7.5868 (2.73); 7.5694 (1.27); 7.5643 (2.16); 7.5567 (3.19); 7.5501 (3.21); 7.5399 (3.31); 7.5275 (3.32); 6.9301 (2.98); 6.9177 (2.88); 3.9045 (14.6); 3.5015 (1.06); 3.4841 (2.54); 3.4697 (2.57); 3.4524 (1.31); 3.428 (0.4); 3.4116 (0.71); 3.3597 (304.29); 3.3124 (0.59); 3.3005 (0.39); 3.1684 (0.53); 2.9509 (1.85); 2.9335 (3.64); 2.9159 (1.69); 2.6731 (0.42); 2.6685 (0.32); 2.5263 (1.39); 2.5128 (25.41); 2.5085 (50.76); 2.5039 (67.15); 2.4994 (50.71); 2.495 (25.94); 2.3353 (0.33); 2.3306 (0.45); 2.3262 (0.36); 2.3127 (0.68); 2.2986 (16); −0.0002 (2.03) |
| 1-20 | 4-(trifluoromethyl)phenyl | CH2 | CH2 | — | H | CAS: 1096213-61-4 |
| 1-21 | 2-methylphenyl | CH2 | CH2 | — | H | CAS: 1328661-91-1 |
| 1-22 | 2,4,6-trimethylphenyl | CH2 | CH2 | — | H | spectrometer: 399.95 MHz 8.1607 (0.39); 8.1464 (0.82); 8.1319 (0.43); 7.5696 (1.94); 7.5572 (2.04); 6.9699 (1.97); 6.9575 (1.94); 6.8089 (4.27); 3.9096 (10.74); 3.3940 (2.46); 3.3686 (187.69); 3.2424 (0.58); 3.2277 (0.94); 3.2229 (0.80); 3.2141 (0.92); 3.2071 (0.78); 3.2008 (1.00); 3.1868 (0.67); 3.1739 (0.53); 2.8005 (1.09); 2.7871 (0.85); 2.7796 (1.09); 2.7744 (0.91); 2.7597 (0.94); 2.5488 (2.24); 2.5317 (0.96); 2.5183 (16.56); 2.5139 (33.04); 2.5094 (43.72); 2.5048 (33.10); |

TABLE 1-continued

Compounds of the formula I-1

I-1

| Ex. No. | X | L¹ | L² | L³ | Y | Physical data: $^1$H-NMR, δ [ppm] or CAS or patent No. |
|---|---|---|---|---|---|---|
| | | | | | | 2.5005 (17.04); 2.4189 (10.37); 2.3362 (0.36); 2.3078 (16.00); 2.1865 (7.38) |
| 1-23 | 3,4-bismethoxy-phenyl | CH2 | CH2 | — | H | CAS: 1023537-11-2 |
| 1-24 | phenyl | CH2 | CH2 | — | H | CAS: 1090485-43-0 |
| 1-25 | 4-chlorophenyl | C(CH2—CH2) | CH2 | — | H | |
| 1-26 | 2,4-dichlorophenyl | C(CH2—CH2) | CH2 | — | H | |
| 1-27 | 4-chlorophenyl | CH2 | C(CH2—CH2) | — | H | |
| 1-28 | 2,4-dichlorophenyl | CH2 | C(CH2—CH2) | — | H | |
| 1-29 | 4-chlorophenyl | O | CH2 | CH2 | H | |
| 1-30 | 2,4-dichlorophenyl | O | CH2 | CH2 | H | compound No. 1-30, solvent: spectrometer: 399.95 MHz 8.0722 (0.7); 8.0589 (1.33); 8.0455 (0.71); 7.5707 (4.23); 7.5637 (3.95); 7.5605 (3.47); 7.3834 (1.58); 7.377 (1.49); 7.3613 (2.18); 7.3548 (2.12); 7.2495 (3.61); 7.2272 (2.64); 6.9582 (3.13); 6.9457 (3.03); 4.2136 (2.09); 4.1987 (4.6); 4.1838 (2.29); 3.624 (1.18); 3.6095 (3.26); 3.5951 (3.15); 3.5804 (1.07); 3.3333 (10.63); 2.5436 (10.77); 2.5086 (6.89); 2.5042 (9.01); 2.4998 (6.82); 2.4061 (16); −0.0002 (0.4) |
| 1-31 | 4-chlorophenyl | CH2 | CH2 | CH2 | H | |
| 1-32 | 4-chlorophenyl | NCH3 | CH2 | CH2 | H | |
| 1-33 | 2,4-dichlorophenyl | NCH3 | CH2 | CH2 | H | |
| 1-34 | 4-chlorophenyl | CH(OCH3) | CH2 | — | H | |
| 1-35 | 2,4-dichlorophenyl | CH(OCH3) | CH2 | — | H | |
| 1-36 | 2-thienyl | CH2 | CH2 | — | H | CAS: 1182416-85-8 |
| 1-37 | 3-thienyl | CH2 | CH2 | — | H | |
| 1-38 | 2-furyl | CH2 | CH2 | — | H | |
| 1-39 | 3-furyl | CH2 | CH2 | — | H | |
| 1-40 | phenyl | CH2 | CH2 | CH(CH3) | H | |
| 1-41 | phenyl | CH2 | CH2 | CH2 | H | |
| 1-42 | 2-Cl-phenyl | CH2 | CH2 | CH(CH3) | H | |
| 1-43 | 4-t-butylphenyl | CH2 | CH2 | CH2 | H | |
| 1-44 | 4-methylphenyl | CH2 | CH2 | CH2 | H | |
| 1-45 | phenyl | CH2 | CH2 | CH(CH2CH3) | H | |
| 1-46 | 2-methoxyphenyl | CH2 | CH2 | CH2 | H | |
| 1-47 | 2-methylphenyl | CH2 | CH2 | CH2 | H | |
| 1-48 | 3-methylphenyl | CH2 | CH2 | CH2 | H | |
| 1-49 | 3-chlorophenyl | CH2 | CH2 | CH2 | H | |
| 1-50 | 2,6-difluorophenyl | CH2 | CH2 | CH2 | H | compound No. 1-50, solvent: spectrometer: 399.95 MHz 8.0032 (0.64); 7.9895 (1.2); 7.976 (0.67); 7.5479 (2.74); 7.5355 (2.88); 7.3477 (0.33); 7.3308 (0.77); 7.3272 (0.73); 7.31 (1.47); 7.2922 (0.79); 7.2892 (0.97); 7.2723 (0.43); 7.0861 (1.99); 7.0662 (3.26); 7.0463 (1.7); 6.9476 (2.95); 6.9352 (2.89); 3.332 (25.1); 3.2604 (1.01); 3.2433 (2.22); 3.2273 (2.24); 3.2103 (1.07); 2.6829 (1.42); 2.6639 (2.36); 2.6444 (1.55); 2.5427 (1.85); 2.5077 (12.73); 2.5032 (17.02); 2.4988 (13.19); 2.4284 (0.38); 2.392 (16); 1.7932 (0.54); 1.7742 (1.43); 1.7556 (1.99); 1.737 (1.35); 1.7185 (0.48) |
| 1-51 | 4-chlorophenyl | CH2 | CH2 | CH2 | H | |
| 1-52 | 2,6-dichlorophenyl | CH2 | CH2 | CH(CH3) | H | |
| 1-53 | 3,5-dichlorophenyl | CH2 | CH2 | CH(CH3) | H | |
| 1-54 | 2,6-dimethylphenyl | CH2 | CH2 | CH2 | H | |
| 1-55 | 2,5-dichlorophenyl | CH2 | CH2 | CH2 | H | |
| 1-56 | 4-isopropoxyphenyl | CH2 | CH2 | CH2 | H | |
| 1-57 | 3-trifluoro-methylphenyl | CH2 | CH2 | CH(CH3) | H | |
| 1-58 | 4-methylphenyl | CH2 | CH2 | CH(CH3) | H | |
| 1-59 | 2-methylphenyl | CH2 | CH2 | CH(CH3) | H | |
| 1-60 | 3,4-dichlorophenyl | CH2 | CH2 | CH(CH3) | H | |
| 1-61 | 3,5-dichlorophenyl | CH2 | CH2 | CH2 | H | |

TABLE 1-continued

Compounds of the formula I-1

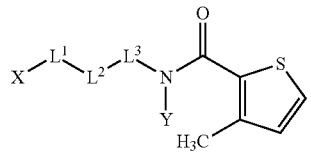

I-1

| Ex. No. | X | $L^1$ | $L^2$ | $L^3$ | Y | Physical data: $^1$H-NMR, δ [ppm] or CAS or patent No. |
|---|---|---|---|---|---|---|
| 1-62 | 2,6-dimethylphenyl | CH2 | CH2 | CH(CH3) | H | |
| 1-63 | 4-trifluoromethylphenyl | CH2 | CH2 | CH(CH3) | H | |
| 1-64 | 2,5-dichlorophenyl | CH2 | CH2 | CH(CH3) | H | |
| 1-65 | 4-phenoxyphenyl | CH2 | CH2 | CH2 | H | |
| 1-66 | 3-chlorophenyl | CH2 | CH2 | CH(CH3) | H | |
| 1-67 | 4-phenoxyphenyl | CH2 | CH2 | CH(CH3) | H | |
| 1-68 | 2,4-dichlorophenyl | CH2 | CH2 | CH(CH3) | H | |
| 1-69 | 2-difluoromethoxyphenyl | CH2 | CH2 | CH(CH3) | H | |
| 1-70 | 4-methoxyphenyl | CH2 | CH2 | CH2 | H | |
| 1-71 | 4-chlorophenyl | CH2 | CH2 | CH(CH3) | H | |
| 1-72 | 4-chlorophenyl | CH2 | CH2 | CH(i-propyl) | H | |
| 1-73 | 4-fluorophenyl | CH2 | CH2 | CH2 | H | |
| 1-74 | 4-chlorophenyl | CH2 | CH2 | CH(n-propyl) | H | |
| 1-75 | 4-chlorophenyl | CH2 | CH2 | CH(t-butyl) | H | |
| 1-76 | 2-chlorophenyl | CH2 | CH2 | CH2 | H | |
| 1-77 | 2-thienyl | CH2 | CH2 | CH2 | H | compound No. 1-77, solvent: spectrometer: 399.95 MHz 8.0057 (0.68); 7.9926 (1.22); 7.9794 (0.73); 7.5501 (2.74); 7.5377 (2.9); 7.3195 (1.89); 7.3171 (1.8); 7.3068 (2.11); 7.3044 (1.92); 6.9512 (4.34); 6.9387 (4.46); 6.9303 (2.09); 6.8872 (2.22); 6.879 (1.86); 3.3316 (21.49); 3.2792 (1.19); 3.2623 (2.71); 3.2467 (2.76); 3.2299 (1.28); 2.857 (2.03); 2.8379 (3.54); 2.8189 (2.24); 2.5412 (3.08); 2.5059 (10.76); 2.5018 (14.05); 2.4977 (11.1); 2.3973 (16); 1.8846 (0.64); 1.8663 (1.92); 1.8478 (2.61); 1.8296 (1.87); 1.8113 (0.59) |
| 1-78 | 2,4-dichlorophenyl | CH2 | CH2 | — | H | WO-A 2007/060166 |
| 1-79 | 4-chloro-2-thienyl | CH2 | CH2 | — | H | compound No. 1-79, solvent: spectrometer: 601.6 MHz 8.0675 (0.49); 8.0583 (0.9); 8.0492 (0.47); 7.5538 (2.72); 7.5455 (2.82); 7.3741 (4.25); 7.3715 (4.3); 6.9466 (2.8); 6.9383 (2.73); 6.9062 (2.59); 6.9049 (2.22); 6.9037 (2.52); 3.4607 (1.01); 3.4491 (2.45); 3.4396 (2.5); 3.4282 (1.11); 3.3253 (249); 3.3101 (0.48); 3.0195 (1.62); 3.0086 (3.14); 3.0077 (3.17); 2.9969 (1.46); 2.653 (0.44); 2.6161 (0.36); 2.613 (0.49); 2.61 (0.35); 2.5474 (1.32); 2.5406 (144.26); 2.5223 (1.16); 2.5192 (1.5); 2.5161 (1.7); 2.5074 (27.92); 2.5044 (58.31); 2.5013 (79.87); 2.4982 (57.12); 2.4952 (26.25); 2.4245 (0.44); 2.3885 (0.37); 2.3854 (0.5); 2.3824 (0.37); 2.3611 (16); 2.0734 (0.47); −0.0002 (5.98) |
| 1-80 | 4-chlorophenyl | N(CH3) | CH2 | CH2 | H | compound No. 1-80, solvent: spectrometer: 399.95 MHz 8.0071 (0.64); 7.9933 (1.25); 7.9795 (0.66); 7.5515 (2.84); 7.5391 (2.93); 7.1827 (0.43); 7.1738 (4.27); 7.1685 (1.41); 7.1563 (1.57); 7.1511 (4.79); 7.1422 (0.51); 6.9457 (2.99); 6.9333 (2.88); 6.7718 (0.52); 6.763 (4.37); 6.7578 (1.48); 6.7403 (3.93); 6.7315 (0.44); 3.4764 (1.14); 3.4596 (2.71); 3.4424 (2.18); 3.3706 (1.25); 3.3551 (2.37); 3.3294 (60.06); 2.915 (15.97); 2.5413 (14.63); 2.5063 (24.52); 2.5019 (31.42); 2.4974 (23.16); 2.3739 (16); −0.0002 (4.01) |

TABLE 2

Compounds of the formula I-2

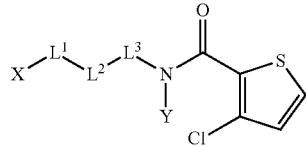

I-2

| Ex. No. | X | $L^1$ | $L^2$ | $L^3$ | Y | Physical data: $^1$H-NMR, δ [ppm] or CAS or patent No. |
|---|---|---|---|---|---|---|
| 2-1 | 3-methyl-2-thienyl | CH2 | CH2 | — | H | |
| 2-2 | 2,4-dichlorophenyl | CH2 | CH2 | CH2 | H | compound No. 2-2, solvent: spectrometer: 399.95 MHz 8.2026 (1.69); 8.1889 (3.11); 8.175 (1.67); 7.8265 (15.43); 7.8133 (16); 7.8078 (0.37); 7.7959 (0.51); 7.7828 (0.47); 7.5677 (10.13); 7.5624 (10.39); 7.426 (5.49); 7.4053 (12.99); 7.3899 (0.44); 7.3803 (9.6); 7.375 (8.72); 7.3597 (3.95); 7.3544 (3.92); 7.1753 (0.46); 7.1623 (0.47); 7.1448 (15.95); 7.1316 (15.49); 3.5143 (0.38); 3.3561 (0.39); 3.3331 (88.56); 3.3198 (3.62); 3.3029 (7.61); 3.2879 (7.63); 3.2708 (3.31); 2.7545 (5.62); 2.7357 (6.9); 2.7158 (6.03); 2.6737 (0.32); 2.544 (14.87); 2.5272 (0.83); 2.5224 (1.34); 2.5138 (17.13); 2.5092 (34.25); 2.5046 (45.37); 2.5 (32.77); 2.4954 (15.38); 2.4798 (0.32); 1.8378 (1.65); 1.8198 (4.34); 1.8009 (5.53); 1.7822 (4.18); 1.7644 (1.46); −0.0002 (5.49) |
| 2-3 | 4-chlorophenyl | CH2 | CH2 | — | H | spectrometer: 399.95 MHz 8.1377 (0.63); 8.1240 (1.15); 8.1101 (0.62); 7.8208 (4.47); 7.8077 (4.66); 7.3703 (0.45); 7.3642 (3.96); 7.3594 (1.50); 7.3482 (1.84); 7.3431 (6.97); 7.3374 (1.07); 7.2906 (0.99); 7.2846 (5.75); 7.2636 (3.41); 7.1343 (4.73); 7.1211 (4.56); 3.9045 (16.00); 3.5002 (1.31); 3.4829 (2.58); 3.4676 (2.57); 3.4498 (1.53); 3.3619 (349.85); 2.8484 (2.20); 2.8302 (3.85); 2.8125 (1.98); 2.6776 (0.36); 2.6732 (0.49); 2.6688 (0.37); 2.5428 (0.32); 2.5264 (1.67); 2.5130 (29.09); 2.5086 (57.80); 2.5041 (76.53); 2.4995 (57.82); 2.4951 (29.49); 2.3352 (0.34); 2.3308 (0.47); 2.3263 (0.34); −0.0002 (1.25) |
| 2-4 | 2,4-dichlorophenyl | CH2 | CH2 | — | H | spectrometer: 399.95 MHz 8.2030 (0.50); 8.1889 (0.94); 8.1751 (0.49); 7.8178 (3.44); 7.8046 (3.60); 7.5878 (2.92); 7.3744 (6.79); 7.3714 (7.04); 7.1316 (3.64); 7.1185 (3.50); 3.9048 (16.00); 3.5280 (0.84); 3.5108 (2.14); 3.4957 (2.20); 3.4786 (0.89); 3.3931 (0.50); 3.3501 (207.99); 2.9699 (1.74); 2.9525 (3.42); 2.9352 (1.57); 2.6726 (0.42); 2.5258 (1.38); 2.5210 (2.13); 2.5124 (24.91); 2.5080 (49.70); 2.5035 (65.74); 2.4989 (49.43); 2.4945 (25.13); 2.3303 (0.40); −0.0002 (7.89) |
| 2-5 | 4-chlorophenyl | CH(OCH3) | CH(CH3) | — | H | compound No. 2-5, solvent: spectrometer: 399.95 MHz 7.8969 (0.63); 7.8755 (0.65); 7.8395 (1.08); 7.8263 (1.16); 7.8054 (1.55); 7.7922 (1.61); 7.7428 (0.45); 7.7222 (0.45); 7.4341 (2.31); 7.4133 (3.65); 7.3501 (4.24); 7.329 (2.67); 7.1597 (1.12); 7.1465 (1.1); 7.1166 (1.63); 7.1034 (1.57); 4.3685 (0.72); 4.3558 (0.82); 4.314 (1.05); 4.2984 (1.23); 4.162 (0.32); 4.1446 (0.41); 4.1279 (0.52); 4.1231 (0.42); 4.1112 (0.37); 4.1065 (0.49); 3.3228 (9.49); 3.2061 (13.22); 2.5066 (21.23); 2.5023 (27.41); 2.498 (20.75); 1.3974 (16); 1.137 (3.55); 1.1202 (3.54); 1.0942 (2.48); 1.0773 (2.42); −0.0002 (4.23) |
| 2-6 | 2,4-dichlorophenyl | CH(OCH3) | CH(CH3) | — | H | |
| 2-7 | 4-chlorophenyl | CH(CH3) | CH2 | — | H | spectrometer: 399.95 MHz 8.0473 (0.68); 8.0332 (1.28); 8.0193 (0.67); 7.8099 (4.58); 7.7967 (4.74); 7.3752 (3.64); 7.3703 (1.40); 7.3590 (1.82); 7.3539 (7.44); 7.3483 (1.19); 7.3161 (1.22); 7.3107 (6.66); 7.3059 (1.87); 7.2941 (1.36); 7.2894 (3.39); 7.1195 (4.85); 7.1063 (4.69); 3.9091 (16.00); 3.5090 (0.43); 3.4617 (0.56); 3.4429 (0.79); 3.4235 (3.81); 3.4050 (6.69); 3.3749 (417.79); 3.1730 (0.36); 3.0954 (0.67); 3.0774 (1.33); 3.0595 (1.26); 3.0415 (0.62); 2.6831 (0.38); 2.6787 (0.51); 2.6743 (0.39); 2.5184 (30.26); 2.5141 (60.39); 2.5096 (80.29); 2.5050 (60.84); 2.5007 (31.19); 2.5319 (1.66); 2.3409 (0.35); 2.3363 (0.49); 2.3319 (0.36); 1.2350 (8.14); 1.2175 (7.98) |
| 2-8 | 2,4- | CH(CH3) | CH2 | — | H | spectrometer: 399.95 MHz |

TABLE 2-continued

Compounds of the formula I-2

I-2

$$\text{X}-\text{L}^1-\text{L}^2-\text{L}^3-\text{N}(\text{Y})-\text{C}(=\text{O})-\text{thiophene-Cl}$$

| Ex. No. | X | L¹ | L² | L³ | Y | Physical data: ¹H-NMR, δ [ppm] or CAS or patent No. |
|---|---|---|---|---|---|---|
| | dichloro-phenyl | | | | | 7.7974 (0.68); 7.7842 (0.70); 7.5640 (0.54); 7.5587 (0.58); 7.4626 (0.64); 7.4268 (0.40); 7.4214 (0.37); 7.1100 (0.71); 7.0969 (0.68); 3.9045 (2.32); 3.5640 (0.34); 3.5473 (0.38); 3.5315 (0.46); 3.5182 (0.47); 3.5010 (0.76); 3.4291 (90.98); 2.5185 (4.75); 2.5141 (9.59); 2.5096 (12.81); 2.5050 (9.84); 2.5008 (5.14); 2.0747 (16.00); 1.2220 (1.09); 1.2053 (1.08) |
| 2-9 | 4-chlorophenyl | CH2 | CH(CH3) | — | H | spectrometer: 399.95 MHz 7.9630 (1.22); 7.9424 (1.27); 7.7924 (4.06); 7.7793 (4.26); 7.3425 (3.49); 7.3378 (1.39); 7.3214 (6.93); 7.2752 (5.94); 7.2542 (3.24); 7.1119 (4.30); 7.0988 (4.20); 4.1713 (0.69); 4.1548 (0.99); 4.1385 (0.75); 4.1185 (0.38); 3.9043 (16.00); 3.4470 (0.40); 3.4286 (0.51); 3.3617 (361.09); 3.3140 (0.82); 3.1746 (0.46); 3.1619 (0.45); 2.8637 (0.63); 2.8435 (0.60); 2.8301 (1.62); 2.8098 (1.65); 2.7957 (1.67); 2.7803 (1.68); 2.7619 (0.65); 2.7468 (0.57); 2.6776 (0.40); 2.6731 (0.53); 2.6688 (0.41); 2.5262 (1.75); 2.5126 (30.67); 2.5085 (59.88); 2.5040 (78.76); 2.4995 (59.69); 2.4953 (30.88); 2.3350 (0.34); 2.3308 (0.48); 2.3263 (0.35); 1.1737 (7.79); 1.1572 (7.72) |
| 2-10 | 2,4-dichlorophenyl | CH2 | CH(CH3) | — | H | |
| 2-11 | 4-chlorophenyl | C(CH3)2 | CH2 | — | H | spectrometer: 399.95 MHz 7.8225 (2.75); 7.8093 (2.84); 7.7385 (0.36); 7.7237 (0.69); 7.7085 (0.36); 7.4631 (2.23); 7.4580 (0.84); 7.4467 (1.16); 7.4413 (3.99); 7.4348 (0.60); 7.3929 (0.56); 7.3863 (4.17); 7.3811 (1.11); 7.3696 (0.83); 7.3645 (2.30); 7.1202 (2.88); 7.1070 (2.78); 3.9093 (12.17); 3.4869 (2.95); 3.4713 (2.90); 3.3711 (239.20); 2.6784 (0.32); 2.5317 (1.02); 2.5183 (19.59); 2.5139 (38.92); 2.5093 (51.34); 2.5048 (38.69); 2.5004 (19.81); 2.3361 (0.32); 1.3129 (16.00) |
| 2-12 | 2,4-dichlorophenyl | C(CH3)2 | CH2 | — | H | spectrometer: 399.95 MHz 7.8018 (3.13); 7.7887 (3.37); 7.7824 (0.47); 7.7666 (0.75); 7.7601 (0.43); 7.7512 (0.38); 7.5497 (2.38); 7.5439 (2.59); 7.4931 (1.53); 7.4714 (2.29); 7.3916 (1.64); 7.3857 (1.53); 7.3700 (1.12); 7.3641 (1.06); 7.0969 (3.23); 7.0837 (3.14); 3.9046 (14.38); 3.8154 (2.85); 3.7997 (2.83); 3.3628 (255.22); 2.6733 (0.37); 2.5266 (1.14); 2.5132 (21.80); 2.5088 (43.66); 2.5042 (57.88); 2.4997 (43.56); 2.4952 (22.23); 2.3310 (0.35); 1.4615 (16.00) |
| 2-13 | 2-chlorophenyl | CH2 | CH2 | — | H | |
| 2-14 | 3,4-dichlorophenyl | CH2 | CH2 | — | H | spectrometer: 399.95 MHz 8.1577 (0.61); 8.1436 (1.18); 8.1300 (0.67); 7.8199 (4.18); 7.8067 (4.38); 7.5614 (3.47); 7.5408 (4.24); 7.5347 (3.30); 7.5299 (3.39); 7.2628 (1.76); 7.2577 (1.77); 7.2422 (1.58); 7.2372 (1.57); 7.1321 (4.41); 7.1189 (4.29); 3.9046 (16.00); 3.5177 (1.16); 3.5006 (2.96); 3.4857 (3.01); 3.4688 (1.33); 3.4388 (0.42); 3.3608 (347.14); 3.1740 (0.40); 3.1622 (0.37); 2.8642 (2.11); 2.8470 (4.26); 2.8297 (1.93); 2.6779 (0.41); 2.6732 (0.53); 2.6688 (0.41); 2.5433 (0.40); 2.5264 (1.84); 2.5128 (31.80); 2.5086 (61.69); 2.5041 (80.66); 2.4996 (60.63); 2.4954 (31.03); 2.3351 (0.36); 2.3309 (0.51); 2.3264 (0.37); −0.0002 (5.83) |

TABLE 2-continued

Compounds of the formula I-2

I-2

| Ex. No. | X | L¹ | L² | L³ | Y | Physical data: ¹H-NMR, δ [ppm] or CAS or patent No. |
|---|---|---|---|---|---|---|
| 2-15 | 3,5-dichloro-phenyl | CH2 | CH2 | — | H | |
| 2-16 | 3-chloro-phenyl | CH2 | CH2 | — | H | spectrometer: 399.95 MHz<br>8.1445 (0.64); 8.1314 (1.17); 8.1183 (0.66); 7.8222 (4.54); 7.8090 (4.73);<br>7.3499(1.14); 7.3308 (5.66); 7.3115 (2.92); 7.2829 (2.38); 7.2782 (1.74); 7.2661 (0.88); 7.2627 (1.07); 7.2582 (0.70); 7.2282 (2.15); 7.2098 (1.50);<br>7.1341 (4.89); 7.1210 (4.79); 3.9043 (16.00); 3.5172 (1.29); 3.4998 (2.92);<br>3.4849 (3.21); 3.4675 (1.70); 3.4498 (0.41); 3.4387 (0.56); 3.3658 (387.37); 3.3078 (0.78); 3.2857 (0.39); 3.1739 (0.33); 2.8676 (2.33); 2.8499 (4.45); 2.8322 (2.20); 2.6779 (0.38); 2.6734 (0.54); 2.6690 (0.39);<br>2.5266 (1.74); 2.5132 (30.49); 2.5088 (60.36); 2.5043 (79.79); 2.4998 (60.13); 2.4954 (30.62); 2.3356 (0.37); 2.3311 (0.51); 2.3266 (0.38); −0.0002 (0.33) |
| 2-17 | 2-fluoro-phenyl | CH2 | CH2 | — | H | spectrometer: 399.95 MHz<br>8.1933 (0.69); 8.1795 (1.28); 8.1656 (0.73); 7.8226 (4.66); 7.8095 (4.87);<br>7.3443 (0.89); 7.3294 (1.55); 7.3251 (1.90); 7.3063 (1.47); 7.2930 (0.53);<br>7.2881 (1.10); 7.2736 (1.12); 7.2679 (1.39); 7.2636 (0.79); 7.2542 (0.78);<br>7.2498 (0.65); 7.1803 (1.50); 7.1596 (3.11); 7.1432 (2.78); 7.1405 (2.70);<br>7.1363 (6.30); 7.1231 (5.81); 3.9084 (16.00); 3.5173 (1.70); 3.5002 (3.08);<br>3.4843 (3.12); 3.4669 (1.92); 3.3799 (457.67); 3.2922 (0.60); 3.1793 (0.73); 3.1668 (0.69); 2.9003 (2.23); 2.8823 (4.00); 2.8645 (2.04); 2.6830<br>(0.41); 2.6785 (0.55); 2.6740 (0.41); 2.5485 (0.41); 2.5315 (1.86); 2.5181<br>(31.81); 2.5139 (62.45); 2.5094 (82.23); 2.5049 (62.52); 2.3405 (0.38); 2.3361 (0.52); 2.3315 (0.39) |
| 2-18 | 2,6-difluoro-phenyl | CH2 | CH2 | — | H | spectrometer: 399.95 MHz<br>7.8107 (0.99); 7.7975 (1.05); 7.3236 (0.37); 7.1264 (1.05); 7.1132 (1.03);<br>7.0797 (0.51); 7.0599 (0.82); 7.0399 (0.45); 3.9037 (3.15); 3.4886 (0.91);<br>3.4718 (1.79); 3.4204 (120.43); 2.9156 (0.41); 2.8983 (0.78); 2.8811 (0.38); 2.5302 (0.44); 2.5170 (6.82); 2.5126 (13.44); 2.5081 (17.68); 2.5035 (13.27); 2.4992 (6.71); 2.0740 (16.00) |
| 2-19 | 2,6-dichloro-phenyl | CH2 | CH2 | — | H | spectrometer: 399.95 MHz<br>8.2795 (0.51); 8.2654 (0.95); 8.2512 (0.49); 7.8182 (3.62); 7.8050 (3.75);<br>7.4669 (4.20); 7.4468 (5.88); 7.3079 (2.06); 7.2888 (2.09); 7.2868 (1.90);<br>7.2677 (1.33); 7.1346 (3.78); 7.1214 (3.63); 3.9095 (16.00); 3.5349 (0.88);<br>3.5183 (2.14); 3.5022 (2.18); 3.4853 (1.14); 3.3672 (282.29); 3.1867 (1.81); 3.1690 (3.28); 3.1517 (1.47); 2.6784 (0.42); 2.5317 (1.42); 2.5183<br>(25.31); 2.5139 (50.14); 2.5093 (65.95); 2.5048 (49.33); 2.5004 (24.84); 2.3361 (0.42) |
| 2-20 | 3-(trifluoro-methyl)phenyl | CH2 | CH2 | — | H | spectrometer: 399.95 MHz<br>8.1552 (0.57); 8.1420 (1.01); 8.1284 (0.54); 7.8190 (3.83); 7.8058 (3.95);<br>7.6056 (2.31); 7.5919 (0.86); 7.5829 (0.97); 7.5682 (4.08); 7.5548 (2.45);<br>7.5421 (0.96); 7.5310 (0.48); 7.5185 (0.32); 7.1293 (4.02); 7.1161 (3.87);<br>3.9045 (16.00); 3.5536 (1.08); 3.5363 (2.64); 3.5216 (2.73); 3.5044 (1.32); |

TABLE 2-continued

Compounds of the formula I-2

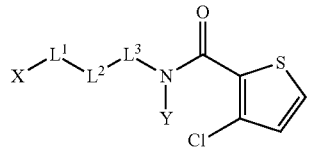

I-2

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 3.3692 (384.74); 3.1744 (0.37); 3.1628 (0.33); 2.9655 (1.88); 2.9481 (3.71); 2.9307 (1.71); 2.6783 (0.36); 2.6740 (0.49); 2.6693 (0.36); 2.5271 (1.74); 2.5137 (30.05); 2.5093 (59.74); 2.5047 (79.00); 2.5002 (59.85); 2.4958 (30.81); 2.3359 (0.37); 2.3314 (0.52); 2.3270 (0.39) |
| 2-21 | 4-(trifluoro-methyl)phenyl | CH2 | CH2 | — | H | spectrometer: 399.95 MHz<br>8.1817 (0.49); 8.1676 (0.91); 8.1538 (0.48); 7.8205 (3.55); 7.8074 (3.67);<br>7.6734 (2.50); 7.6532 (3.05); 7.4918 (2.75); 7.4718 (2.26); 7.1329 (3.74);<br>7.1197 (3.60); 3.9045 (16.00); 3.5502 (0.98); 3.5329 (2.08); 3.5177 (2.07);<br>3.5002 (1.15); 3.4504 (0.42); 3.3701 (329.49); 3.3107 (0.59); 3.1687 (0.49); 2.9563 (1.43); 2.9385 (2.63); 2.9208 (1.28); 2.6740 (0.41); 2.5440 (0.34); 2.5272 (1.46); 2.5138 (24.76); 2.5094 (49.66); 2.5048 (65.83); 2.5003 (49.54); 2.4958 (25.02); 2.3316 (0.42) |
| 2-22 | 2-methylphenyl | CH2 | CH2 | — | H | spectrometer: 399.95 MHz<br>8.2055 (0.56); 8.1914 (1.03); 8.1774 (0.57); 7.8320 (4.41); 7.8188 (4.61);<br>7.1771 (0.88); 7.1689 (1.69); 7.1554 (3.06); 7.1467 (6.97); 7.1392 (1.32);<br>7.1335 (5.44); 7.1284 (3.20); 7.1252 (3.44); 7.1159 (2.95); 7.1098 (1.36);<br>7.1039 (1.71); 3.9042 (14.10); 3.4495 (1.45); 3.4344 (2.40); 3.4312 (2.13);<br>3.4261 (1.89); 3.4160 (2.67); 3.4114 (3.29); 3.3961 (4.40); 3.3681 (316.33); 3.3082 (0.66); 2.8853 (0.33); 3.1749 (0.37); 3.1622 (0.37); 2.8482 (2.20); 2.8286 (2.58); 2.8100 (1.99); 2.6780 (0.33); 2.6736 (0.46);<br>2.6690 (0.34); 2.5268 (1.44); 2.5134 (25.01); 2.5090 (49.94); 2.5044 (65.99); 2.4998 (49.40); 2.4954 (24.78); 2.3244 (16.00); −0.0002 (5.37) |
| 2-23 | 2,4,6-trimethylphenyl | CH2 | CH2 | — | H | spectrometer: 399.95 MHz<br>8.3362 (0.37); 8.3218 (0.76); 8.3073 (0.39); 7.8493 (2.28); 7.8361 (2.39);<br>7.1654 (2.37); 7.1522 (2.31); 6.8107 (4.16); 3.9088 (8.26); 3.3796 (236.40);<br>3.2968 (0.78); 3.2819 (1.10); 3.2684 (1.01); 3.2614 (0.85); 3.2551 (1.02);<br>3.2410 (0.74); 3.1736 (0.50); 2.8176 (1.08); 2.8040 (0.84); 2.7966 (1.09);<br>2.7767 (0.93); 2.5316 (1.03); 2.5180 (16.89); 2.5140 (33.01); 2.5095 (43.47); 2.5050 (32.99); 2.5007 (17.03); 2.3364 (0.34); 2.3086 (16.00); 2.1862 (7.13) |
| 2-24 | 3,4-bismethoxyphenyl | CH2 | CH2 | — | H | spectrometer: 399.95 MHz<br>8.0798 (0.48); 8.0658 (0.95); 8.0519 (0.52); 7.8244 (3.04); 7.8112 (3.20);<br>7.1400 (3.23); 7.1268 (3.15); 6.8786 (2.01); 6.8582 (2.84); 6.8405 (2.24);<br>6.8359 (2.53); 6.7659 (1.43); 6.7612 (1.32); 6.7456 (1.05); 6.7408 (0.98);<br>3.9041 (10.94); 3.7302 (15.17); 3.7118 (16.00); 3.4897 (1.07); 3.4726 (1.98); 3.4550 (2.16); 3.4389 (1.82); 3.3794 (338.51); 3.1752 (0.59); 3.1627 (0.56); 2.7848 (1.52); 2.7663 (2.52); 2.7485 (1.40); 2.6744 (0.40);<br>2.5275 (1.29); 2.5140 (22.66); 2.5097 (44.97); 2.5052 (59.64); 2.5007 (45.41); 2.4964 (23.63); 2.3318 (0.37) |
| 2-25 | phenyl | CH2 | CH2 | — | H | spectrometer: 399.95 MHz<br>7.8131 (0.94); 7.7999 (0.98); 7.2995 (0.82); 7.2815 (0.86); 7.2536 (1.09);<br>7.2366 (0.51); 7.2041 (0.44); 7.1292 (1.00); 7.1160 (0.98); 3.8956 (2.67);<br>3.5033 (0.61); 3.4857 (1.00); 3.4706 (1.25); 3.4669 (1.37); 3.4512 (1.93);<br>3.4109 (103.28); 2.8478 (0.54); 2.8288 (0.80); 2.8109 (0.49); 2.5087 (5.66); 2.5044 (11.35); 2.4998 (15.07); 2.4953 (11.41); 2.4910 (5.85); 2.0658 (16.00) |
| 2-26 | 4-chlorophenyl | C(CH2—CH2) | CH2 | — | H | |

TABLE 2-continued

Compounds of the formula I-2

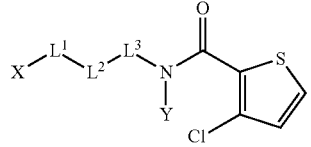

I-2

| Ex. No. | X | L¹ | L² | L³ | Y | Physical data: ¹H-NMR, δ [ppm] or CAS or patent No. |
|---|---|---|---|---|---|---|
| 2-27 | 2,4-dichlorophenyl | C(CH2—CH2) | CH2 | — | H | |
| 2-28 | 4-chlorophenyl | CH2 | C(CH2—CH2) | — | H | |
| 2-29 | 2,4-dichlorophenyl | CH2 | C(CH2—CH2) | — | H | |
| 2-30 | 4-chlorophenyl | O | CH2 | CH2 | H | |
| 2-31 | 2,4-dichlorophenyl | O | CH2 | CH2 | H | compound No. 2-31, solvent: spectrometer: 399.95 MHz 8.2015 (2.25); 8.1882 (4.21); 8.1747 (2.31); 7.8594 (12.24); 7.8462 (12.76); 7.8257 (0.4); 7.8126 (0.38); 7.5737 (10.75); 7.5672 (11.64); 7.3865 (5.52); 7.38 (5.32); 7.3643 (7.63); 7.3579 (7.46); 7.2503 (12.26); 7.2281 (9.04); 7.193 (0.39); 7.18 (0.4); 7.1629 (12.99); 7.1498 (12.64); 4.2325 (7.21); 4.2179 (16); 4.2033 (8.11); 3.6922 (4); 3.6779 (11.3); 3.6635 (11.02); 3.649 (3.76); 3.3342 (54.47); 2.5446 (1.72); 2.5275 (0.63); 2.514 (13.13); 2.5098 (26.04); 2.5054 (34.67); 2.5009 (26.43); 2.4969 (13.89); −0.0002 (1.22) |
| 2-32 | 4-chlorophenyl | CH2 | CH2 | CH2 | H | |
| 2-33 | 4-chlorophenyl | NCH3 | CH2 | CH2 | H | |
| 2-34 | 2,4-dichlorophenyl | NCH3 | CH2 | CH2 | H | |
| 2-35 | 4-chlorophenyl | CH(OCH3) | CH2 | — | H | |
| 2-36 | 2,4-dichlorophenyl | CH(OCH3) | CH2 | — | H | |
| 2-37 | 2-thienyl | CH2 | CH2 | — | H | compound No. 2-37, solvent: spectrometer: 399.95 MHz 8.1958 (2.47); 8.1831 (4.27); 8.1699 (2.52); 7.8355 (11.56); 7.8223 (12.07); 7.802 (0.38); 7.7886 (0.35); 7.357 (7.35); 7.3549 (7.31); 7.3443 (8.02); 7.3422 (7.7); 7.1756 (0.39); 7.1625 (0.44); 7.1454 (12.37); 7.1322 (12.09); 6.974 (5.53); 6.9653 (8.64); 6.9618 (5.98); 6.9529 (8.04); 6.9286 (9.27); 6.9216 (6.48); 3.528 (4.5); 3.5104 (10.49); 3.4953 (10.88); 3.4777 (5.35); 3.3282 (51.56); 3.0758 (9.06); 3.0578 (16); 3.0399 (7.9); 2.6707 (0.4); 2.5413 (3.35); 2.5407 (3.34); 2.5056 (48.75); 2.5015 (63.37); 2.4974 (49.66); 2.3282 (0.42); −0.0002 (1.08) |
| 2-38 | 3-thienyl | CH2 | CH2 | — | H | |
| 2-39 | 2-furyl | CH2 | CH2 | — | H | |
| 2-40 | 3-furyl | CH2 | CH2 | — | H | |
| 2-41 | phenyl | CH2 | CH2 | CH(CH3) | H | compound No. 2-41, solvent: spectrometer: 399.95 MHz⏋ 7.9928 (2.22); 7.9721 (2.24); 7.8193 (7.33); 7.8061 (7.61); 7.2931 (2.88); 7.2744 (7.63); 7.256 (6.79); 7.2108 (8.88); 7.1928 (5.41); 7.1907 (5.41); 7.1679 (3.85); 7.1465 (8.46); 7.1334 (7.49); 3.9791 (0.57); 3.9589 (1.26); 3.9434 (1.66); 3.928 (1.31); 3.9073 (0.6); 3.3467 (186.19); 2.7002 (0.45); 2.6853 (0.67); 2.6766 (0.76); 2.6662 (1.84); 2.6512 (1.83); 2.642 (3.39); 2.6255 (3.16); 2.6186 (2.03); 2.6014 (1.79); 2.59 (0.61); 2.5843 (0.7); 2.5671 (0.65); 2.5426 (34.53); 2.5257 (0.87); 2.5078 (29.8); 2.5033 (39.32); 2.4989 (29.92); 2.0742 (0.39); 1.8911 (0.44); 1.8759 (0.54); 1.8687 (0.78); 1.8565 (1.22); 1.8426 (1.11); 1.8344 (1.66); 1.8206 (1.37); 1.8132 (1.08); 1.7978 (0.88); 1.7922 (0.95); 1.7757 |

TABLE 2-continued

Compounds of the formula I-2

I-2

| Ex. No. | X | L¹ | L² | L³ | Y | Physical data: ¹H-NMR, δ [ppm] or CAS or patent No. |
|---|---|---|---|---|---|---|
| | | | | | | (1.36); 1.7677 (1.03); 1.7612 (1.35); 1.7538 (1.35); 1.7372 (1.15); 1.7278 (0.59); 1.72 (0.61); 1.7037 (0.39); 1.179 (16); 1.1625 (15.89); 0.0079 (0.51); −0.0002 (12.6); −0.0081 (0.51) |
| 2-42 | phenyl | CH2 | CH2 | CH2 | H | compound No. 2-42, solvent: spectrometer: 399.95 MHz 8.1619 (2.22); 8.1492 (3.77); 8.1364 (2.21); 7.8225 (12.02); 7.8093 (12.51); 7.7925 (0.43); 7.7793 (0.36); 7.3039 (4.87); 7.2852 (13.51); 7.2669 (12.29); 7.2291 (16); 7.2116 (8.86); 7.1958 (4.5); 7.1778 (6.66); 7.1601 (2.64); 7.1434 (12.73); 7.1302 (12.26); 3.33 (81.78); 3.2909 (4.21); 3.2739 (9.58); 3.2585 (9.62); 3.2414 (4.44); 2.6714 (0.55); 2.6501 (7.43); 2.6312 (11.09); 2.6116 (7.94); 2.5417 (52.11); 2.5067 (44.47); 2.5024 (57.75); 2.4981 (43.9); 2.3293 (0.35); 2.0751 (0.66); 1.8583 (2.34); 1.8398 (6.48); 1.8211 (8.65); 1.8026(6.12); 1.7845 (2.02); 0.0079 (0.66); −0.0002 (16.13); −0.0083 (0.63) |
| 2-43 | 2-Cl-phenyl | CH2 | CH2 | CH(CH3) | H | |
| 2-44 | 4-t-butylphenyl | CH2 | CH2 | CH2 | H | |
| 2-45 | 4-methyl-phenyl | CH2 | CH2 | CH2 | H | |
| 2-46 | phenyl | CH2 | CH2 | CH(CH2CH3) | H | |
| 2-47 | 2-methoxy-phenyl | CH2 | CH2 | CH2 | H | |
| 2-48 | 2-methyl-phenyl | CH2 | CH2 | CH2 | H | |
| 2-49 | 3-methyl-phenyl | CH2 | CH2 | CH2 | H | |
| 2-50 | 3-chloro-phenyl | CH2 | CH2 | CH2 | H | |
| 2-51 | 2,6-difluoro-phenyl | CH2 | CH2 | CH2 | H | |
| 2-52 | 4-chloro-phenyl | CH2 | CH2 | CH2 | H | |
| 2-53 | 2,6-dichloro-phenyl | CH2 | CH2 | CH(CH3) | H | |
| 2-54 | 3,5-dichloro-phenyl | CH2 | CH2 | CH(CH3) | H | compound No. 2-54, solvent: spectrometer: 399.95 MHz⁻ 7.9656 (2.6); 7.9449 (2.62); 7.8261 (7.86); 7.8129 (8.13); 7.4001 (3.5); 7.3956 (6.47); 7.3909 (3.83); 7.2997 (13.96); 7.295 (12.97); 7.1477 (8.13); 7.1345 (7.85); 3.9691 (0.58); 3.9485 (1.26); 3.934 (1.62); 3.9182 (1.33); 3.8974 (0.61); 3.3344 (29.05); 2.7154 (0.49); 2.7002 (0.6); 2.6924 (0.58); 2.6807 (1.87); 2.6595 (3.09); 2.6431 (3.84); 2.6217 (1.81); 2.6051 (0.63); 2.5872 (0.47); 2.5454 (21.6); 2.5145 (7.6); 2.5105 (14.83); 2.506 (19.57); 2.5015 (14.69); 2.4975 (7.45); 2.0793 (0.86); 1.8865 (0.37); 1.8709 (0.49); 1.8645 (0.77); 1.8518 (1.18); 1.8373 (1.16); 1.8304 (1.93); 1.8152 (1.77); 1.8089 (2); 1.7926 (2.06); 1.7856 (1.23); 1.7776 (1.53); 1.7725 (1.48); 1.7552 (1.24); 1.7441 (0.53); 1.7383 (0.52); 1.7349 (0.49); 1.721 (0.32); 1.1772 (16); 1.1607 (15.86); −0.0002 (6.07) |
| 2-55 | 2,6-dimethyl-phenyl | CH2 | CH2 | CH2 | H | compound No. 2-55, solvent: spectrometer: 399.95 MHz 8.3181 (2.09); 8.2061 (3.02); 8.1928 (5.42); 8.1793 (3); 7.8283 (14.21); 7.8152 (14.72); 7.7982 (0.55); 7.785 (0.44); 7.5008 (13.04); 7.4945 (13.66); 7.4607 (11.99); 7.4393 (16); 7.4263 (0.41); 7.3226 (8.63); 7.3162 (8.14); 7.3012 (6.51); 7.2948 (6.08); 7.177 (0.45); 7.164 (0.52); 7.1465 (14.9); 7.1334 (14.36); 3.3364 (121.82); 3.3094 (12.94); 3.2937 (12.47); 3.2771 (5.11); 2.7645 (8.71); 2.7458 (12.16); 2.7259 (9.31); 2.6742 (0.47); 2.5447 (42.98); 2.5094 (42.43); 2.5053 (54.42); 2.5012 (42.03); 2.3321 (0.36); 2.0782 (1.56); 1.8532 (2.58); 1.8355 (7.45); 1.8163 (9.57); 1.7978 (7.17); 1.7802 (2.28); −0.0002 (8.32) |

TABLE 2-continued

Compounds of the formula I-2

I-2

| Ex. No. | X | L¹ | L² | L³ | Y | Physical data: ¹H-NMR, δ [ppm] or CAS or patent No. |
|---|---|---|---|---|---|---|
| 2-56 | 2,5-dichlorophenyl | CH2 | CH2 | CH2 | H | |
| 2-57 | 4-isopropoxyphenyl | CH2 | CH2 | CH2 | H | |
| 2-58 | 3-trifluoromethylphenyl | CH2 | CH2 | CH(CH3) | H | compound No. 2-58, solvent: spectrometer: 399.95 MHz<br>8.3199 (0.91); 8.0068 (2.56); 7.9862 (2.54); 7.8258 (7.05); 7.8126 (7.3); 7.6239 (0.33); 7.5712 (5.61); 7.5578 (1.06); 7.5285 (15.03); 7.5018 (0.46);<br>7.4925 (0.48); 7.1496 (7.32); 7.1365 (7.06); 3.9918 (0.56); 3.9715 (1.26);<br>3.9561 (1.64); 3.941 (1.32); 3.9204 (0.61); 3.3349 (49.97); 3.3111 (0.7); 2.8065 (0.46); 2.7918 (0.64); 2.7825 (0.64); 2.772 (1.75); 2.7575 (1.88); 2.7481 (3.46); 2.7316 (3.2); 2.7249 (2.16); 2.7074 (1.8); 2.6961 (0.63); 2.6903 (0.69); 2.6734 (0.69); 2.5447 (25.9); 2.5097 (21.29); 2.5053 (27.97); 2.501 (21.36); 2.0779 (0.48); 1.9173 (0.38); 1.9022 (0.5); 1.8946<br>(0.74); 1.8825 (1.2); 1.8689 (1.17); 1.8605 (1.74); 1.8464 (1.52); 1.8387 (1.23); 1.8323 (1.15); 1.8158 (1.52); 1.8079 (1.18); 1.8015<br>(1.5); 1.7944 (1.48); 1.7778 (1.23); 1.7681 (0.59); 1.7605 (0.58); 1.7441 (0.37); 1.2098 (0.47); 1.1881 (16); 1.1716 (15.82); 0.0079 (0.33); −0.0002 (7.99); −0.0082 (0.33) |
| 2-59 | 4-methylphenyl | CH2 | CH2 | CH(CH3) | H | |
| 2-60 | 2-methylphenyl | CH2 | CH2 | CH(CH3) | H | |
| 2-61 | 3,4-dichlorophenyl | CH2 | CH2 | CH(CH3) | H | compound No. 2-61, solvent: spectrometer: 399.95 MHz<br>8.3183 (0.58); 7.9722 (2.55); 7.9515 (2.58); 7.8231 (7.37); 7.81 (7.6); 7.5329 (6.66); 7.5227 (0.38); 7.5123 (7.64); 7.4972 (6.4); 7.4924 (6.61); 7.227 (3.66); 7.2222 (3.6); 7.2064 (3.23); 7.2016 (3.16); 7.1458 (7.72); 7.1326 (7.5); 3.9633 (0.57); 3.9427 (1.24); 3.928 (1.62); 3.9124 (1.33); 3.8917 (0.6); 3.3365 (67.26); 3.313 (0.61); 2.7069 (0.4); 2.6917 (0.6); 2.6838 (0.59); 2.6722 (1.93); 2.6509 (2.99); 2.6345 (3.91); 2.6137 (1.84); 2.5968 (0.64); 2.579 (0.51); 2.5446 (23.11); 2.5272 (0.55); 2.5096 (19.92); 2.5052 (26.41); 2.5007 (20.02); 2.0781<br>(0.85); 1.8847 (0.39); 1.869 (0.51); 1.8628 (0.82); 1.8497 (1.2); 1.8406 (0.78); 1.8354 (1.14); 1.8287 (1.93); 1.8137 (1.66); 1.8072 (1.27); 1.7996 (1.1); 1.7914 (1.12); 1.7826 (1.43); 1.7765 (1.14); 1.7683 (1.47); 1.7635 (1.47); 1.7459 (1.26); 1.7348 1.7292 (0.56); 1.7258<br>(0.53); 1.712 (0.36); 1.1747 (16); 1.1582 (15.98); −0.0002 (5.09) |
| 2-62 | 3,5-dichlorophenyl | CH2 | CH2 | CH2 | H | compound No. 2-62, solvent: spectrometer: 399.95 MHz<br>8.1498 (1.56); 8.1366 (2.79); 8.1233 (1.56); 7.8286 (8.44); 7.8154 (8.79);<br>7.4104 (4.01); 7.406 (7.09); 7.4014 (4.27); 7.3289 (16); 7.3244 (14.18); 7.1458 (8.75); 7.1326 (8.5); 3.3373 (40.62); 3.278 (2.6); 3.2612 (6.29); 3.2459 (6.37); 3.2291 (2.75); 2.6748 (4.59); 2.6562 (7.63); 2.6371 (4.76);<br>2.5459 (24.64); 2.5109 (16.05); 2.5065 (20.86); 2.5021 (15.75); 2.0796 (0.8); 1.8661 (1.37); 1.8481 (4.23); 1.8296 (5.7); 1.8114 (4.02); 1.7937 (1.19); −0.0002 (4.86) |
| 2-63 | 2,6-dimethylphenyl | CH2 | CH2 | CH(CH3) | H | compound No. 2-63, solvent: spectrometer: 399.95 MHz<br>8.032 (0.6); 8.012 (0.61); 7.827 (1.81); 7.8139 (1.91); 7.1533 (1.91); 7.1402 (1.89); 6.9544 (7.38); 4.0757 (0.36); 4.0586 (0.44); 4.0408 (0.37);<br>3.4371 (0.33); 3.4069 (0.64); 3.3327 (1566.67); 3.2526 (0.79); 2.6753 (2.51); 2.6709 (3.44); 2.6667 (2.56); 2.6427 (0.6); 2.632 (0.64); 2.6164 (0.66); 2.6043 (0.67); 2.5877 (0.81); 2.5412 (8.13); 2.524 (10.07); 2.5063<br>(342.36); 2.5018 (450.83); 2.4974 (340.1); 2.333 (2.2); 2.3286 (2.98); 2.3242 (2.23); 2.2892 (0.34); 2.2684 (16); 2.074 (1.53); 1.6333 (0.42); 1.6129 (0.75); 1.5953 (0.83); 1.5745 (0.42); 1.2272 (3.92); 1.2105 (3.81);<br>−0.0002 (14.36) |

TABLE 2-continued

Compounds of the formula I-2

I-2

| Ex. No. | X | L¹ | L² | L³ | Y | Physical data: $^1$H-NMR, δ [ppm] or CAS or patent No. |
|---|---|---|---|---|---|---|
| 2-64 | 4-trifluoro-methyl-phenyl | CH2 | CH2 | CH(CH3) | H | compound No. 2-64, solvent: spectrometer: 399.95 MHz 8.0067 (2.51); 7.9859 (2.51); 7.8239 (7.71); 7.8108 (7.96); 7.6441 (6.59); 7.6238 (8.04); 7.452 (7.31); 7.432 (6.19); 7.147 (8.01); 7.1339 (7.7); 3.9855 (0.56); 3.9649 (1.23); 3.95 (1.59); 3.9344 (1.3); 3.9139 (0.6); 3.3391 (108.58); 3.1416 (0.54); 3.1188 (0.5); 2.7982 (0.34); 2.7829 (0.51); 2.7749 (0.48); 2.7634 (1.56); 2.7433 (2.75); 2.7255 (3.38); 2.705 (1.59); 2.6909 (0.61); 2.67 (0.54); 2.5443 (31.93); 2.5273 (0.69); 2.5136 (12.32); 2.5094 (24.5); 2.5049 (32.71); 2.5005 (24.74); 2.4964 (12.74); 2.077 (0.63); 1.923 (0.4); 1.9073 (0.5); 1.9008 (0.81); 1.8879 (1.13); 1.8787 (0.77); 1.8739 (1.09); 1.8668 (1.76); 1.8519 (1.5); 1.8453 (1.15); 1.8308 (1.44); 1.815 (1.37); 1.8081 (1.1); 1.8008 (1.39); 1.7948 (1.37); 1.7777 (1.19); 1.7672 (0.59); 1.761 (0.57); 1.7439 (0.37); 1.1872 (15.95); 1.1707 (16); −0.0002 (5.54) |
| 2-65 | 2,5-dichloro-phenyl | CH2 | CH2 | CH(CH3) | H | compound No. 2-65, solvent: spectrometer: 399.95 MHz⌐ 8.0047 (2.66); 7.984 (2.69); 7.8266 (7.82); 7.8135 (8.07); 7.4572 (6.76); 7.4506 (12.88); 7.4292 (8.59); 7.312 (4.56); 7.3056 (4.19); 7.2907 (3.38); 7.2842 (3.13); 7.1485 (8.14); 7.1353 (7.92); 4.03 (0.63); 4.0109 (1.35); 3.9946 (1.87); 3.9783 (1.44); 3.9592 (0.66); 3.337 (33.58); 2.8178 (0.53); 2.8018 (0.69); 2.7949 (0.75); 2.7834 (1.75); 2.7681 (1.8); 2.7601 (2.24); 2.7527 (1.93); 2.7443 (1.99); 2.7351 (2.36); 2.7294 (1.88); 2.7123 (1.81); 2.7002 (0.8); 2.6959 (0.69); 2.6778 (0.67); 2.5459 (21.32); 2.5291 (0.42); 2.5111 (14.05); 2.5066 (18.48); 2.5022 (13.85); 2.0797 (1.06); 1.8417 (0.35); 1.8237 (1.25); 1.8093 (2); 1.8 (2.44); 1.7954 (2.45); 1.7871 (2.82); 1.7808 (2.77); 1.7729 (2.03); 1.7659 (1.51); 1.756 (1.33); 1.7399 (0.34); 1.2061 (16); 1.1895 (15.93); −0.0002 (5.28) |
| 2-66 | 4-phenoxy-phenyl | CH2 | CH2 | CH2 | H | |
| 2-67 | 3-chloro-phenyl | CH2 | CH2 | CH(CH3) | H | |
| 2-68 | 4-phenoxy-phenyl | CH2 | CH2 | CH(CH3) | H | |
| 2-69 | 2,4-dichloro-phenyl | CH2 | CH2 | CH(CH3) | H | |
| 2-70 | 2-difluoro-methoxy-phenyl | CH2 | CH2 | CH(CH3) | H | compound No. 2-70, solvent: spectrometer: 399.95 MHz⌐ 8.3169 (0.83); 7.9735 (2.48); 7.9528 (2.5); 7.8211 (8.06); 7.8079 (8.36); 7.3656 (3.83); 7.3272 (2.7); 7.3233 (3.07); 7.3086 (3.46); 7.3047 (3.93); 7.2864 (1.41); 7.2821 (1.36); 7.2671 (3.42); 7.2628 (3.05); 7.2477 (2.97); 7.2433 (2.47); 7.1952 (2.86); 7.1925 (3.33); 7.1796 (8.97); 7.174 (5.06); 7.1526 (5.06); 7.1455 (9.38); 7.1323 (11.35); 6.9939 (3.94); 3.9968 (0.59); 3.9773 (1.28); 3.9613 (1.77); 3.9452 (1.36); 3.9256 (0.61); 3.3351 (80.76); 3.3113 (0.69); 2.7451 (0.57); 2.7303 (0.72); 2.7209 (0.8); 2.7108 (1.67); 2.6961 (1.56); 2.6865 (1.8); 2.6709 (2.03); 2.6504 (1.83); 2.6427 (1.62); 2.6268 (1.64); 2.6161 (0.79); 2.6086 (0.76); 2.5924 (0.67); 2.5423 (33.94); 2.5255 (0.69); 2.5118 (11.77); 2.5075 (23.24); 2.503 (30.78); 2.4985 (23.06); 2.4942 (11.62); 2.0754 (1.11); 1.8303 (0.44); 1.8219 (0.49); 1.8114 (1.2); 1.7969 (1.17); 1.7877 (1.66); 1.7771 (1.65); 1.7731 (1.52); 1.7665 (2.34); 1.7505 (1.84); 1.7409 (1.62); 1.7309 (0.81); 1.7252 (1.09); 1.7164 (0.42); 1.7077 (0.54); 1.1919 (16); 1.1753 (15.87); −0.0002 (6.33) |
| 2-71 | 4-methoxy-phenyl | CH2 | CH2 | CH2 | H | |
| 2-72 | 4-chloro-phenyl | CH2 | CH2 | CH(CH3) | H | compound No. 2-72, solvent: spectrometer: 399.95 MHz⌐ 7.9867 (2.32); 7.9661 (2.36); 7.8197 (7.69); 7.8066 (8.01); 7.3355 (7.83); 7.3309 (2.86); 7.3192 (3.58); 7.3145 (12.43); 7.3085 (1.76); 7.2423 (10.76); 7.2214 (6.89); 7.1448 (8.08); 7.1316 (7.83); 3.9585 (0.56); 3.9379 (1.2); 3.9232 (1.56); 3.9074 (1.25); 3.887 (0.57); 3.3692 (0.6); 3.3315 (338.35); |

TABLE 2-continued

Compounds of the formula I-2

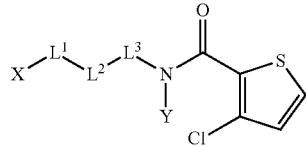

I-2

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 3.2986 (0.6); 2.7118 (0.33); 2.6914 (0.43); 2.6761 (1.11); 2.671 (1.14); 2.6673 (1.05); 2.6571 (1.73); 2.6419 (2); 2.6349 (3.2); 2.6186 (3.68); 2.5962 (1.77); 2.5832 (0.68); 2.5788 (0.73); 2.5608 (0.77); 2.5415 (69.61); 2.5246 (2.52); 2.511 (43.01); 2.5067 (84.57); 2.5022 (111.66); 2.4977 (83.25); 2.4934 (41.77); 2.3334 (0.52); 2.3289 (0.73); 2.3245 (0.53); 2.0746 (0.52); 1.8747 (0.4); 1.8591 (0.51); 1.8526 (0.8); 1.8401 (1.14); 1.8261 (1.03); 1.8186 (1.69); 1.804 (1.42); 1.7971 (1.05); 1.7804 (1.16); 1.7621 (1.26); 1.7553 (0.99); 1.7478 (1.32); 1.7418 (1.29); 1.7245 (1.12); 1.7141 (0.56); 1.7078 (0.57); 1.6909 (0.37); 1.1707 (16); 1.1542 (15.9); 0.0079 (0.47); −0.0002 (12.91); −0.0085 (0.49) |
| 2-73 | 4-chloro-phenyl | CH2 | CH2 | CH (i-propyl) | H | compound No. 2-73, solvent: spectrometer: 399.95 MHz 7.8783 (1.86); 7.8552 (1.89); 7.8267 (4.97); 7.8135 (5.15); 7.3278 (5.08); 7.3234 (1.93); 7.3068 (8.36); 7.3012 (1.31); 7.2428 (7.42); 7.2218 (4.62); 7.1557 (5.24); 7.1426 (5.07); 3.8106 (0.37); 3.7973 (0.6); 3.7872 (1.02); 3.7746 (1.18); 3.7628 (1.01); 3.7518 (0.64); 3.7389 (0.38); 3.3356 (51.87); 2.691 (0.46); 2.6766 (0.69); 2.6686 (0.67); 2.6559 (1.09); 2.6415 (0.96); 2.6351 (0.92); 2.6197 (0.8); 2.5656 (0.8); 2.5434 (16.86); 2.5252 (1.33); 2.5086 (15.1); 2.5041 (19.29); 2.4997 (14.5); 2.4957 (7.55); 2.0766 (0.66); 1.8277 (0.33); 1.8115 (0.99); 1.7946 (1.75); 1.7793 |
| 2-74 | 4-fluoro-phenyl | CH2 | CH2 | CH2 | H | compound No. 2-74, solvent: spectrometer: 399.95 MHz⌐ 8.1571 (2.3); 8.1445 (3.97); 8.1314 (2.32); 7.8233 (13.46); 7.8101 (14); 7.7932 (0.52); 7.7801 (0.41); 7.2736 (6.93); 7.2686 (3.51); 7.2592 (8.85); 7.2522 (10); 7.238 (8.69); 7.1744 (0.47); 7.1614 (0.51); 7.1437 (14.16); 7.1306 (14.46); 7.1211 (10.44); 7.1159 (3.53); 7.0987 (16); 7.0931 (4.15); 7.0813 (3.4); 7.0766 (7.52); 7.069 (0.99); 3.3804 (0.36); 3.3684 (0.65); 3.3369 (163.66); 3.298 (0.48); 3.2807 (4.34); 3.2637 (9.62); 3.2486 (9.89); 3.2314 (4.51); 2.6774 (0.37); 2.6727 (0.48); 2.6685 (0.4); 2.6413 (6.93); 2.6225 (11.06); 2.6031 (7.46); 2.5431 (57.57); 2.5261 (1.62); 2.5122 (25.08); 2.5082 (46.38); 2.5038 (58.81); 2.4993 (43.77); 2.3305 (0.39); 2.0761 (0.8); 1.842 (2.3); 1.8236 (6.48); 1.8051 (8.74); 1.7868 (6.2); 1.7686 (2.03); −0.0002 (7.35) |
| 2-75 | 4-chloro-phenyl | CH2 | CH2 | CH (n-propyl) | H | compound No. 2-75, solvent: spectrometer: 399.95 MHz⌐ 7.913 (2.57); 7.8908 (2.61); 7.8173 (7.32); 7.8042 (7.58); 7.3287 (7.24); 7.3242 (2.78); 7.3123 (3.44); 7.3077 (11.59); 7.3019 (1.79); 7.2372 (10.16); 7.2162 (6.51); 7.1456 (7.76); 7.1325 (7.5); 3.934 (0.76); 3.9158 (1.37); 3.8985 (1.39); 3.8803 (0.8); 3.3318 (66.92); 2.687 (0.51); 2.6681 (1.18); 2.6522 (1.5); 2.6336 (2.24); 2.6145 (2.4); 2.5944 (2.63); 2.574 (1.47); 2.5596 (1.23); 2.5427 (30.42); 2.5259 (0.81); 2.5122 (12.8); 2.5079 (25.23); 2.5034 (33.46); 2.4988 (25.21); 2.4945 (12.78); 2.0761 (0.7); 1.7893 (1.87); 1.7697 (3.93); 1.7521 (4.42); 1.7329 (1.74); 1.5174 (0.93); 1.5077 (1.11); 1.5022 (1.44); 1.4936 (2.52); 1.4751 (3.44); 1.4574 (2); 1.3922 (0.39); 1.3749 (0.68); 1.359 (1.34); 1.3408 (1.88); 1.3332 (1.34);1.3234 (1.73); 1.3153 (1.85); 1.3097 (1.31); 1.2973 (1.52); 1.2927 (1.32); 1.2815 (0.85); 1.2751 (0.93); 1.2636 (0.48); 1.2594 (0.51); 0.8802 (7.91); 0.862 (16); 0.8437 (6.75); 0.0079 (0.5); −0.0002 (13.95); −0.0084 (0.56) |
| 2-76 | 4-chloro-phenyl | CH2 | CH2 | CH (t-butyl) | H | compound No. 2-76, solvent: spectrometer: 399.95 MHz 7.8382 (0.75); 7.8328 (2.07); 7.8196 (2.18); 7.8147 (0.8); 7.3251 (1.73); 7.3205 (0.67); 7.304 (3.07); 7.2498 (2.74); 7.2287 (1.61); 7.1615 (1.96); 7.1484 (1.9); 3.7538 (0.64); 3.7297 (0.33); 3.3375 (20.94); 2.6423 (0.42); 2.5436 (5.53); 2.5129 (2.71); 2.5088 (5.29); 2.5043 (6.98); 2.4998 (5.29); 2.4957 (2.88); 2.4775 (0.4); 2.4722 (0.39); 2.4543 (0.34); 1.8132 (0.35); 0.8896 (16); −0.0002 (1.78) |
| 2-77 | 2-chloro-phenyl | CH2 | CH2 | CH2 | H | compound No. 2-77, solvent: spectrometer: 399.95 MHz 8.3164 (1.67); 8.2073 (2.43); 8.1943 (4.32); 8.1807 (2.43); 7.825 (15.3); |

TABLE 2-continued

Compounds of the formula I-2

I-2

| Ex. No. | X | L¹ | L² | L³ | Y | Physical data: ¹H-NMR, δ [ppm] or CAS or patent No. |
|---|---|---|---|---|---|---|
| | | | | | | 7.8118 (15.85); 7.7946 (0.56); 7.7814 (0.47); 7.4225 (6.56); 7.4191 (6.47); 7.4033 (8.42); 7.3997 (8.42); 7.3877 (5.38); 7.3833 (5.76); 7.369 (7.45); 7.3647 (7.89); 7.3035 (3.37); 7.3001 (3.73); 7.2852 (8.28); 7.2816 (7.74); 7.2668 (5.54); 7.263 (4.67); 7.2539 (6.07); 7.2491 (6.17); 7.2348 (6.74); 7.2303 (6.52); 7.2161 (2.64); 7.2116 (2.32); 7.1756 (0.5); 7.1625 (0.55); 7.1452 (16); 7.132 (15.45); 7.1237 (0.48); 3.3931 (0.48); 3.3741 (1.12); 3.341 (242.72); 3.3129 (11.63); 3.2976 (11); 3.2806 (4.82); 2.77 (8.21); 2.7511 (10.28); 2.7311 (8.72); 2.7137 (0.41); 2.6775 (0.46); 2.6731 (0.59); 2.5434 (63.34); 2.5263 (1.92); 2.5128 (26.19); 2.5086 (50.46); 2.5041 (66.35); 2.4996 (49.74); 2.4953 (25.17); 2.3309 (0.42); 2.0761 (1.44); 1.8538 (2.51); 1.8356 (6.53); 1.8167 (8.34); 1.798 (6.21); 1.78 (2.14); 0.0079 (0.4); −0.0002 (9.67); −0.0085 (0.36) |
| 2-78 | 2-thienyl | CH2 | CH2 | CH2 | H | compound No. 2-78, solvent: spectrometer: 399.95 MHz 8.1901 (2.91); 8.1777 (5); 8.1657 (3.06); 7.8261 (12.85); 7.825 (12.4); 7.8129 (13.52); 7.8119 (13.05); 7.7953 (0.6); 7.7822 (0.44); 7.3203 (8.78); 7.3076 (9.55); 7.1752 (0.42); 7.1621 (0.47); 7.1455 (13.66); 7.1445 (13.08); 7.1323 (13.35); 7.1313 (12.76); 6.9515 (6.41); 6.9427 (8.97); 6.9391 (7.19); 6.9302 (8.23); 6.8872 (10.26); 6.8791 (8.24); 3.3314 (106.28); 3.3073 (13.58); 3.2915 (13.3); 3.2749 (5.96); 2.872 (9.41); 2.853 (16); 2.8339 (10.05); 2.6709 (0.58); 2.5417 (2.78); 2.5407 (2.62); 2.502 (75.43); 2.4981 (60.55); 2.3286 (0.49); 1.9003 (2.93); 1.8821 (9.04); 1.8636 (12.17); 1.8453 (8.71); 1.8273 (2.7); −0.0002 (0.7) |
| 2-79 | 2,6-difluoro-phenyl | CH2 | CH(CH3) | — | H | spectrometer: 399.95 MHz 7.9988 (3.15); 7.9778 (3.21); 7.7997 (7.73); 7.7866 (8.07); 7.7711 (0.4); 7.3519 (0.8); 7.3316 (2.07); 7.3143 (3.69); 7.2939 (2.51); 7.2767 (1.05); 7.1338 (0.37); 7.1153 (8.38); 7.1022 (8.12); 7.0815 (0.95); 7.0692 (5.57); 7.0498 (8.8); 7.03 (4.77); 7.0178 (0.82); 4.2991 (0.8); 4.2811 (1.87); 4.263 (2.47); 4.245 (1.98); 4.2275 (0.89); 3.3347 (26.57); 2.9301 (0.44); 2.8921 (5.54); 2.876 (6.4); 2.8396 (0.39); 2.6724 (0.5); 2.5073 (57.25); 2.5032 (75.74); 2.4992 (61.74); 2.33 (0.51); 1.336 (0.44); 1.2491 (0.44); 1.2325 (0.34); 1.1897 (15.85); 1.173 (16); 0.0078 (1.35); −0.0002 (27.44) |
| 2-80 | 4-chloro-phenyl | CH2 | CH2 | — | CH3 | compound No. 2-80, solvent: spectrometer: 399.95 MHz 8.3205 (0.33); 7.7755 (5.45); 7.7655 (5.62); 7.3258 (9.27); 7.1826 (0.48); 7.0807 (9.65); 7.0682 (9.73); 4.0378 (0.69); 4.02 (0.69); 3.6776 (3.09); 3.5874 (0.71); 3.4941 (2.32); 3.3355 (59.17); 3.0207 (4.31); 2.8772 (10.16); 2.6765 (0.74); 2.6724 (0.97); 2.6681 (0.75); 2.5077 (99.47); 2.5033 (128.84); 2.4989 (96.92); 2.3344 (0.65); 2.3302 (0.86); 2.3258 (0.64); 2.08 (0.37); 2.0357 (0.37); 1.9901 (2.95); 1.397 (16); 1.3364 (0.65); 1.2491 (0.76); 1.1929 (0.8); 1.1751 (1.54); 1.1573 (0.76); 0.1459 (0.32); 0.0079 (3.23); −0.0002 (69.14); −0.008 (3.38) |
| 2-81 | 4-chloro-phenyl | CH2 | CH2 | - | CH2CH3 | compound No. 2-81, solvent: spectrometer: 399.95 MHz 7.7744 (5.47); 7.7613 (5.66); 7.3331 (4.15); 7.0949 (4.31); 7.0821 (4.33); 3.6253 (1.16); 3.4958 (1.18); 3.4703 (1.16); 3.461 (1.16); 3.3349 (23.98); 3.1896 (1.01); 2.8679 (1.6); 2.6723 (0.39); 2.5076 (42.89); 2.5032 (56.18); 2.4988 (43.26); 2.3301 (0.37); 1.99 (0.39); 1.3969 (16); 1.1925 (0.58); 1.1747 (1.07); 1.1563 (1.39); 1.1382 (1.45); 1.0351 (1.92); 0.0076 (1.23); −0.0002 (27.9); −0.0081 (1.7) |
| 2-82 | 2,4-dichloro-phenyl | CH2 | CH2 | - | CH3 | compound No. 2-82, solvent: spectrometer: 399.95 MHz 7.7789 (1.34); 7.768 (1.36); 7.5866 (0.34); 7.4841 (0.42); 7.3806 (1.21); 7.3627 (1.15); 7.3 (0.4); 7.0753 (1.27); 3.7028 (0.63); 3.552 (0.68); 3.3362 (10.02); 3.0647 (1.36); 3.0082 (1.02); 2.908 (1.77); 2.5125 (10.77); 2.5084 (20.65); 2.5039 (26.86); 2.4995 (20.26); 2.4955 (10.59); 1.9906 (1.01); 1.3968 (16); 1.1755 (0.52); 0.0079 (0.69); −0.0002 (15.22); −0.0082 (0.77) |

TABLE 2-continued

Compounds of the formula I-2

I-2

| Ex. No. | X | L¹ | L² | L³ | Y | Physical data: ¹H-NMR, δ [ppm] or CAS or patent No. |
|---|---|---|---|---|---|---|
| 2-83 | 4-fluoro-phenyl | CH2 | CH2 | CH(CH3) | H | compound No. 2-83, solvent: spectrometer: 399.95 MHz<br>7.9847 (2.32); 7.964 (2.34); 7.8206 (7.99); 7.8075 (8.3); 7.2518 (3.78); 7.2468 (1.98); 7.2375 (4.78); 7.2304 (5.75); 7.2216 (2.28); 7.2162 (4.99);<br>7.146 (8.38); 7.1329 (8.13); 7.1185 (0.76); 7.111 (5.83); 7.1059 (1.95); 7.0944 (2.19); 7.0887 (9.22); 7.083 (2.33); 7.0715 (1.62); 7.0665 (4.36);<br>7.059 (0.52); 3.967 (0.57); 3.9466 (1.26); 3.9312 (1.62); 3.9159 (1.29); 3.8953 (0.59); 3.3367 (86.22); 2.6906 (0.41); 2.6753 (0.71); 2.6674 (0.66); 2.6556 (1.69); 2.6407 (1.87); 2.6329 (3.28); 2.6164 (3.4); 2.5935 (1.7); 2.5808 (0.58); 2.5764 (0.66);<br>2.5589 (0.64); 2.5432 (28.9); 2.5262 (0.6); 2.5125 (10.86); 2.5083 (21.49);<br>2.5038 (28.59); 2.4993 (21.7); 2.4951 (11.17); 2.0762 (0.68); 1.8757 (0.44); 1.8603 (0.54); 1.8534 (0.84); 1.841 (1.21); 1.827 (1.09); 1.8194 (1.73); 1.805 (1.45); 1.7979 (1.09); 1.7825 (0.88); 1.777 (0.95); 1.7601 (1.33); 1.7529 (1.04); 1.7459 (1.36); 1.7394 (1.35); 1.7225 (1.17); 1.7123<br>(0.59); 1.7057 (0.6); 1.7029 (0.57); 1.6888 (0.39); 1.1742 (16);1.1577 (15.87); 0.0079 (0.37); −0.0002 (10.23); −0.0083 (0.43) |
| 2-84 | 4-chloro-phenyl | CF2 | CH2 | — | H | compound No. 2-84, solvent: spectrometer: 399.95 MHz<br>8.4971 (0.48); 8.4816 (0.94); 8.466 (0.47); 8.8552 (2.26); 7.842 (2.34); 7.5789 (16); 7.1512 (2.37); 7.138 (2.3); 6.5757 (0.41); 4.0669 (0.61); 4.0511 (0.63); 4.0313 (1.35); 4.0155 (1.31); 3.9954 (0.69); 3.9796 (0.65); 3.3486 (47.96); 2.9452 (2.52); 2.5086 (10.05); 2.5044 (13.29); 2.5001 (10.38) |
| 2-85 | 2-thienyl | CH2 | CH2 | — | CH3 | compound No. 2-85, solvent: spectrometer: 601.6 MHz<br>19.9671 (0.42); 8.3173 (2.02); 7.7769 (7.1); 7.3518 (10.48); 7.0829 (14.02); 6.9538(14.91); 6.9485 (14.76); 6.7584 (4.17); 5.4222 (0.41); 4.6286 (0.4); 4.6186 (0.42); 4.2709 (0.36); 4.0466 (0.39); 4.0346 (1.08); 4.0227 (1.07); 4.0108 (0.34); 3.8995 (0.35); 3.6964 (8.82); 3.5095 (7.68);<br>3.3745 (0.46); 3.3655 (0.42); 3.327 (604.31); 3.2896 (0.8); 3.2808 (0.43);<br>3.2182 (0.4); 3.1085 (12.03); 3.0584 (12.67); 3.0313 (15.74); 2.8975 (16);<br>2.7797 (0.49); 2.6166 (4.14); 2.6136 (5.62); 2.6106 (4.1); 2.5414 (1.05); 2.5229 (11.06); 2.5198 (14); 2.5167 (14.69); 2.5079 (270.99); 2.5049 (588.91); 2.5019 (812.04); 2.4988 (583.52); 2.4958 (265.01); 2.389 (3.73);<br>2.386 (5.26); 2.383 (3.82); 2.3799 (1.78); 1.989 (4.36); 1.3975 (3.17); 1.3358 (1.82); 1.2978 (0.58); 1.2584 (0.62); 1.2492 (2.58); 1.1866 (1.59);<br>1.1748 (2.59); 1.1629 (1.26); 0.948 (1.65); 0.937 (2.01); 0.8385 (0.77); 0.8266 (1.55); 0.814 (0.87); −0.0002 (6.18) |
| 2-86 | 4-chloro-phenyl | CH(OCH3) | CH3 | — | H | compound No. 2-86, solvent: spectrometer: 399.95 MHz<br>8.0412 (0.54); 8.0273 (1.04); 8.0134 (0.55); 7.8389 (2.94); 7.8257 (3.07);<br>7.4555 (2.97); 7.4512 (1.16); 7.4344 (5.07); 7.373 (4.53); 7.3519 (2.79); 7.1478 (3.09); 7.1346 (2.99); 4.4505 (0.88); 4.4347 (1.8); 4.4193 (0.93); 3.4926 (1.9); 3.4779 (3.23); 3.4625 (1.65); 3.3232 (6.6); 3.1925 (16); 2.5248 (0.43); 2.5112 (7.1); 2.507 (13.86); 2.5025 (18.31); 2.4981 (13.72); 2.4939 (6.96); −0.0002(1.07) |
| 2-87 | 5-chloro-2-thienyl | CH2 | CH2 | — | H | compound No. 2-87, solvent: spectrometer: 399.95 MHz<br>8.3161 (0.49); 8.2262 (2.13); 8.2126 (3.88); 8.1986 (2.13); 7.835 (15.07);<br>7.8219 (15.59); 7.8018 (0.43); 7.7888 (0.41); 7.3813 (14.21); 7.3775 (14.34); 7.1746 (0.48); 7.1615 (0.55); 7.1443 (16); 7.1312 (15.45); 6.9241<br>(11.01); 6.9211 (10.85); 4.056 (0.42); 4.0383 (1.28); 4.0204 (1.29); 4.0027<br>(0.43); 3.5237 (4.24); 3.5064 (10.83); 3.4917 (11.18); 3.4746 (4.85); 3.3243 (37.3); 3.0576 (0.44); 3.0424 (8.08); 3.0251 (15.23); 3.0079 (6.89);<br>2.6757 (0.33); 2.6713 (0.45); 2.6668 (0.32); 2.5244 (1.46); 2.5112 (25.96);<br>2.5068 (51.54); 2.5022 (67.31); 2.4977 (48.22); 2.4932 (23.01); 2.329 (0.43); 1.9892 (5.54); 1.3363 (0.61); 1.2494 (0.75); 1.1929 (1.52); |

TABLE 2-continued

Compounds of the formula I-2

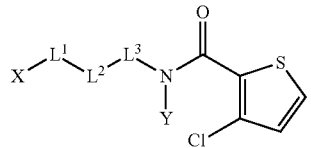

I-2

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 1.1751 (2.95); 1.1573 (1.45); 0.0079 (2.28); −0.0002 (62.76); −0.0086 (2.09) |
| 2-88 | 4-chloro-phenyl | CH(CF3) | CH2 | — | H | compound No. 2-88, solvent: spectrometer: 399.95 MHz 8.1852 (1.39); 8.171 (2.43); 8.1568 (1.34); 7.8144 (7.54); 7.8013 (7.77); 7.4825 (4.15); 7.4769 (2); 7.4663 (3.34); 7.4608 (16); 7.4444 (11.93); 7.4227 (3.38); 7.4026 (0.33); 7.3938 (0.58); 7.1028 (8); 7.0897 (7.68); 4.1295 (0.78); 4.1145 (1.03); 4.1062 (1.33); 4.0908 (1.46); 4.0825 (1.08); 4.0672 (1.02); 4.0562 (1.19); 4.0382 (2.87); 4.0204 (2.82); 4.0027 (0.95); 3.9342 (0.98); 3.9203 (1.62); 3.9058 (1.18); 3.9002 (1.8); 3.8862 (2.62); 3.8721 (1.41); 3.8153 (1.55); 3.7991 (1.72); 3.7928 (1.52); 3.781 (1.34); 3.7768 (1.59); 3.7653 (1.05); 3.7588 (0.95); 3.7427 (0.82); 3.3234 (33.43); 2.6755 (0.35); 2.6711 (0.48); 2.6666 (0.34); 2.5108 (29.52); 2.5066 (56.22); 2.5021 (72.01); 2.4976 (51.93); 2.4933 (25.34); 2.3334 (0.35); 2.3288 (0.47); 2.3244 (0.35); 1.9892 (11.86); 1.3362 (0.44); 1.2493 (0.48); 1.1925 (3.18); 1.1747 (6.21); 1.1569 (3.05); 0.0078 (0.56); −0.0002 (12.89); −0.0083 (0.46) |
| 2-89 | 4-chloro-2-thienyl | CH2 | CH2 | — | H | compound No. 2-89, solvent: spectrometer: 601.6 MHz 8.2192 (1.85); 8.2101 (3.42); 8.2009 (1.88); 7.8322 (15.73); 7.8234 (16); 7.799 (0.4); 7.7904 (0.42); 7.3809 (14.42); 7.3783 (14.95); 7.1724 (0.39); 7.1638 (0.41); 7.1423 (15.96); 7.1336 (15.48); 6.9235 (9.52); 6.9213 (10.04); 3.5135 (4.02); 3.502 (10.07); 3.4923 (10.33); 3.4809 (4.58); 3.359 (0.44); 3.3471 (1.05); 3.3244 (1184.4); 3.0355 (6.84); 3.0239 (13.54); 3.0125 (6.23); 2.6529 (2.02); 2.619 (0.86); 2.616 (1.93); 2.613 (2.75); 2.6099 (2.01); 2.6069 (0.94); 2.5568 (0.46); 2.5406 (602.61); 2.5223 (5.01); 2.5192 (6.23); 2.5161 (5.92); 2.5073 (142.84); 2.5043 (310.99); 2.5012 (430.85); 2.4982 (317.8); 2.4952 (149.21); 2.4243 (2.08); 2.3914 (0.82); 2.3884 (1.89); 2.3854 (2.66); 2.3823 (1.93); 2.3794 (0.88); 2.0735 (1.8); 0.0052 (0.79); −0.0002 (27.37); −0.0058 (0.82) |
| 2-90 | 4-bromo-phenyl | CH2 | CH2 | — | H | compound No. 2-90, solvent: spectrometer: 399.95 MHz 8.1254 (1.64); 8.1114 (2.96); 8.098 (1.58); 7.8191 (11.94); 7.8059 (12.35); 7.7851 (0.39); 7.7721 (0.4); 7.5 (1.64); 7.4936 (13.56); 7.4891 (4.57); 7.4774 (4.83); 7.4728 (16); 7.4665 (1.88); 7.232 (2.14); 7.2256 (13.05); 7.2047 (11.17); 7.1611 (0.44); 7.148 (0.44); 7.1311 (12.58); 7.118 (12.11); 4.0378 (0.35); 4.02 (0.35); 3.4987 (3.04); 3.4814 (6.52); 3.4664 (6.37); 3.4484 (3.36); 3.3228 (89.09); 2.832 (5.84); 2.8139 (10.28); 2.7961 (5.26); 2.6753 (0.74); 2.6707 (1.02); 2.6663 (0.74); 2.662 (0.36); 2.524 (3.23); 2.5106 (57.68); 2.5062 (114.89); 2.5017 (150.1); 2.4971 (107.93); 2.4926 (51.79); 2.333 (0.68); 2.3284 (0.95); 2.3238 (0.69); 2.3193 (0.33); 1.9888 (1.56); 1.3355 (0.36); 1.2492 (0.46); 1.1925 (0.42); 1.1747 (0.81); 1.1569 (0.4); 0.0079 (2.31); −0.0002 (63.05); −0.0085 (2.15) |
| 2-91 | 4-chloro-phenyl | CH2 | C(CH3)2 | — | H | compound No. 2-91, solvent: spectrometer: 399.95 MHz 7.7942 (2); 7.7937 (1.96); 7.781 (2.13); 7.479 (0.83); 7.3998 (1.54); 7.3369 (2.48); 7.3161 (3.41); 7.1964 (3.15); 7.1756 (2.48); 7.116 (2.01); 7.103 (2); 5.3272 (0.4); 3.3499 (30.78); 3.3455 (30.99); 3.3393 (29.64); 3.3302 (12.71); 3.0776 (5.05); 2.5065 (13.57); 2.5026 (18); 2.4987 (15.17); 1.3346 (0.5); 1.3178 (16); −0.0002 (3.62); −0.0012 (3.61) |
| 2-92 | 2,4-dichloro-phenyl | CH2 | C(CH3)2 | — | H | compound No. 2-92, solvent: spectrometer: 399.95 MHz 7.8127 (2.03); 7.8119 (1.97); 7.7996 (2.18); 7.7987 (2.09); 7.5885 (1.94); 7.5833 (2.15); 7.5469 (1.81); 7.366 (0.84); 7.361 (0.84); 7.3452 (1.45); 7.3402 (1.51); 7.2883 (2.5); 7.2674 (1.51); 7.1329 (2.23); 7.1198 (2.2); 4.0387 (0.54); 4.0209 (0.55); 3.3322 (20.83); 3.269 (5.62); 2.5073 (7.09); 2.5032 (9.69); 2.499 (7.85); 1.9896 (2.27); 1.35 (16); 1.1938 (0.62); 1.1929 (0.61); 1.176 (1.2); 1.1751 (1.15); 1.1582 (0.6); −0.0002 (2.55); −0.0013 (2.37) |
| 2-93 | 2-(trifluoro-methyl)-4-chloro-phenyl | CH2 | CH2 | — | H | compound No. 2-93, solvent: spectrometer: 399.95 MHz 8.2642 (1.96); 8.2498 (3.72); 8.2357 (1.92); 7.8279 (15.21); 7.8147 (15.83); 7.7488 (6.83); 7.7434 (10.04); 7.7323 (4.84); 7.7267 (2.66); 7.7115 (5.13); 7.7061 (3.97); 7.5482 (6.98); 7.5275 (5.7); 7.1385 (16); 7.1254 (15.5); 3.5401 (2.97); 3.5233 (6.91); 3.5071 (6.93); 3.4898 (3.3); |

TABLE 2-continued

Compounds of the formula I-2

I-2

| Ex. No. | X | L¹ | L² | L³ | Y | Physical data: ¹H-NMR, δ [ppm] or CAS or patent No. |
|---|---|---|---|---|---|---|
| | | | | | | 3.3246 (34.18); 3.3123 (0.54); 3.304 (4.59); 3.2957 (0.38); 3.2862 (3.62); 3.0151 (4.29); 2.9976 (7.73); 2.98 (3.73); 2.6964 (14.95); 2.6769 (0.42); 2.6724 (0.55); 2.6678 (0.39); 2.5257 (1.76); 2.521 (2.72); 2.5124 (30.57); 2.5079 (60.58); 2.5033 (79.28); 2.4987 (56.52); 2.4941 (26.25); 2.3346 (0.37); 2.3301 (0.52); 2.3253 (0.35); 2.1981 (1.63); 2.1781 (3.1); 2.1576 (2.19); 1.9396 (0.85); 1.9214 (2.12); 1.9182 (1.5); 1.9126 (0.39); 1.9029 (2.26); 1.8923 (0.35); 1.883 (1.91); 1.8798 (0.87); 1.864 (0.57); 1.3365 (2.02); 1.2587 (0.39); 1.2496 (2.47); 1.2334 (0.42); 1.1881 (0.78); 0.008 (0.87); −0.0002 (25.1); −0.0085 (0.69) |
| 2-94 | 2,4-dichlorophenyl | O | CH2 | CH(CH3) | H | compound No. 2-94, solvent: spectrometer: 399.95 MHz 8.0435 (2.25); 8.0237 (2.28); 7.8444 (8.97); 7.8313 (9.29); 7.5738 (7.85); 7.5674 (8.35); 7.386 (3.73); 7.3795 (3.44); 7.3638 (5); 7.3574 (4.75); 7.2389 (7.4); 7.2166 (5.53); 7.1533 (9.63); 7.1401 (9.23); 4.3985 (0.56); 4.3832 (1.22); 4.3662 (1.53); 4.3476 (1.31); 4.332 (0.66); 4.1699 (1.65); 4.1548 (1.49); 4.1455 (3.5); 4.1304 (3.06); 4.1114 (3.5); 4.0974 (3.32); 4.087 (1.78); 4.073 (1.45); 3.3802 (0.32); 3.3735 (0.47); 3.3343 (380.72); 3.2974 (0.41); 2.6762 (0.59); 2.6716 (0.8); 2.6672 (0.57); 2.5419 (14.79); 2.525 (2.2); 2.5202 (3.54); 2.5117 (46.3); 2.5072 (93.4); 2.5026 (123); 2.498 (88.09); 2.4934 (41.35); 2.3339 (0.57); 2.3293 (0.81); 2.3247 (0.58); 1.2919 (16); 1.2749 (15.85); 0.008 (0.75); −0.0002 (23.38); −0.0086 (0.66) |
| 2-95 | 4-chlorophenyl | O | CH2 | CH(CH3) | H | compound No. 2-96, solvent: spectrometer: 399.95 MHz 8.1037 (2.62); 8.0836 (2.64); 7.8406 (8.35); 7.8274 (8.63); 7.6262 (7.86); 7.6205 (8.15); 7.5734 (5.55); 7.5519 (7.26); 7.4258 (4.73); 7.4201 (4.43); 7.4043 (3.64); 7.3986 (3.44); 7.1488 (8.79); 7.1356 (8.49); 4.1854 (0.67); 4.1681 (1.49); 4.1503 (1.96); 4.1328 (1.53); 4.1153 (0.7); 3.3486 (0.62); 3.3298 (110.3); 3.3052 (2.03); 3.2872 (1.82); 3.272 (3.23); 3.2538 (3.07); 3.1986 (3.29); 3.183 (3.35); 3.1653 (2); 3.1496 (1.83); 2.672 (0.36); 2.5422 (20.2); 2.5253 (1.27); 2.5119 (21.46); 2.5075 (42); 2.5029 (54.69); 2.4983 (39.66); 2.4939 (19.17); 2.3296 (0.34); 1.3058 (16); 1.2892 (15.83); −0.0002 (6.66) |
| 2-96 | 2,4-dichlorophenyl | S | CH2 | CH(CH3) | H | compound No. 2-96, solvent: spectrometer: 399.95 MHz 8.1037 (2.62); 8.0836 (2.64); 7.8406 (8.35); 7.8274 (8.63); 7.6262 (7.86); 7.6205 (8.15); 7.5734 (5.55); 7.5519 (7.26); 7.4258 (4.73); 7.4201 (4.43); 7.4043 (3.64); 7.3986 (3.44); 7.1488 (8.79); 7.1356 (8.49); 4.1854 (0.67); 4.1681 (1.49); 4.1503 (1.96); 4.1328 (1.53); 4.1153 (0.7); 3.3486 (0.62); 3.3298 (110.3); 3.3052 (2.03); 3.2872 (1.82); 3.272 (3.23); 3.2538 (3.07); 3.1986 (3.29); 3.183 (3.35); 3.1653 (2); 3.1496 (1.83); 2.672 (0.36); 2.5422 (20.2); 2.5253 (1.27); 2.5119 (21.46); 2.5075 (42); 2.5029 (54.69); 2.4983 (39.66); 2.4939 (19.17); 2.3296 (0.34); 1.3058 (16); 1.2892 (15.83); −0.0002 (6.66) |
| 2-97 | 4-chlorophenyl | S | CH2 | CH(CH3) | H | compound No. 2-97, solvent: spectrometer: 399.95 MHz 8.0313 (2.28); 8.0111 (2.27); 7.8351 (7.34); 7.8276 (0.77); 7.822 (7.61); 7.4468 (0.36); 7.4416 (0.39); 7.4184 (5.41); 7.4131 (2.2); 7.4022 (3.25); 7.3966 (13.89); 7.3911 (2.42); 7.3736 (2.38); 7.3681 (14.46); 7.3625 (3.43); 7.3516 (2.29); 7.3463 (5.62); 7.3404 (0.88); 7.3333 (0.67); 7.3158 (0.37); 7.1509 (0.57); 7.1443 (7.83); 7.1379 (0.74); 7.1311 (7.56); 4.1367 (0.71); 4.1196 (1.54); 4.1015 (1.92); 4.0835 (1.56); 4.0664 (0.72); 3.3511 (0.6); 3.3303 (126.34); 3.2924 (0.34); 3.2547 (2.01); 3.2369 (1.94); 3.2209 (3.27); 3.2031 (3.13); 3.1345 (3.43); 3.1187 (3.44); 3.1008 (2.14); 3.0849 (1.99); 2.6713 (0.39); 2.5417 (12.91); 2.5244 (1.23); 2.5112 (23.65); 2.5069 (46.72); 2.5024 (61.31); 2.4978 (44.84); 2.4935 (22.01); 2.3291 (0.39); 1.3123 (0.69); 1.2957 (0.74); 1.2793 (1.26); 1.2672 (16); 1.2505 (15.69); −0.0002 (6.61) |
| 2-98 | 4-chlorophenyl | N(CH3) | CH2 | CH2 | H | compound No. 2-98, solvent: spectrometer: 399.95 MHz 8.1784 (0.63); 8.1644 (1.19); 8.1511 (0.64); 7.832 (3.85); 7.8188 (3.97); 7.1823 (0.46); 7.1735 (4.39); 7.1681 (1.47); 7.1561 (1.75); 7.1508 (4.9); 7.1399 (4.35); 7.1267 (3.97); 6.78 (0.54); 6.7713 (4.48); 6.766 (1.59); |

TABLE 2-continued

Compounds of the formula I-2

I-2

| Ex. No. | X | L¹ | L² | L³ | Y | Physical data: ¹H-NMR, δ [ppm] or CAS or patent No. |
|---|---|---|---|---|---|---|
| | | | | | | 6.7536 (1.52); 6.7485(4.03); 6.7396 (0.46); 3.4961 (0.89); 3.4802 (2.47); 3.4646 (2.25); 3.4296 (1.28); 3.4143 (2.21); 3.3992 (1.71); 3.3837 (0.55); 3.3285 (37.94); 2.9175 (16); 2.5417 (14.97); 2.5245 (0.68); 2.5111 (10.02); 2.5068 (18.95); 2.5023 (24.27); 2.4977 (17.83); 2.4934 (8.9); −0.0002 (3.85) |
| 2-99 | 3-chloro-4-(trifluoromethyl)phenyl | CH2 | CH2 | — | H | compound No. 2-99, solvent: spectrometer: 399.95 MHz 7.8169 (0.34); 7.8037 (0.35); 7.1258 (0.35); 7.1126 (0.34); 5.7548 (16); 3.3218 (3.21); 2.5111 (2.65); 2.5067 (5.19); 2.5021 (6.78); 2.4975 (4.91); 2.4931 (2.38) |
| 2-100 | 4-chloro-3-(trifluoromethyl)phenyl | CH2 | CH2 | — | H | compound No. 2-100, solvent: spectrometer: 399.95 MHz 8.1546 (1.81); 8.1411 (3.36); 8.1274 (1.79); 7.8227 (15.02); 7.8095 (15.47); 7.7309 (7.67); 7.7263 (7.96); 7.6656 (5.24); 7.645 (9.1); 7.5935 (5.17); 7.589 (4.84); 7.5729 (2.99); 7.5683 (2.88); 7.1311 (16); 7.1179 (15.44); 3.5543 (3.34); 3.5374 (8.85); 3.5227 (9.01); 3.506 (3.66); 3.3342 (43.7); 2.9569 (6.23); 2.94 (12.45); 2.923 (5.53); 2.679 (0.4); 2.5323 (1.33); 2.5275 (2.04); 2.519 (22.77); 2.5144 (45.98); 2.5099 (60.71); 2.5052 (43.75); 2.5007 (20.76); 2.3367 (0.4); 1.343 (0.48); 1.2558 (0.62) |
| 2-101 | 2-chloro-4-(trifluoromethyl)phenyl | O | CH2 | C(CH3)2 | H | compound No. 2-101, solvent: spectrometer: 399.95 MHz 7.8286 (1.28); 7.8232 (1.39); 7.818 (2.64); 7.8048 (2.63); 7.7272 (1.41); 7.6873 (0.62); 7.6829 (0.58); 7.6655 (0.71); 7.6612 (0.65); 7.3709 (1.12); 7.3493 (1); 7.1335 (2.69); 7.1203 (2.57); 4.3465 (4.75); 3.3445 (101.81); 2.5432 (4.46); 2.5263 (0.44); 2.5129 (9.11); 2.5085 (17.92); 2.5039 (23.2); 2.4993 (16.52); 2.4948 (7.76); 1.4956 (16) |
| 2-102 | 4-chloro-2-(trifluoromethyl)phenyl | O | CH3 | C(CH3)3 | H | compound No. 2-102, solvent: spectrometer: 399.95 MHz 7.8202 (2.3); 7.8071 (2.37); 7.7033 (0.56); 7.6966 (0.73); 7.6811 (0.56); 7.6745 (0.92); 7.659 (1.7); 7.6526 (1.1); 7.6064 (1.44); 7.3238 (1.18); 7.3016 (1.05); 7.1421 (2.41); 7.1289 (2.32); 4.3057 (4.74); 3.3418 (117.7); 2.5428 (6.37); 2.5259 (0.54); 2.5125 (11.26); 2.5081 (22.46); 2.5035 (29.35); 2.4989 (21.13); 2.4944 (10.06); 1.456 (16) |
| 2-103 | 2-chloro-4-(trifluoromethyl)phenyl | O | CH2 | CH2 | H | compound No. 2-103, solvent: spectrometer: 399.95 MHz 8.233 (2.33); 8.2195 (4.37); 8.206 (2.37); 7.8593 (13.55); 7.8461 (15.38); 7.8411 (9.06); 7.8357 (9.06); 7.7032 (4.25); 7.6988 (4.02); 7.6816 (4.96); 7.6771 (4.61); 7.5239 (0.41); 7.417 (7.79); 7.3953 (6.77); 7.1625 (14.26); 7.1493 (13.74); 4.3372 (7.53); 4.3228 (16); 4.3084 (7.71); 3.7244 (4.06); 3.7102 (11.54); 3.6959 (11.21); 3.6816 (3.73); 3.3337 (199.43); 2.6777 (0.45); 2.6733 (0.61); 2.669 (0.44); 2.5432 (2.51); 2.5263 (1.9); 2.5129 (37.99); 2.5086 (72.9); 2.5042 (93.47); 2.4998 (67.94); 2.3355 (0.44); 2.3309 (0.58); 2.3267 (0.42); 1.234 (0.34); −0.0002 (0.46) |

TABLE 3

Compounds of the formula I-3

I-3

| Ex. No. | X | L¹ | L² | L³ | Y | Physical data: ¹H-NMR, δ [ppm] or CAS or patent No. |
|---|---|---|---|---|---|---|
| 3-1 | 3-methyl-2-thienyl | CH2 | CH2 | — | H | WO-A 2006/108791 |

TABLE 3-continued

Compounds of the formula I-3

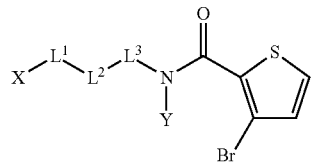

I-3

| Ex. No. | X | L¹ | L² | L³ | Y | Physical data: ¹H-NMR, δ [ppm] or CAS or patent No. |
|---|---|---|---|---|---|---|
| 3-2 | 2,4-di-chlorophenyl | CH2 | CH2 | CH2 | H | compound No. 3-2, solvent: [DMSO], spectrometer: 399.95 MHz 8.2727 (2.08); 8.2589 (3.84); 8.2451 (2.05); 7.7968 (15.36); 7.7838 (15.9); 7.5676 (10.89); 7.5623 (11.33); 7.4294 (6.33); 7.4087 (14.31); 7.3945 (0.46); 7.3819 (10.21); 7.3766 (9.45); 7.3613 (4.36); 7.356 (4.36); 7.176 (16); 7.163 (15.43); 7.1514 (0.4); 3.5162 (0.4); 3.3364 (45.86); 3.3131 (3.59); 3.2962 (8.61); 3.2811 (8.71); 3.2643 (3.65); 2.7678 (6.35); 2.7489 (7.94); 2.729 (6.83); 2.5457 (19.24); 2.5288 (0.62); 2.5239 (1.02); 2.5154 (10.87); 2.5109 (21.41); 2.5064 (28.22); 2.5018 (20.57); 2.4973 (9.85); 1.8383 (1.86); 1.8208 (4.99); 1.8015 (6.21); 1.7827 (4.82); 1.7651 (1.63); −0.0002 (3.74) |
| 3-3 | 4-chlorophenyl | CH2 | CH2 | — | H | CAS: 1270975-99-9 |
| 3-4 | 2,4-di-chlorophenyl | CH2 | CH2 | — | H | WO-A 2007/060166 |
| 3-5 | 4-chlorophenyl | CH(OCH3) | CH(CH3) | — | H | compound No. 3-5, solvent: [DMSO], spectrometer: 399.95 MHz 8.0161 (0.68); 7.9946 (0.69); 7.856 (0.53); 7.8357 (0.53); 7.8077 (1.18); 7.7946 (1.22); 7.7765 (1.55); 7.7635 (1.6); 7.437 (2.83); 7.416 (4.81); 7.3603 (2.38); 7.3542 (3.14); 7.3389 (1.66); 7.333 (1.84); 7.1868 (1.23); 7.1737 (1.18); 7.1492 (1.66); 7.1362 (1.6); 6.5742 (0.41); 4.3623 (0.79); 4.3497 (0.91); 4.305 (1.07); 4.2895 (1.24); 4.1795 (0.33); 4.1314 (0.36); 4.1149 (0.51); 4.0938 (0.49); 3.3227 (9.24); 3.2125 (9.84); 3.2106 (9.39); 2.5065 (21.67); 2.5023 (28.08); 2.4982 (21.85); 1.9892 (0.43); 1.3974 (16); 1.131 (3.58); 1.1142 (3.57); 1.0897 (2.69); 1.0728 (2.64); −0.0002 (4.39) |
| 3-6 | 2,4-di-chlorophenyl | CH(OCH3) | CH(CH3) | — | H | |
| 3-7 | 4-chlorophenyl | CH(CH3) | CH2 | — | H | |
| 3-8 | 2,4-di-chlorophenyl | CH(CH3) | CH2 | — | H | [DMSO], spectrometer: 399.95 MHz 8.2200 (0.51); 8.2055 (1.01); 8.1919 (0.52); 7.7723 (3.38); 7.7593 (3.55); 7.5710 (2.72); 7.5657 (2.98); 7.4893 (1.62); 7.4681 (3.24); 7.4306 (1.96); 7.4253 (1.88); 7.4095 (0.99); 7.4042 (0.99); 7.1453 (3.60); 7.1323 (3.48); 3.9087 (16.00); 3.5751 (0.47); 3.5581 (0.87); 3.5409 (1.02); 3.5251 (0.96); 3.5145 (0.73); 3.4966 (1.18); 3.4815 (1.62); 3.4726 (1.13); 3.4657 (1.16); 3.4579 (1.46); 3.4394 (1.70); 3.3784 (388.06); 3.2888 (0.55); 3.2500 (0.40); 3.1729 (0.36); 2.6830 (0.37); 2.6785 (0.49); 2.6741 (0.37); 2.5485 (0.37); 2.5316 (1.75); 2.5181 (28.84); 2.5139 (56.51); 2.5094 (74.12); 2.5049 (55.80); 2.5006 (28.43); 2.3406 (0.34); 2.3361 (0.47); 2.3316 (0.34); 1.2349 (5.47); 1.2182 (5.38) |
| 3-9 | 4-chlorophenyl | CH2 | CH(CH3) | — | H | WO-A 2007060164 |
| 3-10 | 2,4-di-chlorophenyl | CH2 | CH(CH3) | — | H | |
| 3-11 | 4-chlorophenyl | C(CH3)2 | CH2 | — | H | [DMSO], spectrometer: 399.95 MHz 7.8445 (0.41); 7.8294 (0.74); 7.8145 (0.39); 7.7912 (2.73); 7.7781 (2.84); 7.4685 (2.32); 7.4635 (0.88); 7.4519 (1.07); 7.4467 (3.97); 7.4402 (0.57); 7.3902 (0.53); 7.3836 (4.13); 7.3784 (1.11); 7.3669 (0.85); 7.3619 (2.46); 7.1507 (2.90); 7.1376 (2.80); 3.9086 (11.97); 3.4833 (3.04); 3.4678 (3.11); 3.4543 (0.72); 3.3806 (307.12); 3.3012 (0.34); 2.6786 (0.35); 2.5317 (1.03); 2.5183 (20.55); 2.5139 (40.88); 2.5094 (54.15); 2.5049 (40.96); 2.5005 (20.99); 2.3361 (0.34); 1.3245 (16.00) |
| 3-12 | 2,4-di-chlorophenyl | C(CH3)2 | CH2 | — | H | [DMSO], spectrometer: 399.95 MHz 7.8724 (0.40); 7.8577 (0.80); 7.8423 (0.43); 7.7717 (2.77); 7.7587 (2.80); 7.5436 (2.18); 7.5378 (2.41); 7.5058 (1.54); 7.4841 (2.22); 7.3904 (1.46); 7.3845 (1.45); 7.3688 (1.09); 7.3630 (1.08); 7.1284 (2.82); 7.1154 (2.72); 3.9041 (12.41); 3.8138 (2.83); 3.7982 (2.80); 3.5113 (0.43); 3.4965 (0.43); 3.3807 (353.39); 2.6745 (0.43); 2.5141 (24.73); 2.5099 (47.13); 2.5054 (61.05); 2.5009 (45.64); 2.4967 (23.22); 2.3322 (0.37); 1.4735 (16.00) |
| 3-13 | 2-chlorophenyl | CH2 | CH2 | — | H | [DMSO], spectrometer: 399.95 MHz 8.2809 (0.61); 8.2679 (1.16); 8.2543 (0.64); 7.7889 (4.14); 7.7759 (4.33); 7.4471 (1.48); 7.4430 (1.28); 7.4288 (1.96); 7.4241 (1.98); 7.3873 (1.14); 7.3820 (1.39); 7.3690 (1.55); 7.3641 (2.01); 7.3171 (0.59); 7.3129 (0.83); 7.2987 (1.99); 7.2945 (1.98); 7.2818 (2.41); 7.2772 (2.61); 7.2648 (1.72); 7.2597 (1.56); 7.2463 (0.58); 7.2414 (0.48); 7.1690 (4.39); 7.1560 (4.26); 3.9081 (16.00); 3.5315 (1.41); |

TABLE 3-continued

Compounds of the formula I-3

I-3

| Ex. No. | X | L¹ | L² | L³ | Y | Physical data: ¹H-NMR, δ [ppm] or CAS or patent No. |
|---|---|---|---|---|---|---|
| | | | | | | 3.5145 (3.10); 3.4991 (2.92); 3.4813 (1.92); 3.3866 (495.05); 3.2836 (0.44); 2.9923 (2.25); 2.9743 (3.88); 2.9566 (2.02); 2.6830 (0.39); 2.6785 (0.53); 2.6742 (0.40); 2.5485 (0.40); 2.5317 (1.79); 2.5183 (30.82); 2.5140 (60.87); 2.5095 (80.28); 2.5050 (60.66); 2.5007 (30.97); 2.3406 (0.38); 2.3363 (0.52); 2.3319 (0.39) |
| 3-14 | 3,4-di-chlorophenyl | CH2 | CH2 | — | H | [DMSO], spectrometer: 399.95 MHz<br>8.2310 (0.72); 8.2172 (1.39); 8.2034 (0.78); 7.7885 (4.47); 7.7755 (4.68); 7.5654 (3.69); 7.5445 (6.89); 7.5388 (3.87); 7.3454 (0.34); 7.3407 (0.34); 7.2753 (1.92); 7.2703 (1.94); 7.2547 (1.70); 7.2498 (1.73); 7.1647 (4.90); 7.1517 (4.79); 3.9071 (16.00); 3.5150 (1.83); 3.4981 (4.09); 3.4832 (4.21); 3.4662 (2.98); 3.3988 (569.18); 3.2438 (0.36); 3.2267 (0.36); 3.1783 (0.44); 3.1665 (0.43); 2.8667 (2.27); 2.8496 (4.53); 2.8324 (2.10); 2.6833 (0.42); 2.6787 (0.57); 2.6741 (0.44); 2.5183 (32.31); 2.5140 (63.85); 2.5095 (84.66); 2.5050 (64.88); 2.5008 (34.15); 2.3406 (0.41); 2.3363 (0.55); 2.3317 (0.41) |
| 3-15 | 3,5-di-chlorophenyl | CH2 | CH2 | — | H | CAS: 1318048-71-3 |
| 3-16 | 3-chlorophenyl | CH2 | CH2 | — | H | [DMSO], spectrometer: 399.95 MHz<br>8.2233 (0.45); 8.2093 (0.83); 8.1955 (0.46); 7.7940 (3.28); 7.7810 (3.41); 7.3563 (0.82); 7.3478 (1.31); 7.3433 (2.17); 7.3374 (2.94); 7.3181 (2.00); 7.2909 (1.03); 7.2877 (1.53); 7.2828 (1.18); 7.2709 (0.63); 7.2661 (0.71); 7.2628 (0.50); 7.2409 (1.49); 7.2224 (1.05); 7.1686 (3.58); 7.1556 (3.46); 3.9090 (16.00); 3.5146 (1.04); 3.4973 (2.23); 3.4827 (2.30); 3.4652 (1.28); 3.3763 (317.99); 3.3214 (0.62); 3.2964 (0.38); 2.8720 (1.54); 2.8543 (3.00); 2.8367 (1.46); 2.6786 (0.42); 2.5319 (1.43); 2.5184 (24.35); 2.5140 (48.71); 2.5094 (64.51); 2.5049 (48.63); 2.5005 (24.82); 2.3361 (0.40) |
| 3-17 | 2-fluorophenyl | CH2 | CH2 | — | H | CAS: 1275755-97-9 |
| 3-18 | 2,6-di-fluorophenyl | CH2 | CH2 | — | H | [DMSO], spectrometer: 399.95 MHz<br>8.3218 (0.53); 8.3074 (1.03); 8.2937 (0.57); 7.7811 (3.58); 7.7680 (3.75); 7.3461 (0.67); 7.3421 (0.65); 7.3252 (1.34); 7.3080 (0.69); 7.3044 (0.88); 7.2876 (0.40); 7.1586 (3.84); 7.1456 (3.69); 7.0840 (1.88); 7.0642 (3.00); 7.0532 (0.43); 7.0443 (1.63); 3.9043 (16.00); 3.4972 (0.35); 3.4725 (1.15); 3.4555 (2.68); 3.4396 (2.90); 3.4228 (1.83); 3.3665 (342.01); 3.1746 (0.55); 3.1618 (0.54); 2.9117 (1.44); 2.8943 (2.75); 2.8770 (1.31); 2.6779 (0.35); 2.6734 (0.48); 2.6689 (0.37); 2.5265 (1.71); 2.5131 (27.34); 2.5088 (53.82); 2.5043 (70.92); 2.4998 (53.48); 2.4955 (27.28); 2.3310 (0.44); −0.0002 (1.23) |
| 3-19 | 2,6-di-chlorophenyl | CH2 | CH2 | — | H | [DMSO], spectrometer: 399.95 MHz<br>8.3537 (0.50); 8.3393 (1.04); 8.3250 (0.58); 7.7812 (3.52); 7.7681 (3.77); 7.4649 (4.46); 7.4449 (6.20); 7.3049 (2.08); 7.2856 (2.05); 7.2839 (2.10); 7.2646 (1.38); 7.1626 (3.73); 7.1496 (3.67); 3.9043 (16.00); 3.5128 (0.94); 3.4962 (2.13); 3.4794 (2.24); 3.4629 (1.20); 3.3686 (385.44); 3.2638 (0.35); 3.2399 (0.34); 3.1807 (1.93); 3.1627 (3.54); 3.1455 (1.57); 2.6782 (0.40); 2.6736 (0.53); 2.6692 (0.41); 2.5268 (1.86); 2.5134 (29.37); 2.5090 (57.84); 2.5045 (76.07); 2.5000 (57.08); 2.4956 (28.84); 2.3357 (0.33); 2.3312 (0.45); 2.3268 (0.33) |
| 3-20 | 3-(trifluoro-methyl)phenyl | CH2 | CH2 | — | H | [DMSO], spectrometer: 399.95 MHz<br>8.2347 (0.52); 8.2214 (0.99); 8.2078 (0.57); 7.7906 (3.47); 7.7776 (3.67); 7.6157 (2.15); 7.5973 (0.78); 7.5904 (0.84); 7.5753 (3.32); 7.5612 (2.39); 7.5510 (0.68); 7.5432 (0.86); 7.5246 (0.40); 7.1634 (3.68); 7.1504 (3.59); 3.9086 (16.00); 3.5513 (1.14); 3.5341 (2.61); 3.5194 (2.73); 3.5023 (1.34); 3.3800 (440.79); 3.1791 (0.40); 3.1671 (0.37); 2.9689 (1.80); 2.9515 (3.54); 2.9341 (1.65); 2.6829 (0.42); 2.6786 (0.56); 2.6741 (0.43); 2.5317 (1.97); 2.5183 (31.67); 2.5139 (61.89); 2.5094 (81.18); 2.5049 (60.98); 2.5005 (30.95); 2.3405 (0.37); 2.3364 (0.53); 2.3316 (0.36) |
| 3-21 | 4-(trifluoro-methyl)-phenyl | CH2 | CH2 | — | H | [DMSO], spectrometer: 399.95 MHz<br>8.2576 (0.53); 8.2434 (1.04); 8.2301 (0.59); 7.7888 (3.63); 7.7757 (3.85); 7.6781 (2.65); 7.6579 (3.41); 7.5038 (3.04); 7.4837 (2.56); 7.1658 (3.90); 7.1528 (3.80); 3.9076 (16.00); 3.5464 (1.21); 3.5291 (2.50); 3.5139 (2.46); 3.4967 (1.49); 3.3908 (499.03); 3.2632 (0.61); 3.1775 (0.42); 2.9594 (1.57); 2.9417 (2.93); 2.9240 (1.43); 2.6829 (0.42); 2.6785 (0.57); 2.6741 (0.42); 2.5482 (0.50); 2.5317 (2.05); |

TABLE 3-continued

Compounds of the formula I-3

I-3

[Structure: X-L¹-L²-L³-N(Y)-C(=O)-thiophene(3-Br)]

| Ex. No. | X | L¹ | L² | L³ | Y | Physical data: ¹H-NMR, δ [ppm] or CAS or patent No. |
|---|---|---|---|---|---|---|
| | | | | | | 2.5182 (32.24); 2.5139 (62.79); 2.5094 (82.03); 2.5048 (61.25); 2.5005 (30.81); 2.3406 (0.37); 2.3360 (0.51); 2.3314 (0.36) |
| 3-22 | 2-methyl-phenyl | CH2 | CH2 | — | H | [DMSO], spectrometer: 399.95 MHz<br>8.2822 (0.51); 8.2685 (0.94); 8.2545 (0.50); 7.8035 (3.62); 7.7905 (3.76); 7.1905 (0.80); 7.1822 (4.83); 7.1692 (5.54); 7.1628 (1.58); 7.1536 (1.80); 7.1476 (0.86); 7.1360 (2.33); 7.1318 (2.71); 7.1229 (2.90); 7.1161 (1.08); 7.1107 (1.18); 3.9099 (16.00); 3.4460 (1.27); 3.4307 (2.21); 3.4229 (1.71); 3.4123 (2.38); 3.4080 (2.97); 3.3677 (281.55); 3.1741 (0.41); 2.8542 (1.84); 2.8346 (2.21); 2.8162 (1.66); 2.6788 (0.43); 2.5320 (1.46); 2.5187 (24.89); 2.5142 (49.62); 2.5097 (65.63); 2.5051 (49.58); 2.5007 (25.38); 2.3301 (13.30) |
| 3-23 | 2,4,6-tri-methylphenyl | CH2 | CH2 | — | H | [DMSO], spectrometer: 399.95 MHz<br>8.3946 (0.38); 8.3800 (0.77); 8.3655 (0.42); 7.8104 (2.38); 7.7973 (2.52); 7.1900 (2.48); 7.1770 (2.43); 6.8079 (4.13); 3.9039 (11.15); 3.3682 (250.25); 3.2803 (0.75); 3.2657 (1.06); 3.2609 (0.93); 3.2521 (1.00); 3.2449 (0.83); 3.2386 (1.06); 3.2246 (0.72); 3.1748 (0.36); 3.1622 (0.34); 2.8149 (1.08); 2.8015 (0.84); 2.7939 (1.10); 2.7888 (0.91); 2.7740 (0.94); 2.6735 (0.32); 2.5266 (1.04); 2.5132 (18.68); 2.5089 (37.14); 2.5043 (49.26); 2.4998 (37.65); 2.4955 (19.67); 2.3311 (0.38); 2.3265 (0.33); 2.3030 (16.00); 2.1822 (7.09) |
| 3-24 | 3,4-bis-methoxy-phenyl | CH2 | CH2 | — | H | [DMSO], spectrometer: 399.95 MHz<br>8.1597 (0.49); 8.1461 (0.96); 8.1328 (0.53); 7.7919 (3.25); 7.7789 (3.41); 7.1699 (3.46); 7.1569 (3.37); 6.8788 (1.99); 6.8583 (2.87); 6.8433 (2.25); 6.8386 (2.55); 6.7706 (1.43); 6.7659 (1.34); 6.7503 (1.04); 6.7456 (0.98); 3.9042 (14.99); 3.7347 (15.37); 3.7119 (16.00); 3.4798 (0.94); 3.4628 (1.75); 3.4456 (1.90); 3.4293 (1.30); 3.3655 (318.64); 3.2789 (0.42); 3.1746 (0.77); 3.1620 (0.74); 2.7839 (1.49); 2.7655 (2.48); 2.7476 (1.37); 2.6777 (0.32); 2.6733 (0.46); 2.6687 (0.34); 2.5265 (1.65); 2.5131 (26.50); 2.5087 (51.83); 2.5042 (68.11); 2.4996 (51.37); 2.4953 (26.43); 2.3309 (0.43); 2.3263 (0.32) |
| 3-25 | phenyl | CH2 | CH2 | — | H | [DMSO], spectrometer: 399.95 MHz<br>8.2035 (0.62); 8.1902 (1.10); 8.1767 (0.62); 7.7903 (4.18); 7.7773 (4.38); 7.3256 (1.23); 7.3072 (3.59); 7.2938 (1.16); 7.2892 (3.89); 7.2655 (4.90); 7.2487 (2.19); 7.2316 (0.95); 7.2279 (1.26); 7.2104 (1.89); 7.2046 (0.51); 7.1968 (0.43); 7.1928 (0.66); 7.1669 (4.49); 7.1539 (4.30); 3.9043 (16.00); 3.4997 (1.27); 3.4824 (2.50); 3.4674 (2.42); 3.4638 (2.55); 3.4486 (1.65); 3.4288 (0.62); 3.4125 (0.95); 3.3598 (330.60); 3.1744 (0.41); 3.1616 (0.38); 2.8544 (2.28); 2.8355 (3.54); 2.8175 (2.09); 2.6772 (0.37); 2.6730 (0.51); 2.6684 (0.37); 2.5258 (1.62); 2.5124 (29.32); 2.5082 (57.61); 2.5037 (76.03); 2.4992 (57.88); 2.4949 (30.21); 2.3348 (0.34); 2.3304 (0.47); 2.3260 (0.35); −0.0002 (5.83) |
| 3-26 | 4-chlorophenyl | C(CH2—CH2) | CH2 | — | H | |
| 3-27 | 2,4-di-chlorophenyl | C(CH2—CH2) | CH2 | — | H | |
| 3-28 | 4-chlorophenyl | CH2 | C(CH2—CH2) | — | H | |
| 3-29 | 2,4-di-chlorophenyl | CH2 | C(CH2—CH2) | — | H | |
| 3-30 | 4-chlorophenyl | O | CH2 | CH2 | H | |
| 3-31 | 2,4-di-chlorophenyl | O | CH2 | CH2 | H | compound No. 3-31, solvent: [DMSO], spectrometer: 399.95 MHz<br>8.2822 (2.3); 8.269 (4.38); 8.2557 (2.41); 7.8242 (11.81); 7.8111 (12.3); 7.5752 (10.56); 7.5688 (11.67); 7.387 (5.34); 7.3806 (5.18); 7.3649 (7.31); 7.3585 (7.25); 7.2464 (12.19); 7.2241 (9.05); 7.1919 (12.59); 7.1789 (12.26); 4.2268 (7.16); 4.2123 (16); 4.1979 (8.1); 3.679 (4.02); 3.6647 (11.39); 3.6505 (11.04); 3.6362 (3.72); 3.3278 (103.05); 2.6761 (0.4); 2.6719 (0.55); 2.6676 (0.42); 2.5423 (12.35); 2.5249 (1.63); 2.5073 (61.31); 2.5029 (81.63); 2.4985 (62.83); 2.3338 (0.36); 2.3297 (0.5); 2.3255 (0.38); −0.0003 (2.91) |
| 3-32 | 4-chlorophenyl | CH2 | CH2 | CH2 | H | |
| 3-33 | 4-chlorophenyl | NCH3 | CH2 | CH2 | H | |
| 3-34 | 2,4-di-chlorophenyl | NCH3 | CH2 | CH2 | H | |
| 3-35 | 4-chlorophenyl | CH(OCH3) | CH2 | — | H | |
| 3-36 | 2,4-di-chlorophenyl | CH(OCH3) | CH2 | — | H | |

TABLE 3-continued

Compounds of the formula I-3

I-3

$$X-L^1-L^2-L^3-N(Y)-C(=O)-[3-bromothien-2-yl]$$

| Ex. No. | X | L$^1$ | L$^2$ | L$^3$ | Y | Physical data: $^1$H-NMR, δ [ppm] or CAS or patent No. |
|---|---|---|---|---|---|---|
| 3-37 | 2-thienyl | CH2 | CH2 | — | H | compound No. 3-37, solvent: [DMSO], spectrometer: 399.95 MHz 8.2709 (2.47); 8.2578 (4.4); 8.2445 (2.58); 7.8021 (13.53); 7.7891 (14.28); 7.3587 (7.31); 7.3558 (7.48); 7.3461 (8.13); 7.3431 (7.99); 7.1762 (14.66); 7.1632 (14.2); 6.9754 (5.68); 6.9668 (9.25); 6.9629 (5.93); 6.9542 (9.21); 6.9359 (9.39); 6.9294 (6.21); 3.5179 (4.53); 3.5002 (10.66); 3.4854 (10.84); 3.4677 (5.39); 3.3265 (108.64); 3.0742 (8.92); 3.0562 (16); 3.0383 (7.79); 2.675 (0.54); 2.6706 (0.72); 2.6667 (0.55); 2.5409 (1.07); 2.5238 (2.27); 2.506 (81.37); 2.5015 (109.31); 2.4972 (84.86); 2.3326 (0.54); 2.3283 (0.72); 2.3242 (0.55); −0.0002 (2.19) |
| 3-38 | 3-thienyl | CH2 | CH2 | — | H | |
| 3-39 | 2-furyl | CH2 | CH2 | — | H | |
| 3-40 | 3-furyl | CH2 | CH2 | — | H | |
| 3-41 | phenyl | CH2 | CH2 | CH(CH3) | H | |
| 3-42 | phenyl | CH2 | CH2 | CH2 | H | |
| 3-43 | 2-Cl-phenyl | CH2 | CH2 | CH(CH3) | H | |
| 3-44 | 4-t-butylphenyl | CH2 | CH2 | CH2 | H | |
| 3-45 | 4-methylphenyl | CH2 | CH2 | CH2 | H | |
| 3-46 | phenyl | CH2 | CH2 | CH(CH2CH3) | H | |
| 3-47 | 2-methoxy-phenyl | CH2 | CH2 | CH2 | H | |
| 3-48 | 2-methylphenyl | CH2 | CH2 | CH2 | H | |
| 3-49 | 3-methylphenyl | CH2 | CH2 | CH2 | H | |
| 3-50 | 3-chlorophenyl | CH2 | CH2 | CH2 | H | |
| 3-51 | 2,6-difluorophenyl | CH2 | CH2 | CH2 | H | compound No. 3-51, solvent: [DMSO], spectrometer: 399.95 MHz 8.2507 (3.15); 8.2373 (5.71); 8.2241 (3.3); 7.8265 (0.35); 7.8135 (0.47); 7.7965 (14.71); 7.7835 (15.45); 7.3512 (1.55); 7.3339 (3.69); 7.3306 (3.69); 7.3134 (7.02); 7.2929 (4.7); 7.2758 (2.05); 7.2022 (0.4); 7.1894 (0.43); 7.1745 (15.6); 7.1614 (15.22); 7.1442 (0.47); 7.1223 (0.48); 7.1015 (1.47); 7.0884 (10.05); 7.0688 (16); 7.0491 (8.53); 7.0355 (1.22); 6.5622 (0.48); 3.3305 (79.53); 3.3 (5.1); 3.2829 (11.73); 3.2669 (11.92); 3.2501 (5.38); 2.7104 (6.98); 2.6911 (11.79); 2.6719 (8.33); 2.543 (4.06); 2.5078 (60.23); 2.5037 (79.89); 2.4996 (63.31); 2.3306 (0.52); 1.8103 (2.64); 1.7917 (7.39); 1.7729 (10.06); 1.7542 (7.14); 1.7362 (2.4); −0.0002 (1.04) |
| 3-52 | 4-chlorophenyl | CH2 | CH2 | CH2 | H | |
| 3-53 | 2,6-dichlorophenyl | CH2 | CH2 | CH(CH3) | H | |
| 3-54 | 3,5-dichlorophenyl | CH2 | CH2 | CH(CH3) | H | |
| 3-55 | 2,6-dimethylphenyl | CH2 | CH2 | CH2 | H | |
| 3-56 | 2,5-dichlorophenyl | CH2 | CH2 | CH2 | H | |
| 3-57 | 4-isopropoxyphenyl | CH2 | CH2 | CH2 | H | |
| 3-58 | 3-trifluoromethylphenyl | CH2 | CH2 | CH(CH3) | H | |
| 3-59 | 4-methylphenyl | CH2 | CH2 | CH(CH3) | H | |
| 3-60 | 2-methylphenyl | CH2 | CH2 | CH(CH3) | H | |
| 3-61 | 3,4-dichlorophenyl | CH2 | CH2 | CH(CH3) | H | |
| 3-62 | 3,5-dichlorophenyl | CH2 | CH2 | CH2 | H | |
| 3-63 | 2,6-dimethylphenyl | CH2 | CH2 | CH(CH3) | H | |
| 3-64 | 4-trifluoromethylphenyl | CH2 | CH2 | CH(CH3) | H | |
| 3-65 | 2,5-dichlorophenyl | CH2 | CH2 | CH(CH3) | H | |
| 3-66 | 4-phenoxyphenyl | CH2 | CH2 | CH2 | H | |
| 3-67 | 3-chlorophenyl | CH2 | CH2 | CH(CH3) | H | |
| 3-68 | 4-phenoxyphenyl | CH2 | CH2 | CH(CH3) | H | |

TABLE 3-continued

Compounds of the formula I-3

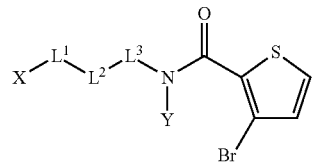

I-3

| Ex. No. | X | L$^1$ | L$^2$ | L$^3$ | Y | Physical data: $^1$H-NMR, δ [ppm] or CAS or patent No. |
|---|---|---|---|---|---|---|
| 3-69 | 2,4-di-chlorophenyl | CH2 | CH2 | CH(CH3) | H | |
| 3-70 | 2-difluoro-methoxyphenyl | CH2 | CH2 | CH(CH3) | H | |
| 3-71 | 4-methoxy-phenyl | CH2 | CH2 | CH2 | H | |
| 3-72 | 4-chlorophenyl | CH2 | CH2 | CH(CH3) | H | |
| 3-73 | 4-chlorophenyl | CH2 | CH2 | CH(i-propyl) | H | |
| 3-74 | 4-fluorophenyl | CH2 | CH2 | CH2 | H | |
| 3-75 | 4-chlorophenyl | CH2 | CH2 | CH(n-propyl) | H | |
| 3-76 | 4-chlorophenyl | CH2 | CH2 | CH(t-butyl) | H | |
| 3-77 | 2-chlorophenyl | CH2 | CH2 | CH2 | H | |
| 3-78 | 2-thienyl | CH2 | CH2 | CH2 | H | compound No. 3-78, solvent: [DMSO], spectrometer: 399.95 MHz 8.2574 (2.91); 8.2444 (5.08); 8.2319 (3.03); 7.795 (15.03); 7.782 (15.69); 7.3229 (8.64); 7.3203 (8.19); 7.3101 (9.55); 7.3076 (8.65); 7.175 (16); 7.162 (15.51); 6.9532 (6.85); 6.9446 (9.61); 6.9406 (7.2); 6.932 (8.69); 6.8918 (9.94); 6.8839 (8.05); 3.3293 (77.96); 3.3137 (5.96); 3.2968 (13.1); 3.2815 (13.26); 3.2648 (5.7); 2.8872 (9.12); 2.8681 (15.69); 2.8491 (9.99); 2.6712 (0.52); 2.5413 (3.88); 2.5061 (54.67); 2.5019 (71.28); 2.4977 (54.62); 2.3289 (0.45); 1.8988 (2.88); 1.8809 (8.81); 1.8623 (11.75); 1.8439 (8.49); 1.826 (2.61); −0.0002 (0.81) |
| 3-79 | 4-chlorophenyl | CF2 | CH2 | — | H | compound No. 3-79, solvent: [DMSO], spectrometer: 399.95 MHz 8.576 (0.68); 8.5604 (1.35); 8.5448 (0.7); 7.8206 (3.69); 7.8075 (3.86); 7.6075 (0.57); 7.5835 (16); 7.5685 (0.76); 7.5596 (0.63); 7.1796 (3.87); 7.1666 (3.76); 6.5757 (0.42); 4.0637 (0.84); 4.048 (0.87); 4.028 (1.88); 4.0122 (1.84); 3.9922 (0.97); 3.9764 (0.91); 3.3393 (75.51); 2.9456 (1.74); 2.5078 (20.84); 2.5034 (27.3); 2.4989 (20.68) |
| 3-80 | 2-thienyl | CH2 | CH2 | — | CH3 | compound No. 3-80, solvent: [DMSO], spectrometer: 601.6 MHz 8.3171 (0.72); 7.7515 (6.42); 7.3562 (7.76); 7.1159 (11.38); 6.9622 (12.26); 6.8603 (0.55); 6.7564 (4.07); 5.7572 (0.42); 3.7 (8.1); 3.4844 (7.36); 3.3293 (377.32); 3.2181 (0.36); 3.1186 (10.28); 3.038 (16); 2.8784 (15.2); 2.6168 (1.63); 2.6138 (2.24); 2.6108 (1.63); 2.5414 (0.34); 2.5231 (3.99); 2.52 (4.92); 2.5169 (4.71); 2.508 (104.72); 2.5051 (230.25); 2.5021 (319.21); 2.499 (230.97); 2.4961 (106.28); 2.3892 (1.51); 2.3862 (2.11); 2.3832 (1.51); 1.336 (1.49); 1.2984 (0.4); 1.2582 (0.56); 1.2492 (1.84); 1.1875 (0.32); −0.0002 (2.45) |
| 3-81 | 5-chloro-2-thienyl | CH2 | CH2 | — | H | compound No. 3-81, solvent: [DMSO], spectrometer: 399.95 MHz 8.316 (0.52); 8.2988 (2.07); 8.2851 (3.82); 8.2712 (2.08); 7.8017 (15.07); 7.7887 (15.57); 7.3823 (13.33); 7.3785 (13.5); 7.1745 (16); 7.1615 (15.29); 6.9307 (10.42); 6.9277 (10.44); 3.5147 (4.05); 3.4975 (10.45); 3.4829 (10.74); 3.4658 (4.65); 3.3232 (27.64); 3.0565 (0.4); 3.0404 (7.54); 3.023 (14.29); 3.006 (6.44); 2.6756 (0.33); 2.6711 (0.46); 2.6665 (0.33); 2.5244 (1.35); 2.5197 (2.08); 2.5111 (25.96); 2.5066 (52.36); 2.5021 (68.84); 2.4975 (49.18); 2.4929 (23.27); 2.3288 (0.44); 1.3363 (0.55); 1.2494 (0.68); 0.008 (2.43); −0.0002 (67.03); −0.0085 (2.09) |
| 3-82 | 4-chlorophenyl | CH(CF3) | CH2 | — | H | compound No. 3-82, solvent: [DMSO], spectrometer: 399.95 MHz 8.2644 (1.3); 8.2504 (2.34); 8.2362 (1.31); 7.7767 (7.71); 7.7637 (8.01); 7.4848 (3.65); 7.479 (1.78); 7.4688 (2.95); 7.4629 (16); 7.4485 (11.94); 7.4267 (3.09); 7.3972 (0.55); 7.1347 (8.26); 7.1217 (7.96); 4.112 (0.79); 4.0969 (0.99); 4.0884 (1.3); 4.0734 (1.39); 4.0645 (1.07); 4.0559 (1.23); 4.0497 (1); 4.0382 (2.79); 4.0204 (2.67); 4.0026 (0.88); 3.9198 (0.92); 3.906 (1.52); 3.8918 (1.06); 3.8858 (1.74); 3.872 (2.54); 3.8581 (1.32); 3.8106 (1.49); 3.7944 (1.68); 3.7877 (1.44); 3.7763 (1.23); 3.7718 (1.5); 3.7605 (0.98); 3.7539 (0.88); 3.7377 (0.77); 3.3243 (51.99); 2.6755 (0.36); 2.6711 (0.49); 2.6665 (0.36); 2.541 (0.33); 2.5241 (1.83); 2.5109 (28.37); 2.5065 (55.26); 2.502 (71.53); 2.4975 (51.75); 2.4931 (25.32); 2.3332 (0.34); 2.3288 (0.46); 2.3241 (0.35); 1.9892 (10.92); 1.3362 (0.43); 1.2492 (0.51); 1.1925 (2.96); 1.1747 (5.8); 1.1569 (2.85); 0.0079 (0.55); −0.0002 (13.71); −0.0085 (0.49) |
| 3-83 | 4-chloro-2-thienyl | CH2 | CH2 | — | H | compound No. 3-83, solvent: [DMSO], spectrometer: 601.6 MHz 8.2915 (1.78); 8.2824 (3.27); 8.2731 (1.76); 7.7989 (15.81); 7.7902 |

TABLE 3-continued

Compounds of the formula I-3

I-3

| Ex. No. | X | L$^1$ | L$^2$ | L$^3$ | Y | Physical data: $^1$H-NMR, δ [ppm] or CAS or patent No. |
|---|---|---|---|---|---|---|
| | | | | | | (15.77); 7.3818 (15.13); 7.3793 (15.15); 7.1725 (15.74); 7.1638 (16); 6.9301 (9.11); 6.929 (8.54); 6.9279 (9.01); 3.5052 (3.7); 3.4937 (9.16); 3.484 (9.36); 3.4726 (4.09); 3.3547 (0.52); 3.3501 (0.72); 3.3266 (979.51); 3.3046 (1.02); 3.3 (0.57); 3.2923 (0.32); 3.0339 (6.1); 3.0223 (12.02); 3.0112 (5.63); 2.6531 (1.55); 2.6192 (0.58); 2.6163 (1.28); 2.6132 (1.78); 2.6101 (1.26); 2.6071 (0.58); 2.5541 (0.65); 2.5408 (489.74); 2.5345 (2.17); 2.5292 (0.67); 2.5225 (3.38); 2.5194 (4.3); 2.5163 (4.19); 2.5075 (96.46); 2.5045 (205.3); 2.5014 (283.65); 2.4984 (204.29); 2.4953 (94.77); 2.4247 (1.54); 2.3917 (0.57); 2.3887 (1.26); 2.3856 (1.74); 2.3826 (1.24); 2.3796 (0.55); 2.0735 (1.17); 0.0052 (0.62); −0.0002 (52.25); −0.0058 (0.54) |
| 3-84 | 4-bromo- phenyl | CH2 | CH2 | — | H | compound No. 3-84, solvent: [DMSO], spectrometer: 399.95 MHz 8.1965 (1.91); 8.1834 (3.45); 8.1699 (1.88); 7.785 (11.42); 7.7719 (11.87); 7.4945 (13.49); 7.4902 (5.13); 7.478 (5.31); 7.4737 (16); 7.2336 (13.63); 7.2127 (11.65); 7.1609 (12.19); 7.1479 (11.79); 3.4906 (3.21); 3.4734 (7.36); 3.4581 (7.32); 3.4406 (3.55); 3.3229 (66.74); 2.8314 (6.16); 2.8135 (11.19); 2.7957 (5.56); 2.6753 (0.67); 2.6707 (0.91); 2.6664 (0.69); 2.5062 (103.94); 2.5017 (134.01); 2.4973 (98.17); 2.3327 (0.63); 2.3285 (0.85); 2.3241 (0.61); 1.9889 (1.26); 1.3355 (0.37); 1.2494 (0.45); 1.1925 (0.33); 1.1748 (0.66); 1.157 (0.34); 0.0079 (2.32); −0.0002 (52.25); −0.0084 (2.1) |
| 3-85 | 2-(trifluoro- methyl)- 4-chloro- phenyl | CH2 | CH2 | — | H | compound No. 3-85, solvent: [DMSO], spectrometer: 399.95 MHz 8.5752 (2.51); 8.5607 (4.96); 8.5462 (2.48); 7.8976 (15.64); 7.8929 (15.71); 7.7434 (7.7); 7.7381 (11.7); 7.7281 (5.7); 7.7228 (3.05); 7.7074 (5.8); 7.702 (4.53); 7.5824 (0.4); 7.5239 (8.07); 7.5033 (6.71); 6.8431 (16); 6.8384 (15.81); 5.7576 (1.8); 3.4777 (3.27); 3.461 (7.38); 3.4428 (7.25); 3.4266 (3.69); 3.3266 (36.26); 2.9946 (5.04); 2.9767 (8.59); 2.9587 (4.31); 2.6736 (0.44); 2.6692 (0.33); 2.5269 (1.37); 2.5136 (24.65); 2.5092 (48.76); 2.5047 (64.15); 2.5001 (46.88); 2.4957 (22.73); 2.3315 (0.42); 1.3372 (1.37); 1.25 (1.65); 1.2333 (0.39); 0.0079 (0.66); −0.0002 (18.26); −0.0084 (0.6) |
| 3-86 | 2,4-di- chlorophenyl | O | CH2 | CH(CH3) | H | compound No. 3-86, solvent: [DMSO], spectrometer: 399.95 MHz 8.1467 (2.33); 8.1269 (2.35); 7.8124 (9.53); 7.8046 (0.44); 7.7994 (9.96); 7.5734 (8.49); 7.567 (9.01); 7.3855 (3.9); 7.379 (3.61); 7.3633 (5.2); 7.3568 (4.97); 7.2379 (7.37); 7.2156 (5.51); 7.1821 (10.39); 7.1691 (9.94); 4.3873 (0.55); 4.3721 (1.22); 4.355 (1.55); 4.3363 (1.3); 4.3206 (0.66); 4.1536 (1.46); 4.1384 (1.32); 4.1292 (3.54); 4.114 (3.17); 4.1024 (3.57); 4.0882 (3.34); 4.078 (1.6); 4.0639 (1.26); 3.3812 (0.35); 3.3642 (0.72); 3.3295 (564.99); 3.2865 (0.37); 2.6803 (0.48); 2.6757 (1.03); 2.671 (1.43); 2.6665 (1.02); 2.662 (0.47); 2.5413 (16.36); 2.5245 (4.04); 2.5197 (6.26); 2.5111 (80.2); 2.5066 (162.64); 2.502 (215.3); 2.4974 (154.32); 2.4928 (72.38); 2.3378 (0.48); 2.3333 (1.01); 2.3288 (1.41); 2.3242 (0.99); 2.3196 (0.45); 1.2912 (16); 1.2743 (15.84); 0.008 (0.41); −0.0002 (13.21); −0.0085 (0.38) |
| 3-87 | 4-chloro- phenyl | O | CH2 | CH(CH3) | H | compound No. 3-87, solvent: [DMSO], spectrometer: 399.95 MHz 8.1732 (2.21); 8.1535 (2.23); 7.8088 (9.31); 7.7957 (9.67); 7.3463 (0.9); 7.3374 (10.82); 7.3318 (3.17); 7.3205 (3.39); 7.3149 (12.46); 7.306 (1.07); 7.1808 (9.77); 7.1678 (9.3); 7.0183 (1.08); 7.0094 (11.04); 7.0038 (3.18); 6.9925 (2.96); 6.9869 (9.63); 6.978 (0.84); 4.3431 (0.52); 4.3274 (1.18); 4.3103 (1.51); 4.2927 (1.25); 4.2766 (0.62); 4.0704 (1.79); 4.0549 (1.68); 4.0461 (3.05); 4.0306 (2.67); 3.9864 (3.11); 3.9725 (3.07); 3.962 (2.01); 3.9481 (1.72); 3.3724 (0.35); 3.3657 (0.44); 3.33 (343.39); 3.2974 (0.4); 2.6757 (0.58); 2.671 (0.81); 2.6665 (0.57); 2.5413 (7.01); 2.5244 (2.47); 2.5196 (3.96); 2.5111 (46.34); 2.5065 (93.01); 2.5019 (122.87); 2.4973 (88.34); 2.4928 (41.73); 2.3333 (0.58); 2.3287 (0.8); 2.3242 (0.58); 1.2637 (16); 1.2468 (15.88); 0.008 (0.36); −0.0002 (11.39); −0.0085 (0.34) |
| 3-88 | 2,4-di- chloro- phenyl | S | CH2 | CH(CH3) | H | compound No. 3-88, solvent: [DMSO], spectrometer: 399.95 MHz 8.2127 (2.51); 8.1927 (2.51); 7.8093 (8.4); 7.7962 (8.74); 7.629 (7.53); 7.6233 (7.85); 7.5753 (5.55); 7.5538 (7.31); 7.4289 (4.64); 7.4232 (4.33); 7.4075 (3.56); 7.4018 (3.38); 7.1795 (8.94); 7.1665 (8.56); 4.1732 (0.66); 4.1562 (1.46); 4.1382 (1.88); 4.1206 (1.5); 4.1032 (0.69); 3.3331 (88.06); 3.2873 (1.73); 3.2693 (1.69); 3.254 |

TABLE 3-continued

Compounds of the formula I-3

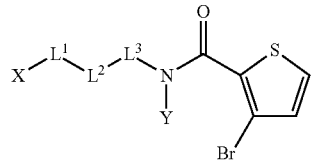

I-3

| Ex. No. | X | L¹ | L² | L³ | Y | Physical data: ¹H-NMR, δ [ppm] or CAS or patent No. |
|---|---|---|---|---|---|---|
| | | | | | | (3.22); 3.236 (3.06); 3.1907 (3.27); 3.175 (3.32); 3.1574 (1.88); 3.1417 (1.71); 2.5427 (22.56); 2.5259 (0.78); 2.5211 (1.24); 2.5126 (15.06); 2.5081 (30.14); 2.5035 (39.5); 2.4989 (28.24); 2.4943 (13.19); 1.3053 (16); 1.2886 (15.72); −0.0002 (4.02) |
| 3-89 | 4-chlorophenyl | S | CH2 | CH(CH3) | H | compound No. 3-89, solvent: [DMSO], spectrometer: 399.95 MHz-8.143 (2.14); 8.1229 (2.13); 7.8094 (0.61); 7.8038 (8.51); 7.7965 (0.76); 7.7908 (8.78); 7.4512 (0.33); 7.4293 (0.67); 7.4233 (5.42); 7.4179 (2.19); 7.4071 (3.22); 7.4014 (14.11); 7.3957 (2.32); 7.3894 (0.37); 7.3783 (2.34); 7.3726 (14.83); 7.3669 (3.31); 7.3561 (2.31); 7.3507 (5.74); 7.3448 (0.86); 7.3386 (0.62); 7.3211 (0.36); 7.1814 (0.6); 7.1752 (9); 7.1684 (0.71); 7.1622 (8.62); 4.1245 (0.67); 4.1076 (1.46); 4.0887 (1.73); 4.0713 (1.48); 4.0544 (0.68); 3.3341 (98.05); 3.239 (1.95); 3.2214 (1.87); 3.2053 (3.23); 3.1877 (3.09); 3.1258 (3.35); 3.1098 (3.38); 3.0921 (2.06); 3.0762 (1.91); 2.5424 (14); 2.5255 (0.62); 2.5207 (1); 2.5122 (13.34); 2.5077 (27.12); 2.5031 (36.01); 2.4985 (25.94); 2.4939 (12.29); 1.3121 (0.7); 1.2954 (0.73); 1.2784 (1.18); 1.266 (16); 1.2493 (15.71); −0.0002 (3.14) |
| 3-90 | 4-chlorophenyl | N(CH3) | CH2 | CH2 | H | compound No. 3-90, solvent: [DMSO], spectrometer: 399.95 MHz 8.2498 (0.67); 8.2363 (1.24); 8.2229 (0.65); 7.7972 (3.49); 7.7842 (3.63); 7.1863 (0.53); 7.1775 (4.44); 7.1709 (4.92); 7.1576 (5.8); 6.7757 (0.57); 6.7671 (4.46); 6.7444 (3.95); 3.4981 (1.03); 3.4816 (2.75); 3.4655 (2.31); 3.4179 (1.25); 3.4033 (2.51); 3.3874 (1.93); 3.3716 (0.77); 3.3291 (101.38); 2.9226 (16); 2.6713 (0.33); 2.5414 (19.11); 2.5065 (40.27); 2.5021 (50.72); 2.4977 (36.93); 2.329 (0.32); 0.0078 (0.37); −0.0002 (7.39) |

TABLE 4

Compounds of the formula I-4

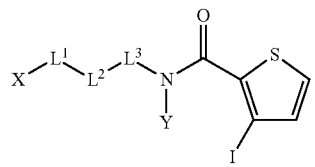

I-4

| Ex. No. | X | L¹ | L² | L³ | Y | Physical data: ¹H-NMR, δ [ppm] or CAS or patent No. |
|---|---|---|---|---|---|---|
| 4-1 | 3-methyl-2-thienyl | CH2 | CH2 | — | H | WO-A 2006/108791 |
| 4-2 | 3-chloro-2-thienyl | CH2 | CH2 | — | H | WO-A 2006/108791 |
| 4-3 | 2,4-dichlorophenyl | CH2 | CH2 | CH2 | H | WO-A 2008/101976 |
| 4-4 | 4-chlorophenyl | CH2 | CH2 | — | H | |
| 4-5 | 2,4-dichlorophenyl | CH2 | CH2 | — | H | WO-A 2007/108483 |
| 4-6 | 4-chlorophenyl | CH(OCH3) | CH(CH3) | — | H | |
| 4-7 | 2,4-dichlorophenyl | CH(OCH3) | CH(CH3) | — | H | |
| 4-8 | 4-chlorophenyl | CH(CH3) | CH2 | — | H | compound No. 4-8, solvent: [DMSO], spectrometer: 399.95 MHz 8.1978 (1.28); 8.1836 (2.49); 8.1694 (1.27); 7.6731 (9.43); 7.6604 (9.81); 7.3745 (0.77); 7.3688 (6.87); 7.3638 (2.5); 7.3527 (3.53); 7.3475 (15.13); 7.3419 (2.2); 7.3161 (2.24); 7.3108 (13.08); 7.3056 (3.36); 7.2943 (2.33); 7.2894 (6.14); 7.1873 (10.07); 7.1745 (9.59); 3.4045 (0.36); 3.3904 (3); 3.3871 (2.85); 3.3719 (5.93); 3.3549 (4.25); 3.3334 (135.39); 3.0838 (1.26); 3.0659 (2.5); 3.0481 (2.41); 3.0302 (1.12); 2.6716 (0.37); 2.5418 (34.95); 2.5249 (1.18); 2.5201 (1.86); 2.5115 (22.13); 2.507 |

TABLE 4-continued

Compounds of the formula I-4

I-4

$$\text{X}-\text{L}^1-\text{L}^2-\text{L}^3-\text{N}(\text{Y})-\text{C}(=\text{O})-\text{[3-iodothiophen-2-yl]}$$

| Ex. No. | X | L¹ | L² | L³ | Y | Physical data: ¹H-NMR, δ [ppm] or CAS or patent No. |
|---|---|---|---|---|---|---|
| | | | | | | (44.23); 2.5025 (58.05); 2.4979 (41.77); 2.4934 (19.73); 2.3293 (0.37); 1.2521 (16); 1.2346 (15.76); −0.0002 (7.44) |
| 4-9 | 2,4-dichlorophenyl | CH(CH3) | CH2 | — | H | compound No. 4-9, solvent: [DMSO], spectrometer: 399.95 MHz 8.2659 (1.43); 8.2517 (2.78); 8.2379 (1.37); 7.6708 (11.05); 7.6581 (11.5); 7.5626 (8.69); 7.5572 (9.18); 7.4833 (4.64); 7.4621 (8.93); 7.4228 (5.83); 7.4173 (5.36); 7.4017 (2.99); 7.3962 (2.83); 7.1832 (11.46); 7.1705 (10.82); 3.5655 (0.99); 3.5479 (2.21); 3.5307 (2.6); 3.5134 (1.78); 3.5092 (1.48); 3.4948 (1.4); 3.4771 (2.63); 3.4615 (3); 3.4453 (3.26); 3.4306 (2.49); 3.4125 (2.42); 3.3982 (1.06); 3.3796 (0.79); 3.3691 (0.46); 3.3297 (402.14); 3.2983 (0.41); 2.6802 (0.32); 2.6755 (0.69); 2.671 (0.95); 2.6664 (0.69); 2.6618 (0.32); 2.5413 (62.58); 2.5243 (2.87); 2.5195 (4.52); 2.511 (53.88); 2.5065 (108.84); 2.5019 (144.25); 2.4973 (104.06); 2.4927 (49.39); 2.3332 (0.66); 2.3286 (0.93); 2.3241 (0.65); 1.2414 (16); 1.2245 (15.82); 0.008 (0.5); −0.0002 (14.84); −0.0085 (0.45) |
| 4-10 | 4-chlorophenyl | CH2 | CH(CH3) | — | H | compound No. 4-10, solvent: [DMSO], spectrometer: 399.95 MHz 8.1201 (2.15); 8.0997 (2.16); 7.6702 (8.96); 7.6575 (9.35); 7.3518 (0.84); 7.3459 (7.05); 7.3409 (2.57); 7.3299 (3.49); 7.3247 (14.43); 7.319 (2.05); 7.2817 (11.16); 7.2767 (3.02); 7.2653 (2.24); 7.2605 (5.63); 7.1814 (9.66); 7.1687 (9.22); 4.1703 (0.59); 4.1538 (1.11); 4.1508 (1.23); 4.1341 (1.75); 4.1176 (1.27); 4.0979 (0.57); 3.3292 (373.27); 2.856 (1.31); 2.8363 (1.27); 2.8225 (2.79); 2.8028 (2.75); 2.7753 (2.78); 2.7597 (2.85); 2.7417 (1.32); 2.7261 (1.19); 2.6797 (0.41); 2.6754 (0.91); 2.6707 (1.26); 2.6662 (0.89); 2.6616 (0.42); 2.541 (11.06); 2.5242 (4.05); 2.5194 (6.28); 2.5108 (70.9); 2.5063 (142.56); 2.5017 (188.15); 2.497 (134.78); 2.4925 (63.12); 2.3376 (0.41); 2.333 (0.89); 2.3284 (1.22); 2.3238 (0.87); 2.3193 (0.4); 1.1641 (16); 1.1476 (15.9); 0.008 (0.56); −0.0002 (17.08); −0.0086 (0.5) |
| 4-11 | 2,4-dichlorophenyl | CH2 | CH(CH3) | — | H | compound No. 4-11, solvent: [DMSO], spectrometer: 399.95 MHz 8.1715 (2.47); 8.1501 (2.54); 7.6701 (9.62); 7.6574 (10.06); 7.5702 (6.37); 7.5652 (6.68); 7.4002 (2.84); 7.3795 (9.34); 7.365 (7.41); 7.3599 (6.8); 7.3444 (2.34); 7.3393 (2.44); 7.1782 (10.2); 7.1655 (9.72); 4.3099 (0.56); 4.2893 (1.25); 4.273 (1.72); 4.2568 (1.19); 4.2523 (1.03); 4.2363 (0.58); 3.3755 (0.44); 3.3304 (524.28); 3.2932 (0.66); 3.28 (0.37); 2.995 (0.76); 2.9591 (0.59); 2.944 (0.89); 2.9247 (4.16); 2.9161 (4.42); 2.9099 (4.06); 2.8956 (3.55); 2.8819 (0.7); 2.8614 (0.77); 2.6801 (0.53); 2.6755 (1.11); 2.6709 (1.52); 2.6663 (1.09); 2.6616 (0.5); 2.5412 (72.37); 2.5243 (4.63); 2.5196 (7.08); 2.511 (85.7); 2.5064 (173.71); 2.5018 (229.57); 2.4972 (164.3); 2.4926 (76.96); 2.3377 (0.52); 2.3332 (1.11); 2.3286 (1.52); 2.324 (1.08); 2.3195 (0.49); 1.2349 (0.56); 1.213 (16); 1.1963 (15.76); 0.0081 (0.66); −0.0002 (19.69); −0.0085 (0.52) |

TABLE 4-continued

Compounds of the formula I-4

I-4

| Ex. No. | X | L¹ | L² | L³ | Y | Physical data: $^1$H-NMR, δ [ppm] or CAS or patent No. |
|---|---|---|---|---|---|---|
| 4-12 | 4-chlorophenyl | C(CH3)2 | CH2 | — | H | |
| 4-13 | 2,4-dichlorophenyl | C(CH3)2 | CH2 | — | H | |
| 4-14 | 2-chlorophenyl | CH2 | CH2 | — | H | |
| 4-15 | 3,4-dichlorophenyl | CH2 | CH2 | — | H | compound No. 4-15, solvent: [DMSO], spectrometer: 399.95 MHz 8.2748 (1.63); 8.2609 (3.12); 8.247 (1.61); 7.6903 (12.52); 7.6776 (12.97); 7.5589 (9.91); 7.5486 (0.57); 7.5381 (16); 7.5316 (8.43); 7.2734 (4.72); 7.2683 (4.54); 7.2528 (4.08); 7.2478 (3.97); 7.2011 (13.09); 7.1884 (12.55); 3.4944 (2.7); 3.4772 (6.94); 3.4626 (7.1); 3.4456 (2.94); 3.3623 (0.52); 3.3573 (0.55); 3.3317 (219.19); 3.31 (0.65); 2.8624 (5.18); 2.8452 (10.47); 2.8279 (4.63); 2.6761 (0.45); 2.6716 (0.61); 2.6669 (0.47); 2.5418 (54.74); 2.5248 (1.69); 2.5201 (2.77); 2.5116 (34.23); 2.5071 (68.94); 2.5025 (90.9); 2.4979 (65.17); 2.4933 (30.68); 2.3337 (0.43); 2.3292 (0.6); 2.3246 (0.41); −0.0002 (8.21) |
| 4-16 | 3,5-dichlorophenyl | CH2 | CH2 | — | H | |
| 4-17 | 3-chlorophenyl | CH2 | CH2 | — | H | |
| 4-18 | 2-fluorophenyl | CH2 | CH2 | — | H | |
| 4-19 | 2,6-difluorophenyl | CH2 | CH2 | — | H | compound No. 4-19, solvent: [DMSO], spectrometer: 399.95 MHz-8.3762 (1.84); 8.3617 (3.57); 8.3473 (1.83); 7.6858 (15.23); 7.6731 (15.98); 7.3627 (1.16); 7.3459 (2.52); 7.3418 (2.17); 7.3289 (1.79); 7.325 (4.81); 7.321 (1.91); 7.308 (2.29); 7.3041 (3.05); 7.2874 (1.45); 7.2011 (16); 7.1884 (15.11); 7.1023 (0.61); 7.0979 (0.9); 7.0858 (6.51); 7.0776 (1.25); 7.0659 (10.15); 7.0547 (1.26); 7.0458 (5.46); 7.0333 (0.71); 7.03 (0.52); 3.4505 (3); 3.4337 (7.14); 3.4175 (7.17); 3.4006 (3.27); 3.3603 (0.48); 3.3506 (0.96); 3.3316 (197.25); 3.3076 (0.42); 2.9097 (4.61); 2.8922 (8.53); 2.8747 (4.12); 2.6762 (0.37); 2.6717 (0.52); 2.6671 (0.37); 2.5418 (14.06); 2.525 (1.6); 2.5202 (2.5); 2.5117 (29.79); 2.5072 (59.77); 2.5026 (78.58); 2.4979 (56.22); 2.4934 (26.35); 2.3339 (0.37); 2.3293 (0.52); 2.3247 (0.36); −0.0002 (6.98) |
| 4-20 | 2,6-dichlorophenyl | CH2 | CH2 | — | H | |
| 4-21 | 3-(trifluoromethyl)phenyl | CH2 | CH2 | — | H | |
| 4-22 | 4-(trifluoromethyl)phenyl | CH2 | CH2 | — | H | |
| 4-23 | 2-methylphenyl | CH2 | CH2 | — | H | |
| 4-24 | 2,4,6-trimethylphenyl | CH2 | CH2 | — | H | |
| 4-25 | 3,4-bismethoxyphenyl | CH2 | CH2 | — | H | |
| 4-26 | phenyl | CH2 | CH2 | — | H | |
| 4-27 | 4-chlorophenyl | C(CH2—CH2) | CH2 | — | H | |
| 4-28 | 2,4-dichlorophenyl | C(CH2—CH2) | CH2 | — | H | |
| 4-29 | 4-chlorophenyl | CH2 | C(CH2—CH2) | — | H | |
| 4-30 | 2,4-dichlorophenyl | CH2 | C(CH2—CH2) | — | H | |
| 4-31 | 4-chlorophenyl | O | CH2 | CH2 | H | |
| 4-32 | 2,4-dichlorophenyl | O | CH2 | CH2 | H | compound No. 4-32, solvent: [DMSO], spectrometer: 399.95 MHz-8.3422 (2.49); 8.3288 (4.8); 8.3156 (2.57); 7.7222 (12.7); 7.7094 (13.41); 7.5727 (11.06); 7.5663 (12.06); 7.3863 (5.61); 7.3799 (5.35); 7.3642 (7.64); 7.3577 (7.48); 7.2441 (12.4); 7.2298 (14.09); 7.2218 (10.16); 7.2171 (14.12); 4.2214 (7.21); 4.2069 (16); 4.1924 (8); 3.6582 (4.04); 3.6439 (11.17); 3.6297 (10.84); 3.6154 (3.67); 3.3273 (96.57); 2.6761 (0.38); 2.6718 (0.51); 2.6675 (0.39); 2.542 (5.91); 2.5246 (1.61); 2.5071 (57.98); 2.5027 (76.93); 2.4983 (58.65); 2.3339 |

TABLE 4-continued

Compounds of the formula I-4

I-4

| Ex. No. | X | L¹ | L² | L³ | Y | Physical data: ¹H-NMR, δ [ppm] or CAS or patent No. |
|---|---|---|---|---|---|---|
| | | | | | | (0.36); 2.3294 (0.48); 2.325 (0.37); −0.0002 (3.39) |
| 4-33 | 4-chlorophenyl | CH2 | CH2 | CH2 | H | |
| 4-34 | 4-chlorophenyl | NCH3 | CH2 | CH2 | H | |
| 4-35 | 2,4-dichlorophenyl | NCH3 | CH2 | CH2 | H | |
| 4-36 | 4-chlorophenyl | CH(OCH3) | CH2 | — | H | |
| 4-37 | 2,4-dichlorophenyl | CH(OCH3) | CH2 | — | H | |
| 4-38 | 2-thienyl | CH2 | CH2 | — | H | compound No. 4-38, solvent: [DMSO], spectrometer: 399.95 MHz 8.3451 (2.74); 8.3316 (5.03); 8.3181 (2.84); 7.7043 (15.02); 7.6916 (15.87); 7.3568 (8.12); 7.3538 (8); 7.3442 (9.03); 7.3411 (8.48); 7.2174 (16); 7.2047 (15.26); 6.9763 (6.01); 6.9677 (10.12); 6.9638 (5.89); 6.9551 (10.17); 6.9408 (9.96); 6.9335 (6.3); 3.4995 (4.52); 3.4819 (10.28); 3.4671 (10.58); 3.4493 (5.31); 3.3305 (31.33); 3.0738 (9.05); 3.0558 (15.86); 3.0378 (7.85); 2.5411 (5.79); 2.524 (0.86); 2.5063 (28.38); 2.5018 (37.56); 2.4974 (28.52); −0.0002 (0.8) |
| 4-39 | 3-thienyl | CH2 | CH2 | — | H | |
| 4-40 | 2-furyl | CH2 | CH2 | — | H | |
| 4-41 | 3-furyl | CH2 | CH2 | — | H | |
| 4-42 | phenyl | CH2 | CH2 | CH(CH3) | H | |
| 4-43 | phenyl | CH2 | CH2 | CH2 | H | |
| 4-44 | 2-Cl-phenyl | CH2 | CH2 | CH(CH3) | H | |
| 4-45 | 4-t-butylphenyl | CH2 | CH2 | CH2 | H | |
| 4-46 | 4-methylphenyl | CH2 | CH2 | CH2 | H | |
| 4-47 | phenyl | CH2 | CH2 | CH(CH2CH3) | H | |
| 4-48 | 2-methoxyphenyl | CH2 | CH2 | CH2 | H | |
| 4-49 | 2-methylphenyl | CH2 | CH2 | CH2 | H | |
| 4-50 | 3-methylphenyl | CH2 | CH2 | CH2 | H | |
| 4-51 | 3-chlorophenyl | CH2 | CH2 | CH2 | H | |
| 4-52 | 2,6-difluorophenyl | CH2 | CH2 | CH2 | H | compound No. 4-52, solvent: [DMSO], spectrometer: 399.95 MHz-8.289 (3.25); 8.2754 (6.02); 8.2617 (3.36); 7.7312 (0.36); 7.7184 (0.45); 7.7002 (14.81); 7.6875 (15.63); 7.3533 (1.47); 7.3359 (3.65); 7.3329 (3.54); 7.3156 (6.68); 7.2952 (4.43); 7.278 (1.94); 7.2407 (0.44); 7.228 (0.48); 7.2108 (16); 7.198 (15.4); 7.1445 (0.34); 7.1223 (0.48); 7.1034 (1.35); 7.0904 (9.74); 7.0708 (15.16); 7.0513 (8.19); 7.0373 (1.2); 6.5636 (0.55); 3.3363 (59.45); 3.2877 (4.72); 3.2706 (10.64); 3.2546 (10.82); 3.2377 (5.03); 2.7211 (6.7); 2.7019 (11.21); 2.6825 (7.59); 2.5446 (8.86); 2.5095 (32.46); 2.5053 (42.82); 2.501 (33.42); 1.815 (2.56); 1.7961 (6.96); 1.7775 (9.62); 1.7588 (6.71); 1.7405 (2.35); −0.0002 (0.39) |
| 4-53 | 4-chlorophenyl | CH2 | CH2 | CH2 | H | |
| 4-54 | 2,6-dichlorophenyl | CH2 | CH2 | CH(CH3) | H | |
| 4-55 | 3,5-dichlorophenyl | CH2 | CH2 | CH(CH3) | H | |
| 4-56 | 2,6-dimethylphenyl | CH2 | CH2 | CH2 | H | |
| 4-57 | 2,5-dichlorophenyl | CH2 | CH2 | CH2 | H | |
| 4-58 | 4-isopropoxyphenyl | CH2 | CH2 | CH2 | H | |
| 4-59 | 3-trifluoromethylphenyl | CH2 | CH2 | CH(CH3) | H | |
| 4-60 | 4-methylphenyl | CH2 | CH2 | CH(CH3) | H | |
| 4-61 | 2-methylphenyl | CH2 | CH2 | CH(CH3) | H | |
| 4-62 | 3,4-dichlorophenyl | CH2 | CH2 | CH(CH3) | H | |
| 4-63 | 3,5-dichlorophenyl | CH2 | CH2 | CH2 | H | |
| 4-64 | 2,6-dimethylphenyl | CH2 | CH2 | CH(CH3) | H | |
| 4-65 | 4-trifluoromethylphenyl | CH2 | CH2 | CH(CH3) | H | |
| 4-66 | 2,5-dichlorophenyl | CH2 | CH2 | CH(CH3) | H | |
| 4-67 | 4-phenoxyphenyl | CH2 | CH2 | CH2 | H | |
| 4-68 | 3-chlorophenyl | CH2 | CH2 | CH(CH3) | H | |

TABLE 4-continued

Compounds of the formula I-4

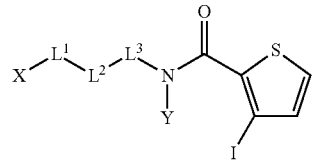

I-4

| Ex. No. | X | $L^1$ | $L^2$ | $L^3$ | Y | Physical data: $^1$H-NMR, δ [ppm] or CAS or patent No. |
|---|---|---|---|---|---|---|
| 4-69 | 4-phenoxyphenyl | CH2 | CH2 | CH(CH3) | H | |
| 4-70 | 2,4-dichlorophenyl | CH2 | CH2 | CH(CH3) | H | |
| 4-71 | 2-difluoromethoxyphenyl | CH2 | CH2 | CH(CH3) | H | |
| 4-72 | 4-methoxyphenyl | CH2 | CH2 | CH2 | H | |
| 4-73 | 4-chlorophenyl | CH2 | CH2 | CH(CH3) | H | |
| 4-74 | 4-chlorophenyl | CH2 | CH2 | CH(i-propyl) | H | |
| 4-75 | 4-fluorophenyl | CH2 | CH2 | CH2 | H | |
| 4-76 | 4-chlorophenyl | CH2 | CH2 | CH(n-propyl) | H | |
| 4-77 | 4-chlorophenyl | CH2 | CH2 | CH(t-butyl) | H | |
| 4-78 | 2-chlorophenyl | CH2 | CH2 | CH2 | H | |
| 4-79 | 4-chlorophenyl | CH2 | CH(CH3) | — | cyclopropyl | WO-A 2007/060164 |
| 4-80 | 2-thienyl | CH2 | CH2 | CH2 | H | compound No. 4-80, solvent: [DMSO], spectrometer: 399.95 MHz-8.2883 (3.21); 8.2753 (5.82); 8.2622 (3.42); 7.6997 (14.19); 7.6984 (13.56); 7.687 (14.99); 7.6858 (14.27); 7.3213 (9.12); 7.3093 (9.89); 7.2101 (15.06); 7.209 (14.6); 7.1974 (14.74); 7.1962 (14.13); 6.9542 (6.4); 6.9453 (9.34); 6.9423 (7.53); 6.9333 (8.71); 6.8987 (10.86); 6.8907 (8.47); 3.3289 (59.48); 3.2994 (5.47); 3.2828 (13.42); 3.2674 (13.55); 3.2509 (5.79); 2.9046 (9.38); 2.8856 (16); 2.8664 (10.3); 2.6709 (0.49); 2.5411 (5.09); 2.5398 (4.82); 2.5011 (68.2); 2.4974 (55.76); 2.3281 (0.44); 1.8989 (2.91); 1.881 (9.05); 1.8622 (12.17); 1.844 (8.84); 1.8262 (2.7); −0.0002 (0.92); −0.0015 (0.88) |
| 4-81 | 4-bromophenyl | CH2 | CH2 | — | H | compound No. 4-81, solvent: [DMSO], spectrometer: 399.95 MHz 8.2659 (1.89); 8.2521 (3.57); 8.2382 (1.87); 7.6881 (11.61); 7.6754 (12.18); 7.5003 (1.69); 7.494 (13.45); 7.4896 (4.69); 7.4777 (4.96); 7.4732 (16); 7.4671 (2.05); 7.2381 (13.04); 7.2173 (11.31); 7.2023 (12.33); 7.1896 (11.63); 4.0378 (0.54); 4.02 (0.55); 3.4707 (2.96); 3.4535 (6.6); 3.4383 (6.52); 3.4207 (3.18); 3.3229 (55.32); 2.8306 (5.69); 2.8126 (10.26); 2.7948 (5.12); 2.6751 (0.53); 2.6707 (0.71); 2.6662 (0.53); 2.5238 (2.53); 2.5104 (42.3); 2.5061 (82.96); 2.5017 (107.91); 2.4972 (78.3); 2.4929 (38.31); 2.3328 (0.51); 2.3283 (0.69); 2.324 (0.52); 1.9889 (2.44); 1.2584 (0.37); 1.2491 (0.34); 1.1925 (0.64); 1.1747 (1.25); 1.1569 (0.63); 0.0079 (1.74); −0.0002 (44.61); −0.0085 (1.59) |
| 4-82 | 4-chlorophenyl | CH2 | C(CH3)2 | — | H | compound No. 4-82, solvent: [DMSO], spectrometer: 399.95 MHz 7.6667 (2.46); 7.654 (2.62); 7.5355 (1.71); 7.3362 (2.54); 7.3317 (1.01); 7.3151 (3.63); 7.2185 (3.4); 7.1975 (2.5); 7.1805 (2.68); 7.1678 (2.52); 3.3365 (20.24); 3.3294 (25.49); 3.0901 (4.92); 2.5063 (12.56); 2.502 (15.88); 2.4976 (11.94); 1.3354 (0.48); 1.314 (16); −0.0002 (4.44) |
| 4-83 | 2,4-dichlorophenyl | CH2 | C(CH3)2 | — | H | compound No. 4-83, solvent: [DMSO], spectrometer: 399.95 MHz-,7.6871 (2.66); 7.6797 (2.07); 7.675 (3.39); 7.5904 (1.85); 7.5854 (2.22); 7.3686 (0.59); 7.3636 (0.58); 7.3479 (1.79); 7.3428 (2.06); 7.3286 (3.03); 7.3078 (0.97); 7.1961 (2.31); 7.1834 (2.26); 3.3548 (62.71); 3.3461 (49.33); 3.3409 (49.17); 3.3339 (34.47); 3.2763 (5.46); 2.5073 (23.38); 2.5032 (31.78); 2.4991 (26.77); 1.9891 (1); 1.3507 (16); 1.1752 (0.54); −0.0002 (7.13) |
| 4-84 | 2-(trifluoromethyl)-4-chlorophenyl | CH2 | CH2 | — | H | compound No. 4-84, solvent: [DMSO], spectrometer: 399.95 MHz 8.383 (2.04); 8.3687 (3.97); 8.3546 (1.99); |

TABLE 4-continued

Compounds of the formula I-4

I-4

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 8.3164 (0.35); 7.7528 (6.84); 7.7474 (9.86); 7.7346 (4.64); 7.7293 (2.73); 7.714 (5.2); 7.7084 (4.18); 7.6994 (15.25); 7.6866 (15.78); 7.5619 (6.76); 7.5412 (5.43); 7.2103 (16); 7.1976 (15.19); 7.187 (0.43); 7.1816 (0.43); 5.7568 (1.06); 3.509 (2.76); 3.4923 (6.41); 3.4763 (6.43); 3.4591 (3.03); 3.323 (95.71); 3.3035 (4.12); 3.2952 (0.44); 3.2857 (3.28); 3.0133 (4.15); 2.996 (7.49); 2.9784 (3.61); 2.6956 (13.62); 2.6802 (0.39); 2.6758 (0.78); 2.6712 (1.07); 2.6666 (0.76); 2.6621 (0.35); 2.5246 (3.29); 2.5199 (5.09); 2.5113 (57.87); 2.5067 (115.78); 2.5021 (152.53); 2.4975 (109.23); 2.493 (50.69); 2.3381 (0.36); 2.3335 (0.75); 2.3289 (1.01); 2.3243 (0.72); 2.3198 (0.33); 2.1972 (1.42); 2.1773 (2.71); 2.1569 (1.91); 1.9391 (0.72); 1.9208 (1.87); 1.9176 (1.37); 1.9118 (0.34); 1.9024 (1.96); 1.8994 (1.59); 1.8852 (0.65); 1.8823 (1.68); 1.8792 (0.77); 1.8635 (0.5); 1.3358 (4.81); 1.2984 (0.49); 1.2586 (0.86); 1.2495 (5.9); 1.2344 (1.02); 1.1874 (1.93); 0.008 (1.56); −0.0002 (47.94); −0.0085 (1.37) |
| 4-85 | 4-chlorophenyl | N(CH3) | CH2 | CH2 | H | compound No. 4-85, solvent: [DMSO], spectrometer: 399.95 MHz 8.3095 (0.73); 8.2956 (1.36); 8.2814 (0.7); 7.6991 (3.86); 7.6864 (4); 7.2124 (4.09); 7.1997 (3.94); 7.1915 (0.59); 7.1826 (4.31); 7.1599 (4.68); 7.1511 (0.53); 6.7634 (4.39); 6.7406 (3.91); 3.4974 (1.23); 3.4807 (2.99); 3.4642 (2.31); 3.3992 (1.39); 3.3836 (2.95); 3.3677 (3.11); 3.3355 (303.57); 3.2852 (0.41); 3.2753 (0.34); 2.9276 (16); 2.676 (0.43); 2.6715 (0.57); 2.5417 (28.45); 2.5068 (68.26); 2.5024 (86.24); 2.4979 (63.01); 2.3337 (0.41); 2.3293 (0.56); 2.3247 (0.41); 0.0078 (0.65); −0.0002 (13.43); −0.0084 (0.57) |
| 4-86 | 3-chloro-4-(trifluoromethyl)phenyl | CH2 | CH2 | — | H | compound No. 4-86, solvent: [DMSO], spectrometer: 399.95 MHz 8.3159 (1.13); 8.3109 (1.84); 8.2967 (3.57); 8.2828 (1.84); 7.7891 (7.25); 7.7689 (8.48); 7.7483 (0.44); 7.6916 (15.23); 7.6789 (16); 7.6296 (8.18); 7.546 (0.53); 7.4507 (4.39); 7.4307 (3.86); 7.358 (0.32); 7.2005 (15.96); 7.1877 (15.29); 3.539 (2.93); 3.5219 (7.7); 3.5073 (7.92); 3.4905 (3.23); 3.3239 (53.87); 3.2047 (0.7); 3.1898 (0.72); 2.9553 (4.99); 2.9383 (9.85); 2.9212 (4.4); 2.7977 (0.33); 2.7802 (0.59); 2.6765 (0.5); 2.6718 (0.68); 2.6672 (0.49); 2.5251 (2.19); 2.5204 (3.32); 2.5118 (37.85); 2.5073 (76.06); 2.5027 (100.26); 2.4981 (71.49); 2.4935 (33.32); 2.3341 (0.47); 2.3295 (0.64); 2.3249 (0.44); 1.336 (3.03); 1.3299 (5.74); 1.299 (0.49); 1.2697 (0.39); 1.2589 (0.85); 1.2498 (2.68); 1.2339 (0.51); 1.2116 (0.42); 1.188 (0.49) |

TABLE 4-continued

Compounds of the formula I-4

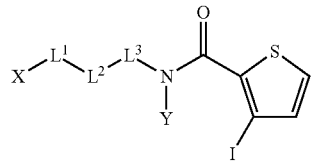

I-4

| Ex. No. | X | L¹ | L² | L³ | Y | Physical data: ¹H-NMR, δ [ppm] or CAS or patent No. |
|---|---|---|---|---|---|---|
| 4-87 | 4-chloro-3-(trifluoromethyl)phenyl | CH2 | CH2 | — | H | compound No. 4-87, solvent: [DMSO], spectrometer: 399.95 MHz<br>8.2897 (2.17); 8.276 (4.12); 8.2624 (2.16); 7.736 (8.36); 7.7315 (8.67); 7.6972 (15.06); 7.6844 (15.74); 7.6656 (5.48); 7.645 (10.25); 7.6029 (5.8); 7.5986 (5.48); 7.5824 (3.08); 7.5779 (2.96); 7.2045 (16); 7.1918 (15.22); 5.7641 (0.79); 3.5293 (3.38); 3.5124 (8.83); 3.4976 (9); 3.481 (3.6); 3.3339 (42.56); 2.9747 (0.38); 2.9521 (6.46); 2.9352 (12.81); 2.9181 (5.67); 2.6835 (0.35); 2.6789 (0.47); 2.6743 (0.35); 2.5321 (1.78); 2.5188 (26.97); 2.5144 (53.04); 2.5098 (69.14); 2.5052 (49.99); 2.5007 (23.99); 2.3365 (0.43); 1.9964 (0.51); 1.3435 (0.51); 1.2563 (0.69) |
| 4-88 | 2-chloro-4-(trifluoromethyl)phenyl | O | CH2 | C(CH3)2 | H | compound No. 4-88, solvent: [DMSO], spectrometer: 399.95 MHz<br>7.8748 (1.62); 7.8251 (1.38); 7.8201 (1.46); 7.6895 (2.54); 7.6769 (2.47); 7.6643 (0.8); 7.6599 (0.74); 7.3646 (1.25); 7.343 (1.13); 7.1933 (2.36); 7.1806 (2.22); 4.3632 (4.84); 3.3302 (38.37); 2.5421 (4.27); 2.5251 (0.4); 2.5117 (8.48); 2.5074 (16.74); 2.5029 (21.85); 2.4984 (16.2); 2.4944 (8.12); 1.4942 (16); 1.4718 (0.33); 1.4664 (0.61) |
| 4-89 | 4-chloro-2-(trifluoromethyl)phenyl | O | CH3 | C(CH3)3 | H | compound No. 4-89, solvent: [DMSO], spectrometer: 399.95 MHz<br>7.8044 (1.53); 7.7025 (0.59); 7.6957 (0.8); 7.6883 (2.87); 7.6803 (0.7); 7.6755 (3.55); 7.6604 (1.81); 7.6539 (1.1); 7.3165 (1.19); 7.2943 (1.07); 7.1974 (2.96); 7.1847 (2.85); 4.3156 (4.63); 3.3281 (49.55); 2.5417 (6.3); 2.5248 (0.58); 2.52 (0.91); 2.5115 (11.41); 2.5069 (22.83); 2.5023 (29.89); 2.4977 (21.3); 2.4932 (9.93); 1.4545 (16); 1.4259 (0.69) |
| 4-90 | 2-chloro-4-(trifluoromethyl)phenyl | O | CH2 | CH2 | H | compound No. 4-90, solvent: [DMSO], spectrometer: 399.95 MHz<br>8.3684 (1.98); 8.3548 (3.86); 8.3416 (2.02); 7.8377 (7.1); 7.8328 (7.68); 7.7229 (15.04); 7.7102 (16); 7.7044 (3.72); 7.6989 (3.42); 7.6814 (4.1); 7.6771 (3.85); 7.6674 (0.48); 7.5236 (0.32); 7.5183 (0.34); 7.4413 (0.38); 7.4093 (6.44); 7.3876 (5.68); 7.2302 (15.98); 7.2175 (15.09); 4.3275 (5.82); 4.3131 (12.95); 4.2988 (6.26); 3.6945 (3.18); 3.6803 (9.06); 3.6662 (8.84); 3.652 (3); 3.365 (0.37); 3.3286 (261.25); 2.6806 (0.33); 2.6762 (0.72); 2.6716 (0.97); 2.6671 (0.7); 2.5419 (19.71); 2.525 (2.86); 2.5202 (4.63); 2.5117 (56.62); 2.5072 (112.56); 2.5026 (146.97); 2.498 (105.33); 2.4935 (49.52); 2.3385 (0.34); 2.3339 (0.7); 2.3294 (0.94); 2.3248 (0.68); 1.2343 (0.52); −0.0002 (1.06) |

TABLE 5

Compounds of the formula I-5

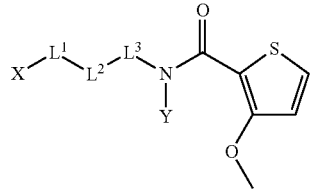

I-5

| Ex. No. | X | L¹ | L² | L³ | Y | Physical data: ¹H-NMR, δ [ppm] or CAS or patent No. |
|---|---|---|---|---|---|---|
| 5-1 | 3-methyl-2-thienyl | CH2 | CH2 | — | H | |
| 5-2 | 2,4-dichlorophenyl | CH2 | CH2 | CH2 | H | compound No. 5-2, solvent: [DMSO], spectrometer: 399.95 MHz 7.697 (3.12); 7.6832 (3.24); 7.5658 (2.74); 7.5605 (2.68); 7.5518 (0.84); 7.5372 (0.43); 7.4228 (1.38); 7.4021 (3.09); 7.3743 (2.13); 7.369 (1.95); 7.3537 (0.91); 7.3484 (0.9); 7.1176 (3.41); 7.1038 (3.28); 3.9577 (16); 3.337 (35.89); 3.3209 (1.01); 3.3037 (1.78); 3.2879 (1.77); 3.2709 (0.81); 2.7282 (1.35); 2.7097 (1.8); 2.6899 (1.45); 2.5436 (4.79); 2.5218 (0.45); 2.5133 (5); 2.5088 (9.88); 2.5042 (13.04); 2.4996 (9.47); 2.4951 (4.5); 1.8224 (0.39); 1.8039 (1.03); 1.7855 (1.37); 1.7673 (0.97); 1.749 (0.34); −0.0002 (0.56) |
| 5-3 | 4-chlorophenyl | CH2 | CH2 | — | H | |
| 5-4 | 2,4-dichlorophenyl | CH2 | CH2 | — | H | |
| 5-5 | 4-chlorophenyl | CH(OCH3) | CH(CH3) | — | H | |
| 5-6 | 2,4-dichlorophenyl | CH(OCH3) | CH(CH3) | — | H | |
| 5-7 | 4-chlorophenyl | CH(CH3) | CH2 | — | H | |
| 5-8 | 2,4-dichlorophenyl | CH(CH3) | CH2 | — | H | |
| 5-9 | 4-chlorophenyl | CH2 | CH(CH3) | — | H | |
| 5-10 | 2,4-dichlorophenyl | CH2 | CH(CH3) | — | H | |
| 5-11 | 4-chlorophenyl | C(CH3)2 | CH2 | — | H | |
| 5-12 | 2,4-dichlorophenyl | C(CH3)2 | CH2 | — | H | |
| 5-13 | 2-chlorophenyl | CH2 | CH2 | — | H | |
| 5-14 | 3,4-dichlorophenyl | CH2 | CH2 | — | H | |
| 5-15 | 3,5-dichlorophenyl | CH2 | CH2 | — | H | |
| 5-16 | 3-chlorophenyl | CH2 | CH2 | — | H | |
| 5-17 | 2-fluorophenyl | CH2 | CH2 | — | H | |
| 5-18 | 2,6-difluorophenyl | CH2 | CH2 | — | H | |
| 5-19 | 2,6-dichlorophenyl | CH2 | CH2 | — | H | |
| 5-20 | 3-(trifluoromethyl)phenyl | CH2 | CH2 | — | H | |
| 5-21 | 4-(trifluoromethyl)phenyl | CH2 | CH2 | — | H | |
| 5-22 | 2-methylphenyl | CH2 | CH2 | — | H | |
| 5-23 | 2,4,6-trimethylphenyl | CH2 | CH2 | — | H | |
| 5-24 | 3,4-bismethoxyphenyl | CH2 | CH2 | — | H | |
| 5-25 | phenyl | CH2 | CH2 | — | H | |
| 5-26 | 4-chlorophenyl | C(CH2—CH2) | CH2 | — | H | |
| 5-27 | 2,4-dichlorophenyl | C(CH2—CH2) | CH2 | — | H | |
| 5-28 | 4-chlorophenyl | CH2 | C(CH2—CH2) | — | H | |
| 5-29 | 2,4-dichlorophenyl | CH2 | C(CH2—CH2) | — | H | |
| 5-30 | 4-chlorophenyl | O | CH2 | CH2 | H | |
| 5-31 | 2,4-dichlorophenyl | O | CH2 | CH2 | H | compound No. 5-31, solvent: [DMSO], spectrometer: 399.95 MHz 7.7368 (3.04); 7.723 (3.67); 7.7075 (1.23); 7.6932 (0.64); 7.5902 (2.45); 7.5838 (2.66); 7.388 (1.32); 7.3815 (1.26); 7.3658 (1.81); 7.3593 (1.79); 7.2512 (3.06); 7.2289 (2.26); 7.1361 (3.32); 7.1223 (3.24); 4.1952 (1.81); 4.1806 (4.03); 4.1662 (2.05); 3.9646 (16); 3.7044 (1.03); 3.69 (2.92); 3.6754 (2.84); 3.6608 (0.95); 3.3343 (12.36); 2.5452 (8.06); 2.5101 (6.38); 2.5057 (8.56); 2.5013 (6.61); −0.0002 (0.35) |
| 5-32 | 4-chlorophenyl | CH2 | CH2 | CH2 | H | |
| 5-33 | 4-chlorophenyl | NCH3 | CH2 | CH2 | H | |
| 5-34 | 2,4-dichlorophenyl | NCH3 | CH2 | CH2 | H | |
| 5-35 | 4-chlorophenyl | CH(OCH3) | CH2 | — | H | |
| 5-36 | 2,4-dichlorophenyl | CH(OCH3) | CH2 | — | H | |
| 5-37 | 2-thienyl | CH2 | CH2 | — | H | compound No. 5-37, solvent: [DMSO], spectrometer: 399.95 MHz 7.7084 (2.75); 7.6946 (2.9); 7.6176 (0.54); 7.6034 (1.01); 7.5895 (0.58); 7.3724 (1.54); 7.3698 (1.55); 7.3597 (1.72); 7.357 (1.64); 7.1144 (3.13); 7.1006 (3.03); 6.9939 (1.3); 6.9853 (1.79); 6.9813 |

TABLE 5-continued

Compounds of the formula I-5

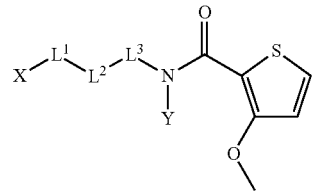

I-5

| Ex. No. | X | L¹ | L² | L³ | Y | Physical data: ¹H-NMR, δ [ppm] or CAS or patent No. |
|---|---|---|---|---|---|---|
| | | | | | | (1.37); 6.9726 (1.66); 6.9295 (1.84); 6.9221 (1.5); 3.9191 (16); 3.5354 (1); 3.5179 (2.4); 3.5026 (2.47); 3.4851 (1.17); 3.3301 (19.26); 3.0521 (1.89); 3.0343 (3.43); 3.0166 (1.68); 2.5415 (0.53); 2.5065 (10.07); 2.5021 (13.37); 2.4978 (10.39) |
| 5-38 | 3-thienyl | CH2 | CH2 | — | H | |
| 5-39 | 2-furyl | CH2 | CH2 | — | H | |
| 5-40 | 3-furyl | CH2 | CH2 | — | H | |
| 5-41 | phenyl | CH2 | CH2 | CH(CH3) | H | |
| 5-42 | phenyl | CH2 | CH2 | CH2 | H | |
| 5-43 | 2-Cl-phenyl | CH2 | CH2 | CH(CH3) | H | |
| 5-44 | 4-t-butylphenyl | CH2 | CH2 | CH2 | H | |
| 5-45 | 4-methylphenyl | CH2 | CH2 | CH2 | H | |
| 5-46 | phenyl | CH2 | CH2 | CH(CH2CH3) | H | |
| 5-47 | 2-methoxyphenyl | CH2 | CH2 | CH2 | H | |
| 5-48 | 2-methylphenyl | CH2 | CH2 | CH2 | H | |
| 5-49 | 3-methylphenyl | CH2 | CH2 | CH2 | H | |
| 5-50 | 3-chlorophenyl | CH2 | CH2 | CH2 | H | |
| 5-51 | 2,6-difluorophenyl | CH2 | CH2 | CH2 | H | compound No. 5-51, solvent: [DMSO], spectrometer: 399.95 MHz<br>7.699 (2.76); 7.6853 (2.89); 7.6047 (0.51); 7.5902 (0.96); 7.5757 (0.53); 7.3315 (0.63); 7.3283 (0.61); 7.3109 (1.18); 7.2902 (0.78);<br>7.2733 (0.35); 7.1187 (3.18); 7.1048 (3.18); 7.0898 (1.68); 7.0698<br>(2.67); 7.05 (1.37); 3.9774 (0.42); 3.9593 (16); 3.3301 (31.44); 3.2955 (0.86); 3.2788 (1.98); 3.2619 (1.97); 3.2452 (0.87); 2.6756<br>(1.24); 2.6567 (2.12); 2.6377 (1.25); 2.5074 (16.9); 2.503 (22.52);<br>2.4986 (17.23); 1.7884 (0.44); 1.7699 (1.29); 1.7515 (1.78); 1.7332 (1.22); 1.7151 (0.38) |
| 5-52 | 4-chlorophenyl | CH2 | CH2 | CH2 | H | |
| 5-53 | 2,6-dichlorophenyl | CH2 | CH2 | CH(CH3) | H | |
| 5-54 | 3,5-dichlorophenyl | CH2 | CH2 | CH(CH3) | H | |
| 5-55 | 2,6-dimethylphenyl | CH2 | CH2 | CH2 | H | |
| 5-56 | 2,5-dichlorophenyl | CH2 | CH2 | CH2 | H | |
| 5-57 | 4-isopropoxyphenyl | CH2 | CH2 | CH2 | H | |
| 5-58 | 3-trifluoromethylphenyl | CH2 | CH2 | CH(CH3) | H | |
| 5-59 | 4-methylphenyl | CH2 | CH2 | CH(CH3) | H | |
| 5-60 | 2-methylphenyl | CH2 | CH2 | CH(CH3) | H | |
| 5-61 | 3,4-dichlorophenyl | CH2 | CH2 | CH(CH3) | H | |
| 5-62 | 3,5-dichlorophenyl | CH2 | CH2 | CH2 | H | |
| 5-63 | 2,6-dimethylphenyl | CH2 | CH2 | CH(CH3) | H | |
| 5-64 | 4-trifluoromethylphenyl | CH2 | CH2 | CH(CH3) | H | |
| 5-65 | 2,5-dichlorophenyl | CH2 | CH2 | CH(CH3) | H | |
| 5-66 | 4-phenoxyphenyl | CH2 | CH2 | CH2 | H | |
| 5-67 | 3-chlorophenyl | CH2 | CH2 | CH(CH3) | H | |
| 5-68 | 4-phenoxyphenyl | CH2 | CH2 | CH(CH3) | H | |
| 5-69 | 2,4-dichlorophenyl | CH2 | CH2 | CH(CH3) | H | |
| 5-70 | 2-difluoromethoxyphenyl | CH2 | CH2 | CH(CH3) | H | |
| 5-71 | 4-methoxyphenyl | CH2 | CH2 | CH2 | H | |
| 5-72 | 4-chlorophenyl | CH2 | CH2 | CH(CH3) | H | |
| 5-73 | 4-chlorophenyl | CH2 | CH2 | CH(i-propyl) | H | |
| 5-74 | 4-fluorophenyl | CH2 | CH2 | CH2 | H | |
| 5-75 | 4-chlorophenyl | CH2 | CH2 | CH(n-propyl) | H | |
| 5-76 | 4-chlorophenyl | CH2 | CH2 | CH(t-butyl) | H | |
| 5-77 | 2-chlorophenyl | CH2 | CH2 | CH2 | H | |
| 5-78 | 2-thienyl | CH2 | CH2 | CH2 | H | compound No. 5-78, solvent: [DMSO], spectrometer: 399.95 MHz<br>7.6992 (2.67); 7.6854 (2.81); 7.5655 (0.5); 7.5515 (0.93); 7.5369 (0.53); 7.3207 (1.41); 7.318 (1.5); 7.308 (1.58); 7.3052 (1.59); 7.1195 (3.07); 7.1056 (2.96); 6.9505 (1.23); 6.942 (1.68); 6.9379 |

TABLE 5-continued

Compounds of the formula I-5

I-5

| Ex. No. | X | L¹ | L² | L³ | Y | Physical data: ¹H-NMR, δ [ppm] or CAS or patent No. |
|---|---|---|---|---|---|---|
| 5-79 | 2,6-difluorophenyl | CH2 | CH(CH3) | — | H | (1.28); 6.9293 (1.57); 6.8857 (1.69); 6.8793 (1.35); 3.9627 (16); 3.3285 (39.07); 3.315 (2.61); 3.2972 (2.23); 3.2808 (1.03); 2.8407 (1.59); 2.8217 (2.79); 2.8027 (1.71); 2.5064 (18.69); 2.5019 (25.1); 2.4975 (19.4); 1.8814 (0.51); 1.8627 (1.48); 1.8444 (1.98); 1.8264 (1.4); 1.8079 (0.46); −0.0002 (0.35) [DMSO], spectrometer: 399.95 MHz 7.6897 (2.73); 7.6759 (2.87); 7.3397 (0.77); 7.3225 (1.32); 7.3021 (0.99); 7.2848 (0.44); 7.263 (1.32); 7.2424 (1.34); 7.1118 (3.25); 7.098 (3.3); 7.091 (2.38); 7.0715 (3.23); 7.0517 (1.74); 4.2493 (0.71); 4.2314 (0.93); 4.2136 (0.74); 4.1963 (0.33); 3.9594 (16); 3.3402 (27.46); 2.8908 (2.98); 2.8731 (2.73); 2.5041 (17.82); 2.5 (15.57); 1.1927 (5.75); 1.1763 (5.8); −0.0002 (6.51) |
| 5-80 | 4-chlorophenyl | N(CH3) | CH2 | CH2 | H | |

TABLE 6

Compounds of the formula I-6

I-6

| Ex. No. | X | L¹ | L² | L³ | Y | Physical data: ¹H-NMR, δ [ppm] or CAS or patent No. |
|---|---|---|---|---|---|---|
| 6-1 | 3-methyl-2-thienyl | CH2 | CH2 | — | H | |
| 6-2 | 2,4-dichlorophenyl | CH2 | CH2 | CH2 | H | compound No. 6-2, solvent: spectrometer: 399.95 MHz 7.6931 (5.88); 7.6793 (6.11); 7.5677 (4.29); 7.5625 (4.38); 7.5055 (0.8); 7.4911 (1.52); 7.4767 (0.79); 7.4167 (2.38); 7.396 (5.89); 7.3731 (4.19); 7.3679 (3.82); 7.3525 (1.62); 7.3472 (1.61); 7.1121 (6.09); 7.0982 (5.83); 4.2841 (2.28); 4.2666 (7.51); 4.2491 (7.58); 4.2317 (2.34); 3.3386 (81.64); 3.3287 (4.96); 3.3131 (3.75); 3.2963 (1.48); 2.7431 (2.5); 2.7244 (3.13); 2.7046 (2.67); 2.5439 (4.54); 2.5271 (0.54); 2.5223 (0.86); 2.5137 (9.69); 2.5092 (19.29); 2.5046 (25.6); 2.5 (18.54); 2.4954 (8.72); 1.8254 (0.72); 1.8079 (1.93); 1.7888 (2.4); 1.77 (1.87); 1.7525 (0.63); 1.3855 (7.72); 1.3681 (16); 1.3506 (7.5); −0.0002 (0.89) |
| 6-3 | 4-chlorophenyl | CH2 | CH2 | — | H | |
| 6-4 | 2,4-dichlorophenyl | CH2 | CH2 | — | H | |
| 6-5 | 4-chlorophenyl | CH(OCH3) | CH(CH3) | — | H | |
| 6-6 | 2,4-dichlorophenyl | CH(OCH3) | CH(CH3) | — | H | |
| 6-7 | 4-chlorophenyl | CH(CH3) | CH2 | — | H | [DMSO]: 7.69, d, 1H; 7.37, d, 2H; 7.25, d, 2H; 7.18, d, NH; 7.09, d, 1H; 4.25-4.14, m, 3H; 2.82, d, 2H; 1.29, t, 3H; 1.14, d, 3H |
| 6-8 | 2,4-dichlorophenyl | CH(CH3) | CH2 | — | H | |
| 6-9 | 4-chlorophenyl | CH2 | CH(CH3) | — | H | |
| 6-10 | 2,4-dichlorophenyl | CH2 | CH(CH3) | — | H | |
| 6-11 | 4-chlorophenyl | C(CH3)2 | CH2 | — | H | |

TABLE 6-continued

Compounds of the formula I-6

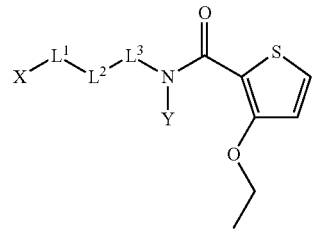

I-6

| Ex. No. | X | $L^1$ | $L^2$ | $L^3$ | Y | Physical data: $^1$H-NMR, δ [ppm] or CAS or patent No. |
|---|---|---|---|---|---|---|
| 6-12 | 2,4-dichlorophenyl | C(CH3)2 | CH2 | — | H | |
| 6-13 | 2-chlorophenyl | CH2 | CH2 | — | H | |
| 6-14 | 3,4-dichlorophenyl | CH2 | CH2 | — | H | |
| 6-15 | 3,5-dichlorophenyl | CH2 | CH2 | — | H | |
| 6-16 | 3-chlorophenyl | CH2 | CH2 | — | H | |
| 6-17 | 2-fluorophenyl | CH2 | CH2 | — | H | |
| 6-18 | 2,6-difluorophenyl | CH2 | CH2 | — | H | |
| 6-19 | 2,6-dichlorophenyl | CH2 | CH2 | — | H | |
| 6-20 | 3-(trifluoromethyl)phenyl | CH2 | CH2 | — | H | CAS: 1022443-07-7 |
| 6-21 | 4-(trifluoromethyl)phenyl | CH2 | CH2 | — | H | |
| 6-22 | 2-methylphenyl | CH2 | CH2 | — | H | |
| 6-23 | 2,4,6-trimethylphenyl | CH2 | CH2 | — | H | |
| 6-24 | 3,4-bismethoxyphenyl | CH2 | CH2 | — | H | |
| 6-25 | phenyl | CH2 | CH2 | — | H | |
| 6-26 | 4-chlorophenyl | C(CH2—CH2) | CH2 | — | H | |
| 6-27 | 2,4-dichlorophenyl | C(CH2—CH2) | CH2 | — | H | |
| 6-28 | 4-chlorophenyl | CH2 | C(CH2—CH2) | — | H | |
| 6-29 | 2,4-dichlorophenyl | CH2 | C(CH2—CH2) | — | H | |
| 6-30 | 4-chlorophenyl | O | CH2 | CH2 | H | |
| 6-31 | 2,4-dichlorophenyl | O | CH2 | CH2 | H | compound No. 6-31, solvent: [DMSO], spectrometer: 399.95 MHz 7.7264 (5.52); 7.7126 (5.85); 7.6937 (1.09); 7.6796 (2.14); 7.6653 (1.13); 7.5916 (5.02); 7.5851 (5.41); 7.3872 (2.53); 7.3807 (2.41); 7.365 (3.43); 7.3586 (3.35); 7.2439 (5.76); 7.2216 (4.3); 7.1218 (5.95); 7.108 (5.75); 4.2743 (2.4); 4.2568 (7.71); 4.2393 (7.81); 4.2218 (2.54); 4.1994 (3.23); 4.1857 (6.99); 4.1721 (3.66); 3.7205 (1.81); 3.7067 (4.99); 3.6927 (4.87); 3.6788 (1.67); 3.3285 (79.46); 2.5424 (7.29); 2.5254 (0.83); 2.5117 (17.49); 2.5076 (34.69); 2.5031 (46.14); 2.4987 (35.2); 1.3303 (7.85); 1.3128 (16); 1.2954 (7.69); −0.0002 (1.17) |
| 6-32 | 4-chlorophenyl | CH2 | CH2 | CH2 | H | |
| 6-33 | 4-chlorophenyl | NCH3 | CH2 | CH2 | H | |
| 6-34 | 2,4-dichlorophenyl | NCH3 | CH2 | CH2 | H | |
| 6-35 | 4-chlorophenyl | CH(OCH3) | CH2 | — | H | |
| 6-36 | 2,4-dichlorophenyl | CH(OCH3) | CH2 | — | H | |
| 6-37 | 2-thienyl | CH2 | CH2 | — | H | compound No. 6-37, solvent: [DMSO], spectrometer: 399.95 MHz 7.6972 (5.59); 7.6834 (5.88); 7.5202 (1.04); 7.5062 (1.95); 7.4922 (1.09); 7.3773 (3.09); 7.3745 (3.05); 7.3646 (3.39); 7.3617 (3.18); 7.0945 (6.15); 7.0806 (5.93); 6.9891 (2.46); 6.9805 (3.59); 6.9765 (2.5); 6.9678 (3.37); 6.9381 (3.6); 6.9305 (2.69); 4.2217 (2.47); 4.2041 (7.85); 4.1866 (7.97); 4.1692 (2.6); 3.5802 (1.96); 3.5634 (5.28); 3.5481 (5.52); 3.5315 (2.23); 3.3282 (54.19); 3.0541 (3.58); 3.0371 (7); 3.0201 (3.22); 2.5064 (28.37); 2.502 (37.77); 2.4976 (28.92); 1.2767 (7.89); 1.2592 (16); 1.2417 (7.77); −0.0002 (0.57) |
| 6-38 | 3-thienyl | CH2 | CH2 | — | H | |
| 6-39 | 2-furyl | CH2 | CH2 | — | H | |
| 6-40 | 3-furyl | CH2 | CH2 | — | H | |
| 6-41 | phenyl | CH2 | CH2 | CH(CH3) | H | |
| 6-42 | phenyl | CH2 | CH2 | CH2 | H | |
| 6-43 | 2-Cl-phenyl | CH2 | CH2 | CH(CH3) | H | |
| 6-44 | 4-t-butylphenyl | CH2 | CH2 | CH2 | H | |
| 6-45 | 4-methylphenyl | CH2 | CH2 | CH2 | H | |
| 6-46 | phenyl | CH2 | CH2 | CH(CH2CH3) | H | |
| 6-47 | 2-methoxyphenyl | CH2 | CH2 | CH2 | H | |
| 6-48 | 2-methylphenyl | CH2 | CH2 | CH2 | H | |
| 6-49 | 3-methylphenyl | CH2 | CH2 | CH2 | H | |
| 6-50 | 3-chlorophenyl | CH2 | CH2 | CH2 | H | |
| 6-51 | 2,6-difluorophenyl | CH2 | CH2 | CH2 | H | compound No. 6-51, solvent: [DMSO], spectrometer: 399.95 MHz |

TABLE 6-continued

Compounds of the formula I-6

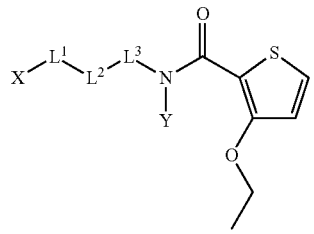

I-6

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 7.6975 (5.44); 7.6837 (5.71); 7.5395 (1.16); 7.5254 (2.18); 7.5113 (1.2); 7.3505 (0.57); 7.3333 (1.35); 7.33 (1.3); 7.3127 (2.54); 7.2921 (1.67); 7.2751 (0.75); 7.1166 (6.24); 7.1028 (6.27); 7.091 (3.65); 7.0712 (5.73); 7.0514 (2.99); 7.038 (0.41); 4.2897 (2.53); 4.2722 (7.97); 4.2547 (8.09); 4.2373 (2.63); 3.332 (25.51); 3.3187 (2.12); 3.302 (4.8); 3.2862 (4.85); 3.2697 (1.88); 2.6936 (2.46); 2.6748 (4.71); 2.656 (2.72); 2.5441 (0.45); 2.509 (18.73); 2.5046 (24.99); 2.5003 (19.41); 1.7933 (0.94); 1.7757 (2.93); 1.7569 (3.9); 1.7387 (2.84); 1.7212 (0.84); 1.3934 (7.91); 1.3759 (16); 1.3664 (1.16); 1.3584 (7.85); −0.0002 (0.45) |
| 6-52 | 4-chlorophenyl | CH2 | CH2 | CH2 | H | |
| 6-53 | 2,6-dichlorophenyl | CH2 | CH2 | CH(CH3) | H | |
| 6-54 | 3,5-dichlorophenyl | CH2 | CH2 | CH(CH3) | H | |
| 6-55 | 2,6-dimethylphenyl | CH2 | CH2 | CH2 | H | |
| 6-56 | 2,5-dichlorophenyl | CH2 | CH2 | CH2 | H | |
| 6-57 | 4-isopropoxyphenyl | CH2 | CH2 | CH2 | H | |
| 6-58 | 3-trifluoromethylphenyl | CH2 | CH2 | CH(CH3) | H | |
| 6-59 | 4-methylphenyl | CH2 | CH2 | CH(CH3) | H | |
| 6-60 | 2-methylphenyl | CH2 | CH2 | CH(CH3) | H | |
| 6-61 | 3,4-dichlorophenyl | CH2 | CH2 | CH(CH3) | H | |
| 6-62 | 3,5-dichlorophenyl | CH2 | CH2 | CH2 | H | |
| 6-63 | 2,6-dimethylphenyl | CH2 | CH2 | CH(CH3) | H | |
| 6-64 | 4-trifluoromethylphenyl | CH2 | CH2 | CH(CH3) | H | |
| 6-65 | 2,5-dichlorophenyl | CH2 | CH2 | CH(CH3) | H | |
| 6-66 | 4-phenoxyphenyl | CH2 | CH2 | CH2 | H | |
| 6-67 | 3-chlorophenyl | CH2 | CH2 | CH(CH3) | H | |
| 6-68 | 4-phenoxyphenyl | CH2 | CH2 | CH(CH3) | H | |
| 6-69 | 2,4-dichlorophenyl | CH2 | CH2 | CH(CH3) | H | |
| 6-70 | 2-difluoromethoxyphenyl | CH2 | CH2 | CH(CH3) | H | |
| 6-71 | 4-methoxyphenyl | CH2 | CH2 | CH2 | H | |
| 6-72 | 4-chlorophenyl | CH2 | CH2 | CH(CH3) | H | |
| 6-73 | 4-chlorophenyl | CH2 | CH2 | CH(i-propyl) | H | |
| 6-74 | 4-fluorophenyl | CH2 | CH2 | CH2 | H | |
| 6-75 | 4-chlorophenyl | CH2 | CH2 | CH(n-propyl) | H | |
| 6-76 | 4-chlorophenyl | CH2 | CH2 | CH(t-butyl) | H | |
| 6-77 | 2-chlorophenyl | CH2 | CH2 | CH2 | H | |
| 6-78 | 2-thienyl | CH2 | CH2 | CH2 | H | compound No. 6-78, solvent: [DMSO], spectrometer: 399.95 MHz 7.696 (5.55); 7.6822 (5.86); 7.4984 (1.13); 7.4843 (2.09); 7.4701 (1.17); 7.325 (3.18); 7.3232 (2.97); 7.3223 (3.01); 7.3122 (3.52); 7.3104 (3.17); 7.3095 (3.19); 7.1147 (6.22); 7.1008 (5.96); 6.9534 (2.59); 6.9448 (3.55); 6.9408 (2.68); 6.9322 (3.22); 6.8846 (3.65); 6.8775 (2.97); 4.2878 (2.52); 4.2703 (7.94); 4.2528 (8.07); 4.2354 (2.65); 3.347 (2.19); 3.3295 (31.18); 3.3146 (5.41); 3.2979 (2.23); 2.8611 (3.39); 2.842 (5.86); 2.8229 (3.7); 2.5246 (0.61); 2.5069 (19.67); 2.5026 (25.81); 2.4984 (19.91); 1.8865 (1.08); 1.8686 (3.25); 1.8498 (4.32); 1.8316 (3.17); 1.8137 (1); 1.3951 (7.95); 1.3776 (16); 1.3601 (7.86); −0.0002 (0.45) |

TABLE 7

Compounds of the formula I-7

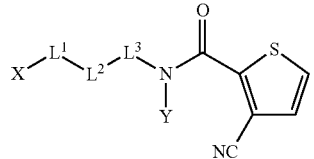

I-7

| Ex. No. | X | L$^1$ | L$^2$ | L$^3$ | Y | Physical data: $^1$H-NMR, δ [ppm] or CAS or patent No. |
|---|---|---|---|---|---|---|
| 7-1 | 3-methyl-2-thienyl | CH2 | CH2 | — | H | |
| 7-2 | 2,4-dichlorophenyl | CH2 | CH2 | CH2 | H | |
| 7-3 | 4-chlorophenyl | CH2 | CH2 | — | H | [DMSO], spectrometer: 399.95 MHz 8.7637 (1.66); 8.7502 (3.17); 8.7364 (1.7); 7.9252 (10.03); 7.9123 (10.75); 7.5535 (10.65); 7.5407 (10.07); 7.3609 (8.8); 7.3562 (3.53); 7.3448 (4.38); 7.3398 (16); 7.334 (2.76); 7.2856 (13.93); 7.2645 (8.1); 3.4844 (2.63); 3.4672 (5.67); 3.4522 (5.54); 3.4342 (2.92); 3.3357 (35.3); 2.8535 (5.02); 2.8353 (8.73); 2.8174 (4.53); 2.6767 (0.4); 2.6723 (0.55); 2.6679 (0.42); 2.5256 (1.69); 2.5119 (27.98); 2.5077 (55.22); 2.5032 (72.9); 2.4987 (54.91); 2.4945 (28.18); 2.3347 (0.34); 2.33 (0.48); 2.3255 (0.35); 0.0079 (0.49); −0.0002 (13.72); −0.0084 (0.58) |
| 7-4 | 2,4-dichlorophenyl | CH2 | CH2 | — | H | [DMSO], spectrometer: 399.95 MHz 8.791 (1.29); 8.7773 (2.55); 8.7634 (1.36); 7.9238 (7.38); 7.911 (7.94); 7.5902 (5.62); 7.5516 (7.8); 7.5388 (7.38); 7.392 (0.43); 7.3731 (16); 7.3526 (0.37); 7.3486 (0.5); 5.7585 (0.68); 3.5117 (1.9); 3.4947 (4.75); 3.4796 (4.87); 3.4626 (2.18); 3.4101 (0.4); 3.3554 (231.44); 2.9775 (3.9); 2.96 (7.5); 2.9426 (3.52); 2.6739 (0.39); 2.5272 (1.22); 2.5135 (21.16); 2.5094 (42.13); 2.5049 (55.83); 2.5004 (42.57); 2.4962 (22.27); 2.3316 (0.38); 1.3362 (0.33); 1.249 (0.41); 0.0079 (0.4); −0.0002 (10.88); −0.0084 (0.49) |
| 7-5 | 4-chlorophenyl | CH(OCH3) | CH(CH3) | — | H | |
| 7-6 | 2,4-dichlorophenyl | CH(OCH3) | CH(CH3) | — | H | |
| 7-7 | 4-chlorophenyl | CH(CH3) | CH2 | — | H | |
| 7-8 | 2,4-dichlorophenyl | CH(CH3) | CH2 | — | H | |
| 7-9 | 4-chlorophenyl | CH2 | CH(CH3) | — | H | |
| 7-10 | 2,4-dichlorophenyl | CH2 | CH(CH3) | — | H | |
| 7-11 | 4-chlorophenyl | C(CH3)2 | CH2 | — | H | |
| 7-12 | 2,4-dichlorophenyl | C(CH3)2 | CH2 | — | H | |
| 7-13 | 2-chlorophenyl | CH2 | CH2 | — | H | |
| 7-14 | 3,4-dichlorophenyl | CH2 | CH2 | — | H | |
| 7-15 | 3,5-dichlorophenyl | CH2 | CH2 | — | H | |
| 7-16 | 3-chlorophenyl | CH2 | CH2 | — | H | |
| 7-17 | 2-fluorophenyl | CH2 | CH2 | — | H | |
| 7-18 | 2,6-difluorophenyl | CH2 | CH2 | — | H | [DMSO], spectrometer: 399.95 MHz 8.8536 (2.47); 8.8394 (4.77); 8.8253 (2.54); 7.9229 (14.9); 7.9101 (15.96); 7.552 (16); 7.5391 (15.07); 7.3681 (1.28); 7.3512 (2.93); 7.3473 (2.78); 7.3303 (5.68); 7.3131 (2.98); 7.3096 (3.65); 7.2927 (1.65); 7.1043 (0.78); 7.0998 (1.07); 7.0876 (8.02); 7.0679 (12.59); 7.057 (1.95); 7.048 (6.83); 7.0356 (1.02); 5.7606 (0.46); 3.4601 (3.72); 3.4432 (9.39); 3.4273 (9.56); 3.4105 (4.19); 3.3369 (50.68); 2.9207 (5.93); 2.9033 (11.25); 2.8858 (5.46); 2.6772 (0.44); 2.6729 (0.61); 2.6685 (0.45); 2.5261 (2.15); 2.5125 (34.74); 2.5083 (68.66); 2.5038 (90.7); 2.4993 (68.58); 2.495 (35.71); 2.3349 (0.43); 2.3305 (0.61); 2.326 (0.45); 1.3363 (0.51); 1.2496 (0.6); 0.0079 (0.6); −0.0002 (16.59); −0.0084 (0.78) |
| 7-19 | 2,6-dichlorophenyl | CH2 | CH2 | — | H | [DMSO], spectrometer: 399.95 MHz 8.8706 (1.58); 8.8566 (3.12); 8.8422 (1.63); 7.923 (9.28); 7.9102 (9.9); 7.5517 (10.16); 7.5388 (9.57); 7.4689 (11.6); 7.4489 (16); 7.4285 (0.32); 7.3095 (5.44); 7.2903 (5.71); 7.2884 (5.66); 7.2803 (0.56); 7.2692 (3.63); 7.2618 (0.38); 5.7598 (1.47); 3.5105 (2.09); 3.4939 (5.53); 3.4771 (5.61); 3.4609 (2.57); 3.3736 (0.52); 3.3434 (148.2); 3.189 (4.65); 3.1712 (8.14); 3.154 (3.8); 2.9768 (0.44); 2.6733 (0.43); 2.6688 (0.33); 2.5086 (47.99); 2.5042 (63.51); 2.4997 (48.43); 2.4956 (25.51); 2.331 (0.42); 1.2494 (0.37); −0.0002 (8.94); −0.0084 (0.43) |

TABLE 7-continued

Compounds of the formula I-7

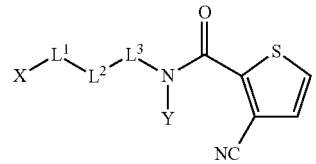

I-7

| Ex. No. | X | L¹ | L² | L³ | Y | Physical data: ¹H-NMR, δ [ppm] or CAS or patent No. |
|---|---|---|---|---|---|---|
| 7-20 | 3-(trifluoromethyl)phenyl | CH2 | CH2 | — | H | |
| 7-21 | 4-(trifluoromethyl)phenyl | CH2 | CH2 | — | H | |
| 7-22 | 2-methylphenyl | CH2 | CH2 | — | H | |
| 7-23 | 2,4,6-trimethylphenyl | CH2 | CH2 | — | H | |
| 7-24 | 3,4-bismethoxyphenyl | CH2 | CH2 | — | H | |
| 7-25 | phenyl | CH2 | CH2 | — | H | |
| 7-26 | 4-chlorophenyl | C(CH2—CH2) | CH2 | — | H | |
| 7-27 | 2,4-dichlorophenyl | C(CH2—CH2) | CH2 | — | H | |
| 7-28 | 4-chlorophenyl | CH2 | C(CH2—CH2) | — | H | |
| 7-29 | 2,4-dichlorophenyl | CH2 | C(CH2—CH2) | — | H | |
| 7-30 | 4-chlorophenyl | O | CH2 | CH2 | H | |
| 7-31 | 2,4-dichlorophenyl | O | CH2 | CH2 | H | [DMSO], spectrometer: 399.95 MHz 8.8522 (1.07); 8.8389 (2.09); 8.8258 (1.1); 8.1029 (1.26); 8.0993 (1.04); 8.0903 (1.05); 8.0868 (1.31); 7.9491 (6.61); 7.9363 (7.1); 7.919 (0.55); 7.6307 (0.37); 7.5719 (14.11); 7.5656 (7.94); 7.5591 (7.26); 7.5441 (0.38); 7.5377 (0.35); 7.5041 (0.57); 7.4912 (0.49); 7.3874 (2.9); 7.3809 (2.79); 7.3773 (1.56); 7.3705 (1.38); 7.3652 (4.09); 7.3587 (4.04); 7.3551 (2.09); 7.3485 (1.63); 7.3406 (0.34); 7.3351 (0.33); 7.2462 (6.01); 7.2239 (4.49); 7.2093 (0.34); 7.1932 (0.47); 7.1872 (2.26); 7.1649 (1.81); 6.5864 (1.34); 6.5827 (1.08); 6.5777 (0.8); 6.574 (1.09); 6.5702 (1.33); 5.7607 (1.41); 4.3737 (0.33); 4.2346 (3.15); 4.2201 (7.07); 4.2057 (3.51); 4.1882 (0.39); 4.1142 (0.42); 4.1045 (0.37); 4.0894 (0.39); 4.0184 (1.55); 4.0041 (3.2); 3.9898 (1.62); 3.7464 (0.48); 3.6652 (1.75); 3.6511 (4.89); 3.637 (4.76); 3.6227 (1.68); 3.5065 (0.59); 3.4891 (0.33); 3.3356 (11.99); 3.0722 (0.34); 3.0672 (0.41); 3.0541 (0.37); 2.9425 (16); 2.9058 (1.58); 2.8915 (3.16); 2.8771 (1.58); 2.677 (0.39); 2.6725 (0.55); 2.668 (0.4); 2.5259 (1.55); 2.5122 (30.72); 2.5079 (61.96); 2.5034 (82.32); 2.4989 (62.24); 2.4946 (32.17); 2.4309 (0.33); 2.3481 (0.55); 2.3303 (0.78); 2.3257 (0.52); 2.1891 (0.75); 2.1818 (3.87); 2.1725 (0.55); 2.0965 (0.49); 2.0722 (3.69); 2.0592 (1.1); 1.8245 (0.48); 1.7375 (2.42); 1.6581 (0.35); 1.325 (0.48); 1.2271 (6.23); 1.1838 (0.45); 1.1659 (0.92); 1.148 (0.44); 1.0533 (0.61); 1.0352 (1.28); 1.0171 (0.58); 0.9532 (1.71); 0.9368 (1.74); 0.0079 (0.58); −0.0002 (17.26); −0.0085 (0.78) |
| 7-32 | 4-chlorophenyl | CH2 | CH2 | CH2 | H | |
| 7-33 | 4-chlorophenyl | NCH3 | CH2 | CH2 | H | |
| 7-34 | 2,4-dichlorophenyl | NCH3 | CH2 | CH2 | H | |
| 7-35 | 4-chlorophenyl | CH(OCH3) | CH2 | — | H | |
| 7-36 | 2,4-dichlorophenyl | CH(OCH3) | CH2 | — | H | |
| 7-37 | 2-thienyl | CH2 | CH2 | — | H | compound No. 7-37, solvent: [DMSO], spectrometer: 399.95 MHz 8.839 (2.59); 8.8256 (4.79); 8.8124 (2.64); 8.3189 (0.4); 7.9395 (14.92); 7.9266 (16); 7.5661 (15.86); 7.5532 (14.91); 7.3585 (7.66); 7.3555 (7.79); 7.3459 (8.58); 7.3429 (8.24); 6.9743 (6.13); 6.9657 (9.59); 6.9617 (6.17); 6.9531 (9.46); 6.9321 (9.27); 6.9259 (6.25); 3.5065 (4.36); 3.4888 (10.03); 3.4742 (10.22); 3.4564 (5.21); 3.3375 (161.8); 3.0819 (8.6); 3.064 (15.33); 3.046 (7.4); 2.6765 (0.71); 2.672 (0.95); 2.6676 (0.73); 2.5252 (3.11); 2.5074 (102.9); 2.503 (135.05); 2.4985 (102.17); 2.334 (0.66); 2.3298 (0.9); 2.3252 (0.67); 1.336 (0.54); 1.2493 (0.67); 0.0079 (0.65); −0.0002 (17.56); −0.0083 (0.81) |
| 7-38 | 3-thienyl | CH2 | CH2 | — | H | |
| 7-39 | 2-furyl | CH2 | CH2 | — | H | |
| 7-40 | 3-furyl | CH2 | CH2 | — | H | |
| 7-41 | phenyl | CH2 | CH2 | CH(CH3) | H | |
| 7-42 | phenyl | CH2 | CH2 | CH2 | H | |
| 7-43 | 2-Cl-phenyl | CH2 | CH2 | CH(CH3) | H | |
| 7-44 | 4-t-butylphenyl | CH2 | CH2 | CH2 | H | |

TABLE 7-continued

Compounds of the formula I-7

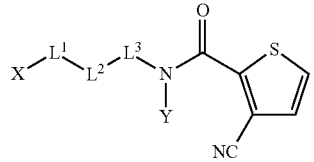

I-7

| Ex. No. | X | L¹ | L² | L³ | Y | Physical data: ¹H-NMR, δ [ppm] or CAS or patent No. |
|---|---|---|---|---|---|---|
| 7-45 | 4-methylphenyl | CH2 | CH2 | CH2 | H | |
| 7-46 | phenyl | CH2 | CH2 | CH(CH2CH3) | H | |
| 7-47 | 2-methoxyphenyl | CH2 | CH2 | CH2 | H | |
| 7-48 | 2-methylphenyl | CH2 | CH2 | CH2 | H | |
| 7-49 | 3-methylphenyl | CH2 | CH2 | CH2 | H | |
| 7-50 | 3-chlorophenyl | CH2 | CH2 | CH2 | H | |
| 7-51 | 2,6-difluorophenyl | CH2 | CH2 | CH2 | H | [DMSO], spectrometer: 399.95 MHz 8.7549 (2.05); 8.7414 (3.86); 8.7278 (2.09); 8.3188 (0.37); 7.9666 (0.33); 7.9538 (0.41); 7.9341 (14.91); 7.9269 (0.85); 7.9212 (15.91); 7.5855 (0.37); 7.5726 (0.39); 7.5573 (16); 7.5444 (15.04); 7.3519 (1.2); 7.335 (2.69); 7.3311 (2.41); 7.3141 (5.04); 7.3104 (2.27); 7.2967 (2.47); 7.2933 (3.34); 7.2765 (1.51); 7.105 (0.76); 7.1006 (0.94); 7.088 (6.68); 7.0679 (10.99); 7.0559 (1.48); 7.0478 (5.67); 7.0347 (0.81); 6.5468 (0.52); 3.3468 (249.02); 3.2962 (3.34); 3.2789 (6.79); 3.2634 (6.76); 3.246 (3.44); 2.7069 (4.52); 2.6878 (7.65); 2.6688 (5.31); 2.5441 (0.41); 2.5273 (1.94); 2.5225 (2.98); 2.5139 (33.76); 2.5094 (68.38); 2.5049 (90.84); 2.5003 (67.84); 2.4959 (34.13); 2.3361 (0.43); 2.3317 (0.61); 2.3271 (0.44); 1.8234 (1.73); 1.8044 (4.61); 1.786 (6.51); 1.7672 (4.31); 1.7488 (1.53); 1.3367 (0.51); 1.2498 (0.63); 0.008 (0.5); −0.0002 (15.55); −0.0085 (0.6) |
| 7-52 | 4-chlorophenyl | CH2 | CH2 | CH2 | H | [DMSO], spectrometer: 399.95 MHz 8.7403 (1.6); 8.7272 (2.97); 8.7136 (1.63); 7.9373 (9.86); 7.9244 (10.54); 7.5592 (10.41); 7.5463 (9.86); 7.3552 (1.07); 7.3492 (8.86); 7.3444 (3.56); 7.3331 (4.47); 7.3281 (16); 7.3223 (2.8); 7.309 (0.44); 7.273 (14); 7.2519 (8.27); 7.2312 (0.34); 3.345 (103.91); 3.2734 (2.65); 3.2562 (6.23); 3.2416 (6.24); 3.2245 (2.8); 2.678 (0.38); 2.6736 (0.52); 2.6593 (4.6); 2.6406 (7.03); 2.621 (5.08); 2.5271 (1.2); 2.5135 (20.13); 2.5092 (40.08); 2.5047 (52.88); 2.5002 (39.87); 2.4959 (20.52); 2.3314 (0.35); 1.8483 (1.39); 1.8303 (4); 1.8114 (5.31); 1.793 (3.88); 1.7751 (1.25); 1.337 (0.39); 1.2494 (0.47); −0.0002 (7.86); −0.0084 (0.33) |
| 7-53 | 2,6-dichlorophenyl | CH2 | CH2 | CH(CH3) | H | |
| 7-54 | 3,5-dichlorophenyl | CH2 | CH2 | CH(CH3) | H | |
| 7-55 | 2,6-dimethylphenyl | CH2 | CH2 | CH2 | H | |
| 7-56 | 2,5-dichlorophenyl | CH2 | CH2 | CH2 | H | |
| 7-57 | 4-isopropoxyphenyl | CH2 | CH2 | CH2 | H | |
| 7-58 | 3-trifluoromethylphenyl | CH2 | CH2 | CH(CH3) | H | |
| 7-59 | 4-methylphenyl | CH2 | CH2 | CH(CH3) | H | |
| 7-60 | 2-methylphenyl | CH2 | CH2 | CH(CH3) | H | |
| 7-61 | 3,4-dichlorophenyl | CH2 | CH2 | CH(CH3) | H | |
| 7-62 | 3,5-dichlorophenyl | CH2 | CH2 | CH2 | H | |
| 7-63 | 2,6-dimethylphenyl | CH2 | CH2 | CH(CH3) | H | |
| 7-64 | 4-trifluoromethylphenyl | CH2 | CH2 | CH(CH3) | H | |
| 7-65 | 2,5-dichlorophenyl | CH2 | CH2 | CH(CH3) | H | |
| 7-66 | 4-phenoxyphenyl | CH2 | CH2 | CH2 | H | |
| 7-67 | 3-chlorophenyl | CH2 | CH2 | CH(CH3) | H | |
| 7-68 | 4-phenoxyphenyl | CH2 | CH2 | CH(CH3) | H | |
| 7-69 | 2,4-dichlorophenyl | CH2 | CH2 | CH(CH3) | H | |
| 7-70 | 2-difluoromethoxyphenyl | CH2 | CH2 | CH(CH3) | H | |
| 7-71 | 4-methoxyphenyl | CH2 | CH2 | CH2 | H | |
| 7-72 | 4-chlorophenyl | CH2 | CH2 | CH(CH3) | H | |
| 7-73 | 4-chlorophenyl | CH2 | CH2 | CH(i-propyl) | H | |
| 7-74 | 4-fluorophenyl | CH2 | CH2 | CH2 | H | |
| 7-75 | 4-chlorophenyl | CH2 | CH2 | CH(n-propyl) | H | |
| 7-76 | 4-chlorophenyl | CH2 | CH2 | CH(t-butyl) | H | |
| 7-77 | 2-chlorophenyl | CH2 | CH2 | CH2 | H | |

TABLE 7-continued

Compounds of the formula I-7

I-7

$$X-L^1-L^2-L^3-N(Y)-C(=O)-\text{(3-NC-thiophen-2-yl)}$$

| Ex. No. | X | $L^1$ | $L^2$ | $L^3$ | Y | Physical data: $^1$H-NMR, δ [ppm] or CAS or patent No. |
|---|---|---|---|---|---|---|
| 7-78 | 4-chlorophenyl | N(CH3) | CH2 | CH2 | H | compound No. 7-78, solvent: [DMSO], spectrometer: 399.95 MHz<br>8.7475 (0.68); 8.7339 (1.34); 8.7201 (0.71); 7.9284 (3.31); 7.9155 (3.52); 7.554 (3.57); 7.5412 (3.35); 7.1828 (0.44); 7.1742 (4.37); 7.1691 (1.48); 7.1516 (4.8); 7.1428 (0.53); 6.7631 (0.63); 6.7544 (4.51); 6.7318 (4.02); 6.7229 (0.47); 3.5155 (1.15); 3.4986 (2.94); 3.4826 (2.24); 3.4183 (1.22); 3.4033 (2.51); 3.3878 (2.05); 3.3716 (0.74); 3.3307 (60.01); 2.9199 (16); 2.8746 (0.79); 2.542 (19); 2.507 (25.15); 2.5027 (31.73); 2.4983 (23.27); 2.3743 (0.39); −0.0002 (3.58) |

TABLE 8

Compounds of the formula I-8

I-8

$$X-L^1-L^2-L^3-N(Y)-C(=O)-\text{(3-CH}_3\text{-furan-2-yl)}$$

| Ex. No. | X | $L^1$ | $L^2$ | $L^3$ | Y | Physical data: $^1$H-NMR, δ [ppm] or CAS or patent No. |
|---|---|---|---|---|---|---|
| 8-1 | 3-methyl-2-thienyl | CH2 | CH2 | — | H | |
| 8-2 | 2,4-dichlorophenyl | CH2 | CH2 | CH2 | H | compound No. 8-2, solvent: [DMSO], spectrometer: 399.95 MHz<br>8.2244 (0.52); 8.2099 (1); 8.1955 (0.52); 7.6582 (2.82); 7.6541 (2.8); 7.5613 (3.05); 7.556 (3.13); 7.4276 (1.91); 7.4069 (3.86); 7.3725 (2.72); 7.3672 (2.5); 7.3518 (1.3); 7.3465 (1.28); 6.4852 (3); 6.4811 (2.98); 3.337 (46.88); 3.254 (0.97); 3.2368 (2.09); 3.2211 (2.08); 3.2039 (0.99); 2.7131 (1.76); 2.6946 (2.19); 2.6745 (1.94); 2.5436 (10.74); 2.5267 (0.35); 2.5219 (0.56); 2.5134 (6.94); 2.5089 (13.88); 2.5042 (18.41); 2.4996 (13.29); 2.4951 (6.22); 2.2699 (16); 1.8033 (0.5); 1.7844 (1.26); 1.7662 (1.7); 1.7479 (1.18); 1.7294 (0.44); −0.0002 (1.59) |
| 8-3 | 4-chlorophenyl | CH2 | CH2 | — | H | CAS: 1330848-74-2 |
| 8-4 | 2,4-dichlorophenyl | CH2 | CH2 | — | H | [DMSO], spectrometer: 601.6 MHz<br>8.2533 (0.55); 8.2437 (1.08); 8.2341 (0.56); 7.6534 (2.78); 7.6506 (2.81); 7.5762 (2.58); 7.5730 (2.69); 7.3713 (0.79); 7.3680 (0.66); 7.3575 (3.11); 7.3543 (3.31); 7.3480 (4.41); 7.3343 (1.03); 6.4800 (2.88); 6.4772 (2.88); 3.4549 (0.97); 3.4436 (1.99); 3.4330 (1.93); 3.4213 (1.06); 3.3283 (23.69); 2.9365 (1.93); 2.9244 (3.25); 2.9126 (1.79); 2.5434 (7.05); 2.5101 (3.42); 2.5071 (7.69); 2.5041 (10.83); 2.5010 (7.79); 2.4980 (3.55); 2.2571 (16.00); −0.0002 (8.63) |
| 8-5 | 4-chlorophenyl | CH(OCH3) | CH(CH3) | — | H | |
| 8-6 | 2,4-dichlorophenyl | CH(OCH3) | CH(CH3) | — | H | |
| 8-7 | 4-chlorophenyl | CH(CH3) | CH2 | — | H | [DMSO], spectrometer: 601.6 MHz<br>8.1009 (0.58); 8.0913 (1.11); 8.0817 (0.58); 7.6309 (2.83); 7.6281 (2.77); 7.3559 (0.46); 7.3515 (3.81); 7.3483 (1.30); 7.3407 (1.56); 7.3374 (5.63); 7.3332 (0.69); 7.2773 (0.73); 7.2731 (5.14); 7.2699 (1.46); 7.2621 (1.26); 7.2591 (3.56); 7.2547 (0.39); 6.4671 (2.96); 6.4644 (2.85); 3.3811 (0.42); 3.3708 (0.53); |

TABLE 8-continued

Compounds of the formula I-8

I-8

[Structure: X-L¹-L²-L³-N(Y)-C(=O)-furan with 3-CH₃ substituent]

| Ex. No. | X | L¹ | L² | L³ | Y | Physical data: ¹H-NMR, δ [ppm] or CAS or patent No. |
|---|---|---|---|---|---|---|
| | | | | | | 3.3689 (0.56); 3.3590 (1.16); 3.3489 (1.02); 3.3471 (1.10); 3.3367 (1.16); 3.3269 (67.15); 3.3167 (1.04); 3.3069 (0.97); 3.3042 (0.96); 3.2946 (1.27); 3.2851 (0.47); 3.2824 (0.52); 3.2728 (0.45); 3.0742 (0.56); 3.0622 (1.11); 3.0503 (1.09); 3.0384 (0.51); 2.5417 (12.80); 2.5233 (0.33); 2.5203 (0.40); 2.5171 (0.43); 2.5083 (7.97); 2.5054 (16.93); 2.5023 (23.20); 2.4993 (16.75); 2.4963 (7.73); 2.2443 (16.00); 1.1791 (7.28); 1.1675 (7.25); 0.0050 (0.39); −0.0002 (9.65); −0.0057 (0.32) |
| 8-8 | 2,4-dichlorophenyl | CH(CH3) | CH2 | — | H | [DMSO], spectrometer: 601.6 MHz<br>8.1820 (0.66); 8.1723 (1.24); 8.1625 (0.64); 7.6318 (2.92); 7.6291 (2.79); 7.5490 (2.92); 7.5455 (2.93); 7.4479 (1.92); 7.4338 (3.89); 7.4107 (2.32); 7.4071 (2.09); 7.3967 (1.11); 7.3931 (1.08); 6.4670 (3.04); 6.4642 (2.92); 3.5460 (0.52); 3.5341 (1.13); 3.5223 (1.24); 3.5105 (0.69); 3.4201 (1.37); 3.4143 (1.36); 3.4096 (1.70); 3.4044 (1.53); 3.4019 (1.35); 3.3986 (1.21); 3.3919 (1.19); 3.3269 (69.14); 3.3091 (0.97); 2.5421 (9.32); 2.5236 (0.75); 2.5206 (0.93); 2.5175 (1.05); 2.5087 (9.41); 2.5058 (18.83); 2.5028 (25.35);<br>2.4997 (18.16); 2.4968 (8.55); 2.4842 (0.97); 2.2433 (16.00); 1.1680 (7.51); 1.1565 (7.49); 0.0050 (0.37); −0.0002 (8.14); −0.0056 (0.33) |
| 8-9 | 4-chlorophenyl | CH2 | CH(CH3) | — | H | [DMSO], spectrometer: 601.6 MHz<br>7.9941 (1.08); 7.9798 (1.10); 7.6414 (2.71); 7.6386 (2.78); 7.3234 (0.34); 7.3191 (3.63); 7.3160 (1.24); 7.3084 (1.40); 7.3052 (5.46); 7.3011 (0.68); 7.2467 (0.59); 7.2427 (4.72); 7.2396 (1.42); 7.2318 (1.12); 7.2287 (3.33); 7.2246 (0.39); 6.4645 (2.83); 6.4617 (2.85); 4.1700 (0.46); 4.1672 (0.56); 4.1562 (0.83); 4.1454 (0.58); 4.1426 (0.48); 3.3297 (111.93); 2.8835<br>(0.86); 2.8699 (0.86); 2.8610 (1.11); 2.8475 (1.08); 2.7225 (1.08); 2.7122 (1.11); 2.7001 (0.86); 2.6897 (0.83); 2.5418 (13.67); 2.5204 (0.33); 2.5085 (7.69); 2.5055 (17.49); 2.5024 (24.75); 2.4994 (17.97); 2.4964 (8.28); 2.2240 (16.00); 1.1286 (7.02); 1.1176 (7.03); −0.0002 (9.01) |
| 8-10 | 2,4-dichlorophenyl | CH2 | CH(CH3) | — | H | |
| 8-11 | 4-chlorophenyl | C(CH3)2 | CH2 | — | H | [DMSO], spectrometer: 601.6 MHz<br>7.6613 (0.33); 7.6509 (0.67); 7.6399 (0.39); 7.6352 (1.85); 7.6324 (1.81); 7.4262 (2.18); 7.4228 (0.77); 7.4153 (0.95); 7.4117 (3.81); 7.4073 (0.46); 7.3731 (0.44); 7.3686 (3.79); 7.3651 (0.95); 7.3575 (0.77); 7.3542 (2.28); 6.4718 (1.81); 6.4690 (1.80); 3.4008 (2.66); 3.3900 (2.66); 3.3311 (73.50); 2.5420 (6.69); 2.5086 (5.02); 2.5056 (11.04); 2.5026 (15.37); 2.4996<br>(11.02); 2.4966 (5.02); 2.2348 (10.09); 1.2561 (16.00); −0.0002 (4.16) |
| 8-12 | 2,4-dichlorophenyl | C(CH3)2 | CH2 | — | H | [DMSO], spectrometer: 601.6 MHz<br>7.7625 (0.35); 7.7518 (0.69); 7.7412 (0.39); 7.6249 (1.80); 7.6221 (1.78); 7.5364 (2.21); 7.5325 (2.32); 7.4594 (1.56); 7.4450 (2.10); 7.3650 (1.43); 7.3611 (1.36); 7.3507 (1.11); 7.3468 (1.08); 6.4625 (1.84); 6.4598 (1.83); 3.7328 (2.62); 3.7220 (2.61); 3.3285 (246.39); 3.3149 (0.46); 2.5413 (8.83); 2.5230 (0.53);<br>2.5199 (0.63); 2.5168 (0.57); 2.5080 (14.39); 2.5050 (32.45); 2.5019 (45.35); 2.4989 (32.42); 2.4958 (14.43); 2.2178 (10.38); 1.4075 (16.00); 0.0052 (0.51); −0.0002 (19.26); −0.0057 (0.57) |

TABLE 8-continued

Compounds of the formula I-8

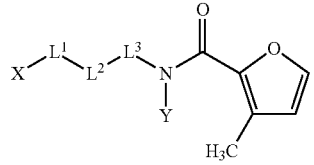

I-8

| Ex. No. | X | L¹ | L² | L³ | Y | Physical data: ¹H-NMR, δ [ppm] or CAS or patent No. |
|---|---|---|---|---|---|---|
| 8-13 | 2-chlorophenyl | CH2 | CH2 | — | H | [DMSO], spectrometer: 601.6 MHz<br>8.2580 (0.48); 8.2487 (0.92); 8.2392 (0.49); 7.6540 (2.63); 7.6512 (2.61); 7.4295 (1.40); 7.4270 (1.30); 7.4168 (1.75); 7.4142 (1.69); 7.3410 (1.01); 7.3379 (1.18); 7.3287 (1.47); 7.3256 (1.67); 7.2908 (0.70); 7.2884 (0.81); 7.2786 (1.79); 7.2761 (1.72); 7.2665 (1.22); 7.2638 (1.05); 7.2605 (1.35); 7.2572 (1.36); 7.2478 (1.43); 7.2447 (1.42); 7.2354 (0.55); 7.2324 (0.49); 6.4816 (2.73); 6.4788 (2.73); 3.4608 (1.04); 3.4505 (1.70); 3.4389 (1.55); 3.4364 (1.82); 3.4264 (1.13); 3.3310 (181.76); 2.9524 (1.91); 2.9397 (2.58);<br>2.9278 (1.77); 2.5416 (15.14); 2.5233 (0.38); 2.5202 (0.47); 2.5171 (0.44); 2.5083 (10.29); 2.5053 (23.29);<br>2.5022 (32.98); 2.4992 (23.49); 2.4962 (10.64); 2.2634 (16.00); −0.0002 (4.03) |
| 8-14 | 3,4-dichlorophenyl | CH2 | CH2 | — | H | [DMSO], spectrometer: 601.6 MHz<br>8.2047 (0.54); 8.1951 (1.03); 8.1858 (0.54); 7.6519 (2.75); 7.6491 (2.78); 7.5429 (3.21); 7.5292 (3.54); 7.5015 (2.66); 7.4981 (2.76); 7.2266 (1.51); 7.2232 (1.50); 7.2129 (1.39); 7.2096 (1.40); 6.4806 (2.86); 6.4778 (2.82); 3.4456 (1.01); 3.4340 (2.18); 3.4239 (2.16); 3.4122 (1.10); 3.3316 (204.25); 3.3131 (0.35);<br>2.8338 (1.79); 2.8219 (3.35); 2.8101 (1.68); 2.5418 (15.80); 2.5235 (0.42); 2.5204 (0.51); 2.5173 (0.47); 2.5084 (12.10); 2.5055 (27.47); 2.5024 (39.05); 2.4994 (28.35); 2.4964 (13.25); 2.2537 (16.00); −0.0002 (4.73) |
| 8-15 | 3,5-dichlorophenyl | CH2 | CH2 | — | H | [DMSO], spectrometer: 601.6 MHz<br>8.2134 (0.53); 8.2041 (1.03); 8.1946 (0.53); 7.6572 (2.71); 7.6544 (2.70); 7.4295 (1.39); 7.4264 (2.74); 7.4232 (1.50); 7.2998 (5.88); 7.2966 (5.65); 6.4830 (2.85); 6.4802 (2.76); 3.4567 (0.97); 3.4451 (2.22); 3.4350 (2.23); 3.4234 (1.06); 3.3345 (121.94); 2.8476<br>(1.71); 2.8359 (3.32); 2.8242 (1.61); 2.5426 (11.75); 2.5093 (6.44); 2.5063 (14.44); 2.5032 (20.30); 2.5002<br>(14.66); 2.4972 (6.66); 2.2543 (16.00); −0.0002 (3.03) |
| 8-16 | 3-chlorophenyl | CH2 | CH2 | — | H | CAS: 1043374-79-3 |
| 8-17 | 2-fluorophenyl | CH2 | CH2 | — | H | CAS: 1043270-08-1 |
| 8-18 | 2,6-difluorophenyl | CH2 | CH2 | — | H | [DMSO], spectrometer: 601.6 MHz<br>8.2999 (0.51); 8.2901 (0.98); 8.2805 (0.51); 7.6472 (2.70); 7.6444 (2.68); 7.3275 (0.64); 7.3248 (0.61); 7.3136 (1.21); 7.3024 (0.64); 7.2998 (0.72); 7.0656 (1.69); 7.0526 (2.62); 7.0449 (0.34); 7.0394 (1.51); 6.4765 (2.83); 6.4737 (2.81); 3.4012 (0.93); 3.3903 (1.99); 3.3777 (1.95); 3.3672 (1.02); 3.3395 (142.03);<br>2.8751 (1.33); 2.8630 (2.35); 2.8512 (1.24); 2.5430 (13.70); 2.5097 (6.17); 2.5067 (13.45); 2.5036 (18.62); 2.5006 (13.27); 2.4976 (5.94); 2.2531 (16.00); −0.0002 (0.79) |
| 8-19 | 2,6-dichlorophenyl | CH2 | CH2 | — | H | [DMSO], spectrometer: 601.6 MHz<br>8.3392 (0.53); 8.3294 (1.05); 8.3197 (0.54); 7.6538 (2.65); 7.6511 (2.71); 7.4513 (5.52); 7.4379 (6.67); 7.2889 (2.12); 7.2756 (2.61); 7.2621 (1.59); 6.4793 (2.75); 6.4765 (2.82); 3.4316 (0.94); 3.4212 (1.85); 3.4172 (1.06); 3.4097 (1.51); 3.4071 (1.92); 3.3972 (1.09); 3.3352 (90.12); 3.3346 (94.30); 3.1452 (1.99);<br>3.1323 (2.48); 3.1207 (1.72); 2.5427 (10.35); 2.5094 (6.80); 2.5064 (15.36); 2.5034 (21.69); 2.5003 |

TABLE 8-continued

Compounds of the formula I-8

I-8

| Ex. No. | X | L¹ | L² | L³ | Y | Physical data: ¹H-NMR, δ [ppm] or CAS or patent No. |
|---|---|---|---|---|---|---|
| | | | | | | (15.57); 2.4973 (7.13); 2.2610 (16.00); −0.0002 (4.04) |
| 8-20 | 3-(trifluoromethyl)phenyl | CH2 | CH2 | — | H | [DMSO], spectrometer: 601.6 MHz 8.2219 (0.57); 8.2125 (1.05); 8.2030 (0.56); 7.6499 (2.92); 7.6472 (2.84); 7.5688 (2.78); 7.5578 (0.96); 7.5546 (1.52); 7.5401 (2.57); 7.5376 (3.85); 7.5253 (1.05); 6.4792 (3.00); 6.4764 (2.89); 3.4759 (1.07); 3.4645 (2.14); 3.4542 (2.10); 3.4421 (1.20); 3.3360 (129.83); 2.9322 (1.87); 2.9200 (3.20); 2.9081 (1.78); 2.5428 (14.60); 2.5214 (0.32); 2.5094 (7.43); 2.5064 (16.06); 2.5034 (22.23); 2.5004 (16.13); 2.4974 (7.56); 2.2605 (0.69); 2.2520 (16.00); −0.0002 (3.79) |
| 8-21 | 4-(trifluoromethyl)phenyl | CH2 | CH2 | — | H | CAS: 1325832-12-9 |
| 8-22 | 2-methylphenyl | CH2 | CH2 | — | H | CAS: 1043269-68-6 |
| 8-23 | 2,4,6-trimethylphenyl | CH2 | CH2 | — | H | [DMSO], spectrometer: 601.6 MHz 8.3712 (0.61); 7.6759 (1.40); 7.6732 (1.40); 6.7975 (3.13); 6.4963 (1.46); 6.4936 (1.46); 3.3334 (97.86); 3.2078 (0.43); 3.1980 (0.70); 3.1944 (0.55); 3.1888 (0.67); 3.1839 (0.54); 3.1797 (0.71); 3.1701 (0.49); 2.7659 (0.85); 2.7570 (0.61); 2.7518 (0.83); 2.7476 (0.62); 2.7383 (0.77); 2.5415 (5.51); 2.5081 (5.27); 2.5052 (11.49); 2.5022 (15.98); 2.4991 (11.53); 2.4962 (5.33); 2.2934 (16.00); 2.1786 (5.69); −0.0002 (2.22) |
| 8-24 | 3,4-bismethoxyphenyl | CH2 | CH2 | — | H | CAS: 1036695-62-1 |
| 8-25 | phenyl | CH2 | CH2 | — | H | CAS: 1060941-00-5 |
| 8-26 | 4-chlorophenyl | C(CH2—CH2) | CH2 | — | H | |
| 8-27 | 2,4-dichlorophenyl | C(CH2—CH2) | CH2 | — | H | |
| 8-28 | 4-chlorophenyl | CH2 | C(CH2—CH2) | — | H | |
| 8-29 | 2,4-dichlorophenyl | CH2 | C(CH2—CH2) | — | H | |
| 8-30 | 4-chlorophenyl | O | CH2 | CH2 | H | CAS: 1325531-65-4 |
| 8-31 | 2,4-dichlorophenyl | O | CH2 | CH2 | H | compound No. 8-31, solvent: [DMSO], spectrometer: 399.95 MHz 8.2551 (0.73); 8.2413 (1.4); 8.2273 (0.74); 7.6878 (3.16); 7.6842 (3.17); 7.5671 (2.97); 7.5607 (3.19); 7.3816 (1.54); 7.3752 (1.45); 7.3594 (2.09); 7.353 (2.01); 7.24 (3.54); 7.2177 (2.63); 6.5049 (3.33); 6.5013 (3.32); 4.1896 (2.12); 4.1741 (4.72); 4.1587 (2.35); 3.6071 (1.2); 3.5921 (3.32); 3.5772 (3.21); 3.562 (1.08); 3.334 (25.86); 2.5438 (13.28); 2.5267 (0.33); 2.5089 (10.22); 2.5046 (13.23); 2.5002 (10.08); 2.2826 (16); −0.0002 (0.33) |
| 8-32 | 4-chlorophenyl | CH2 | CH2 | CH2 | H | |
| 8-33 | 4-chlorophenyl | NCH3 | CH2 | CH2 | H | |
| 8-34 | 2,4-dichlorophenyl | NCH3 | CH2 | CH2 | H | |
| 8-35 | 4-chlorophenyl | CH(OCH3) | CH2 | — | H | |
| 8-36 | 2,4-dichlorophenyl | CH(OCH3) | CH2 | — | H | |
| 8-37 | 2-thienyl | CH2 | CH2 | — | H | CAS: 1015949-54-8 |
| 8-38 | 3-thienyl | CH2 | CH2 | — | H | |
| 8-39 | 2-furyl | CH2 | CH2 | — | H | CAS: 1016026-83-7 |
| 8-40 | 3-furyl | CH2 | CH2 | — | H | |
| 8-41 | phenyl | CH2 | CH2 | CH(CH3) | H | |
| 8-42 | phenyl | CH2 | CH2 | CH2 | H | |
| 8-43 | 2-Cl-phenyl | CH2 | CH2 | CH(CH3) | H | |
| 8-44 | 4-t-butylphenyl | CH2 | CH2 | CH2 | H | |
| 8-45 | 4-methylphenyl | CH2 | CH2 | CH2 | H | |
| 8-46 | phenyl | CH2 | CH2 | CH(CH2CH3) | H | |
| 8-47 | 2-methoxyphenyl | CH2 | CH2 | CH2 | H | |
| 8-48 | 2-methylphenyl | CH2 | CH2 | CH2 | H | |
| 8-49 | 3-methylphenyl | CH2 | CH2 | CH2 | H | |
| 8-50 | 3-chlorophenyl | CH2 | CH2 | CH2 | H | |
| 8-51 | 2,6-difluorophenyl | CH2 | CH2 | CH2 | H | compound No. 8-51, solvent: [DMSO], spectrometer: 399.95 MHz |

TABLE 8-continued

Compounds of the formula I-8

I-8

| Ex. No. | X | L¹ | L² | L³ | Y | Physical data: ¹H-NMR, δ [ppm] or CAS or patent No. |
|---|---|---|---|---|---|---|
| | | | | | | 8.2012 (0.65); 8.1868 (1.21); 8.173 (0.66); 7.6566 (3); 7.653 (2.98); 7.3419 (0.33); 7.3249 (0.79); 7.3215 (0.73); 7.3042 (1.45); 7.2835 (0.94); 7.2666 (0.42); 7.0797 (2.03); 7.0598 (3.28); 7.0399 (1.68); 6.4825 (3.22); 6.4789 (3.24); 3.3291 (43.27); 3.2425 (1.02); 3.2257 (2.16); 3.2081 (2.18); 3.1914 (1.07); 2.6559 (1.43); 2.6367 (2.4); 2.6173 (1.57); 2.5071 (24.4); 2.5027 (32.29); 2.4983 (24.78); 2.2874 (0.37); 2.2627 (16); 1.7727 (0.55); 1.7532 (1.42); 1.7349 (2.05); 1.7162 (1.33); 1.6975 (0.48); −0.0002 (0.34) |
| 8-52 | 4-chlorophenyl | CH2 | CH2 | CH2 | H | |
| 8-53 | 2,6-dichlorophenyl | CH2 | CH2 | CH(CH3) | H | |
| 8-54 | 3,5-dichlorophenyl | CH2 | CH2 | CH(CH3) | H | |
| 8-55 | 2,6-dimethylphenyl | CH2 | CH2 | CH2 | H | |
| 8-56 | 2,5-dichlorophenyl | CH2 | CH2 | CH2 | H | |
| 8-57 | 4-isopropoxyphenyl | CH2 | CH2 | CH2 | H | |
| 8-58 | 3-trifluoromethylphenyl | CH2 | CH2 | CH(CH3) | H | |
| 8-59 | 4-methylphenyl | CH2 | CH2 | CH(CH3) | H | |
| 8-60 | 2-methylphenyl | CH2 | CH2 | CH(CH3) | H | |
| 8-61 | 3,4-dichlorophenyl | CH2 | CH2 | CH(CH3) | H | |
| 8-62 | 3,5-dichlorophenyl | CH2 | CH2 | CH2 | H | |
| 8-63 | 2,6-dimethylphenyl | CH2 | CH2 | CH(CH3) | H | |
| 8-64 | 4-trifluoromethylphenyl | CH2 | CH2 | CH(CH3) | H | |
| 8-65 | 2,5-dichlorophenyl | CH2 | CH2 | CH(CH3) | H | |
| 8-66 | 4-phenoxyphenyl | CH2 | CH2 | CH2 | H | |
| 8-67 | 3-chlorophenyl | CH2 | CH2 | CH(CH3) | H | |
| 8-68 | 4-phenoxyphenyl | CH2 | CH2 | CH(CH3) | H | |
| 8-69 | 2,4-dichlorophenyl | CH2 | CH2 | CH(CH3) | H | |
| 8-70 | 2-difluoromethoxyphenyl | CH2 | CH2 | CH(CH3) | H | |
| 8-71 | 4-methoxyphenyl | CH2 | CH2 | CH2 | H | |
| 8-72 | 4-chlorophenyl | CH2 | CH2 | CH(CH3) | H | |
| 8-73 | 4-chlorophenyl | CH2 | CH2 | CH(i-propyl) | H | |
| 8-74 | 4-fluorophenyl | CH2 | CH2 | CH2 | H | |
| 8-75 | 4-chlorophenyl | CH2 | CH2 | CH(n-propyl) | H | |
| 8-76 | 4-chlorophenyl | CH2 | CH2 | CH(t-butyl) | H | |
| 8-77 | 2-chlorophenyl | CH2 | CH2 | CH2 | H | |
| 8-78 | 4-chlorophenyl | CH2 | CH(CH3) | — | cyclopropyl | |
| 8-79 | 2-thienyl | CH2 | CH2 | CH2 | H | compound No. 8-79, solvent: [DMSO], spectrometer: 399.95 MHz 8.221 (0.63); 8.2071 (1.15); 8.1929 (0.64); 7.6601 (2.99); 7.6565 (3.01); 7.3135 (1.85); 7.3107 (1.85); 7.3007 (2.05); 7.2979 (1.95); 6.9452 (1.53); 6.9367 (2.1); 6.9325 (1.56); 6.924 (1.94); 6.8841 (2.07); 6.8822 (2.07); 6.876 (1.67); 6.487 (3.15); 6.4834 (3.17); 3.3298 (24.93); 3.2682 (1.16); 3.2515 (2.62); 3.235 (2.63); 3.2183 (1.23); 2.8303 (1.94); 2.8111 (3.31); 2.792 (2.12); 2.5418 (1.02); 2.5245 (0.38); 2.5068 (13.21); 2.5024 (17.54); 2.498 (13.39); 2.2729 (16); 1.8665 (0.62); 1.848 (1.79); 1.8294 (2.39); 1.8113 (1.72); 1.7928 (0.57) |
| 8-80 | 4-chloro-2-thienyl | CH2 | CH2 | — | H | compound No. 8-80, solvent: [DMSO], spectrometer: 601.6 MHz 8.2854 (0.55); 8.2761 (1.03); 8.2669 (0.54); 7.6694 (2.74); 7.6667 (2.72); 7.3628 (3.72); 7.3602 (3.83); 6.8983 (2.61); 6.8971 (2.5); 6.896 (2.67); 6.492 (2.8); 6.4894 (2.87); 3.4515 (1.07); 3.4397 (2.48); 3.4298 (2.5); 3.4181 (1.16); 3.3249 (297.13); 3.0042 (1.78); 2.9924 (3.36); 2.9811 (1.58); 2.6529 (0.53); 2.6162 (0.46); 2.6131 (0.62); 2.6101 (0.45); 2.5408 (159.37); 2.5224 (1.46); 2.5193 (1.94); 2.5162 (2.27); 2.5074 (35.62); 2.5044 (73.23); 2.5014 (100.26); 2.4983 |

TABLE 8-continued

Compounds of the formula I-8

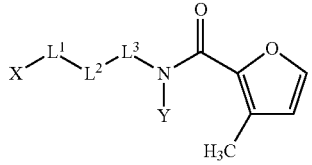

I-8

| Ex. No. | X | $L^1$ | $L^2$ | $L^3$ | Y | Physical data: $^1$H-NMR, δ [ppm] or CAS or patent No. |
|---|---|---|---|---|---|---|
| 8-81 | 4-chlorophenyl | N(CH3) | CH2 | CH2 | H | (73.35); 2.4953 (34.47); 2.4244 (0.53); 2.3886 (0.45); 2.3856 (0.62); 2.3825 (0.45); 2.2685 (16); 2.0736 (0.38); −0.0002 (6.04) compound No. 8-81, solvent: [DMSO], spectrometer: 399.95 MHz 8.2378 (0.68); 8.2238 (1.29); 8.2099 (0.68); 7.6642 (3.05); 7.6607 (2.89); 7.1804 (0.49); 7.1717 (4.21); 7.1665 (1.43); 7.149 (4.63); 7.1402 (0.51); 6.774 (0.59); 6.7656 (4.48); 6.7429 (3.98); 6.4866 (3.24); 6.4831 (3.01); 3.4418 (1.08); 3.4248 (2.45); 3.4071 (2.29); 3.3521 (1.68); 3.3299 (50.37); 3.3052 (0.87); 2.9004 (16); 2.5418 (11.39); 2.5068 (22.85); 2.5024 (28.29); 2.498 (20.57); 2.2758 (15.31); −0.0002 (3.19) |

TABLE 9

Compounds of the formula I-9

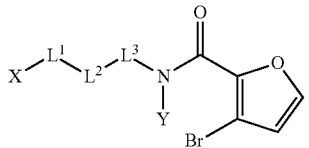

I-9

| Ex. No. | X | $L^1$ | $L^2$ | $L^3$ | Y | Physical data: $^1$H-NMR, δ [ppm] or CAS or patent No. |
|---|---|---|---|---|---|---|
| 9-1 | 3-methyl-2-thienyl | CH2 | CH2 | — | H | |
| 9-2 | 2,4-dichlorophenyl | CH2 | CH2 | CH2 | H | compound No. 9-2, solvent: [DMSO], spectrometer: 399.95 MHz 8.4664 (2.17); 8.4522 (4.21); 8.438 (2.2); 7.8913 (15.07); 7.8865 (15.06); 7.5619 (11.18); 7.5566 (11.52); 7.4291 (7.37); 7.4084 (14.84); 7.3742 (9.98); 7.3689 (9.31); 7.3536 (4.8); 7.3482 (4.73); 6.84 (16); 6.8352 (15.71); 3.516 (0.61); 3.3411 (75.64); 3.2676 (3.72); 3.2505 (8.4); 3.2349 (8.41); 3.2177 (3.87); 2.7236 (6.71); 2.7051 (8.66); 2.6851 (7.33); 2.5465 (32.88); 2.5296 (0.71); 2.5248 (1.1); 2.5163 (14.33); 2.5118 (28.9); 2.5072 (38.46); 2.5026 (28.04); 2.498 (13.4); 1.8153 (1.91); 1.7967 (5.02); 1.7783 (6.69); 1.7599 (4.75); 1.7416 (1.7); −0.0002 (3.86) |
| 9-3 | 4-chlorophenyl | CH2 | CH2 | — | H | compound No. 9-3, solvent: [DMSO], spectrometer: 399.95 MHz 8.4476 (1.57); 8.4333 (2.98); 8.4191 (1.54); 7.8832 (10.65); 7.8784 (10.58); 7.3633 (1.16); 7.3569 (10.15); 7.3523 (3.58); 7.3409 (4.33); 7.336 (16); 7.3299 (2.03); 7.2686 (2.05); 7.2627 (14.04); 7.2462 (3.26); 7.2417 (8.9); 6.8358 (11.21); 6.831 (11); 3.4432 (2.92); 3.4261 (5.63); 3.4106 (5.3); 3.4074 (5.52); 3.3919 (3.26); 3.3341 (429.8); 3.2919 (0.4); 2.8278 (5.24); 2.8092 (8.27); 2.7912 (4.66); 2.7119 (1.53); 2.6761 (0.81); 2.6715 (1.1); 2.6671 (0.81); 2.5727 (0.63); 2.5418 (347.78); 2.5249 (3.65); 2.5199 (5.37); 2.5114 (62.94); |

TABLE 9-continued

Compounds of the formula I-9

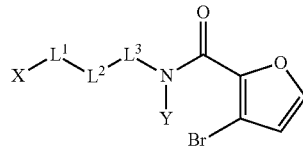

I-9

| Ex. No. | X | L¹ | L² | L³ | Y | Physical data: $^1$H-NMR, δ [ppm] or CAS or patent No. |
|---|---|---|---|---|---|---|
| | | | | | | 2.507 (126.53); 2.5025 (166.36); 2.498 (120.67); 2.4936 (58.56); 2.3682 (1.56); 2.3381 (0.38); 2.3337 (0.79); 2.3292 (1.07); 2.3248 (0.78); 2.0746 (0.75); 0.008 (0.53); −0.0002 (15.19); −0.0086 (0.43) |
| 9-4 | 2,4-dichlorophenyl | CH2 | CH2 | — | H | compound No. 9-4, solvent: [DMSO], spectrometer: 399.95 MHz 8.5057 (1.91); 8.4914 (3.79); 8.477 (1.92); 7.883 (15.24); 7.8782 (15.44);7.5843 (8.45); 7.58 (9.26); 7.3849 (1.98); 7.3803 (1.42); 7.3642 (12.12); 7.3595 (14.17); 7.3558 (16); 7.3354 (2.11); 6.8351 (15.97); 6.8303 (15.9); 3.4689 (3.33); 3.4519 (7.31); 3.4362 (7.18); 3.4186 (4.05); 3.3455 (1196.3); 3.2764 (0.55); 3.2619 (0.48); 2.947 (6.38); 2.929 (10.97); 2.9114 (5.59); 2.7125 (1.77); 2.6815 (0.6); 2.6769 (1.19); 2.6723 (1.68); 2.6677 (1.25); 2.6632 (0.62); 2.5942 (0.33); 2.5826 (0.51); 2.5426 (476.9); 2.5312 (2.43); 2.5304 (2.5); 2.5255 (5.45); 2.5208 (8.28); 2.5123 (92.1); 2.5078 (186.91); 2.5032 (246.51); 2.4986 (177.91); 2.4941 (84.91); 2.3687 (1.75); 2.3392 (0.53); 2.3345 (1.13); 2.3299 (1.58); 2.3254 (1.14); 2.321 (0.55); 2.0744 (1.1); 1.2348 (0.37); 0.0081 (0.87); −0.0001 (24.05); −0.0084 (0.68) |
| 9-5 | 4-chlorophenyl | CH(OCH3) | CH(CH3) | — | H | |
| 9-6 | 2,4-dichlorophenyl | CH(OCH3) | CH(CH3) | — | H | |
| 9-7 | 4-chlorophenyl | CH(CH3) | CH2 | — | H | |
| 9-8 | 2,4-dichlorophenyl | CH(CH3) | CH2 | — | H | compound No. 9-8, solvent: [DMSO], spectrometer: 399.95 MHz 8.4383 (1.22); 8.4239 (2.52); 8.4093 (1.3); 7.8649 (9.5); 7.8602 (9.81); 7.5579 (7.09); 7.5527 (7.65); 7.4577 (3.26); 7.4365 (9.51); 7.4185 (6.03); 7.4132 (5.54); 7.3973 (2.05); 7.3921 (2.08); 6.8223 (9.99); 6.8175 (10.05); 3.5571 (0.95); 3.5389 (2.05); 3.5212 (2.39); 3.5039 (1.42); 3.4866 (0.38); 3.426 (4.8); 3.4108 (6.07); 3.393 (3.53); 3.3311 (719.9); 2.7113 (1.55); 2.6801 (0.71); 2.6757 (1.45); 2.6711 (1.99); 2.6666 (1.49); 2.662 (0.75); 2.5415 (416.13); 2.5244 (6.83); 2.5196 (10.09); 2.5111 (110.28); 2.5066 (222.85); 2.502 (294.79); 2.4974 (212.26); 2.4929 (102.2); 2.3675 (1.53); 2.338 (0.64); 2.3333 (1.39); 2.3287 (1.9); 2.3242 (1.38); 2.3197 (0.65); 2.0746 (1.36); 1.235 (0.4); 1.1833 (16); 1.1661 (15.73); 0.008 (0.94); −0.0002 (24.94); −0.0084 (0.75) |
| 9-9 | 4-chlorophenyl | CH2 | CH(CH3) | — | H | compound No. 9-9, solvent: [DMSO], spectrometer: 399.95 MHz 8.2709 (2.54); 8.2499 (2.53); 7.8735 (9.69); 7.8687 (9.65); 7.3359 (0.97); 7.3298 (8.1); 7.3249 (2.87); 7.3137 (3.72); 7.3086 (14.16); 7.3027 (1.8); 7.2562 (1.96); 7.2504 (12.3); 7.2455 (3.42); 7.2339 (2.64); 7.2292 (7.08); 6.8197 (10.3); 6.8149 (10.08); 4.1826 (0.62); 4.1662 (1.14); 4.1622 (1.32); 4.1459 (1.93); 4.1294 (1.37); 4.1254 (1.12); 4.1092 (0.64); 3.3915 (0.36); 3.3783 (0.52); 3.3335 (390.11); 3.3041 (0.63); 2.8867 (1.85); 2.8664 (1.81); 2.8531 (2.77); 2.8328 (2.68); 2.7432 (2.76); 2.7277 (2.81); 2.7108 (2.57); 2.694 (1.77); |

TABLE 9-continued

Compounds of the formula I-9

I-9

[Structure: X—L¹—L²—L³—N(Y)—C(=O)—(3-bromofuran-2-yl)]

| Ex. No. | X | L¹ | L² | L³ | Y | Physical data: ¹H-NMR, δ [ppm] or CAS or patent No. |
|---------|---|----|----|----|---|------------------------------------------------------|
| | | | | | | 2.6805 (0.41); 2.676 (0.76); 2.6715 (1.01); 2.6669 (0.74); 2.6625 (0.34); 2.5797 (0.38); 2.5761 (0.44); 2.5661 (0.91); 2.5418 (336.04); 2.5249 (3.4); 2.5199 (5.02); 2.5114 (55.84); 2.507 (112.23); 2.5024 (147.1); 2.4978 (105.38); 2.4933 (49.81); 2.3678 (1.22); 2.3337 (0.68); 2.3291 (0.94); 2.3245 (0.65); 2.0747 (0.75); 1.1413 (16); 1.1248 (15.82); 0.008 (0.51); −0.0002 (15.04); −0.0085 (0.45) |
| 9-10 | 2,4-dichlorophenyl | CH2 | CH(CH3) | — | H | compound No. 9-10, solvent: [DMSO], spectrometer: 399.95 MHz 8.3289 (2.32); 8.307 (2.34); 7.88 (8.38); 7.8752 (8.32); 7.561 (5.66); 7.3598 (0.58); 7.3405 (16); 7.3365 (8.81); 7.3156 (0.51); 6.8195 (8.93); 6.8148 (8.69); 4.3154 (0.51); 4.2994 (0.95); 4.2948 (1.05); 4.2785 (1.56); 4.2619 (1.14); 4.2581 (0.91); 4.2415 (0.52); 3.3296 (152.91); 2.9677 (0.81); 2.9473 (0.7); 2.9334 (3.42); 2.9171 (4.18); 2.9132 (4.26); 2.902 (3.69); 2.8831 (0.87); 2.8677 (0.63); 2.6761 (0.44); 2.6715 (0.6); 2.6671 (0.45); 2.5418 (27.6); 2.5249 (2.15); 2.52 (3.35); 2.5116 (36.55); 2.5071 (72.87); 2.5025 (95.04); 2.498 (67.94); 2.4935 (32.18); 2.3339 (0.43); 2.3292 (0.6); 2.3248 (0.43); 2.0753 (0.58); 1.1815 (13.11); 1.1649 (12.95); −0.0002 (9.58) |
| 9-11 | 4-chlorophenyl | C(CH3)2 | CH2 | — | H | compound No. 9-11, solvent: [DMSO], spectrometer: 399.95 MHz 7.9517 (0.35); 7.9364 (0.69); 7.9209 (0.36); 7.8692 (2.81); 7.8644 (2.83); 7.4361 (2.06); 7.4308 (0.79); 7.4197 (1.03); 7.4142 (4.3); 7.408 (0.63); 7.3785 (0.6); 7.3723 (4.38); 7.3669 (1.05); 7.3556 (0.74); 7.3504 (2.07); 6.8234 (2.96); 6.8186 (2.93); 3.4123 (2.77); 3.3962 (2.74); 3.3287 (66.42); 2.5414 (8.25); 2.5244 (0.87); 2.5197 (1.35); 2.5112 (14.71); 2.5067 (29.55); 2.5021 (38.8); 2.4975 (28.08); 2.4931 (13.5); 1.2687 (16); −0.0002 (3.64) |
| 9-12 | 2,4-dichlorophenyl | C(CH3)2 | CH2 | — | H | compound No. 9-12, solvent: [DMSO], spectrometer: 399.95 MHz 8.0394 (0.42); 8.0236 (0.83); 8.0079 (0.41); 7.8579 (2.66); 7.8532 (2.64); 7.5397 (2.36); 7.5339 (2.47); 7.4674 (1.48); 7.4457 (2.27); 7.3728 (1.51); 7.367 (1.41); 7.3513 (0.98); 7.3455 (0.93); 6.8124 (2.75); 6.8077 (2.68); 3.7514 (2.8); 3.7352 (2.76); 3.3316 (61.88); 2.5422 (46.11); 2.5244 (0.68); 2.5113 (11.34); 2.507 (22.12); 2.5026 (28.66); 2.4981 (20.81); 2.4938 (10.15); 1.4198 (16); −0.0002 (2.32) |
| 9-13 | 2-chlorophenyl | CH2 | CH2 | — | H | compound No. 9-13, solvent: [DMSO], spectrometer: 399.95 MHz 8.5179 (2.16); 8.504 (4.01); 8.4898 (2.06); 7.8875 (15.25); 7.8828 (15.26); 7.4382 (5.48); 7.434 (4.36); 7.4199 (7.32); 7.4152 (6.93); 7.351 (3.61); 7.3454 (4.58); 7.3325 (5.41); 7.3276 (7.5); 7.3126 (0.4); 7.3038 (2.45); 7.2995 (3.3); 7.2856 (7.62); 7.2813 (6.98); 7.2712 (7.14); 7.2683 (6.92); 7.2649 (7.54); 7.2527 (5.87); 7.2473 (5.02); 7.2342 (1.87); 7.2292 (1.45); 6.8375 (16); 6.8328 (15.7); 3.4774 (4.04); 3.4611 (7.57); 3.4449 (6.98); 3.4412 (7.64); 3.426 (4.55); 3.3982 (0.59); 3.335 (667.51); 2.9654 (7.85); 2.9463 (11.13); 2.9286 (6.76); 2.7119 (2.07); 2.6805 (0.57); 2.6761 (1.14); 2.6716 (1.52); 2.6671 (1.1); |

TABLE 9-continued

Compounds of the formula I-9

I-9

$$X-L^1-L^2-L^3-N(Y)-C(=O)-\text{[3-bromofuran-2-yl]}$$

| Ex. No. | X | L¹ | L² | L³ | Y | Physical data: ¹H-NMR, δ [ppm] or CAS or patent No. |
|---|---|---|---|---|---|---|
| | | | | | | 2.6629 (0.56); 2.605 (0.32); 2.5969 (0.35); 2.5896 (0.44); 2.5808 (0.7); 2.5418 (478.25); 2.5286 (2.83); 2.5249 (5.27); 2.5199 (7.96); 2.5115 (86.26); 2.507 (172.44); 2.5025 (225.33); 2.4979 (162.09); 2.4935 (77.45); 2.3681 (2.01); 2.3383 (0.49); 2.3338 (1.04); 2.3292 (1.42); 2.3246 (1.02); 2.3202 (0.48); 2.0747 (0.97); 0.0078 (0.74); −0.0002 (20.55); −0.0086 (0.6) |
| 9-14 | 3,4-dichlorophenyl | CH2 | CH2 | — | H | compound No. 9-14, solvent: [DMSO], spectrometer: 399.95 MHz 8.4539 (1.96); 8.4397 (3.7); 8.4256 (1.85); 7.8853 (15.38); 7.8805 (15.18); 7.5624 (0.32); 7.5521 (11.8); 7.5419 (0.51); 7.5315 (13.52); 7.5131 (10.11); 7.5081 (10.24); 7.2376 (5.9); 7.2325 (5.64); 7.217 (5.16); 7.2119 (4.93); 6.8366 (16); 6.8318 (15.7); 3.4648 (3.5); 3.4475 (7.91); 3.4324 (7.94); 3.4148 (3.86); 3.334 (451.38); 3.2947 (0.46); 2.8462 (6.27); 2.8285 (11.81); 2.8108 (5.59); 2.7121 (1.69); 2.6808 (0.5); 2.6764 (0.94); 2.6718 (1.29); 2.6672 (0.98); 2.6625 (0.49); 2.5421 (435.01); 2.5251 (4.29); 2.5203 (6.45); 2.5118 (72.78); 2.5073 (146.59); 2.5027 (192.43); 2.4981 (137.67); 2.4936 (65.14); 2.4647 (0.44); 2.3682 (1.66); 2.3383 (0.42); 2.334 (0.88); 2.3294 (1.2); 2.3248 (0.86); 2.3203 (0.41); 2.0751 (0.95); 1.2343 (0.33); 0.008 (0.64); −0.0002 (19.48); −0.0085 (0.55) |
| 9-15 | 3,5-dichlorophenyl | CH2 | CH2 | — | H | compound No. 9-15, solvent: [DMSO], spectrometer: 399.95 MHz 8.4586 (1.5); 8.4444 (2.86); 8.4305 (1.47); 7.8902 (9.3); 7.8855 (9.22); 7.4381 (3.79); 7.4335 (7.33); 7.4288 (4.2); 7.3104 (16); 7.3058 (14.94); 6.8386 (9.68); 6.8338 (9.46); 3.4749 (2.45); 3.4577 (6.05); 3.4425 (6.16); 3.4253 (2.74); 3.3931 (0.39); 3.3857 (0.43); 3.3345 (369.91); 3.2875 (0.41); 2.8585 (4.53); 2.841 (8.8); 2.8235 (4.05); 2.7117 (1.19); 2.6761 (0.76); 2.6715 (0.97); 2.667 (0.72); 2.6627 (0.38); 2.5849 (0.34); 2.542 (280.12); 2.5248 (3.63); 2.5114 (56.72); 2.507 (111.12); 2.5025 (144.2); 2.4979 (104.8); 2.4935 (51.15); 2.3679 (1.2); 2.338 (0.35); 2.3337 (0.71); 2.3292 (0.95); 2.3248 (0.68); 2.0748 (0.58); 0.008 (0.46); −0.0002 (11.7); −0.0084 (0.43) |
| 9-16 | 3-chlorophenyl | CH2 | CH2 | — | H | compound No. 9-16, solvent: [DMSO], spectrometer: 399.95 MHz 8.4568 (2); 8.4431 (3.7); 8.4294 (1.96); 7.8873 (13.82); 7.8825 (14.02); 7.3569 (0.48); 7.343 (3.53); 7.3359 (0.88); 7.3235 (8.94); 7.3048 (16); 7.2775 (4.67); 7.2743 (6.57); 7.2689 (3.75); 7.2625 (0.89); 7.2577 (2.83); 7.2547 (2.52); 7.2528 (2.64); 7.2497 (1.93); 7.2414 (0.37); 7.205 (6.54); 7.1864 (4.31); 6.8376 (14.52); 6.8328 (14.26); 3.4619 (3.76); 3.4447 (7.43); 3.4294 (7.12); 3.4265 (7.24); 3.4109 (4.42); 3.3914 (0.71); 3.3825 (0.74); 3.3337 (631.19); 3.3035 (0.95); 3.2912 (0.5); 2.8484 (6.66); 2.8299 (11); 2.812 (6.09); 2.7116 (2.09); 2.6804 (0.6); 2.6759 (1.18); 2.6714 (1.59); 2.667 (1.22); 2.6622 (0.62); 2.5927 (0.37); 2.5418 (489.07); 2.5247 (5.31); 2.5197 |

TABLE 9-continued
Compounds of the formula I-9
I-9
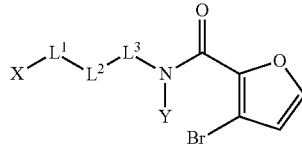
| Ex. No. | X | L¹ | L² | L³ | Y | Physical data: ¹H-NMR, δ [ppm] or CAS or patent No. |
|---|---|---|---|---|---|---|
| | | | | | | (7.89); 2.5113 (88.21); 2.5069 (176.46); 2.5023 (231.72); 2.4978 (167.78); 2.4933 (80.85); 2.3678 (2.05); 2.3381 (0.51); 2.3337 (1.07); 2.3291 (1.48); 2.3246 (1.08); 2.3204 (0.5); 2.0747 (1.09); 1.2353 (0.35); 0.0081 (0.66); −0.0002 (19); −0.0083 (0.59) |
| 9-17 | 2-fluorophenyl | CH2 | CH2 | — | H | compound No. 9-17, solvent: [DMSO], spectrometer: 399.95 MHz 8.5015 (2.01); 8.4875 (3.76); 8.4731 (1.98); 7.8846 (15.25); 7.8798 (15.41); 7.3218 (2.07); 7.3178 (2.63); 7.3032 (4.2); 7.2986 (5.86); 7.2912 (1.72); 7.2781 (4.94); 7.2626 (3.21); 7.2569 (4.02); 7.2524 (2.13); 7.2432 (2.29); 7.2387 (1.78); 7.1717 (4.2); 7.1498 (8.85); 7.1334 (7.61); 7.1303 (7.46); 7.1253 (2.95); 7.115 (3.17); 7.112 (2.74); 6.836 (15.97); 6.8312 (16); 3.4541 (3.8); 3.4374 (7.19); 3.4212 (6.64); 3.4178 (7.33); 3.4025 (4.32); 3.3342 (625.22); 3.2939 (0.64); 3.2701 (0.34); 2.8724 (5.93); 2.8538 (9.52); 2.8356 (5.19); 2.7117 (2.13); 2.6805 (0.56); 2.676 (1.14); 2.6715 (1.55); 2.6669 (1.14); 2.6623 (0.59); 2.5919 (0.32); 2.5904 (0.37); 2.5897 (0.37); 2.589 (0.38); 2.5882 (0.38); 2.5875 (0.4); 2.5868 (0.41); 2.586 (0.43); 2.5846 (0.48); 2.5839 (0.48); 2.5831 (0.47); 2.5809 (0.61); 2.5794 (0.68); 2.5787 (0.7); 2.578 (0.7); 2.5773 (0.71); 2.5765 (0.71); 2.5758 (0.71); 2.575 (0.73); 2.5736 (0.83); 2.5728 (0.86); 2.5721 (0.9); 2.5713 (0.96); 2.5706 (1); 2.5699 (1.03); 2.5691 (1.08); 2.5632 (2.06); 2.5625 (2.13); 2.5418 (539.77); 2.5248 (5.45); 2.5197 (7.8); 2.5114 (85.7); 2.5069 (172.68); 2.5024 (227.41); 2.4978 (165.24); 2.4933 (79.96); 2.4533 (0.41); 2.3678 (2.12); 2.3381 (0.53); 2.3337 (1.07); 2.3291 (1.47); 2.3245 (1.07); 2.0747 (1.21); 1.2347 (0.36); 0.008 (0.7); −0.0002 (19.73); −0.0085 (0.61) |
| 9-18 | 2,6-difluorophenyl | CH2 | CH2 | — | H | compound No. 9-18, solvent: [DMSO], spectrometer: 399.95 MHz 8.5562 (2.09); 8.5417 (4.02); 8.527 (2.04); 7.8822 (15.22); 7.8775 (15.11); 7.3578 (1.21); 7.3409 (2.69); 7.3369 (2.43); 7.3201 (5.16); 7.303 (2.56); 7.2992 (3.32); 7.2824 (1.54); 7.096 (0.71); 7.0916 (1.01); 7.0794 (7.23); 7.0595 (11.38); 7.0483 (1.4); 7.0395 (6); 7.0269 (0.76); 6.8335 (16); 6.8287 (15.61); 3.4179 (3.76); 3.4014 (8.33); 3.3832 (8.36); 3.3671 (5.35); 3.3349 (585.57); 3.2812 (0.32); 2.8879 (5.34); 2.8699 (9.42); 2.8522 (4.73); 2.712 (2.13); 2.6808 (0.55); 2.6762 (1.07); 2.6717 (1.4); 2.6672 (1.07); 2.6627 (0.54); 2.588 (0.44); 2.542 (493); 2.5249 (4.6); 2.5201 (6.98); 2.5117 (78.39); 2.5072 (157.19); 2.5026 (205.6); 2.4981 (147.59); 2.4936 (70.16); 2.3682 (2.04); 2.3383 (0.44); 2.3339 (0.93); 2.3294 (1.3); 2.3248 (0.92); 2.3203 (0.41); 2.0748 (1.01); 0.008 (0.67); −0.0002 (19.34); −0.0085 (0.55) |
| 9-19 | 2,6-dichlorophenyl | CH2 | CH2 | — | H | compound No. 9-19, solvent: [DMSO], spectrometer: 399.95 MHz 8.6015 (1.33); 8.5872 (2.57); 8.5723 (1.29); 7.8872 (9.54); 7.8825 (9.59); 7.4606 (11.42); 7.4405 (16); 7.3004 (5.5); 7.2813 (5.18); |

TABLE 9-continued

Compounds of the formula I-9

I-9

$$X{-}L^1{-}L^2{-}L^3{-}\underset{Y}{N}{-}C(O){-}\text{(3-bromofuran-2-yl)}$$

| Ex. No. | X | $L^1$ | $L^2$ | $L^3$ | Y | Physical data: $^1$H-NMR, δ [ppm] or CAS or patent No. |
|---|---|---|---|---|---|---|
|  |  |  |  |  |  | 7.2792 (4.96); 7.2601 (3.53); 6.8351 (10.07); 6.8303 (9.96); 3.4497 (2.02); 3.4334 (4.64); 3.4285 (2.89); 3.4175 (4.01); 3.4133 (4.62); 3.3984 (2.6); 3.3325 (381.04); 3.1556 (4.55); 3.1361 (6.36); 3.1191 (3.55); 2.7116 (1.08); 2.6804 (0.35); 2.676 (0.73); 2.6715 (1.01); 2.6669 (0.73); 2.6626 (0.37); 2.5764 (0.42); 2.5418 (296); 2.5249 (3.38); 2.52 (5.06); 2.5114 (57.11); 2.507 (115.45); 2.5024 (152.39); 2.4978 (110.49); 2.4933 (53.18); 2.3678 (1.11); 2.3381 (0.34); 2.3337 (0.71); 2.3291 (0.96); 2.3246 (0.72); 2.0749 (0.71); 0.0079 (0.52); −0.0002 (14.88); −0.0085 (0.43) |
| 9-20 | 3-(trifluoromethyl)phenyl | CH2 | CH2 | — | H | compound No. 9-20, solvent: [DMSO], spectrometer: 399.95 MHz 8.471 (1.61); 8.4567 (3.07); 8.4427 (1.64); 7.8939 (0.34); 7.8832 (10.52); 7.8784 (10.51); 7.6474 (0.36); 7.5735 (7.94); 7.565 (3.34); 7.557 (5.99); 7.5441 (16); 7.5259 (2.34); 7.5085 (0.7); 7.4697 (0.38); 7.4499 (0.33); 6.8453 (0.35); 6.8344 (11.18); 6.8297 (10.84); 3.4925 (2.8); 3.4753 (6.23); 3.4598 (6.12); 3.4419 (3.22); 3.3339 (731.94); 2.9713 (0.34); 2.9437 (5.32); 2.9256 (9.17); 2.9078 (4.68); 2.7118 (1.97); 2.676 (1.31); 2.6714 (1.8); 2.667 (1.32); 2.5871 (0.52); 2.5416 (452.24); 2.5247 (6.28); 2.5112 (104.74); 2.5069 (205.43); 2.5024 (266.14); 2.4979 (191.89); 2.4936 (93); 2.3681 (1.96); 2.3336 (1.27); 2.3291 (1.71); 2.3246 (1.26); 2.0745 (1.17); 1.2353 (0.36); 0.0079 (0.91); −0.0003 (22.68); −0.0086 (0.63) |
| 9-21 | 4-(trifluoromethyl)phenyl | CH2 | CH2 | — | H | compound No. 9-21, solvent: [DMSO], spectrometer: 399.95 MHz 8.491 (1.96); 8.477 (3.76); 8.4631 (1.93); 7.8956 (0.32); 7.8854 (15.37); 7.8806 (15.55); 7.6672 (9.34); 7.6471 (11.37); 7.47 (10.52); 7.45 (8.76); 6.8382 (16); 6.8334 (15.78); 3.4932 (3.38); 3.4761 (6.94); 3.4608 (6.56); 3.4581 (6.62); 3.4423 (3.72); 3.3343 (578.23); 3.2864 (0.44); 2.936 (5.37); 2.9178 (9.28); 2.8998 (4.66); 2.7119 (1.87); 2.6806 (0.47); 2.6763 (0.98); 2.6717 (1.38); 2.6671 (1.01); 2.6626 (0.52); 2.5922 (0.33); 2.5855 (0.46); 2.5848 (0.46); 2.5804 (0.55); 2.5796 (0.56); 2.5767 (0.7); 2.576 (0.71); 2.5745 (0.73); 2.5708 (1.06); 2.5701 (1.1); 2.5693 (1.13); 2.5686 (1.15); 2.5583 (3.11); 2.542 (479.54); 2.5295 (2.61); 2.525 (5.02); 2.5202 (7.57); 2.5117 (78.31); 2.5072 (157.79); 2.5026 (208.43); 2.498 (150.66); 2.4935 (72.42); 2.3682 (1.91); 2.3384 (0.48); 2.3339 (1); 2.3294 (1.36); 2.3248 (0.98); 2.3203 (0.48); 2.2815 (1.07); 2.1479 (1.13); 2.0749 (0.96); 0.008 (0.7); −0.0002 (20.15); −0.0084 (0.62) |
| 9-22 | 2-methylphenyl | CH2 | CH2 | — | H | compound No. 9-22, solvent: [DMSO], spectrometer: 399.95 MHz 8.5278 (0.56); 8.5134 (1.06); 8.4991 (0.55); 7.897 (4.61); 7.8922 (4.67); 7.1652 (0.72); 7.1578 (0.91); 7.1522 (1.49); 7.1501 (1.46); 7.1433 (2.02); 7.1337 (3.02); 7.1267 (1.47); 7.1222 (3.59); 7.1191 (3.65); 7.1088 (2.44); 7.104 (1.39); 7.0975 (1.26); 6.8452 (4.91); 6.8404 (4.87); 3.386 (1.15); 3.3709 (2.06); |

TABLE 9-continued

Compounds of the formula I-9

I-9

$$\text{X}-\text{L}^1-\text{L}^2-\text{L}^3-\text{N}(\text{Y})-\text{C}(=\text{O})-\text{[3-bromofuran-2-yl]}$$

| Ex. No. | X | L¹ | L² | L³ | Y | Physical data: ¹H-NMR, δ [ppm] or CAS or patent No. |
|---|---|---|---|---|---|---|
| | | | | | | 3.3668 (1.75); 3.3612 (1.6); 3.3512 (2.81); 3.346 (4.57); 3.3338 (167.79); 2.8188 (2.09); 2.8041 (1.55); 2.7989 (2.25); 2.7797 (1.86); 2.7114 (0.55); 2.6712 (0.43); 2.6666 (0.32); 2.5416 (150.93); 2.5248 (1.47); 2.5198 (2.15); 2.5113 (24.6); 2.5068 (50.05); 2.5022 (66.15); 2.4976 (47.84); 2.493 (22.98); 2.3674 (0.56); 2.3334 (0.44); 2.3287 (0.68); 2.3175 (16); 2.0744 (0.36); −0.0002 (6.67) |
| 9-23 | 2,4,6-trimethylphenyl | CH2 | CH2 | — | H | compound No. 9-23, solvent: [DMSO], spectrometer: 399.95 MHz 8.6412 (0.37); 8.6261 (0.74); 8.6113 (0.36); 7.9121 (3.07); 7.9074 (3.09); 6.8536 (3.23); 6.8488 (3.19); 6.8029 (3.91); 3.3324 (98.38); 3.2252 (0.49); 3.2107 (0.81); 3.2055 (0.65); 3.1964 (0.83); 3.1894 (0.64); 3.1827 (0.82); 3.1687 (0.58); 2.7804 (1.02); 2.7674 (0.77); 2.7592 (0.97); 2.7533 (0.79); 2.739 (0.85); 2.5415 (83.1); 2.5246 (0.91); 2.5198 (1.28); 2.5113 (14.15); 2.5067 (28.63); 2.5021 (37.64); 2.4975 (27); 2.493 (12.79); 2.2945 (16); 2.1802 (6.91); −0.0002 (3.74) |
| 9-24 | 3,4-bismethoxyphenyl | CH2 | CH2 | — | H | compound No. 9-24, solvent: [DMSO], spectrometer: 399.95 MHz 8.4036 (0.5); 8.3898 (0.96); 8.3756 (0.48); 7.8864 (3.18); 7.8817 (3.15); 6.8699 (2.07); 6.8495 (2.8); 6.8384 (3.38); 6.8337 (3.28); 6.813 (2.21); 6.8082 (2.44); 6.7402 (1.39); 6.7355 (1.24); 6.7199 (1.03); 6.7152 (0.94); 3.7217 (16); 3.7097 (15.93); 3.4305 (0.79); 3.4143 (1.52); 3.3972 (1.41); 3.3939 (1.54); 3.3786 (0.95); 3.3692 (0.36); 3.3344 (128.3); 2.7616 (1.47); 2.7422 (2.09); 2.7244 (1.3); 2.7117 (0.5); 2.5417 (105.77); 2.5245 (1.04); 2.5113 (18.38); 2.5068 (36.29); 2.5023 (47.29); 2.4978 (34.09); 2.4934 (16.38); 2.3679 (0.48); −0.0002 (3.92) |
| 9-25 | phenyl | CH2 | CH2 | — | H | compound No. 9-25, solvent: [DMSO], spectrometer: 399.95 MHz 8.4513 (1.78); 8.4374 (3.32); 8.4233 (1.8); 7.8857 (15.05); 7.8809 (15.27); 7.3174 (4.61); 7.3135 (2.02); 7.299 (11.17); 7.2855 (3.59); 7.2809 (11.21); 7.2413 (8.94); 7.2376 (14.49); 7.2203 (11.08); 7.207 (2.6); 7.2019 (6.15); 7.1964 (1.62); 7.1876 (1.43); 7.184 (2.24); 7.1805 (1.18); 6.8376 (16); 6.8328 (15.93); 3.4499 (4.03); 3.4345 (6.67); 3.4316 (6.04); 3.4277 (4.3); 3.4167 (5.87); 3.4125 (7.32); 3.3976 (4.64); 3.3351 (608.2); 3.2783 (0.35); 3.2713 (0.35); 2.8322 (6.91); 2.8125 (8.97); 2.7945 (6.16); 2.7116 (2.04); 2.6804 (0.56); 2.6759 (1.14); 2.6713 (1.55); 2.6668 (1.17); 2.6622 (0.56); 2.5943 (0.4); 2.5842 (0.43); 2.5247 (5.07); 2.5199 (7.8); 2.5416 (553.82); 2.5113 (85.67); 2.5068 (174.07); 2.5022 (229.82); 2.4976 (165.61); 2.4931 (78.84); 2.3678 (2.01); 2.3382 (0.53); 2.3336 (1.08); 2.329 (1.48); 2.3243 (1.09); 2.32 (0.53); 2.0744 (1.24); 1.2347 (0.33); 0.008 (0.83); −0.0002 (24.03); −0.0085 (0.66) |
| 9-26 | 4-chlorophenyl | C(CH2—CH2) | CH2 | — | H | |
| 9-27 | 2,4-dichlorophenyl | C(CH2—CH2) | CH2 | — | H | |
| 9-28 | 4-chlorophenyl | CH2 | C(CH2—CH2) | — | H | |
| 9-29 | 2,4-dichlorophenyl | CH2 | C(CH2—CH2) | — | H | |
| 9-30 | 4-chlorophenyl | O | CH2 | CH2 | H | |

TABLE 9-continued

Compounds of the formula I-9

I-9

$$\text{X}-\text{L}^1-\text{L}^2-\text{L}^3-\text{N}(\text{Y})-\text{C}(=\text{O})-\text{[3-bromofuran-2-yl]}$$

| Ex. No. | X | L¹ | L² | L³ | Y | Physical data: ¹H-NMR, δ [ppm] or CAS or patent No. |
|---|---|---|---|---|---|---|
| 9-31 | 2,4-dichlorophenyl | O | CH2 | CH2 | H | compound No. 9-31, solvent: [DMSO], spectrometer: 399.95 MHz<br>8.5029 (2.45); 8.4891 (4.79); 8.4753 (2.53); 7.9192 (13.04); 7.9145 (13.54); 7.567 (9.73); 7.5606 (10.61); 7.384 (5.33); 7.3775 (5.12); 7.3618 (7.19); 7.3554 (7.06); 7.2385 (12.33); 7.2162 (9.27); 6.8616 (13.39); 6.8568 (13.7); 4.2028 (7.13); 4.1876 (16); 4.1725 (7.94); 3.6229 (3.98); 3.6081 (11.19); 3.5934 (10.88); 3.5784 (3.68); 3.3342 (50.52); 2.5453 (47.37); 2.5283 (0.77); 2.5104 (25.95); 2.5059 (34.95); 2.5015 (26.98); −0.0002 (1.22) |
| 9-32 | 4-chlorophenyl | CH2 | CH2 | CH2 | H | compound No. 9-32, solvent: [DMSO], spectrometer: 399.95 MHz<br>8.423 (1.43); 8.4087 (2.66); 8.3948 (1.37); 7.8835 (11.11); 7.8788 (11.28); 7.3448 (1.08); 7.3386 (8.69); 7.3338 (3.46); 7.3226 (4.14); 7.3175 (16); 7.3117 (2.42); 7.2683 (2.14); 7.2626 (13.33); 7.2578 (4.09); 7.2462 (2.84); 7.2415 (7.72); 6.8357 (11.61); 6.8309 (11.57); 3.3996 (0.35); 3.3342 (448.7); 3.3001 (0.49); 3.2271 (2.59); 3.21 (5.56); 3.1943 (5.43); 3.1773 (2.62); 2.7114 (1.42); 2.6802 (0.4); 2.6759 (0.81); 2.6714 (1.13); 2.6669 (0.84); 2.6625 (0.43); 2.6131 (4.49); 2.5944 (6.82); 2.5749 (5.33); 2.5668 (1.31); 2.5653 (1.27); 2.5646 (1.26); 2.5608 (1.68); 2.5419 (360.69); 2.529 (2.13); 2.5246 (3.78); 2.5113 (61.29); 2.5069 (124.75); 2.5023 (165.59); 2.4978 (121.75); 2.4932 (59.55); 2.3676 (1.4); 2.3382 (0.37); 2.3336 (0.77); 2.3291 (1.06); 2.3244 (0.78); 2.3201 (0.38); 2.0747 (0.88); 1.8153 (1.33); 1.7965 (3.66); 1.7782 (4.9); 1.7598 (3.42); 1.7415 (1.18); 0.008 (0.53); −0.0002 (15.45); −0.0085 (0.53) |
| 9-33 | 4-chlorophenyl | NCH3 | CH2 | CH2 | H | |
| 9-34 | 2,4-dichlorophenyl | NCH3 | CH2 | CH2 | H | |
| 9-35 | 4-chlorophenyl | CH(OCH3) | CH2 | — | H | |
| 9-36 | 2,4-dichlorophenyl | CH(OCH3) | CH2 | — | H | |
| 9-37 | 2-thienyl | CH2 | CH2 | — | H | compound No. 9-37, solvent: [DMSO], spectrometer: 399.95 MHz<br>8.5182 (2.84); 8.5044 (5.3); 8.4905 (2.95); 7.9013 (15.16); 7.8965 (15.5); 7.3461 (7.95); 7.3448 (7.29); 7.3433 (7.82); 7.3334 (8.86); 7.3306 (8.28); 6.967 (6.54); 6.9584 (9.31); 6.9543 (6.8); 6.9457 (8.72); 6.9105 (9.45); 6.9032 (7.42); 6.8485 (15.84); 6.8437 (16); 3.4762 (4.72); 3.4585 (10.28); 3.4432 (10.35); 3.425 (5.63); 3.3339 (45.64); 3.053 (9.22); 3.0347 (15.39); 3.0164 (7.97); 2.5429 (13.03); 2.508 (27.67); 2.5036 (36.84); 2.4993 (28.59); −0.0002 (0.59) |
| 9-38 | 3-thienyl | CH2 | CH2 | — | H | |
| 9-39 | 2-furyl | CH2 | CH2 | — | H | |
| 9-40 | 3-furyl | CH2 | CH2 | — | H | |
| 9-41 | phenyl | CH2 | CH2 | CH(CH3) | H | |
| 9-42 | phenyl | CH2 | CH2 | CH2 | H | |
| 9-43 | 2-Cl-phenyl | CH2 | CH2 | CH(CH3) | H | |
| 9-44 | 4-t-butylphenyl | CH2 | CH2 | CH2 | H | |
| 9-45 | 4-methylphenyl | CH2 | CH2 | CH2 | H | |
| 9-46 | phenyl | CH2 | CH2 | CH(CH2CH3) | H | |
| 9-47 | 2-methoxyphenyl | CH2 | CH2 | CH2 | H | |
| 9-48 | 2-methylphenyl | CH2 | CH2 | CH2 | H | |
| 9-49 | 3-methylphenyl | CH2 | CH2 | CH2 | H | |
| 9-50 | 3-chlorophenyl | CH2 | CH2 | CH2 | H | |

TABLE 9-continued

Compounds of the formula I-9

I-9

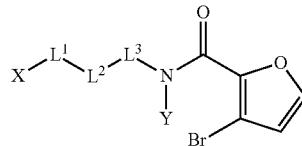

| Ex. No. | X | L¹ | L² | L³ | Y | Physical data: $^1$H-NMR, δ [ppm] or CAS or patent No. |
|---|---|---|---|---|---|---|
| 9-51 | 2,6-difluorophenyl | CH2 | CH2 | CH2 | H | compound No. 9-51, solvent: [DMSO], spectrometer: 399.95 MHz 8.443 (2.14); 8.4285 (3.98); 8.4142 (2.08); 7.8867 (15.33); 7.882 (15.59); 7.345 (1.2); 7.3282 (2.66); 7.3241 (2.47); 7.3072 (5.08); 7.2899 (2.53); 7.2864 (3.35); 7.2696 (1.5); 7.0989 (0.75); 7.0944 (1.09); 7.0818 (6.83); 7.0617 (11.33); 7.0497 (1.52); 7.0416 (5.76); 7.0283 (0.76); 6.837 (15.95); 6.8322 (16); 3.4158 (0.48); 3.4042 (0.68); 3.3356 (798.74); 3.289 (0.81); 3.2517 (3.51); 3.2348 (7.08); 3.2173 (7.01); 3.2008 (3.5); 2.7124 (2.13); 2.6766 (1.66); 2.6664 (5.52); 2.6464 (8.01); 2.627 (5.3); 2.5427 (499.5); 2.5255 (7.14); 2.5121 (91.75); 2.5078 (181.6); 2.5032 (238.19); 2.4987 (175.98); 2.4943 (87.47); 2.4471 (0.45); 2.3686 (2.05); 2.3389 (0.57); 2.3345 (1.13); 2.3299 (1.55); 2.3254 (1.16); 2.0754 (1.15); 1.7839 (1.84); 1.7646 (4.7); 1.7463 (6.69); 1.7273 (4.26); 1.7089 (1.55); 1.2349 (0.37); 0.0085 (0.81); 0.0004 (20.11); −0.0078 (0.73) |
| 9-52 | 4-chlorophenyl | CH2 | CH2 | CH2 | H | |
| 9-53 | 2,6-dichlorophenyl | CH2 | CH2 | CH(CH3) | H | |
| 9-54 | 3,5-dichlorophenyl | CH2 | CH2 | CH(CH3) | H | |
| 9-55 | 2,6-dimethylphenyl | CH2 | CH2 | CH2 | H | |
| 9-56 | 2,5-dichlorophenyl | CH2 | CH2 | CH2 | H | |
| 9-57 | 4-isopropoxyphenyl | CH2 | CH2 | CH2 | H | |
| 9-58 | 3-trifluoromethylphenyl | CH2 | CH2 | CH(CH3) | H | |
| 9-59 | 4-methylphenyl | CH2 | CH2 | CH(CH3) | H | |
| 9-60 | 2-methylphenyl | CH2 | CH2 | CH(CH3) | H | |
| 9-61 | 3,4-dichlorophenyl | CH2 | CH2 | CH(CH3) | H | |
| 9-62 | 3,5-dichlorophenyl | CH2 | CH2 | CH2 | H | |
| 9-63 | 2,6-dimethylphenyl | CH2 | CH2 | CH(CH3) | H | |
| 9-64 | 4-trifluoromethylphenyl | CH2 | CH2 | CH(CH3) | H | |
| 9-65 | 2,5-dichlorophenyl | CH2 | CH2 | CH(CH3) | H | |
| 9-66 | 4-phenoxyphenyl | CH2 | CH2 | CH2 | H | |
| 9-67 | 3-chlorophenyl | CH2 | CH2 | CH(CH3) | H | |
| 9-68 | 4-phenoxyphenyl | CH2 | CH2 | CH(CH3) | H | |
| 9-69 | 2,4-dichlorophenyl | CH2 | CH2 | CH(CH3) | H | |
| 9-70 | 2-difluoromethoxyphenyl | CH2 | CH2 | CH(CH3) | H | |
| 9-71 | 4-methoxyphenyl | CH2 | CH2 | CH2 | H | |
| 9-72 | 4-chlorophenyl | CH2 | CH2 | CH(CH3) | H | |
| 9-73 | 4-chlorophenyl | CH2 | CH2 | CH(i-propyl) | H | |
| 9-74 | 4-fluorophenyl | CH2 | CH2 | CH2 | H | |
| 9-75 | 4-chlorophenyl | CH2 | CH2 | CH(n-propyl) | H | |
| 9-76 | 4-chlorophenyl | CH2 | CH2 | CH(t-butyl) | H | |
| 9-77 | 2-chlorophenyl | CH2 | CH2 | CH2 | H | |
| 9-78 | 4-chlorophenyl | CH2 | CH(CH3) | — | cyclopropyl | |
| 9-79 | 2-thienyl | CH2 | CH2 | CH2 | H | compound No. 9-79, solvent: [DMSO], spectrometer: 399.95 MHz 8.4599 (2.61); 8.4461 (4.83); 8.4323 (2.69); 7.8913 (15.42); 7.8865 (15.68); 7.3171 (7.72); 7.3143 (7.67); 7.3044 (8.56); 7.3015 (8.12); 6.9479 (6.27); 6.9393 (8.65); 6.9352 (6.4); 6.9266 (8.01); 6.8879 (8.55); 6.8859 (8.57); 6.8797 (6.9); 6.8409 (16); 6.8361 (15.96); 3.3334 (63.52); 3.2786 (4.65); 3.2618 (10.55); 3.2457 (10.61); 3.2289 (4.88); 2.8423 (7.82); 2.8231 (13.43); 2.8041 (8.47); 2.5431 (10.08); 2.526 (0.99); 2.5082 (33.08); 2.5038 (43.76); 2.4994 (33.35); 1.8771 (2.49); 1.8587 (7.26); 1.8402 (9.71); 1.822 (6.95); 1.8036 (2.23); −0.0002 (0.41) |
| 9-80 | 4-chloro-2-thienyl | CH2 | CH2 | — | H | compound No. 9-80, solvent: [DMSO], spectrometer: 601.6 MHz |

TABLE 9-continued

Compounds of the formula I-9

I-9

X—L¹—L²—L³—N(Y)—C(=O)—[3-bromofuran-2-yl]

| Ex. No. | X | L¹ | L² | L³ | Y | Physical data: ¹H-NMR, δ [ppm] or CAS or patent No. |
|---|---|---|---|---|---|---|
| | | | | | | 8.528 (1.75); 8.5186 (3.38); 8.5091 (1.76); 7.9005 (15.38); 7.8973 (15.32); 7.3685 (13.84); 7.366 (14.11); 6.9083 (8.96); 6.9071 (7.97); 6.9059 (8.74); 6.847 (15.57); 6.8438 (16); 3.4617 (3.43); 3.4499 (8.05); 3.4402 (8.31); 3.4285 (3.81); 3.4089 (0.45); 3.3255 (899.24); 3.3034 (0.66); 3.0139 (5.58); 3.0021 (10.72); 2.9909 (5.08); 2.6532 (1.68); 2.6194 (0.56); 2.6164 (1.25); 2.6133 (1.73); 2.6103 (1.26); 2.6073 (0.59); 2.5596 (0.36); 2.541 (531.04); 2.5323 (1.2); 2.5227 (3.3); 2.5195 (4.08); 2.5164 (3.99); 2.5077 (92.61); 2.5046 (197.84); 2.5016 (274.23); 2.4985 (197.76); 2.4955 (92.09); 2.4249 (1.7); 2.3919 (0.53); 2.3888 (1.21); 2.3858 (1.68); 2.3827 (1.18); 2.3797 (0.53); 2.0738 (1.5); 1.9005 (0.51); 0.0052 (0.57); −0.0002 (18.84); −0.0057 (0.59) |
| 9-81 | 4-bromophenyl | CH2 | CH2 | — | H | compound No. 9-81, solvent: [DMSO], spectrometer: 399.95 MHz 8.4449 (1.85); 8.4308 (3.49); 8.4168 (1.78); 7.8832 (12.49); 7.8784 (12.44); 7.4943 (1.73); 7.4879 (13.75); 7.4833 (4.7); 7.4717 (4.89); 7.4671 (16); 7.4609 (2.07); 7.2044 (13.74); 7.1835 (11.82); 6.8349 (13.52); 6.8301 (13.28); 4.0557 (0.51); 4.038 (1.57); 4.0202 (1.59); 4.0023 (0.53); 3.4412 (3.09); 3.4242 (6.16); 3.4085 (5.83); 3.4057 (5.97); 3.39 (3.34); 3.323 (72.57); 2.8109 (5.74); 2.7923 (9.21); 2.7743 (5.07); 2.6755 (0.68); 2.6711 (0.94); 2.6666 (0.68); 2.5241 (3.63); 2.5109 (53.76); 2.5065 (105.2); 2.502 (136.77); 2.4975 (98.67); 2.4931 (47.86); 2.3332 (0.64); 2.3288 (0.87); 2.3244 (0.63); 1.989 (6.85); 1.2494 (0.39); 1.1926 (1.75); 1.1749 (3.5); 1.157 (1.73); 0.0079 (2.42); −0.0001 (57.31); −0.0081 (2.28) |
| 9-82 | 4-chlorophenyl | CH2 | C(CH3)2 | — | H | compound No. 9-82, solvent: [DMSO], spectrometer: 399.95 MHz 7.8243 (2.83); 7.8219 (1.84); 7.8198 (2.29); 7.3673 (1.97); 7.3263 (2.65); 7.3056 (3.19); 7.1597 (3.23); 7.1394 (2.56); 6.8242 (1.69); 6.8213 (2.88); 6.8199 (2.01); 6.8169 (2.2); 3.3535 (27.39); 3.346 (34.5); 3.3448 (34.76); 3.0844 (5.32); 2.5076 (12.64); 2.5036 (13.03); 1.9924 (0.93); 1.9896 (1.1); 1.3031 (16); 1.1934 (0.33); 1.1786 (0.52); 1.1756 (0.61); 1.0444 (0.51); 0.0027 (2.14); −0.0002 (2.59) |
| 9-83 | 2,4-dichlorophenyl | CH2 | C(CH3)2 | — | H | compound No. 9-83, solvent: [DMSO], spectrometer: 399.95 MHz 7.8483 (2.55); 7.8436 (2.82); 7.5845 (1.96); 7.5791 (2.27); 7.5258 (1.74); 7.3596 (0.99); 7.3541 (1.03); 7.3388 (1.42); 7.3333 (1.5); 7.2401 (2.4); 7.2192 (1.77); 6.8343 (2.58); 6.8295 (2.82); 4.0384 (0.44); 4.0206 (0.45); 3.334 (39.24); 3.2661 (5.25); 2.5253 (0.44); 2.5116 (8.41); 2.5074 (17.69); 2.503 (24.77); 2.4985 (20.32); |

TABLE 9-continued

Compounds of the formula I-9

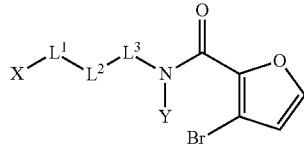

I-9

| Ex. No. | X | L$^1$ | L$^2$ | L$^3$ | Y | Physical data: $^1$H-NMR, δ [ppm] or CAS or patent No. |
|---|---|---|---|---|---|---|
| | | | | | | 1.9892 (1.86); 1.34 (16); 1.1932 (0.51); 1.1754 (1.04); 1.1576 (0.51); −0.0002 (6.16) |
| 9-84 | 4-chlorophenyl | N(CH3) | CH2 | CH2 | H | compound No. 9-84, solvent: [DMSO], spectrometer: 399.95 MHz 8.4718 (0.67); 8.4575 (1.31); 8.4436 (0.68); 7.8928 (3.67); 7.8881 (3.64); 7.182 (0.43); 7.1732 (4.25); 7.1681 (1.43); 7.1557 (1.57); 7.1506 (4.62); 7.1418 (0.51); 6.8399 (3.82); 6.8351 (3.71); 6.7707 (0.52); 6.762 (4.49); 6.7393 (4); 6.7304 (0.44); 3.4566 (1.01); 3.4397 (2.44); 3.4222 (2.25); 3.3646 (1.31); 3.3491 (2.48); 3.3289 (65.35); 3.3024 (0.37); 2.9026 (16); 2.5418 (17.46); 2.507 (27.64); 2.5025 (35.44); 2.4981 (26.2); −0.0002 (4.42) |
| 9-85 | 3-chloro-4-(trifluoromethyl)phenyl | CH2 | CH2 | — | H | compound No. 9-85, solvent: [DMSO], spectrometer: 399.95 MHz 8.4902 (2.25); 8.4761 (4.36); 8.4619 (2.24); 8.3168 (0.35); 7.8879 (15.32); 7.8831 (15.26); 7.7818 (8.24); 7.7616 (9.15); 7.6074 (10.12); 7.4137 (5.4); 7.3934 (4.85); 6.838 (16); 6.8332 (15.64); 5.7573 (0.8); 3.5102 (3.65); 3.493 (9.1); 3.4779 (9.31); 3.4607 (3.99); 3.3279 (112.91); 2.9401 (6.14); 2.9227 (11.74); 2.9052 (5.33); 2.6774 (0.49); 2.6728 (0.67); 2.6683 (0.49); 2.526 (2.57); 2.5127 (38.56); 2.5083 (75.1); 2.5037 (97.54); 2.4991 (70.05); 2.4947 (33.28); 2.335 (0.46); 2.3305 (0.62); 2.3259 (0.44); 1.99 (0.88); 1.3368 (1.28); 1.2499 (1.59); 1.2348 (0.37); 1.1758 (0.49); −0.0002 (0.49) |
| 9-86 | 4-chloro-3-(trifluoromethyl)phenyl | CH2 | CH2 | — | H | compound No. 9-86, solvent: [DMSO], spectrometer: 399.95 MHz 8.4594 (2.9); 8.4454 (5.41); 8.4314 (2.86); 7.8825 (15.43); 7.8778 (15.39); 7.6988 (10.7); 7.6948 (11.01); 7.6481 (7.13); 7.6275 (11); 7.5584 (6.89); 7.5547 (6.58); 7.5379 (4.46); 7.534 (4.27); 6.8335 (16); 6.8287 (15.69); 5.7579 (1.29); 3.4899 (4.18); 3.4729 (10.84); 3.4575 (11.06); 3.4406 (4.56); 3.3289 (48.16); 2.9442 (1.1); 2.9301 (8.13); 2.9128 (15.55); 2.8954 (7.11); 2.6782 (0.39); 2.6736 (0.51); 2.6692 (0.4); 2.509 (58.37); 2.5046 (74.08); 2.5002 (55.32); 2.3356 (0.36); 2.3314 (0.47); 2.3266 (0.36); 1.9905 (0.69); 1.3374 (0.53); 1.2501 (0.6); 1.1764 (0.37); −0.0002 (14.43) |
| 9-87 | 2-chloro-4-(trifluoromethyl)phenyl | O | CH2 | C(CH3)2 | H | compound No. 9-87, solvent: [DMSO], spectrometer: 399.95 MHz 7.8739 (2.54); 7.8691 (2.57); 7.8233 (1.29); 7.8182 (1.4); 7.6962 (1.58); 7.6831 (0.72); 7.6786 (0.66); 7.6612 (0.75); 7.6569 (0.69); 7.3608 (1.18); 7.3391 (1.05); 6.833 (2.71); 6.8282 (2.7); 4.3456 (4.8); 3.3316 (47.93); 2.5427 (4.6); 2.5257 (0.39); 2.5124 (7.84); 2.5079 (15.89); 2.5033 (21.01); 2.4987 (15.26); 2.4942 (7.33); 1.4822 (16) |

TABLE 9-continued

Compounds of the formula I-9

I-9

| Ex. No. | X | L¹ | L² | L³ | Y | Physical data: ¹H-NMR, δ [ppm] or CAS or patent No. |
|---|---|---|---|---|---|---|
| 9-88 | 4-chloro-2-(trifluoromethyl)phenyl | O | CH3 | C(CH3)3 | H | compound No. 9-88, solvent: [DMSO], spectrometer: 399.95 MHz 7.8729 (2.68); 7.8681 (2.67); 7.7015 (0.62); 7.695 (0.8); 7.6794 (0.62); 7.6728 (0.97); 7.6549 (1.82); 7.6484 (1.24); 7.5767 (1.65); 7.3093 (1.28); 7.287 (1.15); 6.831 (2.75); 6.8262 (2.69); 4.2914 (4.85); 3.3302 (35.11); 2.5427 (2.57); 2.5258 (0.35); 2.5123 (7.32); 2.5079 (14.41); 2.5034 (18.74); 2.4988 (13.43); 2.4943 (6.37); 1.4433 (16) |
| 9-89 | 2-chloro-4-(trifluoromethyl)phenyl | O | CH2 | CH2 | H | compound No. 9-89, solvent: [DMSO], spectrometer: 399.95 MHz 8.5338 (2.32); 8.5198 (4.6); 8.5059 (2.42); 7.9202 (14.68); 7.9154 (15.09); 7.9097 (1.09); 7.8332 (8.15); 7.8278 (8.77); 7.7008 (4.01); 7.696 (3.85); 7.6792 (4.94); 7.6743 (4.43); 7.6595 (0.43); 7.5122 (0.41); 7.5084 (0.43); 7.4044 (7.67); 7.3827 (6.75); 6.8631 (15.53); 6.8583 (15.5); 4.3081 (7.13); 4.2931 (16); 4.2782 (7.52); 3.656 (3.88); 3.6413 (11.28); 3.6268 (11.04); 3.612 (3.68); 3.3324 (153.26); 3.3074 (0.45); 2.6779 (0.39); 2.6733 (0.56); 2.6688(0.39); 2.5436 (28.1); 2.5267 (1.57); 2.5217(2.61); 2.5133 (33.56); 2.5088 (67.1); 2.5043(88); 2.4997 (63.47); 2.4952 (30.25); 2.3356(0.43); 2.331 (0.6); 2.3265 (0.44); 1.234 (0.39); −0.0002 (0.56) |

TABLE 10

Compounds of the formula I-10

I-10

| Ex. No. | X | L¹ | L² | L³ | Y | Physical data: ¹H-NMR, δ [ppm] or CAS or patent No. |
|---|---|---|---|---|---|---|
| 10-1 | 3-methyl-2-thienyl | CH2 | CH2 | — | H | |
| 10-2 | 2,4-dichlorophenyl | CH2 | CH2 | CH2 | H | |
| 10-3 | 4-chlorophenyl | CH2 | CH2 | — | H | |
| 10-4 | 2,4-dichlorophenyl | CH2 | CH2 | — | H | |
| 10-5 | 4-chlorophenyl | CH(OCH3) | CH(CH3) | — | H | |
| 10-6 | 2,4-dichlorophenyl | CH(OCH3) | CH(CH3) | — | H | |
| 10-7 | 4-chlorophenyl | CH(CH3) | CH2 | — | H | |
| 10-8 | 2,4-dichlorophenyl | CH(CH3) | CH2 | — | H | |
| 10-9 | 4-chlorophenyl | CH2 | CH(CH3) | — | H | |
| 10-10 | 2,4-dichlorophenyl | CH2 | CH(CH3) | — | H | |
| 10-11 | 4-chlorophenyl | C(CH3)2 | CH2 | — | H | |
| 10-12 | 2,4-dichlorophenyl | C(CH3)2 | CH2 | — | H | |
| 10-13 | 2-chlorophenyl | CH2 | CH2 | — | H | |
| 10-14 | 3,4-dichlorophenyl | CH2 | CH2 | — | H | |
| 10-15 | 3,5-dichlorophenyl | CH2 | CH2 | — | H | |
| 10-16 | 3-chlorophenyl | CH2 | CH2 | — | H | |
| 10-17 | 2-fluorophenyl | CH2 | CH2 | — | H | |
| 10-18 | 2,6-difluorophenyl | CH2 | CH2 | — | H | |
| 10-19 | 2,6-dichlorophenyl | CH2 | CH2 | — | H | |
| 10-20 | 3-(trifluoromethyl)phenyl | CH2 | CH2 | — | H | |

TABLE 10-continued

Compounds of the formula I-10

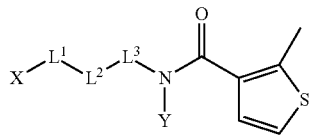

I-10

| Ex. No. | X | L¹ | L² | L³ | Y | Physical data: ¹H-NMR, δ [ppm] or CAS or patent No. |
|---|---|---|---|---|---|---|
| 10-21 | 4-(trifluoromethyl)phenyl | CH2 | CH2 | — | H | |
| 10-22 | 2-methylphenyl | CH2 | CH2 | — | H | |
| 10-23 | 2,4,6-trimethylphenyl | CH2 | CH2 | — | H | |
| 10-24 | 3,4-bismethoxyphenyl | CH2 | CH2 | — | H | |
| 10-25 | phenyl | CH2 | CH2 | — | H | |
| 10-26 | 4-chlorophenyl | C(CH2—CH2) | CH2 | — | H | |
| 10-27 | 2,4-dichlorophenyl | C(CH2—CH2) | CH2 | — | H | |
| 10-28 | 4-chlorophenyl | CH2 | C(CH2—CH2) | — | H | |
| 10-29 | 2,4-dichlorophenyl | CH2 | C(CH2—CH2) | — | H | |
| 10-30 | 4-chlorophenyl | O | CH2 | CH2 | H | |
| 10-31 | 2,4-dichlorophenyl | O | CH2 | CH2 | H | |
| 10-32 | 4-chlorophenyl | CH2 | CH2 | CH2 | H | |
| 10-33 | 4-chlorophenyl | NCH3 | CH2 | CH2 | H | |
| 10-34 | 2,4-dichlorophenyl | NCH3 | CH2 | CH2 | H | |
| 10-35 | 4-chlorophenyl | CH(OCH3) | CH2 | — | H | |
| 10-36 | 2,4-dichlorophenyl | CH(OCH3) | CH2 | — | H | |
| 10-37 | 2-thienyl | CH2 | CH2 | — | H | |
| 10-38 | 3-thienyl | CH2 | CH2 | — | H | |
| 10-39 | 2-furyl | CH2 | CH2 | — | H | |
| 10-40 | 3-furyl | CH2 | CH2 | — | H | |
| 10-41 | phenyl | CH2 | CH2 | CH(CH3) | H | |
| 10-42 | phenyl | CH2 | CH2 | CH2 | H | |
| 10-43 | 2-Cl-phenyl | CH2 | CH2 | CH(CH3) | H | |
| 10-44 | 4-t-butylphenyl | CH2 | CH2 | CH2 | H | |
| 10-45 | 4-methylphenyl | CH2 | CH2 | CH2 | H | |
| 10-46 | phenyl | CH2 | CH2 | CH(CH2CH3) | H | |
| 10-47 | 2-methoxyphenyl | CH2 | CH2 | CH2 | H | |
| 10-48 | 2-methylphenyl | CH2 | CH2 | CH2 | H | |
| 10-49 | 3-methylphenyl | CH2 | CH2 | CH2 | H | |
| 10-50 | 3-chlorophenyl | CH2 | CH2 | CH2 | H | |
| 10-51 | 2,6-difluorophenyl | CH2 | CH2 | CH2 | H | |
| 10-52 | 4-chlorophenyl | CH2 | CH2 | CH2 | H | |
| 10-53 | 2,6-dichlorophenyl | CH2 | CH2 | CH(CH3) | H | |
| 10-54 | 3,5-dichlorophenyl | CH2 | CH2 | CH(CH3) | H | |
| 10-55 | 2,6-dimethylphenyl | CH2 | CH2 | CH2 | H | |
| 10-56 | 2,5-dichlorophenyl | CH2 | CH2 | CH2 | H | |
| 10-57 | 4-isopropoxyphenyl | CH2 | CH2 | CH2 | H | |
| 10-58 | 3-trifluoromethylphenyl | CH2 | CH2 | CH(CH3) | H | |
| 10-59 | 4-methylphenyl | CH2 | CH2 | CH(CH3) | H | |
| 10-60 | 2-methylphenyl | CH2 | CH2 | CH(CH3) | H | |
| 10-61 | 3,4-dichlorophenyl | CH2 | CH2 | CH(CH3) | H | |
| 10-62 | 3,5-dichlorophenyl | CH2 | CH2 | CH2 | H | |
| 10-63 | 2,6-dimethylphenyl | CH2 | CH2 | CH(CH3) | H | |
| 10-64 | 4-trifluoromethylphenyl | CH2 | CH2 | CH(CH3) | H | |
| 10-65 | 2,5-dichlorophenyl | CH2 | CH2 | CH(CH3) | H | |
| 10-66 | 4-phenoxyphenyl | CH2 | CH2 | CH2 | H | |
| 10-67 | 3-chlorophenyl | CH2 | CH2 | CH(CH3) | H | |
| 10-68 | 4-phenoxyphenyl | CH2 | CH2 | CH(CH3) | H | |
| 10-69 | 2,4-dichlorophenyl | CH2 | CH2 | CH(CH3) | H | |
| 10-70 | 2-difluoromethoxyphenyl | CH2 | CH2 | CH(CH3) | H | |
| 10-71 | 4-methoxyphenyl | CH2 | CH2 | CH2 | H | |
| 10-72 | 4-chlorophenyl | CH2 | CH2 | CH(CH3) | H | |
| 10-73 | 4-chlorophenyl | CH2 | CH2 | CH(i-propyl) | H | |
| 10-74 | 4-fluorophenyl | CH2 | CH2 | CH2 | H | |
| 10-75 | 4-chlorophenyl | CH2 | CH2 | CH(n-propyl) | H | |
| 10-76 | 4-chlorophenyl | CH2 | CH2 | CH(t-butyl) | H | |
| 10-77 | 2-chlorophenyl | CH2 | CH2 | CH2 | H | |
| 10-78 | 4-chlorophenyl | CH2 | CH(CH3) | — | cyclopropyl | WO-A 2007/060164 |

TABLE 11

Compounds of the formula I-11

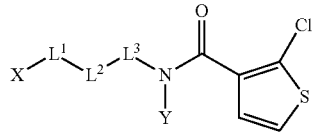

I-11

| Ex. No. | X | $L^1$ | $L^2$ | $L^3$ | Y | Physical data: $^1$H-NMR, δ [ppm] or CAS or patent No. |
|---|---|---|---|---|---|---|
| 11-1 | 3-methyl-2-thienyl | CH2 | CH2 | — | H | |
| 11-2 | 2,4-dichlorophenyl | CH2 | CH2 | CH2 | H | |
| 11-3 | 4-chlorophenyl | CH2 | CH2 | — | H | compound No. 11-3, solvent: [DMSO], spectrometer: 399.95 MHz 8.324 (1.4); 8.3105 (2.59); 8.2971 (1.42); 7.4819 (9.92); 7.4674 (10.93); 7.3651 (1); 7.3588 (9.04); 7.3541 (3.3); 7.3429 (4.14); 7.3378 (16); 7.3319 (2.25); 7.2844 (2.06); 7.2787 (13.94); 7.2739 (3.99); 7.2623 (3.01); 7.2576 (8.33); 7.1841 (11.46); 7.1696 (10.53); 3.454 (2.82); 3.4366 (5.79); 3.4219 (5.7); 3.4038 (3.12); 3.3268 (91.94); 2.8304 (5.17); 2.8122 (9.02); 2.7944 (4.63); 2.6754 (0.35); 2.6708 (0.48); 2.6663 (0.37); 2.5411 (16.41); 2.5241 (1.28); 2.5107 (25.83); 2.5062 (51.84); 2.5017 (69.01); 2.4971 (50.97); 2.4926 (24.86); 2.3331 (0.32); 2.3284 (0.44); 2.3238 (0.32); 2.0747 (0.45); −0.0002 (7.87) |
| 11-4 | 2,4-dichlorophenyl | CH2 | CH2 | — | H | compound No. 11-4, solvent: [DMSO], spectrometer: 399.95 MHz 8.3622 (1.12); 8.3484 (2.12); 8.3344 (1.12); 7.5825 (6.36); 7.5799 (3.86); 7.4827 (7.29); 7.4682 (7.98); 7.3726 (16); 7.3695 (15.8); 7.1861 (8.69); 7.1716 (8.04); 3.4845 (1.92); 3.4673 (4.73); 3.4524 (4.82); 3.4352 (2.13); 3.33 (28.07); 2.9532 (4.09); 2.9358 (7.84); 2.9183 (3.59); 2.5426 (10.86); 2.5256 (0.54); 2.5123 (9.2); 2.5078 (18.09); 2.5032 (23.82); 2.4987 (17.46); 2.4942 (8.49); −0.0002 (2.82) |
| 11-5 | 4-chlorophenyl | CH(OCH3) | CH(CH3) | — | H | |
| 11-6 | 2,4-dichlorophenyl | CH(OCH3) | CH(CH3) | — | H | |
| 11-7 | 4-chlorophenyl | CH(CH3) | CH2 | — | H | compound No. 11-7, solvent: [DMSO], spectrometer: 399.95 MHz 8.2745 (1.71); 8.2608 (3.17); 8.247 (1.75); 7.4645 (7.07); 7.45 (7.68); 7.3619 (7.04); 7.3409 (13.53); 7.2937 (13.14); 7.2726 (7.41); 7.1296 (8); 7.1151 (7.43); 3.4038 (0.52); 3.3856 (0.82); 3.3709 (2.68); 3.3532 (5.26); 3.3369 (5.77); 3.3265 (12.28); 3.3033 (0.9); 3.2886 (0.6); 3.0809 (0.35); 3.0631 (1.51); 3.0454 (2.93); 3.0275 (2.85); 3.0097 (1.37); 2.5023 (34.43); 2.4985 (28.1); 1.9893 (0.45); 1.3969 (1.19); 1.2488 (0.38); 1.2259 (16); 1.2084 (15.92); 1.1753 (0.37); −0.0002 (17.97) |
| 11-8 | 2,4-dichlorophenyl | CH(CH3) | CH2 | — | H | compound No. 11-8, solvent: [DMSO], spectrometer: 399.95 MHz 8.3291 (1.78); 8.3149 (3.46); 8.3011 (1.85); 7.558 (6.34); 7.5528 (6.84); 7.4712 (4.61); 7.4635 (7.51); 7.4495 (15.86); 7.4173 (5.42); 7.4122 (5.15); 7.3962 (2.53); 7.3911 (2.49); 7.1338 (7.92); 7.1192 (7.36); 4.0385 (0.77); 4.0208 (0.78); 3.5511 (1.19); 3.5336 (2.64); 3.5162 (3.05); 3.4991 (1.9); 3.4859 (1.53); 3.4717 (1.35); 3.4541 (2.88); 3.4385 (3.59); 3.4224 (3.86); 3.4074 (2.92); 3.3895 (2.56); 3.3749 (1.09); 3.3567 (0.7); 3.3263 (22.58); 2.5028 (45.05); 1.9897 (3.21); 1.3972 (12.85); 1.2492 (0.33); 1.2167 (15.99); 1.1997 (16); 1.1755 (1.91); 1.1576 (0.94); −0.0002 (20.68) |
| 11-9 | 4-chlorophenyl | CH2 | CH(CH3) | — | H | compound No. 11-9, solvent: [DMSO], spectrometer: 399.95 MHz 8.1383 (2.47); 8.1177 (2.5); 7.4695 (8.58); 7.4551 (9.27); 7.3752 (0.42); 7.3469 (0.87); |

TABLE 11-continued

Compounds of the formula I-11

I-11

[Structure of formula I-11: X–L¹–L²–L³–N(Y)–C(=O)– attached to a thiophene ring with Cl substituent]

| Ex. No. | X | L¹ | L² | L³ | Y | Physical data: ¹H-NMR, δ [ppm] or CAS or patent No. |
|---|---|---|---|---|---|---|
| | | | | | | 7.3408 (7.51); 7.3361 (2.74); 7.3247 (3.61); 7.3198 (13.82); 7.3141 (2.01); 7.2672 (12.32); 7.2461 (6.96); 7.1445 (9.23); 7.13 (8.54); 4.1754 (0.66); 4.1557 (1.41); 4.1392 (2.05); 4.1226 (1.49); 4.103 (0.67); 3.3281 (112.12); 2.9958 (0.65); 2.8303 (1.33); 2.8106 (1.27); 2.7967 (3.33); 2.7769 (3.33); 2.7601 (3.34); 2.7445 (3.38); 2.7265 (1.35); 2.711 (1.31); 2.671 (0.39); 2.5413 (31.42); 2.5244 (1.22); 2.5108 (22.6); 2.5065 (44.94); 2.5019 (59.63); 2.4974 (44.12); 2.493 (21.73); 2.3286 (0.38); 1.1422 (16); 1.1256 (15.88); −0.0002 (6.23) |
| 11-10 | 2,4-dichlorophenyl | CH2 | CH(CH3) | — | H | compound No. 11-11, solvent: [DMSO], spectrometer: 399.95 MHz 8.0755 (0.35); 8.0602 (0.68); 8.0447 (0.35); 7.4556 (2.62); 7.4409 (4.82); 7.4352 (0.88); 7.424 (1.07); 7.4186 (4.21); 7.412 (0.54); 7.3689 (0.53); 7.3623 (4.21); 7.3569 (1.03); 7.3456 (0.79); 7.3405 (2.34); 7.1089 (2.97); 7.0945 (2.75); 3.4168 (2.88); 3.4009 (2.86); 3.326 (22.44); 2.5411 (5.12); 2.5241 (0.37); 2.5193 (0.58); 2.5108 (7.15); 2.5063 (14.26); 2.5017 (18.89); 2.4971 (13.79); 2.4927 (6.62); 1.2964 (16); −0.0002 (2.31) |
| 11-11 | 4-chlorophenyl | C(CH3)2 | CH2 | — | H | compound No. 11-12, solvent: [DMSO], spectrometer: 399.95 MHz 8.0743 (0.37); 8.0588 (0.74); 8.0432 (0.38); 7.5223 (2.56); 7.5165 (2.75); 7.4778 (1.68); 7.4561 (2.46); 7.4438 (3.17); 7.4294 (3.37); 7.3712 (1.69); 7.3654 (1.57); 7.3497 (1.17); 7.3438 (1.11); 7.0774 (3.61); 7.0629 (3.37); 3.7598 (2.9); 3.7439 (2.88); 3.3254 (19.78); 2.5413 (3.21); 2.5244 (0.34); 2.5197 (0.51); 2.511 (6.19); 2.5065 (12.62); 2.5019 (16.92); 2.4972 (12.39); 2.4927 (5.95); 1.4489 (16); −0.0002 (2.31) |
| 11-12 | 2,4-dichlorophenyl | C(CH3)2 | CH2 | — | H | compound No. 11-13, solvent: [DMSO], spectrometer: 399.95 MHz 8.3829 (2.11); 8.3691 (3.81); 8.3557 (2.11); 7.4823 (13.81); 7.4678 (15.22); 7.458 (0.49); 7.4401 (5.35); 7.4361 (4.23); 7.4219 (7.19); 7.4171 (6.67); 7.4 (0.38); 7.368 (4.01); 7.3625 (4.87); 7.3495 (5.47); 7.3447 (7.06); 7.3074 (2.33); 7.3032 (3.01); 7.2891 (7.34); 7.2848 (6.8); 7.2742 (7.49); 7.272 (7.63); 7.2681 (8.03); 7.2557 (6); 7.2504 (5.12); 7.2372 (2.01); 7.2322 (1.55); 7.2012 (16); 7.1867 (14.67); 3.4886 (4.03); 3.4715 (8.18); 3.4566 (8.03); 3.4537 (7.57); 3.4382 (4.56); 3.3673 (0.33); 3.327 (146.98); 2.9718 (7.96); 2.9534 (12.73); 2.9358 (6.97); 2.6753 (0.51); 2.671 (0.66); 2.6665 (0.49); 2.5412 (37.44); 2.5242 (2.74); 2.5108 (39.44); 2.5064 (75.52); 2.5019 (97.85); 2.4973 (71.6); 2.4929 (35.07); 2.3332 (0.48); 2.3286 (0.64); 2.3241 (0.46); 2.0747 (0.38); 0.0079 (0.48); −0.0002 (11.2); −0.0085 (0.4) |
| 11-13 | 2-chlorophenyl | CH2 | CH2 | — | H | compound No. 11-14, solvent: [DMSO], spectrometer: 399.95 MHz 8.3194 (2.09); 8.3057 (3.86); 8.292 (2.08); 7.5558 (12.09); 7.5453 (0.61); 7.5352 (14.39); 7.5286 (11.07); 7.5236 (11.23); 7.4847 (14.74); 7.4702 (16); 7.257 (6.32); 7.2519 (6.09); 7.2364 (5.54); 7.2313 (5.33); 7.1627 (15.77); 7.1482 (14.57); 3.477 (3.74); |

TABLE 11-continued

Compounds of the formula I-11

I-11

| Ex. No. | X | L¹ | L² | L³ | Y | Physical data: ¹H-NMR, δ [ppm] or CAS or patent No. |
|---|---|---|---|---|---|---|
| | | | | | | 3.4599 (9.58); 3.4452 (9.79); 3.4283 (4.08); 3.3274 (110.78); 2.8471 (7.04); 2.8299 (14.14); 2.8126 (6.27); 2.676 (0.41); 2.6714 (0.55); 2.6667 (0.46); 2.5417 (32.72); 2.5247 (1.78); 2.5114 (31.21); 2.5069 (61.08); 2.5024 (80.34); 2.4978 (58.66); 2.4933 (28.25); 2.3337 (0.38); 2.3291 (0.52); 2.3246 (0.38); 2.0755 (0.34); 0.008 (0.34); −0.0002 (9.07) |
| 11-14 | 3,4-dichlorophenyl | CH2 | CH2 | — | H | compound No. 11-15, solvent: [DMSO], spectrometer: 399.95 MHz 8.3216 (1.26); 8.3082 (2.37); 8.2947 (1.26); 7.4877 (10.15); 7.4732 (11.05); 7.4407 (3.67); 7.436 (7.35); 7.4312 (4.19); 7.3284 (16); 7.3236 (14.68); 7.1511 (11.7); 7.1366 (10.87); 3.487 (2.32); 3.47 (6.1); 3.4555 (6.24); 3.4388 (2.55); 3.3465 (0.34); 3.3273 (80.76); 3.3112 (0.45); 2.8597 (4.25); 2.8427 (8.64); 2.8257 (3.84); 2.6713 (0.38); 2.5416 (8.3); 2.5248 (1.09); 2.5199 (1.67); 2.5113 (20.85); 2.5068 (41.83); 2.5022 (55.49); 2.4976 (40.29); 2.493 (19.11); 2.3289 (0.36); −0.0002 (7.54) |
| 11-15 | 3,5-dichlorophenyl | CH2 | CH2 | — | H | compound No. 11-16, solvent: [DMSO], spectrometer: 399.95 MHz 8.3321 (1.58); 8.3187 (2.87); 8.3052 (1.58); 7.4839 (14.27); 7.4694 (15.38); 7.359 (0.35); 7.3448 (3.19); 7.3378 (0.88); 7.3247 (15.14); 7.3198 (5.47); 7.3066 (7.88); 7.2798 (4.31); 7.2767 (6.14); 7.2745 (4.01); 7.2716 (4.33); 7.26 (2.29); 7.2564 (2.53); 7.2549 (2.51); 7.2516 (1.75); 7.225 (3.71); 7.2216 (5.76); 7.2064 (2.76); 7.2028 (4.04); 7.1998 (2.42); 7.1841 (0.59); 7.174 (16); 7.1651 (0.58); 7.1595 (14.79); 3.473 (3.4); 3.4555 (7.36); 3.4411 (7.38); 3.4232 (3.88); 3.3282 (144.3); 3.3127 (0.6); 2.8515 (6.04); 2.8337 (11.28); 2.816 (5.48); 2.6755 (0.43); 2.6709 (0.63); 2.6664 (0.43); 2.554 (0.38); 2.5412 (42.89); 2.5243 (1.78); 2.5196 (2.86); 2.511 (31.99); 2.5064 (64.24); 2.5018 (85.45); 2.4972 (61.99); 2.4926 (29.23); 2.3332 (0.42); 2.3286 (0.56); 2.3241 (0.4); 2.0746 (0.37); 0.008 (0.37); −0.0002 (11.24); −0.0085 (0.32) |
| 11-16 | 3-chlorophenyl | CH2 | CH2 | — | H | compound No. 11-17, solvent: [DMSO], spectrometer: 399.95 MHz 8.3767 (1.9); 8.3634 (3.37); 8.3495 (1.86); 7.4811 (11.89); 7.4666 (13.01); 7.339 (2.1); 7.3352 (2.47); 7.3205 (4.24); 7.316 (5.16); 7.2973 (3.78); 7.2847 (1.38); 7.2799 (2.86); 7.2653 (2.86); 7.2597 (3.62); 7.2552 (1.99); 7.246 (2.03); 7.2415 (1.67); 7.1895 (13.78); 7.175 (16); 7.1526 (8.37); 7.1361 (6.92); 7.1334 (6.68); 7.1178 (2.86); 7.115 (2.54); 3.4647 (3.72); 3.4477 (7.58); 3.4323 (7.23); 3.4141 (4.05); 3.3283 (141.3); 2.878 (5.94); 2.8599 (10.29); 2.8418 (5.24); 2.6755 (0.46); 2.6709 (0.58); 2.6664 (0.42); 2.5413 (37.08); 2.5107 (34.65); 2.5064 (67.03); 2.5019 (88.23); 2.4974 (65.69); 2.4931 (32.79); 2.3333 (0.42); 2.3286 (0.56); 2.3242 (0.41); −0.0002 (7.45) |
| 11-17 | 2-fluorophenyl | CH2 | CH2 | — | H | compound No. 11-18, solvent: [DMSO], spectrometer: 399.95 MHz 8.4295 (1.87); 8.4151 (3.52); 8.4009 (1.86); 7.4813 (14.56); 7.4668 (16); 7.3601 (1.18); |

TABLE 11-continued

Compounds of the formula I-11

I-11

| Ex. No. | X | L¹ | L² | L³ | Y | Physical data: $^1$H-NMR, δ [ppm] or CAS or patent No. |
|---|---|---|---|---|---|---|
| | | | | | | 7.3433 (2.58); 7.3391 (2.31); 7.3224 (5.03); 7.3185 (2.04); 7.3053 (2.42); 7.3016 (3.18); 7.2848 (1.5); 7.1731 (15.19); 7.1586 (14.02); 7.0998 (0.65); 7.0953 (0.93); 7.0831 (6.82); 7.0751 (1.31); 7.0632 (10.87); 7.0518 (1.34); 7.0431 (5.77); 7.0305 (0.76); 3.4342 (3.37); 3.4174 (8.24); 3.4011 (8.25); 3.3842 (3.75); 3.3542 (0.4); 3.3485 (0.67); 3.3276 (165.07); 3.3094 (0.55); 3.3036 (0.36); 2.8962 (5.11); 2.8786 (9.51); 2.8611 (4.56); 2.6757 (0.41); 2.6711 (0.56); 2.6666 (0.41); 2.5415 (1.8); 2.5243 (1.8); 2.5111 (32.75); 2.5066 (64.62); 2.502 (85.44); 2.4974 (62.13); 2.4929 (29.71); 2.3334 (0.39); 2.3288 (0.55); 2.3243 (0.39); −0.0002 (8.23) |
| 11-18 | 2,6-difluorophenyl | CH2 | CH2 | — | H | compound No. 11-19, solvent: [DMSO], spectrometer: 399.95 MHz 8.4545 (1.91); 8.4408 (3.47); 8.4271 (1.91); 7.484 (6.03); 7.4822 (6.36); 7.4675 (16); 7.4458 (13.27); 7.3032 (4.03); 7.2836 (6.08); 7.2637 (2.64); 7.2223 (6.73); 7.2208 (6.83); 7.2078 (6.04); 7.2063 (6.15); 3.4725 (2.41); 3.4559 (6.31); 3.4397 (6.75); 3.4227 (3.01); 3.3312 (92.15); 3.1678 (5.53); 3.1503 (9.02); 3.1324 (4.42); 2.675 (0.38); 2.5437 (6.69); 2.5419 (6.94); 2.5061 (57.13); 2.5027 (58.98); 2.3299 (0.38); 0.0015 (2.92); −0.0002 (3.07) |
| 11-19 | 2,6-dichlorophenyl | CH2 | CH2 | — | H | compound No. 11-20, solvent: [DMSO], spectrometer: 399.95 MHz 8.3374 (2.21); 8.3242 (3.94); 8.3107 (2.11); 7.6684 (0.41); 7.6481 (0.56); 7.597 (8.84); 7.5858 (3.27); 7.5768 (3.53); 7.5622 (16); 7.5494 (9.65); 7.5371 (3.76); 7.5256 (1.78); 7.5133 (1.26); 7.4932 (0.47); 7.4801 (14.24); 7.4656 (15.49); 7.1809 (0.59); 7.1663 (0.71); 7.156 (15.92); 7.1415 (14.7); 3.5098 (4.08); 3.4924 (10.09); 3.4779 (10.2); 3.4606 (4.58); 3.3562 (0.52); 3.3286 (201.14); 3.3061 (0.64); 2.949 (7.48); 2.9315 (14.75); 2.9141 (6.7); 2.6761 (0.54); 2.6714 (0.73); 2.6668 (0.53); 2.5416 (50.7); 2.5246 (2.16); 2.5113 (41.94); 2.5069 (82.27); 2.5023 (108.16); 2.4978 (78.98); 2.4933 (38.15); 2.3335 (0.48); 2.329 (0.68); 2.3245 (0.48); 2.0749 (0.47); 0.0079 (0.44); −0.0002 (11.06); −0.0084 (0.35) |
| 11-20 | 3-(trifluoromethyl)phenyl | CH2 | CH2 | — | H | compound No. 11-21, solvent: [DMSO], spectrometer: 399.95 MHz 8.3587 (1.15); 8.345 (2.15); 8.331 (1.14); 7.6683 (5.85); 7.6483 (7.14); 7.4864 (7.11); 7.4832 (14.15); 7.4686 (16); 7.1809 (11.51); 7.1664 (10.68); 3.5062 (2.2); 3.4889 (4.78); 3.4743 (4.78); 3.4564 (2.44); 3.3283 (114.84); 2.9386 (3.41); 2.9209 (6.32); 2.9031 (3); 2.6714 (0.4); 2.5416 (1.14); 2.5248 (1.33); 2.5201 (2.07); 2.5115 (22.77); 2.5069 (45.71); 2.5023 (60.81); 2.4977 (44.06); 2.4931 (20.85); 2.3291 (0.4); −0.0002 (8.15) |
| 11-21 | 4-(trifluoromethyl)phenyl | CH2 | CH2 | — | H | compound No. 11-22, solvent: [DMSO], spectrometer: 399.95 MHz 8.3927 (0.54); 8.3785 (1); 8.3649 (0.54); 7.4914 (4.51); 7.4769 (4.99); 7.224 (5.11); 7.2095 (4.71); 7.1729 (0.82); 7.1649 (1.47); 7.1617 (1.1); 7.1537 (2.34); 7.1505 (2.52); |

TABLE 11-continued

Compounds of the formula I-11

I-11

| Ex. No. | X | L¹ | L² | L³ | Y | Physical data: ¹H-NMR, δ [ppm] or CAS or patent No. |
|---|---|---|---|---|---|---|
| | | | | | | 7.144 (2.2); 7.1362 (1.07); 7.1301 (0.82); 7.125 (3); 7.1214 (3.18); 7.1183 (1.49); 7.1122 (2.9); 7.1059 (1.29); 7.1 (1.47); 3.4032 (1.17); 3.3881 (1.96); 3.3846 (1.6); 3.3798 (1.13); 3.3727 (1.28); 3.3698 (1.58); 3.365 (2.11); 3.3504 (1.4); 3.3279 (50.23); 2.8321 (2.25); 2.8168 (1.73); 2.8124 (2.5); 2.7938 (2.01); 2.5408 (12.42); 2.524 (0.59); 2.5191 (0.91); 2.5106 (11.37); 2.5061 (22.79); 2.5015 (30.32); 2.4968 (22.05); 2.4923 (10.49); 2.3193 (16); −0.0002 (3.87) |
| 11-22 | 2-methylphenyl | CH2 | CH2 | — | H | compound No. 11-23, solvent: [DMSO], spectrometer: 399.95 MHz 8.4846 (0.48); 8.4704 (0.88); 8.4564 (0.48); 7.5054 (1.96); 7.4908 (2.16); 7.2682 (2.2); 7.2537 (2); 6.8072 (4.44); 3.3271 (31.98); 3.2443 (0.62); 3.2295 (1.12); 3.2158 (1.08); 3.2087 (0.96); 3.2031 (1.11); 3.1888 (0.7); 2.8004 (1.25); 2.7867 (1.05); 2.7792 (1.32); 2.7596 (1.02); 2.5409 (4.06); 2.5056 (16.7); 2.5014 (20.02); 2.4971 (15.02); 2.297 (16); 2.1819 (7.29); −0.0002 (1.53) |
| 11-23 | 2,4,6-trimethylphenyl | CH2 | CH2 | — | H | compound No. 11-25, solvent: [DMSO], spectrometer: 399.95 MHz 8.3377 (1.59); 8.3247 (2.81); 8.3109 (1.58); 7.4827 (13.01); 7.4682 (14.31); 7.3191 (3.86); 7.3153 (1.65); 7.3008 (10.29); 7.2874 (3.19); 7.2828 (10.7); 7.256 (9.52); 7.252 (13.53); 7.2467 (2.78); 7.2352 (6.55); 7.2256 (3.21); 7.2219 (3.53); 7.2181 (1.9); 7.2092 (2.15); 7.204 (5.95); 7.1998 (16); 7.1853 (15.1); 3.4592 (3.82); 3.4413 (5.92); 3.4268 (5.78); 3.4227 (6.18); 3.4078 (4.19); 3.3276 (137.01); 2.8379 (6.65); 2.8187 (9.34); 2.8007 (5.92); 2.6752 (0.47); 2.6705 (0.61); 2.666 (0.43); 2.5408 (30.04); 2.5239 (1.92); 2.519 (2.92); 2.5105 (34.19); 2.506 (68.14); 2.5014 (90.31); 2.4968 (65.75); 2.4923 (31.2); 2.3327 (0.42); 2.3282 (0.58); 2.3236 (0.41); 2.0741 (0.68); 0.008 (0.38); −0.0002 (11.51); −0.0085 (0.32) |
| 11-24 | 3,4-bismethoxyphenyl | CH2 | CH2 | — | H | compound No. 11-7, solvent: [DMSO], spectrometer: 399.95 MHz 8.2745 (1.71); 8.2608 (3.17); 8.247 (1.75); 7.4645 (7.07); 7.45 (7.68); 7.3619 (7.04); 7.3409 (13.53); 7.2937 (13.14); 7.2726 (7.41); 7.1296 (8); 7.1151 (7.43); 3.4038 (0.52); 3.3856 (0.82); 3.3709 (2.68); 3.3532 (5.26); 3.3369 (5.77); 3.3265 (12.28); 3.3033 (0.9); 3.2886 (0.6); 3.0809 (0.35); 3.0631 (1.51); 3.0454 (2.93); 3.0275 (2.85); 3.0097 (1.37); 2.5023 (34.43); 2.4985 (28.1); 1.9893 (0.45); 1.3969 (1.19); 1.2488 (0.38); 1.2259 (16); 1.2084 (15.92); 1.1753 (0.37); −0.0002 (17.97) |
| 11-25 | phenyl | CH2 | CH2 | — | H | compound No. 11-8, solvent: [DMSO], spectrometer: 399.95 MHz 8.3291 (1.78); 8.3149 (3.46); 8.3011 (1.85); 7.558 (6.34); 7.5528 (6.84); 7.4712 (4.61); 7.4635 (7.51); 7.4495 (15.86); 7.4173 (5.42); 7.4122 (5.15); 7.3962 (2.53); 7.3911 (2.49); 7.1338 (7.92); 7.1192 (7.36); 4.0385 (0.77); 4.0208 (0.78); 3.5511 (1.19); 3.5336 (2.64); 3.5162 (3.05); 3.4991 (1.9); 3.4859 (1.53); 3.4717 (1.35); 3.4541 (2.88); 3.4385 (3.59); 3.4224 (3.86); 3.4074 (2.92); 3.3895 (2.56); |

TABLE 11-continued

Compounds of the formula I-11

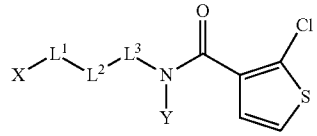

I-11

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 3.3749 (1.09); 3.3567 (0.7); 3.3263 (22.58); 2.5028 (45.05); 1.9897 (3.21); 1.3972 (12.85); 1.2492 (0.33); 1.2167 (15.99); 1.1997 (16); 1.1755 (1.91); 1.1576 (0.94); −0.0002 (20.68) |
| 11-26 | 4-chlorophenyl | C(CH2—CH2) | CH2 | — | H | |
| 11-27 | 2,4-dichlorophenyl | C(CH2—CH2) | CH2 | — | H | |
| 11-28 | 4-chlorophenyl | CH2 | C(CH2—CH2) | — | H | |
| 11-29 | 2,4-dichlorophenyl | CH2 | C(CH2—CH2) | — | H | |
| 11-30 | 4-chlorophenyl | O | CH2 | CH2 | H | |
| 11-31 | 2,4-dichlorophenyl | O | CH2 | CH2 | H | |
| 11-32 | 4-chlorophenyl | CH2 | CH2 | CH2 | H | |
| 11-33 | 4-chlorophenyl | NCH3 | CH2 | CH2 | H | |
| 11-34 | 2,4-dichlorophenyl | NCH3 | CH2 | CH2 | H | |
| 11-35 | 4-chlorophenyl | CH(OCH3) | CH2 | — | H | |
| 11-36 | 2,4-dichlorophenyl | CH(OCH3) | CH2 | — | H | |
| 11-37 | 2-thienyl | CH2 | CH2 | — | H | compound No. 11-37, solvent: [DMSO], spectrometer: 399.95 MHz 8.4093 (1.8); 8.3956 (3.2); 8.3822 (1.77); 7.4959 (13.95); 7.4813 (15.41); 7.3512 (6.88); 7.3481 (7.15); 7.3384 (7.63); 7.3354 (7.39); 7.2335 (16); 7.219 (14.45); 6.9708 (5.81); 6.9623 (8.32); 6.9581 (5.41); 6.9496 (8.12); 6.9238 (6.96); 6.9215 (7.3); 6.9155 (4.9); 6.913 (4.71); 3.4761 (4.02); 3.4583 (8.51); 3.4439 (8.66); 3.4404 (6.22); 3.4258 (4.68); 3.3277 (170.52); 3.3062 (0.39); 3.0561 (7.24); 3.0383 (12.69); 3.0202 (6.06); 2.675 (0.47); 2.6705 (0.64); 2.6658 (0.47); 2.5408 (45.14); 2.5238 (1.96); 2.5189 (3.11); 2.5104 (36.74); 2.5059 (73.63); 2.5013 (97.89); 2.4968 (71.63); 2.4923 (34.49); 2.3327 (0.44); 2.3281 (0.61); 2.3235 (0.45); 2.0742 (0.49); 0.008 (0.35); −0.0002 (10.89) |
| 11-38 | 3-thienyl | CH2 | CH2 | — | H | |
| 11-39 | 2-furyl | CH2 | CH2 | — | H | |
| 11-40 | 3-furyl | CH2 | CH2 | — | H | |
| 11-41 | phenyl | CH2 | CH2 | CH(CH3) | H | |
| 11-42 | phenyl | CH2 | CH2 | CH2 | H | |
| 11-43 | 2-Cl-phenyl | CH2 | CH2 | CH(CH3) | H | |
| 11-44 | 4-t-butylphenyl | CH2 | CH2 | CH2 | H | |
| 11-45 | 4-methylphenyl | CH2 | CH2 | CH2 | H | |
| 11-46 | phenyl | CH2 | CH2 | CH(CH2CH3) | H | |
| 11-47 | 2-methoxyphenyl | CH2 | CH2 | CH2 | H | |
| 11-48 | 2-methylphenyl | CH2 | CH2 | CH2 | H | |
| 11-49 | 3-methylphenyl | CH2 | CH2 | CH2 | H | |
| 11-50 | 3-chlorophenyl | CH2 | CH2 | CH2 | H | |
| 11-51 | 2,6-difluorophenyl | CH2 | CH2 | CH2 | H | |
| 11-52 | 4-chlorophenyl | CH2 | CH2 | CH2 | H | |
| 11-53 | 2,6-dichlorophenyl | CH2 | CH2 | CH(CH3) | H | |
| 11-54 | 3,5-dichlorophenyl | CH2 | CH2 | CH(CH3) | H | |
| 11-55 | 2,6-dimethylphenyl | CH2 | CH2 | CH2 | H | |
| 11-56 | 2,5-dichlorophenyl | CH2 | CH2 | CH2 | H | |
| 11-57 | 4-isopropoxyphenyl | CH2 | CH2 | CH2 | H | |
| 11-58 | 3-trifluoromethylphenyl | CH2 | CH2 | CH(CH3) | H | |
| 11-59 | 4-methylphenyl | CH2 | CH2 | CH(CH3) | H | |
| 11-60 | 2-methylphenyl | CH2 | CH2 | CH(CH3) | H | |
| 11-61 | 3,4-dichlorophenyl | CH2 | CH2 | CH(CH3) | H | |
| 11-62 | 3,5-dichlorophenyl | CH2 | CH2 | CH2 | H | |
| 11-63 | 2,6-dimethylphenyl | CH2 | CH2 | CH(CH3) | H | |
| 11-64 | 4-trifluoromethylphenyl | CH2 | CH2 | CH(CH3) | H | |
| 11-65 | 2,5-dichlorophenyl | CH2 | CH2 | CH(CH3) | H | |
| 11-66 | 4-phenoxyphenyl | CH2 | CH2 | CH2 | H | |
| 11-67 | 3-chlorophenyl | CH2 | CH2 | CH(CH3) | H | |
| 11-68 | 4-phenoxyphenyl | CH2 | CH2 | CH(CH3) | H | |
| 11-69 | 2,4-dichlorophenyl | CH2 | CH2 | CH(CH3) | H | |

TABLE 11-continued

Compounds of the formula I-11

I-11

| Ex. No. | X | L¹ | L² | L³ | Y | Physical data: ¹H-NMR, δ [ppm] or CAS or patent No. |
|---|---|---|---|---|---|---|
| 11-70 | 2-difluoromethoxyphenyl | CH2 | CH2 | CH(CH3) | H | |
| 11-71 | 4-methoxyphenyl | CH2 | CH2 | CH2 | H | |
| 11-72 | 4-chlorophenyl | CH2 | CH2 | CH(CH3) | H | |
| 11-73 | 4-chlorophenyl | CH2 | CH2 | CH(i-propyl) | H | |
| 11-74 | 4-fluorophenyl | CH2 | CH2 | CH2 | H | |
| 11-75 | 4-chlorophenyl | CH2 | CH2 | CH(n-propyl) | H | |
| 11-76 | 4-chlorophenyl | CH2 | CH2 | CH(t-butyl) | H | |
| 11-77 | 2-chlorophenyl | CH2 | CH2 | CH2 | H | |
| 11-78 | 4-chlorophenyl | CH2 | CH(CH3) | — | cyclopropyl | |
| 11-79 | 4-chlorophenyl | CH(OCH3) | CH2 | — | H | compound No. 11-79, solvent: [DMSO], spectrometer: 399.95 MHz 8.346 (0.51); 8.3319 (0.98); 8.3169 (0.52); 7.4778 (2.93); 7.4632 (3.31); 7.4523 (2.92); 7.4479 (1.11); 7.436 (1.26); 7.4312 (4.69); 7.4257 (0.71); 7.36 (4.42); 7.3389 (2.8); 7.1917 (3.31); 7.1772 (3.03); 4.4049 (0.83); 4.3894 (1.47); 4.373 (0.88); 3.4211 (0.97); 3.4123 (1.06); 3.4068 (1.24); 3.4041 (1.33); 3.3976 (1.8); 3.3899 (1.01); 3.3829 (0.95); 3.3214 (14.07); 3.1713 (16); 2.5238 (0.82); 2.5104 (12.71); 2.506 (25.27); 2.5015 (33.73); 2.497 (25.32); 2.4927 (12.7); −0.0002 (1.91) |
| 11-80 | 4-chlorophenyl | N(CH3) | CH2 | CH2 | H | compound No. 11-80, solvent: [DMSO], spectrometer: 399.95 MHz 8.3571 (0.64); 8.3429 (1.2); 8.3295 (0.65); 8.3151 (0.39); 7.4802 (3.24); 7.4657 (3.5); 7.1859 (0.54); 7.1768 (4.22); 7.1716 (1.62); 7.156 (6.44); 7.1418 (3.48); 6.764 (0.58); 6.7555 (4.42); 6.7328 (3.91); 6.7239 (0.45); 3.4846 (1.24); 3.4676 (2.95); 3.4512 (2.23); 3.378 (1.52); 3.3628 (3.09); 3.3268 (337.58); 3.2827 (0.56); 2.9343 (0.72); 2.9132 (16); 2.6751 (0.92); 2.6707 (1.23); 2.6666 (0.91); 2.5409 (7.25); 2.5061 (147.5); 2.5017 (188.35); 2.4973 (139.99); 2.3328 (0.95); 2.3285 (1.25); 2.3241 (0.93); 0.0077 (1.16); −0.0003 (24.24); −0.0086 (1.12) |

TABLE 12

Compounds of the formula I-12

I-12

| Ex. No. | X | L¹ | L² | L³ | Y | Physical data: ¹H-NMR, δ [ppm] or CAS or patent No. |
|---|---|---|---|---|---|---|
| 12-1 | 3-methyl-2-thienyl | CH2 | CH2 | — | H | |
| 12-2 | 2,4-dichlorophenyl | CH2 | CH2 | CH2 | H | compound No. 12-2, solvent: [DMSO], spectrometer: 399.95 MHz 8.3521 (1.86); 8.3384 (3.5); 8.3246 (1.85); 7.6354 (13.63); 7.6211 (14.47); 7.5685 (9); 7.5632 (9.4); 7.433 (6.12); 7.4123 (13.13); 7.3828 (8.55); 7.3775 (7.98); 7.3621 (3.81); 7.3568 (3.76); 7.207 (16); 7.1988 (0.63); 7.1927 (15.22); 3.5145 (0.52); 3.3343 (52.66); 3.2728 (3.31); 3.2557 (7.93); 3.2409 (7.97); 3.2238 (3.44); 2.7614 (5.95); 2.7425 (7.24); 2.7226 (6.35); 2.544 (28.04); 2.5271 (0.65); 2.5222 (0.99); 2.5136 (12.37); 2.5091 (25.04); 2.5045 (33.42); 2.4999 (24.37); |

TABLE 12-continued

Compounds of the formula I-12

![Structure of formula I-12: X-L¹-L²-L³-N(Y)-C(=O)-(2-bromothiophen-3-yl)]

I-12

| Ex. No. | X | L¹ | L² | L³ | Y | Physical data: ¹H-NMR, δ [ppm] or CAS or patent No. |
|---|---|---|---|---|---|---|
| 12-3 | 4-chloro-phenyl | CH2 | CH2 | — | H | 2.4954 (11.58); 1.819 (1.71); 1.8011 (4.5); 1.7821 (5.68); 1.7634 (4.33); 1.7456 (1.51); −0.0002 (4.14) [DMSO], spectrometer: 399.95 MHz 8.3531 (1.66); 8.3395 (3.09); 8.3258 (1.65); 7.6271 (10.73); 7.6128 (11.25); 7.3689 (1.14); 7.3627 (9.27); 7.3579 (3.66); 7.3466 (4.48); 7.3416 (16.00); 7.3357 (2.73); 7.2857 (14.23); 7.2692 (3.39); 7.2645 (8.46); 7.1601 (11.40); 7.1458 (10.88); 3.4522 (2.83); 3.4349 (5.97); 3.4200 (5.81); 3.4020 (3.12); 3.3459 (18.77); 2.8345 (5.41); 2.8164 (9.21); 2.7985 (4.75); 2.5436 (4.58); 2.5266 (0.41); 2.5218 (0.61); 2.5131 (7.31); 2.5087 (14.83); 2.5042 (19.72); 2.4997 (14.85); 2.4953 (7.53); −0.0002 (6.24) |
| 12-4 | 2,4-di-chloro-phenyl | CH2 | CH2 | — | H | [DMSO], spectrometer: 399.95 MHz 8.3827 (1.20); 8.3689 (2.31); 8.3551 (1.19); 7.6272 (7.73); 7.6130 (8.21); 7.5924 (3.75); 7.5898 (6.55); 7.5869 (4.05); 7.3796 (16.00); 7.3766 (15.68); 7.1564 (8.02); 7.1421 (7.63); 3.4760 (1.81); 3.4588 (4.60); 3.4437 (4.66); 3.4267 (2.04); 3.3355 (126.32); 3.3131 (0.35); 2.9517 (3.91); 2.9342 (7.57); 2.9168 (3.44); 2.6759 (0.61); 2.6713 (0.84); 2.6668 (0.62); 2.5418 (12.45); 2.5247 (2.68); 2.5112 (45.90); 2.5068 (93.39); 2.5022 (124.88); 2.4977 (93.92); 2.4933 (47.45); 2.3336 (0.59); 2.3290 (0.83); 2.3246 (0.62); 0.0080 (1.23); −0.0002 (39.06); −0.0085 (1.53) |
| 12-5 | 4-chloro-phenyl | CH(OCH3) | CH(CH3) | — | H | [DMSO], spectrometer: 399.95 MHz 8.1677 (1.14); 8.1461 (1.16); 8.0316 (0.91); 8.0115 (0.92); 7.6200 (2.69); 7.6058 (2.90); 7.5969 (3.53); 7.5827 (3.63); 7.4445 (2.70); 7.4403 (1.05); 7.4270 (4.17); 7.4235 (5.00); 7.4107 (1.49); 7.4059 (5.32); 7.3445 (4.85); 7.3238 (6.23); 7.3031 (2.59); 7.1741 (2.82); 7.1598 (2.70); 7.0188 (3.55); 7.0046 (3.45); 4.3154 (1.44); 4.3003 (1.83); 4.2305 (1.96); 4.2139 (2.72); 4.1965 (0.69); 4.1777 (0.64); 4.1611 (0.39); 4.0941 (0.57); 4.0773 (0.89); 4.0728 (0.70); 4.0604 (0.63); 4.0559 (0.90); 4.0391 (0.52); 3.3426 (14.99); 3.1828 (16.00); 3.1636 (12.86); 2.5435 (4.51); 2.5130 (5.58); 2.5087 (11.35); 2.5041 (15.15); 2.4996 (11.48); 2.4953 (5.90); 1.1524 (6.20); 1.1355 (6.18); 0.9758 (4.73); 0.9587 (4.70); −0.0002 (4.29) |
| 12-6 | 2,4-di-chloro-phenyl | CH(OCH3) | CH(CH3) | — | H | |
| 12-7 | 4-chloro-phenyl | CH(CH3) | CH2 | — | H | [DMSO], spectrometer: 399.95 MHz 8.3039 (1.48); 8.2899 (2.87); 8.2756 (1.51); 7.6091 (9.53); 7.5948 (10.00); 7.3722 (0.88); 7.3663 (7.56); 7.3614 (2.91); 7.3501 (3.85); 7.3450 (14.62); 7.3393 (2.53); 7.3055 (2.22); 7.3002 (13.56); 7.2953 (4.05); 7.2835 (2.78); 7.2789 (7.33); 7.1006 (9.98); 7.0863 (9.59); 3.4004 (0.53); 3.3850 (0.69); 3.3818 (0.76); 3.3673 (2.66); 3.3438 (21.19); 3.3339 (5.14); 3.3169 (2.93); 3.3022 (0.66); 3.2985 (0.77); 3.2842 (0.59); 3.0643 (1.39); 3.0465 (2.77); 3.0287 (2.68); 3.0108 (1.26); 2.5434 (3.93); 2.5265 (0.36); 2.5215 (0.54); 2.5130 (7.13); 2.5086 (14.55); 2.5040 (19.46); 2.4995 (14.72); 2.4952 (7.56); 1.2340 (16.00); 1.2165 (15.81); −0. 0002 (5.65) |
| 12-8 | 2,4-di-chloro-phenyl | CH(CH3) | CH2 | — | H | [DMSO], spectrometer: 399.95 MHz 8.3540 (1.52); 8.3397 (2.97); 8.3255 (1.54); 8.3223 (1.47); 7.6089 (9.43); 7.5946 (9.98); 7.5638 (7.41); 7.5585 (7.90); 7.4769 (4.67); 7.4557 (9.53); 7.4215 (5.64); 7.4161 (5.24); 7.4004 (2.71); 7.3951 (2.63); 7.1065 (10.03); 7.0922 (9.64); 3.5477 (1.10); 3.5303 (2.51); 3.5130 (2.89); 3.4958 (1.76); 3.4830 (1.42); 3.4687 (1.31); 3.4511 (2.77); 3.4356 (3.09); 3.4170 (2.67); 3.4016 (2.58); 3.3835 (2.49); 33.3691 (1.09); 3.3660 (1.00); .3405 (28.82); 2.5434 (5.88); 2.5264 (0.75); 2.5129 (12.07); 2.5086(24.01); 2.5040 (31.64); 2.4995 (23.61); 2.4952 (11.92); 1.4586 (0.34);1.2241 (16.00); 1.2071 (15.79); −0.0002 (8.22); −0.0085 (0.34) |
| 12-9 | 4-chloro-phenyl | CH2 | CH(CH3) | — | H | [DMSO], spectrometer: 399.95 MHz 8.1645 (2.67); 8.1440 (2.71); 7.6151 (9.36); 7.6009 (9.83); 7.4696 (0.47); 7.3522 (0.85); 7.3462 (7.80); 7.3415 (2.95); 7.3301 (3.80); 7.3251 (14.28); 7.3194 (2.28); 7.2725 (12.62); 7.2514 (7.20); 7.1143 (9.87);7.1001 (9.41); 4.1697 (0.66); 4.1503 (1.45); 4.1336 (2.09); 4.1169 (1.53); 4.0976 (0.70); 3.3395 (50.45); 2.9978 (0.55); 2.8343 (1.45); 2.8147 (1.41); 2.8007 (3.21); 2.7811 (3.19); 2.7553 (3.23); 2.7396 (3.31); 2.7217 (1.50); 2.7060 (1.35); 2.5423 (26.31); 2.5254 |

TABLE 12-continued

Compounds of the formula I-12

I-12

| Ex. No. | X | L¹ | L² | L³ | Y | Physical data: ¹H-NMR, δ [ppm] or CAS or patent No. |
|---|---|---|---|---|---|---|
| | | | | | | (0.90); 2.5205 (1.33); 2.5118 (17.41); 2.5074 (35.27); 2.5029 (46.85); 2.4983 (35.21); 2.4939 (17.89); 1.1401 (16.00); 1.1236 (15.93); 0.0080 (0.38); −0.0002 (12.17); −0.0085 (0.50) |
| 12-10 | 2,4-di-chlorophenyl | CH2 | CH(CH3) | — | H | [DMSO], spectrometer: 399.95 MHz
8.2004 (2.78); 8.1790 (2.87); 7.6185 (9.67); 7.6042 (10.31); 7.5727 (6.11); 7.5682 (6.35); 7.5573 (0.58); 7.5523 (0.33); 7.3941 (1.81); 7.3735 (10.64); 7.3678 (8.82); 7.3630 (8.00); 7.3471 (1.37); 7.3423 (1.67); 7.1163 (9.94); 7.1021 (9.58); 4.3105 (0.60); 4.2898 (1.42); 4.2735 (1.87); 4.2576 (1.31); 4.2367 (0.64); 3.3379 (793.49); 2.9388 (0.95); 2.9239 (1.21); 2.9045 (4.14); 2.8893 (7.23); 2.8679 (3.64); 2.8546 (1.03); 2.8338 (1.09); 2.6759 (2.15); 2.6713 (3.02); 2.6668 (2.27); 2.5417 (6.08); 2.5248 (8.92); 2.5200 (13.44); 2.5112 (158.61); 2.5068 (325.54); 2.5023 (436.98); 2.4977 (330.10); 2.4933 (167.93); 2.3379 (0.97); 2.3336 (2.09); 2.3290 (2.90); 2.3245 (2.19); 1.1868 (16.00); 1.1702 (15.87); 0.0080 (2.04); −0.0002 (61.12); −0.0085 (2.26) |
| 12-11 | 4-chlorophenyl | C(CH3)2 | CH2 | — | H | [DMSO], spectrometer: 399.95 MHz
8.1110 (0.51); 8.0956 (1.00); 8.0801 (0.51); 7.5962 (3.37); 7.5820 (3.53); 7.4555 (0.35); 7.4487 (2.98); 7.4436 (1.15); 7.4321 (1.42); 7.4269 (4.94); 7.4203 (0.77); 7.3711 (0.69); 7.3645 (4.97); 7.3593 (1.46); 7.3477 (1.09); 7.3427 (2.99); 7.3360 (0.37); 7.0825 (3.55); 7.0683 (3.41); 3.4141 (3.37); 3.3982 (3.35); 3.3440 (6.40); 2.5433 (2.11); 2.5128 (2.24); 2.5084 (4.44); 2.5039 (5.84); 2.4994 (4.38); 2.4951 (2.20); 1.3075 (16.00); −0.0002 (1.51) |
| 12-12 | 2,4-di-chlorophenyl | C(CH3)2 | CH2 | — | H | [DMSO], spectrometer: 399.95 MHz
8.1079 (0.60); 8.0923 (1.19); 8.0767 (0.60); 7.5849 (3.47); 7.5707 (3.62); 7.5197 (2.71); 7.5139 (2.93); 7.4941 (2.06); 7.4724 (2.84); 7.3706 (1.81); 7.3648 (1.73); 7.3490 (1.33); 7.3432 (1.29); 7.0520 (3.91); 7.0378 (3.78); 3.7589 (3.57); 3.7430 (3.55); 3.3450 (6.00); 2.5443 (2.75); 2.5138 (1.93); 2.5095 (3.90); 2.5050 (5.19); 2.5005 (3.94); 2.4963 (2.03); 1.4603 (16.00); −0.0002 (1.31) |
| 12-13 | 2-chlorophenyl | CH2 | CH2 | — | H | [DMSO], spectrometer: 399.95 MHz
8.4127 (2.48); 8.3990 (4.61); 8.3852 (2.47); 7.6280 (15.19); 7.6137 (16.00); 7.4427 (5.76); 7.4388 (5.01); 7.4243 (7.64); 7.4197 (7.42); 7.3771 (4.40); 7.3719 (5.36); 7.3585 (6.21); 7.3539 (7.66); 7.3115 (2.49); 7.3074 (3.25); 7.2932 (7.49); 7.2891 (7.31); 7.2759 (11.33); 7.2705 (10.51); 7.2574 (6.18); 7.2523 (5.81); 7.2388 (2.14); 7.2340 (1.79); 7.1805 (15.75); 7.1662 (14.99); 3.4881 (4.06); 3.4711 (8.61); 3.4557 (8.12); 3.4531 (8.32); 3.4376 (4.61); 3.3496 (21.16); 2.9774 (8.27); 2.9589 (13.18); 2.9413 (7.23); 2.5443 (11.48); 2.5273 (0.45); 2.5137 (7.95); 2.5094 (16.09); 2.5049 (21.36); 2.5004 (16.25); 2.4962 (8.34); −0.0002 (5.49) |
| 12-14 | 3,4-di-chlorophenyl | CH2 | CH2 | — | H | [DMSO], spectrometer: 399.95 MHz
8.3492 (2.08); 8.3354 (3.92); 8.3217 (2.09); 7.6322 (11.80); 7.6179 (12.44); 7.5574 (8.96); 7.5363 (16.00); 7.5302 (9.94); 7.2643 (5.49); 7.2593 (5.34); 7.2438 (4.80); 7.2387 (4.73); 7.1441 (13.25); 7.1298 (12.72); 3.4797 (3.29); 3.4626 (8.30); 3.4479 (8.48); 3.4309 (3.63); 3.3536 (12.70); 2.8534 (6.22); 2.8362 (12.12); 2.8188 (5.64); 2.5468 (8.28); 2.5249 (0.46); 2.5163 (5.42); 2.5120 (10.84); 2.5075 (14.28); 2.5029 (10.66); 2.4986 (5.37); −0.0002 (3.77) |
| 12-15 | 3,5-di-chlorophenyl | CH2 | CH2 | — | H | [DMSO], spectrometer: 399.95 MHz
8.3492 (1.63); 8.3356 (3.08); 8.3218 (1.63); 7.6359 (9.82); 7.6216 (10.28); 7.4403 (3.65); 7.4356 (7.02); 7.4309 (4.37); 7.3343 (16.00); 7.3296 (15.16); 7.1307 (10.96); 7.1165 (10.51); 3.4879 (2.44); 3.4710 (6.52); 3.4563 (6.56); 3.4395 (2.73); 3.3475 (9.73); 2.8644 (4.63); 2.8474 (9.16); 2.8302 (4.22); 2.5452 (0.46); 2.5148 (5.16); 2.5104 (10.48); 2.5059 (13.97); 2.5014 (10.59); 2.4972 (5.44); −0.0002 (4.02) |
| 12-16 | 3-chlorophenyl | CH2 | CH2 | — | H | [DMSO], spectrometer: 399.95 MHz
8.3626 (2.09); 8.3491 (3.90); 8.3356 (2.16); 7.6299 (12.83); 7.6156 (13.56); 7.3625 (0.43); 7.3479 (3.43); 7.3411 (1.31); 7.3290 (16.00); 7.3096 (8.19); 7.2816 (4.61); 7.2786 (6.59); 7.2738 (4.89); 7.2618 (2.62); 7.2572 (3.02); 7.2539 (2.13); 7.2285 (6.48); 7.2100 (4.52); 77.1617 (0.57); .1525 (14.20); 7.1383 (13.63); 3.4730 (3.57); 3.4556 (7.97); 3.4409 (8.00); 3.4232 (4.10); 3.3497 (19.51); 2.8568 (6.66); 2.8390 (12.06); 2.8211 (6.12); 2.5439 (12.22); 2.5270 (0.35); 2.5134 (6.93); 2.5091 (13.86); 2.5046 (18.26); 2.5000 (13.73); 2.4958 (6.97); −0.0002 (5.23) |

TABLE 12-continued

Compounds of the formula I-12

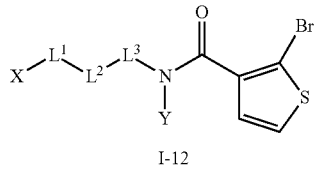

I-12

| Ex. No. | X | $L^1$ | $L^2$ | $L^3$ | Y | Physical data: $^1$H-NMR, δ [ppm] or CAS or patent No. |
|---|---|---|---|---|---|---|
| 12-17 | 2-fluoro-phenyl | CH2 | CH2 | — | H | [DMSO], spectrometer: 399.95 MHz<br>8.4105 (1.69); 8.3967 (3.11); 8.3828 (1.70); 7.6274 (10.97); 7.6132 (11.61); 7.3487 (1.78); 7.3447 (2.10); 7.3300 (3.59); 7.3255 (4.34); 7.3097 (2.13); 7.3064 (2.55); 7.3014 (1.24); 7.2967 (1.00); 7.2874 (1.15); 7.2827 (2.44); 7.2681 (2.42); 7.2624 (3.15); 7.2579 (1.77); 7.2487 (1.77); 7.2442 (1.47); 7.1789 (3.54); 7.1696 (11.64); 7.1554 (16.00); 7.1408 (6.06); 7.1379 (5.90); 7.1324 (2.58); 7.1225 (2.63); 7.1195 (2.29); 3.4660 (2.91); 3.4489 (5.89); 3.4334 (5.60); 3.4306 (5.72); 3.4151 (3.26); 3.3508 (9.28); 2.8851 (4.76); 2.8669 (8.04); 2.8487 (4.26); 2.5445 (10.46); 2.5140 (5.33); 2.5097 (10.66); 2.5051 (14.07); 2.5006 (10.63); 2.4963 (5.45); −0.0002 (4.31) |
| 12-18 | 2,6-di-fluoro-phenyl | CH2 | CH2 | — | H | [DMSO], spectrometer: 399.95 MHz<br>8.4664 (2.25); 8.4520 (4.28); 8.4375 (2.26); 7.6305 (14.40); 7.6162 (15.19); 7.3635 (1.19); 7.3466 (2.69); 7.3427 (2.51); 7.3257 (5.15); 7.3083 (2.69); 7.3049 (3.37); 7.2881 (1.52); 7.1557 (16.00); 7.1414 (15.19); 7.1059 (0.68); 7.1016 (0.98); 7.0893 (7.19); 7.0695 (11.20); 7.0584 (1.62); 7.0495 (6.17); 7.0368 (0.91); 3.4332 (3.52); 3.4165 (8.35); 3.3996 (8.31); 3.3830 (3.90); 3.3493 (15.48); 3.0039 (0.62); 2.9017 (5.53); 2.8839 (9.98); 2.8664 (5.00); 2.5457 (48.45); 2.5291 (0.44); 2.5241 (0.53); 2.5152 (6.36); 2.5109 (13.14); 2.5063 (17.60); 2.5018 (13.32); 2.4974 (6.83); −0.0002 (5.32) |
| 12-19 | 2,6-di-chloro-phenyl | CH2 | CH2 | — | H | [DMSO], spectrometer: 399.95 MHz<br>8.4813 (5.51); 8.4717 (6.76); 7.6432 (4.18); 7.6408 (4.68); 7.6373 (4.42); 7.6306 (11.07); 7.6165 (8.63); 7.4771 (8.04); 7.4674 (13.54); 7.4605 (11.53); 7.4577 (11.13); 7.4473 (16.00); 7.3162 (2.79); 7.3138 7(3.13); .3034 (5.48); 7.2951 (5.19); 7.2929 (4.95); 7.2840 (7.19); 7.2634 (3.36); 7.2160 (4.84); 7.2136 (5.48); 7.2102 (5.22); 7.2039 (11.34); 7.1997 (7.87); 7.1901 (8.73); 3.4516 (11.11); 3.4373 (10.24); 3.4202 (4.23); 3.3591 (7.73); 3.3569 (7.79); 3.3501 (14.35); 3.1542 (12.93); 3.1373 (6.04); 2.5588 (3.42); 2.5564 (3.78); 2.5531 (3.35); 2.5493 (4.50); 2.5466 (5.87); 2.5116 (26.16); 0.0 128 (1.90); 0.0103 (2.09); 0.0069 (1.81); 0.0031 (2.34); −0.0002 (2.93) |
| 12-20 | 3-(tri-fluoro-methyl)phenyl | CH2 | CH2 | — | H | [DMSO], spectrometer: 399.95 MHz<br>8.3732 (2.25); 8.3596 (4.09); 8.3459 (2.18); 7.6733 (0.40); 7.6533 (0.57); 7.6414 (0.52); 7.6293 (14.31); 7.6150 (16.00); 7.6061 (8.70); 7.5919 (2.71); 7.5885 (2.82); 7.5824 (3.33); 7.5670 (13.64); 7.5542 (9.11); 7.5429 (2.88); 7.5367 (2.18); 7.5178 (1.30); 7.4960 (0.47); 7.4759 (0.38); 7.1613 (0.56); 7.1470 (0.66); 7.1370 (14.42); 7.1227 (13.77); 3.5114 (3.59); 3.4940 (8.81); 3.4794 (8.80); 3.4620 (4.13); 3.3522 (15.80); 2.9556 (6.78); 2.9380 (12.80); 2.9204 (6.09); 2.5461 (16.30); 2.5292 (0.41); 2.5244 (0.61); 2.5157 (7.12); 2.5113 (14.54); 2.5068 (19.44); 2.5022 (14.72); 2.4979 (7.52); −0.0002 (6.35) |
| 12-21 | 4-(tri-fluoro-methyl)phenyl | CH2 | CH2 | — | H | [DMSO], spectrometer: 399.95 MHz<br>8.3905 (2.28); 8.3768 (4.30); 8.3631 (2.28); 7.6732 (10.42); 7.6531 (12.81); 7.6305 (14.27); 7.6162 (15.04); 7.4955 (11.97); 7.4755 (9.94);<br>7.1598 (16.00); 7.1455 (15.29); 3.5068 (3.65); 3.4894 (8.31); 3.4746 (8.25); 3.4569 (4.11); 3.3486 (17.26); 2.9447 (6.12); 2.9269 (11.15); 2.9091 (5.42); 2.5456 (0.65); 2.5287 (0.50); 2.5239 (0.76); 2.5152 (8.81); 2.5108 (17.77); 2.5062 (23.54); 2.5017 (17.68); 2.4973 (8.95); −0.0002 (8.01) |
| 12-22 | 2-methyl-phenyl | CH2 | CH2 | — | H | [DMSO], spectrometer: 399.95 MHz<br>8.4223 (0.79); 8.4084 (1.48); 8.3945 (0.80); 7.6351 (4.68); 7.6209 (4.99); 7.2019 (5.30); 7.1876 (5.10); 7.1795 (1.17); 7.1714 (1.73); 7.1677 (1.68); 7.1561 (3.52); 7.1462 (2.76); 7.1407 (1.34); 7.1286 (3.25); 7.1236 (3.88); 7.1150 (3.97); 7.1072 (1.73); 7.1056 (1.79); 7.1024 (1.59); 7.0897 (0.34); 3.4021 (1.35); 3.3869 (2.36); 3.3788 (1.50); 3.3687 (1.99); 3.3639 (2.51); 3.3479 (7.52); 2.8379 (2.66); 2.8180 (3.12); 2.7994 (2.37); 2.5420 (3.48); 2.5114 (2.36); 2.5072 (4.75); 2.5027 (6.30); 2.4982 (4.76); 2.4941 (2.44); 2.3229 (16.00); −0.0002 (1.93) |
| 12-23 | 2,4,6-tri-methyl-phenyl | CH2 | CH2 | — | H | [DMSO], spectrometer: 399.95 MHz<br>8.5114 (0.56); 8.4970 (1.11); 8.4825 (0.58); 7.6494 (2.65); 7.6352 7(2.84); .2473 (2.77); 7.2330 (2.63); 6.8076 (5.31); 3.3461 (4.45); 3.2423 (0.67); 3.2276 (1.18); 3.2139 (1.17); 3.2070 (1.00); 3.2006 (1.27); 3.1866 (0.81); 2.8069 (1.42); 2.7936 (1.11); 2.7858 (1.44); 2.7809 (1.23); 2.7659 (1.21); 2.5424 (3.52); 2.5075 (3.25); 2.5031 |

TABLE 12-continued

Compounds of the formula I-12

I-12

| Ex. No. | X | L¹ | L² | L³ | Y | Physical data: ¹H-NMR, δ [ppm] or CAS or patent No. |
|---|---|---|---|---|---|---|
| 12-24 | 3,4-bis-methoxy-phenyl | CH2 | CH2 | — | H | (4.33); 2.4989 (3.39); 2.3006 (16.00); 2.1828 (8.30); −0.0002 (1.07) [DMSO], spectrometer: 399.95 MHz 8.3289 (0.63); 8.3153 (1.23); 8.3016 (0.64); 7.6315 (3.39); 7.6172 (3.58); 7.1806 (3.65); 7.1663 (3.47); 6.8748 (2.32); 6.8544 (3.19); 6.8313 (2.61); 6.8267 (2.95); 6.7596 (1.68); 6.7550 (1.56); 6.7393 (1.22); 6.7347 (1.15); 3.7316 (16.00); 3.7117 (16.00); 3.4332 (0.90); 3.4165 (1.79); 3.3974 (1.80); 3.3820 (1.00); 3.3407 (7.66); 2.7700 (1.76); 2.7510 (2.68); 2.7331 (1.59); 2.5419 (0.54); 2.5112 (3.87); 2.5071 (7.71); 2.5026 (10.21); 2.4982 (7.74); −0.0002 (2.88) |
| 12-25 | phenyl | CH2 | CH2 | — | H | [DMSO], spectrometer: 399.95 MHz 8.3699 (2.08); 8.3564 (3.75); 8.3429 (2.10); 7.6266 (14.06); 7.6123 (14.88); 7.3222 (4.38); 7.3185 (1.98); 7.3038 (11.81); 7.2904 (3.91); 7.2859 (12.24); 7.2617 (11.43); 7.2578 (15.34); 7.2410 (7.56); 7.2272 (3.32); 7.2236 (4.14); 7.2199 (2.35); 7.2108 (2.48); 7.2059 (6.20); 7.2002 (1.68); 7.1921 (1.59); 7.1881 (2.32); 7.1844 (1.48); 7.1769 (16.00); 7.1626 (15.25); 3.4580 (4.10); 3.4419 (6.80); 3.4403 (6.74); 3.4255 (6.55); 3.4214 (7.14); 3.4065 (4.58); 3.3472 (15.79); 2.8433 (7.45); 2.8240 (10.47); 2.8060 (6.70); 2.5419 (5.14); 2.5250 (0.37); 2.5115 (7. 2.5071 (14.03); 2.5026 (18.53); 2.4980 (13.81); 2.4936 (6.90); −0.0002 (6.21) |
| 12-26 | 4-chloro-phenyl | C(CH2—CH2) | CH2 | — | H | |
| 12-27 | 2,4-di-chloro-phenyl | C(CH2—CH2) | CH2 | — | H | |
| 12-28 | 4-chloro-phenyl | CH2 | C(CH2—CH2) | — | H | |
| 12-29 | 2,4-di-chloro-phenyl | CH2 | C(CH2—CH2) | — | H | |
| 12-30 | 4-chloro-phenyl | O | CH2 | CH2 | H | |
| 12-31 | 2,4-di-chloro-phenyl | O | CH2 | CH2 | H | compound No. 12-31, solvent: [DMSO], spectrometer: 399.95 MHz 8.4586 (2.37); 8.4454 (4.52); 8.4321 (2.46); 7.6461 (12.06); 7.6319 (12.91); 7.5719 (10.04); 7.5654 (11.06); 7.386 (5.31); 7.3795 (5.1); 7.3638 (7.1); 7.3574 (7.07); 7.2393 (12.88); 7.2345 (15.08); 7.2199 (15.12); 4.2102 (7.19); 4.1955 (16); 4.181 (7.99); 3.6247 (4.03); 3.6104 (11.36); 3.5962 (11.04); 3.5818 (3.73); 3.3308 (89.55); 2.6724 (0.35); 2.5426 (64.52); 2.5253 (1.19); 2.5075 (39.39); 2.5031 (53); 2.4987 (41.18); 2.33 (0.34); −0.0002 (1.92) |
| 12-32 | 4-chloro-phenyl | CH2 | CH2 | CH2 | H | |
| 12-33 | 4-chloro-phenyl | NCH3 | CH2 | CH2 | H | |
| 12-34 | 2,4-di-chloro-phenyl | NCH3 | CH2 | CH2 | H | |
| 12-35 | 4-chloro-phenyl | CH(OCH3) | CH2 | — | H | |
| 12-36 | 2,4-di-chloro-phenyl | CH(OCH3) | CH2 | — | H | |
| 12-37 | 2-thienyl | CH2 | CH2 | — | H | compound No. 12-37, solvent: [DMSO], spectrometer: 399.95 MHz 8.4262 (2.73); 8.413 (4.89); 8.3996 (2.79); 7.6376 (13.67); 7.6233 (14.65); 7.3506 (7.69); 7.3483 (7.69); 7.338 (8.41); 7.3355 (8.13); 7.2098 (15.14); 7.1955 (14.48); 6.9721 (6.1); 6.9635 (9.35); 6.9596 (6.31); 6.9509 (8.87); 6.9273 (9.83); 6.9205 (6.8); 3.4749 (4.72); 3.4571 (10.55); 3.4423 (10.87); 3.4245 (5.66); 3.3326 (27.99); 3.0595 (9.29); 3.0414 (16); 3.0234 (8); 2.5408 (9.54); 2.5056 (22.54); 2.5013 (29.54); 2.497 |
| 12-38 | 3-thienyl | CH2 | CH2 | — | H | |
| 12-39 | 2-furyl | CH2 | CH2 | — | H | |
| 12-40 | 3-furyl | CH2 | CH2 | — | H | |
| 12-41 | phenyl | CH2 | CH2 | CH(CH3) | H | |
| 12-42 | phenyl | CH2 | CH2 | CH2 | H | |
| 12-43 | 2-Cl-phenyl | CH2 | CH2 | CH(CH3) | H | |

TABLE 12-continued

Compounds of the formula I-12

| Ex. No. | X | L¹ | L² | L³ | Y | Physical data: $^1$H-NMR, δ [ppm] or CAS or patent No. |
|---|---|---|---|---|---|---|
| 12-44 | 4-t-butyl-phenyl | CH2 | CH2 | CH2 | H | |
| 12-45 | 4-methyl-phenyl | CH2 | CH2 | CH2 | H | |
| 12-46 | phenyl | CH2 | CH2 | CH(CH2CH3) | H | |
| 12-47 | 2-methoxy-phenyl | CH2 | CH2 | CH2 | H | |
| 12-48 | 2-methyl-phenyl | CH2 | CH2 | CH2 | H | |
| 12-49 | 3-methyl-phenyl | CH2 | CH2 | CH2 | H | |
| 12-50 | 3-chloro-phenyl | CH2 | CH2 | CH2 | H | |
| 12-51 | 2,6-difluoro-phenyl | CH2 | CH2 | CH2 | H | compound No. 12-51, solvent: [DMSO], spectrometer: 399.95 MHz 8.3439 (3.57); 8.3309 (6.36); 8.3178 (3.69); 7.6616 (0.33); 7.6471 (0.66); 7.634 (13.3); 7.6212 (13.4); 7.6198 (14.21); 7.3509 (1.47); 7.333 (4.06); 7.3131 (6.87); 7.2937 (4.81); 7.2758 (2.27); 7.2618 (0.44); 7.197 (15.35); 7.1827 (14.55); 7.1425 (0.32); 7.1208 (0.5); 7.1009 (1.56); 7.0882 (10.47); 7.0686 (16); 7.0493 (8.79); 7.0349 (1.36); 6.5486 (0.63); 3.3361 (29.78); 3.2664 (5.24); 3.2496 (11.89); 3.2332 (12.11); 3.2164 (5.54); 2.7079 (7.58); 2.6887 (12.66); 2.6694 (8.51); 2.5446 (9.47); 2.5056 (37.84); 1.7988 (2.81); 1.7801 (7.74); 1.7614 (10.65); 1.7426 (7.42); 1.7243 (2.52); −0.0002 (0.54) |
| 12-52 | 4-chloro-phenyl | CH2 | CH2 | CH2 | H | |
| 12-53 | 2,6-dichloro-phenyl | CH2 | CH2 | CH(CH3) | H | |
| 12-54 | 3,5-dichloro-phenyl | CH2 | CH2 | CH(CH3) | H | |
| 12-55 | 2,6-dimethyl-phenyl | CH2 | CH2 | CH2 | H | |
| 12-56 | 2,5-dichloro-phenyl | CH2 | CH2 | CH2 | H | |
| 12-57 | 4-isopropoxy-phenyl | CH2 | CH2 | CH2 | H | |
| 12-58 | 3-trifluoromethyl-phenyl | CH2 | CH2 | CH(CH3) | H | |
| 12-59 | 4-methyl-phenyl | CH2 | CH2 | CH(CH3) | H | |
| 12-60 | 2-methyl-phenyl | CH2 | CH2 | CH(CH3) | H | |
| 12-61 | 3,4-dichloro-phenyl | CH2 | CH2 | CH(CH3) | H | |
| 12-62 | 3,5-dichloro-phenyl | CH2 | CH2 | CH2 | H | |
| 12-63 | 2,6-dimethyl-phenyl | CH2 | CH2 | CH(CH3) | H | |
| 12-64 | 4-trifluoromethyl-phenyl | CH2 | CH2 | CH(CH3) | H | |
| 12-65 | 2,5-dichloro-phenyl | CH2 | CH2 | CH(CH3) | H | |

TABLE 12-continued

Compounds of the formula I-12

I-12

| Ex. No. | X | L¹ | L² | L³ | Y | Physical data: ¹H-NMR, δ [ppm] or CAS or patent No. |
|---|---|---|---|---|---|---|
| 12-66 | 4-phenoxyphenyl | CH2 | CH2 | CH2 | H | |
| 12-67 | 3-chlorophenyl | CH2 | CH2 | CH(CH3) | H | |
| 12-68 | 4-phenoxyphenyl | CH2 | CH2 | CH(CH3) | H | |
| 12-69 | 2,4-dichlorophenyl | CH2 | CH2 | CH(CH3) | H | |
| 12-70 | 2-difluoromethoxyphenyl | CH2 | CH2 | CH(CH3) | H | |
| 12-71 | 4-methoxyphenyl | CH2 | CH2 | CH2 | H | |
| 12-72 | 4-chlorophenyl | CH2 | CH2 | CH(CH3) | H | |
| 12-73 | 4-chlorophenyl | CH2 | CH2 | CH(i-propyl) | H | |
| 12-74 | 4-fluorophenyl | CH2 | CH2 | CH2 | H | |
| 12-75 | 4-chlorophenyl | CH2 | CH2 | CH(n-propyl) | H | |
| 12-76 | 4-chlorophenyl | CH2 | CH2 | CH(t-butyl) | H | |
| 12-77 | 2-chlorophenyl | CH2 | CH2 | CH2 | H | |
| 12-78 | 4-chlorophenyl | CH2 | CH(CH3) | — | cyclopropyl | WO-A 2007/060164 |
| 12-79 | 2-thienyl | CH2 | CH2 | CH2 | H | compound No. 12-79, solvent: [DMSO], spectrometer: 399.95 MHz 8.3298 (2.96); 8.3169 (5.26); 8.3042 (3.1); 7.6325 (14.47); 7.6183 (15.49); 7.3211 (8.42); 7.3186 (7.65); 7.3083 (9.3); 7.3058 (8.14); 7.2108 (16); 7.1966 (15.18); 6.9528 (6.49); 6.9442 (9.31); 6.9403 (6.93); 6.9316 (8.34); 6.8914 (10.08); 6.8833 (8.16); 3.328 (186.81); 3.2777 (5.37); 3.2609 (12.9); 3.2458 (13.23); 3.229 (5.65); 2.8831 (9.11); 2.864 (15.57); 2.8449 (9.91); 2.6708 (0.98); 2.5408 (3.11); 2.5058 (106.56); 2.5016 (136.82); 2.4976 (105.49); 2.3285 (0.9); 1.8804 (2.82); 1.8625 (8.73); 1.8438 (11.62); 1.8255 (8.42); 1.8075 (2.56); −0.0002 (1.36) |
| 12-80 | 5-chloro-2-thienyl | CH2 | CH2 | — | H | compound No. 12-80, solvent: [DMSO], spectrometer: 399.95 MHz 8.432 (1.82); 8.4184 (3.38); 8.4047 (1.79); 8.3155 (1.88); 7.6414 (15.17); 7.6271 (16); 7.3751 (14.36); 7.3713 (14.43); 7.3638 (0.37); 7.2076 (0.36); 7.1958 (15.71); 7.1815 (14.83); 6.9256 (9.98); 6.9239 (8.92); 6.922 (9.73); 3.4729 (3.5); 3.4555 (8.91); 3.441 (9.18); 3.4239 (4.02); 3.3222 (44.18); 3.0393 (0.33); 3.0233 (6.68); 3.0058 (12.63); 2.9887 (5.62); 2.6753 (0.39); 2.6707 (0.53); 2.6661 (0.38); 2.5239 (1.8); 2.5191 (2.81); 2.5106 (32.21); 2.5062 (64.19); 2.5016 (83.82); 2.497 (59.36); 2.4924 (27.72); 2.3329 (0.4); 2.3283 (0.55); 2.3237 (0.41); 1.9887 (0.99); 1.3357 (0.35); 1.2494 (0.43); 1.1749 (0.53); 0.1459 (0.33); 0.008 (2.83); −0.0002 (78.68); −0.0085 (2.37); −0.1496 (0.33) |
| 12-81 | 4-chloro-2-thienyl | CH2 | CH2 | — | H | compound No. 12-81, solvent: [DMSO], spectrometer: 601.6 MHz 8.4249 (1.78); 8.4158 (3.3); 8.4066 (1.74); 7.639 (15.4); 7.6295 (16); 7.3751 (13.88); 7.3725 (13.92); 7.1923 (15.77); 7.1828 (15.35); 6.9252 (9.32); 6.924 (8.25); 6.9228 (9.13); 3.464 (3.67); 3.4524 (8.92); 3.4428 (9.08); 3.4314 (4.07); 3.3535 (0.49); 3.3256 (836.97); 3.3031 (0.84); 3.0173 (5.99); 3.0056 (11.69); 2.9947 (5.41); 2.6531 (1.58); 2.6192 (0.57); 2.6162 (1.19); 2.6131 (1.66); 2.61 (1.22); 2.607 (0.58); 2.5407 (486.63); 2.5224 (3.63); 2.5193 (4.8); 2.5161 (5.78); 2.5075 (92.82); 2.5044 (192.64); 2.5014 (263.85); 2.4983 (189.46); 2.4953 (88.15); 2.4245 (1.58); 2.3916 (0.56); 2.3886 (1.18); 2.3855 (1.63); 2.3825 (1.15); 2.3795 (0.51); 2.0735 (0.57); 0.0053 (0.56); −0.0002 (15.95); (0.45) −0.0057 |

TABLE 12-continued

Compounds of the formula I-12

$$X-L^1-L^2-L^3-N(Y)-C(=O)-\text{[2-bromothiophen-3-yl]}$$

I-12

| Ex. No. | X | L¹ | L² | L³ | Y | Physical data: ¹H-NMR, δ [ppm] or CAS or patent No. |
|---|---|---|---|---|---|---|
| 12-82 | 4-chloro-phenyl | N(CH3) | CH2 | CH2 | H | compound No. 12-82, solvent: [DMSO], spectrometer: 399.95 MHz 8.2813 (0.73); 8.2674 (1.4); 8.2535 (0.75); 7.8316 (3.37); 7.8264 (3.35); 7.1794 (4.23); 7.157 (4.61); 7.1488 (0.56); 6.8767 (3.52); 6.8715 (3.44); 6.7524 (4.57); 6.7299 (4.09); 3.4651 (1.31); 3.4485 (3.06); 3.4314 (2.35); 3.3556 (1.46); 3.3279 (46.87); 2.9073 (16); 2.5415 (20.17); 2.5064 (30.6); 2.5024 (38.46); −0.0002 (4.87) |
| 12-83 | 3-(tri-fluoro-methyl)phenyl | O | CH2 | CH(CH2CH3) | H | compound No. 12-83, solvent: [DMSO], spectrometer: 399.95 MHz 8.3165 (0.38); 8.1187 (2.84); 8.099 (2.84); 7.8058 (6.33); 7.7928 (6.56); 7.785 (1.18); 7.5428 (1.9); 7.5232 (4.2); 7.5036 (2.82); 7.4898 (0.46); 7.3461 (0.34); 7.2982 (6.29); 7.2784 (5.13); 7.2686 (8.11); 7.1795 (6.69); 7.1665 (6.51); 7.15 (0.77); 4.2211 (0.85); 4.2081 (1.31); 4.2001 (1.72); 4.1867 (2.03); 4.1687 (3.2); 4.1455 (4.52); 4.1306 (3.15); 4.1162 (3.62); 4.1033 (3.3); 4.0927 (2.02); 4.0795 (1.14); 3.3274 (85.66); 2.6715 (0.48); 2.5421 (8.14); 2.5025 (75.15); 2.4986 (60.82); 2.329 (0.51); 1.7771 (0.84); 1.7587 (1.27); 1.7434 (1.92); 1.7301 (1.65); 1.7247 (1.75); 1.712 (1.37); 1.6939 (0.56); 1.6778 (0.34); 1.6605 (0.5); 1.6457 (1.3); 1.6263 (1.94); 1.6077 (1.72); 1.5919 (1.41); 1.5727 (0.89); 0.9905 (8.04); 0.9722 (16); 0.9536 (7.45); 0.9419 (1.2); −0.0002 (9.15); −0.0018 (7.67) |

TABLE 13

Compounds of the formula I-13

$$X-L^1-L^2-L^3-N(Y)-C(=O)-\text{[2-iodothiophen-3-yl]}$$

I-13

| Ex. No. | X | L¹ | L² | L³ | Y | Physical data: ¹H-NMR, δ [ppm] or CAS or patent No. |
|---|---|---|---|---|---|---|
| 13-1 | 3-methyl-2-thienyl | CH2 | CH2 | — | H | WO-A 2006/108791 |
| 13-2 | 2,4-di-chloro-phenyl | CH2 | CH2 | CH2 | H | compound No. 13-2, solvent: [DMSO], spectrometer: 399.95 MHz 8.2987 (1.89); 8.2849 (3.6); 8.271 (1.85); 7.7558 (15.43); 7.7487 (0.67); 7.7421 (16); 7.5825 (0.33); 7.5726 (10.55); 7.5673 (11.03); 7.4427 (6.72); 7.422 (13.06); 7.4149 (0.91); 7.3841 (9.11); 7.3787 (8.54); 7.3634 (4.59); 7.3581 (4.56); 7.1268 (15.9); 7.1131 (15.34); 3.5119 (1.39); 3.4113 (0.38); 3.3318 (475.8); 3.2911 (0.54); 3.2673 (3.24); 3.2503 (7.5); 3.2354 (7.53); 3.2184 (3.21); 2.7694 (5.51); 2.7505 (6.8); 2.7307 (5.96); 2.7121 (0.34); 2.6805 (0.44); 2.6759 (0.89); 2.6714 (1.21); 2.6667 (0.9); 2.662 (0.41); 2.5416 (59.45); 2.5247 (3.74); 2.5199 (5.99); 2.5114 (67.36); 2.5069 (134.03); 2.5022 (177.24); 2.4976 (127.83); 2.4931 (59.8); 2.3382 (0.42); 2.3336 (0.87); 2.329 (1.19); 2.3244 (0.83); 2.3198 (0.37); 2.103 (0.34); 1.821 (1.61); 1.8031 (4.28); 1.7842 (5.47); 1.7655 (4.13); 1.7475 (1.44); 0.008 (0.69); −0.0002 (20.21); −0.0085 (0.54) |
| 13-3 | 4-chloro-phenyl | CH2 | CH2 | — | H | compound No. 13-3, solvent: [DMSO], spectrometer: 399.95 MHz 8.3053 (1.38); 8.2916 (2.62); 8.2776 (1.36); 7.749 (11.36); 7.7418 (0.44); 7.7353 (11.67); 7.3674 (0.94); 7.3612 (8.6); 7.3562 (3.01); |

TABLE 13-continued

Compounds of the formula I-13

I-13

| Ex. No. | X | L¹ | L² | L³ | Y | Physical data: ¹H-NMR, δ [ppm] or CAS or patent No. |
|---|---|---|---|---|---|---|
| | | | | | | 7.3452 (4.05); 7.34 (16); 7.334 (2.14); 7.294 (2.07); 7.2882 (13.58); 7.283 (3.52); 7.2718 (2.81); 7.267 (7.48); 7.2609 (0.8); 7.0851 (11.42); 7.0714 (11.09); 3.5117 (0.89); 3.4442 (2.49); 3.4269 (4.88); 3.4122 (4.9); 3.3938 (2.78); 3.3314 (322.94); 2.8373 (4.56); 2.819 (7.6); 2.8011 (4.04); 2.6756 (0.6); 2.671 (0.8); 2.6665 (0.57); 2.5413 (10.27); 2.5244 (2.31); 2.5196 (3.74); 2.5111 (44.51); 2.5066 (88.79); 2.5019 (117.47); 2.4973 (84.7); 2.4928 (39.68); 2.3333 (0.56); 2.3287 (0.77); 2.3241 (0.53); 0.008 (0.56); −0.0002 (16.55); −0.0086 (0.45) |
| 13-4 | 2,4-dichlorophenyl | CH2 | CH2 | — | H | WO-A 2007/060166 |
| 13-5 | 4-chlorophenyl | CH(OCH3) | CH(CH3) | — | H | |
| 13-6 | 2,4-dichlorophenyl | CH(OCH3) | CH(CH3) | — | H | |
| 13-7 | 4-chlorophenyl | CH(CH3) | CH2 | — | H | compound No. 13-7, solvent: [DMSO], spectrometer: 399.95 MHz 8.2561 (1.25); 8.2419 (2.48); 8.2274 (1.26); 7.7295 (9.88); 7.7223 (0.4); 7.7158 (10.23); 7.3705 (0.75); 7.3644 (7.1); 7.3594 (2.54); 7.3483 (3.46); 7.3431 (14.93); 7.3373 (2.09); (4.46); 2.511 (50.16); 2.5064 (100.33); 2.5018 (133.07); 2.4972 (95.94); 2.4926 (44.84); 2.3332 (0.64); 2.3286 (0.88); 2.324 (0.62); 1.141 (16); 1.1244 (15.88); 0.0079 (0.32); −0.0002 (9.55) |
| 13-10 | 2,4-dichlorophenyl | CH2 | CH(CH3) | — | H | compound No. 13-10, solvent: [DMSO], spectrometer: 399.95 MHz 8.1392 (2.75); 8.1178 (2.77); 7.7411 (10.84); 7.7339 (0.46); 7.7273 (11.11); 7.568 (6.98); 7.563 (7.13); 7.5573 (0.67); 7.5545 (0.45); 7.5523 (0.51); 7.5495 (0.39); 7.3982 (3); 7.3775 (10.29); 7.3644 (8.1); 7.3594 (7.16); 7.3438 (2.16); 7.3387 (2.59); 7.3331 (0.46); 7.0476 (10.87); 7.0339 (10.68); 4.3083 (0.62); 4.2884 (1.37); 4.2718 (1.86); 4.2553 (1.26); 4.2513 (1.14); 4.2349 (0.62); 3.5115 (2.3); 3.4774 (0.32); 3.423 (0.41); 3.4109 (0.46); 3.3835 (0.41); 3.3766 (0.5); 3.3304 (476.05); 2.9417 (0.51); 2.926 (0.82); 2.9164 (0.79); 2.9073 (4.66); 2.901 (4.94); 2.892 (4.23); 2.881 (3.98); 2.8668 (0.61); 2.8467 (0.69); 2.6801 (0.46); 2.6755 (0.93); 2.6709 (1.28); 2.6664 (0.93); 2.6618 (0.42); 2.5412 (22.75); 2.5244 (3.71); 2.5196 (5.74); 2.511 (71.64); 2.5065 (144.49); 2.5018 (192.3); 2.4972 (139.06); 2.4927 (65.54); 2.3378 (0.43); 2.3332 (0.92); 2.3287 (1.26); 2.324 (0.89); 2.3196 (0.4); 1.1898 (16); 1.1732 (15.93); 1.1521 (0.32); 0.008 (0.39); −0.0002 (12.59); −0.0086 (0.35) |
| 13-11 | 4-chlorophenyl | C(CH3)2 | CH2 | — | H | compound No. 13-11, solvent: [DMSO], spectrometer: 399.95 MHz 8.0581 (0.38); 8.0427 (0.75); 8.0272 (0.37); 7.7146 (3.15); 7.7009 (3.23); 7.4519 (2.62); 7.4466 (0.88); 7.4354 (1.12); 7.43 (4.47); 7.4232 (0.52); 7.3708 (0.55); 7.364 (4.49); 7.3587 (1.08); 7.3474 (0.86); 7.3422 (2.69); 7.0015 (3.3); 6.9878 (3.22); 3.4045 (2.79); 3.3886 (2.74); 3.3305 (58.74); 2.5412 (13.3); 2.5243 (0.43); 2.5195 (0.68); 2.511 (8.82); 2.5065 (17.88); 2.5018 (23.87); 2.4972 (17.33); 2.4926 (8.2); 1.3153 (16); −0.0002 (1.51) |

TABLE 13-continued

Compounds of the formula I-13

$$\text{X}-\text{L}^1-\text{L}^2-\text{L}^3-\text{N}(\text{Y})-\text{C}(=\text{O})-\text{[2-iodothiophen-3-yl]}$$

I-13

| Ex. No. | X | L¹ | L² | L³ | Y | Physical data: ¹H-NMR, δ [ppm] or CAS or patent No. |
|---|---|---|---|---|---|---|
| 13-12 | 2,4-di-chloro-phenyl | C(CH3)2 | CH2 | — | H | compound No. 13-12, solvent: [DMSO], spectrometer: 399.95 MHz 8.0559 (0.52); 8.0404 (1.01); 8.0247 (0.5); 7.7024 (3.26); 7.6887 (3.34); 7.52 (2.8); 7.5141 (2.91); 7.5002 (1.88); 7.4785 (2.52); 7.3695 (1.74); 7.3636 (1.57); 7.3479 (1.29); 7.342 (1.18); 6.9686 (3.36); 6.9549 (3.29); 3.7487 (3.12); 3.7328 (3.06); 3.3337 (20.32); 2.5423 (16.32); 2.5121 (3.68); 2.5077 (6.98); 2.5031 (9.01); 2.4985 (6.55); 2.4941 (3.16); 1.4696 (16); −0.0002 (0.69) |
| 13-13 | 2-chloro-phenyl | CH2 | CH2 | — | H | compound No. 13-13, solvent: [DMSO], spectrometer: 399.95 MHz 8.3611 (1.83); 8.3468 (3.5); 8.3328 (1.79); 7.7495 (15.4); 7.7421 (0.6); 7.7357 (16); 7.4425 (4.95); 7.4386 (3.91); 7.424 (7.06); 7.4194 (6.32); 7.3805 (3.65); 7.3752 (4.51); 7.3619 (4.8); 7.3572 (6.14); 7.3114 (2.22); 7.3073 (2.84); 7.2931 (6.69); 7.2889 (6.34); 7.2756 (10.83); 7.2701 (9.19); 7.2568 (5.39); 7.2517 (5.07); 7.2382 (1.86); 7.2334 (1.52); 7.1032 (15.46); 7.0894 (15.02); 3.5117 (1.17); 3.4786 (3.37); 3.4617 (6.34); 3.4468 (6.04); 3.4432 (6.06); 3.4281 (3.75); 3.4108 (0.42); 3.3331 (448.32); 3.2697 (0.34); 2.9789 (6.53); 2.9602 (9.91); 2.9426 (5.64); 2.6804 (0.34); 2.6758 (0.7); 2.6711 (0.96); 2.6665 (0.68); 2.5414 (52.44); 2.5245 (2.8); 2.5198 (4.51); 2.5112 (52.97); 2.5067 (106.54); 2.502 (141.67); 2.4974 (102.33); 2.4929 (47.92); 2.3334 (0.67); 2.3288 (0.93); 2.3242 (0.65); −0.0002 (3.71) |
| 13-14 | 3,4-di-chloro-phenyl | CH2 | CH2 | — | H | compound No. 13-14, solvent: [DMSO], spectrometer: 399.95 MHz 8.2994 (1.97); 8.2855 (3.84); 8.2716 (1.98); 7.7536 (14.19); 7.7463 (0.6); 7.7399 (14.7); 7.5549 (10.77); 7.5445 (0.53); 7.5341 (16); 7.5272 (10.25); 7.2648 (5.81); 7.2596 (5.62); 7.2442 (5.04); 7.2391 (4.96); 7.0699 (15.43); 7.0561 (15.03); 3.5136 (0.7); 3.4695 (3.22); 3.4522 (7.96); 3.4375 (8.1); 3.4203 (3.51); 3.3359 (88.36); 2.8542 (6.07); 2.8368 (12.01); 2.8194 (5.46); 2.5431 (44.95); 2.5263 (0.6); 2.5214 (0.96); 2.5128 (13.13); 2.5083 (26.83); 2.5037 (36.02); 2.4991 (26.35); 2.4946 (12.64); −0.0002 (3.02) |
| 13-15 | 3,5-di-chloro-phenyl | CH2 | CH2 | — | H | compound No. 13-15, solvent: [DMSO], spectrometer: 399.95 MHz 8.2988 (1.57); 8.2851 (2.98); 8.2713 (1.55); 7.7573 (8.92); 7.7436 (9.16); 7.4369 (3.65); 7.4323 (7.01); 7.4275 (4.12); 7.329 (16); 7.3243 (14.78); 7.056 (9.44); 7.0423 (9.26); 3.5115 (1.37); 3.4764 (2.57); 3.4593 (6.18); 3.4446 (6.44); 3.4276 (2.74); 3.4112 (0.53); 3.3849 (0.75); 3.3336 (504.34); 2.8637 (4.44); 2.8465 (8.92); 2.8293 (3.97); 2.6755 (0.84); 2.6711 (1.11); 2.6666 (0.82); 2.5415 (20.02); 2.5065 (125.79); 2.502 (162.85); 2.4975 (120.54); 2.4932 (59.35); 2.3333 (0.79); 2.3288 (1.07); 2.3243 (0.75); −0.0002 (3.04) |
| 13-16 | 3-chloro-phenyl | CH2 | CH2 | — | H | compound No. 13-16, solvent: [DMSO], spectrometer: 399.95 MHz 8.3173 (1.98); 8.3037 (3.72); 8.2901 (2); 7.7524 (13.05); 7.7387 (13.54); 7.361 (0.39); 7.3476 (3.48); 7.3397 (1.02); 7.3274 (16); 7.3221 (6.31); 7.3092 (8.47); 7.2883 (0.72); 7.2797 (4.31); 7.2767 (6.34); 7.2718 (4.72); 7.26 (2.46); 7.255 |

TABLE 13-continued

Compounds of the formula I-13

| Ex. No. | X | L¹ | L² | L³ | Y | Physical data: ¹H-NMR, δ [ppm] or CAS or patent No. |
|---|---|---|---|---|---|---|
| | | | | | | (2.92); 7.2518 (2.01); 7.2297 (6.42); 7.2141 (3.21); 7.2109 (4.46); 7.0878 (0.83); 7.081 (13.81); 7.074 (1.01); 7.0673 (13.43); 3.5129 (0.64); 3.4647 (3.49); 3.4474 (7.27); 3.4326 (7.23); 3.4145 (4.03); 3.3362 (80.45); 2.8591 (6.55); 2.841 (11.42); 2.8231 (5.99); 2.5422 (35.15); 2.5251 (0.65); 2.5118 (13.37); 2.5073 (26.75); 2.5028 (35.56); 2.4982 (26.02); 2.4937 (12.5); −0.0002 (3.04) |
| 13-17 | 2-fluoro-phenyl | CH2 | CH2 | — | H | compound No. 13-17, solvent: [DMSO], spectrometer: 399.95 MHz 8.3625 (2.93); 8.3491 (5.38); 8.3353 (2.96); 7.7494 (15.29); 7.7357 (16); 7.3475 (3.34); 7.3323 (5.91); 7.3283 (6.81); 7.3092 (4.07); 7.3003 (1.66); 7.296 (1.56); 7.2819 (3.83); 7.2797 (3.82); 7.2672 (3.89); 7.2615 (4.95); 7.2478 (2.7); 7.2437 (2.33); 7.1781 (5.29); 7.1571 (11.37); 7.1407 (9.26); 7.1379 (9.6); 7.1224 (4); 7.1195 (3.76); 7.1099 (0.46); 7.0953 (15.7); 7.0816 (15.32); 3.513 (0.71); 3.4573 (4.34); 3.4402 (9.63); 3.4222 (9.61); 3.4063 (4.88); 3.3353 (109.15); 2.8859 (7.7); 2.8676 (13.14); 2.8495 (6.88); 2.6718 (0.35); 2.5421 (19.64); 2.5072 (40.84); 2.5028 (52.67); 2.4984 (41.42); 2.3296 (0.33); −0.0002 (3.3) |
| 13-18 | 2,6-di-fluoro-phenyl | CH2 | CH2 | — | H | compound No. 13-18, solvent: [DMSO], spectrometer: 399.95 MHz 8.4194 (1.58); 8.4049 (3.04); 8.3906 (1.56); 7.7512 (11.16); 7.7374 (11.56); 7.3616 (0.9); 7.3447 (2.04); 7.3407 (1.77); 7.3238 (3.83); 7.3066 (1.94); 7.303 (2.44); 7.2862 (1.14); 7.1048 (0.53); 7.1004 (0.75); 7.0883 (5.54); 7.0792 (13.16); 7.0655 (16); 7.0573 (1.28); 7.0485 (4.48); 7.0358 (0.61); 3.5123 (1.02); 3.4222 (2.6); 3.4056 (5.96); 3.3882 (5.72); 3.3717 (3.02); 3.3344 (184.38); 2.8991 (3.93); 2.8812 (7.01); 2.8636 (3.47); 2.6763 (0.33); 2.6717 (0.46); 2.5419 (12.12); 2.525 (1.42); 2.5202 (2.3); 2.5117 (26.3); 2.5072 (51.9); 2.5026 (68.37); 2.498 (49.52); 2.4935 (23.41); 2.334 (0.33); 2.3293 (0.44); −0.0002 (4.55) |
| 13-19 | 2,6-di-chloro-phenyl | CH2 | CH2 | — | H | compound No. 13-19, solvent: [DMSO], spectrometer: 399.95 MHz 8.43 (1.73); 8.4158 (3.4); 8.4015 (1.77); 7.7507 (8.75); 7.737 (9.15); 7.4659 (12.07); 7.4457 (16); 7.3012 (5.39); 7.282 (6.3); 7.2803 (5.6); 7.2609 (3.54); 7.1251 (9.59); 7.1113 (9.36); 3.4641 (2.26); 3.4477 (5.74); 3.4292 (5.71); 3.4138 (2.96); 3.3323 (41.62); 3.176 (5.34); 3.1574 (8.32); 3.1403 (4.23); 2.5429 (1.1); 2.5081 (24.3); 2.5036 (31.79); 2.4992 (24.46); −0.0002 (3.6) |
| 13-20 | 3-(tri-fluoro-methyl)phenyl | CH2 | CH2 | — | H | compound No. 13-20, solvent: [DMSO], spectrometer: 399.95 MHz 8.3278 (2.13); 8.3141 (3.93); 8.3002 (2.01); 7.762 (0.54); 7.7504 (15.29); 7.7367 (15.65); 7.6712 (0.37); 7.6513 (0.47); 7.6 (7.88); 7.5873 (2.74); 7.5809 (3.05); 7.5655 (12.74); 7.5528 (8.63); 7.5425 (2.38); 7.5348 (2.41); 7.5165 (1.26); 7.4979 (0.46); 7.478 (0.35); 7.0868 (0.61); 7.0729 (0.82); 7.0642 (16); 7.0505 (15.64); 3.5139 (0.98); 3.4986 (3.51); 3.4813 (7.94); 3.4667 (7.96); 3.4489 (3.95); 3.3328 (77.08); 2.9553 (6.5); 2.9375 (11.89); 2.9198 (5.72); 2.5427 (55.96); 2.5258 (0.88); 2.521 (1.52); 2.5125 (17.59); 2.508 (34.92); 2.5034 (46.06); 2.4988 (33.34); 2.4943 (15.66); −0.0002 (5.77) |

TABLE 13-continued

Compounds of the formula I-13

| Ex. No. | X | L¹ | L² | L³ | Y | Physical data: $^1$H-NMR, δ [ppm] or CAS or patent No. |
|---|---|---|---|---|---|---|
| 13-21 | 4-(tri-fluoro-methyl)phenyl | CH2 | CH2 | — | H | compound No. 13-21, solvent: [DMSO], spectrometer: 399.95 MHz 8.345 (2.07); 8.3312 (3.97); 8.3174 (2.05); 7.7521 (15.19); 7.7449 (0.74); 7.7384 (15.59); 7.6713 (9.55); 7.6512 (11.82); 7.4978 (11.02); 7.4778 (8.98); 7.0868 (16); 7.073 (15.56); 3.5139 (1.01); 3.498 (3.41); 3.4808 (7.29); 3.4661 (7.13); 3.4479 (3.7); 3.3331 (76.49); 2.9475 (5.5); 2.9296 (9.85); 2.9117 (4.79); 2.5428 (44.99); 2.5258 (0.91); 2.5126 (16.8); 2.5081 (33.52); 2.5034 (44.47); 2.4988 (32.31); 2.4943 (15.37); −0.0002 (6.57) |
| 13-22 | 2-methyl-phenyl | CH2 | CH2 | — | H | compound No. 13-22, solvent: [DMSO], spectrometer: 399.95 MHz 8.3703 (0.6); 8.3563 (1.15); 8.3423 (0.6); 7.7585 (4.85); 7.7448 (5.06); 7.1827 (0.86); 7.1753 (1.22); 7.1694 (1.38); 7.1602 (2.44); 7.1559 (1.67); 7.1472 (2.14); 7.1404 (0.91); 7.1289 (2.83); 7.123 (8.3); 7.1151 (4.17); 7.1091 (5.65); 7.102 (1.37); 7.0892 (0.34); 3.5115 (0.38); 3.3955 (1.17); 3.3805 (1.97); 3.3769 (1.69); 3.3719 (1.25); 3.3652 (1.39); 3.3621 (1.63); 3.357 (2.2); 3.3419 (2.94); 3.3299 (102.26); 2.8401 (2.17); 2.825 (1.72); 2.8203 (2.41); 2.8017 (1.92); 2.5409 (25.53); 2.524 (0.91); 2.5192 (1.47); 2.5107 (16.02); 2.5062 (31.84); 2.5016 (42.21); 2.4969 (30.62); 2.4924 (14.51); 2.325 (16); −0.0002 (3.65) |
| 13-23 | 2,4,6-tri-methyl-phenyl | CH2 | CH2 | — | H | compound No. 13-23, solvent: [DMSO], spectrometer: 399.95 MHz 8.4542 (0.37); 8.4396 (0.75); 8.4253 (0.37); 7.7732 (2.68); 7.7594 (2.77); 7.1638 (2.72); 7.1499 (2.66); 6.8104 (4); 3.3309 (67.4); 3.2389 (0.49); 3.2244 (0.85); 3.2192 (0.67); 3.2104 (0.84); 3.2038 (0.66); 3.1971 (0.88); 3.1832 (0.58); 2.8112 (1.04); 2.7979 (0.79); 2.7901 (1.01); 2.7846 (0.81); 2.7703 (0.87); 2.541 (22.19); 2.5241 (0.58); 2.5194 (0.92); 2.5108 (10.83); 2.5063 (21.64); 2.5017 (28.71); 2.497 20.92 2.4925 (9.98); 2.3028 (16); 2.184 (6.91); −0.0002(2.34) |
| 13-24 | 3,4-bis-methoxy-phenyl | CH2 | CH2 | — | H | compound No. 13-24, solvent: [DMSO], spectrometer: 399.95 MHz 8.2848 (0.48); 8.2711 (0.94); 8.2571 (0.47); 7.7541 (3.74); 7.7404 (3.9); 7.1101 (3.68); 7.0963 (3.59); 6.8752 (2.04); 6.8548 (2.81); 6.8288 (2.13); 6.8239 (2.36); 6.7622 (1.4); 6.7573 (1.23); 6.7419 (1); 6.737 (0.9); 3.7324 (15.85); 3.7123 (16); 3.5114 (0.32); 3.4266 (0.73); 3.4106 (1.35); 3.3941 (1.2); 3.3902 (1.32); 3.3751 (0.79); 3.3277 (62.85); 2.7742 (1.36); 2.7548 (1.93); 2.737 (1.2); 2.5408 (19.82); 2.5239 (0.63); 2.5192 (0.98); 2.5106 (11.81); 2.5061 (23.72); 2.5015 (31.56); 2.4968 (22.87); 2.4923 (10.76); −0.0002 (4.16) |
| 13-25 | phenyl | CH2 | CH2 | — | H | compound No. 13-25, solvent: [DMSO], spectrometer: 399.95 MHz 8.3241 (1.84); 8.3103 (3.44); 8.2964 (1.85); 7.7503 (15.44); 7.7433 (0.68); 7.7366 (15.88); 7.3228 (4.07); 7.319 (1.78); 7.3044 (11.1); 7.2912 (3.43); 7.2866 (11.73); 7.2635 (10.5); 7.2595 (14.77); 7.254 (3.02); 7.2429 (6.75); 7.2271 (2.89); 7.2233 (3.78); 7.2195 (2.09); 7.2108 (2.18); 7.2057 (5.81); 7.1999 (1.44); 7.1919 (1.29); 7.188 (2.08); 7.1843 (1.06); 7.1017 (16); 7.0879 (15.4); 3.5114 (1.14); 3.4485 |

TABLE 13-continued

Compounds of the formula I-13

| Ex. No. | X | L¹ | L² | L³ | Y | Physical data: ¹H-NMR, δ [ppm] or CAS or patent No. |
|---|---|---|---|---|---|---|
| | | | | | | (3.78); 3.4329 (6.08); 3.4305 (5.84); 3.4269 (4.22); 3.416 (5.74); 3.4116 (6.65); 3.3968 (4.31); 3.3702 (0.54); 3.3307 (368.55); 2.8452 (6.83); 2.8257 (9.14); 2.8078 (6.09); 2.6797 (0.35); 2.6753 (0.71); 2.6706 (0.98); 2.6661 (0.72); 2.6616 (0.36); 2.541 (61); 2.524 (2.99); 2.5193 (4.87); 2.5107 (52.17); 2.5062 (104.15); 2.5016 (138.37); 2.4969 (100.75); 2.4924 (48.16); 2.3329 (0.66); 2.3283 (0.92); 2.3237 (0.64); 0.008 (0.4); −0.0002 (11.65); −0.0085 (0.33) |
| 13-26 | 4-chlorophenyl | C(CH2—CH2) | CH2 | — | H | |
| 13-27 | 2,4-dichlorophenyl | C(CH2—CH2) | CH2 | — | H | |
| 13-28 | 4-chlorophenyl | CH2 | C(CH2—CH2) | — | H | |
| 13-29 | 2,4-dichlorophenyl | CH2 | C(CH2—CH2) | — | H | |
| 13-30 | 4-chlorophenyl | O | CH2 | CH2 | H | |
| 13-31 | 2,4-dichlorophenyl | O | CH2 | CH2 | H | compound No. 13-31, solvent: [DMSO], spectrometer: 399.95 MHz 8.4226 (2.55); 8.4093 (4.92); 8.3959 (2.59); 7.7714 (12.28); 7.7577 (12.83); 7.5717 (10.86); 7.5653 (11.79); 7.386 (5.53); 7.3795 (5.32); 7.3638 (7.47); 7.3574 (7.31); 7.2398 (12.67); 7.2175 (9.52); 7.1676 (12.98); 7.1538 (12.55); 4.2096 (7.17); 4.1949 (16); 4.1803 (7.92); 3.6208 (3.98); 3.6065 (11.08); 3.5923 (10.76); 3.5778 (3.63); 3.3705 (0.32); 3.3316 (159.11); 2.7121 (0.38); 2.6762 (0.37); 2.672 (0.5); 2.6673 (0.37); 2.5421 (80.13); 2.5252 (1.63); 2.5072 (55.73); 2.5028 (73.58); 2.4984 (56.36); 2.3683 (0.38); 2.3341 (0.34); 2.3295 (0.47); 2.3253 (0.36); −0.0002 (1.71) |
| 13-32 | 4-chlorophenyl | CH2 | CH2 | CH2 | H | |
| 13-33 | 4-chlorophenyl | NCH3 | CH2 | CH2 | H | |
| 13-34 | 2,4-dichlorophenyl | NCH3 | CH2 | CH2 | H | |
| 13-35 | 4-chlorophenyl | CH(OCH3) | CH2 | — | H | |
| 13-36 | 2,4-dichlorophenyl | CH(OCH3) | CH2 | — | H | |
| 13-37 | 2-thienyl | CH2 | CH2 | — | H | compound No. 13-37, solvent: [DMSO], spectrometer: 399.95 MHz 8.3969 (2.78); 8.3833 (5.22); 8.3696 (2.88); 7.7643 (15.35); 7.7505 (16); 7.3519 (8.28); 7.349 (8.09); 7.3393 (9.16); 7.3363 (8.55); 7.1406 (15.8); 7.1269 (15.34); 6.9738 (6.19); 6.9652 (9.7); 6.9612 (6.2); 6.9526 (9.38); 6.9326 (9.72); 6.931 (9.7); 6.9246 (6.81); 3.4692 (4.45); 3.4515 (9.93); 3.4367 (10.12); 3.4186 (5.26); 3.3291 (51.64); 3.0625 (8.98); 3.0443 (15.33); 3.0262 (7.65); 2.6706 (0.35); 2.5408 (15.47); 2.5058 (38.81); 2.5014 (50.88); 2.497 (38.5); −0.0002 (0.99) |
| 13-38 | 3-thienyl | CH2 | CH2 | — | H | |
| 13-39 | 2-furyl | CH2 | CH2 | — | H | |
| 13-40 | 3-furyl | CH2 | CH2 | — | H | |
| 13-41 | phenyl | CH2 | CH2 | CH(CH3) | H | |

TABLE 13-continued

Compounds of the formula I-13

I-13

| Ex. No. | X | L¹ | L² | L³ | Y | Physical data: $^1$H-NMR, δ [ppm] or CAS or patent No. |
|---|---|---|---|---|---|---|
| 13-42 | phenyl | CH2 | CH2 | CH2 | H | |
| 13-43 | 2-Cl-phenyl | CH2 | CH2 | CH(CH3) | H | |
| 13-44 | 4-t-butyl-phenyl | CH2 | CH2 | CH2 | H | |
| 13-45 | 4-methyl-phenyl | CH2 | CH2 | CH2 | H | |
| 13-46 | phenyl | CH2 | CH2 | CH(CH2CH3) | H | |
| 13-47 | 2-methoxy-phenyl | CH2 | CH2 | CH2 | H | |
| 13-48 | 2-methyl-phenyl | CH2 | CH2 | CH2 | H | |
| 13-49 | 3-methyl-phenyl | CH2 | CH2 | CH2 | H | |
| 13-50 | 3-chloro-phenyl | CH2 | CH2 | CH2 | H | |
| 13-51 | 2,6-di fluoro-phenyl | CH2 | CH2 | CH2 | H | compound No. 13-51, solvent: [DMSO], spectrometer: 399.95 MHz 8.2922 (3.17); 8.2786 (5.88); 8.2649 (3.23); 7.7845 (0.37); 7.7707 (0.45); 7.7558 (15.29); 7.7421 (16); 7.3509 (1.52); 7.3338 (3.63); 7.3304 (3.4); 7.3131 (6.65); 7.2951 (3.82); 7.2924 (4.41); 7.2755 (1.93); 7.2133 (0.34); 7.1995 (0.34); 7.14 (0.51); 7.1253 (15.58); 7.1116 (15.3); 7.1021 (1.76); 7.0887 (9.35); 7.069 (14.86); 7.0492 (7.93); 7.0356 (1.16); 6.5422 (0.68); 3.337 (21.45); 3.2628 (4.51); 3.2457 (9.72); 3.2291 (9.77); 3.2124 (4.74); 2.712 (6.57); 2.6928 (10.9); 2.6735 (7.35); 2.5448 (10.46); 2.5096 (22.82); 2.5053 (30.14); 2.501 (23.5); 1.8059 (2.44); 1.7867 (6.52); 1.7683 (9.14); 1.7494 (6.14); 1.7309 (2.16); −0.0002 (0.58) |
| 13-52 | 4-chloro phenyl | CH2 | CH2 | CH2 | H | |
| 13-53 | 2,6-di chloro-phenyl | CH2 | CH2 | CH(CH3) | H | |
| 13-54 | 3,5-di chloro-phenyl | CH2 | CH2 | CH(CH3) | H | |
| 13-55 | 2,6-di methyl-phenyl | CH2 | CH2 | CH2 | H | |
| 13-56 | 2,5-di chloro-phenyl | CH2 | CH2 | CH2 | H | |
| 13-57 | 4-iso propoxy-phenyl | CH2 | CH2 | CH2 | H | |
| 13-58 | 3-tri fluoro-methyl-phenyl | CH2 | CH2 | CH(CH3) | H | |
| 13-59 | 4-methyl-phenyl | CH2 | CH2 | CH(CH3) | H | |
| 13-60 | 2-methyl-phenyl | CH2 | CH2 | CH(CH3) | H | |
| 13-61 | 3,4-di chloro-phenyl | CH2 | CH2 | CH(CH3) | H | |
| 13-62 | 3,5-di chloro-phenyl | CH2 | CH2 | CH2 | H | |
| 13-63 | 2,6-di methyl-phenyl | CH2 | CH2 | CH(CH3) | H | |

TABLE 13-continued

Compounds of the formula I-13

| Ex. No. | X | L¹ | L² | L³ | Y | Physical data: ¹H-NMR, δ [ppm] or CAS or patent No. |
|---|---|---|---|---|---|---|
| 13-64 | 4-tri-fluoro-methyl-phenyl | CH2 | CH2 | CH(CH3) | H | |
| 13-65 | 2,5-di-chloro-phenyl | CH2 | CH2 | CH(CH3) | H | |
| 13-66 | 4-phenoxy-phenyl | CH2 | CH2 | CH2 | H | |
| 13-67 | 3-chloro-phenyl | CH2 | CH2 | CH(CH3) | H | |
| 13-68 | 4-phenoxy-phenyl | CH2 | CH2 | CH(CH3) | H | |
| 13-69 | 2,4-di-chloro-phenyl | CH2 | CH2 | CH(CH3) | H | |
| 13-70 | 2-di-fluoro-methoxy-phenyl | CH2 | CH2 | CH(CH3) | H | |
| 13-71 | 4-methoxy-phenyl | CH2 | CH2 | CH2 | H | |
| 13-72 | 4-chloro-phenyl | CH2 | CH2 | CH(CH3) | H | |
| 13-73 | 4-chloro-phenyl | CH2 | CH2 | CH(i-propyl) | H | |
| 13-74 | 4-fluoro-phenyl | CH2 | CH2 | CH2 | H | |
| 13-75 | 4-chloro-phenyl | CH2 | CH2 | CH(n-propyl) | H | |
| 13-76 | 4-chloro-phenyl | CH2 | CH2 | CH(t-butyl) | H | |
| 13-77 | 2-chloro-phenyl | CH2 | CH2 | CH2 | H | |
| 13-78 | 4-chloro-phenyl | CH2 | CH(CH3) | — | cyclo-propyl | WO-A 2007/060164 |
| 13-79 | 2-thienyl | CH2 | CH2 | CH2 | H | compound No. 13-79, solvent: [DMSO], spectrometer: 399.95 MHz 8.2788 (2.87); 8.2654 (5.26); 8.252 (2.96); 7.7525 (14.98); 7.7387 (15.7); 7.3199 (7.88); 7.3171 (8.06); 7.3072 (8.7); 7.3044 (8.53); 7.1374 (16); 7.1236 (15.6); 6.9537 (6.59); 6.9451 (9.28); 6.941 (6.86); 6.9324 (8.74); 6.8987 (9.21); 6.8973 (9.39); 6.8909 (7.3); 3.3332 (29.69); 3.2794 (4.86); 3.2624 (11.62); 3.2474 (11.69); 3.2306 (5.2); 2.8959 (8.31); 2.8768 (14.02); 2.8577 (9.05); 2.5408 (18.14); 2.5238 (0.68); 2.5059 (21.46); 2.5015 (28.83); 2.4971 (22.39); 1.8886 (2.63); 1.8706 (7.84); 1.8517 (10.41); 1.8335 (7.68); 1.8156 (2.43); −0.0002 (0.53) |
| 13-80 | 4-chloro-phenyl | CH(CF3) | CH2 | — | H | compound No. 13-80, solvent: [DMSO], spectrometer: 399.95 MHz 8.4106 (1.21); 8.3962 (2.12); 8.3821 (1.17); 8.3165 (8.26); 7.725 (8.06); 7.7113 (8.28); 7.4792 (4.61); 7.4736 (2.06); 7.4631 (3.24); 7.4574 (16); 7.4382 (11.72); 7.4165 (3.66); 6.9354 (8.49); 6.9216 (8.27); 4.0537 (0.76); 4.0387 (0.96); 4.0304 (1.28); 4.0153 (1.37); 4.0066 (1.02); 3.9918 (0.93); 3.9827 (0.35); 3.8704 (0.88); 3.857 (1.49); 3.843 (1.01); 3.8364 (1.49); 3.823 (2.22); 3.8094 (1.21); 3.7387 (1.21); |

TABLE 13-continued
Compounds of the formula I-13
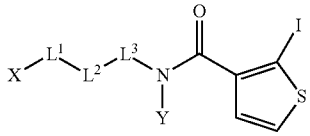
I-13
| Ex. No. | X | L¹ | L² | L³ | Y | Physical data: ¹H-NMR, δ [ppm] or CAS or patent No. |
|---|---|---|---|---|---|---|
| | | | | | | 3.7225 (1.45); 3.7163 (1.26); 3.7047 (1.39); 3.7003 (1.38); 3.6886 (0.92); 3.6823 (0.86); 3.666 (0.72); 3.3218 (50.2); 3.2981 (3.38); 2.6795 (0.35); 2.6749 (0.67); 2.6706 (0.93); 2.666 (0.67); 2.5238 (3.65); 2.5105 (53.97); 2.5061 (106.26); 2.5015 (138.08); 2.4969 (98.64); 2.4925 (46.97); 2.3328 (0.65); 2.3282 (0.9); 2.3237 (0.64); 0.008 (0.68); −0.0002 (19.32); −0.0085 (0.63) |
| 13-81 | 4-chloro-2-thienyl | CH2 | CH2 | — | H | compound No. 13-81, solvent: [DMSO], spectrometer: 601.6 MHz 8.3946 (2.08); 8.3853 (4.02); 8.376 (2.1); 7.7651 (15.61); 7.756 (16); 7.3742 (14.08); 7.3717 (14.19); 7.1256 (15.83); 7.1165 (15.6); 6.9282 (10.18); 6.927 (9.69); 6.9259 (10.09); 3.4591 (3.81); 3.4475 (9.26); 3.4378 (9.49); 3.4263 (4.25); 3.3523 (0.67); 3.3253 (1063.51); 3.3017 (0.95); 3.2969 (0.51); 3.0211 (6.61); 3.0094 (12.8); 2.998 (6); 2.6531 (2.09); 2.6191 (0.74); 2.6161 (1.6); 2.6131 (2.23); 2.61 (1.59); 2.6071 (0.72); 2.5605 (0.47); 2.5407 (617.38); 2.5224 (4.3); 2.5193 (5.21); 2.5162 (5.18); 2.5074 (120.61); 2.5044 (259.43); 2.5013 (360.76); 2.4983 (262.2); 2.4953 (122.46); 2.4246 (2.1); 2.3916 (0.73); 2.3886 (1.6); 2.3855 (2.23); 2.3825 (1.59); 2.3795 (0.73); 2.0735 (1.11); 0.0052 (0.55); −0.0002 (20.16); −0.0057 (0.62) |
| 13-82 | 4-chloro-phenyl | N(CH3) | CH2 | CH2 | H | compound No. 13-82, solvent: [DMSO], spectrometer: 399.95 MHz 8.3356 (0.74); 8.3212 (1.42); 8.3074 (0.73); 7.7465 (3.22); 7.7328 (3.28); 7.1828 (4.27); 7.1603 (4.59); 7.1519 (0.5); 7.0478 (3.52); 7.0341 (3.4); 6.7577 (4.58); 6.735 (4.07); 3.49 (1.35); 3.4733 (3.17); 3.4567 (2.25); 3.3732 (1.34); 3.3578 (2.76); 3.3283 (54.15); 2.9194 (16); 2.5412 (18.68); 2.5065 (26.77); 2.5022 (33.81); 2.499 (25.6); −0.0002 (4.41) |
| 13-83 | 4-(tri-fluoro-methy-oxy)phenyl | CH2 | CH2 | — | H | compound No. 13-83, solvent: [DMSO], spectrometer: 399.95 MHz 8.3322 (1.93); 8.3184 (3.8); 8.3047 (1.91); 7.7488 (13.18); 7.735 (13.59); 7.3986 (1.12); 7.3918 (10.13); 7.3869 (3.75); 7.3753 (4.63); 7.3702 (16); 7.3636 (2.05); 7.2969 (10.34); 7.2771 (6.77); 7.0854 (13.36); 7.0716 (13.06); 5.7561(1.42); 3.4657 (2.96); 3.4486 (6.08); 3.4336(5.93); 3.4152 (3.3); 3.3257 (74.47); 2.8816(5.71); 2.8632 (9.52); 2.8453 (5.09); 2.676 (0.34); 2.6713 (0.46); 2.6667 (0.34); 2.5417(7.2); 2.5246 (1.25); 2.5113 (25.89); 2.5068(51.79); 2.5022 (68.85); 2.4977 (50.2); 2.4932(23.97); 2.3336 (0.33); 2.329 (0.44); 0.008 (1.53); −0.0002 (45.08); −0.0085 (1.45) |

TABLE 14

Compounds of the formula I-14

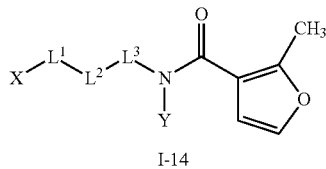

I-14

| Ex. No. | X | $L^1$ | $L^2$ | $L^3$ | Y | Physical data: $^1$H-NMR, δ [ppm] or CAS or patent No. |
|---|---|---|---|---|---|---|
| 14-1 | 3-methyl-2-thienyl | CH2 | CH2 | — | H | |
| 14-2 | 2,4-dichlorophenyl | CH2 | CH2 | CH2 | H | [DMSO], spectrometer: 399.95 MHz<br>8.1005 (0.59); 8.0862 (1.15); 8.0720 (0.59); 7.5886 (2.50); 7.5837 (2.62); 7.4979 (3.01); 7.4929 (3.05); 7.3827 (0.84); 7.3776 (0.71); 7.3620 (2.87); 7.3570 (3.02); 7.3454 (4.17); 7.3247 (1.15); 6.7737 (2.91); 6.7687 (2.89); 3.4388 (0.87); 3.4219 (1.99); 3.4063 (1.93); 3.3887 (0.99); 3.3344 (14.10); 2.9293 (1.87); 2.9112 (3.15); 2.8936 (1.63); 2.5257 (0.50); 2.5209 (0.78); 2.5122 (9.39); 2.5078 (18.89); 2.5033 (24.71); 2.4987 (17.98); 2.4942 (8.73); 2.4740 (16.00); 0.0080 (0.32); −0.0002 (9.56); −0.0085 (0.34) |
| 14-3 | 4-chlorophenyl | CH2 | CH2 | — | H | US 20090163545 |
| 14-4 | 2,4-dichlorophenyl | CH2 | CH2 | — | H | WO-A 2007/060166 |
| 14-5 | 4-chlorophenyl | CH(OCH3) | CH(CH3) | — | H | [DMSO], spectrometer: 399.95 MHz<br>7.7853 (1.01); 7.7637 (1.03); 7.6221 (0.82); 7.6019 (0.84); 7.4943 (2.12); 7.4892 (2.18); 7.4713 (2.63); 7.4663 (2.66); 7.4317 (2.74); 7.4270 (0.88); 7.4152 (1.02); 7.4106 (3.89); 7.4044 (3.22); 7.3997 (1.00); 7.3881 (1.22); 7.3832 (4.95); 7.3775 (0.67); 7.3287 (0.65); 7.3232 (4.39); 7.3184 (1.19); 7.3065 (0.92); 7.3021(2.62); 7.2728 (0.41); 7.2669 (3.21); 7.2623 (0.95); 7.2502 (0.84); 7.2458 (2.52); 6.8700 (1.95); 6.8650 (1.93); 6.7930 (2.44); 6.7880 (2.42); 4.3047 (1.21); 4.2893 (1.71); 4.2345 (2.04); 4.2182 (2.54); 4.1982 (0.55); 4.1819 (0.33); 4.0897 (0.49); 4.0731 (0.75); 4.0684 (0.57); 4.0564 (0.52); 4.0516 (0.75); 4.0350 (0.45); 3.3333 (70.82); 3.1727 (16.00);<br>3.1476 (13.43); 2.7121 (0.33); 2.5422 (81.19); 2.5255 (0.60); 2.5206<br>(0.77); 2.5119 (11.03); 2.5074 (22.78); 2.5028 (30.62); 2.4982 (22.57); 2.4937(10.85); 2.4687 (10.78); 2.3951 (13.43); 2.3683 (0.38); 1.1356 (5.61); 1.1187 (5.61); 0.9433 (4.40); 0.9262 (4.39); 0.0080 (0.50); −0.0002 (16.90); −0.0085 (0.52) |
| 14-6 | 2,4-dichlorophenyl | CH(OCH3) | CH(CH3) | — | H | |
| 14-7 | 4-chlorophenyl | CH(CH3) | CH2 | — | H | [DMSO], spectrometer: 399.95 MHz<br>8.0032 (0.58); 7.9889 (1.14); 7.9746 (0.59); 7.4821 (3.03); 7.4772 (3.07); 7.3650 (0.39); 7.3588 (3.39); 7.3540 (1.19); 7.3426 (1.57); 7.3376 (5.86); 7.3315 (0.80); 7.2828 (0.83); 7.2769 (5.47); 7.2720 (1.53); 7.2604 (1.20); 7.2557 (3.30); 7.2497 (0.39); 6.7627 (2.99); 6.7577 (2.94); 3.3647 (0.35); 3.3337 (42.38); 3.3139 (1.33); 3.3060 (0.98); 3.2984 (1.08); 3.2917 (1.05); 3.2877 (1.03); 3.2732 (1.17); 3.2547 (0.36); 3.0451 (0.56); 3.0272 (1.12); 3.0094 (1.07); 2.9915 (0.50); 2.5421 (55.53); 2.5252 (0.38); 2.5205 (0.55); 2.5119 (7.47); 2.5074 (15.12); 2.5028 (20.09); 2.4982 (14.83); 2.4938 (7.16); 2.4520 (16.00); 1.1981 (6.91); 1.1807 (6.81); 0.0080 (0.35); −0. 0002 (10.15) |
| 14-8 | 2,4-dichlorophenyl | CH(CH3) | CH2 | — | H | [DMSO], spectrometer: 399.95 MHz<br>8.0329 (0.65); 8.0186 (1.30); 8.0043 (0.65); 7.5550 (2.99); 7.5499 (3.01); 7.4798 (3.22); 7.4748 (3.12); 7.4572 (1.53); 7.4361 (4.23); 7.4173 (2.70); 7.4121 (2.37); 7.3962 (0.91); 7.3910 (0.87); 6.7579 (3.17); 6.7529 (2.98); 3.5198 (0.49); 3.5023 (1.12); 3.4849 (1.26); 3.4676 (0.72); 3.4452 (0.46); 3.4303 (0.46); 3.4127 (1.19); 3.3971 (1.29); 3.3860 (1.13); 3.3803 (0.95); 3.3715 (1.25); 3.3536 (1.29); 3.3333 (48.84); 2.5426 (52.28); 2.5257 (0.44); 2.5119 (8.88); 2.5076 (16.98); 2.5031 (21.92); 2.4986 (16.10); 2.4942 (7.74); 2.4485 (16.00); 1.1873 (6.96); 1.1702 (6.84); 0.0079 (0.41); −0.0002 (10.74); −0.0085 (0.34) |
| 14-9 | 4-chlorophenyl | CH2 | CH(CH3) | — | H | WO-A 2007/060164 |
| 14-10 | 2,4-dichlorophenyl | CH2 | CH(CH3) | — | H | [DMSO], spectrometer: 399.95 MHz<br>7.8107 (1.22); 7.7892 (1.24); 7.5607 (2.45); 7.5563 (2.41); 7.4908 (3.01); 7.4858 (3.03); 7.3656 (0.60); 7.3450 (4.88); 7.3418 (4.10); 7.3369 (3.10); 7.3207 (0.40); 7.3162 (0.48); 6.8160 (3.01); 6.8110 |

TABLE 14-continued

Compounds of the formula I-14

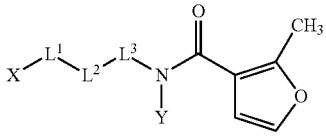

I-14

| Ex. No. | X | L¹ | L² | L³ | Y | Physical data: ¹H-NMR, δ [ppm] or CAS or patent No. |
|---|---|---|---|---|---|---|
| | | | | | | (2.94); 4.2915 (0.59); 4.2741 (0.79); 4.2537 (0.56); 3.3317 (127.65); 2.8915 (3.24); 2.8761 (2.11); 2.8712 (2.06); 2.6714 (0.36); 2.5416 (4.90); 2.5246 (0.96); 2.5111 (20.57); 2.5068 (39.98); 2.5023 (52.16); 2.4978 (38.47); 2.4934 (18.78); 2.4161 (16.00); 2.3291 (0.34); 1.1619 (6.39); 1.1453 (6.35); 0.0078 (0.58); −0.0002 (15.16); −0.0084 (0.50) |
| 14-11 | 4-chloro-phenyl | C(CH3)2 | CH2 | — | H | [DMSO], spectrometer: 399.95 MHz 7.7450 (0.40); 7.7293 (0.81); 7.7135 (0.40); 7.4834 (2.27); 7.4784 (2.28); 7.4241 (2.24); 7.4188 (0.82); 7.4077 (1.13); 7.4022 (4.69); 7.3959 (0.67); 7.3673 (0.65); 7.3610 (4.70); 7.3555 (1.09); 7.3444 (0.81); 7.3391 (2.25); 6.7966 (2.18); 6.7916 (2.13); 3.3752 (2.86); 3.3592 (2.87); 3.3335 (29.94); 2.5422 (39.05); 2.5202 (0.37); 2.5118 (5.39); 2.5073 (10.92); 2.5027 (14.51); 2.4982 (10.65); 2.4937 (5.11); 2.4261 (11.72); 1.2582 (16.00); −0.0002 (7.76) |
| 14-12 | 2,4-di-chloro-phenyl | C(CH3)2 | CH2 | — | H | [DMSO], spectrometer: 399.95 MHz 7.7346 (0.44); 7.7188 (0.91); 7.7029 (0.44); 7.5332 (2.44); 7.5274 (2.60); 7.4699 (2.42); 7.4648 (2.45); 7.4544 (1.64); 7.4328 (2.53); 7.3640 (1.71); 7.3582 (1.61); 7.3425 (1.10); 7.3366 (1.06); 6.7625 (2.29); 6.7575 (2.27); 3.7172 (2.85); 3.7011 (2.82); 3.3342 (36.20); 2.5425 (34.60); 2.5208 (0.40); 2.5122 (5.45); 2.5077 (11.08); 2.5031 (14.82); 2.4985 (10.91); 2.4941 (5.24); 2.4102 (12.19); 1.4076 (16.00); −0.0002 (6.46) |
| 14-13 | 2-chloro-phenyl | CH2 | CH2 | — | H | [DMSO], spectrometer: 399.95 MHz 8.1233 (2.80); 8.1093 (5.37); 8.0954 (2.82); 7.4992 (15.95); 7.4942 (16.00); 7.4398 (6.98); 7.4358 (5.14); 7.4218 (9.64); 7.4169 (8.86); 7.4014 (0.41); 7.3420 (4.40); 7.3362 (5.93); 7.3234 (7.10); 7.3185 (10.40); 7.3021 (3.55); 7.2978 (4.59); 7.2840 (10.82); 7.2796 (9.52); 7.2710 (9.52); 7.2667 (9.41); 7.2646 (9.80); 7.2613 (6.16); 7.2524 (8.16); 7.2470 (6.78); 7.2341 (2.70); 7.2289 (2.08); 6.7953 (15.49); 6.7903 (15.18); 3.4475 (5.04); 3.4316 (9.29); 3.4153 (8.52); 3.4112 (9.56); 3.3963 (5.85); 3.3621 (0.58); 3.3349 (206.81); 3.3115 (0.51); 2.9492 (10.46); 2.9299 (14.13); 2.9123 (9.09); 2.8907 (0.91); 2.7320 (0.68); 2.7122 (1.23); 2.6765 (0.54); 2.6720 (0.67); 2.6674 (0.56); 2.6431 (0.59); 2.5826 (0.32); 2.5686 (0.69); 2.5615 (1.13); 2.5422 (270.64); 2.5254 (1.92); 2.5205 (2.33); 2.5119 (34.55); 2.5074 (69.97); 2.5028 (92.97); 2.4983 (68.09); 2.4937 (32.87); 2.4833 (84.56); 2.3685 (1.18); 2.3341 (0.45); 2.3297 (0.62); 2.3250 (0.47); 2.3201 (0.66); 0.0079 (1.68); −0.0002 (51.87); −0.0086 (1.55) |
| 14-14 | 3,4-di-chloro-phenyl | CH2 | CH2 | — | H | [DMSO], spectrometer: 399.95 MHz 8.0559 (0.60); 8.0420 (1.15); 8.0280 (0.59); 7.5514 (2.92); 7.5309 (3.33); 7.5078 (2.86); 7.5002 (3.65); 7.4947 (3.01); 7.2304 (1.61); 7.2254 (1.54); 7.2098 (1.42); 7.2048 (1.36); 6.7694 (2.98); 6.7644 (2.87); 3.4345 (1.03); 3.4173 (2.30); 3.4022 (2.35); 3.3849 (1.27); 3.3401 (146.07); 2.8254 (1.83); 2.8077 (3.43); 2.7900 (1.63); 2.7122 (0.37); 2.5422 (79.74); 2.5249 (0.91); 2.5117 (16.17); 2.5074 (31.11); 2.5029 (40.60); 2.4983 (29.98); 2.4940 (14.65); 2.4679 (16.00); 2.3684 (0.36); 0.0075 (0.46); −0.0002 (10.57); −0.0085 (0.34) |
| 14-15 | 3,5-di-chloro-phenyl | CH2 | CH2 | — | H | [DMSO], spectrometer: 399.95 MHz 8.0618 (0.56); 8.0480 (1.09); 8.0340 (0.56); 7.5030 (3.07); 7.4980 (3.08); 7.4391 (1.36); 7.4343 (2.72); 7.4296 (1.54); 7.3030 (6.08); 7.2982 (5.74); 6.7674 (2.96); 6.7624 (2.93); 3.4453 (0.91); 3.4280 (2.18); 3.4132 (2.21); 3.3959 (1.00); 3.3367 (59.76); 2.8379 (1.72); 2.8204 (3.32); 2.8028 (1.53); 2.5426 (53.55); 2.5257 (0.33); 2.5207 (0.55); 2.5122 (7.18); 2.5077 (14.57); 2.5031 (19.50); 2.4986 (14.37); 2.4941 (6.93); 2.4668 (16.00); −0.0002 (5.83) |
| 14-16 | 3-chloro-phenyl | CH2 | CH2 | — | H | US 20090163545 |
| 14-17 | 2-fluoro-phenyl | CH2 | CH2 | — | H | CAS: 1088190-17-3 |

TABLE 14-continued

Compounds of the formula I-14

I-14

| Ex. No. | X | L¹ | L² | L³ | Y | Physical data: $^1$H-NMR, δ [ppm] or CAS or patent No. |
|---|---|---|---|---|---|---|
| 14-18 | 2,6-difluorophenyl | CH2 | CH2 | — | H | CAS: 1197478-54-8 |
| 14-19 | 2,6-dichlorophenyl | CH2 | CH2 | — | H | [DMSO], spectrometer: 399.95 MHz<br>8.1857 (0.57); 8.1712 (1.12); 8.1569 (0.57); 7.4946 (2.99); 7.4896 (2.98); 7.4627 (4.66); 7.4426 (6.42); 7.3002 (2.26); 7.2811 (2.21); 7.2792 (2.11); 7.2600 (1.48); 6.7910 (2.95); 6.7860 (2.87); 3.4301 (0.86); 3.4139 (1.91); 3.4087 (1.15); 3.3981 (1.69); 3.3937 (1.91); 3.3790 (1.12); 3.3405 (76.83); 3.1400 (1.96); 3.1205 (2.67); 3.1035 (1.53); 2.5429 (51.41); 2.5260 (0.42); 2.5126 (8.08); 2.5081 (16.01);<br>2.5035 (21.17); 2.4989 (15.52); 2.4945 (7.45); 2.4795 (16.00); −0.0002 (6.48) |
| 14-20 | 3-(trifluoromethyl)phenyl | CH2 | CH2 | — | H | [DMSO], spectrometer: 399.95 MHz<br>8.0845 (0.58); 8.0705 (1.06); 8.0569 (0.55); 7.5785 (2.44); 7.5747 (2.43); 7.5658 (1.02); 7.5575 (1.52); 7.5419 (5.32); 7.5245 (0.81); 7.4993 (3.09); 7.4943 (3.11); 6.7706 (2.96); 6.7656 (2.89); 3.4655 (1.01); 3.4483 (2.10); 3.4335 (2.10); 3.4154 (1.11); 3.3419 (67.23); 2.9274 (1.86); 2.9094 (3.22); 2.8916 (1.83); 2.5431 (55.77); 2.5214 (0.51); 2.5129 (6.99); 2.5085 (14.07); 2.5039 (18.66); 2.4993 (13.63); 2.4948 (6.53); 2.4751 (0.81); 2.4642 (16.00); −0.0002 (6.39) |
| 14-21 | 4-(trifluoromethyl)phenyl | CH2 | CH2 | — | H | CAS:1007769-64-3 |
| 14-22 | 2-methylphenyl | CH2 | CH2 | — | H | [DMSO], spectrometer: 399.95 MHz<br>8.1484 (0.61); 8.1343 (1.17); 8.1203 (0.61); 7.5084 (3.47); 7.5034 (3.53); 7.1648 (0.76); 7.1578 (0.98); 7.1502 (1.82); 7.1427 (2.14); 7.1340 (3.07); 7.1258 (1.29); 7.1216 (3.55); 7.1181 (3.61); 7.1081 (2.67); 7.1027 (1.42); 7.0965 (1.18); 6.8060 (3.37); 6.8010 (3.34); 3.3644 (1.45); 3.3411 (76.78); 3.3255 (2.67); 3.3110 (1.35); 2.8058 (2.23); 2.7911 (1.71); 2.7859 (2.39); 2.7669 (1.98); 2.5421 (59.24); 2.5254 (0.42); 2.5205 (0.61); 2.5117 (7.72); 2.5072 (15.80); 2.5026 (21.96); 2.4983 (30.70); 2.4938 (8.81); 2.3199 (16.00); -0.0002 (7.31) |
| 14-23 | 2,4,6-trimethylphenyl | CH2 | CH2 | — | H | [DMSO], spectrometer: 399.95 MHz<br>8.2303 (0.41); 8.2158 (0.83); 8.2012 (0.42); 7.5185 (2.11); 7.5135 (2.15); 6.8170 (2.10); 6.8117 (2.37); 6.8043 (4.37); 3.3396 (48.79); 3.2143 (0.52); 3.1998 (0.92); 3.1950 (0.75); 3.1860 (0.89); 3.1791 (0.74); 3.1726 (0.96); 3.1586 (0.63); 2.7717 (1.12); 2.7584 (0.85); 2.7507 (1.10); 2.7452 (0.89); 2.7308 (1.02); 2.5420 (33.55); 2.5145 (11.87); 2.5071 (9.55); 2.5025 (12.60); 2.4980 (9.40); 2.4935 (4.67);<br>2.2973 (16.00); 2.1809 (7.31); −0.0002 (4.69) |
| 14-24 | 3,4-bismethoxyphenyl | CH2 | CH2 | — | H | Chemische Berichte (1986), 119(8), 2553-65<br>[DMSO], spectrometer: 399.95 MHz<br>8.0475 (0.51); 8.0337 (1.01); 8.0198 (0.51); 7.5024 (2.60); 7.4974 (2.65); 6.8695 (2.09); 6.8491 (2.78); 6.8088 (4.43); 6.8040 (4.50); 6.7378 (1.38); 6.7330 (1.25); 6.7175 (1.04); 6.7127 (0.95); 3.7181 (15.83); 3.7091 (16.00); 3.3989 (0.79); 3.3829 (1.50); 3.3659 (1.55);<br>3.3624 (1.74); 3.3388 (115.29); 2.7441 (1.42); 2.7247 (2.02); 2.7069 (1.30); 2.5418 (69.00); 2.5249 (0.58); 2.5201 (0.80); 2.5115 (10.33); 2.5070 (21.00); 2.5024 (28.16); 2.4978 (20.98); 2.4934 (10.56); 2.4851 (14.30); −0.0002 (7.72) |
| 14-25 | phenyl | CH2 | CH2 | — | H | CAS: 541523-79-9 |
| 14-26 | 4-chlorophenyl | C(CH2—CH2) | CH2 | — | H | |
| 14-27 | 2,4-dichlorophenyl | C(CH2—CH2) | CH2 | — | H | |
| 14-28 | 4-chlorophenyl | CH2 | C(CH2—CH2) | — | H | |
| 14-29 | 2,4-dichlorophenyl | CH2 | C(CH2—CH2) | — | H | |

TABLE 14-continued

Compounds of the formula I-14

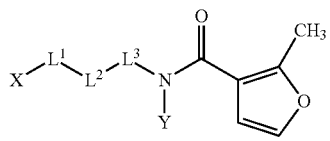

I-14

| Ex. No. | X | L¹ | L² | L³ | Y | Physical data: ¹H-NMR, δ [ppm] or CAS or patent No. |
|---|---|---|---|---|---|---|
| 14-30 | 4-chloro-phenyl | O | CH2 | CH2 | H | |
| 14-31 | 2,4-di-chloro-phenyl | O | CH2 | CH2 | H | compound No. 14-31, solvent: [DMSO], spectrometer: 399.95 MHz 8.1991 (2.44); 8.1856 (4.74); 8.1721 (2.51); 7.5692 (10.73); 7.5627 (11.64); 7.5192 (11.22); 7.5142 (11.71); 7.3808 (5.45); 7.3743 (5.19); 7.3586 (7.5); 7.3522 (7.37); 7.2458 (12.65); 7.2235 (9.28); 6.8287 (11.22); 6.8238 (11.45); 4.1873 (7.13); 4.1722 (16); 4.1572 (7.9); 3.589 (3.92); 3.5743 (10.95); 3.5599 (10.65); 3.545 (3.62); 3.3329 (48.62 002)(1.63) 2.6604 (0.37); 2.544 (41.84); 2.509 (30.08); 2.5003 (78.98); 2.3368(0.51); −0.0002 (1.63) |
| 14-32 | 4-chloro-phenyl | CH2 | CH2 | CH2 | H | |
| 14-33 | 4-chloro-phenyl | NCH3 | CH2 | CH2 | H | |
| 14-34 | 2,4-di-chloro-phenyl | NCH3 | CH2 | CH2 | H | |
| 14-35 | 4-chloro-phenyl | CH(OCH3) | CH2 | — | H | |
| 14-36 | 2,4-di-chloro-phenyl | CH(OCH3) | CH2 | — | H | |
| 14-37 | 2-thienyl | CH2 | CH2 | — | H | CAS: 1036192-62-7; compound No. 14-37, solvent: [DMSO], spectrometer: 399.95 MHz 8.1549 (2.8); 8.1411 (5.13); 8.1277 (2.85); 7.5103 (13.94); 7.5053 (14.05); 7.3436 (8.86); 7.3407 (8.33); 7.3308 (9.73); 7.3279 (8.6); 6.9666 (7.13); 6.9581 (9.85); 6.9539 (7.12); 6.9454 (8.99); 6.9046 (9.56); 6.9026 (9.21); 6.8962 (7.64); 6.8081 (14.18); 6.8032 (13.97); 3.4417 (4.84); 3.424 (10.35); 3.4092 (10.55); 3.3909 (5.74); 3.3313 (114.75); 3.0349 (9.53); 3.0166 (16); 2.9985 (8.11); 2.6758 (0.39); 2.6712 (0.5); 2.6668 (0.37); 2.6529 (0.45); 2.5414 (26.01); 2.5243 (1.99); 2.5066 (56.04); 2.5021 (73.51); 2.4974 (60.73); 2.4927 (97.05); 2.3293 (0.87); −0.0002 (1.26) |
| 14-38 | 3-thienyl | CH2 | CH2 | — | H | |
| 14-39 | 2-furyl | CH2 | CH2 | — | H | DE 2006471 |
| 14-40 | 3-furyl | CH2 | CH2 | — | H | |
| 14-41 | phenyl | CH2 | CH2 | CH(CH3) | H | US 20090163545 |
| 14-42 | phenyl | CH2 | CH2 | CH2 | H | |
| 14-43 | 2-Cl-phenyl | CH2 | CH2 | CH(CH3) | H | |
| 14-44 | 4-t-butyl-phenyl | CH2 | CH2 | CH2 | H | |
| 14-45 | 4-methyl-phenyl | CH2 | CH2 | CH2 | H | |
| 14-46 | phenyl | CH2 | CH2 | CH(CH2CH3) | H | |
| 14-47 | 2-methoxy-phenyl | CH2 | CH2 | CH2 | H | |
| 14-48 | 2-methyl-phenyl | CH2 | CH2 | CH2 | H | |
| 14-49 | 3-methyl-phenyl | CH2 | CH2 | CH2 | H | |
| 14-50 | 3-chloro-phenyl | CH2 | CH2 | CH2 | H | |
| 14-51 | 2,6-di-fluoro-phenyl | CH2 | CH2 | CH2 | H | compound No. 14-51, solvent: [DMSO], spectrometer: 399.95 MHz 8.0323 (3.22); 8.0184 (6.02); 8.0048 (3.33); 7.5324 (0.4); 7.5275 (0.41); 7.5013 (15.34); 7.4964 (15.51); 7.3451 (1.63); 7.328 (3.84); 7.3246 (3.58); 7.3073 (7.14); 7.2866 (4.63); 7.2696 (2.07); 7.1377 (0.34); 7.1164 (0.46); 7.1001 (1); 7.0958 (1.45); 7.083 (10); 7.0631 (16); 7.0433 (8.28); 7.0297 (1.15); 6.8867 (0.35); 6.8816 (0.35); 6.7981 (15.55); 6.7933 (15.34); 6.5018 (0.35); 6.496 (0.68); 3.3608 (0.43); 3.3327 (113.68); 3.2342 (4.87); 3.2176 (9.88); 3.2 (9.94); 3.1832 (5.13); 2.6715 (7.4); 2.6523 (11.98); 2.633 (7.7); 2.5434 (15.29); 2.5084 (61.17); 2.504 (80.08); 2.4996 (60.68); |

TABLE 14-continued

Compounds of the formula I-14

| Ex. No. | X | L¹ | L² | L³ | Y | Physical data: $^1$H-NMR, δ [ppm] or CAS or patent No. |
|---|---|---|---|---|---|---|
| | | | | | | 2.4836 (81.14); 2.3353 (0.43); 2.3308 (0.56); 2.3263 (0.45); 2.3203 (0.69); 1.7725 (2.67); 1.7532 (6.95); 1.7348 (10.07); 1.7159 (6.46); 1.6973 (2.32); −0.0002 (1.34) |
| 14-52 | 4-chlorophenyl | CH2 | CH2 | CH2 | H | |
| 14-53 | 2,6-dichlorophenyl | CH2 | CH2 | CH(CH3) | H | |
| 14-54 | 3,5-dichlorophenyl | CH2 | CH2 | CH(CH3) | H | |
| 14-55 | 2,6-dimethylphenyl | CH2 | CH2 | CH2 | H | |
| 14-56 | 2,5-dichlorophenyl | CH2 | CH2 | CH2 | H | |
| 14-57 | 4-isopropoxyphenyl | CH2 | CH2 | CH2 | H | |
| 14-58 | 3-trifluoromethylphenyl | CH2 | CH2 | CH(CH3) | H | |
| 14-59 | 4-methylphenyl | CH2 | CH2 | CH(CH3) | H | |
| 14-60 | 2-methylphenyl | CH2 | CH2 | CH(CH3) | H | |
| 14-61 | 3,4-dichlorophenyl | CH2 | CH2 | CH(CH3) | H | |
| 14-62 | 3,5-dichlorophenyl | CH2 | CH2 | CH2 | H | |
| 14-63 | 2,6-dimethylphenyl | CH2 | CH2 | CH(CH3) | H | |
| 14-64 | 4-trifluoromethylphenyl | CH2 | CH2 | CH(CH3) | H | |
| 14-65 | 2,5-dichlorophenyl | CH2 | CH2 | CH(CH3) | H | |
| 14-66 | 4-phenoxyphenyl | CH2 | CH2 | CH2 | H | |
| 14-67 | 3-chlorophenyl | CH2 | CH2 | CH(CH3) | H | |
| 14-68 | 4-phenoxyphenyl | CH2 | CH2 | CH(CH3) | H | |
| 14-69 | 2,4-dichlorophenyl | CH2 | CH2 | CH(CH3) | H | |
| 14-70 | 2-difluoromethoxyphenyl | CH2 | CH2 | CH(CH3) | H | |
| 14-71 | 4-methoxyphenyl | CH2 | CH2 | CH2 | H | |
| 14-72 | 4-chlorophenyl | CH2 | CH2 | CH(CH3) | H | |
| 14-73 | 4-chlorophenyl | CH2 | CH2 | CH(i-propyl) | H | |
| 14-74 | 4-fluorophenyl | CH2 | CH2 | CH2 | H | |
| 14-75 | 4-chlorophenyl | CH2 | CH2 | CH(n-propyl) | H | |

TABLE 14-continued
Compounds of the formula I-14
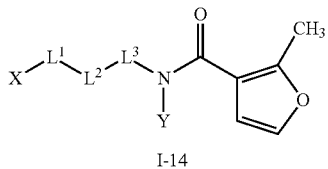
I-14
| Ex. No. | X | L¹ | L² | L³ | Y | Physical data: ¹H-NMR, δ [ppm] or CAS or patent No. |
|---|---|---|---|---|---|---|
| 14-76 | 4-chloro-phenyl | CH2 | CH2 | CH(t-butyl) | H | |
| 14-77 | 2-chloro-phenyl | CH2 | CH2 | CH2 | H | |
| 14-78 | 4-chloro-phenyl | CH2 | CH(CH3) | — | cyclo-propyl | WO-A 2007/060164 |
| 14-79 | 2-thienyl | CH2 | CH2 | CH2 | H | compound No. 14-79, solvent: [DMSO], spectrometer: 399.95 MHz 8.0171 (3); 8.0039 (5.46); 7.9908 (3.16); 7.506 (13.76); 7.5012 (14.16); 7.3189 (8.22); 7.3166 (7.79); 7.3061 (9.13); 7.3039 (8.3); 6.9506 (6.59); 6.942 (9.3); 6.9381 (7.06); 6.9294 (8.33); 6.8849 (9.82); 6.8769 (8.12); 6.8296 (14.52); 6.8249 (14.59); 6.6403 (0.36); 3.3277 (177.24); 3.2788 (0.32); 3.2567 (5.21); 3.2399 (11.67); 3.2241 (11.82); 3.2072 (5.66); 2.8452 (9.12); 2.826 (16); 2.807 (10); 2.6709 (1.15); 2.6668 (0.92); 2.652 (0.52); 2.5412 (3.07); 2.5061 (125.99); 2.5019 (163.82); 2.4976 (130.24); 2.4925 (132.62); 2.3287 (1.52); 1.8629 (2.88); 1.8444 (8.58); 1.826 (11.62); 1.8078 (8.24); 1.7893 (2.67); −0.0002 (2.3) |
| 14-80 | 4-chloro-2-thienyl | CH2 | CH2 | — | H | compound No. 14-80, solvent: [DMSO], spectrometer: 601.6 MHz 19.9748 (0.32); 8.5435 (1.84); 8.1811 (0.53); 8.1329 (0.44); 7.8134 (0.37); 7.7811 (4.16); 7.5088 (0.96); 7.5054 (0.98); 7.3929 (1.4); 7.3903 (2.11); 7.3877 (1.36); 7.384 (11.28); 7.3814 (11.53); 7.3748 (1.67); 7.3703 (2.55); 7.3677 (2.64); 7.3667 (2.58); 7.364 (2.54); 7.3609 (1.36); 7.3583 (2.12); 7.3558 (2.06); 7.3193 (0.54); 7.3105 (0.53); 6.9507 (0.46); 6.9167 (5.02); 6.9051 (1.66); 6.9026 (1.67); 6.8973 (1.83); 6.8736 (0.7); 6.8356 (1.19); 6.796 (0.99); 6.7927 (0.99); 6.7442 (0.39); 6.6313 (0.73); 6.6251 (0.37); 6.613 (0.37); 6.579 (0.7); 6.5069 (6.56); 6.4758 (0.74); 6.3956 (1.37); 6.1166 (0.43); 6.1073 (0.37); 5.5824 (0.84); 5.5744 (0.66); 5.5696 (0.76); 4.9338 (0.37); 4.9239 (0.32); 4.2175 (0.37); 4.1973 (0.42); 4.0375 (0.39); 4.0275 (0.64); 4.0176 (0.38); 3.8042 (0.34); 3.7954 (0.33); 3.5638 (0.39); 3.5318 (1.53); 3.5278 (1.53); 3.4296 (2.98); 3.4196 (3.25); 3.408 (2.33); 3.3962 (1.41); 3.3669 (1.94); 3.3556 (3.37); 3.3263 (1521.55); 3.2793 (2.17); 3.2689 (1.59); 3.0844 (0.99); 3.0567 (1.21);2.994 (11.61); 2.9893 (3.86); 2.9778 (6.69); 2.9662 (3.74); 2.9464 (1.64);2.9344 (2.05);2.9225 (1.74); 2.9166 (1.49); 2.9053 (1.88); 2.8939 (1.1); 2.7631 (0.45);2.7448 (0.79);2.7173 (0.63); 2.653 (5.71); 2.6191 (1.65); 2.6161 (3.65); 2.613 (5.07);2.61 (3.6); 2.607 (1.53); 2.5702 (0.39); 2.5407 (1859.34); 2.5224 (10.56); 2.5193 (13.3); 2.5161 (13.34); 2.5074 (276.9); 2.5044 (589.98); 2.5013 (809.48); 2.4982 (584.41); 2.4952 (269.68); 2.4862 (9.63); 2.4736 (2.03); 2.4364 (2.02); 2.4307 (1.21);2.4243 (6.23);2.3916 (1.99); 2.3885 (3.93); 2.3855 (5.36); 2.3824 (3.92); 2.3794 (1.93); 2.3288 (0.8); 2.2921 (2.69); 2.2896 (2.66); 2.2853 (3.73); 2.2813 (1.91);2.2411 (0.63);2.2013 (5.61); 2.1787 (0.59); 2.1379 (5.98); 2.1297 (1.58);2.1266 (1.16);2.1124 (2.08); 2.1077 (2.88); 2.0771 (2.41); 2.0734 (6.05); 2.0541 (1.21);2.0419 (0.92); 1.9378 (0.35); 1.9084 (6.54); 1.6954 (16); 1.5254 (0.34); 1.4886 (0.32);1.2978 (0.33); 1.2762 (0.52); 1.2583 (0.48); 1.2352 (0.88); 1.1862 (0.34);1.1742 (0.63); 0.0052 (1.63); −0.0002 (52.42); −0.0058 (1.46) |

TABLE 15

Compounds of the formula I-15

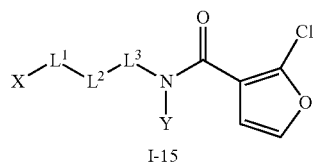

I-15

| Ex. No. | X | $L^1$ | $L^2$ | $L^3$ | Y | Physical data: $^1$H-NMR, δ [ppm] or CAS or patent No. |
|---|---|---|---|---|---|---|
| 15-1 | 3-methyl-2-thienyl | CH2 | CH2 | — | H | |
| 15-2 | 2,4-dichlorophenyl | CH2 | CH2 | CH2 | H | |
| 15-3 | 4-chlorophenyl | CH2 | CH2 | — | H | |
| 15-4 | 2,4-dichlorophenyl | CH2 | CH2 | — | H | |
| 15-5 | 4-chlorophenyl | CH(OCH3) | CH(CH3) | — | H | |
| 15-6 | 2,4-dichlorophenyl | CH(OCH3) | CH(CH3) | — | H | |
| 15-7 | 4-chlorophenyl | CH(CH3) | CH2 | — | H | |
| 15-8 | 2,4-dichlorophenyl | CH(CH3) | CH2 | — | H | |
| 15-9 | 4-chlorophenyl | CH2 | CH(CH3) | — | H | |
| 15-10 | 2,4-dichlorophenyl | CH2 | CH(CH3) | — | H | |
| 15-11 | 4-chlorophenyl | C(CH3)2 | CH2 | — | H | |
| 15-12 | 2,4-dichlorophenyl | C(CH3)2 | CH2 | — | H | |
| 15-13 | 2-chlorophenyl | CH2 | CH2 | — | H | |
| 15-14 | 3,4-dichlorophenyl | CH2 | CH2 | — | H | |
| 15-15 | 3,5-dichlorophenyl | CH2 | CH2 | — | H | |
| 15-16 | 3-chlorophenyl | CH2 | CH2 | — | H | |
| 15-17 | 2-fluorophenyl | CH2 | CH2 | — | H | |
| 15-18 | 2,6-difluorophenyl | CH2 | CH2 | — | H | |
| 15-19 | 2,6-dichlorophenyl | CH2 | CH2 | — | H | |
| 15-20 | 3-(trifluoromethyl)phenyl | CH2 | CH2 | — | H | |
| 15-21 | 4-(trifluoromethyl)phenyl | CH2 | CH2 | — | H | |
| 15-22 | 2-methylphenyl | CH2 | CH2 | — | H | |
| 15-23 | 2,4,6-trimethylphenyl | CH2 | CH2 | — | H | |
| 15-24 | 3,4-bismethoxyphenyl | CH2 | CH2 | — | H | |
| 15-25 | phenyl | CH2 | CH2 | — | H | |
| 15-26 | 4-chlorophenyl | C(CH2—CH2) | CH2 | — | H | |
| 15-27 | 2,4-dichlorophenyl | C(CH2—CH2) | CH2 | — | H | |
| 15-28 | 4-chlorophenyl | CH2 | C(CH2—CH2) | — | H | |
| 15-29 | 2,4-dichlorophenyl | CH2 | C(CH2—CH2) | — | H | |
| 15-30 | 4-chlorophenyl | O | CH2 | CH2 | H | |
| 15-31 | 2,4-dichlorophenyl | O | CH2 | CH2 | H | |
| 15-32 | 4-chlorophenyl | CH2 | CH2 | CH2 | H | |
| 15-33 | 4-chlorophenyl | NCH3 | CH2 | CH2 | H | |
| 15-34 | 2,4-dichlorophenyl | NCH3 | CH2 | CH2 | H | |
| 15-35 | 4-chlorophenyl | CH(OCH3) | CH2 | — | H | |
| 15-36 | 2,4-dichlorophenyl | CH(OCH3) | CH2 | — | H | |
| 15-37 | 2-thienyl | CH2 | CH2 | — | H | |
| 15-38 | 3-thienyl | CH2 | CH2 | — | H | |
| 15-39 | 2-furyl | CH2 | CH2 | — | H | |
| 15-40 | 3-furyl | CH2 | CH2 | — | H | |
| 15-41 | phenyl | CH2 | CH2 | CH(CH3) | H | |
| 15-42 | phenyl | CH2 | CH2 | CH2 | H | |
| 15-43 | 2-Cl-phenyl | CH2 | CH2 | CH(CH3) | H | |
| 15-44 | 4-t-butylphenyl | CH2 | CH2 | CH2 | H | |
| 15-45 | 4-methylphenyl | CH2 | CH2 | CH2 | H | |
| 15-46 | phenyl | CH2 | CH2 | CH(CH2CH3) | H | |
| 15-47 | 2-methoxyphenyl | CH2 | CH2 | CH2 | H | |
| 15-48 | 2-methylphenyl | CH2 | CH2 | CH2 | H | |
| 15-49 | 3-methylphenyl | CH2 | CH2 | CH2 | H | |
| 15-50 | 3-chlorophenyl | CH2 | CH2 | CH2 | H | |
| 15-51 | 2,6-difluorophenyl | CH2 | CH2 | CH2 | H | |
| 15-52 | 4-chlorophenyl | CH2 | CH2 | CH2 | H | |
| 15-53 | 2,6-dichlorophenyl | CH2 | CH2 | CH(CH3) | H | |
| 15-54 | 3,5-dichlorophenyl | CH2 | CH2 | CH(CH3) | H | |
| 15-55 | 2,6-dimethylphenyl | CH2 | CH2 | CH2 | H | |
| 15-56 | 2,5-dichlorophenyl | CH2 | CH2 | CH2 | H | |
| 15-57 | 4-isopropoxyphenyl | CH2 | CH2 | CH2 | H | |
| 15-58 | 3-trifluoromethylphenyl | CH2 | CH2 | CH(CH3) | H | |
| 15-59 | 4-methylphenyl | CH2 | CH2 | CH(CH3) | H | |
| 15-60 | 2-methylphenyl | CH2 | CH2 | CH(CH3) | H | |
| 15-61 | 3,4-dichlorophenyl | CH2 | CH2 | CH(CH3) | H | |
| 15-62 | 3,5-dichlorophenyl | CH2 | CH2 | CH2 | H | |
| 15-63 | 2,6-dimethylphenyl | CH2 | CH2 | CH(CH3) | H | |
| 15-64 | 4-trifluoromethylphenyl | CH2 | CH2 | CH(CH3) | H | |
| 15-65 | 2,5-dichlorophenyl | CH2 | CH2 | CH(CH3) | H | |
| 15-66 | 4-phenoxyphenyl | CH2 | CH2 | CH2 | H | |

TABLE 15-continued

Compounds of the formula I-15

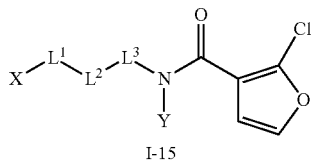

I-15

| Ex. No. | X | L¹ | L² | L³ | Y | Physical data: ¹H-NMR, δ [ppm] or CAS or patent No. |
|---|---|---|---|---|---|---|
| 15-67 | 3-chlorophenyl | CH2 | CH2 | CH(CH3) | H | |
| 15-68 | 4-phenoxyphenyl | CH2 | CH2 | CH(CH3) | H | |
| 15-69 | 2,4-dichlorophenyl | CH2 | CH2 | CH(CH3) | H | |
| 15-70 | 2-difluoromethoxyphenyl | CH2 | CH2 | CH(CH3) | H | |
| 15-71 | 4-methoxyphenyl | CH2 | CH2 | CH2 | H | |
| 15-72 | 4-chlorophenyl | CH2 | CH2 | CH(CH3) | H | |
| 15-73 | 4-chlorophenyl | CH2 | CH2 | CH(i-propyl) | H | |
| 15-74 | 4-fluorophenyl | CH2 | CH2 | CH2 | H | |
| 15-75 | 4-chlorophenyl | CH2 | CH2 | CH(n-propyl) | H | |
| 15-76 | 4-chlorophenyl | CH2 | CH2 | CH(t-butyl) | H | |
| 15-77 | 2-chlorophenyl | CH2 | CH2 | CH2 | H | |
| 15-78 | 4-chlorophenyl | CH2 | CH(CH3) | — | cyclopropyl | |

TABLE 16

Compounds of the formula I-16

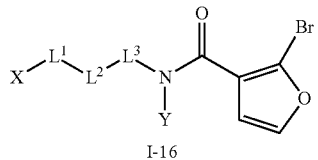

I-16

| Ex. No. | X | L¹ | L² | L³ | Y | Physical data: ¹H-NMR, δ [ppm] or CAS or patent No. |
|---|---|---|---|---|---|---|
| 16-1 | 3-methyl-2-thienyl | CH2 | CH2 | — | H | |
| 16-2 | 2,4-dichlorophenyl | CH2 | CH2 | CH2 | H | compound No. 16-2, solvent: spectrometer: 399.95 MHz<br>8.2265 (2.17); 8.2125 (4.09); 8.1989 (2.11); 7.8375 (15.8); 7.8321 (15.85); 7.5699 (11.89); 7.5647 (12.21); 7.4271 (6.55); 7.4064 (15.53); 7.3811 (10.54); 7.3758 (9.69); 7.3604 (4.25); 7.3552 (4.28); 6.9445 (16); 6.939 (15.83); 3.4406 (0.35); 3.4211 (0.46); 3.3392 (914.76); 3.2877 (0.65); 3.2526 (3.7); 3.2354 (8.13); 3.2202 (8.13); 3.203 (3.76); 2.7346 (6.71); 2.7157 (8.75); 2.7129 (8.89); 2.6961 (7.22); 2.681 (0.86); 2.6764 (1.5); 2.6718 (1.99); 2.6673 (1.49); 2.6628 (0.72); 2.5811 (0.48); 2.5422 (547.01); 2.5293 (3.15); 2.5251 (6.34); 2.5204 (9.64); 2.5118 (108.4); 2.5073 (217.84); 2.5028 (285.86); 2.4982 (204.88); 2.4937 (97.11); 2.3681 (2.18); 2.3386 (0.65); 2.3341 (1.35); 2.3295 (1.84); 2.3249 (1.33); 2.3204 (0.61); 2.0747 (1.58); 1.8031 (1.88); 1.7845 (5.01); 1.766 (6.67); 1.7475 (4.69); 1.7293 (1.67); 1.2346 (0.46); 0.008 (0.78); −0.0001 (23.32); −0.0085 (0.68) |
| 16-3 | 4-chloro-phenyl | CH2 | CH2 | — | H | compound No. 16-3, solvent: spectrometer: 399.95 MHz<br>8.2445 (1.5); 8.2305 (2.78); 8.2166 (1.44); 7.8308 (11.39); 7.8254 (11.53); 7.3664 (1.16); 7.36 (9.59); 7.3552 (3.61); 7.3441 (4.26); 7.339 (16); 7.3329 (2.13); 7.2736 (2.05); 7.2675 (13.43); 7.2627 (4.11); 7.2512 (3.09); 7.2464 (8.65); 6.9182 (11.22); 6.9128 (11.15); 3.4262 (2.78); 3.409 (5.42); 3.3941 (5.2); 3.3909 (5.28); 3.3755 (3.76); 3.3336 (547.71); 2.8154 (4.98); 2.7968 (8); 2.7789 (4.42); 2.7111 (1.67); 2.6802 (0.49); 2.6757 (0.95); 2.6712 (1.32); 2.6666 (0.98); 2.662 (0.49); 2.5802 (0.55); 2.5417 (454.3); 2.5289 (2.7); 2.5282 (2.7); 2.5245 (4.72); 2.5196 (7.15); 2.5111 (73.39); 2.5067 (147.53); 2.5021 (195.1); 2.4975 (141.15); 2.493 (67.83); 2.3673 (1.67); 2.338 (0.45); 2.3334 (0.91); 2.3289 (1.27); 2.3243 (0.91); 2.3201 (0.44); 2.0745 (1.08); 0.008 (0.66); −0.0002 (19.22); −0.0085 (0.58) |

TABLE 16-continued

Compounds of the formula I-16

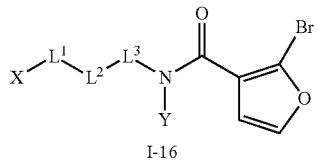

I-16

| Ex. No. | X | L¹ | L² | L³ | Y | Physical data: ¹H-NMR, δ [ppm] or CAS or patent No. |
|---|---|---|---|---|---|---|
| 16-4 | 2,4-dichloro-phenyl | CH2 | CH2 | — | H | compound No. 16-4, solvent: spectrometer: 399.95 MHz<br>8.2802 (2); 8.2663 (3.79); 8.2522 (1.9); 7.8388 (0.4); 7.8288 (14.34); 7.8234 (14.38); 7.5893 (9.07); 7.5847 (9.59); 7.3901 (2.34); 7.3854 (1.75); 7.3695 (12.09); 7.3648 (13.18); 7.3598 (16); 7.3392 (2.51); 6.9057 (14.27); 6.9003 (14.09); 3.4512 (3.36); 3.4343 (7.51); 3.419 (7.4); 3.4013 (4.01); 3.3374 (813.42); 3.2929 (0.6); 3.2715 (0.33); 2.9366 (6.6); 2.9186 (11.55); 2.9011 (5.75); 2.7119 (1.92); 2.6809 (0.59); 2.6763 (1.24); 2.6717 (1.69); 2.6671 (1.25); 2.6626 (0.62); 2.5893 (0.36); 2.582 (0.54); 2.542 (502.66); 2.5299 (2.9); 2.5249 (5.94); 2.5202 (8.82); 2.5117 (97.53); 2.5072 (196.78); 2.5026 (259.04); 2.4981 (187.41); 2.4936 (89.92); 2.4638 (0.46); 2.3682 (1.95); 2.3386 (0.59); 2.3339 (1.22); 2.3293 (1.68); 2.3248 (1.23); 2.3204 (0.6); 2.0746 (1.3); 1.2349 (0.36); 0.008 (0.76); −0.0002 (21.93); −0.0084 (0.65) |
| 16-5 | 4-chloro-phenyl | CH(OCH3) | CH(CH3) | — | H | |
| 16-6 | 2,4-dichloro-phenyl | CH(OCH3) | CH(CH3) | — | H | |
| 16-7 | 4-chloro-phenyl | CH(CH3) | CH2 | — | H | compound No. 16-7, solvent: spectrometer: 399.95 MHz-8.1781 (1.32); 8.1638 (2.52); 8.1494 (1.27); 7.8147 (9.09); 7.8093 (9.1); 7.3697 (0.89); 7.3635 (7.76); 7.3588 (2.77); 7.3473 (3.5); 7.3423 (13.71); 7.3365 (1.78); 7.2919 (1.86); 7.2859 (12.6); 7.2811 (3.49); 7.2695 (2.57); 7.2647 (7.32); 6.8862 (9.03); 6.8808 (8.86); 3.3949 (0.38); 3.3769 (1.15); 3.3582 (2.62); 3.3334 (397.26); 3.3101 (4.09); 3.3041 (3.14); 3.2893 (2.84); 3.2748 (0.77); 3.2707 (0.79); 3.2565 (0.68); 3.0434 (1.3); 3.0255 (2.56); 3.0077 (2.48); 2.9899 (1.14); 2.7118 (1.38); 2.6801 (0.42); 2.6758 (0.84); 2.6713 (1.11); 2.6669 (0.83); 2.6624 (0.41); 2.5864 (0.33); 2.5849 (0.34); 2.5791 (0.49); 2.5769 (0.53); 2.5761 (0.54); 2.5754 (0.55); 2.5746 (0.57); 2.5725 (0.63); 2.5681 (0.89); 2.5674 (0.89); 2.5614 (1.41); 2.5607 (1.46); 2.5415 (319.87); 2.5245 (3.88); 2.5197 (5.75); 2.5113 (63.24); 2.5068 (126.65); 2.5023 (165.95); 2.4978 (120.23); 2.4934 (58.27); 2.368 (1.33); 2.3382 (0.37); 2.3336 (0.76); 2.329 (1.04); 2.3246 (0.77); 2.0744 (0.88); 1.2344 (0.37); 1.2114 (16); 1.1939 (15.75); 0.0079 (0.54); −0.0002 (15.37); −0.0086 (0.46) |
| 16-8 | 2,4-dichloro-phenyl | CH(CH3) | CH2 | — | H | compound No. 16-8, solvent: spectrometer: 399.95 MHz<br>8.2176 (1.32); 8.2031 (2.55); 8.189 (1.27); 7.8121 (9.18); 7.8067 (9.22); 7.5605 (7.36); 7.5553 (7.72); 7.4652 (3.77); 7.4441 (9.57); 7.4213 (5.89); 7.416 (5.32); 7.4002 (2.23); 7.3949 (2.18); 6.8816 (9.33); 6.8762 (9.17); 3.5232 (1.09); 3.5057 (2.49); 3.4883 (2.86); 3.4711 (1.71); 3.4583 (1.53); 3.4437 (1.35); 3.4262 (2.8); 3.4109 (2.75); 3.3936 (1.86); 3.3852 (2.25); 3.3707 (3.08); 3.3681 (2.92); 3.3529 (5.4); 3.3336 (391.24); 3.2951 (0.37); 2.7118 (1.24); 2.6804 (0.39); 2.6762 (0.8); 2.6715 (1.08); 2.667 (0.82); 2.6625 (0.41); 2.5768 (0.45); 2.5419 (314.54); 2.525 (3.6); 2.5201 (5.44); 2.5115 (61.31); 2.5071 (123.34); 2.5025 (162); 2.4979 (116.5); 2.4934 (55.45); 2.368 (1.23); 2.3383 (0.35); 2.3337 (0.74); 2.3292 (1.03); 2.3246 (0.73); 2.3202 (0.33); 2.0749 (0.79); 1.2031 (16); 1.1861 (15.82); 0.008 (0.57); −0.0002 (16.28); −0.0085 (0.48) |
| 16-9 | 4-chloro-phenyl | CH2 | CH(CH3) | — | H | compound No. 16-9, solvent: spectrometer: 399.95 MHz<br>7.9791 (2.49); 7.9585 (2.5); 7.8207 (9.49); 7.8153 (9.53); 7.3426 (0.96); 7.3364 (7.96); 7.3317 (2.87); 7.3204 (3.61); 7.3154 (13.82); 7.3095 (1.79); 7.261 (1.88); 7.2553 (12.01); 7.2505 (3.42); 7.2388 (2.61); 7.2342 (7.06); 6.9428 (9.42); 6.9374 (9.25); 4.1578 (0.64); 4.1388 (1.36); 4.1218 (1.95); 4.1051 (1.41); 4.0857 (0.67); 3.3751 (0.51); 3.3321 (442.52); 3.2936 (0.38); 2.835 (1.56); 2.8156 (1.54); 2.8015 |

TABLE 16-continued

Compounds of the formula I-16

| Ex. No. | X | L¹ | L² | L³ | Y | Physical data: ¹H-NMR, δ [ppm] or CAS or patent No. |
|---|---|---|---|---|---|---|
| | | | | | | (2.95); 2.7821 (2.9); 2.74 (2.97); 2.7242 (3.02); 2.711 (0.98); 2.7066 (1.64); 2.6907 (1.49); 2.6804 (0.46); 2.6758 (0.86); 2.6713 (1.14); 2.6666 (0.84); 2.6621 (0.41); 2.5415 (187.72); 2.5245 (3.94); 2.5198 (6.17); 2.5112 (65.95); 2.5068 (131.89); 2.5022 (173.03); 2.4976 (124.2); 2.4931 (59.01); 2.3678 (0.66); 2.338 (0.39); 2.3335 (0.81); 2.3289 (1.1); 2.3243 (0.81); 2.3201 (0.37); 2.0746 (0.82); 1.1277 (16); 1.1111 (15.8); 0.008 (0.63); −0.0002 (17.51); −0.0085 (0.5) |
| 16-10 | 2,4-dichloro-phenyl | CH2 | CH(CH3) | — | H | compound No. 16-10, solvent: spectrometer: 399.95 MHz 8.0222 (2.87); 8.0009 (2.88); 7.8225 (9.36); 7.8171 (9.38); 7.5632 (6.4); 7.5591 (6.39); 7.3754 (1.37); 7.3677 (0.44); 7.3548 (12.36); 7.3476 (8.02); 7.3313 (0.83); 7.3268 (1.08); 6.9322 (9.4); 6.9268 (9.24); 4.2982 (0.63); 4.2783 (1.42); 4.2617 (1.95); 4.2452 (1.34); 4.225 (0.65); 3.329 (272.05); 2.9356 (0.67); 2.9202 (0.95); 2.9015 (4.68); 2.8923 (4.99); 2.8863 (4.69); 2.8723 (4.08); 2.8584 (0.75); 2.8383 (0.84); 2.6757 (0.72); 2.6711 (0.98); 2.6666 (0.72); 2.6623 (0.36); 2.5413 (60.01); 2.5243 (3.82); 2.511 (58.91); 2.5066 (116.35); 2.5021 (151.66); 2.4976 (109.48); 2.4931 (52.84); 2.3333 (0.71); 2.3288 (0.98); 2.3244 (0.72); 2.0747 (0.65); 1.1716 (16); 1.1549 (15.77); 0.0077 (0.49); −0.0002 (13.39); −0.0085 (0.43) |
| 16-11 | 4-chloro-phenyl | C(CH3)2 | CH2 | — | H | compound No. 16-11, solvent: spectrometer: 399.95 MHz 7.9042 (0.4); 7.8888 (0.76); 7.8729 (0.39); 7.8129 (2.22); 7.8077 (2.27); 7.4348 (2.04); 7.43 (0.84); 7.4183 (1.03); 7.4132 (3.92); 7.4071 (0.65); 7.3711 (0.57); 7.365 (3.9); 7.3601 (1.14); 7.3479 (0.76); 7.3433 (2.1); 6.8863 (2.28); 6.881 (2.3); 3.387 (2.85); 3.3711 (2.97); 3.3318 (118.82); 2.711 (0.37); 2.6709 (0.34); 2.5416 (81.35); 2.5063 (40.7); 2.5019 (53.44); 2.4975 (40.15); 2.3674 (0.36); 2.3286 (0.34); 1.2761 (16); −0.0002 (4.07) |
| 16-12 | 2,4-dichloro-phenyl | C(CH3)2 | CH2 | — | H | compound No. 16-12, solvent: spectrometer: 399.95 MHz 7.9051 (0.38); 7.8905 (0.75); 7.8747 (0.39); 7.7997 (3.06); 7.7943 (3.06); 7.5331 (2.55); 7.5273 (2.7); 7.4702 (1.5); 7.4486 (2.27); 7.3703 (1.57); 7.3645 (1.48); 7.3487 (1.08); 7.3429 (1.01); 6.8516 (3.1); 6.8462 (3.12); 3.7316 (2.67); 3.7156 (2.64); 3.3338 (84.14); 2.7118 (0.34); 2.6715 (0.36); 2.5417 (92.01); 2.5248 (1.39); 2.5199 (2.2); 2.5115 (21.3); 2.507 (42.52); 2.5024 (55.96); 2.4978 (40.68); 2.4933 (20.13); 2.3681 (0.35); 2.3291 (0.34); 1.4263 (16); −0.0002 (5.88) |
| 16-13 | 2-chloro-phenyl | CH2 | CH2 | — | H | compound No. 16-13, solvent: spectrometer: 399.95 MHz 8.3065 (2.1); 8.2927 (3.89); 8.2788 (1.98); 7.8308 (15.98); 7.8254 (15.89); 7.4416 (5.44); 7.4377 (4.19); 7.4234 (7.48); 7.4186 (6.89); 7.3522 (3.47); 7.3467 (4.52); 7.3337 (5.46); 7.3288 (7.43); 7.3136 (0.47); 7.3079 (2.51); 7.3036 (3.37); 7.2896 (7.74); 7.2854 (7.06); 7.2752 (7.12); 7.2725 (6.97); 7.2689 (7.49); 7.2566 (5.91); 7.2512 (5.15); 7.2382 (1.9); 7.2331 (1.5); 6.9286 (16); 6.9231 (15.76); 3.4579 (3.9); 3.4414 (7.26); 3.4258 (6.72); 3.422 (7.37); 3.407 (4.47); 3.3326 (766); 3.2906 (0.46); 3.2753 (0.32); 2.9553 (7.61); 2.9362 (10.86); 2.9187 (6.6); 2.7113 (2.34); 2.6802 (0.7); 2.6758 (1.46); 2.6712 (1.97); 2.6666 (1.47); 2.6624 (0.73); 2.5788 (0.68); 2.5416 (618.96); 2.5306 (3.62); 2.5298 (3.38); 2.529 (3.28); 2.5283 (3.3); 2.5274 (3.41); 2.5246 (6.77); 2.5196 (9.85); 2.5112 (111.13); 2.5067 (225.16); 2.5021 (296.68); 2.4975 (214); 2.493 (102.09); 2.4682 (0.81); 2.4512 (0.41); 2.3676 (2.34); 2.3379 (0.65); 2.3334 (1.37); 2.3289 (1.89); 2.3243 (1.39); 2.3198 (0.64); 2.0745 (1.63); 1.2348 (0.47); 0.0079 (0.96); −0.0002 (29.17); −0. 0085 (0.92) |

TABLE 16-continued

Compounds of the formula I-16

I-16

| Ex. No. | X | L¹ | L² | L³ | Y | Physical data: $^1$H-NMR, δ [ppm] or CAS or patent No. |
|---|---|---|---|---|---|---|
| 16-14 | 3,4-dichloro-phenyl | CH2 | CH2 | — | H | compound No. 16-14, solvent: spectrometer: 399.95 MHz<br>8.235 (2.54); 8.2213 (4.93); 8.2076 (2.59); 7.8323 (14.79); 7.8269 (15.35); 7.5561 (13.07); 7.5456 (0.58); 7.5355 (15.03); 7.5187 (12.31); 7.5138 (13.06); 7.2408 (6.92); 7.2359 (7.06); 7.2202 (6.14); 7.2153 (6.21); 6.9024 (15.31); 6.897 (15.57); 3.4476 (4.33); 3.4303 (10.42); 3.4153 (10.54); 3.3981 (5.06); 3.3341 (888.39); 3.2655 (0.47); 3.237 (0.34); 2.8313 (8.34); 2.8137 (16); 2.7962 (7.48); 2.7114 (2.85); 2.6757 (1.66); 2.6713 (2.31); 2.6669 (1.81); 2.6075 (0.33); 2.6045 (0.37); 2.6031 (0.36); 2.6016 (0.38); 2.6009 (0.39); 2.6001 (0.37); 2.5994 (0.39); 2.5987 (0.39); 2.5979 (0.41); 2.5972 (0.41); 2.5965 (0.43); 2.5957 (0.42); 2.595 (0.44); 2.5928 (0.55); 2.5913 (0.58); 2.5906 (0.59); 2.5899 (0.59); 2.5891 (0.61); 2.5884 (0.66); 2.5877 (0.65); 2.5869 (0.65); 2.5862 (0.66); 2.5855 (0.65); 2.5847 (0.66); 2.584 (0.67); 2.5832 (0.69); 2.5825 (0.72); 2.5817 (0.76); 2.581 (0.84); 2.5803 (0.85); 2.5796 (0.85); 2.5788 (0.86); 2.5766 (1.05); 2.5759 (1.08); 2.5752 (1.11); 2.5745 (1.11); 2.5737 (1.15); 2.5729 (1.21); 2.5722 (1.26); 2.5715 (1.31); 2.5707 (1.37); 2.57 (1.43); 2.5692 (1.52); 2.5678 (1.73); 2.5663 (1.93); 2.5656 (2.03); 2.5648 (2.1); 2.5641 (2.24); 2.5626 (2.54); 2.559 (3.51); 2.5582 (3.64); 2.542 (624.35); 2.5245 (7.46); 2.5109 (127.53); 2.5067 (255.14); 2.5023 (338.71); 2.4979 (250.82); 2.4935 (125.19); 2.4666 (0.77); 2.4614 (0.6); 2.4446 (0.36); 2.4387 (0.33); 2.3677 (2.8); 2.3334 (1.56); 2.329 (2.13); 2.3246 (1.63); 2.075 (1.54); 1.2348 (0.55); 0.0083 (0.96); 0 (26.75); −0.0082 (0.84) |
| 16-15 | 3,5-dichloro-phenyl | CH2 | CH2 | — | H | compound No. 16-15, solvent: spectrometer: 399.95 MHz<br>8.2413 (1.51); 8.2275 (2.87); 8.2135 (1.48); 7.8354 (9.23); 7.83 (9.39); 7.4421 (3.78); 7.4374 (7.5); 7.4327 (4.38); 7.314 (16); 7.3093 (15.27); 6.8979 (9.41); 6.8926 (9.42); 3.4579 (2.49); 3.4406 (6.15); 3.4258 (6.25); 3.4087 (2.76); 3.3343 (406.43); 2.8433 (4.65); 2.826 (9.13); 2.8085 (4.16); 2.7116 (1.25); 2.6804 (0.38); 2.6759 (0.71); 2.6714 (0.97); 2.6669 (0.73); 2.5419 (278.3); 2.5245 (3.3); 2.5112 (55.54); 2.5069 (110.59); 2.5024 (145.42); 2.4979 (106.86); 2.4936 (53.13); 2.3678 (1.26); 2.3335 (0.68); 2.329 (0.95); 2.3246 (0.69); 2.04 6(0.65); 0.0075 (0.42); −0.0002 (11.29); −0.0083 (0.474 ) |
| 16-16 | 3-chlorophenyl | CH2 | CH2 | — | H | compound No. 16-16, solvent: spectrometer: 399.95 MHz<br>8.2557 (2.19); 8.2423 (4); 8.2286 (2.14); 7.833 (14.67); 7.8277 (14.59); 7.3599 (0.54); 7.3555 (0.34); 7.3457 (3.92); 7.3391 (1.01); 7.3262 (9.92); 7.3122 (10.65); 7.3075 (16); 7.2806 (5.14); 7.2774 (7.06); 7.2608 (3.08); 7.256 (3.11); 7.2528 (2.17); 7.2471 (0.47); 7.2082 (7.06); 7.1894 (4.71); 6.9162 (15.14); 6.9108 (14.74); 3.4452 (4.25); 3.428 (8.3); 3.4131 (8.13); 3.4105 (7.99); 3.3947 (5.3); 3.3375 (787.6); 2.8358 (7.39); 2.8174 (12.52); 2.7996 (6.82); 2.7795 (0.34); 2.7118 (2.43); 2.6761 (1.3); 2.6716 (1.73); 2.6671 (1.26); 2.6626 (0.66); 2.6003 (0.34); 2.5848 (0.53); 2.542 (551.34); 2.5249 (5.65); 2.5114 (95.76); 2.507 (191.11); 2.5025 (250.48); 2.4979 (180.46); 2.4935 (86.74); 2.3679 (2.36); 2.3383 (0.55); 2.3338 (1.15); 2.3292 (1.58); 2.3247 (1.14); 2.3204 (0.55); 2.0745 (1.21); 1.2347 (0.4); 0.008 (0.71); −0.0002 (20.67); −0.0084 (0.64) |
| 16-17 | 2-fluorophenyl | CH2 | CH2 | — | H | compound No. 16-17, solvent: spectrometer: 399.95 MHz<br>8.306 (2.32); 8.2924 (4.24); 8.2782 (2.22); 7.8298 (15.72); 7.8244 (15.8); 7.3263 (2.46); 7.3223 (3.02); 7.3077 (4.79); 7.3032 (6.55); 7.2952 (1.92); 7.2838 (5.05); 7.2821 (5.06); 7.2665 (3.48); 7.261 (4.46); 7.2564 (2.34); 7.2472 (2.5); 7.2428 (1.94); 7.1762 (4.74); 7.1539 (10.18); 7.1376 (8.3); 7.1347 (8.56); 7.1192 (3.39); 7.1163 (3); 6.9189 (16); 6.9134 (15.89); 3.4362 (4.39); 3.4196 (8.34); 3.4036 (7.86); |

TABLE 16-continued

Compounds of the formula I-16

[Structure of compound I-16: X–L¹–L²–L³–N(Y)–C(=O)– attached to a furan ring bearing Br]

I-16

| Ex. No. | X | L¹ | L² | L³ | Y | Physical data: ¹H-NMR, δ [ppm] or CAS or patent No. |
|---|---|---|---|---|---|---|
| | | | | | | 3.4001 (8.67); 3.3849 (5.64); 3.3373 (773.29); 2.8615 (6.75); 2.8429 (10.92); 2.8247 (5.95); 2.7116 (2.39); 2.6762 (1.26); 2.6715 (1.65); 2.667 (1.24); 2.5419 (574.76); 2.5248 (5.27); 2.5199 (7.82); 2.5113 (90.74); 2.507 (184.1); 2.5025 (243.84); 2.4979 (179.18); 2.4935 (88.33); 2.3678 (2.34); 2.3337 (1.13); 2.3292 (1.56); 2.3246 (1.15); 2.3204 (0.57); 2.0744 (1.21); 1.2343 (0.39); 0.0079 (0.69); −0.0002 (20.48); −0.0085 (0.7) |
| 16-18 | 2,6-difluoro-phenyl | CH2 | CH2 | — | H | compound No. 16-18, solvent: spectrometer: 399.95 MHz 8.364 (2.34); 8.3494 (4.36); 8.3348 (2.24); 7.8359 (0.47); 7.8264 (15.86); 7.821 (15.92); 7.3625 (1.36); 7.3456 (2.95); 7.3416 (2.73); 7.3247 (5.7); 7.3076 (2.85); 7.3039 (3.68); 7.287 (1.71); 7.1024 (0.81); 7.0981 (1.14); 7.0859 (8.01); 7.0661 (12.58); 7.055 (1.55); 7.0461 (6.67); 7.0334 (0.83); 6.8909 (16); 6.8855 (15.9); 3.4323 (0.4); 3.404 (4.25); 3.3875 (9.46); 3.3692 (10.18); 3.3522 (11.63); 3.3357 (762.69); 2.8773 (5.91); 2.8593 (10.43); 2.8417 (5.22); 2.7118 (2.51); 2.6806 (0.6); 2.6761 (1.22); 2.6716 (1.67); 2.6671 (1.22); 2.6624 (0.64); 2.542 (564.95); 2.5248 (5.69); 2.5199 (8.5); 2.5115 (92.33); 2.507 (186.17); 2.5025 (245.68); 2.498 (178.77); 2.4935 (86.96); 2.368 (2.44); 2.3384 (0.55); 2.3337 (1.13); 2.3292 (1.57); 2.3248 (1.15); 2.3201 (0.54); 2.0747 (1.29); 1.2344 (0.37); 0.0079 (0.75); −0.0002 (21.6); −0.0085 (0.69) |
| 16-19 | 2,6-dichloro-phenyl | CH2 | CH2 | — | H | compound No. 16-19, solvent: spectrometer: 399.95 MHz 8.3769 (1.33); 8.3623 (2.69); 8.3481 (1.38); 7.8267 (8.74); 7.8213 (9.06); 7.4663 (11.72); 7.4462 (16); 7.304 (5.2); 7.2832 (5.24); 7.2638 (3.44); 6.9238 (8.87); 6.9183 (9.01); 3.4417 (2.03); 3.4253 (4.84); 3.4097 (4.35); 3.4059 (4.77); 3.3909 (2.7); 3.3322 (609.35); 3.1465 (4.76); 3.1274 (6.89); 3.1104 (3.7); 2.7113 (1.55); 2.6756 (1.19); 2.6712 (1.62); 2.6666 (1.21); 2.5862 (0.39); 2.5416 (365.51); 2.5243 (4.97); 2.511 (91.04); 2.5066 (183.06); 2.5021 (241.18); 2.4976 (174.7); 2.4931 (84.35); 2.3675 (1.5); 2.3334 (1.11); 2.3288 (1.53); 2.3243 (1.13); 2.0747 (1.17); 1.2348 (0.34); 0.0078 (0.79); −0.0002 (21.03); −0.0086 (0.58) |
| 16-20 | 3-(trifluoro-methyl)phenyl | CH2 | CH2 | — | H | compound No. 16-20, solvent: spectrometer: 399.95 MHz 8.2606 (1.69); 8.2466 (3.12); 8.2329 (1.65); 7.8415 (0.48); 7.8313 (13.29); 7.8259 (13.57); 7.6496 (0.39); 7.5826 (7.88); 7.5796 (7.67); 7.5685 (3.15); 7.5613 (5.86); 7.5476 (16); 7.5444 (9.4); 7.5291 (2.45); 7.5117 (0.79); 7.4741 (0.4); 7.4541 (0.33); 6.9146 (0.57); 6.909 (0.75); 6.9019 (12.98); 6.8964 (12.97); 3.4762 (3.1); 3.459 (6.74); 3.4442 (6.69); 3.4262 (3.69); 3.3919 (0.68); 3.3328 (976.7); 3.2681 (0.42); 2.932 (5.72); 2.914 (10.22); 2.8963 (5.08); 2.7113 (2.51); 2.6804 (0.87); 2.6757 (1.77); 2.6712 (2.47); 2.6666 (1.83); 2.662 (0.9); 2.6005 (0.43); 2.5416 (688.87); 2.5245 (8.94); 2.5198 (13.05); 2.5112 (137.22); 2.5067 (278.51); 2.5021 (368.94); 2.4975 (266.22); 2.493 (127.69); 2.3675 (2.51); 2.338 (0.83); 2.3334 (1.72); 2.3288 (2.38); 2.3243 (1.74); 2.3198 (0.81); 2.0745 (1.98); 1.2348 (0.53); 0.008 (1.26); −0.0002 (37.64); −0.0085 (1.07) |
| 16-21 | 4-(trifluoro-methyl)phenyl | CH2 | CH2 | — | H | compound No. 16-21, solvent: spectrometer: 399.95 MHz 8.2794 (2.07); 8.2661 (4.08); 8.252 (2.17); 7.8319 (15.33); 7.8266 (15.92); 7.6702 (10.32); 7.65 (12.74); 7.4746 (11.64); 7.4546 (9.86); 6.9145 (15.72); 6.9091 (16); 3.4758 (3.75); 3.4586 (7.87); 3.4438 (7.49); 3.4254 (4.33); 3.3336 (1181.31); 3.2726 (0.67); 3.2613 (0.54); 3.2497 (0.46); 2.9229 (6.04); 2.9048 (10.69); 2.887 (5.3); 2.7113 (3.06); 2.6801 (1.14); 2.6757 (2.26); 2.6712 (3.11); 2.6666 (2.36); 2.6621 (1.2); 2.6188 (0.43); 2.6049 (0.56); 2.5938 (0.66); 2.5747 (1.33); 2.5416 (789.94); 2.5245 (10.04); 2.5196 |

TABLE 16-continued

Compounds of the formula I-16

I-16

| Ex. No. | X | L¹ | L² | L³ | Y | Physical data: ¹H-NMR, δ [ppm] or CAS or patent No. |
|---|---|---|---|---|---|---|
| | | | | | | (14.87); 2.5111 (168.63); 2.5067 (343.15); 2.5021 (454.78); 2.4975 (330.74); 2.493 (159.9); 2.3675 (2.92); 2.338 (0.98); 2.3334 (2.07); 2.3289 (2.88); 2.3243 (2.05); 2.3198 (0.99); 2.0744 (2.49); 1.2582 (0.4); 1.2348 (0.71); 0.008 (1.55); −0.0002 (43.58); −0.0086 (1.2) |
| 16-22 | 2-methyl-phenyl | CH2 | CH2 | — | H | compound No. 16-22, solvent: spectrometer: 399.95 MHz 8.3272 (0.6); 8.3132 (1.11); 8.3004 (0.58); 7.8406 (4.19); 7.8352 (4.28); 7.1673 (0.79); 7.1629 (0.99); 7.1545 (2.31); 7.1448 (2.77); 7.1397 (2.8); 7.1325 (1.17); 7.1256 (3.25); 7.122 (3.45); 7.112 (2.59); 7.1067 (1.34); 7.1006 (1.2); 6.9454 (4.2); 6.94 (4.19); 3.3754 (1.44); 3.3602 (2.9); 3.3357 (239.51); 2.8139 (2.12); 2.799 (1.65); 2.7939 (2.36); 2.7752 (1.87); 2.7115 (0.65); 2.6758 (0.38); 2.6712 (0.52); 2.6667 (0.36); 2.5416 (152.36); 2.5246 (1.75); 2.5111 (28.88); 2.5067 (57.57); 2.5022 (75.77); 2.4976 (55.32); 2.4932 (27.06); 2.3676 (0.65); 2.3332 (0.57); 2.3192 (16); 2.0742 (0.41); −0.0002 (5.76) |
| 16-23 | 2,4,6-trimethyl-phenyl | CH2 | CH2 | — | H | compound No. 16-23, solvent: spectrometer: 399.95 MHz 8.4173 (0.36); 8.4026 (0.71); 8.3879 (0.35); 7.8515 (2.35); 7.8461 (2.4); 6.963 (2.36); 6.9576 (2.36); 6.8083 (3.97); 3.3363 (119.23); 3.2235 (0.49); 3.2089 (0.84); 3.2039 (0.71); 3.1952 (0.83); 3.1882 (0.68); 3.1817 (0.88); 3.1678 (0.59); 2.781 (1.03); 2.7676 (0.79); 2.76 (1.01); 2.7543 (0.83); 2.74 (0.86); 2.7115 (0.32); 2.5417 (79.31); 2.5296 (0.53); 2.5247 (0.94); 2.5112 (16.23); 2.5068 (32.68); 2.5022 (43.15); 2.4977 (31.51); 2.4932 (15.43); 2.3677 (0.34); 2.2961 (16); 2.1819 (6.95); −0.0002 (3.57) |
| 16-24 | 3,4-bismethoxy-phenyl | CH2 | CH2 | — | H | compound No. 16-24, solvent: spectrometer: 399.95 MHz 8.2226 (0.5); 8.208 (0.98); 8.1943 (0.5); 7.8349 (3.23); 7.8295 (3.28); 6.9434 (3.24); 6.9379 (3.24); 6.8729 (2.06); 6.8526 (2.75); 6.8156 (2.19); 6.8108 (2.47); 6.7444 (1.39); 6.7396 (1.28); 6.7241 (1.02); 6.7193 (0.96); 3.7235 (15.97); 3.7103 (16); 3.4117 (0.84); 3.3953 (1.51); 3.3755 (1.58); 3.3602 (1.47); 3.3354 (157.64); 3.3019 (0.33); 2.7517 (1.47); 2.7323 (2.14); 2.7144 (1.36); 2.6712 (0.36); 2.5416 (70.4); 2.5311 (0.37); 2.5244 (1.11); 2.5111 (20.3); 2.5067 (41.01); 2.5022 (54.16); 2.4976 (39.63); 2.4931 (19.3); 2.3289 (0.33); −0.0002 (4.43) |
| 16-25 | phenyl | CH2 | CH2 | — | H | compound No. 16-25, solvent: spectrometer: 399.95 MHz 8.2663 (2.05); 8.2526 (3.66); 8.2388 (1.93); 7.833 (15.73); 7.8276 (15.67); 7.3201 (4.91); 7.3164 (2.18); 7.3018 (12.21); 7.2882 (4.01); 7.2836 (12.13); 7.2459 (10.31); 7.2424 (15.72); 7.2254 (11.54); 7.2099 (2.67); 7.2049 (6.44); 7.1994 (1.55); 7.1906 (1.47); 7.187 (2.23); 7.1837 (1.12); 6.947 (0.45); 6.9356 (16); 6.9301 (15.52); 3.4556 (0.39); 3.433 (4.52); 3.4174 (7.23); 3.4149 (6.85); 3.4111 (5.07); 3.4003 (6.85); 3.396 (8); 3.3811 (6.01); 3.3378 (832); 3.2781 (0.38); 2.8224 (7.58); 2.8027 (10.02); 2.7847 (6.73); 2.7117 (2.35); 2.6804 (0.66); 2.676 (1.26); 2.6714 (1.72); 2.6668 (1.27); 2.6623 (0.66); 2.5417 (586.69); 2.5248 (5.85); 2.5199 (8.66); 2.5114 (97.09); 2.5069 (195.08); 2.5023 (255.88); 2.4978 (184.52); 2.4933 (88.29); 2.3679 (2.3); 2.3382 (0.56); 2.3336 (1.2); 2.3291 (1.62); 2.3245 (1.18); 2.3201 (0.56); 2.0741 (1.4); 1.2347 (0.42); 0.0079 (0.73); −0.0002 (21.43); −0.0085 (0.68) |
| 16-26 | 4-chloro-phenyl | C(CH2—CH2) | CH2 | — | H | |
| 16-27 | 2,4-dichloro-phenyl | C(CH2—CH2) | CH2 | — | H | |
| 16-28 | 4-chloro-phenyl | CH2 | C(CH2—CH2) | — | H | |

TABLE 16-continued

Compounds of the formula I-16

I-16

| Ex. No. | X | L¹ | L² | L³ | Y | Physical data: ¹H-NMR, δ [ppm] or CAS or patent No. |
|---|---|---|---|---|---|---|
| 16-29 | 2,4-dichlorophenyl | CH2 | C(CH2—CH2) | — | H | |
| 16-30 | 4-chlorophenyl | O | CH2 | CH2 | H | |
| 16-31 | 2,4-dichlorophenyl | O | CH2 | CH2 | H | compound No. 16-31, solvent: spectrometer: 399.95 MHz 8.3733 (2.22); 8.3598 (4.25); 8.3462 (2.16); 7.86 (0.36); 7.8499 (15.75); 7.8445 (16); 7.5726 (12.99); 7.5662 (13.73); 7.384 (6.39); 7.3775 (5.95); 7.3618 (8.64); 7.3553 (8.26); 7.2427 (13.19); 7.2204 (9.71); 6.9724 (15.47); 6.9669 (15.42); 4.1933 (6.84); 4.1785 (15.69); 4.1637 (7.42); 3.6023 (3.82); 3.5879 (10.74); 3.5736 (10.31); 3.5589 (3.38); 3.436 (0.35); 3.4093 (0.69); 3.4051 (0.73); 3.3396 (959.26); 3.2777 (0.41); 2.7117 (2.2); 2.6808 (0.6); 2.6764 (1.24); 2.6719 (1.72); 2.6673 (1.28); 2.6629 (0.63); 2.5923 (0.34); 2.5917 (0.32); 2.5901 (0.34); 2.5894 (0.37); 2.5887 (0.37); 2.5872 (0.43); 2.5865 (0.45); 2.5857 (0.48); 2.585 (0.51); 2.5843 (0.49); 2.5836 (0.51); 2.5828 (0.51); 2.5821 (0.55); 2.5813 (0.57); 2.5806 (0.59); 2.5799 (0.62); 2.5792 (0.61); 2.5784 (0.6); 2.5776 (0.63); 2.5769 (0.68); 2.5762 (0.72); 2.5754 (0.78); 2.5747 (0.82); 2.574 (0.86); 2.5732 (0.91); 2.5725 (0.97); 2.5718 (1.02); 2.5711 (1.04); 2.5703 (1.1); 2.5695 (1.16); 2.5688 (1.25); 2.5673 (1.48); 2.5666 (1.53); 2.5659 (1.58); 2.5652 (1.61); 2.5644 (1.68); 2.5637 (1.76); 2.5629 (1.85); 2.5622 (1.97); 2.5615 (2.05); 2.5607 (2.19); 2.56 (2.33); 2.557 (3.34); 2.5422 (584.06); 2.5297 (3.19); 2.5288 (3.16); 2.5252 (5.64); 2.5204 (7.98); 2.5118 (94.43); 2.5073 (193.88); 2.5028 (258.34); 2.4982 (189.27); 2.4937 (92.45); 2.4574 (0.45); 2.45 (0.35); 2.3679 (2.2); 2.3386 (0.59); 2.334 (1.21); 2.3295 (1.68); 2.325 (1.24); 2.3206 (0.6); 2.0747 (1.55); 1.2344 (0.47); 0.008 (0.67); −0.0002 (21.1); −0.0085 (0.66) |
| 16-32 | 4-chlorophenyl | CH2 | CH2 | CH2 | H | compound No. 16-32, solvent: spectrometer: 399.95 MHz 8.1773 (1.42); 8.1639 (2.61); 8.15 (1.41); 7.8358 (10.11); 7.8305 (10.24); 7.3511 (0.99); 7.3448 (9.12); 7.3401 (3.33); 7.3289 (4.09); 7.3238 (16); 7.3179 (2.23); 7.2713 (2.03); 7.2655 (13.71); 7.2608 (4); 7.249 (2.94); 7.2445 (8.01); 6.9468 (10.55); 6.9414 (10.43); 3.3385 (536.7); 3.3096 (1.12); 3.2151 (2.67); 3.1978 (5.58); 3.1828 (5.47); 3.1656 (2.73); 2.7119 (1.51); 2.6805 (0.44); 2.6762 (0.86); 2.6718 (1.17); 2.6672 (0.87); 2.6627 (0.47); 2.6287 (4.63); 2.61 (6.98); 2.5905 (5.12); 2.5634 (1.36); 2.5421 (349.18); 2.5249 (3.9); 2.5202 (5.31); 2.5116 (64.09); 2.5072 (129.58); 2.5027 (170.72); 2.4981 (123.82); 2.4936 (59.92); 2.3681 (1.5); 2.3386 (0.38); 2.3338 (0.78); 2.3294 (1.1); 2.3249 (0.8); 2.3204 (0.38); 2.0744 (0.95); 1.8097 (1.4); 1.7909 (3.79); 1.7726 (5.13); 1.7543 (3.55); 1.7361 (1.22); 0.008 (0.5); −0.0002 (14.61); −0.0085 (0.44) |
| 16-33 | 4-chlorophenyl | NCH3 | CH2 | CH2 | H | |
| 16-34 | 2,4-dichlorophenyl | NCH3 | CH2 | CH2 | H | |
| 16-35 | 4-chlorophenyl | CH(OCH3) | CH2 | — | H | |
| 16-36 | 2,4-dichlorophenyl | CH(OCH3) | CH2 | — | H | |
| 16-37 | 2-thienyl | CH2 | CH2 | — | H | compound No. 16-37, solvent: spectrometer: 399.95 MHz 8.3333 (1.5); 8.3197 (2.75); 8.306 (1.49); 7.8428 (11.37); 7.8374 (11.56); 7.3489 (5.55); 7.3459 (5.79); 7.3362 (6.08); 7.3332 (6.06); 6.97 (4.65); 6.9615 (6.42); 6.9573 (4.87); 6.9494 (16); 6.9442 (11.98); 6.9141 (5.3); 6.9118 (5.59); 6.9058 (4.12); 6.9033 (3.93); 3.4524 (2.97); 3.4348 (6.31); 3.4202 (6.3); 3.4019 (3.87); 3.3385 (606.52); 3.2723 (0.34); 3.0423 (5.38); 3.0244 (9.21); 3.0062 (4.53); 2.7115 (1.81); 2.6804 (0.49); 2.6761 (0.92); 2.6714 (1.26); 2.6668 (0.96); |

TABLE 16-continued

Compounds of the formula I-16

*[Structure of compound I-16: X—L¹—L²—L³—N(Y)—C(=O)— connected to 2-bromofuran-3-yl]*

| Ex. No. | X | L¹ | L² | L³ | Y | Physical data: ¹H-NMR, δ [ppm] or CAS or patent No. |
|---|---|---|---|---|---|---|
| | | | | | | 2.6623 (0.46); 2.5816 (0.53); 2.5418 (450.33); 2.5248 (4.92); 2.5198 (6.94); 2.5113 (72.47); 2.5069 (145.82); 2.5023 (192.46); 2.4978 (140.37); 2.4933 (68.41); 2.4648 (0.44); 2.3677 (1.83); 2.3378 (0.46); 2.3336 (0.92); 2.3291 (1.26); 2.3245 (0.93); 2.3203 (0.44); 2.0742 (1.14); 1.2349 (0.33); 0.008 (0.55); −0.0002 (15.05); −0.0085 (0.47) |
| 16-38 | 3-thienyl | CH2 | CH2 | — | H | |
| 16-39 | 2-furyl | CH2 | CH2 | — | H | |
| 16-40 | 3-furyl | CH2 | CH2 | — | H | |
| 16-41 | phenyl | CH2 | CH2 | CH(CH3) | H | |
| 16-42 | phenyl | CH2 | CH2 | CH2 | H | |
| 16-43 | 2-Cl-phenyl | CH2 | CH2 | CH(CH3) | H | |
| 16-44 | 4-t-butyl-phenyl | CH2 | CH2 | CH2 | H | |
| 16-45 | 4-methyl-phenyl | CH2 | CH2 | CH2 | H | |
| 16-46 | phenyl | CH2 | CH2 | CH(CH2CH3) | H | |
| 16-47 | 2-methoxy-phenyl | CH2 | CH2 | CH2 | H | |
| 16-48 | 2-methyl-phenyl | CH2 | CH2 | CH2 | H | |
| 16-49 | 3-methyl-phenyl | CH2 | CH2 | CH2 | H | |
| 16-50 | 3-chloro-phenyl | CH2 | CH2 | CH2 | H | |
| 16-51 | 2,6-difluoro-phenyl | CH2 | CH2 | CH2 | H | compound No. 16-51, solvent: spectrometer: 399.95 MHz 8.2182 (2.22); 8.2044 (4.08); 8.1906 (2.17); 7.8341 (15.73); 7.8287 (15.8); 7.3471 (1.34); 7.3303 (2.93); 7.3263 (2.69); 7.3094 (5.7); 7.2921 (2.82); 7.2886 (3.74); 7.2717 (1.73); 7.1015 (0.79); 7.0971 (1.1); 7.0843 (7.57); 7.0642 (12.49); 7.0523 (1.65); 7.0442 (6.45); 7.0309 (0.93); 7.0279 (0.75); 6.9483 (0.37); 6.9424 (0.46); 6.932 (16); 6.9266 (15.81); 3.4196 (0.58); 3.4076 (0.7); 3.3386 (937.56); 3.2759 (0.66); 3.2628 (0.42); 3.2413 (3.79); 3.224 (7.25); 3.2077 (7.21); 3.1906 (3.91); 2.712 (2.62); 2.6809 (5.78); 2.6715 (3.71); 2.6622 (9.18); 2.6424 (5.7); 2.6247 (0.5); 2.6126 (0.44); 2.5961 (0.57); 2.5422 (618.1); 2.5252 (6.13); 2.5118 (105.87); 2.5073 (213.18); 2.5028 (280.32); 2.4982 (202.97); 2.4938 (97.9); 2.4472 (0.34); 2.3682 (2.59); 2.3384 (0.65); 2.3341 (1.33); 2.3295 (1.8); 2.3251 (1.31); 2.3206 (0.63); 2.2923 (0.32); 2.0747 (1.6); 1.78 (2); 1.7608 (5.09); 1.7425 (7.44); 1.7236 (4.71); 1.7051 (1.8); 1.2345 (0.42); 0.0079 (0.79); −0.0002 (23.26); −0.0085 (0.71) |
| 16-52 | 4-chlorophenyl | CH2 | CH2 | CH2 | H | |
| 16-53 | 2,6-dichlorophenyl | CH2 | CH2 | CH(CH3) | H | |
| 16-54 | 3,5-dichlorophenyl | CH2 | CH2 | CH(CH3) | H | |
| 16-55 | 2,6-dimethylphenyl | CH2 | CH2 | CH2 | H | |
| 16-56 | 2,5-dichlorophenyl | CH2 | CH2 | CH2 | H | |
| 16-57 | 4-isopropoxyphenyl | CH2 | CH2 | CH2 | H | |
| 16-58 | 3-trifluoromethylphenyl | CH2 | CH2 | CH(CH3) | H | |
| 16-59 | 4-methylphenyl | CH2 | CH2 | CH(CH3) | H | |
| 16-60 | 2-methylphenyl | CH2 | CH2 | CH(CH3) | H | |
| 16-61 | 3,4-dichlorophenyl | CH2 | CH2 | CH(CH3) | H | |
| 16-62 | 3,5-dichlorophenyl | CH2 | CH2 | CH2 | H | |
| 16-63 | 2,6-dimethylphenyl | CH2 | CH2 | CH(CH3) | H | |
| 16-64 | 4-trifluoromethylphenyl | CH2 | CH2 | CH(CH3) | H | |
| 16-65 | 2,5-dichlorophenyl | CH2 | CH2 | CH(CH3) | H | |
| 16-66 | 4-phenoxyphenyl | CH2 | CH2 | CH2 | H | |
| 16-67 | 3-chlorophenyl | CH2 | CH2 | CH(CH3) | H | |
| 16-68 | 4-phenoxyphenyl | CH2 | CH2 | CH(CH3) | H | |
| 16-69 | 2,4-dichlorophenyl | CH2 | CH2 | CH(CH3) | H | |
| 16-70 | 2-difluoromethoxyphenyl | CH2 | CH2 | CH(CH3) | H | |
| 16-71 | 4-methoxyphenyl | CH2 | CH2 | CH2 | H | |

TABLE 16-continued

Compounds of the formula I-16

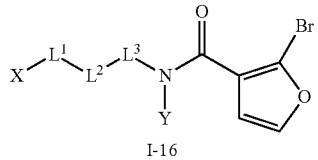

I-16

| Ex. No. | X | L¹ | L² | L³ | Y | Physical data: $^1$H-NMR, δ [ppm] or CAS or patent No. |
|---|---|---|---|---|---|---|
| 16-72 | 4-chlorophenyl | CH2 | CH2 | CH(CH3) | H | |
| 16-73 | 4-chlorophenyl | CH2 | CH2 | CH(i-propyl) | H | |
| 16-74 | 4-fluorophenyl | CH2 | CH2 | CH2 | H | |
| 16-75 | 4-chlorophenyl | CH2 | CH2 | CH(n-propyl) | H | |
| 16-76 | 4-chlorophenyl | CH2 | CH2 | CH(t-butyl) | H | |
| 16-77 | 2-chlorophenyl | CH2 | CH2 | CH2 | H | |
| 16-78 | 4-chlorophenyl | CH2 | CH(CH3) | — | cyclo-propyl | |
| 16-79 | 2-thienyl | CH2 | CH2 | CH2 | H | compound No. 16-79, solvent: spectrometer: 399.95 MHz 8.2073 (1.93); 8.1941 (3.6); 8.1808 (2.04); 7.8384 (15.02); 7.833 (15.64); 7.8221 (0.46); 7.3214 (6.94); 7.3184 (7.71); 7.3087 (7.78); 7.3057 (8.14); 6.9602 (15.15); 6.9547 (16); 6.9437 (8.41); 6.9394 (6.31); 6.9309 (7.83); 6.8888 (6.85); 6.8864 (7.42); 6.8805 (5.63); 6.878 (5.58); 3.341 (1030.45); 3.2639 (4.41); 3.2468 (8.81); 3.2317 (8.63); 3.2146 (4.53); 2.8573 (6.66); 2.8384 (11.53); 2.8193 (7.14); 2.7939 (0.36); 2.7117 (2.58); 2.6762 (1.48); 2.6716 (1.94); 2.6671 (1.44); 2.6627 (0.77); 2.5421 (615.56); 2.525 (6.62); 2.5115 (104.57); 2.5071 (211.52); 2.5026 (280.05); 2.498 (204.18); 2.4935 (99.35); 2.3679 (2.48); 2.3338 (1.29); 2.3294 (1.78); 2.3248 (1.31); 2.2928 (0.39); 2.0743 (1.56); 1.8699 (2.26); 1.8513 (6.3); 1.8328 (8.29); 1.8147 (6); 1.7965 (2.1); 1.2348 (0.46); 0.008 (0.76); −0.0001 (20.6); −0.0085 (0.59) |
| 16-80 | 4-chloro-2-thienyl | CH2 | CH2 | — | H | compound No. 16-80, solvent: spectrometer: 601.6 MHz 8.3297 (1.84); 8.3205 (3.48); 8.3111 (1.83); 7.842 (15.56); 7.8385 (16); 7.372 (14.43); 7.3694 (14.52); 6.9385 (15.47); 6.9348 (15.5); 6.9118 (9.69); 6.9106 (8.64); 6.9094 (9.71); 3.4427 (3.59); 3.431 (8.53); 3.4214 (8.73); 3.4098 (4); 3.3565 (0.5); 3.3506 (0.68); 3.3477 (0.7); 3.3266 (1016.33); 3.3074 (1.22); 3.292 (0.4); 3.0028 (6.03); 2.991 (11.7); 2.9799 (5.43); 2.6532 (1.87); 2.6194 (0.6); 2.6164 (1.31); 2.6134 (1.8); 2.6103 (1.28); 2.6074 (0.59); 2.5498 (2.01); 2.541 (592.11); 2.5332 (1.27); 2.5312 (0.51); 2.5302 (0.57); 2.5279 (0.64); 2.5227 (3.41); 2.5196 (4.23); 2.5165 (4.21); 2.5077 (95.78); 2.5047 (205.59); 2.5016 (283.89); 2.4986 (205.61); 2.4955 (95.24); 2.4249 (1.84); 2.3918 (0.55); 2.3888 (1.23); 2.3858 (1.71); 2.3827 (1.23); 2.3798 (0.55); 2.0736 (1.75); 1.9082 (1.02); 1.2352 (0.36); 0.0053 (0.44); −0.0002 (15.06); −0.0057 (0.46) |
| 16-81 | 4-(trifluoro-methoxy)phenyl | CH2 | CH2 | — | H | compound No. 16-81, solvent: spectrometer: 399.95 MHz 8.2708 (1.44); 8.2572 (2.71); 8.2436 (1.44); 7.832 (7.72); 7.8267 (7.61); 7.3724 (6.65); 7.3508 (11.39); 7.2972 (7.89); 7.2767 (4.71); 6.9227 (8.52); 6.9173 (8.2); 5.7572 (16); 3.4485 (2.25); 3.4316 (4.57); 3.4163 (4.46); 3.4135 (4.31); 3.3977 (2.43); 3.3265 (20.76); 2.861 (4.32); 2.8425 (6.84); 2.8244 (3.78); 2.5122 (18.42); 2.508 (33.91); 2.5035 (42.59); 2.4989 (30.65); 2.4946 (14.78); 1.3371 (0.47); 1.25 (0.57) |

TABLE 17

Compounds of the formula I-17

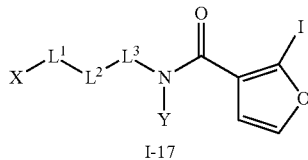

I-17

| Ex. No. | X | L¹ | L² | L³ | Y | Physical data: ¹H-NMR, δ [ppm] or CAS or patent No. |
|---|---|---|---|---|---|---|
| 17-1 | 3-methyl-2-thienyl | CH2 | CH2 | — | H | |
| 17-2 | 2,4-dichlorophenyl | CH2 | CH2 | CH2 | H | compound No. 17-2, solvent: spectrometer: 399.95 MHz<br>8.17 (2.06); 8.156 (3.99); 8.1419 (2.02); 7.9082 (15.62); 7.903 (15.74); 7.5666 (8.93); 7.5614 (9.26); 7.4288 (6.04); 7.4081 (13.21); 7.3941 (0.33); 7.38 (8.59); 7.3747 (7.99); 7.3593 (3.77); 7.354 (3.73); 6.8835 (0.33); 6.8734 (16); 6.8681 (15.76); 3.5158 (0.64); 3.3468 (21.57); 3.2552 (3.13); 3.238 (6.82); 3.2229 (6.82); 3.2056 (3.19); 2.7416 (5.76); 2.723 (7.22); 2.703 (6.2); 2.676 (0.33); 2.5461 (50.15); 2.5294 (0.61); 2.5246 (0.91); 2.5159 (11.4); 2.5114 (23.3); 2.5068 (31.17); 2.5021 (22.71); 2.4976 (10.75); 1.8075 (1.66); 1.7887 (4.29); 1.7703 (5.72); 1.752 (4.03); 1.7335 (1.48); −0.0002 (3.44) |
| 17-3 | 4-chlorophenyl | CH2 | CH2 | — | H | [DMSO], spectrometer: 399.95 MHz<br>8.2153 (0.36); 7.9050 (0.97); 7.8998 (0.97); 7.3625 (0.89); 7.3416 (1.44);<br>7.2769 (1.35); 7.2559 (0.85); 6.8470 (0.97); 6.8418 (0.97); 3.4907 (16.00); 3.4304 (0.43); 3.4133 (0.64); 3.3952 (0.63); 3.3796 (0.36); 2.8214 (0.50); 2.8027 (0.81); 2.7848 (0.45); 2.5552 (2.54); 2.5209 (1.35);<br>2.5165 (1.79); 2.5121 (1.37) |
| 17-4 | 2,4-dichlorophenyl | CH2 | CH2 | — | H | compound No. 17-4, solvent: spectrometer: 399.95 MHz<br>8.2259 (1.64); 8.2118 (3.23); 8.1976 (1.63); 7.8966 (9.93); 7.8914 (10.05); 7.5854 (5.98); 7.582 (6.61); 7.3878 (1.24); 7.3834 (0.84); 7.3672<br>(9.54); 7.3621 (16); 7.3481 (0.42); 7.3404 (1.25); 6.8333 (10); 6.8281 (9.95); 5.7559 (1.39); 3.4479 (2.31); 3.4311 (5.33); 3.4153 (5.28); 3.3981<br>(2.6); 3.3352 (133.8); 2.9377 (4.89); 2.9197 (8.43); 2.9022 (4.3); 2.5262 (1.13); 2.513 (17.16); 2.5085 (33.81); 2.504 (44.7); 2.4994 (33.06); 2.495<br>(16.26); 1.9898 (0.89); 1.2497 (0.4); 1.1757 (0.5); −0.0002 (3.15) |
| 17-5 | 4-chlorophenyl | CH(OCH3) | CH(CH3) | — | H | [DMSO], spectrometer: 399.95 MHz<br>7.9346 (1.29); 7.9132 (1.34); 7.8986 (3.17); 7.8935 (3.16); 7.8787 (3.81);<br>7.8736 (3.79); 7.7754 (1.06); 7.7551 (1.08); 7.4397 (3.09); 7.4182 (5.40);<br>7.3952 (5.46); 7.3336 (4.88); 7.3125 (3.00); 7.2906 (3.65); 7.2696 (2.79);<br>6.9125 (3.03); 6.9073 (2.99); 6.8343 (3.71); 6.8291 (3.66); 4.3054 (1.47);<br>4.2903 (1.95); 4.2506 (1.89); 4.2351 (2.29); 4.2212 (0.50); 4.2041 (0.70);<br>4.1850 (0.65); 4.1687 (0.39); 4.0859 (0.54); 4.0694 (0.82); 4.0650 (0.67);<br>4.0527 (0.62); 4.0483 (0.81); 4.0319 (0.50); 3.3646 (214.06); 3.1876 (16.00); 3.1570 (13.27); 2.5446 (23.99); 2.5274 (0.78); 2.5141 (16.57); 2.5098 (32.70); 2.5053 (42.93); 2.5008 (32.15); 2.4965 (16.12); 1.1261 (6.08); 1.1092 (6.08); 0.9615 (4.80); 0.9444 (4.80); −0.0002 (5.26) |
| 17-6 | 2,4-dichlorophenyl | CH(OCH3) | CH(CH3) | — | H | |
| 17-7 | 4-chlorophenyl | CH(CH3) | CH2 | — | H | [DMSO], spectrometer: 399.95 MHz<br>8.1462 (1.98); 8.1321 (3.29); 8.1178 (1.61); 7.9073 (0.57); 7.9023 (0.70);<br>7.8892 (10.09); 7.8840 (9.22); 7.3662 (8.69); 7.3614 (3.54); 7.3497 (5.91); 7.3449 (13.90); 7.3390 (2.04); 7.2904 (13.43); 7.2856 (4.05); 7.2735 (4.00); 7.2692 (7.52); 6.8214 (9.19); 6.8162 (8.32); 3.3817 (2.45);<br>3.3590 (43.45); 3.3418 (3.25); 3.3234 (4.50); 3.3080 (4.52); 3.2889 (2.72); 3.2744 (0.78); 3.2705 (0.79); 3.2561 (0.61); 3.0661 (0.45); 3.0486<br>(1.60); 3.0308 (2.90); 3.0130 (2.69); 2.9952 (1.22); 2.5650 (0.87); 2.5468<br>(23.00); 2.5162 (8.64); 2.5120 (14.46); 2.5075 (17.35); 2.5030 (12.20); 2.4987 (5.59); 2.0801 (0.53); 1.2175 (16.00); 1.2000 (14.95); −0.0002 (1.94) |
| 17-8 | 2,4-dichlorophenyl | CH(CH3) | CH2 | — | H | [DMSO], spectrometer: 399.95 MHz<br>8.1758 (1.77); 8.1613 (3.49); 8.1473 (1.75); 7.8860 (10.63); 7.8808 (10.75); 7.5603 (7.55); 7.5551 (8.06); 7.4693 (4.38); 7.4482 (10.22); |

TABLE 17-continued

Compounds of the formula I-17

I-17

| Ex. No. | X | L¹ | L² | L³ | Y | Physical data: ¹H-NMR, δ [ppm] or CAS or patent No. |
|---|---|---|---|---|---|---|
| | | | | | | 7.4326 (0.35); 7.4228 (6.21); 7.4175 (5.75); 7.4017 (2.58); 7.3964 (2.55);<br>6.8132 (9.78); 6.8079 (9.75); 3.5263 (1.20); 3.5088 (2.78); 3.4916 (3.14);<br>3.4744 (1.94); 3.4651 (1.63); 3.4505 (1.57); 3.4331 (2.82); 3.4176 (2.76);<br>3.4003 (1.59); 3.3809 (1.92); 3.3657 (3.32); 3.3534 (31.95); 3.3342 (1.68); 3.3171 (0.90); 2.5478 (30.07); 2.5310 (0.41); 2.5260 (0.57); 2.5174 (6.98); 2.5131 (14.06); 2.5085 (18.69); 2.5040 (14.09); 2.4997 (7.17); 2.0819 (0.45); 1.2090 (16.00); 1.1921 (15.93); −0.0002 (1.94) |
| 17-9 | 4-chloro-phenyl | CH2 | CH(CH3) | — | H | [DMSO], spectrometer: 399.95 MHz<br>7.9341 (3.31); 7.9135 (3.39); 7.8967 (10.25); 7.8916 (10.27); 7.3383 (8.48); 7.3337 (3.34); 7.3218 (4.35); 7.3172 (14.38); 7.2595 (13.04); 7.2384 (7.87); 6.8857 (9.59); 6.8805 (9.52); 4.1614 (0.73); 4.1429 (1.62);<br>4.1255 (2.26); 4.1083 (1.70); 4.0898 (0.77); 3.3513 (29.33); 2.8463 (1.85); 2.8271 (1.84); 2.8129 (3.17); 2.7937 (3.09); 2.7358 (3.12); 2.7198 (3.22); 2.7023 (1.91); 2.6863 (1.79); 2.5461 (5.63); 2.5292 (0.35); 2.5156 (7.20); 2.5113 (14.43); 2.5068 (19.08); 2.5022 (14.38); 2.4980 (7.33); 1.1269 (16.00); 1.1103 (15.91); −0.0002 (1.86) |
| 17-10 | 2,4-di-chloro-phenyl | CH2 | CH(CH3) | — | H | |
| 17-11 | 4-chloro-phenyl | C(CH3)2 | CH2 | — | H | [DMSO], spectrometer: 399.95 MHz<br>7.8855 (3.71); 7.8804 (3.81); 7.8730 (0.69); 7.8567 (1.17); 7.8411 (0.58);<br>7.4474 (0.35); 7.4411 (2.83); 7.4360 (1.12); 7.4244 (1.45); 7.4192 (5.07);<br>7.4129 (0.85); 7.3742 (0.75); 7.3679 (5.04); 7.3629 (1.50); 7.3510 (1.08);<br>7.3460 (2.83); 6.8181 (3.59); 6.8129 (3.58); 3.3884 (3.34); 3.3724 (3.35);<br>3.3506 (6.88); 2.5459 (7.32); 2.5154 (2.28); 2.5111 (4.56); 2.5066 (6.03);<br>2.5021 (4.54); 2.4980 (2.31); 1.2846 (16.00); −0.0002 (0.52) |
| 17-12 | 2,4-di-chloro-phenyl | C(CH3)2 | CH2 | — | H | [DMSO], spectrometer: 399.95 MHz<br>7.8724 (3.99); 7.8673 (4.35); 7.8503 (1.31); 7.8345 (0.64); 7.5338 (2.43);<br>7.5281 (2.59); 7.4753 (1.85); 7.4536 (2.70); 7.3702 (1.69); 7.3644 (1.63);<br>7.3486 (1.18); 7.3428 (1.13); 6.7823 (3.77); 6.7771 (3.77); 3.7319 (3.38);<br>3.7159 (3.35); 3.3496 (8.21); 2.5471 (10.07); 2.5166 (2.36); 2.5123 (4.73); 2.5078 (6.26);2.5033 (4.73); 2.4992 (2.42); 1.4336 (16.00) −0.0002 (0.46) |
| 17-13 | 2-chloro-phenyl | CH2 | CH2 | — | H | [DMSO], spectrometer: 399.95 MHz<br>8.2730 (3.03); 8.2592 (5.74); 8.2452 (3.03); 7.9069 (15.65); 7.9018 (16.00); 7.4453 (6.11); 7.4414 (5.58); 7.4270 (7.86); 7.4226 (7.88); 7.4054 (0.35); 7.3586 (4.31); 7.3532 (5.37); 7.3400 (7.02); 7.3354 (9.00);<br>7.3203 (0.55); 7.3104 (2.79); 7.3064 (3.62); 7.2922 (8.16); 7.2882 (7.83);<br>7.2770 (8.74); 7.2751 (8.85); 7.2712 (9.60); 7.2588 (6.59); 7.2536 (5.94);<br>7.2404 (2.24); 7.2355 (1.85); 6.8678 (15.76); 6.8626 (15.98); 3.4600 (4.27); 3.4436 (8.81); 3.4274 (8.22); 3.4242 (8.90); 3.4090 (4.93); 3.3540 (25.43); 2.9612 (8.94); 2.9420 (13.13); 2.9244 (7.88); 2.5472 (38.06); 2.5301 (0.65); 2.5124 (18.26); 2.5080 (24.12); 2.5035 (18.65); 2.0811 (0.64); −0.0002 (1.98) |
| 17-14 | 3,4-di-chloro-phenyl | CH2 | CH2 | — | H | compound No. 17-14, solvent: spectrometer: 399.95 MHz<br>8.1863 (2.74); 8.1724 (5.32); 8.1584 (2.79); 7.9015 (15.73); 7.8963 (15.92); 7.5632 (0.34); 7.5532 (12.94); 7.5433 (0.69); 7.5327 (14.85); 7.5167 (12.06); 7.5118 (12.61); 7.2422 (7.04); 7.2372 (6.94); 7.2216 (6.22); 7.2166 (6.15); 6.8352 (16); 6.8299 (15.99); 5.7581 (3.62); 3.4468 (3.88); 3.4296 (9.23); 3.4144 (9.26); 3.3972 (4.27); 3.3301 (14.93); |

TABLE 17-continued

Compounds of the formula I-17

I-17

| Ex. No. | X | L¹ | L² | L³ | Y | Physical data: ¹H-NMR, δ [ppm] or CAS or patent No. |
|---|---|---|---|---|---|---|
| | | | | | | 2.8348 (7.68); 2.817 (14.34); 2.7994 (6.95); 2.5273 (0.91); 2.5139 (15.91); 2.5096 (31.41); 2.505 (41.48); 2.5005 (30.86); 2.4962 (15.39); 1.9909 (0.36); 1.3379 (0.44); 1.25 (0.54); -0.0002 (2.91) |
| 17-15 | 3,5-di-chlorophenyl | CH2 | CH2 | — | H | compound No. 17-15, solvent: spectrometer: 399.95 MHz 8.1892 (1.68); 8.1751 (3.13); 8.1612 (1.62); 7.9024 (9.49); 7.8973 (9.57); 7.4372 (3.64); 7.4325 (7.17); 7.4277 (4.15); 7.3257 (0.45); 7.3109 (16); 7.3062 (15.6); 6.8462 (0.45); 6.841 (0.52); 6.8277 (9.35); 6.8225 (9.31); 3.4538 (2.27); 3.4366 (5.62); 3.4216 (5.74); 3.4045 (2.62); 3.3236 (18.65); 2.8444 (4.43); 2.8268 (8.57); 2.8093 (4.05); 2.6719 (0.42); 2.5251 (1.34); 2.5115 (21.91); 2.5072 (42.99); 2.5027 (56.75); 2.4982 (42.05); 2.4939 (20.75); 2.3296 (0.37); 1.3363 (0.39); 1.2496 (0.48); 0 .0002 (3.95) |
| 17-16 | 3-chlorophenyl | CH2 | CH2 | — | H | [DMSO], spectrometer: 399.95 MHz 8.2249 (2.76); 8.2111 (5.34); 8.1973 (2.89); 7.9082 (15.77); 7.9031 (16.00); 7.3626 (0.46); 7.3478 (3.64); 7.3419 (1.08); 7.3285 (9.45); 7.3152 (11.43); 7.3100 (14.43); 7.2796 (7.56); 7.2629 (3.23); 7.2581 (3.52); 7.2126 (7.54); 7.1938 (5.32); 6.8562 (15.88); 6.8510 (15.93); 3.4459 (3.89); 3.4290 (8.27); 3.4112 (8.16); 3.3953 (4.50); 3.3551 (29.48); 2.8405 (7.57); 2.8220 (12.55); 2.8041 (7.01); 2.7848 (0.33); 2.5467 (37.80); 2.5302 (0.53); 2.5118 (17.03); 2.5074 (22.52); 2.5029 (17.23); 2.0805 (0.60); 0.0002 (1.57) |
| 17-17 | 2-fluorophenyl | CH2 | CH2 | — | H | [DMSO], spectrometer: 399.95 MHz 8.2765 (2.49); 8.2625 (4.74); 8.2484 (2.48); 7.9060 (15.79); 7.9008 (16.00); 7.3334 (2.38); 7.3295 (2.94); 7.3148 (4.61); 7.3105 (6.26); 7.3033 (1.99); 7.2983 (2.42); 7.2908 (4.50); 7.2847 (3.66); 7.2698 (3.00); 7.2645 (4.26); 7.2601 (2.35); 7.2507 (2.44); 7.2463 (1.93); 7.1821 (4.50); 7.1585 (10.87); 7.1415 (8.18); 7.1388 (9.95); 7.1233 (3.36); 7.1205 (2.96); 6.8587 (14.47); 6.8534 (14.58); 3.4380 (3.67); 3.4216 (7.24); 3.4051 (6.62); 3.4017 (7.33); 3.3865 (4.13); 3.3538 (21.37); 2.8670 (6.33); 2.8483 (9.90); 2.8300 (5.64); 2.5471 (40.41); 2.5304 (0.47); 2.5255 (0.62); 2.5167 (7.78); 2.5124 (15.88); 2.5078 (21.29); 2.5033 (16.19); 2.4991 (8.35); 2.0807 (0.44); -0.0002 (1.98) |
| 17-18 | 2,6-di-fluorophenyl | CH2 | CH2 | — | H | [DMSO], spectrometer: 399.95 MHz 8.3342 (2.88); 8.3196 (5.58); 8.3051 (2.87); 7.9026 (15.84); 7.8975 (16.00); 7.3664 (1.21); 7.3493 (2.96); 7.3460 (2.91); 7.3287 (5.48); 7.3081 (3.63); 7.2912 (1.61); 7.1040 (1.12); 7.0917 (8.22); 7.0720 (12.64); 7.0609 (2.02); 7.0523 (6.99); 7.0393 (1.04); 6.8308 (15.75); 6.8256 (15.91); 3.4058 (3.86); 3.3893 (8.82); 3.3709 (8.98); 3.3545 (32.02); 2.8820 (6.36); 2.8638 (10.95); 2.8461 (5.71); 2.5491 (41.65); 2.5323 (0.55); 2.5142 (16.83); 2.5098 (22.31); 2.5054 (17.15); 2.0827 (0.67); -0.0002 (1.48) |
| 17-19 | 2,6-di-chlorophenyl | CH2 | CH2 | — | H | [DMSO], spectrometer: 399.95 MHz 8.3288 (1.55); 8.3145 (3.12); 8.3000 (1.57); 7.8978 (9.08); 7.8927 (9.37); 7.4685 (11.72); 7.4484 (16.00); 7.3046 (5.36); 7.2854 (5.37); 7.2835 (5.45); 7.2643 (3.55); 6.8498 (9.10); 6.8446 (9.27); 3.4357 (1.95); 3.4193 (4.69); 3.4001 (4.74); 3.3850 (2.68); 3.3443 (255.13); 3.3124 (0.63); 3.1460 (4.54); 3.1268 (6.78); 3.1098 (3.60); 2.6771 (0.46); 2.6727 (0.64); 2.6681 (0.49); 2.5429 (48.46); 2.5260 (1.90); 2.5124 (34.75); 2.5080 (70.93); 2.5035 (95.37); 2.4990 (72.98); 2.4948 (38.02); 2.3347 (0.46); 2.3303 (0.64); 2.3259 (0.48); 2.0770 (0.45); -0.0002 (2.21) |
| 17-20 | 3-(tri-fluoro-methyl)phenyl | CH2 | CH2 | — | H | [DMSO], spectrometer: 399.95 MHz 8.2350 (2.48); 8.2211 (4.60); 8.2072 (2.38); 7.9189 (0.55); 7.9089 (14.27); 7.9037 (14.51); 7.6742 (0.38); 7.6541 (0.53); 7.5885 (10.40); 7.5657 (7.60); 7.5527 (16.00); 7.5341 (3.06); 7.5164 (0.99); 7.4822 (0.46); 7.4624 (0.43); 6.8563 (0.76); 6.8452 (13.05); 6.8400 (13.21); 3.4790 (3.41); 3.4619 (7.67); 3.4465 (7.57); 3.4288 (3.97); 3.3577 (26.92); 2.9395 (6.60); 2.9214 (11.46); 2.9036 (5.97); 2.5490 (41.45); 2.5323 (0.52); 2.5274 (0.63); 2.5185 (8.02); 2.5142 (16.31); 2.5097 (21.74); 2.5052 (16.57); 2.5010 (8.61); 2.0822 (0.92); -0.0002 (1.78) |

TABLE 17-continued

Compounds of the formula I-17

I-17

| Ex. No. | X | L¹ | L² | L³ | Y | Physical data: ¹H-NMR, δ [ppm] or CAS or patent No. |
|---|---|---|---|---|---|---|
| 17-21 | 4-(tri-fluoro-methyl)phenyl | CH2 | CH2 | — | H | [DMSO], spectrometer: 399.95 MHz<br>8.2544 (2.57); 8.2406 (4.94); 8.2266 (2.54); 7.9113 (15.88); 7.9061 (16.00); 7.6742 (10.65); 7.6540 (12.96); 7.4830 (12.41); 7.4629 (10.58); 6.8595 (13.45); 6.8543 (13.40); 3.4818 (3.52); 3.4648 (7.59); 3.4474 (7.40); 3.4313 (3.94); 3.3601 (18.84); 2.9325 (6.19); 2.9142 (10.62); 2.8963 (5.49); 2.5504 (41.32); 2.5337 (0.44); 2.5289 (0.58); 2.5201 (6.63); 2.5157 (13.54 2.5112 (18.14); 2.5066 (13.67); 2.5023 (6.94); 2.0836 (1.04); −0.0002 (1.85)<br>08 00); |
| 17-22 | 2-methyl-phenyl | CH2 | CH2 | — | H | [DMSO], spectrometer: 399.95 MHz<br>8.2893 (0.78); 8.2753 (1.48); 8.2612 (0.77); 7.9142 (4.40); 7.9091 (4.51);<br>7.1690 (1.52); 7.1570 (2.32); 7.1455 (4.19); 7.1396 (1.94); 7.1285 (3.49);<br>7.1242 (4.10); 7.1147 (3.00); 7.1085 (1.64); 7.1054 (1.45); 7.1028 (1.43);<br>6.8805 (4.36); 6.8752 (4.36); 3.3764 (1.19); 3.3612 (2.28); 3.3566 (2.37);<br>3.3480 (8.87); 3.3377 (2.36); 3.3231 (1.32); 2.8169 (2.38); 2.8019 (2.00);<br>2.7969 (2.70); 2.7781 (2.12); 2.5442 (10.51); 2.5136 (3.09); 2.5093 (6.18); 2.5048 (8.22); 2.5003 (6.24); 2.4961 (3.22); 2.3238 (16.00); −0 .0002 (1.07) |
| 17-23 | 2,4,6-tri-methyl-phenyl | CH2 | CH2 | — | H | [DMSO], spectrometer: 399.95 MHz<br>8.3716 (0.56); 8.3571 (1.13); 8.3425 (0.56); 7.9246 (3.20); 7.9195 (3.24);<br>6.8969 (3.16); 6.8916 (3.15); 6.8093 (5.25); 3.3493 (5.65); 3.2268 (0.63);<br>3.2122 (1.13); 3.1985 (1.13); 3.1914 (0.95); 3.1852 (1.19); 3.1712 (0.75);<br>2.7842 (1.35); 2.7708 (1.09); 2.7631 (1.36); 2.7581 (1.16); 2.7433 (1.14);<br>2.5445 (14.01); 2.5140 (1.84); 2.5097 (3.72); 2.5052 (4.96); 2.5007 (3.75); 2.3013 (16.00); 2.1841 (8.24); −0.0002 (0.61) |
| 17-24 | 3,4-bis-methoxy-phenyl | CH2 | CH2 | — | H | [DMSO], spectrometer: 399.95 MHz<br>8.1934 (0.77); 8.1795 (1.52); 8.1655 (0.79); 7.9109 (4.42); 7.9057 (4.46);<br>6.8844 (4.25); 6.8791 (4.46); 6.8754 (3.05); 6.8548 (3.36); 6.8202 (2.95);<br>6.8155 (3.33); 6.7501 (1.89); 6.7454 (1.75); 6.7298 (1.41); 6.7250 (1.34);<br>3.7297 (16.00); 3.7147 (15.91); 3.4141 (0.94); 3.3979 (1.88); 3.3779 (1.94); 3.3621 (1.32); 3.3532 (6.27); 2.7580 (1.87); 2.7385 (2.73); 2.7207 (1.71); 2.5453 (11.49); 2.5149 (2.00); 2.5106 (4.07); 2.5061 (5.45); 2.5016 (4.16); −0.0002 (0.64) |
| 17-25 | phenyl | CH2 | CH2 | — | H | [DMSO], spectrometer: 399.95 MHz<br>8.2349 (2.45); 8.2211 (4.64); 8.2072 (2.45); 7.9072 (15.16); 7.9020 (15.41); 7.3229 (4.79); 7.3045 (12.58); 7.2862 (12.23); 7.2470 (16.00); 7.2285 (11.44); 7.2071 (6.59); 7.1926 (1.60); 7.1892 (2.35); 6.8730 (15.16); 6.8677 (15.29); 3.4314 (3.88); 3.4157 (6.90); 3.3985 (6.16); 3.3942 (7.30); 3.3793 (4.36); 3.3488 (27.85); 2.8251 (7.51); 2.8053 (10.01); 2.7873 (6.71); 2.5441 (33.83); 2.5272 (0.54); 2.5136 (9.76); 2.5093 (19.52); 2.5048 (25.88); 2.5003 (19.58); 2.4961 (10.02); 2.0776 (0.54); −0.0002 (3.28) |
| 17-26 | 4-chloro-phenyl | C(CH2—CH2) | CH2 | — | H | |
| 17-27 | 2,4-di-chloro-phenyl | C(CH2—CH2) | CH2 | — | H | |
| 17-28 | 4-chloro-phenyl | CH2 | C(CH2—CH2) | — | H | |
| 17-29 | 2,4-di-chloro-phenyl | CH2 | C(CH2—CH2) | — | H | |
| 17-30 | 4-chloro-phenyl | O | CH2 | CH2 | H | |

TABLE 17-continued

Compounds of the formula I-17

$$\text{X}-\text{L}^1-\text{L}^2-\text{L}^3-\underset{\underset{Y}{|}}{N}-\overset{\overset{O}{\|}}{C}-\underset{\text{I-17}}{\text{(2-iodofuran-3-yl)}}$$

| Ex. No. | X | L¹ | L² | L³ | Y | Physical data: ¹H-NMR, δ [ppm] or CAS or patent No. |
|---|---|---|---|---|---|---|
| 17-31 | 2,4-di-chlorophenyl | O | CH2 | CH2 | H | compound No. 17-31, solvent: spectrometer: 399.95 MHz<br>8.3198 (2.68); 8.3063 (5.28); 8.2928 (2.73); 7.919 (13.13); 7.9139 (13.58); 7.5705 (11.09); 7.5641 (12.19); 7.3831 (5.65); 7.3766 (5.45); 7.3609 (7.7); 7.3545 (7.63); 7.2428 (12.91); 7.2205 (9.58); 6.9026 (13.27); 6.8974 (13.37); 4.1934 (7.15); 4.1785 (16); 4.1638 (7.93); 3.6025 (3.89); 3.5881 (10.79); 3.5737 (10.5); 3.5591 (3.6); 3.3328 (59.36); 2.7136 (0.32); 2.5439 (68.35); 2.5274 (1.08); 2.509 (33.15); 2.5046 (44.31); 2.5002 (34.03); 2.3703 (0.33); −0.0002 (1.74) |
| 17-32 | 4-chlorophenyl | CH2 | CH2 | CH2 | H | |
| 17-33 | 4-chlorophenyl | NCH3 | CH2 | CH2 | H | |
| 17-34 | 2,4-di-chlorophenyl | NCH3 | CH2 | CH2 | H | |
| 17-35 | 4-chlorophenyl | CH(OCH3) | CH2 | — | H | |
| 17-36 | 2,4-di-chlorophenyl | CH(OCH3) | CH2 | — | H | |
| 17-37 | 2-thienyl | CH2 | CH2 | — | H | [DMSO], spectrometer: 399.95 MHz<br>8.2894 (2.91); 8.2758 (5.41); 8.2620 (2.89); 7.9117 (15.02); 7.9066 (14.86); 7.7491 (0.38); 7.7366 (0.42); 7.7308 (0.43); 7.7212 (0.44); 7.3494 (7.92); 7.3467 (7.79); 7.3367 (8.65); 7.3340 (8.01); 7.1526 (0.35);<br>7.1430 (0.39); 6.9710 (6.64); 6.9625 (9.30); 6.9585 (7.00); 6.9498 (8.54);<br>6.9151 (9.96); 6.9070 (7.48); 6.8780 (16.00); 6.8728 (15.62); 3.4726 (0.57); 3.4472 (4.55); 3.4297 (9.92); 3.4147 (10.07); 3.3965 (5.26); 3.3313 (111.52); 3.0670 (0.51); 3.0409 (9.27); 3.0226 (15.47); 3.0045 (7.69); 2.6758 (0.66); 2.6713 (0.85); 2.6671 (0.63); 2.5067 (96.28); 2.5024 (121.05); 2.4980 (87.99); 2.3290 (0.81); 2.3246 (0.60); 1.3974 (3.19); 0.0078 (1.41); −0.0002 (26.06); −0.0084 (1.01) |
| 17-38 | 3-thienyl | CH2 | CH2 | — | H | |
| 17-39 | 2-furyl | CH2 | CH2 | — | H | |
| 17-40 | 3-furyl | CH2 | CH2 | — | H | |
| 17-41 | phenyl | CH2 | CH2 | CH(CH3) | H | [DMSO], spectrometer: 399.95 MHz<br>7.9127 (9.50); 7.9076 (9.66); 7.8923 (3.15); 7.8716 (3.10); 7.2928 (3.11);<br>7.2742 (8.22); 7.2560 (7.67); 7.2169 (9.97); 7.1996 (5.58); 7.1882 (2.37);<br>7.1850 (2.88); 7.1671 (4.16); 7.1525 (1.07); 7.1492 (1.57); 6.9296 (9.21);<br>6.9244 (9.27); 3.9844 (0.63); 3.9644 (1.41); 3.9487 (1.90); 3.9328 (1.47);<br>3.9127 (0.67); 3.3512 (9.38); 2.6692 (0.44); 2.6533 (0.55); 2.6454 (0.47);<br>2.6346 (1.92); 2.6197 (3.59); 2.6113 (2.75); 2.6028 (2.93); 2.5963 (3.75);<br>2.5804 (2.06); 2.5688 (0.52); 2.5629 (0.67); 2.5442 (27.24); 2.5274 (0.48); 2.5134 (7.30); 2.5093 (14.43); 2.5048 (18.94); 2.5003 (14.42); 1.8535 (0.47); 1.8371 (0.61); 1.8313 (0.86); 1.8196 (1.20); 1.8100 (0.88);<br>1.8042 (1.22); 1.7971 (1.74); 1.7821 (1.43); 1.7765 (1.30); 1.7605 (1.65);<br>1.7444 (1.58); 1.7364 (1.11); 1.7292 (1.54); 1.7217 (1.54); 1.7096 (1.05);<br>1.7053 (1.30); 1.6957 (0.64); 1.6887 (0.68); 1.6722 (0.41); 1.1507 (16.00); 1.1341 (15.91); −0.0002 (2.95) |
| 17-42 | phenyl | CH2 | CH2 | CH2 | H | [DMSO], spectrometer: 399.95 MHz<br>8.1368 (2.49); 8.1231 (4.66); 8.1094 (2.50); 7.9090 (14.35); 7.9038 (14.46); 7.3063 (4.74); 7.2877 (13.13); 7.2695 (12.50); 7.2351 (16.00); 7.2178 (8.62); 7.1973 (4.41); 7.1795 (6.60); 7.1616 (2.42); 6.8846 (14.75); 6.8794 (14.76); 3.3474 (19.82); 3.2286 (3.90); 3.2114 (8.33); 3.1960 (8.33); 3.1853 (1.91); 3.1788 (4.15); 2.6414 (7.03); 2.6225 (10.63); 2.6029 (7.70); 2.5441 (42.85); 2.5275 (0.71); 2.5093 (22.43); 2.5048 (29.37); 2.5004 (22.20); 1.8273 (2.15); 1.8084 (5.85); 1.7900 (8.00); 1.7714 (5.53); 1.7531 (1.93); −0.0002 (4.50) |

TABLE 17-continued
Compounds of the formula I-17
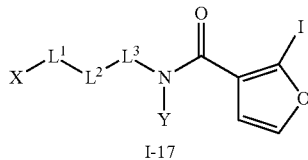
I-17
| Ex. No. | X | L¹ | L² | L³ | Y | Physical data: ¹H-NMR, δ [ppm] or CAS or patent No. |
|---|---|---|---|---|---|---|
| 17-43 | 2-Cl-phenyl | CH2 | CH2 | CH(CH3) | H | [DMSO], spectrometer: 399.95 MHz<br>7.9294 (3.33); 7.9154 (10.19); 7.9102 (11.89); 7.4127 (3.68); 7.4094 (3.74); 7.3935 (4.75); 7.3900 (4.76); 7.3633 (2.79); 7.3589 (3.23); 7.3446 (4.33); 7.3403 (4.71); 7.2924 (1.90); 7.2890 (2.15); 7.2741 (4.59); 7.2706 (4.36); 7.2558 (2.99); 7.2519 (2.61); 7.2437 (3.44); 7.2388 (3.45); 7.2246 (3.72); 7.2200 (3.70); 7.2059 (1.49); 7.2014 (1.35); 6.9319 (9.09); 6.9267 (9.20); 4.0286 (0.72); 4.0116 (1.55); 3.9926 (2.08); 3.9751 (1.67); 3.9575 (0.77); 3.3505 (12.19); 2.7561 (0.48); 2.7433 (2.36); 2.7376 (2.68); 2.7261 (3.82); 2.7159 (4.23); 2.7036 (2.81); 2.6978 (2.63); 2.6850 (0.55); 2.6768 (0.33); 2.5467 (22.42); 2.5297 (0.50); 2.5158 (6.75); 2.5118 (13.34); 2.5073 (17.62); 2.5028 (13.49); 1.7964 (0.38); 1.7844 (1.32); 1.7755 (1.58); 1.7658 (3.15); 1.7483 (3.08); 1.7459 (3.09); 1.7367 (2.84); 1.7262 (1.66); 1.7194 (1.44); 1.7086 (0.37); 1.1794 (16.00); 1.1628 (15.97); −0.0002 (2.80) |
| 17-44 | 4-t-butyl-phenyl | CH2 | CH2 | CH2 | H | [DMSO], spectrometer: 399.95 MHz<br>8.1086 (0.61); 7.9056 (1.74); 7.9005 (1.76); 7.3061 (1.74); 7.2855 (2.27); 7.1515 (2.05); 7.1309 (1.61); 6.8779 (1.72); 6.8727 (1.74); 3.3462 (2.94); 3.2216 (0.43); 3.2046 (0.95); 3.1888 (0.95); 3.1719 (0.45); 2.5985 (0.77); 2.5797 (1.25); 2.5605 (0.84); 2.5442 (1.83); 2.5093 (2.63); 2.5049 (3.45); 2.5005 (2.61); 1.7923 (0.67); 1.7740 (0.91); 1.7556 (0.63); 1.2603 (16.00); −0.0002 (0.55) |
| 17-45 | 4-methyl-phenyl | CH2 | CH2 | CH2 | H | [DMSO], spectrometer: 399.95 MHz<br>8.1177 (0.84); 8.1040 (1.61); 8.0903 (0.85); 7.9061 (4.81); 7.9010 (4.85); 7.1188 (1.26); 7.1127 (0.73); 7.0976 (11.87); 7.0932 (11.01); 7.0718 (1.22); 6.8801 (4.97); 6.8749 (4.98); 3.3461 (6.49); 3.2100 (1.25); 3.1929 (2.69); 3.1773 (2.70); 3.1602 (1.33); 2.5896 (2.25); 2.5708 (3.58); 2.5511 (2.73); 2.5438 (14.58); 2.5090 (7.74); 2.5046 (10.12); 2.5001 (7.69); 2.2601 (16.00); 1.7966 (0.68); 1.7777 (1.91); 1.7595 (2.63); 1.7409 (1.81); 1.7227 (0.62); −0.0002 (1.63) |
| 17-46 | phenyl | CH2 | CH2 | CH(CH2CH3) | H | [DMSO], spectrometer: 399.95 MHz<br>7.9184 (8.52); 7.9133 (8.64); 7.7938 (3.22); 7.7719 (3.28); 7.2878 (3.07); 7.2691 (8.26); 7.2509 (7.54); 7.2127 (10.10); 7.1952 (5.70); 7.1806 (2.98); 7.1626 (4.18); 7.1447 (1.57); 6.9428 (8.82); 6.9377 (9.07); 3.8539 (1.00); 3.8401 (1.66); 3.8339 (1.41); 3.8198 (1.75); 3.8061 (0.98); 3.3471 (13.64); 2.6696 (0.69); 2.6524 (0.92); 2.6482 (0.87); 2.6349 (1.70); 2.6159 (2.42); 2.5958 (1.85); 2.5907 (1.82); 2.5685 (2.70); 2.5447 (23.34); 2.5097 (13.17); 2.5054 (17.07); 2.5011 (13.39); 1.7774 (2.16); 1.7576 (4.32); 1.7388 (3.59); 1.7239 (1.48); 1.7170 (1.31); 1.5828 (0.69); 1.5686 (1.07); 1.5650 (1.06); 1.5493 (1.95); 1.5353 (1.66); 1.5305 (1.79); 1.5170 (1.55); 1.4940 (1.64); 1.4747 (2.32); 1.4557 (1.94); 1.4401 (1.34); 1.4213 (0.83); 0.8711 (7.89); 0.8527 (16.00); 0.8341 (7.15); −0.0002 (2.47) |
| 17-47 | 2-methoxy-phenyl | CH2 | CH2 | CH2 | H | [DMSO], spectrometer: 399.95 MHz<br>8.1191 (0.73); 8.1052 (1.39); 8.0914 (0.74); 7.9055 (3.72); 7.9003 (3.84); 7.1997 (0.68); 7.1959 (0.87); 7.1764 (1.97); 7.1702 (1.96); 7.1571 (1.61); 7.1515 (2.23); 6.9530 (2.31); 6.9330 (2.00); 6.8845 (4.80); 6.8793 (4.01); |

TABLE 17-continued

Compounds of the formula I-17

I-17

| Ex. No. | X | L¹ | L² | L³ | Y | Physical data: ¹H-NMR, δ [ppm] or CAS or patent No. |
|---|---|---|---|---|---|---|
| | | | | | | 6.8679 (2.33); 6.8494 (1.04); 3.7736 (16.00); 3.3485 (7.03); 3.2187 (0.99); 3.2016 (2.09); 3.1848 (2.13); 3.1682 (1.07); 2.6032 (1.84); 2.5844 (2.84); 2.5652 (2.04); 2.5445 (9.41); 2.5094 (5.94); 2.5051 (7.84); 2.5009 (6.13); 1.7730 (0.53); 1.7537 (1.48); 1.7357 (2.10); 1.7168 (1.40); 1.6986 (0.49); −0.0002 (0.98) |
| 17-48 | 2-methyl-phenyl | CH2 | CH2 | CH2 | H | [DMSO], spectrometer: 399.95 MHz<br>8.1622 (0.78); 8.1484 (1.45); 8.1346 (0.77); 7.9092 (4.51); 7.9041 (4.61);<br>7.1697 (0.97); 7.1650 (1.27); 7.1475 (2.45); 7.1254 (2.49); 7.1218 (2.59);<br>7.1119 (2.40); 7.0959 (3.43); 7.0908 (2.68); 7.0787 (1.31); 7.0746 (1.21);<br>7.0609 (0.43); 7.0568 (0.36); 6.8814 (4.59); 6.8763 (4.67); 3.3412 (12.11); 3.2653 (1.11); 3.2482 (2.59); 3.2328 (2.58); 3.2158 (1.19); 2.6194 (2.08); 2.6005 (2.71); 2.5803 (2.29); 2.5427 (15.63); 2.5258 (0.38); 2.5078 (13.05); 2.5033 (17.27); 2.4989 (13.26); 2.2571 (16.00); 1.7732 (0.61); 1.7544 (1.62); 1.7357 (2.13); 1.7170 (1.52); 1.6987 (0.55);<br>−0.0002 (2.60) |
| 17-49 | 3-methyl-phenyl | CH2 | CH2 | CH2 | H | [DMSO], spectrometer: 399.95 MHz<br>8.1261 (0.87); 8.1124 (1.65); 8.0986 (0.88); 7.9076 (4.97); 7.9024 (5.13);<br>7.1833 (1.42); 7.1646 (3.33); 7.1459 (2.14); 7.0322 (3.37); 7.0168 (2.30);<br>6.9972 (3.66); 6.9779 (1.70); 6.8828 (5.15); 6.8776 (5.29); 3.3453 (10.30); 3.2197 (1.29); 3.2025 (2.80); 3.1868 (2.80); 3.1699 (1.38); 2.5970 (2.32); 2.5781 (3.54); 2.5585 (2.58); 2.5436 (12.31); 2.5087 (8.59); 2.5042 (11.48); 2.4998 (8.92); 2.2758 (16.00); 1.8111 (0.70); 1.7921 (1.94); 1.7738 (2.66); 1.7551 (1.84); 1.7370 (0.65); −0.0002 (1.52) |
| 17-50 | 3-chloro-phenyl | CH2 | CH2 | CH2 | H | [DMSO], spectrometer: 399.95 MHz<br>8.1375 (2.05); 8.1238 (3.89); 8.1101 (2.08); 7.9127 (11.29); 7.9075 (11.48); 7.3386 (3.08); 7.3190 (16.00); 7.3000 (6.92); 7.2569 (5.46); 7.2366 (2.93); 7.2157 (5.86); 7.1966 (4.09); 6.8827 (11.57); 6.8775 (11.66); 3.3505 (14.94); 3.2206 (3.03); 3.2035 (6.85); 3.1881 (6.98); 3.1712 (3.18); 2.6569 (5.36); 2.6381 (8.51); 2.6187 (5.85); 2.5466 (34.11); 2.5298 (0.52); 2.5117 (16.03); 2.5073 (20.99); 2.5029 (16.00); 1.8282 (1.62); 1.8096 (4.68); 1.7911 (6.33); 1.7727 (4.47); 1.7546 (1.47);<br>−0.0002 (2.94) |
| 17-51 | 2,6-di-fluoro-phenyl | CH2 | CH2 | CH2 | H | [DMSO], spectrometer: 399.95 MHz<br>8.1763 (2.84); 8.1625 (5.46); 8.1486 (2.86); 7.9383 (0.32); 7.9332 (0.36);<br>7.9093 (15.44); 7.9041 (15.62); 7.3514 (1.34); 7.3344 (3.16); 7.3310 (3.01); 7.3137 (5.89); 7.2930 (3.89); 7.2761 (1.74); 7.1232 (0.33); 7.1063 (0.84); 7.1021 (1.22); 7.0893 (8.41); 7.0694 (13.19); 7.0496 (6.96); 7.0360 (0.98); 6.8676 (15.70); 6.8624 (16.00); 6.5148 (0.56); 3.3516 (23.80); 3.2443 (3.92); 3.2273 (8.04); 3.2098 (8.05); 3.1934 (4.14); 2.6878 (5.86); 2.6688 (9.90); 2.6494 (6.31); 2.5483 (49.22); 2.5313 (0.73); 2.5134 (22.83); 2.5090 (30.10); 2.5046 (23.13); 2.0825 (0.49); 1.7846 (2.16); 1.7653 (5.68); 1.7470 (8.12); 1.7281 (5.29); 1.7096 (1.91);<br>−0.0002 (4.53) |
| 17-52 | 4-chloro-phenyl | CH2 | CH2 | CH2 | H | [DMSO], spectrometer: 399.95 MHz<br>8.1353 (1.90); 8.1216 (3.60); 8.1078 (1.91); 7.9108 (10.72); 7.9057 (10.81); 7.3480 (9.46); 7.3434 (3.76); 7.3315 (4.99); 7.3269 (16.00); 7.2703 (14.47); 7.2492 (8.63); 6.8796 (10.90); 6.8744 (10.94); 3.3507 (15.76); 3.2175 (2.79); 3.2005 (6.27); 3.1852 (6.32); 3.1681 (2.92); 2.6374 (4.98); 2.6186 (7.80); 2.5992 (5.41); 2.5465 (32.60); 2.5296 (0.49); 2.5117 (14.92); 2.5072 (19.57); 2.5028 (14.83); 1.8128 (1.51); 1.7942 (4.29); 1.7758 (5.78); 1.7573 (4.06); 1.7392 (1.34); −0.0002 (3.23) |
| 17-53 | 2,6-di-chloro-phenyl | CH2 | CH2 | CH(CH3) | H | [DMSO], spectrometer: 399.95 MHz<br>7.9701 (3.26); 7.9492 (3.32); 7.9137 (9.17); 7.9086 (9.30); 7.4476 (12.36); 7.4274 (16.00); 7.2717 (5.17); 7.2522 (5.98); 7.2315 (3.53); |

TABLE 17-continued

Compounds of the formula I-17

I-17

| Ex. No. | X | L¹ | L² | L³ | Y | Physical data: ¹H-NMR, δ [ppm] or CAS or patent No. |
|---|---|---|---|---|---|---|
| | | | | | | 6.9302 (9.18); 6.9251 (9.17); 4.1088 (0.72); 4.0919 (1.62); 4.0745 (1.94); |
| | | | | | | 4.0552 (1.61); 4.0384 (0.74); 3.3437 (20.97); 2.9196 (0.41); 2.9041 (3.32); 2.8834 (6.19); 2.8696 (1.83); 2.8624 (3.70); 2.8464 (0.44); 2.5456 |
| | | | | | | (27.97); 2.5285 (0.67); 2.5107 (23.37); 2.5062 (30.62); 2.5018 (23.06); 1.7293 (0.38); 1.7136 (1.61); 1.7077 (1.48); 1.6987 (2.26); 1.6902 (2.74); |
| | | | | | | 1.6776 (2.43); 1.6700 (2.57); 1.6574 (1.45); 1.6485 (1.28); 1.6332 (0.41); |
| | | | | | | 1.2153 (15.51); 1.1986 (15.42); −0.0002 (4.88) |
| 17-54 | 3,5-di-chloro-phenyl | CH2 | CH2 | CH(CH3) | H | [DMSO], spectrometer: 399.95 MHz
7.9154 (9.25); 7.9103 (9.32); 7.8677 (3.43); 7.8470 (3.49); 7.3985 (3.80);
7.3942 (6.77); 7.3898 (4.20); 7.3043 (15.61); 7.2998 (14.40); 6.9135 (9.28); 6.9083 (9.30); 3.9652 (0.67); 3.9456 (1.43); 3.9297 (1.98); 3.9136
(1.53); 3.8938 (0.71); 3.3504 (12.26); 2.6914 (0.37); 2.6697 (0.64); 2.6568 (1.91); 2.6414 (3.71); 2.6339 (2.49); 2.6197 (3.97); 2.6028 (2.04);
2.5894 (0.69); 2.5680 (0.47); 2.5481 (23.90); 2.5310 (0.42); 2.5133 (13.84); 2.5089 (18.18); 2.5044 (13.87); 1.8187 (0.39); 1.8135 (0.60); 1.8011 (1.23); 1.7803 (3.13); 1.7629 (3.66); 1.7503 (1.72); 1.7430 (2.69);
1.7261 (1.32); 1.7141 (0.46); 1.7070 (0.42); 1.1463 (16.00); 1.1297 (15.94); −0.0002 (2.95) |
| 17-55 | 2,6-di-methyl-phenyl | CH2 | CH2 | CH2 | H | [DMSO], spectrometer: 399.95 MHz
8.2139 (0.48); 8.1999 (0.94); 8.1859 (0.48); 7.9149 (2.54); 7.9097 (2.55);
6.9585 (8.29); 6.8842 (2.65); 6.8790 (2.68); 3.3478 (3.48); 3.3182 (0.64);
3.3015 (1.64); 3.2862 (1.65); 3.2695 (0.66); 2.6167 (1.17); 2.6033 (0.97);
2.5962 (1.23); 2.5881 (0.97); 2.5752 (1.26); 2.5441 (6.22); 2.5093 (3.69);
2.5049 (4.78); 2.5006 (3.64); 2.2571 (16.00); 1.6572 (0.33); 1.6395 (0.82); 1.6275 (0.83); 1.6191 (0.96); 1.6117 (0.84); 1.5990 (0.79); −0 .0002 (0.77) |
| 17-56 | 2,5-di-chloro-phenyl | CH2 | CH2 | CH2 | H | [DMSO], spectrometer: 399.95 MHz
8.1790 (2.75); 8.1651 (5.42); 8.1511 (2.80); 7.9110 (15.55); 7.9058 (16.00); 7.5056 (11.96); 7.4992 (12.95); 7.4642 (11.69); 7.4428 (15.63); 7.3259 (8.07); 7.3194 (7.73); 7.3045 (6.07); 7.2980 (5.83); 6.8747 (15.71); 6.8695 (15.98); 3.3409 (54.02); 3.2545 (3.74); 3.2375 (9.03); 3.2220 (9.06); 3.2051 (3.98); 2.7480 (7.09); 2.7293 (9.79); 2.7096 (7.77);
2.6778 (0.48); 2.6734 (0.61); 2.6691 (0.46); 2.5438 (60.65); 2.5264 (1.86); 2.5087 (62.90); 2.5043 (83.39); 2.4998 (63.85); 2.3354 (0.40); 2.3311 (0.54); 2.3267 (0.41); 1.8158 (1.98); 1.7974 (5.61); 1.7788 (7.53);
1.7601 (5.39); 1.7422 (1.81); 0.0080 (0.47); −0.0002 (13.70); −0.0083 (0.63) |
| 17-57 | 4-iso-propoxy-phenyl | CH2 | CH2 | CH2 | H | [DMSO], spectrometer: 399.95 MHz
8.1129 (0.67); 8.0991 (1.30); 8.0853 (0.68); 7.9061 (3.64); 7.9010 (3.71);
7.1187 (3.51); 7.0973 (4.07); 6.8816 (3.64); 6.8764 (3.67); 6.8325 (0.54);
6.8255 (4.39); 6.8041 (3.88); 4.5717 (0.50); 4.5566 (1.28); 4.5415 (1.73);
4.5265 (1.30); 4.5114 (0.52); 3.3459 (5.03); 3.2119 (0.89); 3.1949 (1.96);
3.1790 (1.96); 3.1622 (0.95); 2.5618 (1.61); 2.5448 (11.46); 2.5237 (1.88); 2.5143 (2.54); 2.5100 (4.88); 2.5056 (6.48); 2.5011 (4.98); 1.7872
(0.47); 1.7683 (1.36); 1.7501 (1.85); 1.7317 (1.29); 1.7135 (0.43); 1.2464
(16.00); 1.2313 (16.00); −0.0002 (1.10) |
| 17-58 | 3-tri-fluoro-methyl-phenyl | CH2 | CH2 | CH(CH3) | H | [DMSO], spectrometer: 399.95 MHz
7.9177 (9.64); 7.9126 (10.03); 7.9032 (3.64); 7.8824 (3.43); 7.6218 (0.39); 7.5774 (6.16); 7.5595 (1.29); 7.5335 (12.02); 7.5299 (12.17); 7.5189 (2.87); 7.5029 (0.62); 7.4926 (0.64); 7.4584 (0.35); 6.9287 (9.37); |

TABLE 17-continued
Compounds of the formula I-17
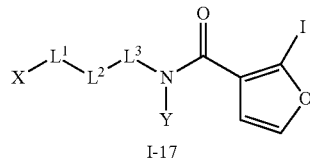
I-17
| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 6.9235 (9.60); 6.9149 (0.77); 3.9956 (0.63); 3.9755 (1.44); 3.9600 (1.90); 3.9443 (1.49); 3.9240 (0.69); 3.3534 (16.27); 2.7807 (0.46); 2.7649 (0.63); 2.7569 (0.64); 2.7461 (1.87); 2.7292 (3.15); 2.7228 (2.93); 2.7064 (3.72); 2.6879 (2.03); 2.6768 (0.69); 2.6712 (0.71); 2.6534 (0.48); 2.5487 (28.87); 2.5319 (0.45); 2.5138 (13.94); 2.5094 (18.54); 2.5050 (14.40); 1.8741 (0.36); 1.8583 (0.50); 1.8515 (0.72); 1.8399 (1.22); 1.8250 (1.32); 1.8178 (1.92); 1.8030 (2.44); 1.7972 (1.75); 1.7867 (1.97); 1.7799 (1.97); 1.7718 (1.81); 1.7647 (1.72); 1.7483 (1.35); 1.7389 (0.59); 1.7307 (0.61); 1.7150 (0.34); 1.1817 (0.51); 1.1608 (16.00); 1.1442 (15.88); −0.0002 (2.85) |
| 17-59 | 4-methyl-phenyl | CH2 | CH2 | CH(CH3) | H | [DMSO], spectrometer: 399.95 MHz<br>7.9137 (9.40); 7.9086 (9.59); 7.8870 (3.27); 7.8662 (3.28); 7.2596 (4.34); 7.2452 (5.33); 7.2381 (6.47); 7.2292 (2.57); 7.2239 (5.66); 7.1180 (0.82); 7.1106 (6.27); 7.1055 (2.21); 7.0940 (2.46); 7.0882 (9.93); 7.0828 (2.71); 7.0711 (1.87); 7.0661 (4.85); 7.0587 (0.64); 6.9256 (9.30); 6.9204 (9.37); 3.9715 (0.65); 3.9514 (1.44); 3.9358 (1.92); 3.9201 (1.50); 3.8999 (0.69); 3.3558 (9.54); 2.6623 (0.36); 2.6466 (0.55); 2.6388 (0.50); 2.6275 (1.88); 2.6124 (3.53); 2.6047 (2.75); 2.5894 (3.81); 2.5731 (2.03); 2.5467 (26.29); 2.5299 (0.51); 2.5158 (6.09); 2.5118 (12.17); 2.5074 (16.17); 2.5029 (12.44); 1.8366 (0.46); 1.8202 (0.60); 1.8146 (0.91); 1.8025 (1.23); 1.7932 (0.90); 1.7872 (1.25); 1.7806 (1.89); 1.7655 (1.57); 1.7596 (1.36); 1.7448 (1.37); 1.7303 (1.60); 1.7229 (1.16); 1.7154 (1.59); 1.7085 (1.57); 1.6918 (1.34); 1.6819 (0.66); 1.6753 (0.67); 1.6586 (0.41); 1.1462 (16.00); 1.1297 (15.96); −0.0002 (2.69) |
| 17-60 | 2-methyl-phenyl | CH2 | CH2 | CH(CH3) | H | |
| 17-61 | 3,4-di-chloro-phenyl | CH2 | CH2 | CH(CH3) | H | [DMSO], spectrometer: 399.95 MHz<br>7.9133 (9.29); 7.9082 (9.50); 7.8746 (3.42); 7.8538 (3.49); 7.5303 (7.20); 7.5201 (0.45); 7.5097 (8.46); 7.5008 (7.28); 7.4960 (7.56); 7.2337 (4.03); 7.2288 (4.02); 7.2130 (3.57); 7.2081 (3.56); 6.9111 (9.56); 6.9059 (9.71); 3.9618 (0.63); 3.9415 (1.40); 3.9263 (1.87); 3.9105 (1.49); 3.8901 (0.69); 3.3482 (20.76); 2.6811 (0.43); 2.6647 (0.54); 2.6584 (0.49); 2.6461 (1.92); 2.6315 (3.40); 2.6236 (2.86); 2.6145 (3.20); 2.6094 (3.54); 2.5934 (2.08); 2.5770 (0.63); 2.5581 (0.54); 2.5473 (16.67); 2.5305 (0.46); 2.5165 (7.65); 2.5125 (15.43); 2.5080 (20.67); 2.5036 (15.94); 1.8368 (0.35); 1.8201 (0.49); 1.8153 (0.74); 1.8027 (1.20); 1.7942 (0.77); 1.7814 (2.15); 1.7658 (2.21); 1.7605 (1.96); 1.7530 (1.90); 1.7452 (1.81); 1.7379 (1.92); 1.7333 (1.73); 1.7157 (1.34); 1.7046 (0.52); 1.6990 (0.52); 1.1441 (15.89); 1.1276 (16.00); −0.0002 (2.67) |
| 17-62 | 3,5-di-chloro-phenyl | CH2 | CH2 | CH2 | H | [DMSO], spectrometer: 399.95 MHz<br>8.1253 (1.68); 8.1116 (3.23); 8.0981 (1.69); 7.9117 (9.06); 7.9066 (9.20); 7.4187 (3.58); 7.4142 (7.05); 7.4095 (4.40); 7.3363 (16.00); 7.3317 (14.77); 6.8716 (9.31); 6.8664 (9.38); 3.3428 (25.62); 3.2070 (2.32); 3.1901 (5.61); 3.1749 (5.61); 3.1581 (2.46); 2.6645 (4.20); 2.6458 (6.99); |

TABLE 17-continued

Compounds of the formula I-17

$$\text{X}-\text{L}^1-\text{L}^2-\text{L}^3-\underset{\underset{Y}{|}}{N}-\underset{\underset{}{\overset{O}{\|}}}{C}-\text{(2-iodo-furan-3-yl)}$$

I-17

| Ex. No. | X | L¹ | L² | L³ | Y | Physical data: ¹H-NMR, δ [ppm] or CAS or patent No. |
|---|---|---|---|---|---|---|
| | | | | | | 2.6266 (4.51); 2.5445 (29.25); 2.5275 (0.91); 2.5096 (28.36); 2.5052 (37.26); 2.5007 (28.41); 1.8263 (1.22); 1.8081 (3.76); 1.7896 (5.10); 1.7714 (3.60); 1.7535 (1.11); −0.0002 (5.72) |
| 17-63 | 2,6-di-methyl-phenyl | CH2 | CH2 | CH(CH3) | H | [DMSO], spectrometer: 399.95 MHz<br>7.9458 (1.00); 7.9201 (3.12); 7.9149 (2.95); 6.9495 (8.61); 6.9341 (2.86);<br>6.9289 (2.85); 4.0731 (0.46); 4.0552 (0.57); 4.0370 (0.46); 3.3484 (3.90);<br>2.5991 (0.60); 2.5875 (0.80); 2.5765 (0.82); 2.5684 (0.82); 2.5582 (0.92);<br>2.5443 (12.30); 2.5095 (3.78); 2.5050 (4.97); 2.5006 (3.79); 2.2564 (16.00); 1.5993 (0.59); 1.5780 (1.35); 1.5604 (1.10); 1.5426 (0.44); 1.5389 (0.43); 1.2042 (4.47); 1.1875 (4.46); −0.0002 (0.86) |
| 17-64 | 4-(tri-fluoro-methyl)phenyl | CH2 | CH2 | CH(CH3) | H | [DMSO], spectrometer: 399.95 MHz<br>7.9159 (9.37); 7.9108 (11.30); 7.8886 (3.51); 7.6422 (7.44); 7.6220 (9.02); 7.4590 (8.52); 7.4389 (7.15); 6.9214 (8.61); 6.9162 (8.74); 3.9910<br>(0.66); 3.9710 (1.47); 3.9556 (1.95); 3.9398 (1.54); 3.9196 (0.71); 3.3562<br>(15.85); 2.7561 (0.50); 2.7376 (1.86); 2.7235 (3.17); 2.7150 (2.91); 2.7024 (3.32); 2.6863 (2.01); 2.6701 (0.60); 2.6515 (0.35); 2.5494 (19.48); 2.5327 (0.40); 2.5145 (11.93); 2.5101 (15.65); 2.5058 (12.13); 1.8834 (0.42); 1.8616 (0.90); 1.8492 (1.22); 1.8464 (1.20); 1.8404 (0.92);<br>1.8277 (2.04); 1.8117 (1.77); 1.8062 (1.76); 1.7887 (2.02); 1.7792 (1.30);<br>1.7709 (1.71); 1.7650 (1.66); 1.7481 (1.40); 1.7375 (0.64); 1.7317 (0.64);<br>1.7146 (0.38); 1.1605 (16.00); 1.1440 (15.96); −0.0002 (2.35) |
| 17-65 | 2,5-di-chloro-phenyl | CH2 | CH2 | CH(CH3) | H | [DMSO], spectrometer: 399.95 MHz<br>7.9161 (12.47); 7.9109 (10.86); 7.8956 (3.51); 7.4585 (7.10); 7.4509 (10.82); 7.4285 (9.20); 7.3111 (4.80); 7.3046 (4.53); 7.2897 (3.59); 7.2833 (3.42); 6.9247 (9.47); 6.9195 (9.66); 4.0229 (0.74); 4.0060 (1.67);<br>3.9863 (2.07); 3.9691 (1.75); 3.9521 (0.79); 3.3489 (14.21); 2.7499 (0.38); 2.7350 (2.34); 2.7299 (2.64); 2.7175 (4.40); 2.7076 (4.32); 2.6956<br>(2.73); 2.6902 (2.62); 2.6758 (0.52); 2.5475 (26.27); 2.5306 (0.47); 2.5259 (0.62); 2.5170 (7.43); 2.5127 (15.17); 2.5082 (20.37); 2.5037 (15.67); 2.4997 (8.27); 1.7760 (2.20); 1.7587 (4.45); 1.7371 (4.35); 1.7190 (2.12); 1.1764 (16.00); 1.1598 (15.96); −0.0002 (3.49) |
| 17-66 | 4-phen-oxy-phenyl | CH2 | CH2 | CH2 | H | [DMSO], spectrometer: 399.95 MHz<br>8.1416 (2.26); 8.1278 (4.38); 8.1140 (2.25); 7.9119 (12.71); 7.9067 (12.91); 7.4000 (1.05); 7.3943 (7.31); 7.3891 (2.86); 7.3816 (1.62); 7.3757 (11.30); 7.3730 (10.98); 7.3592 (3.48); 7.3543 (9.31); 7.3483 (1.35); 7.2570 (12.44); 7.2357 (14.15); 7.1346 (2.60); 7.1323 (4.38); 7.1299 (2.80); 7.1139 (7.39); 7.0978 (2.03); 7.0954 (3.31); 7.0930 (2.02);<br>6.9878 (10.15); 6.9852 (12.61); 6.9660 (11.14); 6.9637 (9.80); 6.9565 (2.71); 6.9486 (16.00); 6.9438 (5.72); 6.9321 (4.90); 6.9273 (14.23); 6.9203 (1.89); 6.8901 (12.33); 6.8849 (12.57); 3.3529 (18.81); 3.2413 (3.04); 3.2243 (6.83); 3.2088 (6.79); 3.1918 (3.21); 2.6380 (5.28); 2.6192<br>(8.32); 2.5998 (5.76); 2.5459 (37.02); 2.5293 (0.53); 2.5242 (0.73); 2.5154 (8.42); 2.5111 (17.04); 2.5066 (22.70); 2.5021 (17.21); 2.4980 (8.84); 1.8327 (1.62); 1.8139 (4.61); 1.7956 (6.24); 1.7771 (4.38); 1.7590 (1.46); −0.0002 (4.51) |
| 17-67 | 3-chloro-phenyl | CH2 | CH2 | CH(CH3) | H | [DMSO], spectrometer: 399.95 MHz<br>7.9148 (9.31); 7.9097 (9.61); 7.8856 (3.41); 7.8649 (3.46); 7.3233 (2.54);<br>7.3038 (6.89); 7.2938 (7.18); 7.2894 (5.52); 7.2850 (6.59); 7.2426 (4.38);<br>7.2386 (3.61); 7.2255 (2.04); 7.2210 (2.42); 7.1934 (4.78); 7.1746 (3.43);<br>6.9228 (9.33); 6.9176 (9.55); 3.9731 (0.65); 3.9530 (1.45); 3.9373 (1.94);<br>3.9216 (1.51); 3.9015 (0.69); 3.3503 (14.85); 2.6819 (0.44); 2.6665 (0.63); 2.6588 (0.55); 2.6477 (1.94); 2.6320 (3.64); 2.6247 (2.88); 2.6090 |

TABLE 17-continued

Compounds of the formula I-17

| Ex. No. | X | L¹ | L² | L³ | Y | Physical data: $^1$H-NMR, δ [ppm] or CAS or patent No. |
|---|---|---|---|---|---|---|
| | | | | | | (4.03); 2.5920 (2.07); 2.5749 (0.70); 2.5570 (0.74); 2.5461 (26.91); 2.5290 (0.48); 2.5109 (14.21); 2.5066 (18.95); 2.5022 (14.74); 2.0803 (0.33); 1.8429 (0.40); 1.8267 (0.54); 1.8209 (0.80); 1.8088 (1.23); 1.7993 (0.85); 1.7934 (1.30); 1.7871 (2.01); 1.7690 (2.21); 1.7511 (2.30); 1.7368 (1.72); 1.7301 (1.65); 1.7135 (1.33); 1.7036 (0.57); 1.6963 (0.60); 1.6803 (0.35); 1.1483 (16.00); 1.1318 (15.96); −0.0002 (3.04) |
| 17-68 | 4-phenoxyphenyl | CH2 | CH2 | CH(CH3) | H | |
| 17-69 | 2,4-dichlorophenyl | CH2 | CH2 | CH(CH3) | H | [DMSO], spectrometer: 399.95 MHz 7.9226 (3.71); 7.9138 (9.65); 7.9087 (9.95); 7.9019 (3.90); 7.5560 (6.70); 7.5513 (6.84); 7.3970 (2.67); 7.3764 (10.70); 7.3663 (7.40); 7.3615 (6.72); 7.3456 (1.65); 7.3408 (1.81); 6.9205 (9.31); 6.9153 (9.31); 4.0118 (0.73); 3.9948 (1.57); 3.9759 (2.10); 3.9585 (1.67); 3.9409 (0.76); 3.3505 (15.85); 2.7400 (0.47); 2.7269 (2.46); 2.7221 (2.75); 2.7098 (4.10); 2.7004 (4.42); 2.6875 (2.87); 2.6824 (2.74); 2.5472 (24.81); 2.5300 (0.52); 2.5122 (16.58); 2.5078 (21.72); 2.5034 (16.52); 2.0817 (0.33); 1.7801 (0.37); 1.7676 (1.32); 1.7600 (1.59); 1.7492 (3.26); 1.7375 (2.74); 1.7297 (3.24); 1.7219 (2.83); 1.7095 (1.62); 1.7046 (1.45); 1.6927 (0.33); 1.1715 (16.00); 1.1549 (15.92); −0.0002 (3.53) |
| 17-70 | 2-difluoromethoxyphenyl | CH2 | CH2 | CH(CH3) | H | [DMSO], spectrometer: 399.95 MHz 7.9109 (10.54); 7.9057 (12.57); 7.8833 (3.48); 7.3646 (4.15); 7.3332 (3.10); 7.3294 (3.60); 7.3146 (3.94); 7.3106 (4.51); 7.2863 (1.47); 7.2820 (1.50); 7.2671 (3.68); 7.2629 (3.45); 7.2476 (3.22); 7.2433 (2.79); 7.1958 (3.12); 7.1931 (3.69); 7.1785 (11.34); 7.1749 (5.90); 7.1523 (5.24); 7.1317 (3.64); 6.9929 (4.28); 6.9275 (9.62); 6.9223 (9.76); 3.9923 (0.70); 3.9737 (1.52); 3.9567 (2.11); 3.9398 (1.60); 3.9211 (0.73); 3.3517 (14.29); 2.6712 (0.41); 2.6546 (3.38); 2.6344 (6.18); 2.6151 (3.77); 2.5987 (0.37); 2.5454 (33.18); 2.5285 (0.38); 2.5239 (0.48); 2.5149 (5.61); 2.5106 (11.41); 2.5061 (15.28); 2.5017 (11.65); 1.7864 (0.74); 1.7726 (1.18); 1.7674 (1.04); 1.7521 (3.00); 1.7331 (3.96); 1.7150 (2.78); 1.6950 (1.44); 1.6822 (0.50); 1.1649 (16.00); 1.1483 (15.94); −0.0002 (2.99) |
| 17-71 | 4-methoxyphenyl | CH2 | CH2 | CH2 | H | [DMSO], spectrometer: 399.95 MHz 8.1154 (0.58); 8.1017 (1.12); 8.0879 (0.59); 7.9071 (3.45); 7.9019 (3.52); 7.1541 (0.38); 7.1470 (3.26); 7.1255 (3.78); 6.8825 (3.56); 6.8773 (3.59); 6.8643 (0.54); 6.8569 (4.21); 6.8520 (1.51); 6.8402 (1.29); 6.8354 (3.69); 6.8281 (0.48); 3.7181 (16.00); 3.3485 (4.93); 3.3464 (4.93); 3.2082 (0.83); 3.1911 (1.79); 3.1755 (1.78); 3.1585 (0.88); 2.5734 (1.51); 2.5546 (2.49); 2.5443 (10.09); 2.5355 (1.82); 2.5137 (2.55); 2.5095 (5.10); 2.5050 (6.78); 2.5005 (5.18); 2.4964 (2.71); 1.7871 (0.45); 1.7681 (1.27); 1.7499 (1.73); 1.7315 (1.19); 1.7133 (0.40); −0.0002 (1.21) |
| 17-72 | 4-chlorophenyl | CH2 | CH2 | CH(CH3) | H | [DMSO], spectrometer: 399.95 MHz 7.9102 (9.37); 7.9051 (9.64); 7.8835 (3.31); 7.8627 (3.32); 7.3334 (8.44); 7.3291 (3.40); 7.3172 (3.89); 7.3124 (14.01); 7.2482 (12.42); 7.2272 (7.78); 6.9151 (9.38); 6.9099 (9.55); 3.9599 (0.62); 3.9398 (1.38); 3.9239 (1.85); 3.9085 (1.44); 3.8883 (0.66); 3.3429 (33.50); 3.3398 (28.83); 2.6732 (0.32); 2.6623 (0.40); 2.6464 (0.52); 2.6390 (0.46); 2.6272 (1.90); 2.6126 (3.44); 2.6044 (2.81); 2.5960 (3.05); 2.5900 (3.56); 2.5742 (2.06); |

TABLE 17-continued
Compounds of the formula I-17
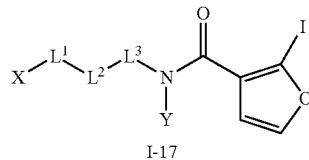
I-17
| Ex. No. | X | L¹ | L² | L³ | Y | Physical data: ¹H-NMR, δ [ppm] or CAS or patent No. |
|---|---|---|---|---|---|---|
| | | | | | | 2.5569 (0.68); 2.5433 (4.69); 2.5263 (0.94); 2.5085 (32.46); 2.5040 (43.18); 2.4996 (33.25); 1.8325 (0.42); 1.8106 (0.87); 1.7981 (1.16); 1.7895 (0.86); 1.7826 (1.23); 1.7766 (1.89); 1.7611 (1.58); 1.7557 (1.39); 1.7469 (1.11); 1.7394 (1.10); 1.7306 (1.61); 1.7235 (1.14); 1.7152 (1.56); 1.7088 (1.53); 1.6922 (1.30); 1.6820 (0.60); 1.6747 (0.62); 1.6586 (0.36); 1.1407 (16.00); 1.1242 (15.98); −0.0002 (6.79); −0.0080 (0.33) |
| 17-73 | 4-chloro-phenyl | CH2 | CH2 | CH(i-propyl) | H | [DMSO], spectrometer: 399.95 MHz<br>7.9210 (6.88); 7.9158 (6.99); 7.7394 (2.51); 7.7167 (2.55); 7.3268 (6.28); 7.3222 (2.46); 7.3103 (3.03); 7.3057 (10.26); 7.2427 (9.13); 7.2216 (5.74); 6.9487 (6.87); 6.9435 (6.92); 3.7815 (0.43); 3.7716 (0.56); 3.7670 (0.62); 3.7573 (1.28); 3.7440 (1.27); 3.7340 (1.27); 3.7246 (0.63); 3.7197 (0.65); 3.7141 (0.46); 3.7101 (0.47); 3.3484 (11.94); 2.6643 (0.55); 2.6508 (0.72); 2.6401 (0.70); 2.6288 (1.30); 2.6164 (1.12); 2.6064 (1.04); 2.5928 (0.93); 2.5468 (12.85); 2.5308 (1.09); 2.5257 (0.72); 2.5120 (10.55); 2.5075 (13.85); 2.5031 (10.20); 2.4988 (5.64); 2.4800 (0.82); 2.4733 (0.88); 2.4559 (0.61); 1.7941 (0.58); 1.7889 (0.52); 1.7768 (1.47); 1.7727 (1.39); 1.7607 (2.36); 1.7553 (1.81); 1.7452 (3.03); 1.7275 (2.17); 1.7249 (2.15); 1.7103 (1.66); 1.6990 (0.89); 1.6861 (0.78); 1.6760 (0.45); 0.8728 (16.00); 0.8557 (15.46); −0.0002 (2.35) |
| 17-74 | 4-fluoro-phenyl | CH2 | CH2 | CH2 | H | [DMSO], spectrometer: 399.95 MHz<br>8.1333 (2.48); 8.1196 (4.75); 8.1058 (2.53); 7.9105 (15.11); 7.9053 (15.43); 7.2880 (0.80); 7.2806 (6.94); 7.2755 (3.27); 7.2663 (8.40); 7.2591 (10.04); 7.2503 (3.89); 7.2449 (8.86); 7.2380 (1.36); 7.1319 (1.17); 7.1243 (10.12); 7.1191 (3.30); 7.1079 (3.67); 7.1020 (16.00); 7.0962 (4.07); 7.0849 (2.87); 7.0798 (7.78); 7.0723 (1.00); 6.8921 (0.37); 6.8819 (15.19); 6.8767 (15.35); 3.3496 (21.88); 3.2187 (3.76); 3.2016 (8.28); 3.1864 (8.41); 3.1691 (4.01); 2.6336 (6.42); 2.6147 (10.23); 2.5953 (7.03); 2.5461 (45.68); 2.5292 (0.68); 2.5155 (10.63); 2.5112 (21.36); 2.5068 (28.40); 2.5023 (21.58); 2.4983 (11.28); 2.0803 (0.35); 1.8108 (2.05); 1.7920 (5.74); 1.7736 (7.78); 1.7551 (5.47); 1.7370 (1.86); −0.0002 (4.63) |
| 17-75 | 4-chloro-phenyl | CH2 | CH2 | CH(n-propyl) | H | [DMSO], spectrometer: 399.95 MHz<br>7.9144 (8.00); 7.9092 (8.05); 7.7826 (3.02); 7.7605 (3.08); 7.3256 (7.35); 7.3211 (2.86); 7.3092 (3.60); 7.3045 (12.10); 7.2426 (10.83); 7.2215 (6.74); 6.9230 (8.00); 6.9178 (8.02); 3.9277 (0.83); 3.9094 (1.48); 3.8925 (1.44); 3.8735 (0.83); 3.3498 (11.45); 2.6567 (0.45); 2.6392 (0.76); 2.6217 (1.49); 2.6033 (2.26); 2.5885 (1.77); 2.5846 (1.81); 2.5684 (2.50); 2.5468 (11.14); 2.5330 (1.00); 2.5252 (0.62); 2.5161 (6.07); 2.5120 (11.61); 2.5075 (15.13); 2.5031 (11.40); 1.7562 (1.82); 1.7366 (3.72); 1.7176 (2.97); 1.7027 (1.20); 1.6966 (1.07); 1.4837 (1.46); 1.4643 (4.13); 1.4466 (4.92); 1.4289 (2.37); 1.3625 (0.35); 1.3452 (0.66); 1.3292 (1.47); 1.3112 (2.42); 1.2927 (2.57); 1.2899 (2.50); 1.2708 (2.00); 1.2528 (1.08); 1.2366 (0.62); 0.8749 (8.05); 0.8567 (16.00); 0.8384 (6.91); −0.0002 (2.85) |
| 17-76 | 4-chloro-phenyl | CH2 | CH2 | CH(t-butyl) | H | [DMSO], spectrometer: 399.95 MHz<br>7.9228 (2.58); 7.9177 (2.61); 7.6241 (0.93); 7.6000 (0.94); 7.3261 (2.22); 7.3216 (0.86); 7.3050 (3.70); 7.2455 (3.30); 7.2244 (2.03); 6.9470 (2.57); 6.9419 (2.58); 3.7681 (0.35); 3.7642 (0.37); 3.7400 (0.76); 3.7159 (0.38); 3.7113 (0.34); 3.3497 (4.20); 2.6099 (0.50); 2.5990 (0.37); 2.5868 (0.36); |

TABLE 17-continued

Compounds of the formula I-17

I-17

| Ex. No. | X | L¹ | L² | L³ | Y | Physical data: ¹H-NMR, δ [ppm] or CAS or patent No. |
|---|---|---|---|---|---|---|
| | | | | | | 2.5467 (4.96); 2.5119 (3.53); 2.5074 (4.65); 2.5030 (3.51); 2.4388 (0.40);<br>2.4345 (0.43); 2.4164 (0.38); 1.7974 (0.33); 1.7918 (0.41); 1.6760 (0.35);<br>0.8714 (16.00); −0.0002 (0.79) |
| 17-77 | 2-chloro-phenyl | CH2 | CH2 | CH2 | H | [DMSO], spectrometer: 399.95 MHz<br>8.1852 (2.64); 8.1712 (5.09); 8.1573 (2.64); 7.9117 (15.90); 7.9065 (16.00); 7.4255 (6.16); 7.4221 (6.15); 7.4062 (7.97); 7.4027 (7.94); 7.3933 (5.09); 7.3889 (5.58); 7.3746 (6.93); 7.3703 (7.57); 7.3057 (3.11);<br>7.3022 (3.47); 7.2873 (7.71); 7.2837 (7.22); 7.2689 (5.15); 7.2651 (4.34);<br>7.2559 (5.61); 7.2510 (5.68); 7.2368 (6.20); 7.2322 (6.12); 7.2180 (2.41);<br>7.2136 (2.18); 6.8936 (0.38); 6.8836 (15.85); 6.8784 (15.89); 3.3493 (25.35); 3.2650 (3.86); 3.2478 (8.57); 3.2323 (8.54); 3.2152 (4.03); 2.7566 (7.33); 2.7379 (9.57); 2.7179 (8.01); 2.5463 (46.61); 2.5295 (0.65); 2.5157 (11.43); 2.5115 (22.76); 2.5070 (30.08); 2.5025 (22.68); 1.8236 (2.10); 1.8047 (5.55); 1.7863 (7.53); 1.7676 (5.20); 1.7493 (1.87);<br>−0.0002 (5.43) |
| 17-78 | 4-chloro-phenyl | CH2 | CH(CH3) | — | cy-clo-pro-pyl | |
| 17-79 | 2-bromo-phenyl | CH2 | CH2 | CH(CH3) | H | [DMSO], spectrometer: 399.95 MHz<br>7.9328 (3.45); 7.9150 (11.67); 7.9099 (12.20); 7.5802 (4.63); 7.5786 (4.57); 7.5605 (5.06); 7.5585 (4.91); 7.3661 (1.84); 7.3613 (2.38); 7.3471<br>(5.66); 7.3422 (5.54); 7.3332 (3.78); 7.3308 (3.66); 7.3153 (4.51); 7.3131<br>(4.49); 7.2966 (1.75); 7.2940 (1.68); 7.1626 (2.45); 7.1576 (2.50); 7.1427<br>(3.33); 7.1396 (3.31); 7.1250 (1.93); 7.1201 (1.83); 6.9353 (9.53); 6.9301<br>(9.50); 4.0370 (0.76); 4.0202 (1.71); 4.0006 (2.07); 3.9833 (1.77); 3.9662<br>(0.79); 3.3495 (13.99); 2.7573 (0.38); 2.7434 (2.39); 2.7378 (2.66); 2.7257 (4.41); 2.7154 (4.49); 2.7035 (2.77); 2.6978 (2.61); 2.6827 (0.46);<br>2.5467 (22.88); 2.5296 (0.35); 2.5160 (6.46); 2.5119 (12.88); 2.5074 (17.03); 2.5029 (12.89); 1.7731 (2.25); 1.7559 (4.51); 1.7505 (3.17); 1.7337 (4.25); 1.7158 (2.15); 1.1849 (16.00); 1.1683 (15.89); −0.0002 (3.03) |
| 17-80 | 3,4-bis-methoxy-phenyl | CH2 | CH2 | CH2 | H | [DMSO], spectrometer: 399.95 MHz<br>8.1153 (0.66); 8.1015 (1.31); 8.0877 (0.68); 7.9095 (3.89); 7.9043 (3.99);<br>6.8878 (3.91); 6.8826 (3.95); 6.8581 (2.42); 6.8377 (3.28); 6.8180 (2.67);<br>6.8134 (3.01); 6.7371 (1.69); 6.7325 (1.60); 6.7168 (1.25); 6.7121 (1.20);<br>3.7419 (15.94); 3.7117 (16.00); 3.3469 (7.03); 3.2211 (0.87); 3.2040 (1.97); 3.1883 (1.97); 3.1715 (0.93); 2.5721 (1.57); 2.5532 (2.64); 2.5442<br>(10.06); 2.5342 (1.87); 2.5230 (0.36); 2.5136 (2.95); 2.5093 (5.98); 2.5048 (8.02); 2.5004 (6.16); 2.4963 (3.25); 1.8073 (0.46); 1.7885 (1.35);<br>1.7703 (1.84); 1.7519 (1.27); 1.7338 (0.41); −0.0002 (1.30) |
| 17-81 | 4-meth-oxy-phenyl | CH2 | CH2 | CH(CH3) | H | compound No. 17-81, solvent: spectrometer: 399.95 MHz<br>7.9111 (3.22); 7.906 (3.26); 7.8715 (1.27); 7.8508 (1.28); 7.1285 (3.39); 7.1071 (3.93); 6.9286 (3.26); 6.9235 (3.27); 6.8512 (0.55); 6.8442 (4.26);<br>6.8227 (3.73); 3.9429 (0.56); 3.9271 (0.76); 3.9111 (0.58); 3.8908 (0.36);<br>3.7132 (16); 3.3486 (4.51); 2.5671 (0.78); 2.545 (9.89); 2.531 (1.41); 2.51 (4.9); 2.5056 (6.27); 2.5012 (4.9); 1.7975 (0.37); 1.7827 (0.47); 1.7767 (0.37); 1.7635 (0.7); 1.748 (0.58); 1.743 (0.5); 1.7264 (0.33); 1.7189 (0.35); 1.7025 (0.59); 1.6953 (0.42); 1.687 (0.61); 1.6805 (0.6); 1.664 (0.52); 1.1391 (5.97); 1.1226 (5.94); −0.0002 (0.97) |

TABLE 17-continued

Compounds of the formula I-17

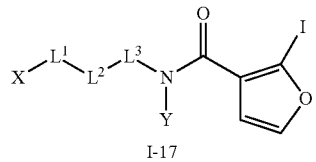

I-17

| Ex. No. | X | L¹ | L² | L³ | Y | Physical data: ¹H-NMR, δ [ppm] or CAS or patent No. |
|---|---|---|---|---|---|---|
| 17-82 | 2-thienyl | CH2 | CH2 | — | CH3 | compound No. 17-82, solvent: spectrometer: 399.95 MHz<br>7.9051 (3.98); 7.8564 (3.87); 7.367 (2.33); 7.3568 (3.14); 7.3412 (3.18); 7.3294 (2.53); 6.9643 (7.41); 6.9431 (3.26); 6.9317 (2.05); 6.786 (3.02); 6.5777 (4.12); 6.2593 (3.96); 3.6581 (2.6); 3.64 (4.75); 3.6216 (3.24); 3.4874 (2.55); 3.4701 (4.58); 3.4522 (2.77); 3.3222 (32.1); 3.1073 (2.88);<br>3.089 (4.93); 3.0707 (3.5); 3.0489 (3.48); 3.0311 (4.81); 3.0136 (2.48); 2.9694 (15.44); 2.8893 (16); 2.675 (0.7); 2.6705 (0.96); 2.666 (0.7); 2.5403 (0.64); 2.5237 (3.17); 2.5103 (52.17); 2.5059 (102.88); 2.5014 (135.96); 2.4968 (100.49); 2.4925 (49.43); 2.3325 (0.66); 2.3282 (0.92); 2.3237 (0.67); 1.3357 (0.6); 1.2585 (0.34); 1.2494 (0.77); 1.235 (0.58); 0.008 (0.32); −0.0002 (8.75) |
| 17-83 | 4-chloro-phenyl | CH(OCH3) | CH3 | — | H | compound No. 17-83, solvent: spectrometer: 399.95 MHz<br>8.2417 (0.6); 8.2275 (1.19); 8.2131 (0.61); 7.8976 (3.22); 7.8924 (3.36); 7.4559 (3.18); 7.4517 (1.33); 7.4395 (1.41); 7.4349 (4.93); 7.3531 (4.57);<br>7.332 (3.12); 6.8935 (3.26); 6.8883 (3.34); 4.3888 (0.87); 4.3749 (1.08); 4.371 (1.3); 4.3574 (0.92); 3.3811 (0.96); 3.3671 (1.72); 3.3579 (1.33); 3.3536 (1.62); 3.3399 (1.04); 3.3228 (7.27); 3.1652 (16); 2.5247 (0.5); 2.5112 (8.17); 2.5069 (16.23); 2.5024 (21.68); 2.4979 (16.58); 2.4937 (8.63); −0.0002 (1.22) |
| 17-84 | 4-chloro-2-thienyl | CH2 | CH2 | — | H | compound No. 17-84, solvent: spectrometer: 601.6 MHz<br>8.2799 (1.85); 8.2706 (3.61); 8.2612 (1.84); 7.9098 (15.38); 7.9064 (16); 7.3715 (14.22); 7.3689 (14.34); 6.9118 (9.2); 6.9106 (8.17); 6.9093 (9.31); 6.8643 (14.88); 6.8609 (15.08); 3.4375 (3.23); 3.4258 (7.59); 3.4162 (7.82); 3.4046 (3.63); 3.3616 (0.32); 3.3259 (1025.33); 3.3013 (0.62); 3.0015 (5.58); 2.9896 (10.71); 2.9783 (5.05); 2.653 (2.1); 2.6193 (0.61); 2.6163 (1.35); 2.6132 (1.88); 2.6102 (1.36); 2.6071 (0.61); 2.5541 (0.78); 2.5409 (672.55); 2.5226 (3.72); 2.5194 (4.5); 2.5163 (4.32); 2.5076 (99.89); 2.5046 (217.41); 2.5015 (301.87); 2.4984 (218.95); 2.4954 (101.36); 2.4247 (2.05); 2.3917 (0.6); 2.3887 (1.32); 2.3856 (1.84); 2.3826 (1.32); 2.3796 (0.6); 2.0736 (1.18); 1.9083 (1.46); 0.0052 (0.48); −0.0002 (17.52); −0.0058 (0.49) |
| 17-85 | 4-chloro-phenyl | N(CH3) | CH2 | CH2 | H | compound No. 17-85, solvent: spectrometer: 399.95 MHz<br>8.2286 (0.82); 8.2146 (1.51); 8.2008 (0.77); 7.8992 (3.63); 7.8941 (3.51);<br>7.1819 (4.35); 7.1593 (4.68); 7.1504 (0.54); 6.7994 (3.77); 6.7942 (3.59);<br>6.7502 (4.64); 6.7275 (4.1); 3.4632 (1.4); 3.4467 (3.07); 3.4297 (2.27); 3.3503 (2.29); 3.3287 (50.01); 3.3035 (0.97); 2.9083 (16); 2.5414 (28.34); 2.5064 (28.93); 2.5021 (36.24); 2.4979 (27.16); 0.0072 (0.37); −0.0002 (5.12) |

TABLE 18

Compounds of the formula I-18

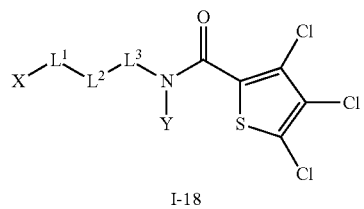

I-18

| Ex. No. | X | L¹ | L² | L³ | Y | Physical data: ¹H-NMR, δ [ppm] or CAS or patent No. |
|---|---|---|---|---|---|---|
| 18-1 | 3-methyl-2-thienyl | CH2 | CH2 | — | H | |
| 18-2 | 2,4-dichloro-phenyl | CH2 | CH2 | CH2 | H | |

TABLE 18-continued

Compounds of the formula I-18

I-18

| Ex. No. | X | L¹ | L² | L³ | Y | Physical data: ¹H-NMR, δ [ppm] or CAS or patent No. |
|---|---|---|---|---|---|---|
| 18-3 | 4-chlorophenyl | CH2 | CH2 | — | H | [DMSO], spectrometer: 399.95 MHz<br>8.3383 (1.45); 8.3244 (2.76); 8.3106 (1.46); 7.3729 (1.04); 7.3667 (9.60); 7.3618 (3.26); 7.3506 (4.25); 7.3456 (16.00); 7.3395 (2.01); 7.2843 (2.02); 7.2785 (13.78); 7.2736 (3.81); 7.2620 (3.18); 7.2574 (8.47); 7.2512 (0.91); 3.5163 (2.66); 3.4991(5.64); 3.4841 (5.63); 3.4661 (2.92); 3.3869 (0.37); 3.3812 (0.38); 3.3577 (1.06); 3.3334 (313.99); 2.8510 (4.86); 2.8329 (8.67); 2.8151 (4.40); 2.6761 (0.62); 2.6717(0.87); 2.6672 (0.63); 2.5419 (8.85); 2.5250 (2.19); 2.5202 (3.29); 2.5116 (45.83); 2.5071 (92.00); 2.5025 (121.96); 2.4979 (89.32); 2.4934 (42.57); 2.3338 (0.57); 2.3293 (0.79); 2.3247 (0.57); 0.0080 (1.38); −0.0002 (42.71); −0.0085 (1.24) |
| 18-4 | 2,4-dichloro-phenyl | CH2 | CH2 | — | H | [DMSO], spectrometer: 399.95 MHz<br>8.4015 (1.11); 8.3872 (2.18); 8.3729 (1.10); 7.5903 (4.21); 7.5864 (4.70); 7.3988(0.87); 7.3945 (0.49); 7.3781 (8.35); 7.3737 (16.00); 7.3529 (0.76); 3.5452 (2.09); 3.5281 (4.99); 3.5130 (5.12); 3.4961 (2.43); 3.3526 (1670.12); 3.2698 (0.76); 3.2279 (0.51); 3.2143 (0.33); 2.9730 (3.68); 2.9558 (7.46); 2.9384 (3.27); 2.7127 (0.59); 2.6816 (0.69); 2.6772 (1.51); 2.6725 (2.08); 2.6680 (1.47); 2.6634 (0.66); 2.5427(177.03); 2.5260 (5.29); 2.5212 (7.81); 2.5125 (109.57); 2.5080 (223.92); 2.5034 (300.01); 2.4988 (219.02); 2.4943 (103.52); 2.3689 (0.63); 2.3393 (0.69); 2.3348 (1.46); 2.3302 (2.02); 2.3256 (1.43); 2.3211 (0.64); 1.2346 (0.40); 0.1460 (0.56); 0.0080 (4.37); −0.0002 (149.93); −0.0085 (4.42); −0.1496 (0.58) |
| 18-5 | 4-chlorophenyl | CH(OCH3) | CH(CH3) | — | H | [DMSO], spectrometer: 399.95 MHz<br>8.1147 (0.61); 8.0932 (0.63); 7.9828 (0.94); 7.9620 (0.95); 7.4465 (3.15); 7.4432 (2.70); 7.4302 (1.39); 7.4254 (5.38); 7.4223 (3.60); 7.3525 (3.98); 7.3430 (2.72); 7.3369 (1.34); 7.3314 (2.64); 7.3265 (0.95); 7.3220 (1.76); 4.3564 (1.46); 4.3433 (1.68); 4.2957 (0.96); 4.2796 (1.15); 4.1896 (0.39); 4.1727 (0.55); 4.1553 (0.53); 4.1522 (0.49); 4.1383 (0.39); 4.1329 (0.38); 4.1158 (0.46); 4.1108 (0.35); 4.0990 (0.32); 4.0941 (0.44); 3.3753 (0.39); 3.3676 (0.42); 3.3334 (280.83); 3.3030 (0.41); 3.1991 (10.71); 3.1954 (16.00); 2.6760 (0.43); 2.6715 (0.60); 2.6669 (0.45); 2.5418 (63.22); 2.5250 (1.48); 2.5201 (2.19); 2.5115 (31.52); 2.5070 (64.55); 2.5024 (86.98); 2.4978 (64.44); 2.4933 (31.34); 2.3337 (0.41); 2.3292 (0.57); 2.3247 (0.42); 1.1526 (3.43); 1.1358 (3.44); 1.0899 (5.40); 1.0729 (5.38); 0.0080 (0.99); −0.0002 (31.93); −0. 0085 (0.99) |
| 18-6 | 2,4-dichloro-phenyl | CH(OCH3) | CH(CH3) | — | H | |
| 18-7 | 4-chlorophenyl | CH(CH3) | CH2 | — | H | [DMSO], spectrometer: 399.95 MHz<br>8.2587 (1.23); 8.2446 (2.41); 8.2302 (1.23); 7.3788 (0.76); 7.3726 (7.48); 7.3676 (2.58); 7.3565 (3.40); 7.3513 (14.45); 7.3453 (1.89); 7.3072 (1.81); 7.3013 (12.95); 7.2962 (3.31); 7.2848 (2.49); 7.2800 (7.06); 7.2741 (0.75); 3.4313 (3.82); 3.4130 (5.92); 3.3981 (5.02); 3.3792 (0.59); 3.3746 (0.55); 3.3667 (0.81); 3.3336 (441.38); 3.3027 (0.50); 3.2970 (0.37); 3.0900 (1.20); 3.0721 (2.38); 3.0542 (2.29); 3.0361 (1.09); 2.6761 (0.72); 2.6715 (1.00); 2.6669 (0.72); 2.6623 (0.32); 2.5418 (75.45); 2.5249 (2.60); 2.5202 (3.74); 2.5115 (52.54); 2.5070 (107.79); 2.5023 (144.94); 2.4977 (106.89); 2.4932 (51.49); 2.3337 (0.67); 2.3291 (0.97); 2.3245 (0.68); 1.2297 (16.00); 1.2121 (15.70); 0.0080 (0.90); −0.0002 (30.79); −0.0085 (0.93) |
| 18-8 | 2,4-dichloro-phenyl | CH(CH3) | CH2 | — | H | |
| 18-9 | 4-chlorophenyl | CH2 | CH(CH3) | — | H | [DMSO], spectrometer: 399.95 MHz<br>8.1684 (2.39); 8.1575 (0.72); 8.1476 (2.42); 7.3554 (0.73); 7.3492 (7.88); 7.3444 (2.76); 7.3331 (3.38); 7.3281 (14.10); 7.3222 (1.89); 7.2691 (11.74); 7.2480 (7.01); 4.1879 (0.58); 4.1676 (1.20); 4.1511 (1.90); 4.1344 (1.38); 4.1147 (0.62); |

TABLE 18-continued

Compounds of the formula I-18

$$\text{X-L}^1\text{-L}^2\text{-L}^3\text{-N(Y)-C(=O)-[3,4,5-trichlorothiophen-2-yl]}$$

I-18

| Ex. No. | X | L¹ | L² | L³ | Y | Physical data: ¹H-NMR, δ [ppm] or CAS or patent No. |
|---|---|---|---|---|---|---|
| | | | | | | 3.4896 (0.32); 3.4577 (0.49); 3.4446 (0.45); 3.4350 (0.52); 3.4276 (0.67); 3.4152 (0.79); 3.4083 (0.83); 3.3772 (2.46); 3.3337 (2834.39); 3.2709 (1.22); 3.2358 (0.55); 3.2193 (0.38); 2.8564 (0.73); 2.8363 (0.65); 2.8224 (3.63); 2.8103 (4.00); 2.8027 (4.16); 2.7947 (4.04); 2.7766 (0.76); 2.7607 (0.57); 2.6801 (2.08); 2.6756 (4.53); 2.6710 (6.32); 2.6665 (4.61); 2.6620 (2.22); 2.6020 (0.34); 2.5413 (21.69); 2.5244 (15.29); 2.5197 (23.07); 2.5110 (323.58); 2.5065 (666.17); 2.5019 (898.26); 2.4973 (661.97); 2.4928 (317.58); 2.3378 (1.97); 2.3333 (4.37); 2.3287 (6.09); 2.3241 (4.39); 2.3197 (2.07); 2.2889 (0.47); 1.2578 (0.44); 1.2351 (0.97); 1.1864 (16.00); 1.1699 (15.83); 0.1459 (0.48); 0.0080 (3.73); −0.0002 (124.43); −0.0085 (3.51); −0.1495 (0.50) |
| 18-10 | 2,4-dichlorophenyl | CH2 | CH(CH3) | — | H | [DMSO], spectrometer: 399.95 MHz<br>8.3159 (0.35); 8.2349 (2.20); 8.2137 (2.22); 7.5731 (3.36); 7.5703 (6.07); 7.5674 (3.69); 7.3687 (16.00); 7.3658 (15.36); 4.3258 (0.44); 4.3042 (1.07); 4.2881 (1.34); 4.2727 (1.05); 4.2517 (0.49); 3.6123 (0.36); 3.5587 (0.37); 3.5460 (0.39); 3.5174 (0.50); 3.5025 (0.59); 3.4877 (0.58); 3.4696 (0.67); 3.4588 (1.03); 3.4418 (1.03); 3.4227 (1.45); 3.3982 (2.57); 3.3351 (5077.54); 3.2907 (3.09); 3.2810 (2.65); 3.2568 (1.10); 3.2516 (1.05); 3.2389 (0.88); 3.2218 (0.60); 3.2087 (0.53); 3.1956 (0.50); 3.1860 (0.43); 3.1793 (0.33); 3.1605 (0.48); 3.1330 (0.33); 2.9947 (0.36); 2.9852 (0.92); 2.9712 (1.12); 2.9510 (3.40); 2.9348 (4.38); 2.9121 (3.04); 2.8995 (0.99); 2.8901 (0.39); 2.8780 (1.04); 2.7099 (0.37); 2.6801 (3.06); 2.6757 (6.56); 2.6711 (9.23); 2.6665 (6.68); 2.6620 (3.14); 2.6417 (0.32); 2.6214 (0.51); 2.6119 (0.54); 2.5966 (0.60); 2.5693 (1.11); 2.5414 (40.35); 2.5245 (23.18); 2.5197 (33.93); 2.5111 (471.06); 2.5066 (969.31); 2.5020 (1306.95); 2.4974 (961.78); 2.4929 (462.06); 2.4530 (1.02); 2.4186 (0.46);<br>2.3379 (2.88); 2.3333 (6.32); 2.3287 (8.86); 2.3241 (6.39); 2.3197 (2.94); 2.2893 (0.71); 1.4338 (0.33); 1.2977 (0.58); 1.2581 (0.99); 1.2320 (14.66); 1.2153 (13.11); 1.1813 (0.35); 1.1656 (0.33); 0.8704 (0.33); 0.8537 (0.47); 0.1460 (0.62); 0.0079 (4.21); −0.0003 (140.87); −0.0085 (4.14); −0.1497 (0.56) |
| 18-11 | 4-chlorophenyl | C(CH3)2 | CH2 | — | H | [DMSO], spectrometer: 399.95 MHz<br>7.9826 (0.42); 7.9676 (0.84); 7.9523 (0.45); 7.4509 (2.05); 7.4343 (1.05); 7.4292 (4.00); 7.3877 (0.55); 7.3814 (4.00); 7.3647 (0.87); 7.3596 (2.18); 3.4783 (2.79); 3.4627 (2.80); 3.3817 (0.38); 3.3708 (0.61); 3.3382 (185.17); 3.2999 (0.37); 2.6718 (0.33); 2.5421 (32.30); 2.5248 (1.10); 2.5071 (35.24); 2.5027 (48.02); 2.4983 (38.24); 2.3294 (0.32); 1.3079 (16.00); −0.0002 (5.06) |
| 18-12 | 2,4-dichlorophenyl | C(CH3)2 | CH2 | — | H | [DMSO], spectrometer: 399.95 MHz<br>8.0483 (0.38); 8.0336 (0.76); 8.0185 (0.38); 7.5470 (2.21); 7.5412 (2.35); 7.4867 (1.60); 7.4650 (2.48); 7.3951 (1.76); 7.3893 (1.62); 7.3735 (1.15); 7.3677 (1.11); 3.8178 (2.76); 3.8020 (2.73); 3.3793 (0.46); 3.3648 (0.85); 3.3383 (270.44); 2.6763 (0.35); 2.6718 (0.49); 2.6671 (0.34); 2.5420 (36.71); 2.5251 (1.23); 2.5204 (1.98); 2.5118 (26.71); 2.5072 (53.98); 2.5026 (71.90); 2.4980 (52.51); 2.4935 (24.80); 2.3340 (0.34); 2.3294 (0.47); 2.3248 (0.33); 1.4601 (16.00); −0.0002 (8.50) |
| 18-13 | 2-chlorophenyl | CH2 | CH2 | — | H | [DMSO], spectrometer: 399.95 MHz<br>8.4047 (2.52); 8.3907 (4.88); 8.3766 (2.61); 7.4404 (6.45); 7.4365 (4.88); 7.4350 (4.64); 7.4222 (9.21); 7.4173 (8.49); 7.4008 (0.37); 7.3654 (4.74); 7.3599 (6.00); 7.3468 (6.72); 7.3421 (9.18); 7.3273 (0.39); 7.3124 (3.08); 7.3081 (4.16); 7.2941 (9.79); 7.2898 (9.16); 7.2798 (9.24); 7.2770 (9.45); 7.2736 (9.93); 7.2719 (7.64); 7.2611 (7.85); 7.2558 (6.91); 7.2427 (2.64); 7.2376 (2.13); 3.5551 (4.91); 3.5380 (10.36); 3.5229 (10.15); 3.5049 (5.55); 3.3678 (1276.41); 3.2303 (0.70);<br>3.1844 (0.39); 3.1732 (0.34); 3.1611 (0.34); 3.1526 (0.34); 2.9921 (9.29); 2.9740 (16.00); 2.9565 (8.30); 2.6830 (0.53); |

TABLE 18-continued

Compounds of the formula I-18

[Structure I-18]

| Ex. No. | X | L¹ | L² | L³ | Y | Physical data: ¹H-NMR, δ [ppm] or CAS or patent No. |
|---|---|---|---|---|---|---|
| | | | | | | 2.6785 (1.12); 2.6739 (1.54); 2.6693 (1.11); 2.6647 (0.54); 2.5440 (26.94); 2.5272 (4.13); 2.5224 (6.63); 2.5138 (78.38); 2.5093 (158.33); 2.5047 (210.97); 2.5001 (154.60); 2.4956 (73.64); 2.3406 (0.53); 2.3361 (1.10); 2.3315 (1.50); 2.3269 (1.07); 2.3223 (0.50); 1.2338 (0.92); 0.0080 (0.68); −0.0002 (18.93); −0.0085 (0.53) |
| 18-14 | 3,4-dichlorophenyl | CH2 | CH2 | — | H | [DMSO], spectrometer: 399.95 MHz 8.3558 (2.16); 8.3425 (4.30); 8.3280 (2.26); 8.3157 (0.59); 7.5658 (13.70); 7.5557 (0.53); 7.5452 (16.00); 7.5367 (11.66); 7.5317 (12.12); 7.2572 (6.90); 7.2520 (6.73); 7.2366 (6.16); 7.2315 (6.00); 3.6967 (0.33); 3.6686 (0.37); 3.6487 (0.44); 3.6021 (0.52); 3.5839 (0.53); 3.5344 (4.32); 3.5171 (10.67); 3.5024 (11.03); 3.4854 (5.22); 3.4631 (1.39); 3.4320 (2.05); 3.4217 (2.24); 3.4018 (4.27); 3.3395 (5202.56); 3.2846 (3.40); 3.2691 (1.97); 3.2381 (0.93); 3.2298 (0.90); 3.2222 (0.97); 3.2102 (0.71); 3.1817 (0.46); 3.1514 (0.46); 3.1348 (0.38); 3.1097 (0.38); 3.0893 (0.33); 2.9294 (0.43); 2.8901 (0.40); 2.8654 (7.26); 2.8483 (14.70); 2.8310 (6.59); 2.7303 (0.44); 2.7111 (0.53); 2.6806 (3.27); 2.6761 (6.70); 2.6715 (9.14); 2.6669 (6.77); 2.6624 (3.28); 2.5417 (67.51); 2.5249 (24.44); 2.5202 (37.04); 2.5115 (469.46); 2.5070 (954.80); 2.5024 (1275.92); 2.4978 (935.38); 2.4932 (444.13); 2.3383 (2.78); 2.3337 (6.15); 2.3291 (8.50); 2.3245 (6.09); 2.3200 (2.74); 2.2906 (0.75); 1.4598 (0.49); 1.4341 (0.34); 1.2974 (0.53); 1.2583 (0.73); 1.2439 (0.83); 1.2344 (2.20); 0.0079 (2.35); −0.0002 (75.50); -0.0085 (2.08) |
| 18-15 | 3,5-dichlorophenyl | CH2 | CH2 | — | H | [DMSO], spectrometer: 399.95 MHz 8.3635 (1.59); 8.3495 (3.02); 8.3358 (1.55); 7.4561 (3.52); 7.4514 (6.76); 7.4467 (3.82); 7.3362 (16.00); 7.3315 (14.73); 3.5441 (2.54); 3.5273 (6.64); 3.5123 (6.80); 3.4957 (2.79); 3.4538 (0.33); 3.4358 (0.44); 3.4020 (0.84); 3.3403 (774.15); 3.3073 (1.15); 3.2955 (0.64); 2.8758 (4.51); 2.8589 (9.13); 2.8420 (4.07); 2.6766 (0.93); 2.6721 (1.22); 2.6676 (0.90); 2.5423 (11.07); 2.5251 (4.02); 2.5118 (70.19); 2.5075 (133.89); 2.5030 (174.54); 2.4985 (128.16); 2.4943 (62.55); 2.3342 (0.84); 2.3297 (1.13); 2.3252 (0.81); 0.0080 (0.39); −0.0002 (7.87) |
| 18-16 | 3-chlorophenyl | CH2 | CH2 | — | H | [DMSO], spectrometer: 399.95 MHz 8.3502 (2.22); 8.3363 (4.27); 8.3224 (2.34); 7.3668 (0.45); 7.3518 (4.27); 7.3458 (0.95); 7.3317 (16.00); 7.3251 (7.19); 7.3136 (10.84); 7.2894 (5.46); 7.2862 (7.75); 7.2812 (5.74); 7.2696 (3.01); 7.2645 (3.28); 7.2611 (2.32); 7.2249 (4.84); 7.2215 (7.70); 7.2066 (3.86); 7.2028 (5.51); 3.5338 (4.43); 3.5164 (9.92); 3.5017 (10.19); 3.4841 (5.10); 3.4659 (0.60); 3.4537 (0.48); 3.4464 (0.55); 3.4364 (0.64); 3.4250 (0.90); 3.3951 (1.97); 3.3446 (1716.20); 3.2744 (0.85); 3.2561 (0.57); 3.2491 (0.55); 3.2412 (0.52); 3.2322 (0.40); 2.8910 (0.54); 2.8694 (7.72); 2.8517 (14.91); 2.8340 (7.33); 2.8151 (0.34); 2.7318 (0.38); 2.7123 (1.48); 2.6812 (0.87); 2.6767 (1.80); 2.6721 (2.50); 2.6676 (1.79); 2.6630 (0.84); 2.5833 (0.45); 2.5767 (0.51); 2.5760 (0.51); 2.5730 (0.52); 2.5701 (0.62); 2.5694 (0.61); 2.5672 (0.69); 2.5665 (0.68); 2.5657 (0.65); 2.5627 (0.90); 2.5621 (0.94); 2.5614 (0.92); 2.5423 (412.00); 2.5307 (1.62); 2.5256 (6.01); 2.5208 (8.89); 2.5121 (124.91); 2.5076 (254.80); 2.5030 (340.40); 2.4984 (248.09); 2.4938 (117.28); 2.3685 (1.43); 2.3389 (0.77); 2.3343 (1.68); 2.3298 (2.33); 2.3252 (1.65); 2.3207 (0.73); 1.2346 (0.40); 0.0080 (0.42); −0.0002 (13.65); −0.0086 (0.34) |
| 18-17 | 2-fluorophenyl | CH2 | CH2 | — | H | [DMSO], spectrometer: 399.95 MHz 8.3957 (2.90); 8.3818 (5.52); 8.3678 (2.98); 7.3361 (3.19); 7.3319 (3.87); 7.3174 (6.62); 7.3128 (8.10); 7.3043 (2.78); 7.2978 (4.46); 7.2936 (5.27); 7.2859 (4.82); 7.2795 (3.29); 7.2712 (4.94); 7.2654 (5.84); 7.2609 (3.14); 7.2518 (3.50); 7.2472 (2.69); 7.1764 (6.27); 7.1566 (11.90); 7.1532 (8.27); 7.1501 (5.99); 7.1406 (11.91); 7.1377 (10.17); 7.1327 (4.90); 7.1298 (4.37); 7.1222 (5.11); 7.1192 (4.17); 3.6834 (0.33); |

TABLE 18-continued

Compounds of the formula I-18

| Ex. No. | X | L¹ | L² | L³ | Y | Physical data: $^1$H-NMR, δ [ppm] or CAS or patent No. |
|---|---|---|---|---|---|---|
| | | | | | | 3.5782 (0.41); 3.5280 (6.02); 3.5109 (12.37); 3.4955 (12.32); 3.4775 (6.60); 3.4568 (1.25); 3.3476 (2316.66); 3.2151 (0.83); 2.8992 (8.80); 2.8814 (16.00); 2.8635 (7.91); 2.7319 (0.57); 2.7122 (2.12); 2.6811 (1.30); 2.6768 (2.57); 2.6721 (3.53); 2.6676 (2.57); 2.6631 (1.29); 2.6135 (0.46); 2.6069 (0.50); 2.5790 (0.94); 2.5425 (525.77); 2.5256 (9.51); 2.5207 (14.47); 2.5121 (181.56); 2.5076 (362.66); 2.5030 (480.12); 2.4984 (349.45); 2.4939 (165.02); 2.3684 (1.93); 2.3389 (1.04); 2.3344 (2.31); 2.3298 (3.19); 2.3253 (2.24); 2.3206 (0.99); 1.2347 (0.54); 0.0079 (0.34); −0.0002 (10.27) |
| 18-18 | 2,6-difluorophenyl | CH2 | CH2 | — | H | |
| 18-19 | 2,6-dichlorophenyl | CH2 | CH2 | — | H | [DMSO], spectrometer: 399.95 MHz<br>8.4790 (1.26); 8.4644 (2.57); 8.4500 (1.31); 7.4643 (11.15); 7.4442 (16.00); 7.4223 (0.44); 7.4174 (0.44); 7.3413 (0.38); 7.3057 (5.89); 7.2938 (0.56); 7.2867 (5.55); 7.2844 (5.33); 7.2714 (0.55); 7.2654 (3.92); 7.2554 (0.36); 3.5541 (2.22); 3.5373 (5.65); 3.5216 (5.80); 3.5048 (2.68); 3.4705 (0.46); 3.4658 (0.45); 3.4373 (0.52); 3.4210 (0.86); 3.3411 (1529.98); 3.2968 (1.65); 3.2504 (0.51); 3.2346 (0.41); 3.2214 (0.35); 3.2060 (0.39); 3.1841 (4.37); 3.1668 (8.06); 3.1495 (3.65); 2.9916 (0.41); 2.9731 (0.67); 2.9558 (0.42); 2.6809 (0.87); 2.6764 (1.83); 2.6718 (2.53); 2.6672 (1.82); 2.6627 (0.88); 2.5420 (39.84); 2.5252 (6.83); 2.5204 (10.41); 2.5118 (129.79); 2.5073 (262.65); 2.5027 (350.05); 2.4981 (255.24); 2.4935 (120.13); 2.3387 (0.77); 2.3341 (1.70); 2.3295 (2.34); 2.3249 (1.68); 2.3204 (0.76); 1.2347 (0.43); 0.0080 (1.16); −0.0002 (36.14); −0.0085 (0.97) |
| 18-20 | 3-(trifluoromethyl)phenyl | CH2 | CH2 | — | H | [DMSO], spectrometer: 399.95 MHz<br>8.3596 (2.58); 8.3455 (4.62); 8.3316 (2.38); 7.6766 (0.93); 7.6566 (1.19); 7.6020 (9.79); 7.5891 (2.76); 7.5766 (5.18); 7.5715 (9.15); 7.5651 (13.92); 7.5613 (11.18); 7.5553 (12.55); 7.5375 (3.49); 7.5267 (0.45); 7.5194 (1.32); 7.4865 (0.98); 7.4665 (0.87); 3.5706 (4.51); 3.5532 (11.20); 3.5385 (11.39); 3.5213 (5.00); 3.4202 (0.65); 3.3409 (891.91); 2.9678 (8.02); 2.9504 (16.00); 2.9330 (7.25); 2.8913 (0.59); 2.7323 (0.48); 2.7128 (1.33); 2.6815 (0.56); 2.6771 (1.13); 2.6724 (1.56); 2.6679 (1.12); 2.6633 (0.54); 2.5841 (0.43); 2.5427 (366.31); 2.5258 (3.99); 2.5211 (5.99); 2.5125 (80.10); 2.5079 (162.32); 2.5033 (216.15); 2.4987 (157.36); 2.4942 (73.95); 2.3690 (1.24); 2.3392 (0.45); 2.3347 (1.01); 2.3301 (1.41); 2.3255 (1.00); 2.3209 (0.43); 0.0080 (1.82); −0.0002 (60.87); −0.0085 (1.71) |
| 18-21 | 4-(trifluoromethyl)phenyl | CH2 | CH2 | — | H | [DMSO], spectrometer: 399.95 MHz<br>8.3826 (2.67); 8.3689 (5.23); 8.3550 (2.75); 7.6766 (13.01); 7.6564 (16.00); 7.4861 (14.81); 7.4660 (12.51); 3.5654 (4.59); 3.5481 (10.38); 3.5329 (10.38); 3.5154 (5.13); 3.4825 (0.34); 3.4664 (0.51); 3.4607 (0.50); 3.4501 (0.46); 3.4333 (0.61); 3.4100 (0.95); 3.3992 (1.04); 3.3366 (1695.91); 3.2803 (1.01); 3.2604 (0.42); 2.9580 (7.44); 2.9402 (13.90); 2.9225 (6.64); 2.6806 (1.15); 2.6761 (2.39); 2.6716 (3.33); 2.6671 (2.42); 2.6625 (1.16); 2.5419 (22.64); 2.5249 (8.60); 2.5201 (12.91); 2.5115 (173.78); 2.5070 (351.71); 2.5025 (470.69); 2.4979 (347.82); 2.4935 (169.16); 2.3383 (1.06); 2.3338 (2.27); 2.3293 (3.17); 2.3247 (2.27); 2.3202 (1.04); 1.2350 (0.53); 0.1461 (0.33); 0.0080 (2.40); −0.0002 (76.44); −0.0084 (2.40) |
| 18-22 | 2-methylphenyl | CH2 | CH2 | — | H | [DMSO], spectrometer: 399.95 MHz<br>8.4044 (0.57); 8.3908 (1.07); 8.3760 (0.56); 7.1690 (1.37); 7.1574 (1.84); 7.1457 (3.82); 7.1393 (1.52); 7.1345 (1.20); 7.1292 (3.37); 7.1265 (3.45); 7.1190 (1.24); 7.1159 (2.25); 7.1115 (1.16); 7.1050 (1.52); 3.4652 (1.06); 3.4501 (1.93); 3.4421 (1.18); 3.4318 (1.61); 3.4272 (2.00); 3.4125 (1.29); 3.3974 (0.44); 3.3925 (0.49); 3.3845 (0.74); 3.3364 (628.44); 3.3074 (0.93); 3.2961 (0.61); 2.8518 (2.05); 2.8364 (1.70); |

TABLE 18-continued

Compounds of the formula I-18

| Ex. No. | X | L¹ | L² | L³ | Y | Physical data: ¹H-NMR, δ [ppm] or CAS or patent No. |
|---|---|---|---|---|---|---|
| | | | | | | 2.8321 (2.36); 2.8135 (1.84); 2.6802 (0.37); 2.6759 (0.82); 2.6713 (1.14); 2.6668 (0.83); 2.6622 (0.36); 2.5416 (5.14); 2.5247 (3.20); 2.5199 (4.87); 2.5113 (61.11); 2.5068 (123.14); 2.5022 (163.88); 2.4976 (120.10); 2.4931 (57.14); 2.3381 (0.45); 2.3335 (0.93); 2.3289 (1.44); 2.3194 (16.00); 0.0080 (0.89); −0.0002 (28.19); −0.0085 (0.82) |
| 18-23 | 2,4,6-trimethyl-phenyl | CH2 | CH2 | — | H | |
| 18-24 | 3,4-bismethoxy-phenyl | CH2 | CH2 | — | H | [DMSO], spectrometer: 399.95 MHz 8.2840 (0.49); 8.2698 (0.94); 8.2559 (0.48); 6.8795 (2.01); 6.8591 (2.74); 6.8349 (2.13); 6.8302 (2.31); 6.7589 (1.36); 6.7542 (1.21); 6.7386 (0.99); 6.7339 (0.88); 3.7305 (15.58); 3.7120 (16.00); 3.5042 (0.78); 3.4874 (1.53); 3.4693 (1.46); 3.4534 (0.86); 3.3957 (0.32); 3.3777 (0.64); 3.3382 (330.27); 3.2953 (0.36); 2.7870 (1.36); 2.7685 (2.24); 2.7505 (1.24); 2.6761 (0.42); 2.6714 (0.58); 2.6671 (0.42); 2.5418 (80.42); 2.5315 (0.67); 2.5249 (1.50); 2.5201 (2.29); 2.5114 (32.05); 2.5070 (64.65); 2.5024 (85.98); 2.4978 (63.63); 2.4934 (30.94); 2.3680 (0.34); 2.3336 (0.40); 2.3292 (0.57); 2.3246 (0.41); 0.0080 (0.36); −0.0002 (12.16); −0.0085 (0.37) |
| 18-25 | phenyl | CH2 | CH2 | — | H | [DMSO], spectrometer: 399.95 MHz 8.3334 (1.80); 8.3197 (3.63); 8.3058 (2.10); 7.3248 (4.55); 7.3210 (1.73); 7.3065 (12.05); 7.2931 (3.50); 7.2885 (12.51); 7.2563 (9.87); 7.2524 (16.00); 7.2334 (10.00); 7.2170 (2.59); 7.2118 (6.73); 7.2062 (1.87); 7.1978 (1.62); 7.1940 (2.54); 3.7304 (0.33); 3.7120 (0.36); 3.5240 (4.33); 3.5072 (7.33); 3.4915 (7.04); 3.4878 (7.57); 3.4727 (5.04); 3.3423 (2075.15); 2.8909 (0.51); 2.8572 (7.70); 2.8382 (11.32); 2.8203 (6.95); 2.7306 (0.47); 2.7120 (1.54); 2.6763 (2.50); 2.6718 (3.33); 2.6671 (2.49); 2.6626 (1.25); 2.5420 (409.43); 2.5252 (8.63); 2.5204 (12.67); 2.5118 (161.71); 2.5072 (328.42); 2.5026 (437.97); 2.4980 (318.47); 2.4935 (149.52); 2.3683 (1.16); 2.3386 (0.86); 2.3340 (2.04); 2.3294 (2.86); 2.3248 (2.00); 2.3203 (0.82); 1.2349 (0.53); 0.0080 (1.34); −0.0002 (37.49); −0.0085 (0.79) |
| 18-26 | 4-chlorophenyl | C(CH2—CH2) | CH2 | — | H | |
| 18-27 | 2,4-dichlorophenyl | C(CH2 CH2) | CH2 | — | H | |
| 18-28 | 4-chlorophenyl | CH2 | C(CH2—CH2) | — | H | |
| 18-29 | 2,4-dichlorophenyl | CH2 | C(CH2—CH2) | — | H | |
| 18-30 | 4-chlorophenyl | O | CH2 | CH2 | H | |
| 18-31 | 2,4-dichlorophenyl | O | CH2 | CH2 | H | |
| 18-32 | 4-chlorophenyl | CH2 | CH2 | CH2 | H | |
| 18-33 | 4-chlorophenyl | NCH3 | CH2 | CH2 | H | |
| 18-34 | 2,4-dichlorophenyl | NCH3 | CH2 | CH2 | H | |
| 18-35 | 4-chlorophenyl | CH(OCH3) | CH2 | — | H | |
| 18-36 | 2,4-dichlorophenyl | CH(OCH3) | CH2 | — | H | |
| 18-37 | 2-thienyl | CH2 | CH2 | — | H | compound No. 18-37, solvent: spectrometer: 399.95 MHz 8.4026 (2.85); 8.3891 (5.07); 8.3758 (2.83); 7.3603 (7.73); 7.3576 (7.29); 7.3476 (8.4); 7.3448 (7.56); 6.9744 (5.8); 6.9657 (8.94); 6.962 (6.02); 6.9532 (8.02); 6.9271 (9.64); 6.9195 (6.84); 3.5416 (4.44); 3.5242 (10.59); 3.509 (11.17); 3.4915 (5.08); 3.3274 (120.31); 3.0811 (8.92); 3.0632 (16); 3.0454 (7.69); 2.6712 (0.67); 2.5416 (1.37); 2.5062 (81.74); 2.5022 (102.18); 2.4981 (77.29); 2.329 (0.7); −0.0002 (1.69) |
| 18-38 | 3-thienyl | CH2 | CH2 | — | H | |
| 18-39 | 2-furyl | CH2 | CH2 | — | H | |
| 18-40 | 3-furyl | CH2 | CH2 | — | H | |
| 18-41 | phenyl | CH2 | CH2 | CH(CH3) | H | |
| 18-42 | phenyl | CH2 | CH2 | CH2 | H | |
| 18-43 | 2-Cl-phenyl | CH2 | CH2 | CH(CH3) | H | |

TABLE 18-continued

Compounds of the formula I-18

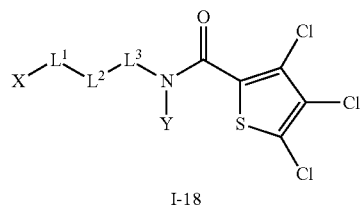

I-18

| Ex. No. | X | $L^1$ | $L^2$ | $L^3$ | Y | Physical data: $^1$H-NMR, δ [ppm] or CAS or patent No. |
|---|---|---|---|---|---|---|
| 18-44 | 4-t-butylphenyl | CH2 | CH2 | CH2 | H | |
| 18-45 | 4-methylphenyl | CH2 | CH2 | CH2 | H | |
| 18-46 | phenyl | CH2 | CH2 | CH(CH2CH3) | H | |
| 18-47 | 2-methoxyphenyl | CH2 | CH2 | CH2 | H | |
| 18-48 | 2-methylphenyl | CH2 | CH2 | CH2 | H | |
| 18-49 | 3-methylphenyl | CH2 | CH2 | CH2 | H | |
| 18-50 | 3-chlorophenyl | CH2 | CH2 | CH2 | H | |
| 18-51 | 2,6-difluorophenyl | CH2 | CH2 | CH2 | H | |
| 18-52 | 4-chlorophenyl | CH2 | CH2 | CH2 | H | |
| 18-53 | 2,6-dichlorophenyl | CH2 | CH2 | CH(CH3) | H | |
| 18-54 | 3,5-dichlorophenyl | CH2 | CH2 | CH(CH3) | H | |
| 18-55 | 2,6-dimethylphenyl | CH2 | CH2 | CH2 | H | |
| 18-56 | 2,5-dichlorophenyl | CH2 | CH2 | CH2 | H | |
| 18-57 | 4-isopropoxyphenyl | CH2 | CH2 | CH2 | H | |
| 18-58 | 3-trifluoromethylphenyl | CH2 | CH2 | CH(CH3) | H | |
| 18-59 | 4-methylphenyl | CH2 | CH2 | CH(CH3) | H | |
| 18-60 | 2-methylphenyl | CH2 | CH2 | CH(CH3) | H | |
| 18-61 | 3,4-dichlorophenyl | CH2 | CH2 | CH(CH3) | H | |
| 18-62 | 3,5-dichlorophenyl | CH2 | CH2 | CH2 | H | |
| 18-63 | 2,6-dimethylphenyl | CH2 | CH2 | CH(CH3) | H | |
| 18-64 | 4-trifluoromethylphenyl | CH2 | CH2 | CH(CH3) | H | |
| 18-65 | 2,5-dichlorophenyl | CH2 | CH2 | CH(CH3) | H | |
| 18-66 | 4-phenoxyphenyl | CH2 | CH2 | CH2 | H | |
| 18-67 | 3-chlorophenyl | CH2 | CH2 | CH(CH3) | H | |
| 18-68 | 4-phenoxyphenyl | CH2 | CH2 | CH(CH3) | H | |
| 18-69 | 2,4-dichlorophenyl | CH2 | CH2 | CH(CH3) | H | |
| 18-70 | 2-difluoromethoxyphenyl | CH2 | CH2 | CH(CH3) | H | |
| 18-71 | 4-methoxyphenyl | CH2 | CH2 | CH2 | H | |
| 18-72 | 4-chlorophenyl | CH2 | CH2 | CH(CH3) | H | |
| 18-73 | 4-chlorophenyl | CH2 | CH2 | CH(i-propyl) | H | |
| 18-74 | 4-fluorophenyl | CH2 | CH2 | CH2 | H | |
| 18-75 | 4-chlorophenyl | CH2 | CH2 | CH(n-propyl) | H | |
| 18-76 | 4-chlorophenyl | CH2 | CH2 | CH(t-butyl) | H | |
| 18-77 | 2-chlorophenyl | CH2 | CH2 | CH2 | H | |
| 18-78 | 4-chlorophenyl | CH2 | CH(CH3) | — | cyclopropyl | |

TABLE 19

Compounds of the formula I-19

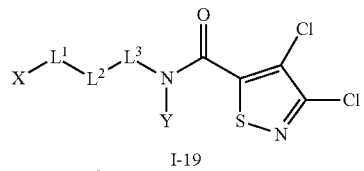

I-19

| Ex. No. | X | L¹ | L² | L³ | Y | Physical data: ¹H-NMR, δ [ppm] or CAS or patent No. |
|---|---|---|---|---|---|---|
| 19-1 | 3-methyl-2-thienyl | CH2 | CH2 | — | H | |
| 19-2 | 2,4-dichlorophenyl | CH2 | CH2 | CH2 | H | WO-A 2008/101976 |
| 19-3 | 4-chlorophenyl | CH2 | CH2 | — | H | [DMSO] spectrometer: 399.95 MHz<br>8.7804 (1.61); 8.7666 (2.98); 8.7533 (1.69); 7.3729 (9.38); 7.3684 (3.79); 7.3566 (4.52); 7.3519 (16.00); 7.3464 (2.86); 7.2909 (14.36); 7.2699 (8.86); 3.5300 (2.87); 3.5127 (6.87); 3.4975 (6.94); 3.4802 (3.25); 3.3432 (53.59); 2.8588 (5.46); 2.8410 (10.32); 2.8233 (5.05); 2.5440 (6.08); 2.5090 (29.64); 2.5046 (39.14); 2.5002 (29.94); 2.0786 (1.17); −0.0002 (4.99) |
| 19-4 | 2,4-dichlorophenyl | CH2 | CH2 | — | H | [DMSO] spectrometer: 399.95 MHz<br>8.8319 (1.09); 8.8182 (2.04); 8.8041 (1.10); 7.6008 (3.91); 7.5980 (5.81); 7.4114 (0.32); 7.3901 (12.93); 7.3871 (16.00); 7.3689 (0.34); 3.5560 (1.82); 3.5389 (4.91); 3.5238 (5.01); 3.5070 (2.05); 3.3452 (150.16); 2.9809 (3.79); 2.9637 (7.76); 2.9464 (3.42); 2.6728 (0.41); 2.5432 (6.83); 2.5262 (1.41); 2.5127 (23.77); 2.5083 (47.67); 2.5038 (62.98); 2.4992 (47.09); 2.4948 (23.94); 2.3306 (0.41); 2.0773 (1.79); 0.0080 (0.34); −0.0002 (10.17); −0.0085 (0.44) |
| 19-5 | 4-chlorophenyl | CH(OCH3) | CH(CH3) | — | H | [DMSO] spectrometer: 399.95 MHz<br>8.6720 (0.83); 8.6503 (0.84); 8.5858 (1.06); 8.5647 (1.07); 7.4562 (3.64); 7.4520 (3.91); 7.4351 (6.33); 7.4309 (4.83); 7.3606 (4.59); 7.3404 (5.97); 7.3199 (2.51); 4.3370 (1.82); 4.3233 (2.21); 4.2540 (1.43); 4.2378 (1.90); 4.2202 (0.54); 4.2031 (0.72); 4.1996 (0.64); 4.1890 (0.56); 4.1854 (0.66); 4.1827 (0.62); 4.1683 (0.46); 4.1301 (0.46); 4.1135 (0.69); 4.1087 (0.53); 4.0968 (0.48); 4.0920 (0.68); 4.0754 (0.40); 3.3409 (73.80); 3.1983 (13.14); 3.1836 (16.00); 2.5431 (4.17); 2.5261 (0.83); 2.5213 (1.23); 2.5127 (14.60); 2.5083 (29.47); 2.5037 (39.10); 2.4992 (29.18); 2.4948 (14.65); 2.0775 (2.35); 1.1695 (4.92); 1.1527 (4.90); 1.0737 (5.89); 1.0566 (5.86); −0.0002 (5.08) |
| 19-6 | 2,4-dichlorophenyl | CH(OCH3) | CH(CH3) | — | H | |
| 19-7 | 4-chlorophenyl | CH(CH3) | CH2 | — | H | [DMSO] spectrometer: 399.95 MHz<br>8.7346 (1.37); 8.7208 (2.60); 8.7066 (1.41); 7.3845 (0.88); 7.3786 (7.46); 7.3738 (2.91); 7.3624 (3.84); 7.3573 (14.36); 7.3515 (2.43); 7.3103 (13.32); 7.3055 (3.96); 7.2935 (2.86); 7.2890 (7.26); 3.4569 (0.35); 3.4429 (2.88); 3.4379 (2.86); 3.4235 (6.11); 3.4081 (3.74); 3.4062 (3.84); 3.3906 (0.38); 3.3874 (0.38); 3.3432 (43.13); 3.0839 (1.34); 3.0661 (2.65); 3.0482 (2.58); 3.0303 (1.24); 2.5442 (5.28); 2.5273 (0.65); 2.5225 (0.99); 2.5137 (11.38); 2.5094 (22.74); 2.5048 (29.96); 2.5003 (22.48); 2.4960 (11.55); 2.0788 (1.96); 1.2453 (16.00); 1.2278 (15.80); −0.0002 (4.41) |
| 19-8 | 2,4-dichlorophenyl | CH(CH3) | CH2 | — | H | [DMSO] spectrometer: 399.95 MHz<br>8.8147 (1.76); 8.8006 (3.14); 8.7893 (1.62); 7.5801 (9.54); 7.5748 (10.09); 7.4937 (5.81); 7.4726 (11.68); 7.4585 (0.32); 7.4369 (7.10); 7.4315 (6.55); 7.4159 (3.48); 7.4104 (3.35); 3.5791 (1.06); 3.5625 (2.52); 3.5467 (3.86); 3.5373 (2.96); 3.5270 (3.67); 3.5124 (3.99); 3.4968 (1.82); 3.4874 (1.70); 3.4733 (1.37); 3.4631 (2.34); 3.4491 (2.88); 3.4355 (1.44); 3.4251 (0.61); 3.4175 (0.49); 3.4109 (0.34); 3.3420 (126.95); 2.6732 (0.41); 2.5437 (7.71); 2.5266 (1.34); 2.5131 (24.03); 2.5087 (48.16); 2.5042 (63.58); 2.4996 (47.39); 2.4952 (24.03); 2.3309 (0.42); 2.0782 (3.45); 1.2396 (15.60); 1.2233 (16.00); −0.0002 (7.21) |
| 19-9 | 4-chlorophenyl | CH2 | CH(CH3) | — | H | [DMSO] spectrometer: 399.95 MHz<br>8.6741 (2.64); 8.6534 (2.68); 7.3663 (0.98); 7.3604 (8.41); 7.3560 (3.27); 7.3442 (3.93); 7.3394 (13.89); 7.3337 (2.30); 7.2747 (12.38); 7.2537 (7.77); 4.2068 (0.71); 4.1886 (1.65); 4.1712 (2.18); 4.1521 (1.64); 4.1349 (0.79); 3.3435 (51.80); 2.8243 (0.45); 2.8066 (8.20); 2.7880 (5.81); 2.7530 (0.34); 2.5442 (5.12); 2.5270 (0.63); 2.5135 (12.25); 2.5093 (24.47); |

TABLE 19-continued

Compounds of the formula I-19

I-19

| Ex. No. | X | L¹ | L² | L³ | Y | Physical data: ¹H-NMR, δ [ppm] or CAS or patent No. |
|---|---|---|---|---|---|---|
| 19-10 | 2,4-dichlorophenyl | CH2 | CH(CH3) | — | H | 2.5048 (32.40); 2.5003 (24.57); 2.4962 (12.91); 2.0787 (3.43); 1.1902 (16.00); 1.1736 (15.92); −0.0002 (4.17) [DMSO] spectrometer: 399.95 MHz 8.7231 (2.60); 8.7020 (2.65); 7.5839 (5.94); 7.5803 (6.44); 7.3996 (1.21); 7.3951 (0.92); 7.3789 (9.06); 7.3736 (14.41); 7.3517 (1.29); 4.3427 (0.56); 4.3210 (1.30); 4.3046 (1.60); 4.2997 (1.06); 4.2905 (1.28); 4.2690 (0.62); 3.3395 (91.34); 2.9978 (0.50); 2.9928 (1.78); 2.9792 (1.95); 2.9586 (3.54); 2.9451 (3.31); 2.9337 (0.34); 2.8990 (3.28); 2.8769 (3.20); 2.8648 (1.81); 2.8427 (1.73); 2.6726 (0.44); 2.6680 (0.32); 2.5431 (14.37); 2.5261 (1.28); 2.5125 (25.11); 2.5081 (50.63); 2.5036 (67.19); 2.4990 (50.39); 2.4946 (25.68); 2.3303 (0.44); 2.3257 (0.33); 2.0776 (0.56); 1.2350 (16.00); 1.2184 (15.83); 0.0080 (0.33); −0.0002 (9.83); −0.0085 (0.42) |
| 19-11 | 4-chlorophenyl | C(CH3)2 | CH2 | — | H | [DMSO] spectrometer: 399.95 MHz 8.5244 (0.45); 8.5093 (0.87); 8.4941 (0.46); 7.4515 (2.38); 7.4299 (4.35); 7.3812 (4.42); 7.3639 (0.95); 7.3596 (2.39); 3.4804 (3.09); 3.4647 (3.08); 3.3427 (14.46); 2.5438 (1.18); 2.5090 (7.49); 2.5047 (9.63); 2.5006 (7.32); 2.0785 (0.56); 1.3199 (16.00); −0.0002 (1.03) |
| 19-12 | 2,4-dichlorophenyl | C(CH3)2 | CH2 | — | H | [DMSO] spectrometer: 399.95 MHz 8.5462 (0.47); 8.5307 (0.91); 8.5155 (0.47); 7.5449 (2.56); 7.5392 (2.75); 7.4817 (1.58); 7.4600 (2.57); 7.3986 (1.75); 7.3928 (1.64); 7.3770 (1.09); 7.3712 (1.04); 3.8267 (3.08); 3.8109 (3.06); 3.3406 (18.90); 2.5439 (1.33); 2.5133 (4.42); 2.5090 (8.72); 2.5045 (11.48); 2.5000 (8.64); 2.4959 (4.44); 2.0787 (0.62); 1.4697 (16.00); −0.0002 (1.49) |
| 19-13 | 2-chlorophenyl | CH2 | CH2 | — | H | [DMSO] spectrometer: 399.95 MHz 8.8495 (2.31); 8.8362 (4.26); 8.8228 (2.56); 7.4483 (5.85); 7.4440 (4.95); 7.4299 (8.03); 7.4253 (7.77); 7.4076 (0.52); 7.3783 (4.41); 7.3729 (5.50); 7.3599 (6.47); 7.3550 (8.44); 7.3210 (2.68); 7.3168 (3.45); 7.3027 (8.15); 7.2985 (7.66); 7.2865 (9.83); 7.2809 (10.41); 7.2685 (7.22); 7.2633 (6.22); 7.2500 (2.55); 7.2450 (1.96); 3.5642 (4.49); 3.5470 (10.21); 3.5319 (10.47); 3.5142 (5.54); 3.3436 (133.06); 3.0006 (8.81); 2.9828 (16.00); 2.9651 (8.39); 2.6780 (0.36); 2.6733 (0.48); 2.6688 (0.36); 2.5435 (12.04); 2.5266 (1.84); 2.5131 (28.79); 2.5087 (57.00); 2.5042 (75.11); 2.4996 (56.62); 2.4952 (30.49); 2.3356 (0.36); 2.3309 (0.49); 2.3263 (0.37); 2.0778 (1.98); −0.0002 (8.63); −0.0085 (0.47) |
| 19-14 | 3,4-dichlorophenyl | CH2 | CH2 | — | H | [DMSO] spectrometer: 399.95 MHz 8.7831 (1.79); 8.7697 (3.26); 8.7563 (1.81); 8.0167 (0.44); 8.0142 (0.46); 7.7686 (0.56); 7.7640 (1.10); 7.5729 (9.10); 7.5518 (16.00); 7.5455 (9.40); 7.5300 (1.00); 7.2724 (5.03); 7.2675 (4.89); 7.2519 (4.43); 7.2469 (4.33); 3.5517 (2.97); 3.5348 (7.98); 3.5198 (8.24); 3.5032 (3.53); 3.4913 (0.56); 3.3421 (68.88); 2.8729 (5.77); 2.8558 (11.58); 2.8387 (5.30); 2.6739 (0.36); 2.5442 (20.13); 2.5269 (1.23); 2.5092 (39.28); 2.5048 (50.84); 2.5003 (38.03); 2.3314 (0.32); −0.0002 (6.05) |
| 19-15 | 3,5-dichlorophenyl | CH2 | CH2 | — | H | [DMSO] spectrometer: 399.95 MHz 8.7911 (1.51); 8.7773 (2.84); 8.7639 (1.57); 7.4621 (3.80); 7.4574 (7.53); 7.4527 (4.51); 7.3510 (16.00); 7.3463 (15.06); 3.5626 (2.41); 3.5462 (6.56); 3.5309 (6.73); 3.5146 (2.74); 3.3448 (76.07); 2.8833 (4.62); 2.8665 (9.15); 2.8497 (4.27); 2.5445 (6.75); 2.5270 (0.83); 2.5096 (27.94); 2.5051 (36.59); 2.5008 (27.67); 2.0790 (3.29); −0.0002 (3.41) |
| 19-16 | 3-chlorophenyl | CH2 | CH2 | — | H | [DMSO] spectrometer: 399.95 MHz 8.7918 (2.09); 8.7786 (3.77); 8.7654 (2.21); 7.3726 (0.45); 7.3575 (3.69); 7.3382 (16.00); 7.3192 (8.92); 7.2947 (4.95); 7.2916 (7.69); 7.2869 (5.41); 7.2749 (2.80); 7.2703 (3.49); 7.2671 (2.30); 7.2343 (6.99); 7.2158 (4.98); 3.5505 (3.89); 3.5331 (9.69); 3.5183 (9.79); 3.5011 (4.46); 3.3496 (96.29); 2.8786 (7.20); 2.8611 (14.18); 2.8435 (6.87); 2.8251 (0.35); 2.5450 (9.80); 2.5280 (0.84); 2.5144 (14.12); 2.5101 (28.09); 2.5056 (37.06); 2.5011 (27.82); 2.4969 (14.31); 2.0791 (2.50); −0.0002 (3.45) |

TABLE 19-continued

Compounds of the formula I-19

X–L¹–L²–L³–N(Y)–C(=O)–[4,3-dichloroisothiazol-5-yl]

I-19

| Ex. No. | X | L¹ | L² | L³ | Y | Physical data: ¹H-NMR, δ [ppm] or CAS or patent No. |
|---|---|---|---|---|---|---|
| 19-17 | 2-fluoro-phenyl | CH2 | CH2 | — | H | [DMSO] spectrometer: 399.95 MHz<br>8.8382 (2.72); 8.8249 (4.94); 8.8114 (2.83); 7.3493 (3.12); 7.3453 (3.77); 7.3307 (6.31); 7.3261 (7.78); 7.3178 (1.32); 7.3110 (5.26); 7.3070 (6.13); 7.2978 (2.28); 7.2930 (4.44); 7.2868 (3.36); 7.2783 (4.56); 7.2725 (5.67); 7.2681 (3.20); 7.2589 (3.29); 7.2544 (2.70); 7.1846 (6.09); 7.1640 (12.14); 7.1479 (10.66); 7.1451 (10.10); 7.1411 (5.38); 7.1380 (4.57); 7.1295 (4.67); 7.1266 (4.17); 3.5382 (5.31); 3.5210 (12.15); 3.5055 (12.02); 3.4881 (5.99); 3.3396 (151.75); 2.9086 (8.60); 2.8908 (16.00); 2.8730 (7.82); 2.6771 (0.50); 2.6726 (0.70); 2.6680 (0.54); 2.5430 (16.86); 2.5338 (0.86); 2.5258 (2.20); 2.5124 (39.67); 2.5080 (79.89); 2.5035 (106.15); 2.4989 (79.67); 2.4945 (40.94); 2.3347 (0.48); 2.3302 (0.67); 2.3257 (0.51); 2.0774 (1.75); 0.0080 (0.57); −0.0002 (16.34); −0.0084 (0.71) |
| 19-18 | 2,6-difluoro-phenyl | CH2 | CH2 | — | H | [DMSO] spectrometer: 399.95 MHz<br>8.9007 (2.81); 8.8864 (5.25); 8.8721 (2.89); 7.3756 (1.65); 7.3588 (3.71); 7.3546 (3.45); 7.3378 (7.21); 7.3205 (3.71); 7.3170 (4.72); 7.3002 (2.18); 7.1144 (0.95); 7.1101 (1.39); 7.0980 (10.03); 7.0899 (2.24); 7.0782 (16.00); 7.0673 (2.34); 7.0581 (8.70); 7.0458 (1.29); 3.5129 (4.77); 3.4960 (13.06); 3.4802 (13.39); 3.4636 (5.42); 3.3679 (0.36); 3.3420 (107.12); 2.9327 (7.50); 2.9155 (14.53); 2.8983 (6.88); 2.6738 (0.44); 2.6694 (0.33); 2.5443 (0.46); 2.5272 (1.38); 2.5137 (25.06); 2.5094 (50.22);2.5048 (66.45); 2.5003 (49.73); 2.4958 (25.33); 2.3316 (0.42); 2.3271 (0.32); 0.0079(0.33); −0.0002 (9.53); −0.0086 (0.39) |
| 19-19 | 2,6-dichloro-phenyl | CH2 | CH2 | — | H | [DMSO] spectrometer: 399.95 MHz<br>8.9373 (1.36); 8.9229 (2.62); 8.9083 (1.40); 7.4765 (11.58); 7.4564 (16.00); 7.3161 (5.43); 7.2970 (5.29); 7.2951 (5.32); 7.2758 (3.58); 3.5576 (2.10); 3.5408 (5.68); 3.5246 (5.85); 3.5080 (2.59); 3.3415 (57.81); 3.1951 (4.63); 3.1777 (8.55); 3.1604 (3.93); 2.5441 (5.45); 2.5270 (0.80); 2.5136 (14.24); 2.5092 (28.83); 2.5046 (38.37); 2.5001 (28.84); 2.4957 (14.83); 2.0788 (2.44); −0.0002 (5.53) |
| 19-20 | 3-(trifluoro-methyl)phenyl | CH2 | CH2 | — | H | [DMSO] spectrometer: 399.95 MHz<br>8.7964 (2.23); 8.7835 (3.96); 8.7703 (2.26); 7.6628 (0.40); 7.6154 (9.26); 7.6001 (3.27); 7.5966 (3.26); 7.5908 (3.88); 7.5760 (16.00); 7.5625 (9.95); 7.5502 (3.78); 7.5387 (1.89); 7.5262 (1.44); 7.4994 (0.38); 3.5867 (3.96); 3.5695 (10.42); 3.5548 (10.75); 3.5378 (4.57); 3.3419 (134.70); 2.9749 (7.43); 2.9576 (14.97); 2.9403 (6.88); 2.6775 (0.51); 2.6729 (0.68); 2.6685 (0.52); 2.5433 (17.34); 2.5263 (2.41); 2.5128 (40.93); 2.5084 (80.03); 2.5039 (104.05); 2.4994 (77.50); 2.4950 (39.59); 2.3351 (0.50); 2.3307 (0.68); 2.3262 (0.49); 2.0778 (0.93); 0.0080 (0.69); −0.0002 (17.79); −0.0085 (0.76) |
| 19-21 | 4-(trifluoro-methyl)phenyl | CH2 | CH2 | — | H | [DMSO] spectrometer: 399.95 MHz<br>8.8177 (2.60); 8.8041 (4.86); 8.7904 (2.63); 7.6831 (13.11); 7.6630 (16.00); 7.4994 (14.89); 7.4794 (12.39); 3.5812 (4.57); 3.5638 (11.19); 3.5489 (11.29); 3.5316 (5.14); 3.3418 (176.25); 2.9659 (7.54); 2.9483 (14.53); 2.9307 (6.82); 2.6778 (0.52); 2.6731 (0.70); 2.6686 (0.55); 2.5436 (18.36); 2.5266 (2.35); 2.5218 (3.55); 2.5131 (40.06); 2.5087 (80.58); 2.5041 (106.74); 2.4996 (79.60); 2.4952 (40.28); 2.3355 (0.48); 2.3310 (0.68); 2.3266 (0.48); 2.0780 (1.55); 0.0080 (0.58); −0.0002 (17.65); −0.0085 (0.75) |
| 19-22 | 2-methyl-phenyl | CH2 | CH2 | — | H | [DMSO] spectrometer: 399.95 MHz<br>8.8388 (0.56); 8.8252 (1.02); 8.8110 (0.57); 7.1762 (1.10); 7.1680 (1.57); 7.1600 (2.17); 7.1529 (3.48); 7.1464 (1.52); 7.1401 (1.15); 7.1353 (3.36); 7.1325 (3.75); 7.1270 (1.42); 7.1222 (2.19); 7.1175 (1.38); 7.1110 (1.65); 3.4793 (1.11); 3.4639 (1.94); 3.4568 (1.23); 3.4460 (1.65); 3.4415 (2.06); 3.4267 (1.23); 3.3398 (36.67); 2.8624 (2.18); 2.8427 (2.65); 2.8243 (1.97); 2.5424 (3.80); 2.5253 (0.57); 2.5119 (9.67); 2.5074 (19.48); 2.5029 (25.78); 2.4983 (19.12); |

TABLE 19-continued

Compounds of the formula I-19

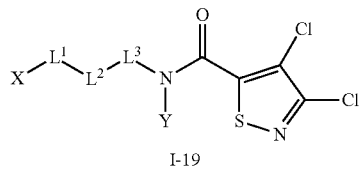

I-19

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 2.4938 (9.54); 2.3216 (16.00); 2.0768 (0.40); −0.0002 (4.25) 2.07 |
| 19-23 | 2,4,6-trimethyl-phenyl | CH2 | CH2 | — | H | |
| 19-24 | 3,4-bismethoxy-phenyl | CH2 | CH2 | — | H | WO-A 1999/24413 |
| 19-25 | phenyl | CH2 | CH2 | — | H | [DMSO] spectrometer: 399.95 MHz 8.7893 (1.92); 8.7766 (3.37); 8.7637 (1.96); 7.3294 (4.40); 7.3257 (2.01); 7.3110 (11.94); 7.2976 (3.73); 7.2929 (12.13); 7.2650 (10.76); 7.2613 (16.00); 7.2443 (7.92); 7.2347 (4.70); 7.2217 (2.41); 7.2166 (6.34); 7.2110 (1.64); 7.2026 (1.43); 7.1989 (2.22); 7.1955 (1.20); 3.5342 (4.15); 3.5169 (7.84); 3.5019 (7.46); 3.4986 (7.53); 3.4832 (4.68); 3.3438 (186.18); 2.8650 (7.54); 2.8463 (12.09); 2.8284 (6.88); 2.6766 (0.41); 2.6723 (0.56); 2.6677 (0.44); 2.5427 (12.25); 2.5257 (1.71); 2.5209 (2.48); 2.5121 (30.51); 2.5078 (62.13); 2.5032 (82.86); 2.4987 (62.25); 2.4942 (31.74); 2.3346 (0.36); 2.3300 (0.52); 2.3255 (0.38); 2.0768 (0.71); −0.0002 (9.93); −0.0084 (0.41) |
| 19-26 | 4-chloro-phenyl | C(CH2—CH2) | CH2 | — | H | |
| 19-27 | 2,4-dichloro-phenyl | C(CH2—CH2) | CH2 | — | H | |
| 19-28 | 4-chloro-phenyl | CH2 | C(CH2—CH2) | — | H | |
| 19-29 | 2,4-dichloro-phenyl | CH2 | C(CH2—CH2) | — | H | |
| 19-30 | 4-chloro-phenyl | O | CH2 | CH2 | H | |
| 19-31 | 2,4-dichloro-phenyl | O | CH2 | CH2 | H | |
| 19-32 | 4-chlorophenyl | CH2 | CH2 | CH2 | H | |
| 19-33 | 4-chlorophenyl | NCH3 | CH2 | CH2 | H | |
| 19-34 | 2,4-dichloro-phenyl | NCH3 | CH2 | CH2 | H | |
| 19-35 | 4-chlorophenyl | CH(OCH3) | CH2 | — | H | |
| 19-36 | 2,4-dichloro-phenyl | CH(OCH3) | CH2 | — | H | |
| 19-37 | 2-thienyl | CH2 | CH2 | — | H | compound No. 19-37, solvent: spectrometer: 399.95 MHz 8.8336 (4.16); 7.3653 (6.75); 7.3528 (7.52); 6.9787 (4.74); 6.97 (7.86); 6.9576 (7.44); 6.937 (9.26); 6.9294 (6.33); 3.5478 (4.27); 3.5305 (10.7); 3.5153 (11.05); 3.4981 (5.03); 3.3931 (0.38); 3.3266 (812.02); 3.2311 (0.42); 3.0886 (8.69); 3.0709 (16); 3.0532 (7.58); 2.6701 (3.3); 2.5397 (2.96); 2.5047 (374.78); 2.501 (476.09); 2.3279 (3.13); 1.2346 (0.43); −0.0002 (5.83 |
| 19-38 | 3-thienyl | CH2 | CH2 | — | H | |
| 19-39 | 2-furyl | CH2 | CH2 | — | H | |
| 19-40 | 3-furyl | CH2 | CH2 | — | H | |
| 19-41 | phenyl | CH2 | CH2 | CH(CH3) | H | |
| 19-42 | phenyl | CH2 | CH2 | CH2 | H | |
| 19-43 | 2-Cl-phenyl | CH2 | CH2 | CH(CH3) | H | |
| 19-44 | 4-t-butylphenyl | CH2 | CH2 | CH2 | H | |
| 19-45 | 4-methylphenyl | CH2 | CH2 | CH2 | H | |
| 19-46 | phenyl | CH2 | CH2 | CH(CH2CH3) | H | |
| 19-47 | 2-methoxy-phenyl | CH2 | CH2 | CH2 | H | |
| 19-48 | 2-methylphenyl | CH2 | CH2 | CH2 | H | |
| 19-49 | 3-methylphenyl | CH2 | CH2 | CH2 | H | |
| 19-50 | 3-chlorophenyl | CH2 | CH2 | CH2 | H | |
| 19-51 | 2,6-difluorophenyl | CH2 | CH2 | CH2 | H | |
| 19-52 | 4-chlorophenyl | CH2 | CH2 | CH2 | H | |
| 19-53 | 2,6-dichlorophenyl | CH2 | CH2 | CH(CH3) | H | |
| 19-54 | 3,5-dichlorophenyl | CH2 | CH2 | CH(CH3) | H | |

TABLE 19-continued

Compounds of the formula I-19

$$X-L^1-L^2-L^3-\underset{Y}{N}-C(O)-\text{(4,5-dichloroisothiazol-3-yl)}$$

I-19

| Ex. No. | X | L¹ | L² | L³ | Y | Physical data: ¹H-NMR, δ [ppm] or CAS or patent No. |
|---|---|---|---|---|---|---|
| 19-55 | 2,6-dimethylphenyl | CH2 | CH2 | CH2 | H | |
| 19-56 | 2,5-dichlorophenyl | CH2 | CH2 | CH2 | H | |
| 19-57 | 4-isopropoxyphenyl | CH2 | CH2 | CH2 | H | |
| 19-58 | 3-trifluoromethylphenyl | CH2 | CH2 | CH(CH3) | H | |
| 19-59 | 4-methylphenyl | CH2 | CH2 | CH(CH3) | H | |
| 19-60 | 2-methylphenyl | CH2 | CH2 | CH(CH3) | H | |
| 19-61 | 3,4-dichlorophenyl | CH2 | CH2 | CH(CH3) | H | |
| 19-62 | 3,5-dichlorophenyl | CH2 | CH2 | CH2 | H | |
| 19-63 | 2,6-dimethylphenyl | CH2 | CH2 | CH(CH3) | H | |
| 19-64 | 4-trifluoromethylphenyl | CH2 | CH2 | CH(CH3) | H | |
| 19-65 | 2,5-dichlorophenyl | CH2 | CH2 | CH(CH3) | H | |
| 19-66 | 4-phenoxyphenyl | CH2 | CH2 | CH2 | H | |
| 19-67 | 3-chlorophenyl | CH2 | CH2 | CH(CH3) | H | |
| 19-68 | 4-phenoxyphenyl | CH2 | CH2 | CH(CH3) | H | |
| 19-69 | 2,4-dichlorophenyl | CH2 | CH2 | CH(CH3) | H | |
| 19-70 | 2-difluoromethoxyphenyl | CH2 | CH2 | CH(CH3) | H | |
| 19-71 | 4-methoxyphenyl | CH2 | CH2 | CH2 | H | |
| 19-72 | 4-chlorophenyl | CH2 | CH2 | CH(CH3) | H | |
| 19-73 | 4-chlorophenyl | CH2 | CH2 | CH(i-propyl) | H | |
| 19-74 | 4-fluorophenyl | CH2 | CH2 | CH2 | H | |
| 19-75 | 4-chlorophenyl | CH2 | CH2 | CH(n-propyl) | H | |
| 19-76 | 4-chlorophenyl | CH2 | CH2 | CH(t-butyl) | H | |
| 19-77 | 2-chlorophenyl | CH2 | CH2 | CH2 | H | |
| 19-78 | 4-chlorophenyl | CH2 | CH(CH3) | — | cyclopropyl | |
| 19-79 | 5-chloro-2-thienyl | CH2 | CH2 | — | H | compound No. 19-79, solvent: spectrometer: 399.95 MHz 8.8608 (2.19); 8.8474 (4.01); 8.8336 (2.24); 7.3913 (15.36); 7.3875 (15.49); 6.9401 (11.63); 6.9369 (11.98); 6.5738 (0.41); 3.5496 (4.49); 3.5324 (11.85); 3.5178 (12.11); 3.5008 (5.14); 3.3233 (38.67); 3.0726 (0.4); 3.0536 (8.3); 3.0363 (16); 3.0194 (7.18); 2.6761 (0.37); 2.6716 (0.5); 2.667 (0.36); 2.525 (1.55); 2.5203 (2.32); 2.5116 (28.26); 2.5072 (57.01); 2.5026 (75.01); 2.498 (53.73); 2.4935 (25.57); 2.334 (0.36); 2.3294 (0.5); 2.3247 (0.37); 1.3361 (1.12); 1.2988 (0.33); 1.2586 (0.47); 1.2494 (1.29); 1.2326 (0.32); 1.1878 (0.37); 0.008 (2.52); −0.0002 (72.28); −0.0085 (2.36) |
| 19-80 | 4-chlorophenyl | CH(CF3) | CH2 | — | H | compound No. 19-80, solvent: spectrometer: 399.95 MHz 8.8846 (2.51); 7.4971 (3.7); 7.4915 (1.85); 7.4753 (16); 7.4611 (12.36); 7.4393 (3.16); 7.4048 (0.67); 4.1116 (0.8); 4.0968 (1.06); 4.0885 (1.33); 4.0736 (1.47); 4.0651 (1.07); 4.0501 (1.02); 4.0414 (0.4); 3.9563 (1.09); 3.9418 (0.97); 3.922 (1.72); 3.9084 (1.42); 3.8182 (1.33); 3.7947 (1.33); 3.763 (0.73); 3.3264 (41.38); 2.6724 (0.32); 2.5117 (19.46); 2.5075 (37.26); 2.5031 (48.06); 2.4986 (35.03); 2.4944 (17.36); 1.3365 (0.91); 1.2492 (0.84); 0.0078 (0.39); −0.0002 (9.03); −0.0084 (0.34) |

TABLE 20

Compounds of the formula I-20

I-20

| Ex. No. | Q | X | L¹ | L² | L³ | Y | Physical data: $^1$H-NMR, δ [ppm] or CAS or patent No. |
|---|---|---|---|---|---|---|---|
| 20-1 | 2,6-difluorphenyl | 4-chlorophenyl | CH2 | CH2 | — | H | CAS: 925125-80-0 |
| 20-2 | 2,6-difluorphenyl | 2,4-dichlorophenyl | CH2 | CH2 | — | H | WO-A 2007/108483 |
| 20-3 | 2,6-difluorphenyl | 4-chlorophenyl | CH2 | CH2 | CH2 | H | |
| 20-4 | 2,6-difluorphenyl | 2,4-dichlorophenyl | CH2 | CH2 | CH2 | H | [DMSO], spectrometer: 399.95 MHz 8.8263 (2.01); 8.8127 (3.75); 8.7992 (2.03); 8.3195 (0.35); 7.5797 (7.62); 7.5754 (7.80); 7.5501 (1.37); 7.5431 (0.37); 7.5334 (2.81); 7.5290 (2.62); 7.5165 (1.97); 7.5123 (5.40); 7.5080 (2.33); 7.4955 (2.66); 7.4912 (3.24); 7.4813 (0.45); 7.4745 (1.46); 7.4443 (0.32); 7.4235 (0.33); 7.4143 (2.32); 7.4066 (0.78); 7.3938 (16.00); 7.3897 (13.57); 7.3850 (11.20); 7.3689 (1.56); 7.3643 (1.92); 7.3549 (0.69); 7.3340 (0.69); 7.2580 (0.83); 7.2374 (0.65); 7.2181 (0.38); 7.2006 (1.69); 7.1931 (8.85); 7.1736 (11.56); 7.1531 (7.40); 7.1452 (1.42); 3.3334 (73.52); 3.3058 (3.23); 3.2892 (8.34); 3.2743 (8.33); 3.2578 (3.38); 3.2429 (0.48); 3.2286 (0.34); 2.7605 (5.97); 2.7413 (7.33); 2.7215 (6.31); 2.6762 (0.65); 2.6718 (0.89); 2.6674 (0.67); 2.6282 (0.33); 2.5421 (0.58); 2.5250 (2.94); 2.5116 (45.53); 2.5072 (89.65); 2.5027 (118.86); 2.4982 (89.41); 2.4939 (45.65); 2.3340 (0.62); 2.3295 (0.85); 2.3251 (0.62); 1.9898 (0.66); 1.8022 (1.81); 1.7852 (4.81); 1.7656 (5.74); 1.7466 (4.63); 1.7293 (1.48); 1.3972 (3.34); 1.1750 (0.35); −0.0002 (4.81) |
| 20-5 | 2,6-difluorphenyl | 4-chlorophenyl | O | CH2 | CH2 | H | CAS: 926794-21-0 |
| 20-6 | 2,6-difluorphenyl | 2,4-dichlorophenyl | O | CH2 | CH2 | H | [DMSO], spectrometer: 399.95 MHz 8.9779 (2.41); 8.9648 (4.49); 8.9517 (2.45); 7.5784 (12.25); 7.5719 (13.18); 7.5473 (1.58); 7.5306 (3.24); 7.5260 (2.99); 7.5139 (2.22); 7.5095 (6.17); 7.5051 (2.47); 7.4927 (3.08); 7.4884 (3.73); 7.4718 (1.67); 7.3861 (6.61); 7.3796 (6.20); 7.3640 (8.78); 7.3575 (8.59); 7.3447 (0.33); 7.2345 (13.85); 7.2122 (10.60); 7.1907 (1.36); 7.1877 (1.82); 7.1803 (10.33); 7.1607 (13.36); 7.1402 (8.65); 7.1325 (1.72); 4.2004 (7.38); 4.1865 (16.00); 4.1727 (8.30); 4.0377 (0.37); 3.6654 (4.11); 3.6516 (11.37); 3.6378 (11.06); 3.6240 (3.84); 3.3342 (45.46); 2.6762 (0.40); 2.6719 (0.56); 2.6673 (0.42); 2.5250 (1.78); 2.5115 (30.26); 2.5072 (60.19); 2.5026 (80.35); 2.4981 (61.14); 2.4937 (31.77); 2.3339 (0.40); 2.3294 (0.53); 2.3249 (0.40); 1.9899 (1.08); 1.3970 (0.40); 1.1750 (0.57); −0.0002 (4.36) |
| 20-7 | 2,6-difluorphenyl | 4-chlorophenyl | CH(OCH3) | CH(CH3) | — | H | |
| 20-8 | 2,6-difluorphenyl | 2,4-dichlorophenyl | CH(OCH3) | CH(CH3) | — | H | |
| 20-9 | 2,6-difluorphenyl | 2-thienyl | CH2 | CH2 | — | H | CAS: 1325338-30-4 |
| 20-10 | 2,6-dichlorophenyl | 4-chlorophenyl | CH2 | CH2 | — | H | CAS: 925089-79-8 |
| 20-11 | 2,6-dichlorophenyl | 2,4-dichlorophenyl | CH2 | CH2 | — | H | |
| 20-12 | 2,6-dichlorophenyl | 4-chlorophenyl | CH2 | CH2 | CH2 | H | |
| 20-13 | 2,6-dichlorophenyl | 2,4-dichlorophenyl | CH2 | CH2 | CH2 | H | |
| 20-14 | 2,6-dichlorophenyl | 4-chlorophenyl | O | CH2 | CH2 | H | |
| 20-15 | 2,6-dichlorophenyl | 2,4-dichlorophenyl | O | CH2 | CH2 | H | |
| 20-16 | 2,6-dichlorophenyl | 4-chlorophenyl | CH(OCH3) | CH(CH3) | — | H | |
| 20-17 | 2,6-dichlorophenyl | 2,4-dichlorophenyl | CH(OCH3) | CH(CH3) | — | H | |

TABLE 20-continued

Compounds of the formula I-20

$$\text{X}-\text{L}^1-\text{L}^2-\text{L}^3-\underset{\text{Y}}{\text{N}}-\overset{\text{O}}{\text{C}}-\text{Q}$$

I-20

| Ex. No. | Q | X | L¹ | L² | L³ | Y | Physical data: ¹H-NMR, δ [ppm] or CAS or patent No. |
|---|---|---|---|---|---|---|---|
| 20-18 | 2,6-dichlorophenyl | 2-thienyl | CH2 | CH2 | — | H | |
| 20-19 | 2-(trifluoro-methyl)phenyl | 4-chlorophenyl | CH2 | CH2 | — | H | WO-A 2007/108483 |
| 20-20 | 2-(trifluoro-methyl)phenyl | 2,4-dichlorophenyl | CH2 | CH2 | — | H | |
| 20-21 | 2-(trifluoro-methyl)phenyl | 4-chlorophenyl | CH2 | CH2 | CH2 | H | |
| 20-22 | 2-(trifluoro-methyl)phenyl | 2,4-dichlorophenyl | CH2 | CH2 | CH2 | H | WO-A 2008/101975 |
| 20-23 | 2-(trifluoro-methyl)phenyl | 4-chlorophenyl | O | CH2 | CH2 | H | CAS: 1099734-75-4 |
| 20-24 | 2-(trifluoro-methyl)phenyl | 2,4-dichlorophenyl | O | CH2 | CH2 | H | |
| 20-25 | 2-(trifluoro-methyl)phenyl | 4-chlorophenyl | CH(OCH3) | CH(CH3) | — | H | |
| 20-26 | 2-(trifluoro-methyl)phenyl | 2,4-dichlorophenyl | CH(OCH3) | CH(CH3) | — | H | [CDCl3], spectrometer: 400.13 MHz 15.1093 (0.48); 8.5572 (0.32); 8.2223 (0.37); 8.1265 (0.34); 8.1070 (0.32); 7.9339 (0.37); 7.8522 (0.52); 7.8429 (0.54); 7.8277 (0.52); 7.7143 (1.89); 7.6949 (2.09); 7.6744 (1.27); 7.6560 (1.51); 7.6211 (0.88); 7.6017 (2.05); 7.5834 (1.94); 7.5530 (2.36); 7.5335 (3.54); 7.5280 (3.38); 7.5180 (3.37); 7.5123 (3.26); 7.4858 (0.72); 7.4816 (0.65); 7.4670 (0.43); 7.4506 (0.32); 7.4238 (3.85); 7.4204 (6.91); 7.4154 (3.78); 7.3909 (1.79); 7.3706 (2.98); 7.3665 (2.66); 7.3589 (0.76); 7.3133 (3.46); 7.2926 (5.56); 7.2884 (5.68); 7.2830 (3.85); 7.2783 (2.62); 7.2593 (320.36); 7.2536 (295.32); 7.2177 (0.33); 6.9953 (1.86); 6.9898 (1.63); 6.2179 (0.40); 6.1986 (1.02); 6.1763 (0.91); 6.0188 (0.64); 5.9948 (0.67); 5.2980 (1.05); 5.2922 (0.92); 4.7474 (2.16); 4.7413 (2.28); 4.6122 (2.57); 4.5815 (0.92); 4.5774 (0.92); 4.5589 (0.87); 4.5538 (0.75); 4.5099 (0.33); 4.4983 (0.68); 4.4919 (0.54); 4.4808 (0.76); 4.4637 (0.62); 4.4577 (0.67); 3.2980 (11.54); 3.2925 (11.18); 3.2858 (16.00); 3.2804 (14.57); 3.2164 (0.38); 3.2101 (0.38); 3.1971 (0.38); 2.8158 (0.70); 1.5876 (0.41); 1.5736 (0.51); 1.5344 (105.05); 1.5297 (91.91); 1.4795 (0.34); 1.4660 (0.32); 1.4098 (4.56); 1.4048 (4.23); 1.3928 (4.72); 1.3879 (4.12); 1.3316 (0.33); 1.2535 (0.41); 1.1374 (0.33); 1.1237 (0.43); 1.0671 (6.78); 1.0623 (6.09); 1.0499 (6.78); 1.0450 (5.96); 0.8472 (0.37); 0.8209 (0.33); 0.1461 (0.66); 0.1410 (0.64); 0.0189 (0.40); 0.0000 (138.31) |
| 20-27 | 2-(trifluoro-methyl)phenyl | 2-thienyl | CH2 | CH2 | — | H | CAS: 1180590-25-3 |
| 20-28 | 2-(difluoro-methyl)phenyl | 4-chlorophenyl | CH2 | CH2 | — | H | compound No. 20-28, solvent: spectrometer: 399.95 MHz 8.6748 (1.05); 8.6614 (1.96); 8.6484 (1.07); 8.3161 (11.05); 7.7031 (2.15); 7.6962 (2.77); 7.6809 (4.08); 7.6373 (0.88); 7.6324 (1.37); 7.6187 (4.41); 7.6137 (6.63); 7.6046 (6.53); 7.5958 (6.35); 7.5769 (1.02); 7.5198 (0.34); 7.5038 (3.53); 7.4963 (2.03); 7.4891 (2.75); 7.4822 (2.27); 7.37 (0.96); 7.364 (8.78); 7.3595 (3.57); 7.3481 (4.13); 7.3431 (16); 7.3375 (2.81); 7.2948 (5.29); 7.2889 (14.58); 7.2679 (8.52); 7.1559 (7); 7.0167 (3.46); 3.5048 (1.84); 3.4874 (4.84); 3.4765 (5.54); 3.4734 (5.65); 3.4591 (2.89); 3.4561 (2.7); 3.3222 (18.88); 3.2983 (2.92); 2.8514 (5.34); 2.8338 (10.46); 2.8163 (4.85); 2.6747 (0.39); 2.6703 (0.56); 2.666 (0.41); 2.5232 (1.53); 2.51 (27.61); 2.5057 (55.63); 2.5012 (74.31); 2.4968 (56.19); 2.4925 (29.47); 2.3323 (0.36); 2.3278 (0.49); 2.3236 (0.38); 0.0075 (0.92); −0.0002 (24.99); −0.0083 (1.27) |
| 20-29 | 2-(difluoro-methyl)phenyl | 2,4-dichlorophenyl | CH2 | CH2 | — | H | [DMSO], spectrometer: 399.95 MHz 8.7190 (1.28); 8.7051 (2.43); 8.6909 (1.28); 7.7105 (1.74); 7.7037 (2.19); 7.6883 (3.14); 7.6439 (0.77); |

TABLE 20-continued

Compounds of the formula I-20

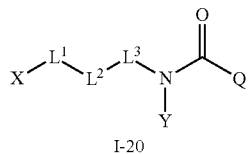

I-20

| Ex. No. | Q | X | $L^1$ | $L^2$ | $L^3$ | Y | Physical data: $^1$H-NMR, δ [ppm] or CAS or patent No. |
|---|---|---|---|---|---|---|---|
| | | | | | | | 7.6390 (1.12); 7.6254 (3.53); 7.6203 (5.06); 7.6112 (5.01); 7.6023 (5.49); 7.5964 (7.93); 7.5837 (1.06); 7.5318 (2.92); 7.5244 (1.58); 7.5168 (2.05); 7.5104 (1.63); 7.3970 (0.54); 7.3779 (16.00); 7.3575 (0.34); 7.3534 (0.47); 7.3217 (2.45); 7.1826 (5.41); 7.0434 (2.66); 3.5390 (1.96); 3.5222 (5.35); 3.5071 (5.49); 3.4905 (2.19); 3.3309 (15.16); 2.9732 (4.24); 2.9563 (8.59); 2.9392 (3.74); 2.5240 (1.03); 2.5108 (13.31); 2.5068 (25.73); 2.5024 (33.46); 2.4979 (24.60); 2.4935 (12.41); 1.9894 (0.40); −0.0002 (6.46) |
| 20-30 | 2-(difluoro-methyl)phenyl | 4-chlorophenyl | CH2 | CH2 | CH2 | H | compound No. 20-30, solvent: spectrometer: 399.95 MHz 8.6396 (1.14); 8.626 (2.12); 8.6119 (1.17); 8.3162 (7.85); 7.7153 (2.16); 7.7058 (3); 7.6931 (3.96); 7.6482 (0.62); 7.6418 (1.22); 7.6296 (5.26); 7.624 (4.86); 7.6179 (4.58); 7.6107 (4.64); 7.6065 (7.73); 7.593 (2.63); 7.5866 (5.14); 7.5735 (2.46); 7.5628 (1.34); 7.4411 (3.25); 7.3524 (9.08); 7.3478 (3.61); 7.3363 (4.21); 7.3314 (16); 7.3257 (2.7); 7.3017 (7.09); 7.2734 (14.23); 7.2524 (8.49); 7.1622 (3.5); 4.0381 (0.37); 4.0204 (0.36); 3.3229 (26.39); 3.2987 (1.9); 3.2701 (2.08); 3.2532 (5.25); 3.239 (5.87); 3.2222 (2.68); 2.6749 (0.45); 2.6707 (0.62); 2.666 (0.56); 2.6531 (4.88); 2.6344 (7.24); 2.6147 (5.28); 2.5238 (1.6); 2.5103 (28.34); 2.5061 (56.45); 2.5016 (75); 2.4972 (56.44); 2.493 (29.4); 2.3331 (0.35); 2.3285 (0.47); 2.3239 (0.38); 1.9888 (1.6); 1.8391 (1.47); 1.8213 (4.26); 1.8021 (5.49); 1.7837 (4.14); 1.7661 (1.29); 1.1928 (0.42); 1.1749 (0.84); 1.1571 (0.42); 0.0079 (0.76); −0.0002 (21.11); −0.0082 (0.96) |
| 20-31 | 2-(difluoro-methyl)phenyl | 2,4-dichlorophenyl | CH2 | CH2 | CH2 | H | compound No. 20-31, solvent: spectrometer: 399.95 MHz 8.6946 (2.25); 8.6809 (4.24); 8.6675 (2.34); 8.3163 (4.8); 7.7197 (3.37); 7.7092 (5.17); 7.6976 (6.25); 7.6532 (0.86); 7.6458 (1.95); 7.6353 (8.89); 7.6283 (8.28); 7.6232 (5.97); 7.618 (8.56); 7.6121 (16); 7.6058 (6.22); 7.6 (9.94); 7.5868 (4.58); 7.577 (12.69); 7.5719 (13.05); 7.4441 (5.22); 7.437 (7.39); 7.4163 (15.96); 7.3907 (10.52); 7.3855 (10.3); 7.3701 (4.41); 7.3649 (4.49); 7.3526 (0.49); 7.3314 (0.58); 7.3048 (10.58); 7.2733 (0.57); 7.2534 (0.37); 7.1654 (5.22); 3.322 (64.94); 3.3093 (4.55); 3.2923 (9.46); 3.2775 (9.74); 3.2608 (4.23); 3.2401 (0.35); 2.7636 (7.41); 2.7447 (9.82); 2.7249 (8); 2.6755 (0.77); 2.671 (1.05); 2.6667 (0.82); 2.5242 (3.23); 2.5106 (53.74); 2.5064 (108.21); 2.5019 (145.28); 2.4974 (113.32); 2.3332 (0.68); 2.3287 (0.95); 2.3242 (0.74); 1.9889 (1.04); 1.8355 (2.26); 1.8179 (6.19); 1.7987 (7.79); 1.7798 (5.96); 1.7624 (1.91); 1.3974 (1.62); 1.1751 (0.55); 0.0079 (1.85); −0.0002 (48.24); −0.0083 (2.91) |
| 20-32 | 2-(difluoro-methyl)phenyl | 4-chlorophenyl | O | CH2 | CH2 | H | |
| 20-33 | 2-(difluoro-methyl)phenyl | 2,4-dichlorophenyl | O | CH2 | CH2 | H | compound No. 20-33, solvent: spectrometer: 399.95 MHz 8.8283 (2.04); 8.8146 (3.93); 8.8013 (2.07); 8.3162 (6.62); 7.7265 (3.04); 7.7188 (4.15); 7.7045 (5.84); 7.6591 (1.2); 7.6529 (2); 7.6413 (5.28); 7.6359 (8.17); 7.6281 (6.64); 7.6183 (10.98); 7.6148 (8.31); 7.598 (8.08); 7.5819 (14.05); 7.5754 (14.37); 7.4377 (4.62); 7.3934 (6); 7.387 (5.67); 7.3713 (8); 7.3648 (7.77); 7.2989 (10.04); 7.2444 (13.18); 7.2221 (9.93); 7.1599 (4.98); 4.2386 (7.22); 4.2244 (16); 4.2102 (8.01); 4.0381 (0.51); 4.0203 (0.46); 3.6674 (3.5); 3.6535 (10.13); 3.6396 (10.08); 3.6255 (3.54); 3.3229 (27.12); 3.2991 (1.99); 2.6753 (0.45); 2.6709 (0.61); 2.6665 (0.45); 2.5239 (1.84); 2.5106 (33.33); 2.5063 (66.36); 2.5018 (87.82); 2.4973 (65.39); 2.4931 (33.55); 2.3331 |

TABLE 20-continued

Compounds of the formula I-20

$$X \diagdown L^1 \diagdown L^2 \diagdown L^3 \diagdown \underset{Y}{N} - \underset{\parallel}{\overset{O}{C}} - Q$$

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (0.41); 2.3286 (0.58); 2.3242 (0.44); 1.9889 (1.87); 1.1928 (0.5); 1.175 (0.98); 1.1572 (0.47); 0.0076 (1.17); −0.0002 (32.23); −0.0084 (1.5) |
| 20-34 | (2-difluoro-methyl)phenyl | 4-chlorophenyl | CH(OCH3) | CH(CH3) | — | H | |
| 20-35 | 2-(difluoro-methyl)phenyl | 2,4-dichlorophenyl | CH(OCH3) | CH(CH3) | — | H | |
| 20-36 | 2-(difluoro-methyl)phenyl | 2-thienyl | CH2 | CH2 | — | H | |
| 20-37 | 2-fluorophenyl | 4-chlorophenyl | CH2 | CH2 | — | H | CAS: 303091-97-6 |
| 20-38 | 2-fluorophenyl | 2,4-dichlorophenyl | CH2 | CH2 | — | H | WO-A 2007/108483 |
| 20-39 | 2-fluorophenyl | 4-chlorophenyl | CH2 | CH2 | CH2 | H | CAS: 932215-55-9 |
| 20-40 | 2-fluorophenyl | 2,4-dichlorophenyl | CH2 | CH2 | CH2 | H | |
| 20-41 | 2-fluorophenyl | 4-chlorophenyl | O | CH2 | CH2 | H | CAS: 1327454-26-1 |
| 20-42 | 2-fluorophenyl | 2,4-dichlorophenyl | O | CH2 | CH2 | H | |
| 20-43 | 2-fluorophenyl | 4-chlorophenyl | CH(OCH3) | CH(CH3) | — | H | |
| 20-44 | 2-fluorophenyl | 2,4-dichlorophenyl | CH(OCH3) | CH(CH3) | — | H | |
| 20-45 | 2-fluorophenyl | 2-thienyl | CH2 | CH2 | — | H | CAS: 883059-03-8 |
| 20-46 | 2-chlorophenyl | 4-chlorophenyl | CH2 | CH2 | — | H | CAS: 329920-38-9 |
| 20-47 | 2-chlorophenyl | 2,4-dichlorophenyl | CH2 | CH2 | — | H | WO-A 2007/108483 |
| 20-48 | 2-chlorophenyl | 4-chlorophenyl | CH2 | CH2 | CH2 | H | CAS: 928982-63-2 |
| 20-49 | 2-chlorophenyl | 2,4-dichlorophenyl | CH2 | CH2 | CH2 | H | |
| 20-50 | 2-chlorophenyl | 4-chlorophenyl | O | CH2 | CH2 | H | |
| 20-51 | 2-chlorophenyl | 2,4-dichlorophenyl | O | CH2 | CH2 | H | |
| 20-52 | 2-chlorophenyl | 4-chlorophenyl | CH(OCH3) | CH(CH3) | — | H | |
| 20-53 | 2-chlorophenyl | 2,4-dichlorophenyl | CH(OCH3) | CH(CH3) | — | H | [CDCl₃], spectrometer: 400.13 MHz 7.6736 (0.75); 7.6688 (0.75); 7.6552 (0.96); 7.6510 (0.83); 7.5184 (0.71); 7.4732 (0.65); 7.4702 (0.70); 7.4516 (0.79); 7.4131 (2.72); 7.4059 (2.52); 7.4009 (2.52); 7.3930 (1.90); 7.3692 (1.87); 7.3666 (1.90); 7.3511 (1.79); 7.3465 (1.53); 7.3332 (1.83); 7.3288 (1.48); 7.3173 (2.79); 7.3090 (0.44); 7.2987 (1.25); 7.2944 (1.19); 7.2798 (0.97); 7.2614 (104.22); 7.2596 (120.45); 7.2462 (1.24); 7.2429 (1.00); 7.2254 (0.53); 7.2092 (1.93); 6.9957 (0.69); 6.6293 (0.40); 6.6066 (0.42); 6.4017 (0.32); 4.7763 (1.27); 4.7674 (1.36); 4.6373 (1.23); 4.6318 (1.33); 4.6097 (0.40); 4.6020 (0.41); 4.5934 (0.37); 4.5860 (0.33); 4.5328 (0.33); 4.5227 (0.35); 4.5170 (0.49); 4.4993 (0.33); 3.3130 (16.00); 2.0058 (1.08); 2.0039 (1.22); 1.5441 (61.86); 1.5428 (64.29); 1.4920 (0.87); 1.4336 (3.42); 1.4167 (3.37); 1.0931 (3.97); 1.0760 (3.96); 0.0018 (37.93); 0.0000 (42.74) |
| 20-54 | 2-chlorophenyl | 2-thienyl | CH2 | CH2 | — | H | CAS: 883059-11-8 |
| 20-55 | 2-bromophenyl | 4-chlorophenyl | CH2 | CH2 | — | H | CAS: 329920-42-5 |
| 20-56 | 2-bromophenyl | 2,4-dichlorophenyl | CH2 | CH2 | — | H | WO-A 2007/108483 |
| 20-57 | 2-bromophenyl | 4-chlorophenyl | CH2 | CH2 | CH2 | H | CAS: 931976-92-0 |
| 20-58 | 2-bromophenyl | 2,4-dichlorophenyl | CH2 | CH2 | CH2 | H | |
| 20-59 | 2-bromophenyl | 4-chlorophenyl | O | CH2 | CH2 | H | CAS: 296273-47-7 |
| 20-60 | 2-bromophenyl | 2,4-dichlorophenyl | O | CH2 | CH2 | H | |
| 20-61 | 2-bromophenyl | 4-chlorophenyl | CH(OCH3) | CH(CH3) | — | H | |
| 20-62 | 2-bromophenyl | 2,4-dichlorophenyl | CH(OCH3) | CH(CH3) | — | H | |
| 20-63 | 2-bromophenyl | 2-thienyl | CH2 | CH2 | — | H | |
| 20-64 | 2-iodophenyl | 4-chlorophenyl | CH2 | CH2 | — | H | WO-A 2001/066553 |
| 20-65 | 2-iodophenyl | 2,4-dichlorophenyl | CH2 | CH2 | — | H | WO-A 2007/108483 |

TABLE 20-continued

Compounds of the formula I-20

I-20

| Ex. No. | Q | X | L¹ | L² | L³ | Y | Physical data: $^1$H-NMR, δ [ppm] or CAS or patent No. |
|---|---|---|---|---|---|---|---|
| 20-66 | 2-iodophenyl | 4-chlorophenyl | CH2 | CH2 | CH2 | H | CAS: 932215-61-7 |
| 20-67 | 2-iodophenyl | 2,4-dichlorophenyl | CH2 | CH2 | CH2 | H | WO-A 2008/101975 |
| 20-68 | 2-iodophenyl | 4-chlorophenyl | O | CH2 | CH2 | H | |
| 20-69 | 2-iodophenyl | 2,4-dichlorophenyl | O | CH2 | CH2 | H | |
| 20-70 | 2-iodophenyl | 4-chlorophenyl | CH(OCH3) | CH(CH3) | — | H | |
| 20-71 | 2-iodophenyl | 2,4-dichlorophenyl | CH(OCH3) | CH(CH3) | — | H | |
| 20-72 | 2-iodophenyl | 2-thienyl | CH2 | CH2 | — | H | CAS: 1180850-78-5 |
| 20-73 | 2-chloro-3-pyridyl | 4-chlorophenyl | CH2 | CH2 | — | H | WO-A 2007/108483 |
| 20-74 | 2-chloro-3-pyridyl | 2,4-dichlorophenyl | CH2 | CH2 | — | H | EP1787981, WO-A 2006/009054 |
| 20-75 | 2-chloro-3-pyridyl | 4-chlorophenyl | CH2 | CH2 | CH2 | H | |
| 20-76 | 2-chloro-3-pyridyl | 2,4-dichlorophenyl | CH2 | CH2 | CH2 | H | WO-A 2008/101976 |
| 20-77 | 2-chloro-3-pyridyl | 4-chlorophenyl | O | CH2 | CH2 | H | CAS: 1280706-56-0 |
| 20-78 | 2-chloro-3-pyridyl | 2,4-dichlorophenyl | O | CH2 | CH2 | H | |
| 20-79 | 2-chloro-3-pyridyl | 4-chlorophenyl | CH(OCH3) | CH(CH3) | — | H | |
| 20-80 | 2-chloro-3-pyridyl | 2,4-dichlorophenyl | CH(OCH3) | CH(CH3) | — | H | [CDCl$_3$], spectrometer: 400.13 MHz 16.6681 (0.46); 16.2155 (0.45); 14.3579 (0.72); 14.3561 (1.20); 10.0965 (0.56); 9.5807 (0.46); 8.4869 (1.28); 8.4816 (1.34); 8.4749 (1.32); 8.4696 (1.39); 8.4501 (0.93); 8.4454 (0.77); 8.4380 (0.97); 8.1345 (1.29); 8.1292 (1.43); 8.1154 (1.43); 8.1099 (1.41); 7.9452 (0.96); 7.9403 (0.86); 7.9257 (0.63); 7.9212 (0.78); 7.5924 (0.48); 7.5606 (0.45); 7.5194 (4.16); 7.4235 (2.42); 7.4184 (3.00); 7.4115 (2.07); 7.4060 (1.55); 7.3936 (2.33); 7.3783 (1.77); 7.3664 (1.55); 7.3592 (1.82); 7.3473 (1.74); 7.3412 (0.95); 7.3317 (1.38); 7.3266 (1.27); 7.3207 (2.05); 7.3093 (4.38); 7.3020 (1.92); 7.2897 (1.72); 7.2807 (1.68); 7.2751 (2.63); 7.2742 (2.29); 7.2717 (3.76); 7.2700 (5.00); 7.2693 (5.79); 7.2685 (6.16); 7.2676 (6.85); 7.2667 (8.28); 7.2606 (749.95); 7.2502 (7.89); 7.2486 (6.63); 7.2478 (6.57); 7.2453 (4.22); 7.2445 (4.18); 7.2420 (3.82); 7.2379 (2.61); 7.2363 (2.79); 7.2258 (1.10); 7.2208 (1.46); 7.2120 (2.36); 6.9966 (4.06); 6.9538 (0.61); 6.9282 (0.56); 6.8835 (0.48); 4.7785 (1.76); 4.7690 (2.00); 4.6423 (1.11); 4.6357 (1.29); 4.6061 (0.58); 4.6031 (0.62); 4.5799 (0.63); 4.5274 (0.48); 4.5181 (0.56); 3.7400 (0.57); 3.3350 (9.58); 3.3291 (16.00); 3.3087 (0.53); 2.3093 (0.53); 2.0635 (0.49); 1.6750 (0.49); 1.5915 (1.09); 1.5438 (268.09); 1.5096 (0.86); 1.4971 (0.81); 1.4603 (0.46); 1.4479 (3.68); 1.4310 (3.73); 1.2843 (0.47); 1.1624 (0.51); 1.1046 (0.47); 1.0955 (6.04); 1.0783 (5.92); 1.0485 (0.63); 0.8443 (0.51); 0.8276 (0.55); 0.1455 (1.37); 0.0487 (1.59); 0.0372 (0.82); 0.0331 (0.73); 0.0193 (1.22); 0.0152 (1.53); 0.0079 (10.51); 0.0053 (5.58) |
| 20-81 | 2-chloro-3-pyridyl | 2-thienyl | CH2 | CH2 | — | H | CAS: 1016515-62-0 |
| 20-82 | 3-chloro-2-pyridyl | 4-chlorophenyl | CH2 | CH2 | — | H | |
| 20-83 | 3-chloro-2-pyridyl | 2,4-dichlorophenyl | CH2 | CH2 | — | H | |
| 20-84 | 3-chloro-2-pyridyl | 4-chlorophenyl | CH2 | CH2 | CH2 | H | |
| 20-85 | 3-chloro-2-pyridyl | 2,4-dichlorophenyl | CH2 | CH2 | CH2 | H | |
| 20-86 | 3-chloro-2-pyridyl | 4-chlorophenyl | O | CH2 | CH2 | H | |

TABLE 20-continued

Compounds of the formula I-20

$$X\underset{L^2}{\overset{L^1}{\diagup}}\underset{L^2}{\overset{L^3}{\diagdown}}\underset{Y}{N}\underset{}{\overset{O}{\diagdown}}Q$$

I-20

Physical data: ¹H-NMR, δ [ppm] or

| Ex. No. | Q | X | L¹ | L² | L³ | Y | CAS or patent No. |
|---|---|---|---|---|---|---|---|
| 20-87 | 3-chloro-2-pyridyl | 2,4-dichlorophenyl | O | CH2 | CH2 | H | |
| 20-88 | 3-chloro-2-pyridyl | 4-chlorophenyl | CH(OCH3) | CH(CH3) | — | H | |
| 20-89 | 3-chloro-2-pyridyl | 2,4-dichlorophenyl | CH(OCH3) | CH(CH3) | — | H | |
| 20-90 | 3-chloro-2-pyridyl | 2-thienyl | CH2 | CH2 | — | H | compound No. 20-90, solvent: spectrometer: 399.95 MHz 8.8102 (2); 8.7969 (3.57); 8.5555 (9.71); 8.5521 (10.14); 8.5439 (10.23); 8.5405 (10.17); 8.0358 (9.45); 8.0324 (9.67); 8.0153 (10.63); 8.0119 (10.2); 7.5563 (11.43); 7.5447 (10.84); 7.5358 (10.42); 7.5242 (10.27); 7.3562 (8.94); 7.3527 (8.99); 7.3439 (9.92); 7.3403 (9.64); 7.3326 (0.52); 7.3228 (0.35); 6.9758 (6.3); 6.9673 (12.58); 6.9636 (5.06); 6.9549 (16); 6.9513 (9.59); 6.948 (10.68); 6.9428 (4.7); 6.9406 (3.88); 3.5307 (5.16); 3.5157 (6.98); 3.5129 (10.36); 3.4982 (10.3); 3.4943 (7.68); 3.4795 (6.03); 3.3275 (282.63); 3.2872 (0.32); 3.074 (8.9); 3.056 (15.41); 3.0375 (7.59); 2.8814 (0.38); 2.6794 (0.35); 2.6752 (0.75); 2.6706 (1.03); 2.6661 (0.73); 2.6614 (0.34); 2.5409 (63.33); 2.524 (3.09); 2.5193 (4.77); 2.5107 (56.86); 2.5062 (114.9); 2.5015 (153.32); 2.4969 (111.2); 2.4924 (52.61); 2.3375 (0.35); 2.3329 (0.75); 2.3283 (1.01); 2.3237 (0.73); 2.319 (0.33); 2.0743 (0.43); 0.008 (0.54); −0.0002 (16.04); −0.0085 (0.45) |
| 20-91 | 2-(difluoromethyl)phenyl | 2-thienyl | CH2 | CH2 | CH2 | H | compound No. 20-91, solvent: spectrometer: 399.95 MHz 8.5671 (3.2); 8.5539 (5.77); 8.5406 (3.33); 7.7868 (7.95); 7.7672 (10.56); 7.7376 (3.51); 7.719 (9.03); 7.7007 (6.5); 7.6564 (6.19); 7.6373 (8.13); 7.6183 (3.11); 7.5222 (9.51); 7.5036 (8.09); 7.3257 (8.36); 7.3238 (8.96); 7.313 (9.28); 7.311 (9.56); 6.9584 (7.59); 6.9499 (9.97); 6.9457 (8.03); 6.9371 (9.24); 6.8814 (10.45); 6.8744 (8.56); 3.3267 (153.05); 3.2886 (5.72); 3.2718 (14.21); 3.2569 (14.23); 3.2403 (5.99); 2.8762 (9.58); 2.8572 (16); 2.838 (10.49); 2.6745 (0.73); 2.67 (0.92); 2.6657 (0.72); 2.5405 (11.03); 2.5052 (95.98); 2.5008 (128.32); 2.4965 (100.07); 2.332 (0.62); 2.3276 (0.83); 2.3234 (0.63); 1.8648 (2.98); 1.8472 (9.01); 1.8282 (11.83); 1.8098 (8.87); 1.7923 (2.72); −0.0002 (2.25) |
| 20-92 | 2-(difluoromethyl)phenyl | 2,6-difluorophenyl | CH2 | CH2 | CH2 | H | compound No. 20-92, solvent: spectrometer: 399.95 MHz 8.5928 (3.25); 8.5793 (6.03); 8.5658 (3.34); 7.7853 (8.08); 7.7657 (10.72); 7.7418 (3.66); 7.7231 (9.13); 7.7045 (6.51); 7.6573 (6.29); 7.6382 (8.15); 7.6194 (3.09); 7.5091 (9.48); 7.4904 (8.06); 7.3579 (1.6); 7.3408 (3.76); 7.3374 (3.57); 7.3202 (7.08); 7.2995 (4.71); 7.2825 (2.12); 7.128 (0.47); 7.1102 (1.39); 7.0972 (10.08); 7.0776 (16); 7.0578 (8.46); 7.0441 (1.14); 6.5523 (0.52); 3.3313 (62.96); 3.2829 (4.85); 3.2659 (11.59); 3.2502 (11.76); 3.2333 (5.14); 2.7073 (7.03); 2.688 (10.99); 2.6683 (8.03); 2.5423 (22.3); 2.5072 (47.4); 2.5028 (62.7); 2.4985 (48.22); 2.3296 (0.41); 1.7824 (2.61); 1.764 (7.07); 1.745 (9.35); 1.7261 (6.81); 1.708 (2.31); −0.0002 (1.23) |
| 20-93 | 2-chloro-3-pyridyl | 2-thienyl | CH2 | CH2 | CH2 | H | compound No. 20-93, solvent: spectrometer: 399.95 MHz 8.6718 (3.1); 8.6585 (5.6); 8.6454 (3.22); 8.4758 (8.48); 8.471 (9.08); 8.4638 (9.26); 8.459 (9.1); 7.9041 (8.97); 7.8993 (9.17); 7.8853 (10.25); 7.8805 (9.87); 7.5068 (9.8); 7.4947 (9.77); 7.488 (9.35); 7.4759 (8.93); 7.3282 (8.94); 7.3254 (8.82); 7.3154 (9.9); 7.3127 (9.38); |

TABLE 20-continued

Compounds of the formula I-20

I-20

| Ex. No. | Q | X | L¹ | L² | L³ | Y | Physical data: $^1$H-NMR, δ [ppm] or CAS or patent No. |
|---|---|---|---|---|---|---|---|
| | | | | | | | 6.9597 (7.48); 6.9512 (10.11); 6.9471 (7.7); 6.9385 (9.32); 6.8921 (10.36); 6.8841 (8.46); 3.3337 (192.94); 3.3095 (6.23); 3.2929 (14.51); 3.278 (14.87); 3.2615 (6.02); 2.908 (9.61); 2.8889 (16); 2.8698 (10.47); 2.6707 (0.52); 2.6663 (0.39); 2.541 (29.76); 2.5239 (1.58); 2.5059 (56.79); 2.5016 (75.45); 2.4972 (58.03); 2.3284 (0.49); 1.8893 (2.96); 1.8719 (9.13); 1.8529 (11.78); 1.8344 (8.87); 1.817 (2.72) |
| 20-94 | 2-chloro-3-pyridyl | 2,6-difluorophenyl | CH2 | CH2 | CH2 | H | compound No. 20-94, solvent: spectrometer: 399.95 MHz 8.7031 (3.23); 8.6894 (5.89); 8.6758 (3.24); 8.4912 (0.37); 8.4766 (8.64); 8.4718 (9.18); 8.4646 (9.27); 8.4598 (9.04); 7.8796 (8.87); 7.8748 (9.07); 7.8608 (10.08); 7.856 (9.71); 7.5112 (9.99); 7.4991 (9.83); 7.4924 (9.19); 7.4803 (8.75); 7.3586 (1.61); 7.3415 (3.75); 7.3381 (3.57); 7.3208 (7.06); 7.3001 (4.69); 7.2832 (2.11); 7.1305 (0.47); 7.115 (0.99); 7.1107 (1.45); 7.0978 (10.04); 7.0781 (16); 7.0582 (8.35); 7.0447 (1.11); 4.1111 (0.33); 3.3304 (78.24); 3.3037 (5.07); 3.2867 (12.08); 3.2713 (12.23); 3.2544 (5.21); 2.7326 (7); 2.7132 (10.88); 2.6935 (7.67); 2.6775 (0.65); 2.6724 (0.63); 2.5425 (6.02); 2.5075 (55.51); 2.5031 (73.74); 2.4987 (56.58); 2.3344 (0.36); 2.3301 (0.48); 1.8048 (2.62); 1.7866 (7.19); 1.7674 (9.3); 1.7485 (6.94); 1.7306 (2.32); −0.0002 (1.2) |
| 20-95 | 2,6-difluorphenyl | 2-thienyl | CH2 | CH2 | CH2 | H | compound No. 20-95, solvent: spectrometer: 399.95 MHz 8.7866 (2.67); 8.7735 (4.65); 8.7608 (2.77); 7.5484 (1.64); 7.5316 (3.62); 7.5274 (3.5); 7.5105 (7.02); 7.4937 (3.64); 7.4895 (4.22); 7.4728 (1.91); 7.3278 (8.06); 7.3251 (7.93); 7.3151 (8.92); 7.3124 (8.41); 7.1979 (1.96); 7.1903 (11.27); 7.1708 (16); 7.1504 (9.58); 7.1424 (1.96); 6.9575 (7.04); 6.949 (9.15); 6.9448 (7.26); 6.9363 (8.37); 6.8801 (9.17); 6.8781 (9.16); 6.8718 (7.9); 3.3278 (164.47); 3.3094 (6.3); 3.2927 (13.31); 3.278 (13.4); 3.2615 (5.42); 2.879 (8.6); 2.86 (14.17); 2.8408 (9.35); 2.6748 (0.7); 2.6704 (0.92); 2.666 (0.69); 2.5407 (13.91); 2.5057 (97.37); 2.5013 (129.07); 2.4969 (98.84); 2.3324 (0.62); 2.3281 (0.85); 2.3238 (0.63); 1.8648 (2.72); 1.8476 (8.31); 1.8284 (10.51); 1.81 (8); 1.7926 (2.48); −0.0002 (1.8) |
| 20-96 | 2,6-difluorphenyl | 2,6-difluorophenyl | CH2 | CH2 | CH2 | H | compound No. 20-96, solvent: spectrometer: 399.95 MHz 8.8193 (2.86); 8.8061 (5.16); 8.793 (3.04); 7.5468 (1.59); 7.53 (3.62); 7.5258 (3.55); 7.5089 (6.85); 7.492 (3.73); 7.488 (4.21); 7.4712 (1.86); 7.3558 (1.44); 7.3389 (3.36); 7.3353 (3.29); 7.3181 (6.42); 7.2975 (4.31); 7.2805 (1.93); 7.2155 (0.34); 7.1946 (2.39); 7.187 (11.02); 7.1673 (16); 7.1471 (9.84); 7.1393 (2.31); 7.1273 (0.75); 7.1048 (1.37); 7.0915 (9.02); 7.0719 (14.49); 7.052 (7.74); 7.0387 (1.18); 3.3299 (80.97); 3.3089 (5.1); 3.2919 (11.57); 3.2766 (11.69); 3.2599 (4.94); 2.7096 (6.49); 2.6901 (9.8); 2.6705 (7.65); 2.5422 (27.45); 2.5071 (59.63); 2.5028 (79.63); 2.4985 (62.94); 2.3297 (0.53); 2.3252 (0.41); 1.7748 (2.41); 1.757 (6.62); 1.7375 (8.36); 1.7184 (6.52); 1.7008 (2.23); −0.0002 (1.19) |
| 20-97 | 3-chloro-2-pyridyl | 4-chlorophenyl | CH(CH3) | CH2 | — | H | compound No. 20-97, solvent: spectrometer: 399.95 MHz 8.6527 (1.15); 8.6382 (2.18); 8.6237 (1.13); 8.524 (4.77); 8.5206 (5.04); 8.5124 (5.01); 8.509 (4.91); 8.0051 (4.61); 8.0017 (4.68); 7.9846 (5.17); 7.9812 (4.91); 7.5252 (5.46); 7.5136 (5.22); 7.5047 (4.94); 7.4931 (4.93); 7.3712 (0.73); 7.3657 (5.87); 7.3604 (2.25); 7.3496 (3.36); 7.3442 (15); 7.3388 (2.37); 7.3198 (2.39); 7.3145 (13.76); 7.3091 (3.14); 7.2982 |

TABLE 20-continued

Compounds of the formula I-20

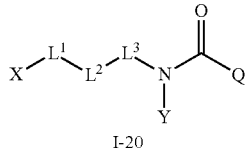

I-20

| Ex. No. | Q | X | L¹ | L² | L³ | Y | Physical data: $^1$H-NMR, δ [ppm] or CAS or patent No. |
|---|---|---|---|---|---|---|---|
| | | | | | | | (2.16); 7.2931 (5.61); 3.4579 (0.52); 3.4427 (0.66); 3.4397 (0.69); 3.4249 (2.62); 3.4074 (4.48); 3.3919 (4.37); 3.3747 (2.74); 3.3601 (0.67); 3.3565 (0.84); 3.3416 (1.25); 3.3261 (91.33); 3.0787 (1.24); 3.0609 (2.5); 3.0431 (2.43); 3.0252 (1.12); 2.6755 (0.33); 2.6709 (0.44); 2.5411 (9.44); 2.5242 (1.49); 2.5194 (2.38); 2.5109 (25.29); 2.5064 (50.25); 2.5018 (66.57); 2.4972 (48.4); 2.4926 (23.09); 2.3286 (0.42); 2.0748 (0.57); 1.2383 (16); 1.2208 (15.67); −0.0002 (8.46) |
| 20-98 | 3-chloro-2-pyridyl | 2,6-difluorophenyl | CH2 | CH2 | — | H | compound No. 20-98, solvent: spectrometer: 399.95 MHz 20.0109 (1.35); 3.3257 (4454.79); 2.6796 (5.86); 2.6751 (11.85); 2.6704 (16); 2.6658 (11.7); 2.6612 (5.68); 2.5407 (14.72); 2.5238 (50.32); 2.5191 (79.38); 2.5105 (854.78); 2.5059 (1704.74); 2.5013 (2262.73); 2.4967 (1622.75); 2.4921 (753); 2.3373 (4.95); 2.3327 (10.69); 2.3281 (14.85); 2.3235 (10.35); 2.3188 (4.51); 2.2876 (1.26); 2.0741 (8.13); 1.2978 (1.71); 1.2582 (2.59); 1.1467 (1.48); 0.008 (9.02); −0.0001 (230.2); −0.0085 (4.9) |
| 20-99 | 3-chloro-2-pyridyl | 2,6-dichlorophenyl | CH2 | CH2 | — | H | compound No. 20-99, solvent: spectrometer: 399.95 MHz 8.879 (1.24); 8.8644 (2.34); 8.85 (1.22); 8.5555 (4.98); 8.5521 (5.26); 8.5439 (5.18); 8.5405 (5.19); 8.0368 (4.91); 8.0334 (4.98); 8.0163 (5.42); 8.0129 (5.24); 7.5576 (5.7); 7.546 (5.41); 7.5371 (5.14); 7.5255 (5.14); 7.4713 (11.44); 7.4513 (16); 7.3098 (5.63); 7.2908 (5.21); 7.2887 (5.09); 7.2695 (3.67); 3.4902 (2.13); 3.4747 (4.25); 3.4665 (2.48); 3.4568 (3.35); 3.4519 (4.42); 3.4374 (2.69); 3.3616 (0.34); 3.3289 (196.23); 3.2997 (0.39); 3.1885 (4.92); 3.1741 (3.82); 3.1684 (5.31); 3.1506 (3.77); 2.9928 (0.4); 2.6759 (0.43); 2.6714 (0.6); 2.6667 (0.44); 2.5417 (3.46); 2.5247 (2.02); 2.5114 (34.95); 2.5069 (69.4); 2.5023 (91.93); 2.4977 (67.13); 2.4932 (32.31); 2.3337 (0.43); 2.3291 (0.59); 2.3244 (0.42); −0.0002 (6.28) |
| 20-100 | 3-chloro-2-pyridyl | 2-thienyl | CH2 | CH2 | CH2 | H | compound No. 20-100, solvent: [DMSO], spectrometer: 399.95 MHz 8.7168 (2.89); 8.7033 (5.09); 8.6899 (2.89); 8.5659 (0.32); 8.555 (11.33); 8.5517 (11.89); 8.5434 (11.97); 8.54 (11.87); 8.5289 (0.39); 8.32 (0.32); 8.0402 (11.39); 8.0368 (11.42); 8.0197 (12.72); 8.0163 (12.03); 7.8261 (0.34); 7.5487 (12.99); 7.537 (12.49); 7.5281 (11.98); 7.5165 (11.77); 7.5051 (0.34); 7.3264 (10.74); 7.3234 (10.9); 7.3136 (11.97); 7.3106 (11.62); 6.9568 (8.97); 6.9483 (11.96); 6.9441 (8.95); 6.9356 (11.41); 6.923 (0.42); 6.8941 (10.56); 6.8915 (10.87); 6.8889 (6.99); 6.8857 (8.56); 6.8831 (8.05); 6.5773 (1.9); 3.3506 (0.55); 3.3346 (35.61); 3.3259 (6.76); 3.3089 (15.07); 3.2939 (15.13); 3.277 (6.37); 2.89 (9.7); 2.8708 (16); 2.8518 (10.42); 2.6762 (0.48); 2.6717 (0.66); 2.6671 (0.49); 2.5417 (0.46); 2.5248 (2.32); 2.5115 (35.66); 2.5071 (71.08); 2.5025 (94.26); 2.498 (70.42); 2.4936 (35.15); 2.3337 (0.46); 2.3292 (0.62); 2.3248 (0.45); 1.8933 (3.31); 1.8757 (9.39); 1.8565 (11.85); 1.8381 (9.11); 1.8205 (2.9); 0.008 (2.01); −0.0002 (56.72); −0.0085 (2.12) |
| 20-101 | 2-chlorophenyl | 2,6-difluorophenyl | CH2 | CH2 | — | H | [CD$_3$CN], spectrometer: 399.95 MHz 7.4371 (1.76); 7.4346 (2.53); 7.4334 (2.70); 7.4310 (2.77); 7.4242 (0.85); 7.4175 (6.85); 7.4155 (8.44); 7.4135 (8.55); 7.4115 (8.75); 7.4090 (6.49); 7.4019 (5.40); 7.3945 (5.99); 7.3873 (8.41); 7.3828 (1.48); 7.3746 (2.32); 7.3722 (1.86); 7.3678 (7.13); 7.3571 (11.42); 7.3540 (16.00); 7.3501 (15.24); 7.3395 (5.36); 7.3353 (4.89); 7.3312 (1.42); 7.3204 (1.20); 7.3163 |

TABLE 20-continued
Compounds of the formula I-20
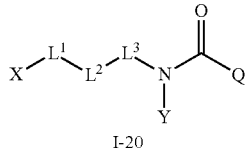
I-20
| Ex. No. | Q | X | L¹ | L² | L³ | Y | Physical data: ¹H-NMR, δ [ppm] or CAS or patent No. |
|---|---|---|---|---|---|---|---|
| | | | | | | | (1.32); 7.3126 (1.46); 7.2960 (2.78); 7.2915 (2.65); 7.2793 (1.79); 7.2750 (5.55); 7.2707 (2.28); 7.2582 (2.69); 7.2541 (3.55); 7.2375 (1.70); 7.0013 (0.80); 6.9969 (1.09); 6.9848 (6.92); 6.9831 (6.20); 6.9765 (1.59); 6.9645 (11.84); 6.9530 (1.94); 6.9442 (6.83); 6.9316 (2.17); 6.9281 (2.07); 6.9115 (1.55); 3.5955 (5.13); 3.5786 (14.04); 3.5623 (14.32); 3.5456 (5.75); 2.9814 (6.83); 2.9643 (12.91); 2.9471 (6.19); 2.1620 (33.13); 1.9649 (1.44); 1.9588 (1.82); 1.9530 (16.67); 1.9469 (31.95); 1.9407 (45.11); 1.9345 (31.42); 1.9283 (16.29); 1.3720 (1.91); 1.3402 (0.53); 1.2846 (0.71); 1.2761 (2.14); 0.0081 (0.86); −0.0002 (24.95); −0.0086 (1.01) |
| 20-102 | 2-bromophenyl | 2,6-difluorophenyl | CH2 | CH2 | — | H | [CD₃CN], spectrometer: 399.95 MHz 7.6127 (5.77); 7.6091 (6.50); 7.6036 (1.81); 7.6006 (1.89); 7.5894 (8.99); 7.4072 (2.86); 7.4043 (3.07); 7.3975 (0.67); 7.3874 (7.17); 7.3868 (7.21); 7.3850 (5.95); 7.3800 (1.03); 7.3700 (7.26); 7.3670 (6.89); 7.3272 (2.78); 7.3224 (9.67); 7.3175 (10.94); 7.3135 (10.59); 7.3053 (8.77); 7.3029 (6.71); 7.2995 (9.00); 7.2941 (8.09); 7.2876 (4.57); 7.2827 (3.70); 7.2764 (6.42); 7.2722 (2.55); 7.2597 (3.10); 7.2555 (3.90); 7.2390 (1.87); 7.0054 (0.85); 7.0009 (1.16); 6.9888 (7.92); 6.9806 (1.72); 6.9686 (13.18); 6.9570 (1.89); 6.9484 (7.10); 6.9356 (1.53); 6.9323 (1.34); 6.8941 (1.93); 5.4488 (1.32); 3.5870 (5.83); 3.5700 (15.66); 3.5535 (16.00); 3.5367 (6.53); 2.9835 (7.84); 2.9662 (14.68); 2.9489 (7.08); 2.1711 (118.64); 2.1083 (0.38); 1.9652 (2.04); 1.9591 (2.81); 1.9533 (23.58); 1.9472 (44.73); 1.9410 (62.83); 1.9348 (43.82); 1.9286 (22.83); 1.7694 (0.36); 1.3719 (1.91); 1.2762 (2.14); 0.0080 (0.99); −0.0002 (26.58); −0.0084 (1.21) |
| 20-103 | 2-iodophenyl | 2,6-difluorophenyl | CH2 | CH2 | — | H | [CD₃CN], spectrometer: 399.95 MHz 7.8836 (7.62); 7.8815 (7.99); 7.8638 (8.08); 7.8616 (8.34); 7.4300 (4.03); 7.4273 (4.06); 7.4112 (9.07); 7.4086 (8.97); 7.3988 (0.51); 7.3923 (5.66); 7.3897 (5.52); 7.3135 (1.53); 7.2968 (3.17); 7.2926 (3.16); 7.2800 (2.15); 7.2759 (6.51); 7.2718 (2.72); 7.2607 (10.21); 7.2568 (11.57); 7.2420 (6.94); 7.2380 (8.66); 7.1493 (4.80); 7.1451 (4.63); 7.1303 (7.26); 7.1261 (7.09); 7.1109 (4.00); 7.1066 (3.77); 7.0077 (0.83); 7.0033 (1.16); 6.9910 (8.12); 6.9709 (13.41); 6.9594 (1.75); 6.9508 (7.13); 6.9381 (1.31); 6.9189 (0.46); 6.8987 (0.50); 6.8553 (1.92); 6.8084 (0.38); 5.4481 (0.51); 3.5767 (6.29); 3.5597 (15.88); 3.5432 (16.00); 3.5263 (6.89); 2.9893 (8.07); 2.9719 (14.90); 2.9545 (7.28); 2.1633 (47.92); 1.9649 (1.38); 1.9587 (1.95); 1.9530 (16.38); 1.9469 (30.82); 1.9407 (43.20); 1.9345 (30.09); 1.9283 (15.53); 1.4359 (0.37); 1.3720 (2.63); 1.2846 (0.41); 1.2760 (2.90); 0.0080 (0.73); −0.0002 (20.73); −0.0085 (0.84) |
| 20-104 | 2-(trifluoromethyl)phenyl | 2,6-difluorophenyl | CH2 | CH2 | — | H | [CD₃CN], spectrometer: 399.95 MHz 7.7400 (6.16); 7.7205 (7.97); 7.6668 (2.61); 7.6492 (6.95); 7.6482 (6.89); 7.6308 (5.47); 7.6035 (5.26); 7.5845 (6.41); 7.5657 (2.23); 7.4252 (7.63); 7.4065 (6.33); 7.3192 (1.51); 7.3026 (3.31); 7.2982 (3.24); 7.2816 (6.65); 7.2776 (2.71); 7.2649 (3.39); 7.2607 (4.16); 7.2441 (1.98); 7.0108 (0.97); 7.0064 (1.34); 6.9942 (8.76); 6.9861 (2.10); 6.9741 (14.69); 6.9624 (2.53); 6.9538 (8.60); 6.9411 (2.78); 6.9377 (2.71); 6.9273 (2.23); 5.4474 (0.58); 3.5774 (6.07); 3.5604 (15.77); 3.5437 (16.00); 3.5269 (6.84); 2.9691 (8.40); 2.9516 (15.43); 2.9342 (7.60); 2.1492 (24.45); 1.9642 (1.04); 1.9579 (1.58); 1.9523 (12.05); 1.9462 (22.63); 1.9400 (31.46); 1.9338 (21.84); 1.9276 (11.33); 1.3724 (3.08); 1.2845 (0.43); 1.2761 (3.32); 0.0079 (0.68); −0.0002 (15.49); −0.0085 (0.64) |

TABLE 20-continued

Compounds of the formula I-20

$$\text{X}-L^1-L^2-L^3-\underset{Y}{N}-\underset{O}{\overset{\displaystyle \|}{C}}-Q$$

I-20

| Ex. No. | Q | X | $L^1$ | $L^2$ | $L^3$ | Y | Physical data: $^1$H-NMR, δ [ppm] or CAS or patent No. |
|---|---|---|---|---|---|---|---|
| 20-105 | 2-(trifluoro-methyl)-3-pyridyl | 2,6-difluorophenyl | CH2 | CH2 | — | H | [CD$_3$CN], spectrometer: 399.95 MHz<br>8.7335 (5.80); 8.7238 (5.79); 8.7218 (5.88); 7.8137 (5.32); 7.8116 (5.51); 7.7942 (6.72); 7.7920 (6.81); 7.6526 (6.31); 7.6407 (6.26); 7.6330 (5.17); 7.6211 (4.91); 7.4201 (0.32); 7.3245 (1.51); 7.3079 (3.19); 7.3034 (3.16); 7.2911 (2.10); 7.2869 (6.53); 7.2827 (2.58); 7.2702 (3.18); 7.2660 (4.06); 7.2572 (0.32); 7.2494 (1.92); 7.0307 (1.96); 7.0148 (2.24); 7.0103 (2.35); 6.9981 (8.83); 6.9899 (2.02); 6.9779 (14.13); 6.9666 (1.86); 6.9577 (7.50); 6.9452 (1.12); 6.9419 (0.91); 5.4484 (0.54); 3.5947 (6.03); 3.5777 (15.78); 3.5612 (16.00); 3.5443 (6.78); 2.9735 (8.07); 2.9560 (15.06); 2.9386 (7.33); 2.1548 (43.11); 2.1084 (0.35); 1.9652 (1.75); 1.9590 (2.35); 1.9533 (20.50); 1.9471 (38.61); 1.9410 (54.32); 1.9348 (37.80); 1.9286 (19.73);<br>1.3722 (5.33); 1.3405 (0.53); 1.2849 (0.79); 1.2764 (5.84); 0.0079 (0.93); −0.0002 (26.02); −0.0084 (1.10) |
| 20-106 | 2-chlorophenyl | 2,6-difluorophenyl | CH2 | CH(CH3) | — | H | spectrometer: 399.95 MHz<br>8.4438 (3.31); 8.4226 (3.36); 7.473 (2.85); 7.4697 (3.19); 7.4532 (6.8); 7.4505 (6.74); 7.4366 (3.01); 7.4323 (3.14); 7.4187 (5.25); 7.4143 (4.95); 7.3994 (3.15); 7.3943 (3.52); 7.3905 (3.91); 7.3862 (3.45); 7.3719 (5.76); 7.3681 (5.89); 7.3537 (3.59); 7.3501 (4.32); 7.3293 (3.87); 7.3087 (2.56); 7.2915 (1.6); 7.2837 (5.55); 7.2804 (5.23); 7.2657 (4.18); 7.2616 (3.65); 7.1028 (1.11); 7.0912 (5.81); 7.0714 (8.95); 7.0518 (4.79); 7.0389 (0.9); 5.7605 (0.99); 4.3148 (0.84); 4.297 (1.97); 4.2789 (2.56); 4.2602 (2.03); 4.2429 (0.92); 3.3372 (17.93); 2.8941 (1.12); 2.8756 (1.22); 2.8607 (3.46); 2.8419 (3.76); 2.8325 (3.85); 2.8152 (3.53); 2.7988 (1.32); 2.7816 (1.11); 2.6717 (0.33); 2.5068 (34.02); 2.5026 (42.22); 2.4984 (32.02); 1.1501 (15.98); 1.1333 (16); 0.0078 (1.03); −0.0002 (18.04); −0.0083 (1.14) |
| 20-107 | 2,6-difluorophenyl | 2,6-difluorophenyl | CH2 | CH(CH3) | — | H | spectrometer: 399.95 MHz<br>8.7305 (3.33); 8.7096 (3.35); 7.5201 (0.97); 7.5034 (2.25); 7.4995 (2.22); 7.4825 (3.92); 7.4657 (2.37); 7.4617 (2.41); 7.4449 (1.1); 7.3628 (0.87); 7.3457 (2.15); 7.3428 (2.13); 7.3253 (3.75); 7.3052 (2.51); 7.2878 (1.12); 7.1488 (6.59); 7.1295 (9.71); 7.1093 (5.82); 7.1011 (1.8); 7.0869 (1.48); 7.0751 (5.92); 7.0556 (8.95); 7.0359 (4.91); 7.0234 (1.03); 5.7601 (2.65); 4.3197 (0.92); 4.3024 (2.06); 4.284 (2.66); 4.2661 (2.11); 4.248 (0.98); 3.3373 (23.33); 2.8796 (1.3); 2.8608 (1.5); 2.8463 (3.43); 2.8277 (3.47); 2.8091 (3.54); 2.7921 (3.46); 2.7757 (1.54); 2.7585 (1.29); 2.6726 (0.37); 2.5071 (44.36); 2.5031 (53.12); 2.3302 (0.37); 1.1388 (16); 1.1221 (15.97); −0.0002 (18.67) |
| 20-108 | 2-(trifluoro-methyl)phenyl | 2,6-difluorophenyl | CH2 | CH(CH3) | — | H | spectrometer: 399.95 MHz<br>8.5208 (3.59); 8.4996 (3.65); 7.7624 (4.49); 7.7427 (6.14); 7.7324 (2.47); 7.7129 (5.08); 7.6946 (3.49); 7.6427 (3.49); 7.6236 (4.61); 7.6046 (1.81); 7.3686 (5.46); 7.362 (3.24); 7.3499 (5.4); 7.3407 (4.33); 7.32 (2.65); 7.303 (1.1); 7.1164 (0.89); 7.1041 (5.75); 7.0846 (9.17); 7.0648 (4.99); 7.0525 (0.88); 4.2957 (0.84); 4.278 (1.97); 4.2595 (2.59); 4.2412 (2.06); 4.2234 (0.9);<br>3.3365 (23.98); 2.9012 (1.45); 2.8825 (1.53); 2.8677 (3.12); 2.8493 (3.06); 2.8145 (3.13); 2.7974 (3.18); 2.7813 (1.61); 2.764 (1.45); 2.6716 (0.38); 2.507 (41.43); 2.5027 (54.72); 2.4986 (44.59); 2.3294 (0.36); 1.1298 (15.95); 1.1131 (16); 0.0078 (1.08); −0.0002 (21.01) |

TABLE 20-continued

Compounds of the formula I-20

$$X-L^1-L^2-L^3-N(Y)-C(=O)-O-Q$$
I-20

| Ex. No. | Q | X | L¹ | L² | L³ | Y | Physical data: ¹H-NMR, δ [ppm] or CAS or patent No. |
|---|---|---|---|---|---|---|---|
| 20-109 | 2-chloro-3-pyridyl | 2,6-difluorophenyl | CH2 | CH(CH3) | — | H | spectrometer: 399.95 MHz<br>8.6234 (3.3); 8.6023 (3.37); 8.4598 (4.87); 8.455 (5.07);<br>8.4478 (5.32); 8.443 (4.86); 7.7344 (4.7); 7.7296 (4.58);<br>7.7156 (5.76); 7.7108 (5.19); 7.5025 (5.18); 7.4904 (5.36); 7.4837 (4.79); 7.4716 (4.46); 7.3741 (0.9); 7.357 (2.17); 7.3537 (2.05); 7.3365 (3.79); 7.3193 (2.34); 7.3159 (2.45); 7.2991 (1.13); 7.1092 (1.04); 7.0976 (5.81); 7.0779 (8.83); 7.0581 (4.82); 7.0457 (1); 5.7609 (0.54); 4.3138 (0.86); 4.2962 (2); 4.2781 (2.6); 4.2597 (2.08); 4.2418 (0.97); 3.3388 (21.6); 2.9002 (1.04); 2.8817 (1.19); 2.8665 (3.63); 2.8459 (5.54); 2.8261 (3.67); 2.8097 (1.28); 2.7924 (1.04); 2.6726 (0.33); 2.5077 (34.68); 2.5035 (42.14); 2.4992 (31.64); 1.9904 (1.19); 1.1929 (0.55); 1.1751 (1.36); 1.1578 (16); 1.1411 (15.75); −0.0002 (16.67) |
| 20-110 | 2-bromophenyl | 2,6-difluorophenyl | CH2 | CH(CH3) | — | H | spectrometer: 399.95 MHz<br>8.4395 (3.53); 8.4184 (3.56); 7.6307 (5.36); 7.6109 (6.18); 7.4354 (2.29); 7.4338 (2.27); 7.4172 (5.65); 7.3987 (4.23); 7.3688 (1.15); 7.353 (4.99); 7.3491 (5.69); 7.3307 (8.3); 7.3148 (4.44); 7.3109 (4.59); 7.294 (1.32); 7.2502 (5.27); 7.2462 (5.11); 7.2316 (4.47); 7.2276 (4.15); 7.0958 (5.89); 7.0762 (9.01); 7.0566 (4.92); 7.0441 (1.03); 4.3013 (0.9); 4.2833 (2.06); 4.265 (2.67); 4.2466 (2.12); 4.2287 (0.96); 3.3372 (18.16); 2.9056 (1.41); 2.8873 (1.61); 2.8722 (3.35); 2.854 (3.27); 2.8277 (3.35); 2.8104 (3.34); 2.7944 (1.63); 2.7769 (1.4); 2.5067 (32.26); 2.5027 (39.54); 1.1474 (16); 1.1306 (15.94); −0.0002 (15.19) |
| 20-111 | 2-(difluoromethyl)phenyl | 2,6-difluorophenyl | CH3 | CH(CH3) | — | H | compound No. 20-111, solvent: [DMSO], spectrometer: 399.95 MHz<br>8.5973 (3.2); 8.576 (3.25); 8.3188 (0.36); 7.6884 (2.21);<br>7.6764 (3.28); 7.6657 (4.13); 7.6282 (1.34); 7.6172 (8.13); 7.6098 (6.21); 7.6034 (6.2); 7.5945 (7.46); 7.585 (1.24); 7.4977 (3.39); 7.4873 (3.31); 7.4766 (2.47); 7.3596 (0.79); 7.3423 (1.9); 7.3392 (2); 7.3221 (3.57); 7.3017 (2.4); 7.2846 (1.02); 7.1282 (3.01); 7.0869 (0.89); 7.0747 (5.48); 7.0551 (8.69); 7.0354 (4.73); 7.0226 (0.77); 6.9892 (6.06); 6.8501 (3.12); 4.3556 (0.79); 4.3376 (1.84); 4.3194 (2.36); 4.3009 (1.88); 4.283 (0.86); 3.3304 (34.98); 2.8634 (8.06); 2.846 (7.36); 2.6755 (0.4); 2.6712 (0.49); 2.5065 (55.44); 2.5023 (71.8); 2.3293 (0.47); 1.3976 (12.9); 1.1985 (16); 1.1817 (15.99); 0.0078 (1.15); −0.0002 (23.5) |
| 20-112 | 2-(difluoromethyl)phenyl | 2,6-dichlorophenyl | CH2 | CH2 | — | H | compound No. 20-112, solvent: [DMSO], spectrometer: 399.95 MHz<br>8.8325 (0.87); 8.8178 (1.69); 8.8033 (0.9); 8.1023 (1.34); 8.0984 (1.06); 8.09 (1.04); 8.086 (1.41); 7.7223 (1.18); 7.7152 (1.61); 7.7006 (2.28); 7.6506 (0.53); 7.6446 (0.83); 7.6331 (1.86); 7.6275 (3.21); 7.6194 (2.93); 7.6097 (4.61); 7.6056 (3.18); 7.5913 (3.22); 7.5752 (1.22); 7.5667 (0.65); 7.5366 (0.45); 7.522 (0.35); 7.5149 (0.44); 7.486 (0.47); 7.4748 (6.75); 7.4547 (9.17); 7.4334 (0.67); 7.4274 (0.63); 7.3851 (1.66); 7.3716 (0.35); 7.3652 (0.37); 7.3527 (0.38); 7.3482 (0.52); 7.3242 (0.44); 7.313 (3.05); 7.3064 (0.61); 7.2922 (3.62); 7.2834 (0.81); 7.2728 (2.28); 7.2649 (0.7); 7.2592 (0.56); 7.2461 (3.66); 7.1854 (0.62); 7.1068 (1.71); 6.5853 (1.45); 6.5813 (1.13); 6.5764 (0.72); 6.573 (1.11); 6.569 (1.46); 5.7589 (0.94);<br>3.5459 (0.35); 3.5364 (1.34); 3.5286 (1.12); 3.5198 (3.43); 3.5032 (3.47); 3.4868 (1.57); 3.3316 (13.6); |

TABLE 20-continued

Compounds of the formula I-20

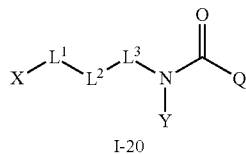

I-20

| Ex. No. | Q | X | L¹ | L² | L³ | Y | Physical data: ¹H-NMR, δ [ppm] or CAS or patent No. |
|---|---|---|---|---|---|---|---|
| 20-113 | 2-(difluoro-methyl)phenyl | 2-chlorophenyl | CH2 | CH2 | — | H | 3.2503 (0.49); 3.1897 (2.92); 3.1722 (4.99); 3.1548 (2.38); 2.9932 (0.54); 2.9757 (0.98); 2.9579 (0.57); 2.9422 (16); 2.5114 (15.32); 2.5072 (30.14); 2.5028 (40.01); 2.4983 (30.7); 2.1225 (0.41); −0.0002 (0.43) compound No. 20-113, solvent: [DMSO], spectrometer: 399.95 MHz 8.7424 (0.88); 8.7288 (1.6); 8.7153 (0.88); 8.3173 (3.76); 8.1014 (1.32); 8.0975 (1.05); 8.0891 (0.99); 8.0851 (1.38); 7.7112 (1.28); 7.7052 (1.59); 7.6892 (2.3); 7.6426 (0.58); 7.638 (0.81); 7.6241 (2.24); 7.619 (3.02); 7.6093 (3.32); 7.6009 (2.97); 7.5953 (2.23); 7.5806 (0.69); 7.5374 (2.14); 7.5215 (1.48); 7.5164 (1.2); 7.4506 (1.9); 7.4464 (1.44); 7.4334 (2.19); 7.4276 (2.49); 7.3716 (1.49); 7.3654 (1.79); 7.3535 (1.81); 7.3484 (2.73); 7.3227 (1.75); 7.3104 (0.73); 7.3057 (1.09); 7.292 (2.76); 7.2873 (2.75); 7.2833 (2.9); 7.276 (4.39); 7.2692 (2.01); 7.2649 (2.4); 7.2596 (1.95); 7.2464 (0.76); 7.2413 (0.6); 7.1836 (3.49); 7.0445 (1.75); 6.586 (1.49); 6.5821 (1.18); 6.5741 (1.46); 6.5697 (1.51); 3.5469 (1.43); 3.5297 (3.57); 3.5146 (3.61); 3.4975 (1.63); 3.351 (107.28); 3.3273 (3.1); 2.9934 (2.96); 2.9759 (5.64); 2.9584 (2.78); 2.942 (16); 2.5079 (21.11); 2.5034 (27.83); 2.499 (21.41); 2.1196 (0.39); 2.1047 (1.11) |
| 20-114 | 2-(difluoro-methyl)phenyl | 2,6-difluorophenyl | CH2 | CH2 | — | H | compound No. 20-114, solvent: [DMSO], spectrometer: 399.95 MHz 8.7976 (2.67); 8.783 (5.05); 8.7685 (2.75); 8.3162 (4.96); 7.7232 (0.47); 7.7126 (4.28); 7.7062 (5.41); 7.6907 (7.95); 7.6445 (1.75); 7.6398 (2.6); 7.6259 (8.26); 7.621 (12.07); 7.6116 (11.86); 7.603 (11.71); 7.5834 (2.06); 7.5172 (7.18); 7.5023 (5.32); 7.4964 (4.42); 7.3681 (1.53); 7.351 (3.58); 7.3475 (3.58); 7.3304 (6.9); 7.3098 (4.64); 7.2988 (6.37); 7.2933 (2.83); 7.1598 (12.75); 7.1013 (1.33); 7.0886 (10.19); 7.069 (16); 7.0579 (2.39); 7.0492 (8.59); 7.0362 (1.3); 7.0207 (6.41); 3.4911 (4.3); 3.4746 (12.35); 3.4588 (13.1); 3.4425 (5.16); 3.3225 (60.57); 3.2986 (1.51); 2.9218 (7.97); 2.9049 (15.53); 2.888 (7.22); 2.675 (0.71); 2.6709 (0.98); 2.6665 (0.74); 2.506 (109.63); 2.5018 (142.43); 2.4975 (107.93); 2.3287 (0.95); 2.3244 (0.73); 1.3979 (1.26); 0.0077 (1.95); −0.0002 (44.93); −0.0075 (2.55) |
| 20-115 | 2-(difluoro-methyl)phenyl | 2,6-difluorophenyl | CH2 | CH2 | CH2 | H | compound No. 20-115, solvent: [DMSO], spectrometer: 399.95 MHz 8.6859 (2.4); 8.6722 (4.39); 8.6588 (2.52); 8.3157 (11.03); 7.7173 (4.29); 7.7069 (5.92); 7.6949 (7.51); 7.6504 (1.37); 7.6443 (2.52); 7.6322 (12.29); 7.6261 (9.65); 7.6203 (9.23); 7.6149 (8.98); 7.6093 (15.36); 7.5966 (3.07); 7.5894 (3.01); 7.5805 (8.02); 7.5685 (5.58); 7.5582 (3.27); 7.4235 (5.92); 7.3534 (1.65); 7.3362 (3.7); 7.3327 (3.65); 7.3156 (7.13); 7.2949 (5.2); 7.2841 (13.11); 7.1448 (6.49); 7.1225 (0.48); 7.1085 (1.03); 7.1042 (1.45); 7.0913 (9.92); 7.0717 (16); 7.0518 (8.5); 7.0384 (1.33); 6.5388 (0.52); 3.3207 (120.85); 3.2977 (7.7); 3.2813 (9.77); 3.2666 (10.82); 3.2496 (5.18); 2.7092 (7.16); 2.69 (11.86); 2.6705 (10.18); 2.5059 (249.54); 2.5015 (326.17); 2.4972 (249.79); 2.3325 (1.58); 2.3282 (2.17); 2.3239 (1.66); 1.9886 (0.4); 1.8168 (2.68); 1.7983 (7.48); 1.7794 (10.07); 1.7606 (7.19); 1.7425 (2.46); 1.3978 (2.07); 0.1461 (0.48); 0.0077 (4.77); −0.0002 (99.46); −0.0078 (6.39); −0.1497 (0.48) |
| 20-116 | 2,6-difluorphenyl | 2,6-difluorophenyl | CH2 | CH2 | — | H | compound No. 20-116, solvent: [DMSO], spectrometer: 399.95 MHz 8.8727 (2.68); 8.8581 (4.9); 8.8442 (2.75); 8.3184 |

TABLE 20-continued
Compounds of the formula I-20
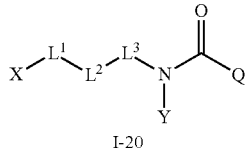
I-20
| Ex. No. | Q | X | $L^1$ | $L^2$ | $L^3$ | Y | Physical data: $^1$H-NMR, δ [ppm] or CAS or patent No. |
|---|---|---|---|---|---|---|---|
| | | | | | | | (1.05); 7.5297 (1.61); 7.513 (3.41); 7.5086 (3.47); 7.492 (6.65); 7.4752 (3.56); 7.471 (4); 7.4543 (1.8); 7.3647 (1.43); 7.3477 (3.27); 7.344 (3.25); 7.3271 (6.26); 7.3064 (4.11); 7.2895 (1.92); 7.1673 (2.25); 7.1601 (11.3); 7.1402 (16); 7.1203 (9.66); 7.1125 (2.08); 7.1012 (1.12); 7.0969 (1.41); 7.0843 (9.15); 7.0648 (14.29); 7.0538 (2.28); 7.045 (7.76); 7.032 (1.16); 4.3621 (0.81); 3.4784 (4.37); 3.4614 (11.35); 3.4452 (11.62); 3.4284 (4.92); 3.3288 (57.35); 3.3054 (0.64); 2.8926 (7.33); 2.8751 (13.83); 2.8576 (6.7); 2.6752 (0.74); 2.6711 (0.98); 2.6667 (0.77); 2.5063 (107.61); 2.502 (140.51); 2.4977 (107.71); 2.3328 (0.68); 2.3288 (0.93); 2.3244 (0.71); 1.9893 (0.4); 1.3358 (0.35); 1.2493 (0.37); 0.0075 (2.3); −0.0002 (48.12); −0.0079 (2.93) |
| 20-117 | 2-(trifluoro-methyl)phenyl | 2,4-dichlorophenyl | CH(OCH3) | CH(CH3) | — | cPr | compound No. 20-117, solvent: +CDCl3+, spectrometer: 400.13MHz 7.6348 (0.95); 7.6238 (1.04); 7.6125 (1.19); 7.5516 (0.32); 7.545 (0.36); 7.5185 (2.65); 7.4603 (1.55); 7.4529 (1.34); 7.4126 (1.87); 7.4028 (1.66); 7.3939 (1.49); 7.3809 (0.38); 7.3593 (0.71); 7.358 (0.35); 7.3571 (0.33); 7.3563 (0.34); 7.3555 (0.35); 7.3538 (0.66); 7.3514 (0.46); 7.3507 (0.47); 7.3499 (0.41); 7.3343 (0.33); 7.3319 (0.33); 7.3311 (0.33); 7.3303 (0.33); 7.3294 (0.34); 7.3286 (0.33); 7.3278 (0.37); 7.327 (0.38); 7.3262 (0.4); 7.3254 (0.45); 7.3245 (0.47); 7.3237 (0.45); 7.3229 (0.5); 7.3221 (0.55); 7.3213 (0.53); 7.3205 (0.53); 7.3197 (0.5); 7.3189 (0.49); 7.318 (0.51); 7.3172 (0.5); 7.3164 (0.49); 7.3156 (0.49); 7.3148 (0.48); 7.314 (0.41); 7.3132 (0.4); 7.3123 (0.39); 7.3115 (0.4); 7.3094 (4.03); 7.3059 (1.7); 7.3042 (1.56); 7.3034 (1.47); 7.3026 (1.45); 7.3018 (1.42); 7.301 (1.43); 7.3001 (1.35); 7.2993 (1.37); 7.2985 (1.36); 7.2977 (1.24); 7.2969 (1.25); 7.296 (1.23); 7.2953 (1.23); 7.2944 (1.15); 7.2937 (1.08); 7.2928 (1.08); 7.292 (1.06); 7.2912 (1.02); 7.2903 (1.05); 7.2895 (1.13); 7.2887 (1.21); 7.2879 (1.17); 7.2871 (1.21); 7.2862 (1.24); 7.2854 (1.31); 7.2846 (1.36); 7.2838 (1.4); 7.283 (1.47); 7.2822 (1.53); 7.2814 (1.54); 7.2806 (1.56); 7.2797 (1.6); 7.2789 (1.64); 7.2781 (1.63); 7.2773 (1.73); 7.2764 (1.91); 7.2756 (1.99); 7.2748 (2.06); 7.274 (2.17); 7.2732 (2.42); 7.2723 (2.63); 7.2715 (3.05); 7.2707 (3.3); 7.2699 (3.71); 7.269 (4.36); 7.2682 (5.11); 7.2598 (427.96); 7.2472 (1.59); 7.2439 (1.05); 7.2423 (0.93); 7.2399 (0.71); 7.2382 (0.56); 7.2374 (0.51); 7.2358 (0.43); 7.235 (0.41); 7.2341 (0.36); 7.2333 (0.35); 7.2325 (0.33); 6.9959 (2.37); 6.5292 (0.32); 5.2988 (1.86); 5.2781 (0.33); 5.2691 (0.32); 4.9815 (0.33); 4.1339 (0.34); 3.4911 (0.55); 3.4204 (0.92); 3.2502 (16); 3.1874 (0.5); 3.0278 (0.52); 3.0155 (0.51); 2.1633 (0.38); 2.1548 (0.39); 2.0052 (0.61); 1.5868 (2.32); 1.5704 (2.48); 1.5363 (24.44); 1.4702 (0.96); 1.4528 (0.91); 1.2683 (0.49); 1.256 (0.79); 0.6284 (0.38); 0.5985 (0.58); 0.5747 (0.43); 0.5708 (0.43); 0.5483 (0.44); 0.4776 (0.38); 0.3062 (0.43); 0.2916 (0.5); 0.2816 (0.42); 0.1679 (0.33); 0.1462 (0.69); 0.0497 (0.93); 0.0174 (0.34); 0.0166 (0.4); 0.0159 (0.48); 0.015 (0.48); 0.0142 (0.49); 0.0134 (0.58); 0.0125 (0.72); 0.0117 (0.82); 0.0109 (1.01); 0.0101 (1.27); 0.0082 (3.77); 0.0069 (2.02); 0.006 |

TABLE 20-continued

Compounds of the formula I-20

$$X-L^1-L^2-L^3-N(Y)-C(=O)-O-Q$$

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (2.42); 0.0051 (3.06); 0.0000 (124.02) |
| 20-118 | 2-(trifluoro-methyl)phenyl | 2,4-dichlorophenyl | CH(OCH3) | C(CH2CH2) | — | H | compound No. 20-118, solvent: [CDCl₃], spectrometer: 400.13 MHz<br>7.665 (0.75); 7.6635 (0.7); 7.6455 (0.94); 7.644 (0.91); 7.5752 (0.81); 7.5734 (0.79); 7.5566 (0.7); 7.5546 (0.62); 7.5289 (0.42); 7.5268 (0.6); 7.525 (0.65); 7.5231 (0.54); 7.5186 (0.5); 7.5076 (0.72); 7.5059 (0.76); 7.5041 (0.64); 7.4726 (0.9); 7.4709 (0.94); 7.4539 (0.66); 7.4521 (0.71); 7.4295 (1.6); 7.4121 (2.32); 7.4073 (3.86); 7.2922 (1.11); 7.2911 (1.18); 7.2857 (1.04); 7.2747 (0.32); 7.2739 (0.39); 7.273 (0.49); 7.2715 (1); 7.27 (1.22); 7.2681 (0.92); 7.2673 (1.14); 7.2658 (1.98); 7.2648 (2.3); 7.2641 (2.59); 7.2598 (71.63); 7.2542 (1.71); 7.2533 (1.37); 7.2525 (1.12); 7.2516 (0.96); 7.2508 (0.87); 7.25 (0.77); 7.2492 (0.71); 7.2484 (0.63); 7.2476 (0.55); 7.2467 (0.48); 7.2459 (0.43); 7.2451 (0.41); 7.2442 (0.39); 7.2434 (0.35); 7.2426 (0.33); 6.9959 (0.41); 6 (0.68); 5.1563 (2.86); 3.2515 (16); 1.5413 (2.81); 1.1056 (0.35); 1.0955 (0.46); 1.0919 (0.57); 1.0762 (0.74); 1.0708 (0.5); 0.9468 (0.32); 0.9319 (0.45); 0.9262 (0.65); 0.9212 (0.93); 0.916 (0.74); 0.9119 (1.24); 0.9101 (1.26); 0.9034 (2.72); 0.893 (0.95); 0.8872 (0.6); 0.877 (0.34); 0.0082 (0.62); 0.0059 (0.33); 0.0051 (0.39) |
| 20-119 | 2,6-difluorophenyl | 4-chlorophenyl | CH(OCH3) | CH2 | — | H | compound No. 20-119, solvent: [DMSO], spectrometer: 399.95 MHz<br>8.8718 (0.55); 8.8577 (1.06); 8.8435 (0.56); 7.5093 (0.65); 7.505 (0.65); 7.4882 (1.26); 7.4715 (0.67); 7.4672 (0.79); 7.452 (3.08); 7.4311 (5.06); 7.3741 (4.76); 7.353 (2.88); 7.1628 (0.37); 7.1551 (2.12); 7.1354 (2.94); 7.1153 (1.81); 7.1073 (0.35); 4.3805 (0.89); 4.365 (1.61); 4.3489 (0.96); 3.4537 (1); 3.4393 (1.44); 3.4371 (1.44); 3.4287 (1.87); 3.4227 (1.15); 3.4141 (0.98); 3.3216 (61 16); 2.506 (15.91); 2.5015 (21.21); 2.4971 (16.22); −0.0002 (1.09) |
| 20-120 | 2-chloro-3-pyridyl | 2,6-difluorophenyl | CH2 | CH2 | — | H | compound No. 20-120, solvent: [CD₃CN], spectrometer: 399.95 MHz<br>8.413 (5.82); 8.4084 (6.01); 8.401 (6.05); 8.3964 (5.98); 7.7501 (6.22); 7.7454 (6.37); 7.7311 (6.93); 7.7265 (6.91); 7.3888 (6.67); 7.3767 (6.62); 7.3701 (6.22); 7.358 (5.91); 7.315 (1.48); 7.2981 (2.8); 7.294 (2.88); 7.2774 (5.64); 7.2605 (3.03); 7.2567 (3.53); 7.24 (1.7); 7.034 (1.71); 7.0019 (1.31); 6.9977 (1.48); 6.9847 (8.12); 6.9652 (12.79); 6.9535 (1.59); 6.9452 (6.91); 6.9321 (0.96); 5.447 (0.69); 3.6072 (5.51); 3.5905 (15.58); 3.574 (16); 3.5574 (6.09); 2.9864 (7.72); 2.9693 (14.57); 2.9521 (6.97); 2.1507 (45.69); 1.9711 (0.52); 1.9639 (1.18); 1.952 (12.63); 1.9459 (23.7); 1.9397 (33.17); 1.9337 (23.28); 1.9276 (12.36); 1.3715 (2.1); 1.3401 (0.39); 1.2844 (0.57); 1.2761 (2.18); −0.0003 (0.35) |
| 20-121 | 2,6-dichlorophenyl | 2,6-difluorophenyl | CH2 | CH2 | — | H | compound No. 20-121, solvent: [CD₃CN], spectrometer: 399.95 MHz<br>7.4155 (0.48); 7.3951 (3.94); 7.3889 (5.15); 7.3717 (16); 7.3474 (6.9); 7.3318 (3.81); 7.3237 (2.35); 7.3081 (2.31); 7.2916 (1.59); 7.2875 (1.66); 7.2708 (3.18); 7.254 (1.73); 7.2501 (2.03); 7.2335 (0.97); 6.9916 (1.52); 6.9879 (1.64); 6.975 (5.18); 6.9555 (7.6); 6.9354 (4.05); 6.9224 (0.7); 5.4464 (0.36); 3.631 (3.11); 3.614 (7.2); 3.596 (7.13); 3.5793 (3.44); 2.9879 (4.6); 2.9696 (8.01); 2.9517 (4.13); 2.1407 (13.38); 1.9635 (0.73); 1.9516 (7.7); 1.9454 (14.55); 1.9393 (20.39); 1.9331 (14.36); 1.927 (7.57); 1.3716 (2.51); 1.3401 (0.44); 1.2846 (0.57); 1.2762 (2.42) |

TABLE 20-continued

Compounds of the formula I-20

$$X-L^1-L^2-L^3-N(Y)-C(=O)-O-Q$$
I-20

| Ex. No. | Q | X | L¹ | L² | L³ | Y | Physical data: ¹H-NMR, δ [ppm] or CAS or patent No. |
|---|---|---|---|---|---|---|---|
| 20-122 | 2-(trifluoro-methoxy)phenyl | 2,6-difluorophenyl | CH2 | CH2 | — | H | compound No. 20-122, solvent: [CD₃CN], spectrometer: 399.95 MHz 7.5826 (5.72); 7.5783 (7.26); 7.5631 (7.35); 7.5596 (11.94); 7.541 (7.35); 7.5365 (5.83); 7.521 (5.42); 7.5169 (4.3); 7.4321 (6.15); 7.4132 (9.06); 7.3956 (3.52); 7.3945 (3.57); 7.3685 (6.23); 7.3479 (4.93); 7.3091 (1.48); 7.2924 (3.11); 7.2882 (3.25); 7.2716 (6.38); 7.2549 (3.28); 7.2508 (3.94); 7.2342 (1.88); 7.0112 (1.97); 6.993 (2.2); 6.9888 (2.27); 6.9761 (9.15); 6.9563 (14.31); 6.9448 (1.73); 6.9363 (7.65); 6.9233 (1.05); 3.5864 (6.21); 3.5695 (15.84); 3.5528 (16); 3.5359 (6.84); 2.9747 (8.49); 2.9571 (15.55); 2.9396 (7.56); 2.1449 (40.42); 2.1432 (39.69); 2.1074 (0.37); 1.9636 (2); 1.9518 (20.41); 1.9456 (37.73); 1.9395 (52.75); 1.9334 (36.61); 1.9273 (18.96); 1.3721 (2.9); 1.3406 (0.43); 1.2851 (0.6); 1.2766 (2.86); −0.0002 (0.62) |
| 20-123 | 2-cyano-phenyl | 2,6-difluorophenyl | CH2 | CH2 | — | H | compound No. 20-123, solvent: [CD₃CN], spectrometer: 399.95 MHz 9.0801 (4.37); 8.3734 (0.34); 8.0779 (0.54); 8.0564 (0.58); 8.0283 (0.48); 8.0072 (0.54); 7.8753 (4.87); 7.8569 (5.91); 7.7506 (2.67); 7.7315 (6.56); 7.7081 (10.99); 7.6858 (8.38); 7.6676 (7.41); 7.6491 (2.51); 7.5314 (0.33); 7.5109 (0.42); 7.4259 (0.8); 7.4202 (0.79); 7.2606 (1.35); 7.24 (3.01); 7.2227 (4.19); 7.2053 (2.67); 7.1852 (1.03); 7.1712 (0.56); 7.165 (0.52); 7.1499 (0.33); 6.8967 (1.05); 6.8841 (6.99); 6.8645 (11.28); 6.845 (5.98); 6.8315 (0.81); 6.3743 (1.52); 5.4473 (1.14); 4.0359 (5.9); 4.0191 (12.18); 4.0024 (6.7); 3.951 (0.72); 3.1122 (5.02); 3.0957 (9.47); 3.0791 (5.04); 3.0257 (0.63); 3.0155 (0.68); 2.4681 (0.9); 2.4632 (1.21); 2.4587 (0.82); 2.156 (225.3); 2.1503 (501.46); 2.1196 (2.74); 2.1135 (2.75); 2.1073 (2.81); 2.101 (1.96); 2.0948 (1.25); 1.9641 (12.84); 1.9521 (136.9); 1.946 (250.5); 1.9399 (342.39); 1.9337 (240.09); 1.9275 (124.67); 1.7806 (0.92); 1.7744 (1.6); 1.7683 (2.15); 1.7621 (1.53); 1.7559 (0.86); 1.3716 (15.13); 1.3403 (2.55); 1.3132 (0.86); 1.2966 (1.15); 1.285 (3.95); 1.2766 (16); 1.2229 (0.42); 1.2167 (0.64); 1.2056 (0.55); 1.1883 (0.38); 1.1304 (0.35); 0.8817 (0.49); 0.8586 (0.52); 0.8409 (0.37); −0.0002 (2.32) |
| 20-124 | 3-(trifluoro-methyl)-2-pyridyl | 2,6-l difluoropheny | CH2 | CH2 | — | H | compound No. 20-124, solvent: [CD₃CN], spectrometer: 399.95 MHz 8.8469 (0.36); 8.8342 (0.37); 8.7487 (6.37); 8.7374 (6.53); 8.208 (6.64); 8.1879 (7.1); 7.8158 (1.77); 7.7015 (0.35); 7.6889 (0.34); 7.6833 (0.37); 7.6687 (0.45); 7.6521 (4.69); 7.6401 (4.76); 7.6319 (4.63); 7.6199 (4.35); 7.6044 (0.32); 7.4259 (0.77); 7.4199 (0.83); 7.3009 (1.46); 7.2843 (3.12); 7.28 (3.31); 7.2633 (6.63); 7.2467 (3.29); 7.2424 (4.38); 7.2361 (0.98); 7.226 (1.89); 7.1713 (0.55); 7.1651 (0.57); 7.1503 (0.37); 7.1441 (0.42); 6.9777 (0.84); 6.9734 (1.15); 6.9609 (8.33); 6.941 (14); 6.9296 (1.93); 6.9209 (7.55); 6.9083 (1.07); 6.3754 (0.56); 4.4849 (0.81); 4.4775 (0.5); 4.4734 (0.88); 4.4692 (0.55); 4.4618 (0.89); 3.7125 (0.88); 3.7054 (0.51); 3.7009 (0.91); 3.6968 (0.57); 3.6893 (0.85); 3.6246 (6.1); 3.6076 (15.27); 3.5901 (15.42); 3.5733 (6.87); 3.5288 (0.42); 3.5113 (1.22); 3.4937 (1.24); 3.4763 (0.43); 2.9902 (8.31); 2.9722 (15.03); 2.9548 (7.65); 2.4688 (0.34); 2.4641 (0.46); 2.4594 (0.36); 2.1646 (105.76); 2.1206 (0.4); 2.1142 (0.46); 2.1079 (0.52); 2.1018 (0.38); 1.9648 (2.06); 1.9585 (2.65); 1.9529 (23.35); 1.9467 (44.62); 1.9406 |

TABLE 20-continued
Compounds of the formula I-20
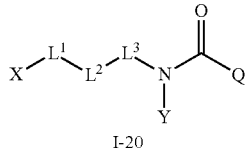
| Ex. No. | Q | X | L¹ | L² | L³ | Y | Physical data: $^1$H-NMR, δ [ppm] or CAS or patent No. |
|---|---|---|---|---|---|---|---|
| | | | | | | | (63.49); 1.9344 (45.42); 1.9282 (24.55); 1.769 (0.41); 1.386 (0.4); 1.3718 (15.25); 1.3405 (2.6); 1.308 (0.65); 1.2915 (0.91); 1.2849 (3.44); 1.2764 (16); 1.2166 (0.59); 1.1548 (1.33); 1.1373 (2.58); 1.1197 (1.36); 0.8805 (0.38); −0.0002 (0.46) |
| 20-125 | 2-fluorophenyl | 5-chloro-2-thienyl | CH2 | CH2 | — | H | compound No. 20-125, solvent: [DMSO], spectrometer: 399.95 MHz 8.4651 (3.06); 8.316 (0.52); 7.603 (3.12); 7.5985 (3.75); 7.5846 (5.99); 7.5799 (7.33); 7.5716 (0.67); 7.5652 (3.95); 7.5609 (4.16); 7.5508 (1.95); 7.5462 (1.77); 7.5375 (2.11); 7.5326 (4.05); 7.5298 (2.81); 7.5279 (2.67); 7.5254 (2.46); 7.5187 (3.11); 7.5147 (2.73); 7.5117 (4.45); 7.5069 (2.31); 7.4983 (2.53); 7.4936 (2.12); 7.3806 (15.87); 7.3767 (16); 7.3046 (5.11); 7.2935 (5.8); 7.291 (6.09); 7.2858 (4.11); 7.2836 (4.82); 7.2803 (5.14); 7.2774 (6.68); 7.2746 (10.59); 7.2725 (8.3); 7.2594 (3.7); 7.2561 (9.16); 7.2536 (3.7); 6.9263 (11.37); 6.9249 (10.3); 6.9228 (11.38); 3.5151 (4.1); 3.4979 (10.57); 3.4832 (10.85); 3.4662 (4.73); 3.3217 (75.88); 3.0523 (0.4); 3.0357 (7.98); 3.0183 (15.2); 3.0015 (6.77); 2.6797 (0.34); 2.6751 (0.71); 2.6705 (0.98); 2.6659 (0.71); 2.6617 (0.32); 2.5239 (3.01); 2.5191 (4.59); 2.5105 (53.81); 2.506 (108.31); 2.5015 (142.01); 2.4968 (100.19); 2.4923 (46.53); 2.3327 (0.68); 2.3282 (0.94); 2.3236 (0.65); 1.2982 (0.41); 1.2586 (0.58); 0.146 (0.57); 0.016 (0.45); 0.008 (4.91); −0.0002 (137.72); −0.0086 (4.08); −0.1497 (0.56) |
| 20-126 | 2,6-difluorophenyl | 5-chloro-2-thienyl | CH2 | CH2 | — | H | compound No. 20-126, solvent: [DMSO], spectrometer: 399.95 MHz 8.8955 (2.25); 8.8821 (4.07); 8.8684 (2.2); 8.3156 (0.5); 7.5431 (1.73); 7.5264 (3.66); 7.5218 (3.28); 7.5097 (2.34); 7.5052 (7.02); 7.5008 (2.44); 7.4885 (3.31); 7.4841 (4.09); 7.4675 (1.9); 7.3865 (15.76); 7.3826 (16); 7.1905 (1.42); 7.1874 (1.96); 7.1799 (11.48); 7.1604 (14.18); 7.1505 (1.68); 7.1398 (9.63); 7.1321 (1.61); 6.9192 (11.69); 6.9159 (11.67); 3.5099 (4.38); 3.4929 (11.66); 3.4784 (11.87); 3.4616 (4.98); 3.3205 (83.35); 3.0294 (0.41); 3.0138 (8.08); 2.9968 (15.71); 2.98 (6.98); 2.6792 (0.43); 2.6748 (0.93); 2.6702 (1.27); 2.6657 (0.92); 2.6611 (0.43); 2.5236 (4.01); 2.5187 (6.09); 2.5102 (72.3); 2.5057 (144.74); 2.5012 (189.52); 2.4966 (134.68); 2.492 (63.46); 2.3371 (0.43); 2.3325 (0.92); 2.3279 (1.26); 2.3234 (0.91); 2.3189 (0.42); 1.2586 (0.37); 0.1459 (0.72); 0.008 (6.22); −0.0002 (170.52); −0.0085 (5.32); −0.0172 (0.44); −0.1497 (0.71) |
| 20-127 | 2-fluorophenyl | 4-chlorophenyl | CH(CF3) | CH2 | — | H | compound No. 20-127, solvent: [DMSO], spectrometer: 399.95 MHz 8.4686 (1.65); 7.5309 (0.78); 7.5263 (0.92); 7.5176 (0.9); 7.5128 (1.83); 7.5081 (1.53); 7.5056 (1.32); 7.4988 (1.41); 7.4972 (1.4); 7.493 (2.29); 7.4868 (4.55); 7.4804 (2.02); 7.4705 (3.22); 7.4647 (16); 7.4503 (13); 7.4449 (5.08); 7.4294 (4.01); 7.3983 (0.56); 7.2636 (2.61); 7.2593 (3.08); 7.2571 (2.46); 7.2408 (5.44); 7.2383 (6.84); 7.2218 (1.95); 7.219 (3.16); 5.7555 (4.12); 4.0995 (0.69); 4.0844 (0.89); 4.0759 (1.15); 4.061 (1.27); 4.0522 (0.92); 4.0375 (0.88); 4.0283 (0.32); 3.9356 (0.88); 3.9219 (1.47); 3.9076 (0.96); 3.9018 (1.43); 3.8879 (2.15); 3.8739 (1.07); 3.7883 (1.25); 3.7723 (1.4); 3.7658 (1.22); 3.754 (1.15); 3.75 (1.31); 3.7385 (0.92); 3.7319 (0.85); 3.7159 (0.74); |

TABLE 20-continued

Compounds of the formula I-20

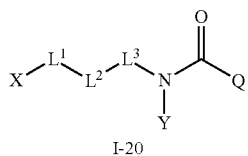

I-20

| Ex. No. | Q | X | L¹ | L² | L³ | Y | Physical data: ¹H-NMR, δ [ppm] or CAS or patent No. |
|---|---|---|---|---|---|---|---|
| 20-128 | 2,6-difluorophenyl | 4-chloro | CH(CF3) | CH2 | — | H | 3.3647 (158.37); 2.5276 (0.53); 2.5144 (9.64); 2.5099 (18.94); 2.5054 (24.49); 2.5008 (17.42); 2.4963 (8.24); −0.0002 (6.78) compound No. 20-128, solvent: [DMSO], spectrometer: 399.95 MHz 8.9291 (1.32); 8.9151 (2.41); 8.9011 (1.31); 7.5162 (0.78); 7.4995 (1.74); 7.4949 (1.83); 7.4868 (3.98); 7.4786 (4.03); 7.4711 (3.62); 7.465 (16); 7.4504 (12.04); 7.4285 (3.19); 7.3981 (0.58); 7.1416 (0.98); 7.1344 (5.14); 7.1146 (7.03); 7.0943 (4.38); 7.087 (0.91); 5.7577 (13.35); 4.0265 (0.75); 4.0124 (1.01); 4.0031 (1.25); 3.9889 (1.5); 3.9798 (0.95); 3.9654 (1.11); 3.9386 (1.37); 3.9248 (1.75); 3.9108 (1); 3.9046 (1.7); 3.8909 (2.5); 3.8771 (1.15); 3.782 (1.32); 3.7662 (1.53); 3.759 (1.33); 3.7478 (1.34); 3.7435 (1.44); 3.7325 (1.08); 3.7252 (0.98); 3.7093 (0.84); 3.3236 (18.92); 2.5102 (18.47); 2.5059 (35.35); 2.5015 (45.5); 2.497 (33.27); 2.4928 (16.71); 0.0078 (0.43); −0.0002 (9.53); −0.0084 (0.4) |
| 20-129 | 2-chlorophenyl | 4-chlorophenyl | CH(CF3) | CH2 | — | H | compound No. 20-129, solvent: [DMSO], spectrometer: 399.95 MHz 8.6377 (1.16); 8.6233 (2.01); 8.6093 (1.15); 7.4938 (2.88); 7.4875 (1.49); 7.478 (2.46); 7.4717 (16); 7.4606 (11.69); 7.4497 (1.65); 7.4452 (2.77); 7.4385 (2.65); 7.4294 (4.85); 7.4249 (6.25); 7.4198 (3.2); 7.4065 (4.07); 7.4024 (3.69); 7.3867 (1.55); 7.3823 (1.62); 7.3588 (2.36); 7.3542 (2.18); 7.3401 (3.23); 7.3359 (3.21); 7.3226 (1.85); 7.3183 (1.73); 7.1883 (3.44); 7.185 (3.3); 7.1699 (3.07); 7.1659 (2.79); 5.7573 (5.72); 4.0615 (0.69); 4.0478 (0.84); 4.038 (1.42); 4.0238 (1.28); 4.0135 (0.92); 3.9999 (0.89); 3.8983 (0.84); 3.885 (1.5); 3.8716 (0.89); 3.8643 (1.56); 3.8511 (2.48); 3.8379 (1.18); 3.7874 (1.36); 3.7712 (1.5); 3.7634 (1.25); 3.7536 (1.04); 3.7472 (1.3); 3.7374 (0.88); 3.7296 (0.79); 3.7133 (0.71); 3.3319 (60.9); 2.5241 (0.6); 2.5193 (0.92); 2.5107 (10.13); 2.5062 (20.21); 2.5017 (26.4); 2.4971 (18.82); 2.4926 (8.91); 1.989 (1.31); 1.1924 (0.36); 1.1746 (0.7); 1.1568 (0.34); −0.0002 (7.69) |
| 20-130 | 2-chloro-3-pyridyl | 4-chlorophenyl | CH(CF3) | CH2 | — | H | compound No. 20-130, solvent: [DMSO], spectrometer: 399.95 MHz 8.8142 (0.81); 8.8 (1.44); 8.7859 (0.77); 8.4443 (2.18); 8.4395 (2.3); 8.4323 (2.33); 8.4274 (2.23); 7.6785 (2.1); 7.6736 (2.12); 7.6596 (2.58); 7.6548 (2.41); 7.5009 (0.86); 7.4928 (0.79); 7.4781 (16); 7.4605 (2.95); 7.4537 (2.82); 7.4417 (2.09); 5.7579 (2.27); 4.0571 (0.46); 4.044 (0.58); 4.0337 (0.77); 4.0202 (0.88); 4.0099 (0.6); 3.9962 (0.61); 3.9361 (0.61); 3.9227 (1.02); 3.909 (0.6); 3.9022 (0.97); 3.8887 (1.51); 3.8753 (0.7); 3.7936 (0.83); 3.7777 (0.92); 3.7699 (0.79); 3.7595 (0.75); 3.7542 (0.84); 3.7439 (0.61); 3.736 (0.54); 3.7201 (0.47); 3.3248 (14.93); 2.5104 (10.72); 2.5062 (20.15); 2.5018 (25.62); 2.4973 (18.62); 2.4931 (9.24); −0.0002 (5.58) |
| 20-131 | 2-(trifluoromethyl)phenyl | 4-chlorophenyl | CH(CF3) | CH2 | — | H | compound No. 20-131, solvent: [DMSO], spectrometer: 399.95 MHz 8.7484 (1.54); 8.7344 (2.8); 8.7202 (1.52); 7.7521 (3.32); 7.7332 (4.46); 7.6965 (1.43); 7.6787 (3.76); 7.6604 (2.94); 7.6367 (2.97); 7.6178 (3.36); 7.599 (1.17); 7.5014 (5.44); 7.4962 (2.37); 7.4851 (3.82); 7.4798 (16); 7.4569 (12.2); 7.4353 (4.49); 7.4074 (0.49); 7.2452 (3.94); 7.2267 (3.57); 5.7568 (2.6); 4.0159 (0.84); 4.0018 (1.11); 3.9927 (1.41); 3.9786 (1.63); 3.9688 (1.09); 3.955 (1.19); 3.9316 (0.44); |

TABLE 20-continued

Compounds of the formula I-20

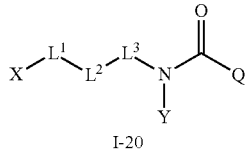

I-20

| Ex. No. | Q | X | L¹ | L² | L³ | Y | Physical data: $^1$H-NMR, δ [ppm] or CAS or patent No. |
|---|---|---|---|---|---|---|---|
| | | | | | | | 3.9175 (1.28); 3.9041 (1.93); 3.8902 (1.13); 3.8837 (1.85); 3.8702 (2.8); 3.8566 (1.31); 3.7657 (1.54); 3.7499 (1.73); 3.7428 (1.5); 3.7315 (1.5); 3.7271 (1.62); 3.7161 (1.19); 3.709 (1.07); 3.693 (0.93); 3.3806 (0.34); 3.3357 (154.02); 2.6713 (0.33); 2.5109 (21); 2.5067 (39.96); 2.5022 (51.06); 2.4977 (36.92); 2.4935 (18.16); 2.329 (0.33); 0.0078 (0.5); −0.0002 (11.07); −0.0085 (0.42) |
| 20-132 | 2-(difluoro-methyl)phenyl | 4-chlorophenyl | CH(CF3) | CH2 | — | H | compound No. 20-132, solvent: [DMSO], spectrometer: 399.95 MHz 8.823 (1.35); 8.8089 (2.32); 8.7946 (1.34); 7.6811 (2.28); 7.6631 (3.73); 7.6269 (1.35); 7.6236 (1.51); 7.6085 (3.34); 7.605 (3.24); 7.5903 (3.97); 7.5858 (4); 7.569 (2.82); 7.5514 (1.09); 7.4941 (3.5); 7.4882 (1.73); 7.478 (3.04); 7.4722 (16); 7.4584 (12.21); 7.4366 (3.08); 7.4051 (0.64); 7.3407 (3.02); 7.3227 (2.66); 7.1923 (2.35); 7.0537 (5.11); 6.9151 (2.57); 4.0957 (0.77); 4.0814 (0.95); 4.072 (1.3); 4.0576 (1.38); 4.048 (1.04); 4.0339 (0.96); 4.0239 (0.36); 3.9048 (0.87); 3.8914 (1.5); 3.8776 (1); 3.8709 (1.7); 3.8574 (2.57); 3.8439 (1.29); 3.8008 (1.48); 3.7844 (1.67); 3.7775 (1.42); 3.7668 (1.17); 3.7612 (1.45); 3.7506 (0.95); 3.7436 (0.86); 3.7273 (0.74); 3.3535 (0.35); 3.3306 (71.62); 2.5241 (0.98); 2.5108 (16.14); 2.5065 (31.11); 2.502 (39.98); 2.4975 (28.79); 2.493 (14.02); 0.0079 (0.34); −0.0002 (7.76) |
| 20-133 | 2,6-difluorophenyl | 2,4-dichlorophenyl | CH(CH3) | CH2 | — | H | compound No. 20-133, solvent: [DMSO], spectrometer: 399.95 MHz 8.7796 (3.23); 7.5736 (11.86); 7.5683 (12.38); 7.5186 (1.44); 7.5019 (2.97); 7.4973 (2.61); 7.4853 (2.06); 7.4808 (5.61); 7.4764 (2.19); 7.4623 (8.11); 7.4411 (16); 7.4165 (9.97); 7.4112 (9.05); 7.3954 (3.99); 7.3901 (3.98); 7.161 (1.09); 7.1577 (1.48); 7.1501 (9.26); 7.1309 (11.3); 7.1102 (7.76); 7.1023 (1.34); 3.505 (1.31); 3.4797 (8.41); 3.4755 (9.89); 3.4692 (9.82); 3.4514 (1.79); 3.4363 (0.72); 3.3218 (56.35); 2.6794 (0.43); 2.675 (0.92); 2.6704 (1.27); 2.6658 (0.92); 2.6612 (0.42); 2.5406 (0.65); 2.5238 (4.44); 2.519 (7.01); 2.5105 (73.48); 2.506 (146.45); 2.5014 (191.21); 2.4968 (135.74); 2.4922 (63.52); 2.3373 (0.42); 2.3327 (0.91); 2.3281 (1.23); 2.3236 (0.9); 2.3191 (0.42); 1.9889 (1); 1.3975 (0.62); 1.3356 (0.78); 1.2583 (0.38); 1.2491 (1.23); 1.2398 (0.93); 1.2216 (15.13); 1.2161 (10.02); 1.2106 (9.7); 1.2052 (13.94); 1.1923 (0.84); 1.1868 (0.81); 1.1745 (0.68); 1.1567 (0.35); 0.1459 (0.36); 0.008 (3.26); −0.0002 (91.11); −0.0085 (2.75); −0.1497 (0.37) |
| 20-134 | 3-(trifluoro-methyl)-2-pyridyl | 2,4-1 dichloropheny | CH2 | CH2 | CH2 | H | WO 2008101976 |
| 20-135 | 2-(trifluoro-methyl)-3-pyridyl | 2,4-dichlorophenyl | CH2 | CH2 | — | H | WO 2007108483 |
| 20-136 | 2,6-difluorophenyl | 4-chloro-2-thienyl | CH2 | CH2 | — | H | compound No. 20-136, solvent: [DMSO], spectrometer: 601.6 MHz 8.8887 (1.7); 8.8797 (3.16); 8.8707 (1.72); 7.5303 (1.31); 7.5192 (2.85); 7.5162 (2.52); 7.5081 (1.83); 7.5052 (5.17); 7.5022 (1.73); 7.4941 (2.62); 7.4911 (3.02); 7.4801 (1.29); 7.3862 (15.73); 7.3836 (16); 7.1788 (1.27); 7.1738 (8.93); 7.161 (10.71); 7.16 (10.17); 7.1472 (7.77); 7.142 (1.21); 6.9188 (10.1); 6.9175 (8.68); 6.9164 (9.93); 3.5016 (3.85); 3.4902 (9.87); 3.4806 (9.96); 3.4694 (4.3); 3.3625 (0.58); 3.3246 (1819.31); 3.3014 (1.26); 3.29 (0.59); 3.0081 |

TABLE 20-continued

Compounds of the formula I-20

$$X\underset{L^2}{\overset{L^1}{\diagup}}\underset{}{\overset{L^3}{\diagdown}}\underset{Y}{N}\underset{}{\overset{O}{\diagdown}}Q$$

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (6.19); 2.9976 (12.3); 2.9966 (12.61); 2.9861 (5.73); 2.6529 (2.69); 2.619 (1.17); 2.616 (2.66); 2.613 (3.72); 2.6099 (2.67); 2.6069 (1.22); 2.5406 (916.49); 2.5223 (7.29); 2.5192 (8.9); 2.5161 (8.38); 2.5073 (196.78); 2.5043 (426.38); 2.5012 (595.96); 2.4981 (428.05); 2.4951 (198.35); 2.4246 (2.78); 2.3915 (1.17); 2.3885 (2.62); 2.3854 (3.66); 2.3823 (2.61); 2.3793 (1.16); 2.0735 (1.44); 1.2584 (0.32); 0.0053 (1.1); −0.0002 (39.2); −0.0057 (1.17) |
| 20-137 | 2-(trifluoro-methyl)phenyl | 4-chloro-2-thienyl | CH2 | CH2 | — | H | compound No. 20-137, solvent: [DMSO], spectrometer: 601.6 MHz 8.6786 (1.8); 8.6695 (3.35); 8.6605 (1.75); 7.7827 (4.89); 7.7697 (5.83); 7.7339 (2.18); 7.7214 (5.27); 7.7088 (3.34); 7.6558 (3.19); 7.6429 (4.75); 7.6302 (1.94); 7.4766 (5.31); 7.4641 (4.79); 7.3938 (16); 7.3912 (15.95); 6.9336 (9.79); 6.9324 (8.4); 6.9311 (9.62); 3.4861 (3.53); 3.4745 (8.84); 3.465 (9); 3.4535 (3.93); 3.3591 (0.44); 3.3496 (1.26); 3.3265 (1092.25); 3.3059 (1.04); 3.3019 (0.46); 3.2949 (0.39); 3.0069 (5.84); 2.9961 (11.39); 2.9952 (11.54); 2.9844 (5.29); 2.6529 (1.75); 2.6191 (0.65); 2.6161 (1.39); 2.613 (1.92); 2.61 (1.37); 2.6069 (0.61); 2.5638 (0.4); 2.5595 (0.53); 2.5407 (587); 2.5336 (2.14); 2.5299 (1.17); 2.5224 (4.02); 2.5192 (5.23); 2.5161 (5.46); 2.5074 (107.08); 2.5043 (223.59); 2.5013 (307.08); 2.4982 (218.71); 2.4952 (101.09); 2.4247 (1.8); 2.4242 (1.8); 2.3915 (0.65); 2.3885 (1.37); 2.3855 (1.89); 2.3824 (1.33); 2.3794 (0.57); 2.0734 (1.47); 0.0053 (0.53); −0.0002 (15.9); −0.0057 (0.45) |
| 20-138 | 3-chloro-2-pyridyl | 4-chloro-2-thienyl | CH2 | CH2 | — | H | compound No. 20-138, solvent: [DMSO], spectrometer: 601.6 MHz 8.808 (1.66); 8.7986 (3.04); 8.7892 (1.65); 8.5512 (8.34); 8.5489 (8.44); 8.5435 (8.71); 8.5412 (8.23); 8.0306 (8.42); 8.0283 (8.32); 8.0169 (8.91); 8.0147 (9.04); 7.5494 (9.27); 7.5417 (8.94); 7.5358 (9.12); 7.5281 (9.28); 7.3788 (15.91); 7.3762 (16); 6.9446 (9.92); 6.9434 (8.41); 6.9421 (9.79); 3.5243 (3.9); 3.5126 (9.74); 3.5029 (10); 3.4913 (4.39); 3.3533 (1.04); 3.347 (1.63); 3.3422 (3.04); 3.3251 (1940.63); 3.3047 (1.5); 3.2871 (0.43); 3.0357 (5.98); 3.025 (11.86); 3.0239 (11.9); 3.0133 (5.54); 2.6529 (2.29); 2.6192 (1.19); 2.6161 (2.63); 2.6131 (3.69); 2.61 (2.64); 2.607 (1.2); 2.5578 (0.65); 2.5407 (787.35); 2.5224 (7.12); 2.5193 (8.95); 2.5162 (8.4); 2.5074 (195.17); 2.5044 (422.79); 2.5013 (588.17); 2.4983 (423.77); 2.4952 (196.78); 2.4247 (2.31); 2.3916 (1.16); 2.3886 (2.58); 2.3855 (3.6); 2.3824 (2.59); 2.3794 (1.14); 2.0736 (2.41); 1.2353 (0.33); 0.0053 (0.94); −0.0002 (34.17); −0.0057 (1) |
| 20-139 | 2-chlorophenyl | 4-chloro-2-thienyl | CH2 | CH2 | — | H | compound No. 20-139, solvent: [DMSO], spectrometer: 601.6 MHz 8.5943 (1.48); 8.5852 (2.77); 8.576 (1.49); 7.4936 (3.73); 7.4923 (4.24); 7.481 (5.45); 7.4794 (7.34); 7.4495 (3.35); 7.4453 (3.61); 7.4385 (4.86); 7.4361 (2.27); 7.4344 (5.3); 7.4319 (2.17); 7.4254 (3.27); 7.4211 (3.83); 7.4117 (0.34); 7.4005 (2.03); 7.3984 (2.03); 7.3869 (16); 7.3843 (14.22); 7.3784 (9.11); 7.377 (7.58); 7.375 (12.27); 7.366 (1.98); 7.3624 (0.8); 6.9399 (7.99); 6.9386 (7.27); 6.9374 (8.35); 3.491 (3.18); 3.4796 (8.18); 3.47 (8.2); 3.4587 (3.58); 3.361 (0.38); 3.3539 (0.75); 3.3499 (1.21); 3.3448 (2.06); 3.3387 (3.67); 3.3258 (982.47); 3.3119 (2.08); 3.3029 (0.74); 3.2994 (0.74); 3.2953 (0.35); 3.2882 (0.33); 3.0243 (5.2); 3.0127 (10.5); 3.0019 (4.65); 2.6527 (1.58); 2.6189 (0.59); 2.616 (1.29); 2.6129 (1.8); 2.6098 (1.31); 2.6068 (0.58); 2.5648 (0.41); 2.5594 (0.69); |

TABLE 20-continued
Compounds of the formula I-20
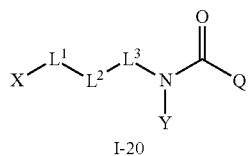
I-20
| Ex. No. | Q | X | L¹ | L² | L³ | Y | Physical data: ¹H-NMR, δ [ppm] or CAS or patent No. |
|---|---|---|---|---|---|---|---|
| | | | | | | | 2.5535 (1.22); 2.5503 (1.52); 2.5489 (1.92); 2.5476 (2.28); 2.5447 (9.34); 2.5406 (521.84); 2.5354 (4.98); 2.529 (1.74); 2.5254 (1.2); 2.5223 (4.02); 2.5191 (5); 2.516 (4.81); 2.5073 (95.82); 2.5042 (206.37); 2.5012 (289.57); 2.4981 (210.67); 2.495 (99.49); 2.4241 (1.56); 2.3914 (0.58); 2.3884 (1.27); 2.3853 (1.76); 2.3823 (1.27); 2.3793 (0.58); 2.0734 (1.8); 0.0052 (0.44); −0.0002 (14.27); −0.0058 (0.47) |
| 20-140 | 2-bromophenyl | 4-chloro-2-thienyl | CH2 | CH2 | — | H | compound No. 20-140, solvent: [DMSO], spectrometer: 601.6 MHz 8.5884 (1.79); 8.5793 (3.33); 8.5701 (1.76); 7.6496 (6.04); 7.6489 (6.73); 7.6369 (6.22); 7.6354 (6.6); 7.4404 (3.17); 7.4386 (3.3); 7.432 (0.35); 7.428 (8.3); 7.4263 (6.15); 7.4156 (5.94); 7.4138 (5.8); 7.3877 (16); 7.3852 (15.99); 7.3649 (3.84); 7.3619 (6.28); 7.3523 (4.86); 7.3491 (10.4); 7.3458 (9.03); 7.3438 (5.04); 7.3392 (2.73); 7.3362 (5.13); 7.3338 (6.94); 7.3314 (4.4); 6.9495 (9.98); 6.9482 (8.47); 6.947 (10.1); 3.4858 (3.69); 3.4743 (9.46); 3.4647 (9.48); 3.4533 (4.11); 3.3642 (0.46); 3.3552 (0.52); 3.3524 (0.45); 3.3491 (1.1); 3.3473 (1.06); 3.3452 (1.17); 3.3424 (1.07); 3.3351 (9.18); 3.3333 (11.46); 3.3262 (963.66); 3.3144 (2.18); 3.3125 (2.53); 3.3065 (1.08); 3.3009 (0.67); 3.2921 (0.38); 3.027 (6.08); 3.0165 (11.65); 3.0155 (12.05); 3.0048 (5.37); 2.6527 (1.7); 2.619 (0.56); 2.616 (1.22); 2.6129 (1.74); 2.6099 (1.27); 2.6068 (0.56); 2.5634 (0.43); 2.5618 (0.34); 2.5596 (0.36); 2.5529 (0.85); 2.5515 (1.55); 2.5495 (3.28); 2.5479 (3.93); 2.5443 (8.85); 2.5406 (571.09); 2.5288 (0.56); 2.5268 (0.9); 2.5253 (1.05); 2.5223 (3.46); 2.5191 (3.91); 2.516 (4.13); 2.5073 (91.35); 2.5043 (196.39); 2.5012 (275.69); 2.4981 (199.43); 2.495 (92.26); 2.4873 (1.26); 2.4844 (1.01); 2.4241 (1.68); 2.3915 (0.52); 2.3884 (1.17); 2.3853 (1.67); 2.3823 (1.2); 2.3793 (0.54); 2.0734 (1.88); 0.0052 (0.41); −0.0002 (14.33); −0.0058 (0.45) |
| 20-141 | 2,6-difluorophenyl | 4-bromophenyl | CH2 | CH2 | — | H | compound No. 20-141, solvent: [DMSO], spectrometer: 399.95 MHz 8.7889 (1.58); 8.7755 (2.88); 8.7621 (1.54); 7.53 (1.15); 7.5133 (2.46); 7.5087 (2.27); 7.4961 (3.03); 7.4893 (14.3); 7.4848 (4.98); 7.4731 (6.07); 7.4685 (16); 7.4622 (2.15); 7.4545 (1.29); 7.2384 (1.85); 7.2324 (12.87); 7.2114 (10.99); 7.176 (1); 7.1729 (1.33); 7.1653 (7.56); 7.146 (9.3); 7.1253 (6.26); 7.1175 (1.13); 3.4874 (2.88); 3.4699 (6.99); 3.4554 (6.98); 3.438 (3.11); 3.3223 (93.04); 2.8072 (5.4); 2.7896 (10.43); 2.7719 (4.75); 2.6749 (0.76); 2.6703 (1.05); 2.6658 (0.78); 2.5236 (4.16); 2.5103 (60.3); 2.5059 (119.33); 2.5013 (155.96); 2.4967 (112.38); 2.4923 (53.93); 2.3326 (0.7); 2.328 (0.97); 2.3235 (0.72); 1.2984 (0.36); 1.2585 (0.5); 1.2493 (0.32); 0.008 (2.78); −0.0001 (69.23); −0.0084 (2.32) |
| 20-142 | 2-chlorophenyl | 4-bromophenyl | CH2 | CH2 | — | H | compound No. 20-142, solvent: [DMSO], spectrometer: 399.95 MHz 8.5005 (1.54); 8.4869 (2.88); 8.4733 (1.53); 8.316 (0.34); 7.5049 (1.49); 7.4984 (12.59); 7.4938 (4.41); 7.4826 (6.59); 7.4776 (16); 7.4713 (2.18); 7.4636 (6.29); 7.4603 (6.82); 7.442 (3.05); 7.4373 (3.42); 7.4242 (5.06); 7.4195 (5.22); 7.4047 (2.82); 7.3997 (3.14); 7.3892 (2.97); 7.3853 (2.88); 7.3705 (5.66); 7.3669 (5.76); 7.3527 (3.31); 7.3491 (3.15); 7.3325 |

TABLE 20-continued

Compounds of the formula I-20

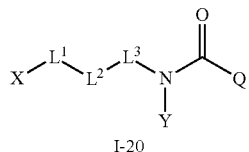
I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (6.5); 7.3276 (5.79); 7.3139 (3.44); 7.3091 (2.7); 7.2507 (1.71); 7.2445 (12.6); 7.24 (4.41); 7.228 (3.65); 7.2235 (10.81); 3.4756 (2.79); 3.458 (6.45); 3.4434 (6.43); 3.4258 (3.06); 3.3222 (93.23); 2.8243 (5.17); 2.8065 (9.8); 2.7888 (4.62); 2.6748 (0.65); 2.6702 (0.91); 2.6656 (0.67); 2.6609 (0.35); 2.5235 (3.09); 2.5186 (4.8); 2.5101 (51.49); 2.5057 (103.8); 2.5011 (136.97); 2.4965 (99.07); 2.492 (47.75); 2.3324 (0.64); 2.3279 (0.88); 2.3233 (0.64); 1.9885 (1.35); 1.1923 (0.38); 1.1745 (0.73); 1.1567 (0.36); 0.008 (2.35); −0.0002 (65.84); −0.0085 (2.2) |
| 20-143 | 2-(trifluoro-methyl)phenyl | 4-bromophenyl | CH2 | CH2 | — | H | compound No. 20-143, solvent: [DMSO], spectrometer: 399.95 MHz 8.5841 (1.71); 8.5704 (3.19); 8.5566 (1.66); 8.3164 (0.44); 7.7723 (4.15); 7.7529 (5.48); 7.7231 (1.83); 7.7049 (4.71); 7.6864 (3.38); 7.6469 (3.36); 7.6278 (4.29); 7.6087 (1.58); 7.511 (1.66); 7.5047 (13.54); 7.5001 (4.5); 7.4885 (4.86); 7.4838 (16); 7.4776 (1.96); 7.4221 (4.96); 7.4035 (4.31); 7.238 (13.61); 7.2172 (11.58); 7.211 (1.48); 3.4708 (2.98); 3.4533 (6.46); 3.4386 (6.46); 3.4207 (3.19); 3.3229 (45.27); 2.808 (5.61); 2.79 (10.08); 2.7722 (4.92); 2.6749 (0.49); 2.6702 (0.69); 2.6658 (0.53); 2.5235 (2.48); 2.5102 (40.2); 2.5058 (79.2); 2.5013 (102.93); 2.4967 (73.79); 2.4923 (35.2); 2.3325 (0.46); 2.328 (0.65); 2.3235 (0.47); 1.9886 (0.35); 0.0078 (1.73); −0.0002 (45.17); −0.0084 (1.51) |
| 20-144 | 2-iodophenyl | 4-bromophenyl | CH2 | CH2 | — | H | compound No. 20-144, solvent: [DMSO], spectrometer: 399.95 MHz 7.851 (0.33); 7.5031 (0.72); 7.4822 (0.88); 7.4222 (0.33); 7.4195 (0.34); 7.2594 (0.72); 7.2385 (0.64); 7.2309 (0.39); 4.0556 (1.26); 4.0378 (3.79); 4.02 (3.83); 4.0022 (1.29); 3.4417 (0.33); 3.427 (0.33); 3.3337 (14.14); 3.3312 (12.46); 2.8224 (0.51); 2.5195 (0.36); 2.511 (4.08); 2.5065 (8.25); 2.5019 (10.88); 2.4973 (7.8); 2.4928 (3.7); 1.9887 (16); 1.1927 (4.68); 1.1749 (8.99); 1.1571 (4.52); −0.0002 (5.43) |
| 20-145 | 2-bromophenyl | 4-bromophenyl | CH2 | CH2 | — | H | compound No. 20-145, solvent: [DMSO], spectrometer: 399.95 MHz 8.4951 (1.59); 8.4816 (2.98); 8.4678 (1.56); 7.6399 (5.1); 7.6373 (5.31); 7.6202 (6.17); 7.6174 (6.09); 7.507 (1.59); 7.5005 (13.33); 7.4958 (4.44); 7.4843 (4.85); 7.4796 (16); 7.4732 (1.87); 7.4312 (2.22); 7.4283 (2.56); 7.4127 (6.18); 7.4097 (6.23); 7.3942 (5); 7.3911 (4.65); 7.3573 (3.76); 7.3525 (4.95); 7.338 (4.32); 7.3331 (5.55); 7.3187 (2.45); 7.3141 (2.49); 7.2987 (6.49); 7.2941 (5.75); 7.2802 (4.81); 7.2756 (4.33); 7.2569 (1.82); 7.2506 (13.29); 7.246 (4.36); 7.2343 (3.89); 7.2297 (11.17); 7.2234 (1.39); 4.0376 (0.37); 4.0198 (0.37); 3.4692 (2.92); 3.4516 (6.46); 3.4371 (6.47); 3.4193 (3.17); 3.3221 (61.64); 2.8287 (5.27); 2.8108 (9.86); 2.793 (4.75); 2.6749 (0.62); 2.6703 (0.85); 2.6657 (0.67); 2.6613 (0.33); 2.5237 (2.87); 2.5189 (4.52); 2.5103 (48.99); 2.5058 (98.6); 2.5012 (129.12); 2.4966 (92.4); 2.4921 (43.72); 2.3326 (0.63); 2.328 (0.84); 2.3234 (0.62); 1.9886 (1.65); 1.2494 (0.32); 1.1924 (0.45); 1.1746 (0.9); 1.1568 (0.44); 0.008 (2.31); −0.0002 (64.37); −0.0085 (2.01) |
| 20-146 | 2-chloro-3-pyridyl | 4-bromophenyl | CH2 | CH2 | — | H | compound No. 20-146, solvent: [DMSO], spectrometer: 399.95 MHz 7.5029 (0.41); 7.4818 (0.63); 7.251 (0.43); 7.2301 (0.36); 4.0557 (1.33); 4.0379 (4.01); 4.0201 (4.04); 4.0023 (1.37); 3.3212 (5.03); 2.8109 (0.34); 2.5104 (3.74); 2.5061 (7.24); 2.5016 (9.33); 2.497 (6.65); |

TABLE 20-continued

Compounds of the formula I-20

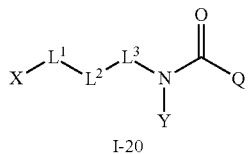

I-20

| Ex. No. | Q | X | L¹ | L² | L³ | Y | Physical data: ¹H-NMR, δ [ppm] or CAS or patent No. |
|---|---|---|---|---|---|---|---|
| 20-147 | 2-(difluoro-methyl)phenyl | 4-bromophenyl | CH2 | CH2 | — | H | 2.4926 (3.14); 1.9888 (16); 1.1927 (4.62); 1.1749 (8.89); 1.1571 (4.47); −0.0002 (4.26) compound No. 20-147, solvent: [DMSO], spectrometer: 399.95 MHz 8.6756 (1.7); 8.6619 (3.21); 8.6479 (1.68); 8.316 (0.33); 7.7034 (2.41); 7.6963 (3.06); 7.681 (4.49); 7.6377 (1.07); 7.6328 (1.57); 7.6191 (5.21); 7.614 (7.36); 7.6049 (7.49); 7.5962 (7.09); 7.5914 (3.99); 7.5772 (1.07); 7.5029 (5.14); 7.496 (15.25); 7.4911 (6.51); 7.48 (6.36); 7.4751 (16); 7.469 (2.04); 7.2948 (3.54); 7.2377 (1.85); 7.2315 (13.49); 7.2107 (11.61); 7.1557 (7.8); 7.0165 (3.86); 3.5014 (2.92); 3.484 (7.2); 3.4694 (7.25); 3.4521 (3.21); 3.3231 (116.28); 2.8336 (5.54); 2.8161 (10.87); 2.7985 (4.94); 2.6749 (0.73); 2.6704 (1.03); 2.6659 (0.75); 2.5237 (3.61); 2.5103 (56.57); 2.5059 (112.86); 2.5014 (148.07); 2.4968 (106.8); 2.4923 (51.39); 2.3327 (0.69); 2.3281 (0.94); 2.3236 (0.7); 1.2493 (0.35); 0.0079 (2.44); −0.0002 (65.07); −0.0085 (2.23) |
| 20-148 | 2-fluorophenyl | 4-bromophenyl | CH2 | CH2 | — | H | compound No. 20-148, solvent: [DMSO], spectrometer: 399.95 MHz 8.3636 (2.28); 8.3165 (2.18); 7.564 (1.98); 7.5596 (2.52); 7.5456 (3.8); 7.5411 (5.24); 7.5319 (1.67); 7.5258 (2.72); 7.5224 (3.94); 7.5184 (3.19); 7.5008 (3.43); 7.4945 (14.44); 7.4901 (5.26); 7.4841 (2.61); 7.4786 (5.7); 7.4737 (16); 7.4675 (2.24); 7.2889 (3.68); 7.2789 (3.86); 7.2767 (4.01); 7.268 (3.6); 7.2605 (8.72); 7.2411 (7.36); 7.2309 (13.69); 7.2101 (11.71); 3.49 (2.73); 3.4726 (6.23); 3.4578 (6.33); 3.4401 (3.14); 3.3235 (46.76); 2.8262 (5.86); 2.8083 (10.62); 2.7905 (5.27); 2.6752 (0.46); 2.6705 (0.64); 2.6661 (0.49); 2.5237 (2.15); 2.5104 (36.73); 2.506 (73.71); 2.5015 (97.24); 2.497 (71.37); 2.4926 (35.42); 2.3329 (0.45); 2.3282 (0.62); 2.3236 (0.46); 1.2492 (0.38); 0.008 (1.41); −0.0002 (39.4); −0.0084 (1.61) |
| 20-149 | 2-(trifluoro-methyl)phenyl | 4-(trifluoro-methoxy)phenyl | CH2 | CH2 | — | H | compound No. 20-149, solvent: [DMSO], spectrometer: 399.95 MHz 8.5882 (1.81); 8.5745 (3.45); 8.5606 (1.79); 7.7677 (4.21); 7.7485 (5.55); 7.7109 (1.79); 7.6936 (4.77); 7.675 (3.56); 7.6431 (3.51); 7.6242 (4.28); 7.6056 (1.64); 7.403 (6.18); 7.3962 (10.38); 7.3909 (4.34); 7.3804 (6.39); 7.3745 (16); 7.3679 (2.18); 7.3058 (10.21); 7.286 (6.51); 3.5028 (3.01); 3.4852 (6.81); 3.4707 (6.87); 3.4529 (3.31); 3.3227 (28.64); 2.8689 (5.7); 2.851 (10.59); 2.8332 (5.06); 2.6749 (0.55); 2.6705 (0.74); 2.6658 (0.51); 2.5238 (2.39); 2.5104 (41.04); 2.5059 (81.05); 2.5014 (105.24); 2.4967 (74.92); 2.4922 (35.14); 2.3327 (0.49); 2.3282 (0.68); 2.3235 (0.51); 1.2492 (0.41); 0.008 (2.57); −0.0002 (68.98); −0.0085 (2.04) |
| 20-150 | 2-fluorophenyl | 4-(trifluoro-methoxy)phenyl | CH2 | CH2 | — | H | compound No. 20-150, solvent: [DMSO], spectrometer: 399.95 MHz 8.3863 (0.42); 7.5561 (0.35); 7.5516 (0.48); 7.5371 (0.75); 7.533 (1.05); 7.5225 (0.35); 7.5179 (0.83); 7.5145 (0.89); 7.5034 (0.48); 7.4969 (0.54); 7.3907 (1.63); 7.3859 (0.64); 7.3742 (0.77); 7.369 (2.63); 7.3626 (0.39); 7.2983 (1.73); 7.2904 (0.83); 7.2783 (1.2); 7.2756 (1.46); 7.2728 (1.14); 7.2699 (0.73); 7.2638 (0.67); 7.2609 (0.69); 7.2562 (1.28); 7.2539 (1.04); 7.243 (0.48); 7.2402 (0.56); 7.2376 (0.69); 7.235 (0.46); 4.0557 (1.23); 4.0379 (3.73); 4.0201 (3.77); 4.0023 (1.27); 3.5122 (0.52); 3.4949 (1.11); 3.48 (1.08); |

TABLE 20-continued

Compounds of the formula I-20

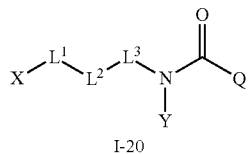

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | 3.4621 (0.56); 3.3226 (18.63); 2.8865 (1.01); 2.8684 (1.76); 2.8506 (0.89); 2.524 (0.78); 2.5193 (1.24); 2.5107 (12.97); 2.5063 (25.98); 2.5017 (34.12); 2.4972 (24.58); 2.4927 (11.79); 1.9887 (16); 1.1926 (4.34); 1.1749 (8.55); 1.157 (4.22); 0.008 (0.55); −0.0002 (15.34); −0.0084 (0.5) |
| 20-151 | 2-chlorophenyl | 4-(trifluoromethoxy)phenyl | CH2 | CH2 | — | H | compound No. 20-151, solvent: [DMSO], spectrometer: 399.95 MHz 8.5116 (1.7); 8.4979 (3.21); 8.4842 (1.69); 7.4806 (3.07); 7.4773 (3.81); 7.4608 (6.94); 7.4575 (7.58); 7.439 (3.52); 7.4345 (3.77); 7.4212 (5.67); 7.4166 (5.88); 7.4113 (1.49); 7.4039 (10.57); 7.397 (5.17); 7.3875 (4.6); 7.3822 (16); 7.3764 (4.96); 7.3615 (6.22); 7.3581 (6.3); 7.3436 (3.65); 7.3401 (3.42); 7.3172 (7.16); 7.3127 (7.28); 7.3018 (10.26); 7.2991 (9.89); 7.2943 (5.04); 7.2821 (6.63); 3.5048 (3.22); 3.4872 (7.13); 3.4727 (7.23); 3.4551 (3.38); 3.3216 (55.25); 2.8855 (5.67); 2.8678 (10.91); 2.8501 (5.1); 2.6791 (0.48); 2.6748 (1); 2.6702 (1.31); 2.6657 (0.96); 2.6611 (0.45); 2.5235 (4.39); 2.5187 (6.84); 2.5102 (74.28); 2.5057 (147.7); 2.5011 (193.1); 2.4966 (138.18); 2.4921 (65.46); 2.337 (0.46); 2.3325 (0.95); 2.3279 (1.3); 2.3233 (0.94); 2.3187 (0.43); 1.2492 (0.41); 1.2354 (0.45); 0.146 (0.5); 0.017 (0.35); 0.008 (4.39); −0.0002 (121.24); −0.0085 (3.82); −0.1497 (0.49) |
| 20-152 | 2-fluorophenyl | 4-chlorophenyl | CH2 | C(CH3)2 | — | H | compound No. 20-152, solvent: [DMSO], spectrometer: 399.95 MHz 7.7103 (1.44); 7.4943 (0.45); 7.4909 (0.58); 7.486 (0.76); 7.4775 (0.86); 7.4715 (1.16); 7.4675 (1.55); 7.4602 (0.88); 7.454 (0.84); 7.4492 (0.86); 7.3439 (2.49); 7.3232 (3.56); 7.2521 (1.65); 7.2344 (1.84); 7.2201 (3.78); 7.1995 (2.86); 3.3305 (18.97); 3.1021 (5.24); 2.5054 (7.31); 2.5013 (10.06); 2.4971 (8.15); 1.2976 (16); −0.0002 (2.26) |
| 20-153 | 2-chlorophenyl | 4-chlorophenyl | CH2 | C(CH3)2 | — | H | compound No. 20-153, solvent: [DMSO], spectrometer: 399.95 MHz 7.8576 (1.52); 7.4679 (0.72); 7.4648 (0.81); 7.4479 (1.45); 7.4456 (1.53); 7.4217 (0.59); 7.4169 (0.63); 7.404 (1.07); 7.3991 (1.13); 7.3848 (0.74); 7.3754 (2.84); 7.3548 (4.49); 7.341 (0.89); 7.3377 (0.77); 7.3289 (1.6); 7.3242 (1.41); 7.3104 (0.76); 7.3054 (0.59); 7.2687 (3.31); 7.2477 (2.3); 3.3313 (33.5); 3.3264 (37.28); 3.1088 (4.84); 2.5235 (0.44); 2.5056 (19.52); 2.5013 (25.61); 2.4969 (19.68); 1.2881 (16); 1.0424 (0.44); −0.0002 (6.24); −0.0084 (0.36) |
| 20-154 | 2-chloro-3-pyridyl | 4-chlorophenyl | CH2 | C(CH3)2 | — | H | compound No. 20-154, solvent: [DMSO], spectrometer: 399.95 MHz 8.4373 (1.03); 8.4356 (1.11); 8.4341 (1.05); 8.4281 (1.03); 8.4265 (1.1); 8.4253 (1.12); 8.4236 (1.14); 8.0286 (1.82); 7.7718 (1); 7.7699 (1.07); 7.7556 (1.09); 7.7531 (1.19); 7.7512 (1.21); 7.4809 (1.03); 7.4797 (1.06); 7.4688 (1.06); 7.4676 (1.09); 7.4622 (1.04); 7.461 (1.03); 7.4502 (0.96); 7.4489 (0.96); 7.3843 (2.3); 7.3641 (3.3); 7.264 (3.21); 7.2436 (2.39); 3.3436 (38.07); 3.3355 (57.01); 3.1014 (5.14); 2.5016 (21.59); 1.9884 (1.16); 1.987 (1.19); 1.2918 (16); 1.191 (0.32); 1.1748 (0.62); 1.1732 (0.63); 1.1554 (0.33); −0.0002 (3.58); −0.002 (3.59); −0.0033 (3.45) |
| 20-155 | 2-bromophenyl | 4-chlorophenyl | CH2 | C(CH3)2 | — | H | compound No. 20-155, solvent: [DMSO], spectrometer: 399.95 MHz 7.8481 (1.63); 7.6241 (1.29); 7.6231 (1.28); 7.6045 (1.47); 7.4201 (0.5); 7.4182 (0.47); 7.4017 (1.37); 7.3997 (1.24); 7.3831 (3.37); 7.3622 (3.56); 7.3372 (0.72); 7.3328 (0.93); 7.3178 (0.96); 7.3134 (1.33); 7.2986 (1.95); 7.2944 (1.67); 7.2763 (4.19); 7.2554 (2.38); 3.3444 (31.89); 3.3338 (38.19); 3.1076 (4.93); |

TABLE 20-continued

Compounds of the formula I-20

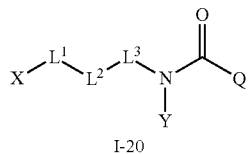

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | 2.5054 (16.45); 2.5014 (20.87); 2.497 (15.85); 1.2898 (16); 1.0424 (0.53); −0.0002 (4.72) |
| 20-156 | 2-fluorophenyl | 4-chlorophenyl | CH2 | C(CH3)2 | — | H | compound No. 20-156, solvent: [DMSO], spectrometer: 399.95 MHz 7.8583 (1.78); 7.5892 (2); 7.5845 (2.14); 7.5487 (0.48); 7.5445 (0.65); 7.5268 (1.33); 7.5203 (0.49); 7.5132 (0.78); 7.5072 (1.03); 7.5001 (0.87); 7.4953 (0.64); 7.4863 (0.73); 7.4813 (0.86); 7.4661 (0.45); 7.4634 (0.39); 7.3852 (0.7); 7.3815 (0.65); 7.3644 (1.72); 7.3606 (1.75); 7.3367 (2.91); 7.3159 (1.22); 7.2725 (1.71); 7.2555 (2.12); 7.2496 (1.21); 7.2462 (1.27); 7.2445 (1.27); 7.2391 (0.88); 7.2368 (1.09); 7.2234 (0.91); 4.0393 (0.55); 4.0215 (0.56); 3.3351 (13.59); 3.2939 (5.9); 2.5038 (6.59); 1.9914 (2.19); 1.9898 (2.27); 1.3348 (16); 1.1956 (0.58); 1.1938 (0.61); 1.1778 (1.19); 1.1759 (1.27); 1.1601 (0.59); 1.1581 (0.62); 0.0019 (1.63); −0.0002 (1.7) |
| 20-157 | 2-chlorophenyl | 4-chlorophenyl | CH2 | C(CH3)2 | — | H | compound No. 20-157, solvent: [DMSO], spectrometer: 399.95 MHz 8.0099 (1.75); 7.5959 (2.15); 7.4846 (0.73); 7.4669 (1.68); 7.4415 (0.55); 7.435 (0.75); 7.4231 (6.06); 7.4124 (1.21); 7.4 (3.27); 7.3941 (2.3); 7.3906 (1.87); 7.3784 (1.03); 3.342 (38.26); 3.3334 (54.14); 3.2976 (5.68); 2.5063 (17.39); 2.502 (23.82); 2.4977 (18.86); 1.9886 (0.35); 1.3215 (16); −0.0002 (4.99) |
| 20-158 | 2-bromophenyl | 4-chlorophenyl | CH2 | C(CH3)2 | — | H | compound No. 20-158, solvent: [DMSO], spectrometer: 399.95 MHz 7.9991 (1.77); 7.6403 (1.39); 7.6205 (1.57); 7.5971 (2.27); 7.4413 (5.56); 7.4389 (5.68); 7.4232 (1.45); 7.4068 (1.24); 7.4048 (1.28); 7.3866 (1.26); 7.3818 (1.95); 7.3678 (0.84); 7.3628 (0.76); 7.3557 (0.97); 7.3506 (0.75); 7.3362 (1.05); 7.3315 (0.94); 7.3182 (0.55); 7.3132 (0.5); 3.3316 (35.22); 3.298 (5.62); 2.506 (15.89); 2.5016 (21.92); 2.4972 (17.56); 1.9886 (0.72); 1.3242 (16); 1.1748 (0.38); −0.0002 (5.31); −0.0081 (0.35) |
| 20-159 | 2-chloro-3-pyridyl | 4-chlorophenyl | CH2 | C(CH3)2 | — | H | compound No. 20-159, solvent: [DMSO], spectrometer: 399.95 MHz 8.4584 (1.13); 8.4537 (1.26); 8.4464 (1.26); 8.4417 (1.29); 8.1801 (1.84); 7.8674 (1.15); 7.8627 (1.23); 7.8487 (1.34); 7.844 (1.35); 7.6041 (1.87); 7.5992 (2.07); 7.5009 (1.28); 7.4888 (1.28); 7.4821 (1.26); 7.4701 (1.19); 7.4561 (0.59); 7.4511 (0.52); 7.4353 (1.85); 7.4302 (1.97); 7.417 (3.15); 7.3962 (0.93); 3.3257 (15.08); 3.2911 (5.49); 2.5059 (11.73); 2.5016 (15.94); 2.4974 (12.66); 1.9888 (0.74); 1.3274 (16); 1.1751 (0.4); 1.0116 (0.47); −0.0002 (3.3) |
| 20-160 | 2-fluorophenyl | 2,4-dichlorophenyl | CH(OCH3) | C(CH3)2 | — | H | compound No. 20-160, solvent: [DMSO], spectrometer: 399.95 MHz 7.8355 (1.24); 7.8289 (1.21); 7.6299 (1.78); 7.627 (3.23); 7.6241 (1.82); 7.5703 (0.52); 7.5654 (0.75); 7.5505 (1.1); 7.5464 (1.37); 7.5324 (0.7); 7.5277 (1.1); 7.5227 (0.4); 7.5139 (0.46); 7.5078 (0.87); 7.5041 (0.63); 7.5021 (0.58); 7.495 (0.82); 7.4933 (0.83); 7.4845 (7.2); 7.4816 (6.81); 7.4749 (0.77); 7.4703 (0.49); 7.2775 (2.52); 7.2603 (1.8); 7.258 (2.62); 7.2508 (1.16); 7.2419 (0.91); 7.2393 (0.88); 7.2301 (0.83); 5.3049 (5.71); 3.3224 (12.63); 3.1235 (16); 2.5247 (0.51); 2.5114 (8.21); 2.5069 (16.17); 2.5023 (21.38); 2.4977 (15.63); 2.4932 (7.47); 1.3348 (9.39); 1.2777 (9.07); −0.0002 (2.38) |
| 20-161 | 2-chlorophenyl | 2,4-dichlorophenyl | CH(OCH3) | C(CH3)2 | — | H | compound No. 20-161, solvent: [DMSO], spectrometer: 399.95 MHz 8.0421 (2.11); 7.6406 (1.76); 7.6377 (3.23); 7.6347 (1.83); 7.4855 (6.92); 7.4825 (6.75); 7.4621 (1.33); 7.4591 (2.47); 7.4568 (1.51); 7.4365 (0.77); 7.4248 |

TABLE 20-continued

Compounds of the formula I-20

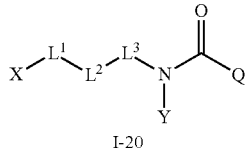

I-20

| Ex. No. | Q | X | L[1] | L[2] | L[3] | Y | Physical data: $^1$H-NMR, δ [ppm] or CAS or patent No. |
|---|---|---|---|---|---|---|---|
| | | | | | | | (1.43); 7.4139 (1.59); 7.406 (0.94); 7.3946 (1.29); 7.3808 (4.34); 7.3714 (2.5); 5.4002 (5.68); 3.3216 (25.14); 3.1227 (16); 2.524 (0.75); 2.5191 (1.19); 2.5106 (13.86); 2.5061 (27.65); 2.5015 (36.85); 2.4969 (27.09); 2.4924 (13.09); 1.3356 (1.03); 1.2979 (0.57); 1.2817 (9.39); 1.2738 (9.77); 1.2585 (0.72); 1.2492 (1.29); −0.0002 (3.89) |
| 20-162 | 2-bromophenyl | 2-(trifluoro-methyl)-4-chlorophenyl | CH2 | CH2 | — | H | compound No. 20-162, solvent: [DMSO], spectrometer: 399.95 MHz 8.6021 (1.54); 8.5879 (2.98); 8.5738 (1.53); 7.9527 (1.91); 7.7555 (13.05); 7.7361 (4.13); 7.7308 (2.82); 7.6546 (2.87); 7.6516 (5.43); 7.6369 (2.18); 7.631 (5.23); 7.5921 (4.65); 7.5724 (3.68); 7.4489 (1.72); 7.4461 (1.9); 7.43 (5.74); 7.4255 (2.8); 7.4119 (4.3); 7.409 (4.12); 7.3718 (2.51); 7.3671 (4.68); 7.3485 (12.06); 7.3315 (5.59); 7.3289 (5.83); 3.5052 (2.29); 3.488 (5.14); 3.472 (5.19); 3.4547 (2.81); 3.3799 (8.01); 3.0189 (3.28); 3.0012 (5.84); 2.9835 (2.86); 2.8906 (16); 2.7309 (12.91); 2.6754 (0.52); 2.671 (0.72); 2.6663 (0.53); 2.5243 (2.05); 2.5109 (39.29); 2.5064 (79.3); 2.5018 (105.67); 2.4973 (77.62); 2.4928 (37.69); 2.3331 (0.52); 2.3286 (0.7); 2.3241 (0.51); 1.4682 (0.5); 1.4606 (0.42); 0.9796 (0.46); 0.9661 (0.39); 0.9326 (0.36); 0.916 (0.74); 0.8983 (0.48); 0.008 (1.68); −0.0002 (48.69); −0.0085 (1.63) |
| 20-163 | 2,6-difluorophenyl | 2-(trifluoro-methyl)-4-chlorophenyl | CH2 | CH2 | — | H | compound No. 20-163, solvent: [DMSO], spectrometer: 399.95 MHz 8.8777 (2.65); 8.8635 (5.04); 8.8495 (2.6); 8.3166 (0.42); 7.9531 (0.68); 7.7574 (10.21); 7.7519 (13.11); 7.7286 (5.86); 7.7232 (4.18); 7.708 (7.88); 7.7023 (6); 7.6787 (0.73); 7.6734 (0.62); 7.5642 (10.01); 7.5426 (10.01); 7.5255 (4.47); 7.521 (4.11); 7.5088 (2.8); 7.5044 (7.75); 7.4999 (2.74); 7.4876 (3.72); 7.4832 (4.57); 7.4667 (2.12); 7.1869 (1.51); 7.1837 (2.09); 7.1763 (12.99); 7.1569 (16); 7.1503 (2.99); 7.1362 (10.71); 7.1285 (1.87); 3.5356 (4.02); 3.5184 (9.6); 3.503 (9.74); 3.4857 (4.43); 3.3242 (108.43); 3.0244 (1.42); 2.9948 (5.91); 2.9773 (10.81); 2.9597 (5.11); 2.9425 (0.46); 2.8909 (5.96); 2.8572 (1.01); 2.8179 (0.36); 2.7899 (1.12); 2.7792 (1.33); 2.7701 (0.74); 2.7589 (0.42); 2.7497 (0.36); 2.7312 (4.61); 2.6801 (0.44); 2.6758 (0.85); 2.6712 (1.14); 2.6666 (0.85); 2.662 (0.42); 2.5245 (3.68); 2.5197 (5.62); 2.5112 (61.16); 2.5067 (121.97); 2.5021 (160.91); 2.4975 (115.62); 2.4929 (54.08); 2.338 (0.35); 2.3334 (0.77); 2.3288 (1.05); 2.3243 (0.75); 1.2338 (0.55); 0.0079 (2.67); −0.0002 (76.75); −0.0086 (2.21) |
| 20-164 | 2-iodophenyl | 2-(trifluoro-methyl) -4-chlorophenyl | CH2 | CH2 | — | H | compound No. 20-164, solvent: [DMSO], spectrometer: 399.95 MHz 8.5662 (2.01); 8.5521 (3.94); 8.5381 (2.02); 7.8837 (6.05); 7.8816 (6.49); 7.8639 (6.57); 7.8618 (6.63); 7.7587 (16); 7.7402 (5.25); 7.735 (3.51); 7.7142 (0.56); 7.7086 (0.88); 7.6991 (0.5); 7.6784 (0.54); 7.6037 (5.43); 7.5829 (4.14); 7.5421 (0.63); 7.5213 (0.46); 7.4578 (2.9); 7.4552 (3.03); 7.4391 (6.62); 7.4365 (6.78); 7.4204 (4.22); 7.4177 (4.18); 7.2879 (5.89); 7.2839 (6.66); 7.269 (5.06); 7.265 (5.08); 7.1832 (3.66); 7.179 (3.57); 7.1639 (5.46); 7.1599 (5.22); 7.1449 (3.18); 7.1407 (2.95); 3.4938 (2.68); 3.4767 (6.03); 3.4606 (5.96); 3.4432 (2.98); 3.3236 (91.35); 3.0318 (4.18); 3.014 (7.2); 2.9946 (4.26); 2.8906 (0.44); 2.7874 (0.77); 2.7758 (0.95); 2.7631 (0.53); 2.7452 (0.34); 2.7371 (1.1); 2.7321 (0.5); 2.6753 (0.68); 2.6709 (0.91); |

TABLE 20-continued

Compounds of the formula I-20

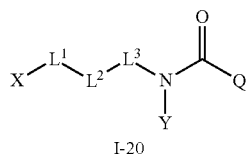

I-20

| Ex. No. | Q | X | L¹ | L² | L³ | Y | Physical data: ¹H-NMR, δ [ppm] or CAS or patent No. |
|---|---|---|---|---|---|---|---|
| 20-165 | 2-fluorophenyl | 2-(trifluoro-methyl)-4-chlorophenyl | CH2 | CH2 | — | H | 2.6663 (0.67); 2.524 (3.98); 2.5107 (50.53); 2.5063 (98.83); 2.5017 (129.88); 2.4972 (95.11); 2.4928 (45.91); 2.3331 (0.63); 2.3285 (0.85); 2.324 (0.62); 0.008 (2.02); −0.0002 (51.37); −0.0085 (1.62) compound No. 20-165, solvent: [DMSO], spectrometer: 399.95 MHz 8.4652 (3.88); 8.317 (0.92); 7.7512 (9.51); 7.7457 (13.96); 7.7339 (6.46); 7.7285 (3.65); 7.7132 (7.02); 7.7078 (5.49); 7.5917 (3.46); 7.5873 (4.21); 7.5734 (6.77); 7.5688 (8.6); 7.5576 (10.86); 7.5493 (5.39); 7.542 (3.5); 7.5369 (8.49); 7.5287 (4.99); 7.5259 (3.53); 7.5239 (3.28); 7.5215 (2.92); 7.5148 (3.85); 7.5132 (3.45); 7.5106 (3.27); 7.5079 (4.91); 7.503 (2.67); 7.4944 (2.91); 7.4898 (2.39); 7.2976 (5.87); 7.2883 (6.9); 7.2858 (6.6); 7.2785 (4.91); 7.2765 (5.64); 7.2728 (6.18); 7.2699 (16); 7.25 (11.9); 3.5358 (3.88); 3.5189 (9.41); 3.5029 (9.56); 3.4859 (4.39); 3.3248 (92.64); 3.0135 (5.94); 2.9959 (10.83); 2.9783 (5.15); 2.6763 (0.59); 2.6717 (0.83); 2.6672 (0.58); 2.5251 (2.6); 2.5203 (4.17); 2.5118 (46.72); 2.5072 (93.12); 2.5027 (122.56); 2.498 (88.07); 2.4935 (41.34); 2.334 (0.59); 2.3295 (0.82); 2.3249 (0.59); 1.3363 (2.16); 1.2587 (0.39); 1.2496 (2.69); 1.2339 (0.46); 1.188 (0.72); 0.008 (1.21); −0.0002 (34.4); −0.0086 (1) |
| 20-166 | 2-chlorophenyl | 2-(trifluoro-methyl)-4-chlorophenyl | CH2 | CH2 | — | H | compound No. 20-166, solvent: [DMSO], spectrometer: 399.95 MHz 8.6068 (2.26); 8.5928 (4.34); 8.5788 (2.23); 7.7516 (16); 7.7296 (6.12); 7.7241 (4.32); 7.5839 (7.88); 7.5637 (6.3); 7.4971 (3.53); 7.496 (3.9); 7.4939 (4.71); 7.4779 (7.36); 7.4753 (12.02); 7.4731 (7.32); 7.4562 (4.48); 7.4488 (4.8); 7.4412 (6.52); 7.4338 (7.7); 7.4286 (1.95); 7.4222 (3.86); 7.414 (5.12); 7.4086 (2.48); 7.4049 (2.48); 7.3898 (10.12); 7.3865 (10.85); 7.382 (11.6); 7.381 (11.27); 7.3748 (15.28); 7.3724 (12.67); 7.3634 (1.81); 7.3561 (0.4); 5.757 (0.94); 3.5162 (3.36); 3.4991 (7.77); 3.4834 (7.84); 3.466 (3.77); 3.3252 (39.7); 3.0152 (4.91); 2.9976 (8.86); 2.9799 (4.23); 2.6762 (0.36); 2.6716 (0.48); 2.667 (0.36); 2.5249 (1.53); 2.5201 (2.44); 2.5116 (27.58); 2.5071 (54.54); 2.5025 (71.35); 2.4979 (51.08); 2.4933 (23.87); 2.3339 (0.32); 2.3293 (0.46); 1.3368 (0.72); 1.2497 (0.94); 0.008 (0.82); −0.0002 (24.28); −0.0085 (0.66) |
| 20-167 | 2-chloro-3-pyridyl | 2-(trifluoro-methyl)-4-chlorophenyl | CH2 | CH2 | — | H | compound No. 20-167, solvent: [DMSO], spectrometer: 399.95 MHz 8.7757 (2.13); 8.7616 (4.13); 8.7474 (2.09); 8.4739 (7.95); 8.4691 (8.53); 8.4619 (8.53); 8.457 (8.31); 8.3164 (0.34); 7.8536 (8.24); 7.8487 (8.46); 7.8348 (9.63); 7.8299 (8.99); 7.7572 (16); 7.7357 (5.69); 7.7303 (4); 7.5908 (7.22); 7.5707 (5.78); 7.509 (9.48); 7.4969 (9.14); 7.4902 (8.58); 7.4781 (8.5); 3.5304 (3.13); 3.5133 (7.18); 3.4976 (3.42); 3.4801 (3.49); 3.3233 (76.93); 3.3038 (0.53); 3.2858 (0.38); 3.018 (4.56); 3.0004 (8.2); 2.9826 (3.92); 2.6957 (1.43); 2.6759 (0.6); 2.6713 (0.82); 2.6667 (0.59); 2.5247 (2.61); 2.5199 (4.06); 2.5114 (44.89); 2.5068 (89.59); 2.5022 (118.23); 2.4976 (84.85); 2.4931 (39.51); 2.3336 (0.57); 2.329 (0.75); 2.3244 (0.53); 1.2496 (0.41); 1.2345 (0.37); 0.008 (1.19); −0.0002 (34.81); −0.0086 (1.01) |
| 20-168 | 2-chloro-3-pyridyl | 2,4-dichlorophenyl | O | CH2 | CH(CH3) | H | |
| 20-169 | 2-chloro-3-pyridyl | 4-chlorophenyl | O | CH2 | CH(CH3) | H | |

TABLE 20-continued

Compounds of the formula I-20

$$X-L^1-L^2-L^3-N(Y)-C(=O)-Q$$

I-20

| Ex. No. | Q | X | L¹ | L² | L³ | Y | Physical data: ¹H-NMR, δ [ppm] or CAS or patent No. |
|---|---|---|---|---|---|---|---|
| 20-170 | 2-chloro-3-pyridyl | 2,4-dichlorophenyl | S | CH2 | CH(CH3) | H | compound No. 20-170, solvent: [DMSO], spectrometer: 399.95 MHz 8.761 (2.56); 8.7414 (2.58); 8.4846 (4.68); 8.4798 (5.03); 8.4726 (5.03); 8.4677 (4.92); 7.8638 (4.71); 7.8589 (4.83); 7.845 (5.47); 7.8401 (5.13); 7.6517 (8.24); 7.646 (8.6); 7.6075 (6.44); 7.5859 (8.23); 7.5183 (5.37); 7.5063 (5.16); 7.4996 (4.9); 7.4875 (4.86); 7.4474 (5.35); 7.4417 (5.02); 7.4259 (4.2); 7.4202 (4.03); 4.1599 (0.72); 4.1431 (1.68); 4.1246 (2.01); 4.1072 (1.71); 4.0903 (0.75); 3.3329 (130.06); 3.2479 (1.64); 3.2305 (1.61); 3.2148 (3.57); 3.1974 (3.44); 3.1702 (3.53); 3.1539 (3.58); 3.137 (1.75); 3.1207 (1.59); 2.6719 (0.34); 2.5421 (44.66); 2.5252 (0.95); 2.5205 (1.52); 2.5119 (19.7); 2.5073 (39.77); 2.5027 (52.6); 2.4981 (37.84); 2.4936 (17.82); 2.3296 (0.34); 1.2899 (16); 1.2732 (15.76); −0.0002 (5.97) |
| 20-171 | 2-chloro-3-pyridyl | 4-chlorophenyl | S | CH2 | CH(CH3) | H | compound No. 20-171, solvent: [DMSO], spectrometer: 399.95 MHz 8.6948 (2.19); 8.675 (2.1); 8.4784 (4.47); 8.4735 (4.79); 8.4663 (4.78); 8.4615 (4.65); 7.829 (0.35); 7.8221 (4.51); 7.8172 (4.63); 7.8103 (0.49); 7.8033 (5.34); 7.7984 (4.94); 7.5031 (5.23); 7.4911 (5.09); 7.4878 (0.94); 7.4843 (4.98); 7.4723 (4.67); 7.453 (0.69); 7.447 (6.45); 7.4414 (2.4); 7.4307 (3.48); 7.425 (16); 7.4192 (2.38); 7.401 (2.37); 7.3953 (15.88); 7.3895 (3.36); 7.3788 (2.42); 7.3731 (6.08); 7.3671 (0.74); 7.3617 (0.6); 7.3431 (0.34); 4.1071 (0.73); 4.0904 (1.68); 4.0735 (1.91); 4.0711 (1.83); 4.0542 (1.65); 4.0373 (0.71); 3.338 (282); 3.3029 (0.42); 3.2056 (2.02); 3.196 (0.34); 3.1885 (2); 3.1721 (3.44); 3.155 (3.31); 3.0935 (3.44); 3.0771 (3.49); 3.06 (2.17); 3.0435 (2.01); 2.6762 (0.39); 2.6717 (0.54); 2.667 (0.37); 2.5419 (51.59); 2.5251 (1.63); 2.5203 (2.45); 2.5117 (30.83); 2.5072 (62.38); 2.5026 (82.24); 2.4979 (58.89); 2.4934 (27.56); 2.3338 (0.38); 2.3293 (0.52); 2.3247 (0.39); 1.2606 (1.19); 1.2492 (15.64); 1.2324 (15.4); −0.0002 (1.31) |
| 20-172 | 2-fluorophenyl | 2,4-dichlorophenyl | O | CH2 | CH(CH3) | H | compound No. 20-172, solvent: [DMSO], spectrometer: 399.95 MHz 8.3453 (1.74); 8.3257 (1.75); 7.5999 (1.54); 7.5955 (1.87); 7.5816 (3.12); 7.5746 (8.3); 7.568 (7.86); 7.5621 (2.08); 7.5577 (1.97); 7.5479 (0.98); 7.5433 (0.88); 7.5346 (1.06); 7.5297 (2.01); 7.5268 (1.44); 7.525 (1.38); 7.5225 (1.18); 7.5157 (1.63); 7.5114 (1.51); 7.5089 (2.08); 7.504 (1.13); 7.4954 (1.24); 7.4908 (1.12); 7.3861 (3.63); 7.3796 (3.32); 7.3639 (4.91); 7.3575 (4.68); 7.2996 (2.54); 7.2907 (3.01); 7.2883 (2.79); 7.2784 (2.53); 7.2722 (7.29); 7.2522 (5.68); 7.2482 (7.98); 7.2259 (5.61); 4.4027 (0.6); 4.3864 (1.37); 4.3691 (1.77); 4.3514 (1.49); 4.3349 (0.68); 4.1324 (1.75); 4.1164 (1.64); 4.1081 (3.75); 4.0921 (3.33); 4.0749 (3.61); 4.06 (3.46); 4.0506 (1.86); 4.0357 (1.49); 3.3803 (0.37); 3.3689 (0.64); 3.3366 (269); 3.2973 (0.47); 2.6762 (0.41); 2.6716 (0.58); 2.667 (0.4); 2.5418 (10.48); 2.5249 (1.82); 2.5201 (2.91); 2.5116 (34.32); 2.5071 (67.98); 2.5025 (88.73); 2.4979 (63.5); 2.4934 (30.01); 2.3338 (0.41); 2.3292 (0.57); 2.3247 (0.41); 1.2724 (16); 1.2555 (15.8); −0.0002 (7.4) |
| 20-173 | 2-fluorophenyl | 4-chlorophenyl | O | CH2 | CH(CH3) | H | compound No. 20-173, solvent: [DMSO], spectrometer: 399.95 MHz 8.3587 (1.62); 8.3396 (1.61); 7.5813 (1.43); 7.5768 (1.81); 7.5631 (2.72); 7.5584 (3.59); 7.5489 (0.41); |

TABLE 20-continued
Compounds of the formula I-20
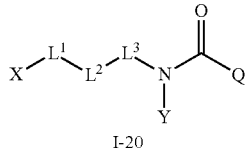
I-20
| Ex. No. | Q | X | L¹ | L² | L³ | Y | Physical data: ¹H-NMR, δ [ppm] or CAS or patent No. |
|---|---|---|---|---|---|---|---|
| | | | | | | | 7.5437 (2.73); 7.5393 (2.88); 7.5307 (1.12); 7.5258 (2.03); 7.523 (1.37); 7.521 (1.24); 7.5186 (1.18); 7.5119 (1.6); 7.5104 (1.38); 7.5078 (1.26); 7.5049 (2.12); 7.5001 (1.11); 7.4915 (1.26); 7.4869 (1.01); 7.3476 (0.87); 7.3386 (10.81); 7.333 (3.09); 7.3217 (3.32); 7.316 (12.36); 7.3071 (1.08); 7.2944 (2.5); 7.2845 (2.89); 7.282 (2.85); 7.2755 (2); 7.2734 (2.36); 7.2703 (2.49); 7.2657 (5.54); 7.2634 (3.87); 7.2494 (1.81); 7.2468 (5.25); 7.0155 (1.1); 7.0066 (12.04); 7.0009 (3.25); 6.9897 (3.06); 6.984 (10.46); 6.9751 (0.82); 4.3635 (0.55); 4.3473 (1.25); 4.33 (1.59); 4.3126 (1.33); 4.2962 (0.63); 4.0503 (2.17); 4.0345 (2.03); 4.0261 (3.45); 4.0102 (3.07); 3.9581 (3.29); 3.9436 (3.23); 3.9338 (2.23); 3.9194 (1.92); 3.3603 (0.38); 3.3296 (209.41); 3.3086 (0.54); 2.6755 (0.42); 2.6709 (0.59); 2.6663 (0.42); 2.5412 (13.76); 2.5243 (1.76); 2.5196 (2.67); 2.511 (33.94); 2.5064 (68.81); 2.5018 (91.1); 2.4972 (65.31); 2.4926 (30.57); 2.3332 (0.44); 2.3286 (0.6); 2.324 (0.43); 1.247 (16); 1.23 (15.85); 0.008 (0.44); −0.0002 (14.27); −0.0085 (0.41) |
| 20-174 | 2-fluorophenyl | 2,4-dichlorophenyl | S | CH2 | CH(CH3) | H | compound No. 20-174, solvent: [DMSO], spectrometer: 399.95 MHz 8.4095 (1.97); 8.3904 (1.99); 7.6355 (8.69); 7.6298 (9.04); 7.5981 (6.41); 7.586 (1.74); 7.5814 (2.44); 7.5766 (8.37); 7.5678 (3.05); 7.5631 (4.04); 7.5531 (1.4); 7.5484 (2.83); 7.5441 (2.37); 7.5398 (1.33); 7.5348 (2.21); 7.5321 (1.58); 7.53 (1.45); 7.5277 (1.29); 7.5209 (1.83); 7.5168 (1.48); 7.514 (2.27); 7.5091 (1.19); 7.5005 (1.35); 7.496 (1.06); 7.4332 (5.46); 7.4275 (5.12); 7.4117 (4.32); 7.406 (4.13); 7.3025 (2.68); 7.2923 (3.14); 7.2898 (3.12); 7.2835 (2.3); 7.2815 (2.6); 7.2783 (2.78); 7.2734 (6.07); 7.2713 (4.39); 7.2572 (2.12); 7.2546 (5.5); 4.1974 (0.66); 4.1803 (1.54); 4.1626 (1.99); 4.145 (1.58); 4.1277 (0.69); 3.3275 (84.73); 3.2701 (1.92); 3.2522 (1.86); 3.237 (3.37); 3.2192 (3.23); 3.1637 (3.35); 3.1477 (3.41); 3.1306 (2.05); 3.1147 (1.89); 2.6713 (0.4); 2.5415 (4.13); 2.5246 (1.2); 2.5198 (1.91); 2.5112 (23.31); 2.5067 (46.67); 2.5021 (61.49); 2.4975 (44.11); 2.493 (20.79); 2.3289 (0.4); 1.2907 (16); 1.274 (15.82); 0.008 (0.47); −0.0002 (14.67); −0.0086 (0.44) |
| 20-175 | 2-fluorophenyl | 4-chlorophenyl | S | CH2 | CH(CH3) | H | compound No. 20-175, solvent: [DMSO], spectrometer: 399.95 MHz 8.3401 (1.7); 8.3201 (1.6); 7.5667 (0.37); 7.5628 (0.46); 7.5565 (1.27); 7.5523 (2.14); 7.5466 (1.49); 7.5418 (1.02); 7.5383 (2.17); 7.5335 (5.23); 7.5279 (2.55); 7.5211 (1.62); 7.5189 (1.58); 7.5139 (4.14); 7.5076 (2.18); 7.5028 (1.08); 7.4942 (1.4); 7.4895 (0.91); 7.4642 (0.67); 7.4603 (0.34); 7.4439 (0.39); 7.4369 (0.73); 7.4309 (6.36); 7.4254 (2.38); 7.4146 (3.48); 7.409 (15.66); 7.403 (2.25); 7.3836 (2.34); 7.3777 (15.44); 7.372 (3.3); 7.3653 (0.55); 7.3613 (2.45); 7.3557 (6.04); 7.3499 (1.05); 7.3458 (0.92); 7.3267 (0.57); 7.3064 (0.32); 7.2949 (2.24); 7.2816 (3.06); 7.2791 (3.38); 7.2741 (2.55); 7.2704 (2.58); 7.2667 (2.28); 7.2627 (5.68); 7.2603 (4.07); 7.2495 (1.86); 7.2466 (1.94); 7.244 (2.97); 7.2415 (1.94); 7.2381 (0.5); 4.1477 (0.68); 4.1307 (1.51); 4.1129 (1.8); 4.0948 (1.49); 4.0775 (0.66); 3.3279 (269.64); 3.3039 (0.6); 3.2953 (0.36); 3.2219 (2.23); 3.2043 (2.12); 3.1884 (3.44); 3.1709 (3.32); 3.096 (3.55); 3.0798 (3.57); 3.0626 (2.29); 3.0463 (2.1); 2.68 (0.32); 2.6754 (0.68); 2.6708 (0.95); 2.6661 (0.68); 2.541 (11.82); 2.5241 |

TABLE 20-continued

Compounds of the formula I-20

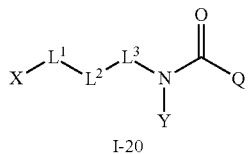

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (2.98); 2.5193 (4.61); 2.5108 (54.34); 2.5063 (109.41); 2.5017 (144.48); 2.497 (103.4); 2.4925 (48.5); 2.3331 (0.68); 2.3284 (0.94); 2.3238 (0.67); 1.2968 (0.88); 1.2801 (0.88); 1.2621 (1.44); 1.2502 (16); 1.2335 (15.83); 0.008 (0.89); −0.0002 (27.8); −0.0086 (0.81) |
| 20-176 | 2,6-difluorophenyl | 2,4-dichlorophenyl | O | CH2 | CH(CH3) | H | compound No. 20-176, solvent: [DMSO], spectrometer: 399.95 MHz 8.8466 (2.46); 8.8275 (2.49); 7.5762 (7.9); 7.5698 (8.4); 7.5411 (0.88); 7.5338 (0.38); 7.5245 (1.83); 7.5199 (1.66); 7.5078 (1.31); 7.5033 (3.4); 7.499 (1.21); 7.4867 (1.65); 7.4822 (1.96); 7.4657 (0.93); 7.431 (0.34); 7.4091 (0.87); 7.3829 (3.9); 7.3765 (3.96); 7.3607 (5.18); 7.3543 (4.96); 7.2354 (7.89); 7.2131 (5.93); 7.1843 (0.66); 7.1812 (0.92); 7.1737 (5.68); 7.1545 (6.93); 7.1338 (4.76); 7.126 (0.79); 4.3688 (0.63); 4.353 (1.49); 4.3356 (1.94); 4.3179 (1.55); 4.3024 (0.72); 4.0626 (8.62); 4.0477 (7.8); 3.356 (0.46); 3.3276 (185.33); 2.6753 (0.47); 2.6707 (0.64); 2.6663 (0.46); 2.5411 (48.61); 2.524 (2.01); 2.5107 (36.77); 2.5062 (73.24); 2.5017 (96.47); 2.4971 (69.51); 2.4925 (33.12); 2.3329 (0.44); 2.3284 (0.62); 2.324 (0.44); 1.2633 (16); 1.2463 (15.96); 1.2338 (1.27); 0.008 (0.57); −0.0002 (15.95); −0.0086 (0.48) |
| 20-177 | 2,6-difluorophenyl | 4-chlorophenyl | O | CH2 | CH(CH3) | H | compound No. 20-177, solvent: [DMSO], spectrometer: 399.95 MHz 8.8278 (2.13); 8.8082 (2.14); 7.5396 (0.81); 7.5229 (1.74); 7.5185 (1.47); 7.5062 (1.11); 7.5018 (3.23); 7.4973 (1.13); 7.4852 (1.51); 7.4806 (1.9); 7.4641 (0.88); 7.3515 (0.89); 7.3425 (10.8); 7.337 (3.03); 7.3257 (3.28); 7.32 (11.85); 7.3111 (1.01); 7.1832 (0.65); 7.18 (0.85); 7.1724 (5.43); 7.1533 (6.55); 7.1324 (4.46); 7.1246 (0.71); 7.0022 (1.08); 6.9933 (11.85); 6.9877 (3.17); 6.9764 (3.04); 6.9707 (10.21); 6.9618 (0.79); 4.3443 (0.59); 4.3288 (1.34); 4.3117 (1.66); 4.2937 (1.27); 4.2781 (0.64); 3.9644 (9.63); 3.9498 (8.22); 3.3302 (369.65); 3.2885 (0.36); 2.6754 (0.68); 2.6708 (0.93); 2.6662 (0.66); 2.541 (38.14); 2.5242 (2.58); 2.5194 (4.22); 2.5109 (53.52); 2.5064 (107.51); 2.5017 (141.36); 2.4971 (100.74); 2.4926 (47.11); 2.3378 (0.33); 2.3332 (0.69); 2.3285 (0.92); 2.324 (0.66); 1.2328 (16); 1.2159 (15.73); 0.008 (0.75); −0.0002 (23.53); −0.0086 (0.66) |
| 20-178 | 2,6-difluorophenyl | 2,4-dichlorophenyl | S | CH2 | CH(CH3) | H | compound No. 20-178, solvent: [DMSO], spectrometer: 399.95 MHz 8.894 (2.47); 8.8747 (2.49); 7.6468 (8.36); 7.6411 (8.67); 7.5852 (6.39); 7.5636 (8.46); 7.5547 (0.99); 7.5381 (1.92); 7.5334 (1.61); 7.5215 (1.27); 7.5169 (3.52); 7.5125 (1.24); 7.5002 (1.68); 7.4958 (2.11); 7.4792 (0.96); 7.4407 (5.6); 7.435 (5.23); 7.4192 (4.3); 7.4135 (4.09); 7.1979 (0.7); 7.1946 (0.97); 7.1873 (5.98); 7.1682 (7.1); 7.1473 (4.9); 7.1396 (0.83); 4.1645 (0.73); 4.1476 (1.68); 4.1297 (2.11); 4.1122 (1.74); 4.0952 (0.75); 3.3309 (33.07); 3.2137 (1.44); 3.1962 (1.41); 3.1807 (3.86); 3.1633 (3.76); 3.1504 (3.77); 3.1343 (3.79); 3.1174 (1.51); 3.1013 (1.37); 2.5424 (4.06); 2.5255 (0.56); 2.5207 (0.89); 2.5122 (10.31); 2.5077 (20.68); 2.5031 (27.29); 2.4984 (19.56); 2.4939 (9.16); 1.2784 (16); 1.2617 (15.76); −0.0002 (6.55) |
| 20-179 | 2,6-difluorophenyl | 4-chlorophenyl | S | CH2 | CH(CH3) | H | compound No. 20-179, solvent: [DMSO], spectrometer: 399.95 MHz 8.8309 (2.12); 8.8114 (2.04); 7.5502 (0.99); 7.5336 (1.83); 7.529 (1.48); 7.5169 (1.32); 7.5124 (3.32); 7.508 |

TABLE 20-continued

Compounds of the formula I-20

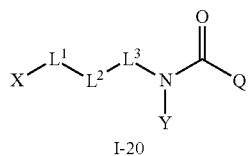

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (1.15); 7.4957 (1.63); 7.4913 (1.95); 7.4745 (1.18); 7.4705 (0.44); 7.4412 (0.65); 7.4358 (5.1); 7.4299 (2.17); 7.4195 (3.29); 7.4136 (16); 7.4083 (2.75); 7.4012 (0.61); 7.3967 (2.75); 7.3913 (15.9); 7.3854 (3.2); 7.375 (2.21); 7.3692 (5.23); 7.3638 (0.64); 7.356 (0.59); 7.3537 (0.7); 7.3508 (0.47); 7.3387 (0.39); 7.193 (0.68); 7.1894 (1.07); 7.1822 (5.56); 7.1632 (6.58); 7.1615 (6.12); 7.1529 (0.84); 7.1486 (0.82); 7.1423 (4.63); 7.1345 (0.79); 4.1017 (0.75); 4.0848 (1.68); 4.0677 (1.94); 4.0661 (1.92); 4.0489 (1.65); 4.0319 (0.73); 3.3337 (85.5); 3.1679 (0.4); 3.163 (1.82); 3.1507 (0.4); 3.1457 (1.77); 3.1297 (3.56); 3.1124 (3.59); 3.0981 (0.41); 3.0748 (3.54); 3.0583 (3.58); 3.0414 (1.9); 3.025 (1.76); 2.5418 (42.3); 2.5249 (0.62); 2.5201 (0.96); 2.5115 (12.21); 2.507 (24.74); 2.5024 (32.76); 2.4978 (23.6); 2.4932 (11.19); 1.284 (0.73); 1.2673 (0.76); 1.2463 (1.33); 1.2349 (15.2); 1.2182 (14.9); −0.0002 (5.31) |
| 20-180 | 2,6-difluorophenyl | 4-chlorophenyl | N(CH3) | CH2 | CH2 | H | compound No. 20-180, solvent: [DMSO], spectrometer: 399.95 MHz 20.0009 (0.57); 8.8407 (1.19); 8.3152 (2.41); 8.2135 (0.83); 7.899 (2); 7.894 (1.98); 7.5308 (0.83); 7.5101 (1.46); 7.489 (0.88); 7.472 (0.46); 7.1882 (4.61); 7.183 (5.54); 7.1652 (8.21); 7.1438 (2.19); 6.7984 (2.1); 6.793 (2.08); 6.7488 (5.97); 6.7265 (5.39); 3.4872 (1.23); 3.471 (3.04); 3.456 (2.74); 3.447 (2.13); 3.4276 (1.57); 3.4118 (1.6); 3.3968 (2.82); 3.3828 (2.71); 3.3258 (2227.56); 2.9278 (16); 2.9082 (9.65); 2.6749 (7.58); 2.6708 (9.86); 2.6666 (7.38); 2.5409 (20.06); 2.5061 (1172.41); 2.5018 (1470.89); 2.4975 (1079.79); 2.3329 (7.31); 2.3286 (9.59); 2.3244 (7.01); 1.2978 (0.52); 1.2584 (0.64); 1.2365 (1.2); 1.1492 (1.1); 0.1468 (1.02); 0.0075 (11.87); −0.0002 (194.85); −0.1492 (0.86) |
| 20-181 | 2-chloro-3-pyridyl | 4-chlorophenyl | N(CH3) | CH2 | CH2 | H | compound No. 20-181, solvent: [DMSO], spectrometer: 399.95 MHz 8.7037 (0.6); 8.6895 (1.15); 8.6756 (0.61); 8.4644 (1.76); 8.4595 (1.88); 8.4524 (1.9); 8.4475 (1.83); 7.6944 (1.75); 7.6895 (1.78); 7.6756 (2.15); 7.6707 (2); 7.4692 (2.01); 7.4571 (1.98); 7.4503 (1.78); 7.4383 (1.71); 7.2024 (0.41); 7.1935 (4.24); 7.1881 (1.37); 7.1761 (1.49); 7.1707 (4.59); 7.1619 (0.48); 6.7739 (0.49); 6.7651 (4.45); 6.7597 (1.45); 6.7475 (1.43); 6.7422 (3.96); 6.7333 (0.42); 3.5152 (1.05); 3.4985 (2.88); 3.4829 (2.13); 3.4203 (1.14); 3.4053 (2.46); 3.3901 (1.99); 3.3743 (0.61); 3.3266 (45.2); 2.9328 (16); 2.5411 (18.17); 2.524 (0.85); 2.5105 (13.57); 2.5063 (26.08); 2.5018 (33.7); 2.4973 (24.92); −0.0002 (5.59) |
| 20-182 | 3-chloro-2-pyridyl | 4-chlorophenyl | N(CH3) | CH2 | CH2 | H | compound No. 20-182, solvent: [DMSO], spectrometer: 399.95 MHz 20.0118 (1.31); 8.3153 (3.2); 3.3267 (3766.5); 2.8989 (1.9); 2.6707 (16); 2.5404 (18.21); 2.5018 (2389.82); 2.3285 (15.29); 1.2377 (1.02); 1.1487 (1.88); 0.1454 (1.47); −0.0002 (250.97); −0.1492 (1.25) |
| 20-183 | 2-chlorophenyl | 4-chlorophenyl | N(CH3) | CH2 | CH2 | H | compound No. 20-183, solvent: [DMSO], spectrometer: 399.95 MHz 8.5194 (0.64); 8.5054 (1.22); 8.4913 (0.65); 7.4933 (1.22); 7.4913 (1.22); 7.4734 (2.55); 7.4458 (1.06); 7.4417 (1.07); 7.4274 (1.65); 7.4235 (1.63); 7.4077 (0.84); 7.4035 (0.81); 7.3628 (1.07); 7.36 (0.97); 7.3441 (1.97); 7.3414 (1.77); 7.3256 (1.01); 7.323 (0.88); 7.2455 (2.02); 7.2416 (1.9); 7.2267 (1.52); 7.2227 (1.34); 7.198 (0.45); 7.1893 (4.17); 7.1843 (1.42); |

TABLE 20-continued

Compounds of the formula I-20

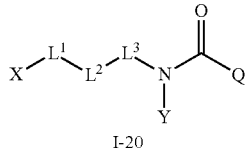

| Ex. No. | Q | X | L¹ | L² | L³ | Y | Physical data: ¹H-NMR, δ [ppm] or CAS or patent No. |
|---|---|---|---|---|---|---|---|
| | | | | | | | 7.1668 (4.56); 7.1575 (0.66); 6.7747 (0.54); 6.766 (4.48); 6.7433 (4); 6.7345 (0.5); 3.5066 (1.22); 3.4896 (3.1); 3.4737 (2.24); 3.4011 (1.23); 3.386 (2.64); 3.3705 (2.23); 3.3536 (1.1); 3.3279 (81.4); 2.9306 (16); 2.9068 (0.86); 2.5409 (10.1); 2.5058 (37.73); 2.5015 (47.42); 2.4972 (34.79); −0.0002 (5.78) |
| 20-184 | 2-bromophenyl | 4-chlorophenyl | N(CH3) | CH2 | CH2 | H | compound No. 20-184, solvent: [DMSO], spectrometer: 399.95 MHz 8.5071 (0.65); 8.4929 (1.17); 8.4791 (0.62); 7.65 (1.64); 7.6472 (1.53); 7.6308 (1.99); 7.6276 (1.83); 7.4043 (0.58); 7.4013 (0.63); 7.386 (1.7); 7.3828 (1.73); 7.3681 (1.7); 7.3642 (1.59); 7.3598 (1.5); 7.3545 (1.61); 7.3407 (1.61); 7.3356 (1.63); 7.3217 (0.66); 7.3168 (0.53); 7.2057 (1.94); 7.2008 (2.18); 7.1928 (4.48); 7.1877 (2.9); 7.1827 (1.86); 7.1755 (1.61); 7.1701 (4.72); 7.1612 (0.53); 6.7783 (0.5); 6.7695 (4.42); 6.752 (1.44); 6.7468 (3.99); 6.738 (0.43); 3.5083 (1.18); 3.4914 (2.98); 3.4751 (2.12); 3.395 (1.12); 3.3797 (2.38); 3.3641 (2.05); 3.3264 (101.83); 2.9342 (16); 2.6706 (0.4); 2.5409 (6.07); 2.5235 (1.54); 2.5103 (25.32); 2.506 (48.19); 2.5015 (62.01); 2.497 (45.67); 2.4928 (22.99 ); 2.3284 (0.41); 0.0078 (0.4); −0.0002 (9.06) −0.0084 (0.4) |
| 20-185 | 2-chlorophenyl | 3,5-dichlorophenyl | O | CH2 | CH2 | H | compound No. 20-185, solvent: [DMSO], spectrometer: 399.95 MHz 8.663 (1.62); 8.65 (2.84); 8.6358 (1.61); 8.3152 (0.41); 7.8103 (0.63); 7.797 (0.63); 7.4997 (2.88); 7.4802 (6.05); 7.4598 (2.02); 7.4526 (2.37); 7.4447 (2.65); 7.4378 (3.56); 7.4245 (1.58); 7.4176 (2.69); 7.4112 (2.09); 7.3976 (9.95); 7.3933 (8.41); 7.381 (3.34); 7.3618 (0.79); 7.3088 (0.43); 7.2888 (0.77); 7.2697 (0.58); 7.1821 (0.76); 7.1634 (6.5); 7.0708 (16); 7.0666 (14.38); 6.9773 (0.93); 6.9576 (0.96); 6.9384 (0.51); 4.1823 (4.58); 4.1685 (9.65); 4.1547 (5.01); 3.9765 (0.37); 3.9633 (0.39); 3.6053 (2.57); 3.5911 (7); 3.5771 (6.77); 3.5635 (2.36); 3.3246 (316.9); 3.2665 (0.51); 2.6709 (1.9); 2.541 (13.01); 2.5059 (246.36); 2.5019 (303.3); 2.4006 (0.45); 2.3285 (2.02); 1.2776 (1.6); 1.2602 (1.61); 1.2366 (0.46); −0.0002 (39.02) |
| 20-186 | 2-chlorophenyl | 3-(trifluoro-methyl)phenyl | O | CH2 | CH(CH2CH3) | H | compound No. 20-186, solvent: [DMSO], spectrometer: 399.95 MHz 8.4502 (2.74); 8.4297 (2.75); 7.5527 (1.77); 7.5333 (3.93); 7.5134 (2.54); 7.4987 (2.98); 7.4783 (6.26); 7.4666 (0.79); 7.4637 (0.77); 7.453 (1.97); 7.4448 (2.42); 7.4388 (2.78); 7.4305 (3.34); 7.4243 (1.53); 7.4201 (1.83); 7.4107 (2.26); 7.402 (1.57); 7.3832 (6.13); 7.38 (7.2); 7.3778 (7.04); 7.3692 (8.3); 7.3592 (1.11); 7.3464 (0.63); 7.343 (0.67); 7.3359 (0.91); 7.3024 (5.18); 7.2951 (3.65); 7.2841 (4.07); 7.2683 (5.65); 4.2071 (0.7); 4.1946 (1.05); 4.1859 (1.43); 4.1731 (1.6); 4.1626 (1.09); 4.1509 (0.85); 4.1381 (0.46); 4.0941 (10.04); 4.0796 (6.82); 3.3261 (89.96); 2.6757 (0.45); 2.6711 (0.59); 2.6665 (0.39); 2.5412 (23.18); 2.5064 (72.37); 2.502 (88.19); 2.4976 (62.74); 2.4595 (0.34); 2.3331 (0.46); 2.3286 (0.57); 2.3245 (0.4); 1.7801 (0.34); 1.7615 (0.9); 1.7491 (1.12); 1.743 (1.06); 1.7301 (1.5); 1.7274 (1.49); 1.7151 (1.35); 1.7085 (1.35); 1.6965 (1.17); 1.6899 (0.56); 1.6778 (0.38); 1.6066 (0.33); 1.5881 (1.17); 1.5694 (1.6); 1.5534 (1.32); 1.5479 (1.42); 1.535 (1.16); 1.5314 (1.12); 1.5135 (0.83); 1.0047 (7.61); 0.9862 (16); 0.9679 (7.15); 0.9521 (0.77); 0.0078 (0.89); −0.0002 (15.13); −0.0084 (0.59) |

TABLE 20-continued

Compounds of the formula I-20

I-20

| Ex. No. | Q | X | L¹ | L² | L³ | Y | Physical data: ¹H-NMR, δ [ppm] or CAS or patent No. |
|---|---|---|---|---|---|---|---|
| 20-187 | 2-fluorophenyl | 3,5-dichlorophenyl | O | CH2 | CH2 | H | compound No. 20-187, solvent: [DMSO], spectrometer: 399.95 MHz 12.9515 (7.81); 12.8762 (0.37); 7.7979 (0.34); 7.6668 (4.85); 7.6634 (5.04); 7.6481 (5.98); 7.6444 (5.97); 7.6243 (0.32); 7.6117 (0.54); 7.6043 (0.63); 7.5893 (4.26); 7.5819 (16); 7.573 (9.12); 7.5696 (9.04); 7.5639 (5.41); 7.5597 (5.28); 7.5548 (7.03); 7.5527 (7.5); 7.546 (12.17); 7.5436 (11.07); 7.526 (2.67); 7.5219 (2.54); 7.5138 (6.51); 7.5116 (5.98); 7.5012 (6.97); 7.4989 (6.12); 7.4808 (4.16); 7.477 (3.84); 7.4624 (5.5); 7.4589 (5.13); 7.4443 (2.41); 7.4406 (2.13); 7.1268 (6.02); 7.1176 (6.29); 7.1143 (6.13); 7.1051 (5.43); 3.3238 (35.51); 3.0765 (1.4); 2.6756 (0.43); 2.6713 (0.58); 2.6668 (0.43); 2.5065 (66.1); 2.5022 (83.42); 2.4978 (60.82); 2.3332 (0.42); 2.3291 (0.55); 2.3246 (0.4); 1.3185 (0.48); 1.106 (4.47); 0.007 (3.34); −0.0002 (60.47); −0.0083 (2.59) |
| 20-188 | 2-fluorophenyl | 3-(trifluoro-methyl)phenyl | O | CH2 | CH(CH2CH3) | H | compound No. 20-188, solvent: [DMSO], spectrometer: 399.95 MHz-8.3163 (0.38); 8.3016 (2.08); 8.2813 (2.12); 7.5666 (1.4); 7.5623 (1.76); 7.5439 (5.17); 7.5364 (1.55); 7.5247 (6.51); 7.5047 (4.19); 7.4973 (1.6); 7.4882 (1.52); 7.4837 (1.38); 7.3332 (0.74); 7.2968 (6.56); 7.2892 (3.86); 7.28 (6.43); 7.2684 (10.33); 7.2637 (10.32); 7.2505 (2.72); 7.2478 (2.79); 7.245 (2.96); 4.2377 (0.67); 4.2244 (0.93); 4.2167 (1.36); 4.2034 (1.49); 4.1954 (0.99); 4.1898 (0.87); 4.182 (0.8); 4.1687 (0.39); 4.1426 (1.6); 4.1272 (1.08); 4.1182 (3.91); 4.1028 (3.34); 4.0961 (4.02); 4.082 (3.2); 4.0715 (1.53); 4.0574 (1.05); 3.3269 (97.68); 2.6758 (0.36); 2.6714 (0.49); 2.667 (0.35); 2.5418 (11.24); 2.511 (31.46); 2.5068 (59.34); 2.5024 (75.97); 2.4979 (55.71); 2.4936 (27.92); 2.3337 (0.37); 2.3291 (0.49); 2.3246 (0.35); 1.7714 (0.8); 1.759 (1.01); 1.7529 (1.09); 1.7375 (1.51); 1.7248 (1.32); 1.7187 (1.33); 1.7063 (1.13); 1.688 (0.39); 1.6319 (0.41); 1.6134 (1.16); 1.5947 (1.51); 1.5786 (1.18); 1.573 (1.38); 1.5602 (1.03); 1.5571 (1.06); 1.5385 (0.79); 0.9806 (7.65); 0.9621 (16); 0.9436 (6.89); 0.0079 (0.66); −0.0002 (14.38); −0.0084 (0.61) |
| 20-189 | 2-fluorophenyl | 4-chlorophenyl | CH(CH3) | CH2 | — | H | compound No. 20-189, solvent: [DMSO], spectrometer: 399.95 MHz 8.7583 (1.18); 8.744 (2.29); 8.7298 (1.2); 7.5192 (0.84); 7.5026 (1.81); 7.498 (1.63); 7.4859 (1.17); 7.4814 (3.41); 7.4771 (1.35); 7.4647 (1.61); 7.4603 (2.05); 7.4437 (0.91); 7.3713 (0.77); 7.3653 (6.93); 7.3604 (2.74); 7.3492 (3.4); 7.344 (14.21); 7.3383 (2.27); 7.3052 (1.95); 7.2995 (12.79); 7.2945 (3.58); 7.283 (2.45); 7.2782 (6.59); 7.1633 (0.62); 7.1601 (0.9); 7.1525 (5.58); 7.1333 (6.75); 7.1126 (4.67); 7.1046 (0.83); 3.4105 (0.37); 3.3989 (4.49); 3.3838 (5.77); 3.3808 (6.27); 3.366 (5.46); 3.3357 (253.14); 3.0333 (1.28); 3.0155 (2.48); 2.9977 (2.4); 2.9799 (1.12); 2.6755 (0.4); 2.671 (0.51); 2.6665 (0.39); 2.5414 (34.24); 2.5244 (1.57); 2.5197 (2.34); 2.511 (28.7); 2.5066 (59.24); 2.502 (79.45); 2.4974 (59.12); 2.4928 (29.56); 2.3334 (0.36); 2.3287 (0.51); 2.3242 (0.38); 1.232 (16); 1.2145 (15.69); −0.0002 (3.72) |
| 20-190 | 2-fluorophenyl | 2,4-dichlorophenyl | CH(CH3) | CH2 | — | H | compound No. 20-190, solvent: [DMSO], spectrometer: 399.95 MHz 8.7811 (3.18); 7.5737 (11.92); 7.5684 (12.49); 7.5624 (0.42); 7.5189 (1.42); 7.5023 (3.04); 7.4978 (2.57); 7.4856 (2.1); 7.4812 (5.66); 7.4767 (2.1); 7.4624 (8.01); |

TABLE 20-continued

Compounds of the formula I-20

$$X-L^1-L^2-L^3-N(Y)-C(=O)-Q$$

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | 7.4412 (16); 7.4266 (0.47); 7.4168 (10.09); 7.4115 (9.06); 7.3957 (3.99); 7.3903 (3.92); 7.1612 (1.1); 7.158 (1.48); 7.1504 (9.35); 7.1313 (11.28); 7.1105 (7.72); 7.1026 (1.24); 3.5054 (1.41); 3.4802 (8.31); 3.476 (9.62); 3.4698 (9.51); 3.4516 (1.72); 3.4366 (0.79); 3.4283 (0.34); 3.3882 (0.44); 3.3735 (0.92); 3.3353 (463.26); 3.3029 (0.69); 2.6805 (0.36); 2.676 (0.74); 2.6713 (1.03); 2.6668 (0.73); 2.6623 (0.34); 2.5416 (90.84); 2.5246 (3.46); 2.5199 (5.28); 2.5114 (58.22); 2.5069 (116.59); 2.5023 (153.29); 2.4977 (109.72); 2.4931 (51.55); 2.3382 (0.34); 2.3336 (0.72); 2.329 (0.99); 2.3244 (0.7); 1.2402 (0.89); 1.2219 (14.9); 1.2162 (9.57); 1.2109 (9.31); 1.2053 (13.62); 1.1872 (0.72); −0.0002 (5.15) |
| 20-191 | 2-fluorophenyl | 4-chloro | CH2 | CH(CH3) | — | H | compound No. 20-191, solvent: [DMSO], spectrometer: 399.95 MHz 8.6712 (2.03); 8.651 (2.04); 7.52 (0.85); 7.5034 (1.86); 7.4989 (1.59); 7.4867 (1.24); 7.4823 (3.57); 7.4779 (1.22); 7.4657 (1.65); 7.4612 (2.22); 7.4446 (0.95); 7.3512 (0.84); 7.3451 (7.36); 7.3402 (2.55); 7.3291 (3.41); 7.324 (13.59); 7.3181 (1.72); 7.2765 (1.82); 7.2707 (11.83); 7.2657 (3); 7.2544 (2.38); 7.2496 (6.51); 7.2436 (0.66); 7.1644 (0.69); 7.1612 (0.96); 7.1535 (5.48); 7.1401 (1.27); 7.1345 (6.52); 7.1137 (4.55); 7.1057 (0.71); 4.1879 (0.65); 4.1711 (1.35); 4.1519 (1.85); 4.1348 (1.44); 4.1168 (0.65); 3.3997 (0.37); 3.3372 (514.41); 3.2924 (0.39); 3.2774 (0.33); 2.8018 (0.57); 2.783 (0.52); 2.7678 (3.79); 2.7585 (3.95); 2.7493 (4.12); 2.7425 (3.95); 2.7245 (0.6); 2.709 (0.47); 2.6802 (0.33); 2.6757 (0.75); 2.6712 (1.01); 2.6668 (0.73); 2.6619 (0.35); 2.5414 (71.83); 2.5246 (2.95); 2.5198 (4.68); 2.5112 (57.61); 2.5067 (115.94); 2.5021 (152.98); 2.4975 (109.79); 2.4929 (51.5); 2.338 (0.34); 2.3334 (0.7); 2.3288 (1); 2.3242 (0.71); 2.3198 (0.33); 1.1293 (16); 1.1127 (15.84); 1.0873 (0.33); −0.0002 (3.21) |
| 20-192 | 2-fluorophenyl | 2,4-dichlorophenyl | CH2 | CH(CH3) | — | H | compound No. 20-192, solvent: [DMSO], spectrometer: 399.95 MHz 8.7079 (2.04); 8.6868 (2.1); 7.5823 (5.63); 7.5791 (4.41); 7.5575 (0.89); 7.5369 (0.99); 7.5304 (0.78); 7.5255 (0.82); 7.5217 (0.85); 7.505 (1.65); 7.5004 (1.44); 7.4884 (1.14); 7.4839 (3.12); 7.4795 (1.17); 7.4672 (1.53); 7.4627 (1.88); 7.4462 (0.85); 7.3813 (0.36); 7.3623 (16); 7.3377 (0.56); 7.2682 (0.45); 7.2628 (0.47); 7.2475 (0.39); 7.2423 (0.41); 7.1654 (0.97); 7.1611 (0.82); 7.1535 (5.25); 7.1466 (1.26); 7.1344 (6.25); 7.1137 (4.4); 7.1056 (0.79); 4.3283 (0.48); 4.3072 (1.11); 4.291 (1.41); 4.2759 (1.08); 4.2549 (0.52); 3.4986 (0.72); 3.4839 (0.68); 3.4673 (0.35); 3.4055 (0.38); 3.3366 (877.92); 2.9191 (1.16); 2.9048 (1.32); 2.8845 (3.52); 2.8702 (3.3); 2.8587 (3.44); 2.8374 (3.39); 2.824 (2.11); 2.8028 (1.34); 2.6803 (0.61); 2.6758 (1.19); 2.6713 (1.63); 2.6667 (1.18); 2.6621 (0.59); 2.5415 (5.09); 2.5246 (5.17); 2.5198 (8.13); 2.5113 (89.76); 2.5068 (179.12); 2.5022 (235.98); 2.4976 (169.29); 2.4931 (79.58); 2.338 (0.52); 2.3335 (1.1); 2.3289 (1.52); 2.3243 (1.08); 2.3198 (0.48); 1.2348 (1.01); 1.1834 (14.03); 1.1668 (13.75); 1.1465 (0.43); −0.0002 (5.81) |
| 20-193 | 2-fluorophenyl | 3,4-dichlorophenyl | CH2 | CH2 | — | H | compound No. 20-193, solvent: [DMSO], spectrometer: 399.95 MHz 8.7765 (1.98); 8.763 (3.72); 8.7494 (1.98); 7.5574 (13.39); 7.5471 (0.57); 7.5368 (16); 7.5305 (11.92); 7.5256 (11.89); 7.5123 (3.38); 7.5076 (2.9); 7.4956 (2.09); 7.4912 (6.3); 7.4867 (2.22); 7.4744 (2.89); 7.47 |

TABLE 20-continued

Compounds of the formula I-20

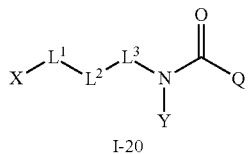

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (3.73); 7.4534 (1.7); 7.2683 (6.59); 7.2631 (6.37); 7.2477 (5.72); 7.2425 (5.57); 7.177 (1.14); 7.1737 (1.63); 7.1661 (10.43); 7.1525 (2.16); 7.1469 (12.48); 7.14 (2.17); 7.1368 (1.44); 7.1261 (8.7); 7.1183 (1.4); 3.5159 (3.79); 3.4991 (9.67); 3.4845 (9.83); 3.4678 (4.1); 3.4058 (0.41); 3.3848 (0.79); 3.3376 (649.05); 2.8411 (7.03); 2.8242 (14.08); 2.8073 (6.32); 2.6803 (0.43); 2.676 (0.89); 2.6714 (1.15); 2.6667 (0.83); 2.6621 (0.52); 2.5416 (3.4); 2.5247 (3.39); 2.5199 (5.19); 2.5114 (63.6); 2.5069 (128.59); 2.5023 (170.29); 2.4976 (122.24); 2.4931 (57.37); 2.3383 (0.36); 2.3336 (0.78); 2.3291 (1.09); 2.3244 (0.77); 2.32 (0.34); −0.0002 (4.11) |
| 20-194 | 2-fluorophenyl | 2,4-dichlorophenyl | CH(CH3) | CH2 | — | H | compound No. 20-194, solvent: [DMSO], spectrometer: 399.95 MHz 8.2773 (1.89); 8.2562 (1.99); 7.5767 (5.78); 7.5725 (5.77); 7.5194 (0.83); 7.5147 (1.02); 7.5062 (0.93); 7.5013 (2.07); 7.4965 (1.55); 7.4939 (1.45); 7.4833 (1.61); 7.4803 (2.29); 7.4755 (1.45); 7.467 (1.19); 7.4623 (1.37); 7.4538 (1.74); 7.4492 (1.73); 7.4353 (3.34); 7.4307 (3.23); 7.4161 (2.55); 7.4117 (2.02); 7.3901 (1.28); 7.3696 (10.68); 7.367 (11.34); 7.3623 (8.54); 7.3462 (1); 7.3417 (1.3); 7.2712 (2.69); 7.2599 (3.13); 7.2574 (3.35); 7.2502 (2.57); 7.2473 (2.84); 7.2445 (3.33); 7.2409 (5.41); 7.2264 (2.03); 7.2226 (4.08); 7.2198 (2.09); 4.3474 (0.53); 4.3267 (1.18); 4.3102 (1.52); 4.2945 (1.14); 4.2733 (0.53); 3.4746 (0.37); 3.4364 (0.48); 3.3364 (3083.87); 3.2046 (0.54); 2.9493 (1.2); 2.9348 (1.42); 2.915 (4.14); 2.9005 (4.25); 2.8959 (4.38); 2.8746 (3.73); 2.8616 (1.23); 2.8403 (1.27); 2.6803 (1.84); 2.6758 (3.74); 2.6711 (5.11); 2.6665 (3.66); 2.662 (1.76); 2.5414 (12.65); 2.5245 (15.39); 2.5198 (23.63); 2.5112 (279.98); 2.5067 (566.47); 2.5021 (750.44); 2.4974 (537.35); 2.4929 (250.69); 2.3379 (1.64); 2.3334 (3.56); 2.3288 (4.9); 2.3242 (3.45); 2.3197 (1.54); 1.2979 (0.32); 1.2583 (0.49); 1.235 (0.8); 1.1986 (16); 1.182 (15.78)( 1.1473 (0.61); 0.008 (0.68); −−0.0001 (20.86); −0.0085 (0.51) |
| 20-195 | 2,6-difluorophenyl | 4-(trifluoro-methoxy)phenyl | CH2 | CH2 | — | H | compound No. 20-195, solvent: [DMSO], spectrometer: 399.95 MHz 8.8112 (1.94); 8.7976 (3.61); 8.7839 (1.94); 8.3161 (0.51); 7.5293 (1.2); 7.5126 (2.6); 7.5081 (2.45); 7.4956 (1.88); 7.4914 (4.98); 7.4873 (1.96); 7.4747 (2.58); 7.4704 (2.97); 7.4537 (1.37); 7.3931 (10.46); 7.3715 (16); 7.3652 (2.33); 7.2927 (10.9); 7.2726 (7.31); 7.1739 (1.17); 7.1709 (1.54); 7.1633 (8.36); 7.1437 (10.97); 7.1234 (7); 7.1156 (1.26); 3.5131 (3.26); 3.4957 (7.89); 3.4811 (7.96); 3.4637 (3.52); 3.3237 (64.61); 2.869 (6.23); 2.8513 (12.02); 2.8337 (5.55); 2.6751 (0.52); 2.6706 (0.69); 2.6665 (0.48); 2.5235 (2.41); 2.5103 (36.06); 2.5061 (69.47); 2.5016 (90.6); 2.4971 (66.54); 2.4928 (32.92); 2.333 (0.44); 2.3283 (0.59); 2.3239 (0.43); 0.0078 (1.05); −0.0002 (24..02; −0.0084 (0.89) |
| 20-196 | 2-(difluoro-methyl)phenyl | 4-(trifluoro-methoxy)phenyl | CH2 | CH2 | — | H | compound No. 20-196, solvent: [DMSO], spectrometer: 399.95 MHz 8.6926 (1.79); 8.6788 (3.42); 8.6651 (1.78); 8.3172 (0.32); 7.701 (2.57); 7.6957 (3.4); 7.679 (4.78); 7.6348 (1.42); 7.6305 (1.84); 7.6163 (5); 7.6119 (5.03); 7.6069 (3.35); 7.6002 (7.95); 7.5934 (4.42); 7.5884 (3.93); 7.5861 (3.99); 7.57 (1.32); 7.4948 (4.24); 7.4922 (4.05); 7.4884 (2.58); 7.4781 (3.25); 7.4737 (2.64); 7.3976 (1.08); 7.3908 (10.07); 7.3859 (3.71); 7.3743 (4.46); 7.3692 (16); 7.3626 (2.14); 7.2985 (10.22); 7.2786 (6.62); 7.2615 (3.84); 7.1224 (8.45); 6.9832 (4.16); |

TABLE 20-continued

Compounds of the formula I-20

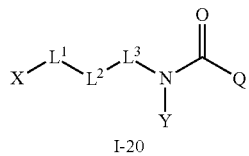

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | 3.5323 (3.01); 3.5149 (7.54); 3.5003 (7.63); 3.4831 (3.35); 3.3254 (35.92); 2.8943 (5.76); 2.8768 (11.43); 2.8593 (5.16); 2.6711 (0.41); 2.5245 (1.28); 2.5197 (1.92); 2.5111 (23.54); 2.5066 (47.55); 2.502 (63.08); 2.4974 (45.73); 2.493 (21.89); 2.3289 (0.4); 1.3369 (0.42); 1.2497 (0.53) |
| 20-197 | 2-fluorophenyl | 3-chloro-4-(trifluoromethyl)phenyl | CH2 | CH2 | — | H | compound No. 20-197, solvent: [DMSO], spectrometer: 399.95 MHz8.4146 (2.38); 8.4027 (4.07); 8.3911 (2.34); 8.3167 (0.44); 7.789 (11.02); 7.7688 (12.34); 7.628 (12.88); 7.5399 (2.61); 7.5357 (7.86); 7.531 (1.45); 7.5203 (11.76); 7.5168 (12.14); 7.5108 (3.43); 7.5018 (11.58); 7.4972 (7.27); 7.4921 (2.71); 7.4834 (3.6); 7.4787 (2.19); 7.442 (6.85); 7.4217 (6.14); 7.2918 (5.42); 7.2775 (7.05); 7.2748 (8.92); 7.2722 (5.9); 7.2694 (4.89); 7.2668 (6.55); 7.2587 (11.47); 7.2562 (10.44); 7.2455 (3.66); 7.243 (4.38); 7.2399 (6.85); 7.2373 (4.7); 5.7568 (0.99); 3.5576 (4.59); 3.5407 (12.22); 3.5258 (12.62); 3.5092 (5.14); 3.3247 (95.24); 2.9518 (8.05); 2.9348 (16); 2.9178 (7.16); 2.6762 (0.62); 2.6716 (0.87); 2.667 (0.64); 2.525 (2.59); 2.5202 (4.03); 2.5117 (48.63); 2.5071 (97.73); 2.5025 (129.03); 2.4979 (92); 2.4934 (42.82); 2.3339 (0.6); 2.3293 (0.84); 2.3247 (0.59); 2.0609 (0.38); 2.0415 (0.35); 1.3365 (1.13); 1.2588 (0.44); 1.2496 (1.45); 1.2341(0.43) |
| 20-198 | 2-chlorophenyl | 3-chloro-4-(trifluoromethyl)phenyl | CH2 | CH2 | — | H | compound No. 20-198, solvent: [DMSO], spectrometer: 399.95 MHz 8.511 (2.7); 8.4972 (5.09); 8.4834 (2.65); 7.7939 (10.74); 7.7737 (12.04); 7.6393 (12.77); 7.481 (5.12); 7.4777 (6.4); 7.4613 (16); 7.4582 (13.81); 7.4433 (6.45); 7.4399 (8.71); 7.4353 (6.57); 7.422 (9.46); 7.4173 (9.37); 7.4094 (0.63); 7.4023 (5.29); 7.3975 (5.65); 7.386 (5.72); 7.3822 (5.46); 7.3771 (0.59); 7.3674 (10.2); 7.3638 (10.34); 7.3494 (5.84); 7.3458 (5.37); 7.3364 (0.34); 7.32 (11.1); 7.316 (9.87); 7.3016 (6.76); 7.2969 (5.48); 5.7564 (2.31); 3.557 (4.72); 3.5405 (11.98); 3.5256 (12.19); 3.5092 (5.18); 3.3248 (43.38); 2.9506 (7.76); 2.9339 (14.95); 2.9171 (6.9); 2.6759 (0.43); 2.6712 (0.6); 2.6666 (0.43); 2.5245 (2.01); 2.5198 (3.06); 2.5112 (33.95); 2.5067 (68.05); 2.5021 (89.6); 2.4975 (64.12); 2.493 (30.2); 2.3335 (0.43); 2.3289 (0.58); 2.3244 (0.4); 1.9892 (0.64); 1.3367 (0.89); 1.2588 (0.36); 1.2497 (1.17); 1.2337 (0.35); 1.1753 (0.38) |
| 20-199 | 2-bromophenyl | 3-chloro-4-(trifluoromethyl)phenyl | CH2 | CH2 | — | H | compound No. 20-199, solvent: [DMSO], spectrometer: 399.95 MHz 8.5053 (3.04); 8.4917 (5.76); 8.4778 (3); 7.7963 (11.33); 7.776 (12.76); 7.649 (14.08); 7.6366 (9.48); 7.6343 (9.54); 7.6169 (10.81); 7.6143 (10.59); 7.4723 (7.45); 7.4521 (6.58); 7.4292 (3.88); 7.4263 (4.21); 7.4107 (10.46); 7.4077 (10.67); 7.3921 (8.46); 7.3891 (7.81); 7.3562 (6.57); 7.3515 (8.21); 7.3365 (7.91); 7.3319 (9.57); 7.3177 (4.18); 7.3131 (4.06); 7.2862 (10.86); 7.2817 (9.77); 7.2675 (8.4); 7.2632 (7.33); 5.7563 (1.63); 3.5514 (4.91); 3.5349 (12.73); 3.52 (12.94); 3.5035 (5.34); 3.3246 (50.97); 2.9529 (8.35); 2.9362 (16); 2.9194 (7.34); 2.6757 (0.47); 2.6711 (0.64); 2.6667 (0.47); 2.5242 (2.43); 2.511 (36.71); 2.5066 (72.13); 2.502 (94.54); 2.4974 (68.73); 2.493 (33.14); 2.3334 (0.44); 2.3288 (0.59); 2.3243 (0.42); 1.9891 (0.61); 1.3364 (0.95); 1.2588 (0.35); 1.2496 (1.17); 1.2339 (0.37); 1.1753 (0.35) |
| 20-200 | 2-iodophenyl | 3-chloro-4-(trifluoromethyl)phenyl | CH2 | CH2 | — | H | compound No. 20-200, solvent: [DMSO], spectrometer: 399.95 MHz 8.4788 (3.08); 8.465 (5.95); 8.4511 (3.02); 7.8692 (10.01); 7.867 (10.49); 7.8495 (10.79); 7.8472 (10.6); |

TABLE 20-continued

Compounds of the formula I-20

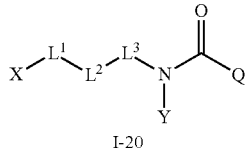

| Ex. No. | Q | X | L¹ | L² | L³ | Y | Physical data: ¹H-NMR, δ [ppm] or CAS or patent No. |
|---|---|---|---|---|---|---|---|
| | | | | | | | 7.7997 (11.51); 7.7795 (13); 7.7683 (0.59); 7.661 (13.75); 7.4828 (7.36); 7.4624 (6.49); 7.4404 (5.13); 7.4377 (5.23); 7.4217 (11.29); 7.419 (11.3); 7.4111 (0.72); 7.4029 (7.01); 7.4002 (6.74); 7.3372 (0.34); 7.2584 (0.37); 7.2206 (9.34); 7.2166 (11.24); 7.2017 (8.47); 7.1976 (8.89); 7.1715 (6.6); 7.1673 (5.81); 7.1524 (9.49); 7.1481 (8.44); 7.1332 (5.61); 7.129 (4.91); 5.7563 (1.07); 3.5381 (4.97); 3.5212 (12.89); 3.5065 (13.12); 3.4899 (5.32); 3.3242 (74.03); 2.9609 (8.14); 2.9441 (16); 2.9272 (7.24); 2.6757 (0.58); 2.6711 (0.79); 2.6665 (0.57); 2.5245 (2.67); 2.5197 (4.15); 2.5111 (44.64); 2.5066 (89.1); 2.5021 (117.31); 2.4975 (83.97); 2.4929 (39.5); 2.3335 (0.56); 2.3289 (0.76); 2.3243 (0.54); 1.3364 (1.02); 1.2588 (0.36); 1.2497 (1.31); 1.235 (0.35) |
| 20-201 | 2,6-difluorophenyl | 3-chloro-4-(trifluoromethyl)phenyl | CH2 | CH2 | — | H | compound No. 20-201, solvent: [DMSO], spectrometer: 399.95 MHz 8.7981 (2.62); 8.7842 (4.9); 8.7703 (2.59); 8.3162 (0.5); 7.7851 (10.6); 7.7649 (11.86); 7.6227 (12.51); 7.5284 (1.93); 7.5118 (4.12); 7.5073 (3.57); 7.4951 (2.73); 7.4906 (7.84); 7.4862 (2.75); 7.474 (3.73); 7.4695 (4.67); 7.4526 (2.94); 7.4453 (6.7); 7.425 (6); 7.1763 (1.56); 7.1731 (2.08); 7.1657 (13.08); 7.1464 (16); 7.1396 (2.87); 7.1364 (1.91); 7.1256 (10.89); 7.1179 (1.87); 5.7564 (0.86); 3.5647 (4.53); 3.5484 (11.52); 3.5333 (11.71); 3.517 (5); 3.3236 (106.45); 2.9342 (7.65); 2.9175 (14.63); 2.9008 (6.78); 2.68 (0.39); 2.6756 (0.78); 2.6711 (1.05); 2.6665 (0.76); 2.6619 (0.37); 2.5244 (3.34); 2.5196 (5.14); 2.5111 (57.3); 2.5066 (114.12); 2.502 (149.98); 2.4974 (107.21); 2.4929 (50.27); 2.3333 (0.69); 2.3287 (0.95); 2.3241 (0.67); 1.3362 (0.96); 1.2987 (0.38); 1.2588 (0.56); 1.2497 (1.16); −0.0002 (0.34) |
| 20-202 | 2-chloro-3-pyridyl | 3-chloro-4-(trifluoromethyl)phenyl | CH2 | CH2 | — | H | compound No. 20-202, solvent: [DMSO], spectrometer: 399.95 MHz 8.6764 (2.27); 8.6628 (4.25); 8.6489 (2.2); 8.4592 (9); 8.4543 (9.56); 8.4471 (9.62); 8.4422 (9.29); 8.3161 (0.32); 7.8006 (16); 7.796 (11.26); 7.7819 (14.57); 7.7773 (15.71); 7.6539 (10.46); 7.4938 (10.79); 7.4818 (10.64); 7.4749 (13.18); 7.4629 (10.11); 7.4516 (4.96); 3.5741 (3.92); 3.5575 (9.92); 3.5427 (10.16); 3.5262 (4.29); 3.324 (68.76); 2.9545 (6.38); 2.9377 (12.33); 2.921 (5.67); 2.676 (0.56); 2.6714 (0.75); 2.6668 (0.53); 2.5248 (2.58); 2.5201 (3.92); 2.5115 (40.93); 2.5069 (81.65); 2.5023 (107.36); 2.4977 (76.49); 2.4932 (35.59); 2.3338 (0.5); 2.3291 (0.69); 2.3245 (0.48); 1.2346 (0.4) |
| 20-203 | 2-fluorophenyl | 4-chloro-3-(trifluoromethyl)phenyl | CH2 | CH2 | — | H | compound No. 20-203, solvent: [DMSO], spectrometer: 399.95 MHz 8.3685 (1.63); 7.7254 (4.36); 7.7209 (4.58); 7.658 (2.84); 7.6374 (5.04); 7.5891 (3.01); 7.5847 (2.86); 7.5684 (1.7); 7.564 (1.64); 7.532 (0.62); 7.5274 (1.05); 7.5174 (1.91); 7.513 (3.09); 7.51 (2.64); 7.4955 (4.99); 7.477 (3.74); 7.2851 (1.85); 7.2833 (2.1); 7.2762 (0.56); 7.2683 (2.73); 7.266 (3.14); 7.2587 (2.65); 7.2491 (4.13); 7.2368 (1.71); 7.2345 (1.58); 7.2309 (2.39); 7.2285 (1.72); 5.757 (16); 4.0389 (0.72); 4.021 (0.73); 3.5404 (1.77); 3.5239 (4.69); 3.5088 (4.8); 3.4925 (1.95); 3.3274 (33.84); 2.9424 (3.57); 2.9256 (7); 2.9087 (3.17); 2.5254 (0.98); 2.512 (13.42); 2.5076 (26.45); 2.5031 (34.87); 2.4985 (25.69); 2.4941 (12.73); 1.9896 (3.14); 1.1934 (0.86); 1.1757 (1.69); 1.1578 (0.83) |
| 20-204 | 2-chlorophenyl | 4-chloro-3-(trifluoromethyl)phenyl | CH2 | CH2 | — | H | compound No. 20-204, solvent: [DMSO], spectrometer: 399.95 MHz 8.4836 (2.64); 8.47 (4.99); 8.4563 (2.63); 7.7429 (10.83); 7.7384 (11.16); 7.6669 (6.44); 7.6463 (13.48); |

TABLE 20-continued

Compounds of the formula I-20

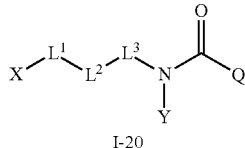

| Ex. No. | Q | X | L¹ | L² | L³ | Y | Physical data: ¹H-NMR, δ [ppm] or CAS or patent No. |
|---|---|---|---|---|---|---|---|
| | | | | | | | 7.6125 (8.02); 7.608 (7.39); 7.5919 (3.83); 7.5873 (3.65); 7.4777 (4.79); 7.4744 (5.8); 7.4578 (10.88); 7.4545 (11.62); 7.4366 (5.28); 7.4322 (5.73); 7.4186 (8.45); 7.4142 (8.5); 7.3988 (4.69); 7.3943 (4.77); 7.3759 (5.36); 7.3722 (5.16); 7.3573 (9.34); 7.3538 (9.27); 7.3391 (5.01); 7.3357 (4.61); 7.2913 (10.06); 7.287 (9.31); 7.2727 (6.85); 7.2683 (5.91); 5.7569 (0.66); 3.5417 (4.47); 3.5256 (11.31); 3.5104 (11.48); 3.4942 (4.9); 3.3263 (51.19); 2.9405 (8.51); 2.9239 (16); 2.9073 (7.56); 2.6758 (0.34); 2.6714 (0.46); 2.6669 (0.34); 2.5247 (1.68); 2.5114 (27.62); 2.5069 (54.57); 2.5023 (71.45); 2.4978 (51.6); 2.4933 (24.71); 2.3336 (0.34); 2.3292 (0.47); 2.3247 (0.33); 1.9894 (1.05); 1.337 (0.46); 1.2497 (0.59); 1.1755 (0.58); −0.0002 (0.41) |
| 20-205 | 2-bromophenyl | 4-chloro-3-(trifluoromethyl)phenyl | CH2 | CH2 | — | H | compound No. 20-205, solvent: [DMSO], spectrometer: 399.95 MHz 8.4785 (2.55); 8.4651 (4.78); 8.4512 (2.52); 8.3163 (0.61); 7.7516 (10.32); 7.7473 (10.52); 7.6699 (5.77); 7.6493 (13.08); 7.6342 (7.94); 7.6316 (8.03); 7.6195 (8.59); 7.6146 (16); 7.5991 (3.59); 7.5946 (3.38); 7.4189 (3.1); 7.416 (3.39); 7.4004 (8.62); 7.3974 (8.66); 7.3819 (6.97); 7.3788 (6.35); 7.3533 (5.57); 7.3485 (6.65); 7.3339 (6.76); 7.3292 (7.61); 7.3148 (3.34); 7.3102 (3.08); 7.2536 (8.8); 7.2491 (8.39); 7.2351 (6.96); 7.2306 (6.4); 5.7565 (0.83); 3.5341 (4.1); 3.5178 (10.62); 3.5028 (10.83); 3.4864 (4.48); 3.3234 (67.7); 2.9413 (7.99); 2.9246 (15.3); 2.9079 (7.04); 2.6797 (0.35); 2.6753 (0.64); 2.6708 (0.87); 2.6662 (0.64); 2.6618 (0.33); 2.524 (3.09); 2.5107 (49.79); 2.5063 (96.59); 2.5017 (125.64); 2.4972 (91.08); 2.4927 (44.05); 2.333 (0.6); 2.3286 (0.81); 2.324 (0.58); 1.9889 (1.1); 1.3361 (0.41); 1.2495 (0.53); 1.175 (0.6); −0.0002 (0.61) |
| 20-206 | 2-iodophenyl | 4-chloro-3-(trifluoromethyl)phenyl | CH2 | CH2 | — | H | compound No. 20-206, solvent: [DMSO], spectrometer: 399.95 MHz 7.6515 (0.34); 5.7552 (16); 3.3268 (22.23); 2.9311 (0.38); 2.5194 (0.43); 2.511 (5.17); 2.5066 (10.31); 2.502 (13.5); 2.4974 (9.68); 2.493 (4.6) |
| 20-207 | 2,6-difluorophenyl | 4-chloro-3-(trifluoromethyl)phenyl | CH2 | CH2 | — | H | compound No. 20-207, solvent: [DMSO], spectrometer: 399.95 MHz 8.7711 (2.66); 8.7576 (4.99); 8.744 (2.67); 7.7304 (11.2); 7.7259 (11.57); 7.6638 (7.27); 7.6432 (13.57); 7.5999 (7.87); 7.5954 (7.37); 7.5793 (4.25); 7.5747 (4.05); 7.53 (1.93); 7.5134 (4.14); 7.5088 (3.63); 7.4967 (2.74); 7.4922 (7.8); 7.4878 (2.84); 7.4755 (3.74); 7.4711 (4.62); 7.4545 (2.12); 7.1729 (1.5); 7.1697 (2.06); 7.1622 (12.76); 7.1429 (15.99); 7.1222 (10.82); 7.1144 (1.86); 3.5576 (4.64); 3.5418 (11.5); 3.5261 (11.46); 3.5103 (5.07); 3.336 (50.94); 2.9315 (8.91); 2.9149 (16); 2.8984 (7.89); 2.6788 (0.42); 2.5322 (1.35); 2.5188 (24.17); 2.5144 (48.32); 2.5098 (63.36); 2.5052 (45.64); 2.5007 (21.7); 2.3366 (0.39); 1.9967 (0.81); 1.3443 (0.52); 1.2569 (0.68); 1.1826 (0.45) |
| 20-208 | 2-chloro-3-pyridyl | 4-chloro-3-(trifluoromethyl)phenyl | CH2 | CH2 | — | H | compound No. 20-208, solvent: [DMSO], spectrometer: 399.95 MHz 8.6587 (2.09); 8.6452 (3.95); 8.6312 (2.08); 8.4642 (6.75); 8.4593 (7.11); 8.4521 (7.2); 8.4473 (6.94); 7.7823 (6.93); 7.7774 (7.11); 7.7634 (16); 7.7586 (15.98); 7.6796 (5.02); 7.659 (10.65); 7.6263 (6.31); 7.6219 (5.79); 7.6056 (2.96); 7.6011 (2.87); 7.4946 (7.83); 7.4825 (7.7); 7.4757 (7.03); 7.4637 (6.84); 5.7645 (2.19); 3.5661 (3.47); 3.5498 (8.9); 3.5346 |

TABLE 20-continued

Compounds of the formula I-20

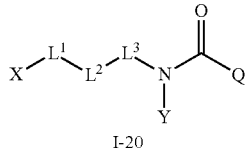

| Ex. No. | Q | X | L¹ | L² | L³ | Y | Physical data: ¹H-NMR, δ [ppm] or CAS or patent No. |
|---|---|---|---|---|---|---|---|
| | | | | | | | (9.03); 3.5184 (3.75); 3.3335 (49.48); 2.9519 (7.51); 2.9355 (12.51); 2.9188 (5.82); 2.6834 (0.33); 2.6788 (0.44); 2.6743 (0.33); 2.532 (1.66); 2.5187 (26.53); 2.5143 (51.52); 2.5097 (66.81); 2.5052 (48.07); 2.5008 (23.02); 2.3409 (0.32); 2.3366 (0.42) |
| 20-209 | 2-fluorophenyl | 4-chlorophenyl | CH2 | C(CH2CH2) | — | H | compound No. 20-209, solvent: [DMSO], spectrometer: 399.95 MHz 8.3568 (4.49); 7.4915 (0.95); 7.4869 (1.13); 7.4782 (1.06); 7.4734 (2.25); 7.4687 (1.73); 7.4661 (1.54); 7.4595 (1.54); 7.4577 (1.52); 7.4538 (2.46); 7.4477 (1.56); 7.4391 (1.28); 7.4344 (1.45); 7.4241 (1.8); 7.4197 (1.77); 7.4054 (3.52); 7.4012 (3.38); 7.3868 (1.84); 7.3828 (2); 7.3596 (0.9); 7.3533 (8.9); 7.3484 (2.99); 7.3373 (3.71); 7.3322 (14.7); 7.3261 (1.84); 7.2696 (1.72); 7.2636 (12.72); 7.2586 (3.45); 7.2472 (2.8); 7.2425 (8.07); 7.2348 (3.6); 7.2303 (3.9); 7.2279 (3.09); 7.2116 (6.94); 7.2093 (8.93); 7.1929 (2.33); 7.1901 (4.62); 3.3262 (84.15); 2.9374 (16); 2.6705 (0.33); 2.5407 (1.6); 2.5239 (0.86); 2.5191 (1.31); 2.5106 (18.22); 2.506 (37.1); 2.5014 (49.66); 2.4968 (36.13); 2.4922 (17.09); 0.8343 (2.26); 0.8267 (1.69); 0.8191 (5.43); 0.8151 (7.12); 0.8052 (4.25); 0.7937 (1.34); 0.7702 (1.45); 0.7584 (3.94); 0.7485 (6.72); 0.7373 (1.7); 0.7296 (1.91); −0.0002 (9.57) |
| 20-210 | 2-fluorophenyl | 3,5-dichlorophenyl | O | CH2 | CH2 | H | compound No. 20-210, solvent: [DMSO], spectrometer: 399.95 MHz 8.9582 (1.12); 8.9452 (2.08); 8.9318 (1.1); 7.5474 (0.75); 7.5308 (1.61); 7.5263 (1.46); 7.5139 (1.11); 7.5096 (3.06); 7.5053 (1.13); 7.4929 (1.52); 7.4885 (1.8); 7.472 (0.82); 7.1916 (0.65); 7.1884 (0.86); 7.181 (5.21); 7.1715 (4.05); 7.1672 (7.93); 7.1623 (9.59); 7.1408 (4.31); 7.1331 (0.74); 7.0575 (16); 7.0531 (14.9); 4.1665 (3.76); 4.1531 (7.87); 4.1396 (4.16); 3.6263 (2.11); 3.6128 (5.63); 3.5992 (5.41); 3.5856 (1.88); 3.3347 (320.34); 3.2913 (0.49); 2.676 (0.59); 2.6716 (0.82); 2.6671 (0.58); 2.5417 (6.89); 2.5248 (2.24); 2.5114 (47.18); 2.507 (93.86); 2.5024 (124.14); 2.4979 (91.68); 2.4935 (44.8); 2.3336 (0.6); 2.3293 (0.8); 2.3247 (0.58); −0.0002 (1.97) |
| 20-211 | 2-(trifluoromethyl)phenyl | phenyl | C(CH3)2 | CH2 | — | H | compound No. 20-211, solvent: [DMSO], spectrometer: 601.6 MHz 8.3712 (0.32); 8.3612 (0.6); 7.7448 (0.86); 7.7319 (1.03); 7.679 (0.38); 7.6665 (0.93); 7.6541 (0.61); 7.6171 (0.6); 7.6043 (0.84); 7.5916 (0.33); 7.4266 (1.45); 7.4246 (1.74); 7.4213 (0.56); 7.4125 (2.19); 7.4107 (1.98); 7.336 (1.5); 7.3327 (0.51); 7.3237 (2.15); 7.3128 (0.62); 7.31 (1.9); 7.2952 (0.87); 7.2159 (0.45); 7.2139 (0.77); 7.212 (0.45); 7.2018 (1.22); 7.1896 (0.54); 3.4473 (2.68); 3.437 (2.66); 3.3529 (192.26); 2.5419 (52.5); 2.5236 (0.43); 2.5206 (0.52); 2.5174 (0.56); 2.5087 (7.11); 2.5057 (14.84); 2.5027 (20.52); 2.4996 (14.91); 2.4966 (7); 1.3128 (16); −0.0002 (1.31) |
| 20-212 | 2-(trifluoromethyl)phenyl | 4-chlorophenyl | C(CH2CH2) | CH2 | — | H | compound No. 20-212, solvent: [DMSO], spectrometer: 601.6 MHz 8.5726 (0.34); 8.5631 (0.64); 8.5535 (0.33); 7.7481 (0.86); 7.7351 (1.04); 7.6999 (0.4); 7.6874 (0.93); 7.6749 (0.58); 7.6258 (0.57); 7.613 (0.84); 7.6003 (0.34); 7.3496 (1.07); 7.3384 (16); 3.4961 (2.13); 3.4863 (2.1); 3.3273 (54.56); 2.5406 (22.25); 2.5223 (0.38); 2.5192 (0.46); 2.516 (0.52); 2.5072 (6.3); 2.5043 (12.78); 2.5013 (17.29); 2.4983 (12.72); 2.4955 (6.06); 0.984 (0.71); 0.9763 (1.97); 0.9736 (2.04); 0.9663 (0.77); 0.7936 (0.79); 0.7863 (1.93); 0.7837 (2.02); 0.7759 (0.63); −0.0002 (0.86) |

TABLE 20-continued

Compounds of the formula I-20

$$\text{X}-\text{L}^1-\text{L}^2-\text{L}^3-\underset{\underset{Y}{|}}{N}-\overset{\overset{O}{\|}}{C}-Q$$

I-20

| Ex. No. | Q | X | L¹ | L² | L³ | Y | Physical data: ¹H-NMR, δ [ppm] or CAS or patent No. |
|---|---|---|---|---|---|---|---|
| 20-213 | 2-(trifluoro-methyl)phenyl | 2,4-dichloro-phenyl | C(CH2CH2) | CH2 | — | H | compound No. 20-213, solvent: [DMSO], spectrometer: 601.6 MHz<br>8.5397 (2.01); 8.5297 (3.92); 8.5197 (1.95); 7.7446 (4.99); 7.7316 (6.04); 7.7057 (2.3); 7.6932 (5.41); 7.6807 (3.37); 7.6269 (3.34); 7.6141 (4.85); 7.6014 (2.04); 7.5611 (13.34); 7.5576 (13.68); 7.427 (0.35); 7.4177 (8.4); 7.4039 (16); 7.3773 (11.18); 7.3737 (10.29); 7.3636 (6.12); 7.3599 (9.03); 7.3451 (5); 3.4554 (4.44); 3.4463 (4.37); 3.3233 (773.98); 3.3042 (0.59); 3.3003 (0.51); 2.6528 (0.85); 2.619 (0.68); 2.616 (1.35); 2.6129 (1.83); 2.6099 (1.33); 2.6068 (0.65); 2.5406 (279.05); 2.5222 (5.54); 2.5191 (7.02); 2.516 (7.69); 2.5073 (97.86); 2.5042 (206.44); 2.5012 (288.66); 2.4981 (208.21); 2.495 (95.86); 2.4241 (0.8); 2.3915 (0.57); 2.3884 (1.25); 2.3854 (1.71); 2.3823 (1.22); 2.3793 (0.53); 2.0736 (0.39); 1.0481 (3.83); 1.0401 (11.37); 1.0377 (12.07); 1.03 (3.95); 0.7727 (4.41); 0.7649 (10.69); 0.7626 (11.23); 0.7545 (3.63); 0.0052 (0.69); −0.0002 (20.39); −0.0057 (0.65) |
| 20-214 | 2-(trifluoro-methyl)phenyl | 4-(trifluoro-1 methyl)pheny | C(CH3)2 | CH2 | — | H | compound No. 20-214, solvent: [DMSO], spectrometer: 601.6 MHz<br>8.398 (0.37); 8.3879 (0.73); 8.3777 (0.36); 7.7345 (0.95); 7.7217 (1.13); 7.6756 (1.04); 7.6612 (4.3); 7.6502 (3.36); 7.6359 (0.95); 7.6121 (0.65); 7.5993 (0.91); 7.5867 (0.36); 7.2984 (1.03); 7.2859 (0.96); 3.5028 (2.67); 3.4924 (2.64); 3.3267 (77.64); 2.5409 (61.72); 2.5226 (0.35); 2.5195 (0.45); 2.5164 (0.48); 2.5077 (8.46); 2.5046 (18.04); 2.5016 (25.25); 2.4985 (18.22); 2.4955 (8.44); 1.3494 (16); −0.0002 (1.75) |
| 20-215 | 2-(trifluoro-methyl)phenyl | 2,5-dichloro-phenyl | C(CH3)2 | CH2 | — | H | compound No. 20-215, solvent: [DMSO], spectrometer: 601.6 MHz<br>8.3664 (0.35); 8.3563 (0.69); 8.346 (0.35); 7.7328 (0.9); 7.7199 (1.09); 7.6759 (0.4); 7.6642 (0.98); 7.6517 (0.64); 7.6113 (0.62); 7.5985 (0.88); 7.5859 (0.35); 7.4331 (2.43); 7.419 (3.37); 7.4113 (1.89); 7.4071 (2.1); 7.3454 (1.76); 7.3411 (1.53); 7.3313 (1.25); 7.3271 (1.18); 7.3117 (0.99); 7.2991 (0.92); 3.7889 (2.65); 3.7785 (2.62); 3.325 (131.07); 2.5406 (81.64); 2.5327 (0.35); 2.5223 (0.64); 2.5192 (0.8); 2.516 (0.84); 2.5073 (14.15); 2.5043 (30.1); 2.5012 (42.22); 2.4981 (30.52); 2.4951 (14.18); 1.465 (16); −0.0002 (3.13) |
| 20-216 | 2-(trifluoro-methyl)phenyl | 4-chlorophenyl | C(CH3)2 | CH2 | — | H | compound No. 20-216, solvent: [DMSO], spectrometer: 601.6 MHz<br>8.3734 (0.36); 8.3632 (0.7); 8.353 (0.35); 7.7416 (0.94); 7.7286 (1.13); 7.6847 (0.41); 7.6727 (1.01); 7.6602 (0.64); 7.6172 (0.63); 7.6044 (0.92); 7.5917 (0.36); 7.4398 (2.65); 7.4363 (0.89); 7.4288 (1.07); 7.4253 (4.02); 7.4206 (0.45); 7.3691 (0.48); 7.3645 (4.06); 7.361 (1.04); 7.3535 (0.88); 7.35 (2.75); 7.3228 (1.02); 7.3103 (0.94); 3.4388 (2.7); 3.4284 (2.67); 3.3265 (68.14); 2.5406 (55.44); 2.5192 (0.4); 2.5161 (0.42); 2.5073 (7.55); 2.5043 (15.85); 2.5012 (21.96); 2.4982 (15.84); 2.4951 (7.33); 1.3026 (16); −0.0002 (1.45) |
| 20-217 | 2-(trifluoro-methyl)phenyl | phenyl | C(CH2CH2) | CH2 | — | H | compound No. 20-217, solvent: [DMSO], spectrometer: 601.6 MHz<br>8.5501 (1.51); 8.5407 (2.84); 8.5312 (1.48); 7.7456 (4.13); 7.7326 (4.97); 7.6896 (1.84); 7.6772 (4.47); 7.6648 (2.86); 7.6206 (2.77); 7.6078 (4.01); 7.5952 (1.6); 7.3335 (7.25); 7.3312 (10.76); 7.3197 (16); 7.3179 (14.72); 7.3031 (9.87); 7.2995 (2.28); 7.2908 (10.7); 7.2803 (2.29); 7.2775 (5.07); 7.2016 (2.13); 7.1993 (3.94); 7.1968 (2.12); 7.1903 (2.23); 7.1874 (5.39); 7.1843 (1.8); 7.1778 (1.37); 7.1754 (2.43); |

TABLE 20-continued

Compounds of the formula I-20

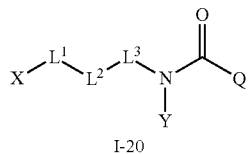

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | 7.1731 (1.23); 3.52 (11.5); 3.5103 (11.38); 3.3536 (0.4); 3.3264 (380.29); 2.6526 (0.91); 2.6157 (0.52); 2.6126 (0.73); 2.6096 (0.53); 2.5609 (0.35); 2.5402 (291.54); 2.5219 (1.7); 2.5188 (2.12); 2.5157 (2.37); 2.507 (40.83); 2.5039 (86.4); 2.5008 (119.69); 2.4978 (86.54); 2.4948 (39.49); 2.4242 (0.88); 2.3881 (0.51); 2.385 (0.7); 2.382 (0.49); 2.073 (0.43); 0.9721 (3.92); 0.9645 (10.49); 0.9616 (10.73); 0.9545 (4.36); 0.79 (4.26); 0.7829 (10); 0.78 (10.5); 0.7724 (3.39); −0.0002 (8.02) |
| 20-218 | 2(trifluoro-methyl)phenyl | 3,4-dichloro-phenyl | C(CH3)2 | CH2 | — | H | compound No. 20-218, solvent: [DMSO], spectrometer: 601.6 MHz 8.3691 (0.37); 8.3589 (0.73); 8.3486 (0.37); 7.7374 (0.99); 7.7245 (1.18); 7.6841 (0.45); 7.6721 (1.06); 7.6597 (0.7); 7.6154 (0.68); 7.602 (3.23); 7.5982 (2.56); 7.5901 (0.43); 7.5591 (2.32); 7.545 (2.82); 7.4116 (1.38); 7.4078 (1.33); 7.3975 (1.16); 7.3937 (1.14); 7.3232 (1.05); 7.3106 (0.98); 3.4588 (2.73); 3.4484 (2.65); 3.3432 (0.49); 3.3238 (270.15); 3.3093 (0.43); 3.3063 (0.36); 2.6528 (0.38); 2.616 (0.47); 2.613 (0.64); 2.6099 (0.46); 2.5406 (117.72); 2.526 (0.33); 2.5223 (1.41); 2.5191 (1.8); 2.516 (2.19); 2.5073 (35.67); 2.5042 (75.52); 2.5012 (105.59); 2.4981 (77.29); 2.4951 (35.91); 2.4243 (0.37); 2.3884 (0.46); 2.3854 (0.63); 2.3823 (0.45); 2.0124 (0.73); 1.3116 (16); −0.0002 (6.06) |
| 20-219 | 2-(trifluoro-methyl)phenyl | 2-chlorophenyl | C(CH3)2 | CH2 | — | H | compound No. 20-219, solvent: [DMSO], spectrometer: 601.6 MHz 8.36 (0.35); 8.3499 (0.66); 8.3396 (0.34); 7.735 (0.9); 7.7222 (1.07); 7.6692 (0.4); 7.657 (0.96); 7.6445 (0.64); 7.6093 (0.63); 7.5965 (0.87); 7.584 (0.34); 7.4873 (0.87); 7.4846 (0.91); 7.4741 (1.03); 7.4714 (1.03); 7.4034 (1.09); 7.4009 (1.14); 7.3904 (1.33); 7.3879 (1.35); 7.3178 (0.57); 7.3152 (0.64); 7.3095 (1.06); 7.3056 (1.16); 7.3031 (1.05); 7.2971 (0.97); 7.2926 (0.86); 7.29 (0.71); 7.2638 (0.82); 7.261 (0.85); 7.251 (0.98); 7.2484 (0.96); 7.2387 (0.48); 7.2359 (0.45); 3.7904 (2.64); 3.78 (2.6); 3.3257 (68.58); 2.5497 (0.44); 2.5403 (49.95); 2.5219 (0.49); 2.5189 (0.6); 2.5158 (0.69); 2.507 (7.76); 2.504 (16.18); 2.501 (22.25); 2.4979 (16.19); 2.4949 (7.46); 1.4689 (16); −0.0002 (1.57) |
| 20-220 | 2-(trifluoro-methyl)phenyl | 4-chlorophenyl | CH2 | C(CH3)2 | — | H | compound No. 20-220, solvent: [DMSO], spectrometer: 399.95 MHz 7.9368 (1.72); 7.7538 (1.1); 7.7341 (1.46); 7.7119 (0.5); 7.6937 (1.24); 7.675 (0.85); 7.6244 (0.83); 7.6051 (1.13); 7.5864 (0.43); 7.4031 (2.46); 7.3821 (3.57); 7.3771 (1.88); 7.3579 (1.18); 7.2511 (3.14); 7.2303 (2.46); 3.3307 (66.15); 3.1011 (5.02); 2.5018 (34.05); 1.2677 (16); −0.0002 (6.51) |
| 20-221 | 2-(trifluoro-methyl)phenyl | 2,4-dichloro-phenyl | CH2 | C(CH3)2 | — | H | compound No. 20-221, solvent: +DMSO+, spectrometer: 399.95 MHz 8.0919 (1.84); 7.7705 (1.14); 7.7508 (1.54); 7.7382 (0.58); 7.7194 (1.27); 7.7008 (0.89); 7.6437 (0.86); 7.6245 (1.19); 7.6147 (2.18); 7.6092 (2.69); 7.493 (1.36); 7.4766 (1.84); 7.472 (1.92); 7.4563 (1.56); 7.4508 (1.65); 7.3901 (2.59); 7.3692 (1.65); 3.3407 (19.92); 3.3376 (21.29); 3.3337 (19.22); 3.2928 (5.54); 2.5067 (10.36); 2.5022 (14.48); 2.4978 (11.95); 1.3016 (16); −0.0002 (3.64) |

TABLE 20-continued

Compounds of the formula I-20

$$\text{X}-\text{L}^1-\text{L}^2-\text{L}^3-\underset{\underset{Y}{|}}{N}-\overset{\overset{O}{||}}{C}-Q$$

I-20

| Ex. No. | Q | X | L¹ | L² | L³ | Y | Physical data: ¹H-NMR, δ [ppm] or CAS or patent No. |
|---|---|---|---|---|---|---|---|
| 20-222 | 2-(trifluoro-methyl)phenyl | 2,4-dichloro-phenyl | CH(OCH3) | C(CH3)2 | — | H | compound No. 20-222, solvent: [DMSO], spectrometer: 399.95 MHz 8.1249 (2.2); 7.764 (1.28); 7.7445 (1.74); 7.7363 (0.65); 7.7176 (1.44); 7.6988 (0.99); 7.6502 (2.93); 7.6476 (1.93); 7.6401 (1.04); 7.6208 (1.3); 7.6016 (0.51); 7.49 (6.37); 7.4872 (7.02); 7.4623 (1.33); 5.4093 (5.45); 3.3212 (16.96); 3.1073 (16); 2.5239 (0.89); 2.5107 (14.77); 2.5062 (28.86); 2.5016 (37.95); 2.4971 (27.67); 2.4926 (13.24); 1.3357 (1.68); 1.2982 (0.38); 1.2644 (9.79); 1.2466 (9.7); −0.0002 (4.05) |
| 20-223 | 2-(trifluoro-methyl)phenyl | 2-(trifluoro-methyl)-4-chlorophenyl | CH2 | CH2 | — | H | compound No. 20-223, solvent: [DMSO], spectrometer: 399.95 MHz 8.6914 (2.57); 8.6774 (5.02); 8.6632 (2.54); 8.3162 (0.96); 7.7842 (6.26); 7.7648 (15.96); 7.7599 (16); 7.7409 (3.28); 7.7345 (7.1); 7.7279 (6); 7.7238 (7.51); 7.705 (5.09); 7.6609 (4.87); 7.6418 (6.27); 7.6228 (2.37); 7.5787 (8.93); 7.5583 (7.28); 7.4849 (7.39); 7.4661 (6.34); 7.3367 (0.42); 7.3321 (0.37); 7.1813 (0.58); 7.1758 (0.39); 3.5065 (3.67); 3.4895 (7.83); 3.4734 (7.66); 3.4557 (4.14); 3.3226 (200.35); 2.9985 (5.53); 2.9806 (9.48); 2.9626 (4.7); 2.6799 (0.64); 2.6754 (1.37); 2.6709 (1.86); 2.6663 (1.32); 2.6617 (0.6); 2.5243 (5.39); 2.5195 (8.41); 2.5109 (101.48); 2.5064 (204.34); 2.5018 (270.53); 2.4972 (194.79); 2.4926 (91.36); 2.3377 (0.65); 2.3331 (1.33); 2.3286 (1.82); 2.324 (1.3); 2.3195 (0.59); 1.3515 (0.41); 1.3358 (6.85); 1.2983 (0.59); 1.2586 (1.06); 1.2495 (8.87); 1.2348 (1.2); 1.1873 (0.53); 0.008 (2.54); −0.0002 (78.69); −0.0085 (2.37) |
| 20-224 | 2-(trifluoro-methyl)phenyl | 4-chlorophenyl | N(CH3) | CH2 | CH2 | H | compound No. 20-224, solvent: [DMSO], spectrometer: 399.95 MHz 8.5833 (0.65); 8.5693 (1.25); 8.5555 (0.67); 7.7815 (1.35); 7.7631 (1.8); 7.7603 (1.63); 7.6881 (0.5); 7.6712 (1.49); 7.6537 (1.97); 7.6498 (2.18); 7.6302 (1.38); 7.6115 (0.45); 7.3078 (1.6); 7.2903 (1.45); 7.2094 (0.44); 7.2006 (4.34); 7.1954 (1.41); 7.183 (1.61); 7.1779 (4.71); 7.169 (0.5); 6.7781 (0.53); 6.7694 (4.55); 6.7642 (1.52); 6.7467 (4.06); 6.738 (0.44); 3.4883 (1.08); 3.4717 (2.81); 3.4556 (2.25); 3.3963 (1.23); 3.3815 (2.43); 3.3657 (1.97); 3.3495 (0.75); 3.3265 (39.84); 2.9281 (16); 2.5409 (17.33); 2.5058 (24.19); 2.5014 (30.73); 2.497 (22.57); −0.0002 (4.72) |
| 20-225 | 2-(trifluoro-methyl)phenyl | 3,5-dichloro-phenyl | O | CH2 | CH2 | H | compound No. 20-225, solvent: [DMSO], spectrometer: 399.95 MHz 8.7362 (1.45); 8.7229 (2.72); 8.7094 (1.45); 7.7839 (3.37); 7.7645 (4.5); 7.7373 (1.5); 7.7189 (3.82); 7.7004 (2.86); 7.6614 (2.7); 7.6425 (3.42); 7.6235 (1.26); 7.5073 (4.07); 7.4886 (3.43); 7.1703 (3.45); 7.1663 (6.46); 7.1622 (3.93); 7.0563 (16); 7.0519 (14.71); 4.1638 (4.37); 4.1501 (9.22); 4.1365 (4.76); 3.6059 (2.44); 3.5922 (6.57); 3.5784 (6.33); 3.5647 (2.19); 3.3284 (64.9); 2.9286 (0.36); 2.5415 (31.56); 2.5066 (38.19); 2.5022 (49.01); 2.4979 (36.35); −0.0003 (6.28) |
| 20-226 | 2-(trifluoro-methyl)phenyl | 3-(trifluoro-l methyl)pheny | O | CH2 | CH(CH2CH3) | H | compound No. 20-226, solvent: [DMSO], spectrometer: 399.95 MHz 8.5298 (2.87); 8.5092 (2.91); 7.7838 (3.39); 7.7644 (4.53); 7.7343 (1.49); 7.7159 (3.75); 7.6973 (2.79); 7.6765 (0.4); 7.6571 (2.91); 7.6379 (3.45); 7.6189 (1.29); 7.5597 (1.81); 7.5401 (4.09); 7.5203 (2.56); 7.4809 (3.98); 7.4623 (3.43); 7.3549 (0.53); 7.3351 (0.96); 7.3087 (3.63); 7.2888 (5.95); 7.2576 (5.29); 4.2022 (0.69); 4.1888 (1.09); 4.1811 (1.4); 4.168 (1.63); |

TABLE 20-continued

Compounds of the formula I-20

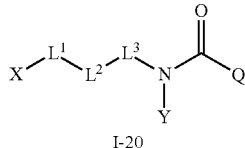

I-20

| Ex. No. | Q | X | L¹ | L² | L³ | Y | Physical data: $^1$H-NMR, δ [ppm] or CAS or patent No. |
|---|---|---|---|---|---|---|---|
| | | | | | | | 4.1569 (1.08); 4.1463 (0.84); 4.1336 (0.43); 4.0839 (9.92); 4.0701 (5.47); 3.3269 (88.33); 2.6755 (0.44); 2.6711 (0.57); 2.5413 (23.4); 2.5065 (69.88); 2.5022 (86.63); 2.4979 (62.85); 2.3291 (0.56); 1.7584 (0.45); 1.7518 (0.82); 1.7395 (1.11); 1.7332 (1.06); 1.7197 (1.56); 1.7052 (1.39); 1.6991 (1.37); 1.6869 (1.23); 1.67 (0.49); 1.5914 (1.16); 1.5725 (1.64); 1.5563 (1.32); 1.5512 (1.47); 1.5379 (1.17); 1.5349 (1.16); 1.5167 (0.82); 0.9882 (7.77); 0.9697 (16); 0.9512 (6.94); 0.0077 (0.75); −0.0003 (13.51); −0.0085 (0.57) |
| 20-227 | 2-(trifluoro-methyl)phenyl | 2,4-dichloro-phenyl | CH(CH3) | CH2 | — | H | compound No. 20-227, solvent: [DMSO], spectrometer: 399.95 MHz 8.4853 (2.14); 8.4642 (2.18); 7.7612 (2.61); 7.7416 (3.53); 7.7244 (1.2); 7.7067 (3); 7.688 (2.06); 7.6415 (2.07); 7.6223 (2.75); 7.6 (4.88); 7.5965 (5.78); 7.5942 (4.18); 7.4248 (0.48); 7.4039 (10.2); 7.4002 (16); 7.3813 (0.44); 7.3189 (3.06); 7.3001 (2.79); 4.3174 (0.49); 4.2979 (1.12); 4.281 (1.55); 4.2641 (1.05); 4.2605 (1.04); 4.244 (0.54); 3.3971 (0.45); 3.3372 (602.52); 3.2859 (0.46); 2.8992 (0.5); 2.8798 (5.86); 2.8648 (3.94); 2.8588 (3.89); 2.8242 (0.4); 2.6805 (0.35); 2.6759 (0.71); 2.6713 (0.96); 2.6668 (0.7); 2.6622 (0.32); 2.5416 (10.43); 2.5247 (3.11); 2.5199 (4.94); 2.5114 (56.02); 2.5069 (112.43); 2.5023 (148.76); 2.4976 (107.69); 2.4931 (51.38); 2.3382 (0.36); 2.3336 (0.7); 2.329 (0.99); 2.3244 (0.71); 2.3198 (0.33); 1.2348 (0.6); 1.1724 (12.85); 1.1558 (12.71); −0.0002 (4.01) |
| 20-228 | 2-(trifluoro-methyl)phenyl | 3-chloro-4-(trifluoromethyl)phenyl | CH2 | CH2 | — | H | compound No. 20-228, solvent: [DMSO], spectrometer: 399.95 MHz 8.5891 (2.45); 8.5752 (4.67); 8.5614 (2.39); 7.7985 (9.5); 7.7888 (0.77); 7.7782 (10.87); 7.7678 (6.38); 7.7484 (7.98); 7.7206 (2.63); 7.7032 (6.75); 7.6846 (4.92); 7.6465 (5.02); 7.6299 (16); 7.609 (2.33); 7.4544 (6.04); 7.4339 (5.36); 7.4104 (7.08); 7.3916 (6.21); 3.5542 (4.1); 3.5374 (10.69); 3.5227 (11.02); 3.506 (4.48); 3.3252 (57.49); 2.9335 (7.06); 2.9165 (13.45); 2.8996 (5.99); 2.6761 (0.47); 2.6715 (0.66); 2.6671 (0.48); 2.5248 (2.16); 2.52 (3.39); 2.5115 (36.96); 2.507 (73.51); 2.5024 (96.47); 2.4978 (68.87); 2.4933 (32.15); 2.3338 (0.44); 2.3292 (0.62); 2.3246 (0.44); 1.3368 (0.88); 1.2498 (1.13) |
| 20-229 | 2-(trifluoro-methyl)phenyl | 4-chloro-3-(trifluoromethyl)phenyl | CH2 | CH2 | — | H | compound No. 20-229, solvent: [DMSO], spectrometer: 399.95 MHz 8.563 (2.85); 8.5494 (5.31); 8.5357 (2.82); 7.771 (6.58); 7.7519 (8.96); 7.7372 (11.25); 7.7328 (11.48); 7.717 (3); 7.6985 (7.47); 7.6779 (11.46); 7.6567 (13.84); 7.6314 (6.82); 7.612 (10.03); 7.5913 (4.29); 7.5869 (4.01); 7.39 (7.76); 7.3713 (6.84); 4.0461 (0.61); 4.0283 (0.62); 3.5475 (4.43); 3.5313 (11.3); 3.5162 (11.58); 3.4999 (4.76); 3.3358 (53.12); 2.9316 (8.47); 2.9149 (16); 2.8982 (7.46); 2.6835 (0.33); 2.679 (0.43); 2.6743 (0.32); 2.5187 (26.92); 2.5144 (50.62); 2.5099 (64.69); 2.5054 (47.17); 2.501 (23.38); 2.3367 (0.4); 1.9967 (2.65); 1.3446 (0.4); 1.257 (0.49); 1.2004 (0.71); 1.1826 (1.4); 1.1648 (0.7) |
| 20-230 | 2-(trifluoro-methyl)phenyl | 4-chlorophenyl | CH2 | C(CH2CH2) | — | H | compound No. 20-230, solvent: [DMSO], spectrometer: 399.95 MHz 8.5652 (5.62); 7.7355 (3.21); 7.7164 (4.32); 7.6865 (1.39); 7.669 (3.7); 7.6504 (2.69); 7.615 (2.65); 7.596 (3.34); 7.5772 (1.22); 7.3902 (0.99); 7.3839 (9.03); 7.3791 (3.04); 7.3679 (3.89); 7.3628 (15.2); 7.3568 (1.9); 7.3091 (4.09); 7.3039 (2.52); 7.2973 (13.55); 7.2921 (6.67); 7.281 (2.94); 7.2762 (8.08); 7.2701 |

TABLE 20-continued

Compounds of the formula I-20

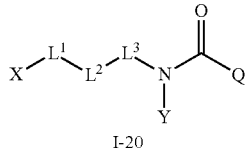

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (0.88); 3.3298 (191); 2.995 (0.59); 2.9457 (16); 2.7109 (0.38); 2.6752 (0.35); 2.6706 (0.47); 2.666 (0.34); 2.5559 (0.52); 2.5408 (100.84); 2.5239 (1.26); 2.5192 (1.98); 2.5106 (26.19); 2.5061 (52.97); 2.5015 (70.49); 2.4968 (51.18); 2.4923 (24.26); 2.3672 (0.37); 2.3329 (0.33); 2.3282 (0.45); 2.3237 (0.32); 0.8257 (2.44); 0.8117 (6); 0.8071 (7.57); 0.7966 (3.93); 0.7684 (0.75); 0.7592 (0.8); 0.7306 (3.69); 0.7202 (7.06); 0.7161 (5.97); 0.7019 (2.04); −0.0002 (6.65) |
| 20-231 | 2-(trifluoro-methyl)-3-pyridyl | 4-chlorophenyl | CH2 | C(CH3)2 | — | H | compound No. 20-231, solvent: [DMSO], spectrometer: 399.95 MHz 8.7694 (1.07); 8.7602 (1.08); 8.758 (1.07); 8.1082 (1.71); 7.8409 (0.74); 7.8382 (0.78); 7.8214 (1.37); 7.8188 (1.33); 7.7767 (1.19); 7.765 (1.16); 7.7572 (0.72); 7.7455 (0.69); 7.4141 (2.75); 7.4098 (1.04); 7.3932 (3.59); 7.3872 (0.58); 7.2526 (3.35); 7.2316 (2.64); 5.7581 (0.99); 3.3252 (8.95); 3.0943 (4.98); 2.5102 (5.82); 2.5059 (11.23); 2.5014 (14.52); 2.4969 (10.79.3); 2.4927 (5.5); 1.9891 (0.54); 1.276 (16); 1.2493 (0.34) |
| 20-232 | 2-(trifluoro-methyl)-3-pyridyl | 4-chloro-2-(trifluoromethyl)phenyl | CH2 | CH2 | — | H | compound No. 20-232, solvent: [DMSO], spectrometer 399.95 MHz 8.8531 (3.08); 8.8392 (5.92); 8.8252 (3.06); 8.8018 (7.54); 8.7922 (7.33); 8.7902 (7.33); 7.9764 (6.39); 7.9742 (6.69); 7.957 (7.98); 7.9548 (7.94); 7.8018 (7.11); 7.79 (7.1); 7.7822 (6.23); 7.7704 (14.82); 7.7655 (16); 7.7598 (8.64); 7.7387 (7.55); 7.7336 (5.8); 7.5891 (10.13); 7.5686 (8.13); 5.759 (0.48); 3.5306 (4.19); 3.5137 (9.15); 3.497 (8.93); 3.4797 (4.64); 3.3277 (69.59); 3.0051 (6.41); 2.987 (11.03); 2.9688 (5.52); 2.6768 (0.46); 2.6724 (0.61); 2.6678 (0.47); 2.5425 (0.41); 2.5255 (2.03); 2.5122 (35.54); 2.5078 (69.77); 2.5033 (90.89); 2.4987 (66.12); 2.4943 (31.84); 2.3345 (0.41); 2.33 (0.56); 2.3253 (0.43); 1.337 (0.57); 1.2498 (0.71); −0.0002 (1.27) |
| 20-233 | 2-(trifluoro-methyl)-3-pyridyl | 4-chloro-3-(trifluoromethyl)phenyl | CH2 | CH2 | — | H | compound No. 20-233, solvent: [DMSO], spectrometer: 399.95 MHz-8.7846 (2.79); 8.7752 (2.72); 8.773 (2.72); 8.7089 (1.13); 8.6954 (2.15); 8.6817 (1.12); 8.1021 (0.88); 8.0861 (0.88); 7.8913 (2.26); 7.8888 (2.35); 7.8718 (3.2); 7.8693 (3.13); 7.7774 (2.92); 7.7657 (2.9); 7.7579 (2.22); 7.7458 (2.58); 7.7393 (4.5); 7.7349 (4.57); 7.6744 (2.78); 7.6539 (5.25); 7.6117 (3.14); 7.6073 (2.9); 7.591 (1.66); 7.5866 (1.56); 6.5865 (1.27); 6.5826 (0.93); 6.5741 (0.92); 6.5702 (1.22); 3.5655 (1.77); 3.5492 (4.57); 3.5341 (4.64); 3.5178 (1.91); 3.3285 (14.34); 2.9429 (16); 2.9273 (3.41); 2.9106 (6.49); 2.8938 (3.01); 2.5252 (0.74); 2.5119 (12.14); 2.5076 (23.36); 2.503 (30.16); 2.4985 (21.74); 2.4941 (10.4); −0.0002 (0.4) |
| 20-234 | 2-(trifluoro-methyl)-3-pyridyl | 4-chlorophenyl | CF2 | CH2 | — | H | compound No. 20-234, solvent: [DMSO], spectrometer: 399.95 MHz 9.1568 (1.26); 9.1415 (2.53); 9.1262 (1.29); 8.8004 (2.96); 8.7906 (3.04); 7.878 (2.33); 7.8604 (3.54); 7.8586 (3.51); 7.7917 (2.96); 7.7799 (2.93); 7.7721 (2.12); 7.7603 (1.97); 7.6316 (1.83); 7.6248 (1); 7.6088 (16); 7.6025 (15.63); 7.5862 (1.13); 7.5797 (1.96); 5.7586 (0.72); 4.0976 (1.51); 4.0819 (1.53); 4.0613 (3.39); 4.0457 (3.31); 4.0249 (1.73); 4.0092 (1.64); 3.3248 (11.06); 2.9419 (0.37); 2.5066 (34.87); 2.5022 (44.93); 2.4978 (33.89); 0.9823 (0.33); −0.0002 (0.52) |
| 20-235 | 2-(trifluoro-methyl)-3-pyridyl | 2,4-dichloro-phenyl | CF2 | CH2 | — | H | compound No. 20-235, solvent: [DMSO], spectrometer: 399.95 MHz 9.1615 (2.9); 9.1459 (5.94); 9.1304 (2.87); 8.7983 (6.21); 8.7958 (6.6); 8.7866 (6.48); 8.7841 (6.4); 7.8585 (4.84); 7.8557 (5.09); 7.839 (8.35); 7.8361 (7.99); |

TABLE 20-continued

Compounds of the formula I-20

$$X-L^1-L^2-L^3-N(Y)-C(=O)-Q$$

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | 7.8161 (9.79); 7.8113 (9.98); 7.7864 (7.68); 7.7747 (7.34); 7.7668 (4.74); 7.7551 (4.58); 7.6722 (9.17); 7.6508 (16); 7.6007 (8.69); 7.5956 (8.14); 7.5794 (4.98); 7.5743 (4.82); 5.7582 (5.57); 4.2439 (3.38); 4.2282 (3.39); 4.2081 (7.66); 4.1924 (7.38); 4.1723 (3.82); 4.1566 (3.58); 4.0384 (0.32); 4.0205 (0.32); 3.3245 (59.16); 2.9421 (0.8); 2.6758 (0.57); 2.6713 (0.78); 2.6667 (0.56); 2.5245 (2.5); 2.5112 (43.34); 2.5068 (85.25); 2.5022 (110.8); 2.4976 (79.2); 2.4931 (37.2); 2.3335 (0.52); 2.3289 (0.71); 2.3244 (0.52); 1.9894 (1.37); 1.3365 (2.06); 1.299 (0.35); 1.2585 (0.57); 1.2495 (2.55); 1.1927 (0.4); 1.1749 (0.77); 1.1571 (0.39); 0.008 (1.89); −0.0002 (51.72); −0.0085 (1.64) |
| 20-236 | 2-(trifluoro-methyl)-3-pyridyl | 2,4,6-trichloro-phenyl | O | CH2 | CH2 | H | compound No. 20-236, solvent: [DMSO], spectrometer: 399.95 MHz 9.002 (0.67); 8.9879 (1.3); 8.9738 (0.66); 8.813 (1.53); 8.8107 (1.62); 8.8013 (1.58); 8.7989 (1.58); 8.0057 (1.4); 8.0032 (1.46); 7.9861 (1.75); 7.9837 (1.72); 7.8167 (1.59); 7.8048 (1.57); 7.7971 (1.35); 7.7853 (1.31); 7.7326 (16); 4.1203 (2.18); 4.1058 (5.08); 4.0914 (2.43); 3.6957 (1.19); 3.6813 (3.34); 3.6669 (3.17); 3.6523 (1); 3.3249 (10.68); 2.5251 (0.52); 2.5117 (9.36); 2.5072 (18.53); 2.5027 (24.22); 2.4981 (17.33); 2.4935 (8.18); 0.008 (0.75); −0.0002 (19.25); −0.0085 (0.59) |
| 20-237 | 2-(trifluoro-methyl)-3-pyridyl | 4-chloro-2-(trifluoromethyl)phenyl | O | CH2 | CH2 | H | compound No. 20-237, solvent: [DMSO], spectrometer: 399.95 MHz 8.8759 (2.53); 8.8628 (4.86); 8.8499 (2.49); 8.8057 (5.7); 8.8034 (6.06); 8.794 (5.88); 8.7917 (5.91); 7.9456 (5.03); 7.943 (5.28); 7.926 (6.75); 7.9235 (6.66); 7.8088 (6.17); 7.797 (6.09); 7.7892 (4.86); 7.7774 (4.67); 7.7296 (4.12); 7.7231 (5.12); 7.7074 (4.35); 7.7008 (6.13); 7.6744 (11.57); 7.6679 (8.54); 7.3672 (8.6); 7.3448 (7.62); 5.7591 (1.35); 4.2772 (7.46); 4.2633 (16); 4.2494 (7.94); 3.6517 (4.17); 3.638 (11.48); 3.6241 (11); 3.6102 (3.67); 3.3267 (34.02); 2.6769 (0.34); 2.6722 (0.47); 2.6677 (0.34); 2.5256 (1.52); 2.5122 (26.37); 2.5077 (52.34); 2.5032 (68.41); 2.4986 (49.1); 2.4941 (23.23); 2.3345 (0.33); 2.3299 (0.43); 1.3375 (0.35); 1.2498 (0.48); 1.2349 (0.36); 0.008 (2.37); −0.0002 (60.82); −0.0085 (1.92) |
| 20-238 | 2-(trifluoro-methyl)-3-pyridyl | 4-chloro-2-(trifluoromethyl)phenyl | O | CH2 | C(CH3)2 | H | ¹H-NMR (d6-DMSO): δ [ppm], 8.95 (t, 1H, NH), 8.80-8.79 (d, 1H), 7.99-7.97 (d, 1H), 7.84 (s, 1H), 7.80-7.77 (dd, 1H), 7.72-7.69 (d, 1H), 7.40-7.38 (d, 1H), 4.30 (t, 2H), 3.70-3.67 (quart, 2H). |
| 20-239 | 2-(trifluoro-methyl)-3-pyridyl | 2-chloro-4-(trifluoromethyl)phenyl | O | CH2 | CH2 | H | compound No. 20-239, solvent: [DMSO], spectrometer: 399.95 MHz-8.951 (0.32); 8.9377 (0.62); 8.8036 (0.77); 8.794 (0.76); 8.792 (0.76); 7.9955 (0.67); 7.9934 (0.7); 7.9761 (0.83); 7.9739 (0.82); 7.8492 (1.11); 7.8441 (1.18); 7.804 (0.73); 7.7921 (0.73); 7.7845 (0.63); 7.7726 (0.6); 7.7181 (0.55); 7.7137 (0.53); 7.6963 (0.64); 7.692 (0.59); 7.4025 (1.02); 7.3808 (0.9); 5.7574 (16); 4.3186 (0.92); 4.305 (1.94); 4.2914 (0.99); 4.0391 (0.42); 4.0213 (0.43); 3.7078 (0.52); 3.6942 (1.4); 3.6805 (1.35); 3.6669 (0.46); 3.3318 (21.81); 2.5123 (4.13); 2.508 (8.08); 2.5035 (10.5); 2.499 (7.65); 2.4947 (3.74); 1.99 (1.83); 1.1935 (0.5); 1.1757 (1); 1.1579 (0.49); −0.0002 (3.87) |
| 20-240 | 2-(trifluoro-methyl)-3-pyridyl | 2-chloro-4-(trifluoromethyl)phenyl | O | CH2 | C(CH3)2 | H | compound No. 20-240, solvent: [DMSO], spectrometer: 399.95 MHz 8.7725 (0.93); 8.7632 (0.91); 8.7611 (0.92); 8.5433 (1.63); 7.8661 (0.81); 7.8558 (1.46); 7.8503 (2.44); 7.7737 (0.97); 7.7619 (0.94); 7.7542 (0.69); 7.7423 |

TABLE 20-continued

Compounds of the formula I-20

$$X-L^1-L^2-L^3-N(Y)-C(=O)-Q$$

I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | (0.66); 7.71 (0.67); 7.7057 (0.66); 7.6883 (0.76); 7.6839 (0.73); 7.3506 (1.22); 7.3289 (1.11); 4.3551 (4.79); 3.3246 (8.95); 2.5247 (0.34); 2.5114 (6.89); 2.507 (13.73); 2.5024 (18.07); 2.4979 (13.26); 2.4935 (6.54); 1.9896 (0.35); 1.4658 (16); −0.0002 (7.67) |
| 20-241 | 2-(trifluoromethyl)-3-pyridyl | 2-chloro-4-4-chlorophenyl | CH2 | C(CH3)2 | — | H | |
| 20-242 | 2-chloro-4-(trifluoromethyl)-3-pyridyl | 4-chloro-2-(trifluoromethyl)phenyl | CH2 | CH2 | — | H | compound No. 20-242, solvent: [DMSO], spectrometer: 399.95 MHz 9.0439 (3.42); 9.0299 (6.6); 9.0159 (3.34); 8.7506 (11.17); 8.7495 (10.82); 8.7376 (11.57); 7.8965 (16); 7.8835 (15.34); 7.8399 (0.45); 7.8355 (0.41); 7.7725 (11.36); 7.7671 (15.91); 7.7537 (7.12); 7.7483 (4.17); 7.733 (8.46); 7.7276 (6.72); 7.6197 (11.83); 7.5989 (8.77); 7.3152 (0.34); 5.7588 (3.52); 3.8307 (1.77); 3.5599 (4.64); 3.5435 (8.9); 3.523 (8.82); 3.5078 (5.19); 3.3256 (75.52); 3.0172 (7.11); 2.9983 (11.12); 2.9798 (6.09); 2.6812 (0.33); 2.6768 (0.62); 2.6723 (0.84); 2.6678 (0.6); 2.5256 (2.62); 2.5122 (46.03); 2.5078 (90.6); 2.5032 (117.63); 2.4987 (84.07); 2.4942 (39.46); 2.3347 (0.54); 2.33 (0.74); 2.3253 (0.52); 2.1844 (0.74); 1.3367 (2.34); 1.2993 (0.89); 1.2589 (1.31); 1.2497 (2.77); 1.2339 (0.41); 1.1382 (5.8); 0.008 (1.9); −0.0002 (53.16); −0.0085 (1.59) |
| 20-243 | 2-chloro-4-(trifluoromethyl)-3-pyridyl | 4-chloro-3-(trifluoromethyl)phenyl | CH2 | CH2 | — | H | compound No. 20-243, solvent: [DMSO], spectrometer: 399.95 MHz 8.8583 (3); 8.8447 (5.73); 8.8309 (2.98); 8.7221 (10); 8.7208 (9.89); 8.7092 (10.38); 7.8632 (14.23); 7.8502 (13.59); 7.748 (11.74); 7.7439 (11.97); 7.6725 (5.96); 7.6518 (16); 7.6307 (9.56); 7.6262 (8.74); 7.6099 (3.56); 7.6054 (3.5); 5.7588 (0.85); 3.6159 (4.32); 3.5997 (11.07); 3.5845 (11.29); 3.5683 (4.65); 3.3266 (40.13); 2.9408 (8.41); 2.9241 (15.96); 2.9074 (7.58); 2.6766 (0.39); 2.6721 (0.52); 2.6675 (0.38); 2.5255 (1.76); 2.5206 (2.85); 2.5121 (29.87); 2.5077 (58.63); 2.5031 (76.27); 2.4986 (55.17); 2.4941 (26.47); 2.3344 (0.36); 2.3298 (0.5); 2.3254 (0.36); 2.1873 (0.58); 1.3371 (1.8); 1.2995 (0.61); 1.2589 (0.9); 1.2498 (2.23); 0.008 (1.46); −0.0002 (37.48); −0.0085 (1.27) |
| 20-244 | 2-chloro-4-(trifluoromethyl)-3-pyridyl | 4-chlorophenyl | CF2 | CH2 | — | H | compound No. 20-244, solvent: [DMSO], spectrometer: 399.95 MHz-9.2553 (1.9); 9.24 (3.77); 9.2246 (1.84); 8.737 (5.97); 8.7359 (5.97); 8.724 (6.15); 7.8753 (8.49); 7.8623 (8.16); 7.6489 (6.1); 7.627 (16); 7.6018 (15.49); 7.58 (5.73); 5.758 (0.43); 4.1597 (2.23); 4.1442 (2.25); 4.1229 (4.63); 4.1073 (4.43); 4.0859 (2.57); 4.0703 (2.41); 4.0558 (0.64); 4.038 (1.71); 4.0202 (1.73); 4.0024 (0.58); 3.3245 (78.05); 2.6755 (0.53); 2.671 (0.69); 2.6665 (0.5); 2.5242 (2.31); 2.5109 (38.2); 2.5064 (75.12); 2.5019 (97.93); 2.4973 (70.45); 2.4929 (33.55); 2.3331 (0.46); 2.3286 (0.62); 2.3242 (0.45); 2.1846 (0.94); 1.9891 (7.45); 1.3361 (3.24); 1.2583 (0.49); 1.2493 (3.95); 1.2369 (0.63); 1.1925 (2.08); 1.1876 (0.4); 1.1747 (4.01); 1.1569 (1.97); 0.9926 (0.45); 0.0079 (0.51); −0.0002 (13.56); −0.0085 (0.43) |
| 20-245 | 2-chloro-4-(trifluoromethyl)- | 2,4-dichlorophenyl | CF2 | CH2 | — | H | compound No. 20-245, solvent: [DMSO], spectrometer: 399.95 MHz 9.296 (1.59); 9.2805 (3.23); 9.2648 (1.54); 8.738 (4.86); |

TABLE 20-continued

Compounds of the formula I-20

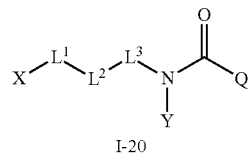

I-20

| Ex. No. | Q | X | L¹ | L² | L³ | Y | Physical data: ¹H-NMR, δ [ppm] or CAS or patent No. |
|---|---|---|---|---|---|---|---|
| | 3-pyridyl | | | | | | 8.7253 (4.97); 7.877 (6.65); 7.8639 (6.36); 7.8307 (5.02); 7.8262 (5.22); 7.6706 (4.09); 7.6492 (7.88); 7.634 (0.38); 7.6094 (4.6); 7.6045 (4.31); 7.5882 (2.31); 7.5832 (2.42); 5.7581 (16); 4.2989 (1.42); 4.2834 (1.49); 4.2623 (3.08); 4.2468 (2.95); 4.2254 (1.67); 4.2099 (1.53); 3.3238 (28.88); 2.6713 (0.43); 2.5107 (24.71); 2.5067 (47.79); 2.5023 (62.23); 2.4978 (45.78); 2.3289 (0.4); 1.9894 (0.67); 1.3362 (2.24); 1.2585 (0.36); 1.2494 (2.58); 1.2349 (0.55); 1.175 (0.39); −0.0002 (7.82) |
| 20-246 | 2-chloro-4-(trifluoromethyl)-3-pyridyl | 2,4,6-trichlorophenyl | O | CH2 | CH2 | H | compound No. 20-246, solvent: [DMSO], spectrometer: 399.95 MHz 9.1761 (0.71); 9.162 (1.4); 9.1478 (0.71); 8.7505 (2.33); 8.7375 (2.42); 7.8959 (3.19); 7.8828 (3.04); 7.7277 (16); 5.7583 (0.34); 4.1267 (2.03); 4.1121 (4.62); 4.0977 (2.29); 3.7314 (1.21); 3.717 (3.34); 3.7024 (3.16); 3.6878 (1.01); 3.3239 (19.86); 2.5246 (0.72); 2.5113 (13.49); 2.507 (26.19); 2.5025 (33.73); 2.4979 (24.58); 2.4939 (11.99); 1.3365 (1.36); 1.2494 (1.49); 1.1877 (0.53); −0.0002 (2.48) |
| 20-247 | 2-chloro-4-(trifluoromethyl)-3-pyridyl | 4-chloro-2-(trifluoromethyl)phenyl | O | CH2 | CH2 | H | |
| 20-248 | 2-chloro-4-(trifluoromethyl)-3-pyridyl | 4-chloro-2-(trifluoromethyl)phenyl | O | CH2 | C(CH3)2 | H | |
| 20-249 | 2-chloro-4-(trifluoromethyl)-3-pyridyl | 2-chloro-4-(trifluoromethyl)phenyl | O | CH2 | CH2 | H | compound No. 20-249, solvent: [DMSO], spectrometer: 399.95 MHz 9.1561 (2.95); 9.1428 (5.74); 9.1293 (2.89); 8.7423 (9.88); 8.7408 (9.79); 8.7293 (10.29); 8.728 (9.87); 7.883 (14.27); 7.8699 (13.68); 7.8473 (10.44); 7.8425 (11.06); 7.7127 (5.05); 7.7114 (5.1); 7.7071 (4.88); 7.6895 (5.91); 7.6853 (5.46); 7.4022 (9.47); 7.3805 (8.35); 6.6413 (0.41); 5.758 (1.17); 4.3178 (8.21); 4.3048 (16); 4.2917 (8.67); 4.0387 (0.39); 4.0209 (0.39); 3.7313 (4.78); 3.7181 (12.19); 3.7048 (11.71); 3.6915 (4.23); 3.3765 (0.49); 3.3332 (368.95); 3.2977 (0.43); 2.6814 (0.32); 2.6768 (0.65); 2.6723 (0.9); 2.6677 (0.64); 2.5256 (2.85); 2.5208 (4.54); 2.5123 (51.37); 2.5078 (102.09); 2.5032 (133.15); 2.4986 (95.12); 2.4941 (44.46); 2.3346 (0.62); 2.3299 (0.84); 2.3254 (0.59); 1.9898 (1.69); 1.3366 (2.06); 1.3138 (0.43); 1.2586 (0.45); 1.2496 (2.41); 1.2356 (0.78); 1.1931 (0.53); 1.1753 (0.96); 1.1575 (0.48); −0.0002 (7.41) |
| 20-250 | 2-chloro-4-(trifluoromethyl)-3-pyridyl | 2-chloro-4-(trifluoromethyl)phenyl | O | CH2 | C(CH3)2 | H | |
| 20-251 | 2-chloro-4-(trifluoromethyl)-5-pyridyl | 4-chlorophenyl | CH2 | C(CH3)2 | — | H | |
| 20-252 | 2-chloro-4-(trifluoromethyl)-5-pyridyl | 4-chloro-2-(trifluoromethyl)phenyl | CH2 | CH2 | — | H | |
| 20-253 | 2-chloro-4-(trifluoromethyl)-5-pyridyl | 4-chloro-3-(trifluoromethyl)phenyl | CH2 | CH2 | — | H | |

TABLE 20-continued

Compounds of the formula I-20

$$\text{X}-\text{L}^1-\text{L}^2-\text{L}^3-\underset{\text{Y}}{\text{N}}-\overset{\overset{\text{O}}{\|}}{\text{C}}-\text{Q}$$

I-20

| Ex. No. | Q | X | L¹ | L² | L³ | Y | Physical data: ¹H-NMR, δ [ppm] or CAS or patent No. |
|---|---|---|---|---|---|---|---|
| 20-254 | 2-chloro-4-(trifluoro-methyl)-5-pyridyl | 4-chlorophenyl | CF2 | CH2 | — | H | |
| 20-255 | 2-chloro-4-(trifluoro-methyl)-5-pyridyl | 2,4-dichloro-phenyl | CF2 | CH2 | — | H | |
| 20-256 | 2-chloro-4-(trifluoro-methyl)-5-pyridyl | 2,4,6-trichloro-phenyl | O | CH2 | CH2 | H | |
| 20-257 | 2-chloro-4-(trifluoro-methyl)-5-pyridyl | 4-chloro-2-(trifluoromethyl)phenyl | O | CH2 | CH2 | H | |
| 20-258 | 2-chloro-4-(trifluoro-methyl)-5-pyridyl | 4-chloro-2-(trifluoromethyl)phenyl | O | CH2 | C(CH3)2 | H | |
| 20-259 | 2-chloro-4-(trifluoro-methyl)-5-pyridyl | 2-chloro-4-(trifluoromethyl)phenyl | O | CH2 | CH2 | H | |
| 20-260 | 2-chloro-4-(trifluoro-methyl)-5-pyridyl | 2-chloro-4-(trifluoromethyl)phenyl | O | CH2 | C(CH3)2 | H | |
| 20-261 | 2-fluorophenyl | 2-chloro-4-(trifluoromethyl)phenyl | O | CH2 | C(CH3)2 | H | compound No. 20-261, solvent: [DMSO], spectrometer: 399.95 MHz 8.0866 (0.97); 7.8342 (1.25); 7.829 (1.33); 7.6904 (0.62); 7.6861 (0.59); 7.6687 (0.71); 7.6644 (0.66); 7.5067 (0.35); 7.5005 (0.54); 7.4958 (0.66); 7.4934 (0.64); 7.4889 (0.7); 7.4817 (0.97); 7.4771 (1.43); 7.4712 (0.68); 7.4625 (0.48); 7.4584 (0.81); 7.363 (1.14); 7.3413 (1.01); 7.262 (0.71); 7.2501 (0.87); 7.2477 (0.87); 7.2424 (0.57); 7.2379 (0.86); 7.2302 (1.4); 7.2163 (0.46); 7.2127 (1.08); 4.3728 (4.74); 3.3302 (39.12); 2.542 (5.13); 2.5251 (0.38); 2.5203 (0.59); 2.5116 (7.72); 2.5071 (15.68); 2.5026 (20.72); 2.498 (15.04); 2.4935 (7.22); 1.4746 (16) |
| 20-262 | 2-fluorophenyl | 4-chloro-2-trifluoro-methyl)phenyl | O | CH3 | C(CH3)3 | H | compound No. 20-262, solvent: [DMSO], spectrometer: 399.95 MHz 7.9991 (1); 7.7034 (0.6); 7.697 (0.8); 7.6814 (0.59); 7.6749 (1.07); 7.6637 (1.85); 7.6574 (1.11); 7.5086 (0.83); 7.5037 (0.5); 7.4957 (0.6); 7.4899 (1.39); 7.4855 (1.03); 7.4783 (0.71); 7.474 (0.78); 7.4703 (0.75); 7.4672 (0.66); 7.4604 (0.44); 7.3145 (1.26); 7.2924 (1.13); 7.2663 (0.71); 7.2564 (0.84); 7.2544 (0.86); 7.2379 (1.55); 7.2184 (1.28); 4.3236 (4.82); 3.3295 (45.22); 2.5417 (4.44); 2.5108 (10.41); 2.5067 (19.44); 2.5023 (24.74); 2.4978 (17.96); 1.4352 (16) |
| 20-263 | 2-fluorophenyl | 2-chloro-4-(trifluoro-methyl)phenyl | O | CH2 | CH2 | H | compound No. 20-263, solvent: [DMSO], spectrometer: 399.95 MHz 8.4918 (2.89); 8.4875 (2.87); 7.8404 (7.83); 7.8352 (8.24); 7.7037 (3.86); 7.6994 (3.67); 7.6819 (4.55); 7.6776 (4.2); 7.6517 (3.03); 7.6472 (3.31); 7.6332 (6); 7.6285 (6.56); 7.6215 (0.73); 7.6137 (3.82); 7.6094 (3.65); 7.5628 (1.62); 7.5582 (1.61); 7.5496 (1.85); 7.5447 (3.65); 7.5418 (2.69); 7.54 (2.6); 7.5375 (2.32); 7.5307 (3.18); 7.5291 (3.02); 7.5268 (3); 7.5238 (4); 7.519 (2.14); 7.5104 (2.22); 7.5058 (1.91); 7.4167 (7.38); 7.395 (6.46); 7.3135 (4.53); 7.3007 (5.21); 7.2982 (5.76); 7.2946 (3.97); 7.2925 (4.35); 7.2887 (4.73); 7.286 (5.35); 7.2816 (9.18); 7.2798 (7.7); 7.2678 (3.46); 7.2632 (5.87); 7.2606 (3.41); 4.3333 (7.15); |

TABLE 20-continued

Compounds of the formula I-20

$$X-L^1-L^2-L^3-N(Y)-C(=O)-Q$$
I-20

| Ex. No. | Q | X | L¹ | L² | L³ | Y | Physical data: ¹H-NMR, δ [ppm] or CAS or patent No. |
|---|---|---|---|---|---|---|---|
| | | | | | | | 4.3188 (16); 4.3043 (7.62); 3.7101 (3.72); 3.6959 (10.66); 3.6818 (10.46); 3.6675 (3.58); 3.3317 (263.4); 2.6764 (0.65); 2.672 (0.87); 2.6673 (0.62); 2.5422 (29.72); 2.5252 (2.46); 2.5203 (4.06); 2.5119 (50.71); 2.5074 (100.78); 2.5028 (131.49); 2.4982 (93.67); 2.4937 (44.06); 2.3342 (0.61); 2.3296 (0.85); 2.325 (0.61); 1.2348 (0.37); −0.0002 (0.78) |
| 20-264 | 2,6-difluorophenyl | 2-chloro-4-(trifluoromethyl)phenyl | O | CH2 | C(CH3)2 | H | compound No. 20-264, solvent: [DMSO], spectrometer: 399.95 MHz 8.592 (1.48); 7.8351 (1.31); 7.8303 (1.41); 7.6905 (0.64); 7.6863 (0.63); 7.6688 (0.74); 7.6646 (0.7); 7.4834 (0.46); 7.479 (0.43); 7.4622 (0.86); 7.4455 (0.44); 7.4412 (0.52); 7.352 (1.17); 7.3304 (1.05); 7.1327 (1.42); 7.1139 (1.84); 7.0932 (1.2); 4.3453 (4.68); 3.3299 (84.45); 2.5413 (8.58); 2.5242 (0.73); 2.5107 (15.63); 2.5064 (30.85); 2.502 (40.14); 2.4974 (29.57); 2.4931 (14.7); 1.4618 (16) |
| 20-265 | 2,6-difluorophenyl | 4-chloro-2-(trifluoromethyl)phenyl | O | CH3 | C(CH3)3 | H | compound No. 20-265, solvent: [DMSO], spectrometer: 399.95 MHz 8.5375 (1.39); 7.7004 (0.52); 7.6938 (0.76); 7.6783 (0.44); 7.6715 (1.19); 7.6658 (1.88); 7.6596 (0.95); 7.48 (0.44); 7.4756 (0.41); 7.4589 (0.84); 7.4422 (0.42); 7.4379 (0.51); 7.3024 (1.14); 7.2804 (1.02); 7.1292 (1.39); 7.1104 (1.72); 7.0897 (1.17); 4.2966 (4.57); 3.3303 (132.8); 2.671 (0.37); 2.5412 (10.41); 2.5242 (1.19); 2.5109 (22.6); 2.5064 (44.89); 2.5019 (58.71); 2.4973 (42.49); 2.4929 (20.42); 2.3287 (0.38); 1.4199 (16) |
| 20-266 | 2,6-difluorophenyl | 2-chloro-4-(trifluoromethyl)phenyl | O | CH2 | CH2 | H | compound No. 20-266, solvent: [DMSO], spectrometer: 399.95 MHz 8.9843 (2.32); 8.9716 (4.42); 8.9582 (2.43); 7.8401 (8.68); 7.8353 (9.2); 7.7014 (4.31); 7.697 (4.13); 7.6796 (4.99); 7.6752 (4.7); 7.5476 (1.6); 7.531 (3.49); 7.5264 (3.11); 7.5142 (2.71); 7.5098 (6.7); 7.5054 (2.39); 7.4931 (3.2); 7.4887 (3.89); 7.4721 (1.79); 7.4014 (8.11); 7.3797 (7.11); 7.19 (1.32); 7.1868 (1.81); 7.1795 (10.93); 7.16 (14.22); 7.1393 (9.11); 7.1317 (1.51); 4.3087 (7.58); 4.295 (16); 4.2813 (8.06); 3.7034 (4.16); 3.6898 (11.54); 3.676 (11.27); 3.6622 (3.99); 3.3857 (0.39); 3.3668 (0.96); 3.3333 (431.43); 2.6805 (0.37); 2.676 (0.78); 2.6715 (1.07); 2.6669 (0.75); 2.6626 (0.36); 2.5418 (48.39); 2.5248 (3.19); 2.5199 (5.02); 2.5114 (62.06); 2.507 (124); 2.5024 (162.49); 2.4978 (117.01); 2.4933 (55.64); 2.3381 (0.37); 2.3337 (0.77); 2.3291 (1.04); 2.3246 (0.75); 1.2352 (0.42); −0.0002 (0.34) |
| 20-267 | 2-chlorophenyl | 2-chloro-4-(trifluoromethyl)phenyl | O | CH2 | C(CH3)2 | H | compound No. 20-267, solvent: [DMSO], spectrometer: 399.95 MHz 8.2838 (1.48); 7.8439 (1.28); 7.8386 (1.33); 7.701 (0.62); 7.6964 (0.59); 7.679 (0.71); 7.6747 (0.66); 7.4612 (0.58); 7.4579 (0.71); 7.4412 (1.29); 7.4383 (1.43); 7.4205 (0.6); 7.4157 (0.66); 7.4029 (0.99); 7.3981 (1); 7.3834 (0.54); 7.3782 (0.61); 7.3671 (0.6); 7.3633 (0.6); 7.3556 (1.2); 7.3485 (1.22); 7.345 (1.19); 7.3312 (1.27); 7.3275 (0.78); 7.3181 (1.4); 7.3134 (1.25); 7.2995 (0.63); 7.2947 (0.47); 4.3796 (4.61); 3.3324 (119.91); 3.3118 (0.57); 2.5414 (8.32); 2.5244 (0.73); 2.5111 (16.7); 2.5066 (32.73); 2.5021 (42.5); 2.4975 (30.6); 2.4931 (14.6); 1.4677 (16) |
| 20-268 | 2-chlorophenyl | 4-chloro-2-(trifluoromethyl)phenyl | O | CH3 | C(CH3)3 | H | compound No. 20-268, solvent: [DMSO], spectrometer: 399.95 MHz 8.2413 (1.48); 7.7116 (0.55); 7.705 (0.77); 7.6896 (0.49); 7.683 (1.06); 7.6738 (1.84); 7.6673 (1.04); 7.4668 (0.63); 7.4632 (0.8); 7.4468 (1.27); 7.4438 (1.45); 7.4228 (0.6); 7.4182 (0.67); 7.4048 (1.11); |

TABLE 20-continued

Compounds of the formula I-20

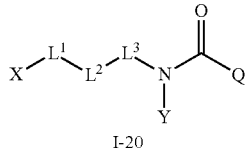

| Ex. No. | Q | X | L¹ | L² | L³ | Y | Physical data: ¹H-NMR, δ [ppm] or CAS or patent No. |
|---|---|---|---|---|---|---|---|
| | | | | | | | 7.4002 (1.09); 7.3854 (0.66); 7.3804 (0.71); 7.375 (0.71); 7.371 (0.68); 7.3565 (1.21); 7.3528 (1.22); 7.3383 (0.63); 7.3348 (0.57); 7.3038 (1.77); 7.2991 (1.19); 7.2848 (1.87); 7.2808 (0.94); 4.3274 (4.62); 3.334 (88.25); 2.5416 (3.24); 2.5247 (0.52); 2.5199 (0.86); 2.5113 (10.97); 2.5068 (21.94); 2.5023 (28.77); 2.4976 (20.67); 2.4931 (9.77); 1.4282 (16) |
| 20-269 | 2-chlorophenyl | 2-chloro-4-(trifluoro-methyl)phenyl | O | CH2 | CH2 | H | compound No. 20-269, solvent: [DMSO], spectrometer: 399.95 MHz 8.6857 (1.94); 8.6727 (3.73); 8.6592 (2.07); 7.8522 (6.96); 7.8473 (7.4); 7.7172 (3.44); 7.7125 (3.34); 7.6951 (4.04); 7.6908 (3.78); 7.5288 (0.42); 7.5083 (3.49); 7.5065 (3.46); 7.4887 (8.2); 7.4686 (3.2); 7.4626 (3.7); 7.4525 (4.23); 7.4464 (5.98); 7.4271 (5.41); 7.4167 (16); 7.4091 (10.21); 7.4053 (7.4); 7.3928 (8.94); 7.3734 (1.47); 7.3703 (1.25); 4.3369 (5.95); 4.3229 (12.79); 4.3089 (6.3); 3.6904 (3.27); 3.6766 (9.28); 3.6627 (9.21); 3.6487 (3.32); 3.3427 (315.93); 2.6831 (0.55); 2.6786 (0.74); 2.6742 (0.54); 2.5488 (34.74); 2.5316 (2.2); 2.5182 (45.59); 2.514 (87.75); 2.5095 (112.19); 2.505 (80.97); 2.5008 (39.04); 2.3406 (0.54); 2.3363 (0.72); 2.3318 (0.51) |
| 20-270 | 2-chloro-3-pyridyl | 2-chloro-4-(trifluoro-methyl)phenyl | O | CH2 | C(CH3)2 | H | compound No. 20-270, solvent: [DMSO], spectrometer: 399.95 MHz-8.4764 (1.47); 8.4475 (1.24); 8.4427 (1.34); 8.4355 (1.34); 8.4306 (1.3); 7.8548 (1.23); 7.8501 (1.31); 7.7675 (1.21); 7.7626 (1.26); 7.7487 (1.46); 7.7438 (1.36); 7.7116 (0.6); 7.7074 (0.58); 7.6899 (0.7); 7.6856 (0.64); 7.4828 (1.42); 7.4707 (1.36); 7.464 (1.26); 7.452 (1.26); 7.3672 (1.08); 7.3458 (0.98); 4.3787 (4.52); 3.3653 (0.55); 3.3409 (148.83); 3.3119 (0.32); 2.5479 (11.64); 2.5311 (0.78); 2.5262 (1.26); 2.5177 (17.1); 2.5132 (34.25); 2.5086 (44.74); 2.504 (31.94); 2.4994 (15.06); 1.4803 (16) |
| 20-271 | 2-chloro-3-pyridyl | 4-chloro-2-(trifluoro-methyl)phenyl | O | CH3 | C(CH3)3 | H | compound No. 20-271, solvent: [DMSO], spectrometer: 399.95 MHz8.4494 (1.21); 8.4445 (1.43); 8.4372 (2.53); 8.4327 (1.95); 7.7322 (1.1); 7.7273 (1.17); 7.7225 (0.64); 7.7136 (1.72); 7.7086 (1.31); 7.7003 (0.53); 7.6939 (1.04); 7.6841 (1.8); 7.6778 (1.03); 7.4939 (1.25); 7.4818 (1.23); 7.4751 (1.11); 7.4631 (1.08); 7.3181 (1.17); 7.296 (1.05); 4.3297 (4.57); 3.389 (0.32); 3.3418 (213.36); 2.6825 (0.32); 2.6778 (0.43); 2.5481 (12.03); 2.5311 (1.11); 2.5177 (25.37); 2.5133 (50.43); 2.5087 (65.7); 2.5042 (47.42); 2.4997 (22.66); 2.3355 (0.42); 1.4395 (16) |
| 20-272 | 2-chloro-3-pyridyl | 2-chloro-4-(trifluoro-methyl)phenyl | O | CH2 | CH2 | H | compound No. 20-272, solvent: [DMSO], spectrometer: 399.95 MHz 8.8792 (2.37); 8.8659 (4.61); 8.8525 (2.5); 8.4849 (8.31); 8.4801 (8.81); 8.4728 (8.86); 8.468 (8.62); 7.8861 (8.63); 7.8812 (8.68); 7.8672 (9.98); 7.8623 (9.87); 7.8554 (8.82); 7.8504 (9.33); 7.72 (4.26); 7.7157 (4.14); 7.6983 (4.97); 7.694 (4.66); 7.5199 (9.72); 7.5079 (9.4); 7.5011 (8.86); 7.489 (8.68); 7.4161 (8.03); 7.3943 (7.08); 4.3399 (7.49); 4.3261 (16); 4.3124 (7.96); 3.7093 (4.15); 3.6956 (11.68); 3.6818 (11.56); 3.668 (4.17); 3.4539 (0.33); 3.4505 (0.33); 3.4276 (0.49); 3.4064 (0.79); 3.3451 (1017.79); 3.2868 (0.37); 2.8964 (0.36); 2.6873 (0.59); 2.683 (1.26); 2.6784 (1.71); 2.6739 (1.22); 2.6693 (0.58); 2.5486 (16.11); 2.5318 (4.86); 2.5269 (7.6); 2.5184 (98.26); 2.5139 (197.2); 2.5094 (258.78); 2.5048 (185.74); 2.5003 (87.65); 2.3452 (0.57); 2.3407 (1.21); 2.3361 (1.67); 2.3315 (1.18); 2.327 (0.53); 1.4402 (0.75); 1.2417 (0.71) |

TABLE 20-continued

Compounds of the formula I-20

$$X-L^1-L^2-L^3-N(Y)-C(=O)-Q$$

I-20

| Ex. No. | Q | X | L¹ | L² | L³ | Y | Physical data: ¹H-NMR, δ [ppm] or CAS or patent No. |
|---|---|---|---|---|---|---|---|
| 20-273 | 2-bromophenyl | 2-chloro-4-(trifluoromethyl)phenyl | O | CH2 | C(CH3)2 | H | compound No. 20-273, solvent: [DMSO], spectrometer: 399.95 MHz 8.2809 (1.54); 7.8447 (1.31); 7.8399 (1.4); 7.7027 (0.64); 7.6985 (0.62); 7.6808 (0.74); 7.6769 (0.7); 7.6167 (1.04); 7.6147 (1.11); 7.5972 (1.23); 7.5948 (1.24); 7.4108 (0.4); 7.408 (0.45); 7.3922 (1.17); 7.3895 (1.18); 7.3738 (0.96); 7.3708 (0.91); 7.3529 (1.17); 7.3375 (0.79); 7.3327 (1.78); 7.3184 (0.86); 7.3136 (1.1); 7.2991 (0.45); 7.2945 (0.49); 7.2874 (1.27); 7.2829 (1.06); 7.269 (0.91); 7.2646 (0.79); 4.3772 (4.64); 3.335 (156.03); 2.5416 (8.9); 2.5246 (0.84); 2.5111 (18.12); 2.5068 (36.48); 2.5023 (47.97); 2.4977 (35.24); 2.4934 (17.29); 1.4716 (16) |
| 20-274 | 2-bromophenyl | 4-chloro-2-(trifluoromethyl)phenyl | O | CH3 | C(CH3)3 | H | compound No. 20-274, solvent: [DMSO], spectrometer: 399.95 MHz 8.2393 (1.48); 7.7135 (0.56); 7.7069 (0.77); 7.6914 (0.51); 7.6849 (1.05); 7.6751 (1.83); 7.6687 (1.05); 7.6235 (1.07); 7.6209 (1.1); 7.6037 (1.28); 7.601 (1.24); 7.4195 (0.44); 7.4166 (0.46); 7.4009 (1.23); 7.3981 (1.19); 7.3824 (0.95); 7.3794 (0.86); 7.3391 (0.73); 7.3345 (0.9); 7.3199 (0.92); 7.3151 (1.08); 7.3026 (1.28); 7.2961 (0.57); 7.2809 (1.1); 7.2727 (1.29); 7.2682 (1.13); 7.2541 (0.98); 7.2497 (0.84); 4.3258 (4.59); 3.33 (70.11); 2.5413 (4.54); 2.5244 (0.61); 2.5194 (1); 2.511 (11.91); 2.5066 (23.51); 2.502 (30.42); 2.4974 (21.73); 2.4929 (10.21); 1.432 (16) |
| 20-275 | 2-bromophenyl | 2-chloro-4-(trifluoromethyl)phenyl | O | CH2 | CH2 | H | compound No. 20-275, solvent: [DMSO], spectrometer: 399.95 MHz 8.677 (2.32); 8.6636 (4.57); 8.6502 (2.43); 7.8463 (8.39); 7.8412 (8.99); 7.7114 (4.09); 7.707 (3.93); 7.6897 (4.78); 7.6851 (4.47); 7.6549 (7.91); 7.6372 (7.44); 7.6348 (8.35); 7.5254 (0.43); 7.5213 (0.43); 7.4501 (2.27); 7.4474 (2.48); 7.4294 (6.83); 7.4133 (9); 7.4103 (12.89); 7.3878 (11.85); 7.3846 (16); 7.3752 (7.87); 7.3699 (7.93); 7.3648 (4.67); 7.3559 (6.33); 7.3524 (4.66); 7.351 (4.86); 7.3381 (3.37); 7.333 (2.86); 4.3298 (7.14); 4.3157 (15.6); 4.3017 (7.58); 3.6763 (3.91); 3.6624 (11.22); 3.6485 (11.13); 3.6344 (3.96); 3.3287 (262.97); 2.6755 (0.84); 2.671 (1.17); 2.6665 (0.85); 2.6623 (0.41); 2.5413 (42.54); 2.5243 (3.43); 2.5109 (67.35); 2.5065 (134.61); 2.5019 (176.63); 2.4974 (127.79); 2.4929 (61.18); 2.3331 (0.81); 2.3287 (1.13); 2.3242 (0.82); 2.32 (0.39); 1.2349 (0.51); −0.0002 (1.21) |
| 20-276 | 2-bromophenyl | 4-chloro-2-(trifluoromethyl)phenyl | O | CH2 | CH2 | H | compound No. 20-276, solvent: [DMSO], spectrometer: 399.95 MHz 8.6012 (1.54); 8.5878 (2.91); 8.5747 (1.48); 7.7241 (2.52); 7.7176 (3.13); 7.7019 (2.67); 7.6953 (3.8); 7.6718 (7.26); 7.665 (5.72); 7.6608 (3.61); 7.6577 (5.54); 7.6428 (2.43); 7.6372 (4.91); 7.4531 (1.79); 7.4502 (1.88); 7.4342 (5.7); 7.4297 (2.72); 7.416 (4.43); 7.4131 (4.07); 7.3762 (7.14); 7.3721 (6.99); 7.3533 (16); 7.336 (5.64); 7.3336 (5.34); 4.2828 (4.61); 4.2682 (10.25); 4.2537 (4.86); 3.627 (2.58); 3.6128 (7.24); 3.5986 (6.94); 3.5841 (2.25); 3.3301 (63.99); 2.5419 (14.61); 2.5249 (0.96); 2.5116 (17.95); 2.5071 (34.96); 2.5026 (45.04); 2.498 (32.13); 2.4934 (15.13); −0.0002 (0.35) |
| 20-277 | 2-iodophenyl | 2-chloro-4-(trifluoromethyl)phenyl | O | CH2 | C(CH3)2 | H | compound No. 20-277, solvent: [DMSO], spectrometer: 399.95 MHz 8.2418 (1.64); 7.8457 (2.44); 7.8442 (2.52); 7.8398 (1.5); 7.8264 (1.29); 7.8242 (1.25); 7.7017 (0.65); 7.6973 (0.62); 7.68 (0.74); 7.6755 (0.68); 7.4208 (0.56); 7.4182 (0.57); 7.4021 (1.28); 7.3995 (1.27); 7.3834 (0.8); 7.3807 (0.77); 7.3469 (1.18); 7.3252 (1.06); |

TABLE 20-continued

Compounds of the formula I-20

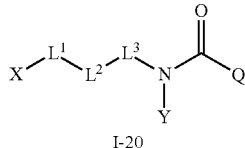

| Ex. No. | Q | X | L¹ | L² | L³ | Y | Physical data: $^1$H-NMR, δ [ppm] or CAS or patent No. |
|---|---|---|---|---|---|---|---|
| | | | | | | | 7.2271 (1.11); 7.223 (1.26); 7.2082 (0.99); 7.2041 (0.98); 7.1507 (0.71); 7.1465 (0.66); 7.1316 (1.07); 7.1274 (0.97); 7.1125 (0.61); 7.1082 (0.54); 4.3755 (4.65); 3.328 (33.38); 2.5414 (6.5); 2.5244 (0.43); 2.5111 (8.02); 2.5066 (15.59); 2.5021 (20.14); 2.4975 (14.32); 2.493 (6.71); 1.4828 (16) |
| 20-278 | 2-iodophenyl | 4-chloro-2-(trifluoromethyl)phenyl | O | CH3 | C(CH3)3 | H | compound No. 20-278, solvent: [DMSO], spectrometer: 399.95 MHz 8.1977 (1.65); 7.851 (1.22); 7.8488 (1.24); 7.8312 (1.33); 7.8291 (1.26); 7.7127 (0.61); 7.7063 (0.82); 7.6906 (0.57); 7.6842 (1.18); 7.6755 (1.97); 7.6693 (1.11); 7.4291 (0.59); 7.4264 (0.58); 7.4104 (1.33); 7.4077 (1.28); 7.3917 (0.83); 7.389 (0.76); 7.2953 (1.24); 7.2732 (1.12); 7.2163 (1.12); 7.2123 (1.26); 7.1974 (1.02); 7.1934 (1); 7.1512 (0.75); 7.147 (0.68); 7.1321 (1.1); 7.128 (0.99); 7.1129 (0.64); 7.1087 (0.56); 4.3279 (4.67); 3.3277 (30.38); 2.5413 (6.24); 2.5242 (0.53); 2.511 (8.58); 2.5066 (16.24); 2.502 (20.68); 2.4974 (14.92); 2.493 (7.19); 1.4429 (16) |
| 20-279 | 2-iodophenyl | 2-chloro-4-(trifluoromethyl)phenyl | O | CH2 | CH2 | H | compound No. 20-279, solvent: [DMSO], spectrometer: 399.95 MHz 8.6416 (1.09); 8.628 (2.2); 8.6148 (1.24); 7.8855 (3.45); 7.8833 (3.79); 7.8657 (3.82); 7.8635 (3.98); 7.8464 (3.91); 7.841 (4.3); 7.8162 (0.33); 7.7121 (1.84); 7.7077 (1.8); 7.6903 (2.24); 7.686 (2.16); 7.4582 (1.57); 7.4555 (1.73); 7.4394 (3.76); 7.4368 (4.01); 7.4207 (2.61); 7.4181 (2.75); 7.4062 (3.66); 7.3844 (3.22); 7.3246 (3.49); 7.3205 (3.89); 7.3056 (2.84); 7.3016 (2.86); 7.1878 (2.08); 7.1835 (2.09); 7.1685 (3.07); 7.1642 (3.08); 7.1495 (1.91); 7.1453 (1.82); 4.3341 (3.12); 4.3199 (7.03); 4.3056 (3.65); 3.6679 (1.71); 3.6539 (4.95); 3.6399 (5.09); 3.6257 (2.1); 3.369 (0.56); 3.3291 (561.58); 3.3006 (20.11); 2.6795 (0.44); 2.6753 (1); 2.6707 (1.41); 2.6661 (1.06); 2.6616 (0.53); 2.5411 (15.33); 2.5241 (3.55); 2.5193 (5.45); 2.5107 (76.72); 2.5062 (160.49); 2.5017 (217.15); 2.4971 (161.5); 2.4926 (81.83); 2.4746 (16); 2.3375 (0.47); 2.333 (1.01); 2.3284 (1.41); 2.3238 (1.07); 2.3194 (0.54); 1.2349 (0.58); [DMSO],0.0002 (1.24) |
| 20-280 | 2-iodophenyl | 4-chloro-2-(trifluoromethyl)phenyl | O | CH2 | CH2 | H | compound No. 20-280, solvent: [DMSO], spectrometer: 399.95 MHz 8.5626 (2.47); 8.5492 (4.83); 8.5357 (2.45); 7.8878 (7.67); 7.8857 (8.04); 7.8681 (8.38); 7.8659 (8.19); 7.7257 (3.93); 7.7192 (4.93); 7.7035 (4.13); 7.697 (6); 7.6738 (11.36); 7.6672 (8.19); 7.4604 (3.7); 7.4577 (3.9); 7.4416 (8.42); 7.4389 (8.59); 7.4229 (5.46); 7.4202 (5.36); 7.3724 (8.27); 7.3501 (7.31); 7.2915 (7.43); 7.2874 (8.23); 7.2725 (6.4); 7.2684 (6.24); 7.1869 (4.84); 7.1827 (4.64); 7.1675 (6.98); 7.1633 (6.64); 7.1487 (4.16); 7.1444 (3.82); 4.2868 (7.05); 4.272 (16); 4.2574 (7.56); 3.6165 (3.93); 3.6021 (11.13); 3.5878 (10.73); 3.5732 (3.52); 3.3274 (257.7); 2.68 (0.37); 2.6754 (0.77); 2.6709 (1.05); 2.6663 (0.76); 2.6617 (0.36); 2.5412 (31.49); 2.5243 (3.27); 2.5108 (61.88); 2.5064 (122.47); 2.5018 (159.53); 2.4972 (114.77); 2.4927 (54.57); 2.3374 (0.36); 2.3332 (0.75); 2.3286 (1.02); 2.324 (0.75); 2.3195 (0.34); 1.2345 (0.55); −0.0002 (1.3) |
| 20-281 | 2-(trifluoromethyl)phenyl | 2-chloro-4-(trifluoromethyl)phenyl | O | CH2 | C(CH3)2 | H | compound No. 20-281, solvent: [DMSO], spectrometer: 399.95 MHz 8.3635 (1.54); 7.8522 (1.32); 7.8472 (1.39); 7.7467 (0.85); 7.7273 (1.15); 7.7043 (1); 7.6842 (1.6); 7.667 (0.7); 7.6262 (0.68); 7.6073 (0.86); 7.4188 (1.02); |

TABLE 20-continued

Compounds of the formula I-20

I-20

| Ex. No. | Q | X | L¹ | L² | L³ | Y | Physical data: ¹H-NMR, δ [ppm] or CAS or patent No. |
|---|---|---|---|---|---|---|---|
| 20-282 | 2-(trifluoro-methyl)phenyl | 4-chloro-2-(trifluoro-methyl)phenyl | O | CH3 | C(CH3)3 | H | 7.4002 (0.89); 7.3415 (1.16); 7.3197 (1.06); 4.3633 (4.65); 3.33 (87.86); 2.5413 (8.46); 2.5243 (0.75); 2.5109 (16.03); 2.5065 (31.63); 2.502 (41.16); 2.4974 (29.71); 2.493 (14.23); 1.4551 (16) compound No. 20-282, solvent: [DMSO], spectrometer: 399.95 MHz 8.3145 (1.55); 7.7476 (0.88); 7.7282 (1.17); 7.7138 (0.75); 7.7085 (1.12); 7.6925 (1.45); 7.6868 (1.33); 7.6776 (2.09); 7.6718 (1.67); 7.6261 (0.67); 7.6071 (0.87); 7.588 (0.33); 7.4014 (1.03); 7.3827 (0.9); 7.29 (1.2); 7.2679 (1.09); 4.3083 (4.63); 3.3349 (172.86); 3.303 (0.4); 2.6711 (0.34); 2.5414 (1.3); 2.5244 (0.91); 2.511 (19.6); 2.5066 (39.33); 2.5021 (51.72); 2.4975 (37.59); 2.493 (18.2); 2.3288 (0.33); 1.4166 (16) |
| 20-283 | 2-(trifluoro-methyl)phenyl | 2-chloro-4-(trifluoro-methyl)phenyl | O | CH2 | CH2 | H | compound No. 20-283, solvent: [DMSO], spectrometer: 399.95 MHz 8.7712 (2.51); 8.7579 (4.81); 8.7445 (2.57); 7.8548 (8.92); 7.8495 (9.08); 7.7923 (5.96); 7.7729 (7.94); 7.7473 (2.59); 7.7294 (7.2); 7.7177 (4.73); 7.711 (5.61); 7.7004 (5.27); 7.6961 (4.6); 7.684 (0.58); 7.6701 (4.72); 7.6511 (5.98); 7.6323 (2.18); 7.525 (7.22); 7.5062 (5.96); 7.4045 (7.99); 7.3829 (7.03); 4.3181 (7.51); 4.3042 (16); 4.2903 (7.8); 3.6854 (4.15); 3.6716 (11.54); 3.6577 (11.37); 3.6438 (4.1); 3.4387 (0.43); 33454 (879.81); 2.6867 (0.57); 2.6823 (1.18); 2.6777 (1.58); 2.6731 (1.13); 2.6686 (0.54); 2.548 (79.94); 2.531 (5.04); 2.5176 (93.91); 2.5132 (182.99); 2.5086 (236.55); 2.504 (168.8); 2.4995 (79.54); 2.3444 (0.54); 2.3399 (1.1); 2.3353 (1.51); 2.3308 (1.07); 2.3263 (0.49); 1.2406 (0.61) |
| 20-284 | 2-(trifluoro-methyl)phenyl | 4-(trifluoro-methyl)phenyl | O | CH2 | CH2 | H | compound No. 20-284, solvent: [DMSO], spectrometer: 399.95 MHz, S, 8.76 (t, 1H, NH), 7.81-7.62 (m, 4H), 7.50 (d, 1H), 7.15 (d, 2H), 4.18 (t, 2H), 3.65-3.61 (q, 2H). |

TABLE 21

Compounds of the formula I-21

I-21

| Ex. No. | X | L¹ | L² | L³ | Y | Physical data: ¹H-NMR, δ [ppm] or CAS or patent No. |
|---|---|---|---|---|---|---|
| 21-1 | 3-methyl-2-thienyl | CH2 | CH2 | — | H | |
| 21-2 | 2,4-dichlorophenyl | CH2 | CH2 | CH2 | H | WO-A 2008/101976 |
| 21-3 | 4-chlorophenyl | CH2 | CH2 | — | H | |
| 21-4 | 2,4-dichlorophenyl | CH2 | CH2 | — | H | WO-A 2007/108483 |
| 21-5 | 4-chlorophenyl | CH(OCH3) | CH(CH3) | — | H | |
| 21-6 | 2,4-dichlorophenyl | CH(OCH3) | CH(CH3) | — | H | |
| 21-7 | 4-chlorophenyl | CH(CH3) | CH2 | — | H | |
| 21-8 | 2,4-dichlorophenyl | CH(CH3) | CH2 | — | H | |
| 21-9 | 4-chlorophenyl | CH2 | CH(CH3) | — | H | |
| 21-10 | 2,4-dichlorophenyl | CH2 | CH(CH3) | — | H | |
| 21-11 | 4-chlorophenyl | C(CH3)2 | CH2 | — | H | |
| 21-12 | 2,4-dichlorophenyl | C(CH3)2 | CH2 | — | H | |

TABLE 21-continued

Compounds of the formula I-21

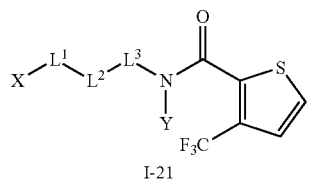

I-21

Physical data: $^1$H-NMR, δ [ppm] or CAS or patent No.

| Ex. No. | X | L$^1$ | L$^2$ | L$^3$ | Y | |
|---|---|---|---|---|---|---|
| 21-13 | 2-chlorophenyl | CH2 | CH2 | — | H | |
| 21-14 | 3,4-dichlorophenyl | CH2 | CH2 | — | H | |
| 21-15 | 3,5-dichlorophenyl | CH2 | CH2 | — | H | |
| 21-16 | 3-chlorophenyl | CH2 | CH2 | — | H | |
| 21-17 | 2-fluorophenyl | CH2 | CH2 | — | H | |
| 21-18 | 2,6-difluorophenyl | CH2 | CH2 | — | H | |
| 21-19 | 2,6-dichlorophenyl | CH2 | CH2 | — | H | |
| 21-20 | 3-(trifluoromethyl)phenyl | CH2 | CH2 | — | H | |
| 21-21 | 4-(trifluoromethyl)phenyl | CH2 | CH2 | — | H | |
| 21-22 | 2-methylphenyl | CH2 | CH2 | — | H | |
| 21-23 | 2,4,6-trimethylphenyl | CH2 | CH2 | — | H | |
| 21-24 | 3,4-bismethoxyphenyl | CH2 | CH2 | — | H | |
| 21-25 | phenyl | CH2 | CH2 | — | H | |
| 21-26 | 4-chlorophenyl | C(CH2—CH2) | CH2 | — | H | |
| 21-27 | 2,4-dichlorophenyl | C(CH2—CH2) | CH2 | — | H | |
| 21-28 | 4-chlorophenyl | CH2 | C(CH2—CH2) | — | H | |
| 21-29 | 2,4-dichlorophenyl | CH2 | C(CH2—CH2) | — | H | |
| 21-30 | 4-chlorophenyl | O | CH2 | CH2 | H | |
| 21-31 | 2,4-dichlorophenyl | O | CH2 | CH2 | H | |
| 21-32 | 4-chlorophenyl | CH2 | CH2 | CH2 | H | |
| 21-33 | 4-chlorophenyl | NCH3 | CH2 | CH2 | H | |
| 21-34 | 2,4-dichlorophenyl | NCH3 | CH2 | CH2 | H | |
| 21-35 | 4-chlorophenyl | CH(OCH3) | CH2 | — | H | |
| 21-36 | 2,4-dichlorophenyl | CH(OCH3) | CH2 | — | H | |
| 21-37 | 2-thienyl | CH2 | CH2 | — | H | |
| 21-38 | 3-thienyl | CH2 | CH2 | — | H | |
| 21-39 | 2-furyl | CH2 | CH2 | — | H | |
| 21-40 | 3-furyl | CH2 | CH2 | — | H | |
| 21-41 | phenyl | CH2 | CH2 | CH(CH3) | H | |
| 21-42 | phenyl | CH2 | CH2 | CH2 | H | |
| 21-43 | 2-Cl-phenyl | CH2 | CH2 | CH(CH3) | H | |
| 21-44 | 4-t-butylphenyl | CH2 | CH2 | CH2 | H | |
| 21-45 | 4-methylphenyl | CH2 | CH2 | CH2 | H | |
| 21-46 | phenyl | CH2 | CH2 | CH(CH2CH3) | H | |
| 21-47 | 2-methoxyphenyl | CH2 | CH2 | CH2 | H | |
| 21-48 | 2-methylphenyl | CH2 | CH2 | CH2 | H | |
| 21-49 | 3-methylphenyl | CH2 | CH2 | CH2 | H | |
| 21-50 | 3-chlorophenyl | CH2 | CH2 | CH2 | H | |
| 21-51 | 2,6-difluorophenyl | CH2 | CH2 | CH2 | H | |
| 21-52 | 4-chlorophenyl | CH2 | CH2 | CH2 | H | |
| 21-53 | 2,6-dichlorophenyl | CH2 | CH2 | CH(CH3) | H | |
| 21-54 | 3,5-dichlorophenyl | CH2 | CH2 | CH(CH3) | H | |
| 21-55 | 2,6-dimethylphenyl | CH2 | CH2 | CH2 | H | |
| 21-56 | 2,5-dichlorophenyl | CH2 | CH2 | CH2 | H | |
| 21-57 | 4-isopropoxyphenyl | CH2 | CH2 | CH2 | H | |
| 21-58 | 3-trifluoromethylphenyl | CH2 | CH2 | CH(CH3) | H | |
| 21-59 | 4-methylphenyl | CH2 | CH2 | CH(CH3) | H | |
| 21-60 | 2-methylphenyl | CH2 | CH2 | CH(CH3) | H | |
| 21-61 | 3,4-dichlorophenyl | CH2 | CH2 | CH(CH3) | H | |
| 21-62 | 3,5-dichlorophenyl | CH2 | CH2 | CH2 | H | |
| 21-63 | 2,6-dimethylphenyl | CH2 | CH2 | CH(CH3) | H | |
| 21-64 | 4-trifluoromethylphenyl | CH2 | CH2 | CH(CH3) | H | |
| 21-65 | 2,5-dichlorophenyl | CH2 | CH2 | CH(CH3) | H | |
| 21-66 | 4-phenoxyphenyl | CH2 | CH2 | CH2 | H | |
| 21-67 | 3-chlorophenyl | CH2 | CH2 | CH(CH3) | H | |
| 21-68 | 4-phenoxyphenyl | CH2 | CH2 | CH(CH3) | H | |
| 21-69 | 2,4-dichlorophenyl | CH2 | CH2 | CH(CH3) | H | |
| 21-70 | 2-difluoromethoxyphenyl | CH2 | CH2 | CH(CH3) | H | |
| 21-71 | 4-methoxyphenyl | CH2 | CH2 | CH2 | H | |
| 21-72 | 4-chlorophenyl | CH2 | CH2 | CH(CH3) | H | |
| 21-73 | 4-chlorophenyl | CH2 | CH2 | CH(i-propyl) | H | |
| 21-74 | 4-fluorophenyl | CH2 | CH2 | CH2 | H | |
| 21-75 | 4-chlorophenyl | CH2 | CH2 | CH(n-propyl) | H | |
| 21-76 | 4-chlorophenyl | CH2 | CH2 | CH(t-butyl) | H | |
| 21-77 | 2-chlorophenyl | CH2 | CH2 | CH2 | H | |

TABLE 21-continued

Compounds of the formula I-21

I-21

| Ex. No. | X | L¹ | L² | L³ | Y | Physical data: ¹H-NMR, δ [ppm] or CAS or patent No. |
|---|---|---|---|---|---|---|
| 21-78 | 4-chlorophenyl | CH2 | CH(CH3) | — | cyclopropyl | |

TABLE 22

Compounds of the formula I-22

I-22

| Ex. No. | Q | X | L¹ | L² | L³ | Y | Physical data: ¹H-NMR, δ [ppm] or source |
|---|---|---|---|---|---|---|---|
| 22-1 | 3-chlorothienyl | 4-chlorophenyl | CH(CH3) | CH2 | - | H | ¹H-NMR (d6-DMSO): δ [ppm], 10.10 (s, 1H, NH), 7.76 (d, 1H), 7.38-7.32 (dd, 4H), 7.05 (d, 1H), 3.91-3.74 (2xm, 2H), 3.37-3.30 (m, 1H), 1.33 (d, 3H). |
| 22-2 | 3-chlorothienyl | 2,4-dichlorophenyl | CH(CH3) | CH3 | - | H | ¹H-NMR (d6-DMSO): δ [ppm], 10.15 (s, 1H, NH), 7.76 (d, 1H), 7.57-7.41 (m, 3H), 7.05 (d, 1H), 3.98-3.79 (m, 3H), 3.37-3.30 (m, 1H), 1.30 (d, 3H). |

TABLE 23

Compounds of the formula I-23

I-23

| Ex. No. | X | L¹ | L² | L³ | Y | Physical data: ¹H-NMR, δ [ppm] or CAS or patent No. |
|---|---|---|---|---|---|---|
| 23-1 | 3-methyl-2-thienyl | CH2 | CH2 | — | H | |
| 23-2 | 2,4-dichlorophenyl | CH2 | CH2 | CH2 | H | |
| 23-3 | 4-chlorophenyl | CH2 | CH2 | — | H | compound No. 23-3, solvent: [DMSO], spectrometer: 399.95 MHz 8.4094 (1.95); 8.3977 (3.36); 8.3841 (1.84); 7.3599 (7.78); 7.34 (12.6); 7.2746 (12.92); 7.262 (15.69); 7.2601 (16); 7.2543 (8.56); 3.441 (3); 3.4243 (6.9); 3.4086 (6.99); 3.3912 (3.64); 3.3363 (1234.04); 3.3339 (1028.02); 3.2344 (0.51); 2.8168 (5.5); 2.7988 (9.82); 2.7811 (4.71); 2.6717 (2.38); 2.5415 (19.39); 2.5397 (18.68); 2.5026 (365.92); 2.3295 (2.26); 2.0741 (0.43); 1.2344 (0.51); −0.0002 (16.17); −0.0019 (15.45) |
| 23-4 | 2,4-dichlorophenyl | CH2 | CH2 | — | H | compound No. 23-4, solvent: [DMSO], spectrometer: 399.95 MHz |

TABLE 23-continued

Compounds of the formula I-23

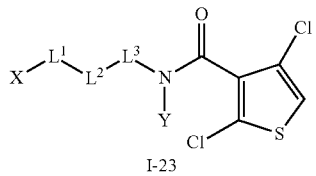

I-23

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 8.4444 (1.12); 8.4302 (2.16); 8.4161 (1.1); 8.316 (0.34); 7.587 (5.6); 7.3967 (0.43); 7.3722 (16); 7.3534 (0.33); 7.2635 (15.9); 3.4685 (1.84); 3.4514 (4.63); 3.4364 (4.68); 3.4193 (2.06); 3.3233 (165.14); 2.9383 (3.93); 2.9209 (7.68); 2.9035 (3.43); 2.6798 (0.41); 2.6753 (0.85); 2.6708 (1.17); 2.6663 (0.86); 2.6616 (0.41); 2.524 (3.72); 2.5107 (65.8); 2.5062 (132.4); 2.5017 (174.38); 2.4972 (125.44); 2.4927 (59.91); 2.3372 (0.38); 2.333 (0.81); 2.3285 (1.13); 2.3239 (0.82); 2.3195 (0.39); 1.3354 (0.4); 1.2493 (0.41); 0.008 (2.55); −0.0002 (72.77); −0.0084 (2.34) |
| 23-5 | 4-chlorophenyl | CH(OCH3) | CH(CH3) | — | H | |
| 23-6 | 2,4-dichlorophenyl | CH(OCH3) | CH(CH3) | — | H | |
| 23-7 | 4-chlorophenyl | CH(CH3) | CH2 | — | H | compound No. 23-7, solvent: [DMSO], spectrometer: 399.95 MHz 8.3694 (1.13); 8.3556 (2.13); 8.3417 (1.1); 7.3647 (6.44); 7.3599 (2.46); 7.3486 (3.12); 7.3435 (11.88); 7.3377 (1.75); 7.2964 (1.73); 7.2906 (10.87); 7.2858 (3.14); 7.2741 (2.26); 7.2694 (6.11); 7.2111 (16); 3.392 (0.68); 3.3769 (1.04); 3.3731 (1.13); 3.3588 (3.86); 3.3346 (379.03); 3.3077 (2.83); 3.2928 (0.87); 3.289 (0.84); 3.2749 (0.61); 3.0386 (1.11); 3.0207 (2.21); 3.0028 (2.12); 2.9848 (0.99); 2.7117 (0.72); 2.6759 (0.62); 2.6713 (0.82); 2.6668 (0.62); 2.5676 (0.49); 2.5416 (198.1); 2.5247 (2.6); 2.5198 (4.34); 2.5113 (48.81); 2.5068 (98.32); 2.5023 (129.34); 2.4977 (94.29); 2.4933 (46.11); 2.4671 (0.33); 2.3679 (0.73); 2.3336 (0.59); 2.329 (0.81); 2.3245 (0.59); 2.0745 (0.51); 1.2203 (13.97); 1.2028 (13.7); −0.0002 (8.06) |
| 23-8 | 2,4-dichlorophenyl | CH(CH3) | CH2 | — | H | compound No. 23-8, solvent: [DMSO], spectrometer: 399.95 MHz 20.0115 (0.42); 8.4185 (1.14); 8.4043 (2.34); 7.5676 (6.37); 7.5623 (6.93); 7.4672 (3.41); 7.446 (8.13); 7.4197 (4.9); 7.4144 (4.67); 7.3987 (2.12); 7.3933 (2.08); 7.2215 (16); 3.5268 (0.91); 3.5095 (2.03); 3.4925 (2.41); 3.4749 (2.34); 3.4598 (1.59); 3.4424 (2.42); 3.4267 (2.78); 3.4105 (1.85); 3.3964 (2.57); 3.3792 (3.85); 3.3646 (7.87); 3.3322 (2494.64); 3.2606 (1.24); 2.7111 (1.91); 2.6755 (4.55); 2.6709 (6.21); 2.6664 (4.54); 2.5412 (475.91); 2.5242 (23.84); 2.5109 (365.49); 2.5064 (724.17); 2.5019 (947); 2.4973 (685.77); 2.4929 (333.49); 2.3674 (1.83); 2.3331 (4.33); 2.3286 (5.98); 2.3241 (4.36); 2.2901 (0.62); 2.0742 (1.94); 1.2585 (0.47); 1.2351 (1); 1.2128 (13.29); 1.196 (13.12); 0.008 (1.33); −0.0001 (31.97); −0.0083 (0.96) |
| 23-9 | 4-chlorophenyl | CH2 | CH(CH3) | — | H | |
| 23-10 | 2,4-dichlorophenyl | CH2 | CH(CH3) | — | H | |
| 23-11 | 4-chlorophenyl | C(CH3)2 | CH2 | — | H | compound No. 23-12, solvent: [DMSO], spectrometer: 399.95 MHz 8.1803 (0.4); 8.1644 (0.81); 8.1492 (0.41); 7.5252 (2.25); 7.5195 (2.43); 7.4713 (1.46); 7.4496 (2.2); 7.3726 (1.46); 7.3667 (1.39); 7.351 (0.97); 7.3452 (0.92); 7.1644 (5.38); 3.7449 (2.75); 3.729 (2.72); 3.3766 (0.59); 3.3352 (262.2); 2.6755 (0.4); 2.6711 (0.56); 2.6669 (0.41); 2.5415 (52.18); 2.5244 (1.83); 2.511 (32.18); 2.5067 (65.15); 2.5021 (86.34); 2.4976 (63.79); 2.4932 (31.7); 2.3334 (0.38); |

TABLE 23-continued

Compounds of the formula I-23

$$\text{X}-\text{L}^1-\text{L}^2-\text{L}^3-\text{N}(\text{Y})-\text{C}(\text{O})-\text{[2,4-dichlorothiophen-3-yl]}$$

I-23

| Ex. No. | X | L¹ | L² | L³ | Y | Physical data: ¹H-NMR, δ [ppm] or CAS or patent No. |
|---|---|---|---|---|---|---|
| 23-12 | 2,4-dichlorophenyl | C(CH3)2 | CH2 | — | H | 2.3289 (0.52); 2.3244 (0.38); 2.0742 (0.36); 1.4397 (16); −0.0002 (3.1) |
| 23-13 | 2-chlorophenyl | CH2 | CH2 | — | H | compound No. 23-13, solvent: [DMSO], spectrometer: 399.95 MHz 15.3304 (0.91); 14.7843 (0.89); 8.4566 (1.23); 8.4447 (1.06); 7.8866 (0.91); 7.442 (2.27); 7.4235 (2.45); 7.4186 (2.68); 7.3595 (1.83); 7.3415 (2.82); 7.3077 (1.14); 7.2929 (2.85); 7.2887 (2.2); 7.2751 (14.86); 7.2598 (2.02); 7.2538 (1.87); 3.9437 (0.86); 3.7152 (1.16); 3.7111 (1.12); 3.6657 (1.33); 3.6279 (0.97); 3.6084 (1.08); 3.5888 (1.4); 3.5481 (1.58); 3.5292 (1.71); 3.4739 (3.46); 3.4572 (4.98); 3.4396 (5.96); 3.4243 (5.58); 3.3369 (4888.75); 3.2607 (2.51); 3.2253 (1.62); 3.2208 (1.54); 3.2035 (1.25); 3.1766 (0.88); 3.1355 (1.06); 3.0607 (1.03); 2.9574 (2.89); 2.9401 (4.58); 2.9213 (2.47); 2.7494 (1.02); 2.7109 (1.79); 2.6756 (11.72); 2.6711 (16); 2.6665 (11.63); 2.6487 (1.41); 2.6168 (1.28); 2.5979 (1.95); 2.5922 (1.93); 2.5414 (434.46); 2.5245 (53.58); 2.5111 (966.23); 2.5067 (1928.89); 2.5021 (2522.35); 2.4975 (1818.19); 2.493 (878.69); 2.4235 (1.24); 2.3848 (0.93); 2.3676 (1.3); 2.3334 (11.4); 2.3289 (15.19); 2.3244 (11.05); 2.2907 (1.19); 2.0739 (8.74); 1.4393 (0.91); 1.258 (1.52); 1.2445 (1.31); 1.2354 (2.36); 0.0079 (1.5); −0.0002 (37.15); −3.2871 (0.87) |
| 23-14 | 3,4-dichlorophenyl | CH2 | CH2 | — | H | compound No. 23-14, solvent: [DMSO], spectrometer: 399.95 MHz 8.4017 (1.01); 8.3886 (1.96); 8.3744 (1.08); 7.7614 (0.52); 7.5594 (5.74); 7.5492 (0.49); 7.5389 (6.81); 7.5281 (5.8); 7.5232 (5.72); 7.2553 (3.23); 7.2503 (3.09); 7.2382 (16); 7.2297 (2.73); 3.4901 (0.39); 3.4648 (2.16); 3.4478 (5.1); 3.4331 (5.43); 3.4161 (2.82); 3.3398 (844.78); 3.2759 (1.01); 3.2373 (0.37); 3.1759 (0.33); 2.8477 (0.4); 2.8323 (3.6); 2.8151 (7.12); 2.7978 (3.15); 2.7117 (1.08); 2.6761 (1.6); 2.6714 (2.17); 2.667 (1.53); 2.6622 (0.74); 2.5924 (0.4); 2.5873 (0.45); 2.5749 (0.5); 2.542 (235.81); 2.5245 (7.84); 2.5113 (134.34); 2.507 (263.42); 2.5025 (342.6); 2.498 (247.23); 2.4936 (119.52); 2.368 (1); 2.3335 (1.56); 2.3293 (2.16); 2.3248 (1.56); 2.0742 (0.7); 1.2346 (0.41); 0.0074 (0.4); −0.0002 (10.23); −0.0087 (0.32) |
| 23-15 | 3,5-dichlorophenyl | CH2 | CH2 | — | H | compound No. 23-16, solvent: [DMSO], spectrometer: 399.95 MHz8.4201 (1.05); 8.4067 (1.91); 8.3933 (1.06); 7.3474 (1.77); 7.3399 (0.51); 7.3274 (5.7); 7.3209 (5.13); 7.3166 (3.52); 7.3092 (4.57); 7.2827 (2.42); 7.2796 (3.41); 7.275 (2.72); 7.2628 (1.44); 7.2599 (1.79); 7.2548 (1.34); 7.2432 (16); 7.2187 (3.38); 7.2001 (2.39); 3.4617 (2.14); 3.4442 (4.72); 3.4297 (4.78); 3.4121 (2.62); 3.3445 (284.99); 2.8382 (3.58); 2.8205 (6.83); 2.8028 (3.26); 2.7121 (0.74); 2.6767 (0.55); 2.6721 (0.73); 2.6676 (0.55); 2.5699 (0.63); 2.5424 (172.33); 2.5118 (42); 2.5075 (83.31); 2.503 (108.79); 2.4985 (79.52); 2.4941 (39.13); 2.3684 (0.69); 2.3342 (0.48); 2.3297 (0.65); 2.3254 (0.48); −0.0002 (0.93) |
| | | | | | | compound No. 23-17, solvent: [DMSO], spectrometer: 399.95 MHz8.4666 (0.86); 8.4532 (1.56); 8.439 (0.83); 7.3365 (0.95); |

TABLE 23-continued
Compounds of the formula I-23
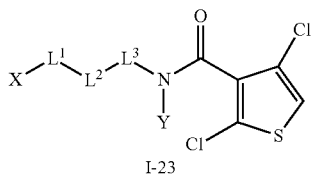
I-23
| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 7.3324 (1.16); 7.3179 (1.94); 7.3133 (2.38); 7.3015 (0.9); 7.2975 (1.57); 7.2942 (1.53); 7.2882 (0.79); 7.2833 (1.44); 7.2767 (1.07); 7.2686 (1.59); 7.2625 (2.46); 7.2588 (16); 7.2492 (1.12); 7.2447 (0.82); 7.1788 (1.48); 7.1763 (1.88); 7.1555 (3.77); 7.15 (1.8); 7.1393 (3.41); 7.1363 (3.04); 7.1328 (1.61); 7.1296 (1.3); 7.1209 (1.43); 7.1179 (1.19); 3.452 (1.75); 3.4347 (3.58); 3.4197 (3.43); 3.4167 (3.32); 3.4014 (2.25); 3.3411 (246.18); 2.8659 (2.58); 2.8478 (4.55); 2.8296 (2.28); 2.6762 (0.46); 2.6718 (0.63); 2.6672 (0.48); 2.5421 (6.08); 2.525 (2.41); 2.5118 (38.02); 2.5073 (76.27); 2.5027 (100.15); 2.4981 (72.48); 2.4936 (35.32); 2.334 (0.46); 2.3295 (0.64); 2.3247 (0.45); −0.0002 (0.9) |
| 23-16 | 3-chloro | CH2 | CH2 | — | H | compound No. 23-18, solvent: [DMSO], spectrometer: 399.95 MHz 8.5227 (0.93); 8.5081 (1.73); 8.4939 (0.91); 7.3651 (0.56); 7.3482 (1.24); 7.3442 (1.11); 7.3273 (2.36); 7.3102 (1.17); 7.3065 (1.52); 7.2897 (0.7); 7.2308 (16); 7.1022 (0.48); 7.0901 (3.28); 7.0702 (5.22); 7.0591 (0.71); 7.0501 (2.73); 7.0374 (0.36); 3.4202 (1.99); 3.4034 (4.4); 3.3873 (4.77); 3.3698 (4.01); 3.342 (300.48); 3.2921 (0.49); 2.8849 (2.46); 2.8675 (4.61); 2.85 (2.18); 2.6763 (0.54); 2.6718 (0.75); 2.6674 (0.55); 2.542 (4.42); 2.525 (2.8); 2.5118 (45.29); 2.5073 (89.72); 2.5028 (117.31); 2.4982 (85.04); 2.4937 (41.62); 2.3338 (0.53); 2.3295 (0.73); 2.3248 (0.55); −0.0002 (0.86) |
| 23-17 | 2-fluorophenyl | CH2 | CH2 | — | H | compound No. 23-19, solvent: [DMSO], spectrometer: 399.95 MHz 19.1408 (0.92); 8.5291 (1.11); 7.4714 (4.01); 7.4516 (5.66); 7.3073 (1.97); 7.2832 (6.17); 7.2679 (0.98); 4.87 (1.07); 4.3055 (0.96); 4.1606 (1.02); 3.7688 (1.03); 3.7288 (0.93); 3.679 (0.98); 3.6295 (1.15); 3.6029 (1.58); 3.562 (1.5); 3.5478 (1.61); 3.5279 (2.65); 3.4948 (2.73); 3.4749 (2.51); 3.4383 (7); 3.426 (6.9); 3.3432 (6877.18); 3.2793 (8.44); 3.2304 (3.47); 3.1713 (1.12); 3.1518 (2.19); 3.1353 (3.17); 3.1176 (2.28); 3.0968 (1.28); 3.0709 (1.46); 3.0604 (0.99); 3.0447 (1.06); 3.0289 (0.95); 2.9409 (1.13); 2.9204 (1.01); 2.9094 (0.93); 2.676 (11.25); 2.6716 (16); 2.6673 (11.67); 2.5964 (1.82); 2.5418 (69.55); 2.5246 (57.73); 2.5113 (953.34); 2.507 (1877.51); 2.5026 (2445.77); 2.4981 (1776.72); 2.4938 (872.51); 2.4384 (2.36); 2.391 (1.34); 2.3673 (1.3); 2.3339 (10.71); 2.3293 (14.87); 2.3247 (10.66); 2.2914 (1.5); 2.0737 (7.17); 1.2978 (0.92); 1.258 (1.34); 1.2356 (1.54); 0.008 (2.92); −0.0002 (64.72); −3.221 (0.96); −3.6597 (0.89) |
| 23-18 | 2,6-difluorophenyl | CH2 | CH2 | — | H | compound No. 23-20, solvent: [DMSO], spectrometer: 399.95 MHz 8.4219 (1.19); 8.4085 (2.09); 8.3958 (1.11); 7.5895 (4.83); 7.5614 (8.2); 7.5514 (5.36); 7.5414 (1.47); 7.5337 (1.06); 7.5255 (0.45); 7.5157 (0.64); 7.2556 (0.57); 7.2173 (16); 3.4981 (2.2); 3.4806 (5.45); 3.4663 (5.53); 3.4491 (2.6); 3.4265 (0.35); 3.3483 (224.96); 3.345 (258.95); 3.2753 (0.34); 2.9348 (3.91); 2.9175 (7.81); 2.9 (3.5); 2.7123 (0.85); 2.6767 |

TABLE 23-continued

Compounds of the formula I-23

![Structure of I-23: X-L¹-L²-L³-N(Y)-C(=O)-thiophene with 2,4-dichloro substituents]

| Ex. No. | X | L¹ | L² | L³ | Y | Physical data: ¹H-NMR, δ [ppm] or CAS or patent No. |
|---|---|---|---|---|---|---|
| | | | | | | (0.51); 2.6723 (0.71); 2.6678 (0.51); 2.5427 (207.19); 2.5255 (2.54); 2.5207 (3.65); 2.5122 (42.66); 2.5078 (86.35); 2.5032 (113.99); 2.4987 (83.14); 2.4942 (40.86); 2.3686 (0.89); 2.3344 (0.51); 2.3298 (0.74); 2.3255 (0.55); 2.0742 (0.65); −0.0002 (5.44) |
| 23-19 | 2,6-dichlorophenyl | CH2 | CH2 | — | H | compound No. 23-21, solvent: [DMSO], spectrometer: 399.95 MHz 8.4426 (1.18); 8.4297 (2.14); 8.4162 (1.14); 7.6703 (5.64); 7.6501 (6.81); 7.4832 (6.41); 7.4632 (5.29); 7.2564 (16); 3.495 (2.04); 3.4777 (4.73); 3.4629 (4.72); 3.4454 (2.22); 3.3365 (221.13); 3.2922 (0.48); 2.9255 (3.31); 2.9078 (6.22); 2.8902 (2.9); 2.6764 (0.5); 2.6717 (0.67); 2.6672 (0.48); 2.542 (10.39); 2.5246 (2.82); 2.5113 (42.35); 2.5071 (81.57); 2.5026 (105.26); 2.4981 (76.57); 2.4939 (37.93); 2.3336 (0.5); 2.3297 (0.66); 2.3249 (0.5); 2.0743 (0.47); −0.0002 (5.32) |
| 23-20 | 3-(trifluoromethyl)phenyl | CH2 | CH2 | — | H | compound No. 23-22, solvent: [DMSO], spectrometer: 399.95 MHz 8.4812 (0.55); 8.4674 (1); 8.454 (0.55); 7.297 (8.12); 7.1679 (1.34); 7.1555 (1.83); 7.1449 (3.91); 7.1376 (1.55); 7.1323 (1.02); 7.1269 (3.06); 7.1239 (3.17); 7.1136 (2.28); 7.1088 (1.22); 7.1027 (1.44); 3.3909 (1.3); 3.3756 (2.45); 3.3723 (2.32); 3.3672 (2.13); 3.3393 (135.72); 2.8204 (2.14); 2.8049 (1.7); 2.8006 (2.45); 2.7821 (1.9); 2.7118 (0.37); 2.6716 (0.39); 2.5611 (0.45); 2.5419 (85.03); 2.5248 (1.52); 2.5197 (2.26); 2.5115 (23.4); 2.5071 (46.59); 2.5026 (61.15); 2.498 (44.67); 2.4936 (22.22); 2.3681 (0.39); 2.3338 (0.33); 2.3292 (0.5); 2.3244 (0.49); 2.3117 (16); −0.0002 (3.22) |
| 23-21 | 4-(trifluoromethyl)phenyl | CH2 | CH2 | — | H | compound No. 23-23, solvent: [DMSO], spectrometer: 399.95 MHz 8.5693 (0.36); 8.5553 (0.7); 8.5404 (0.34); 7.347 (5.6); 6.8086 (3.84); 3.332 (151.28); 3.331 (153.07); 3.2272 (0.51); 3.2132 (0.83); 3.2085 (0.68); 3.1993 (0.82); 3.1923 (0.66); 3.1855 (0.88); 3.1717 (0.57); 2.7881 (1.05); 2.7749 (0.77); 2.7669 (1.01); 2.7613 (0.8); 2.7471 (0.84); 2.6753 (0.45); 2.6708 (0.63); 2.6664 (0.45); 2.5412 (3.48); 2.524 (2.48); 2.5108 (37); 2.5063 (73.94); 2.5018 (96.97); 2.4972 (69.95); 2.4926 (33.72); 2.3331 (0.46); 2.3285 (0.63); 2.3238 (0.46); 2.2873 (16); 2.1811 (6.78); −0.00022 (5.92) |
| 23-22 | 2-methylphenyl | CH2 | CH2 | — | H | compound No. 23-25, solvent: [DMSO], spectrometer: 399.95 MHz 8.4296 (0.87); 8.4161 (1.52); 8.4022 (0.85); 7.32 (2.13); 7.3161 (0.95); 7.3017 (5.36); 7.2883 (1.9); 7.2836 (5.53); 7.2716 (16); 7.2511 (4.62); 7.2472 (7.01); 7.2419 (1.67); 7.2277 (4.16); 7.2114 (1.12); 7.2062 (2.81); 7.2005 (0.7); 7.1921 (0.62); 7.1884 (0.99); 7.1849 (0.5); 3.4471 (2); 3.4294 (3.2); 3.415 (3.12); 3.4108 (3.25); 3.3959 (2.24); 3.3378 (122.84); 3.3346 (136.02); 3.3327 (135.44); 2.8256 (3.4); 2.8065 (4.9); 2.7886 (3.03); 2.6756 (0.49); 2.6711 (0.66); 2.6665 (0.49); 2.5414 (12.22); 2.5242 (2.74); 2.511 (39.9); 2.5065 (79.55); 2.502 (104.35); 2.4974 (75.24); 2.4928 (36.63); 2.3334 (0.48); 2.3287 (0.66); 2.324 (0.47); 2.074 (0.46); −0.0002 (6.11) |

TABLE 23-continued

Compounds of the formula I-23

I-23

| Ex. No. | X | L¹ | L² | L³ | Y | Physical data: $^1$H-NMR, δ [ppm] or CAS or patent No. |
|---|---|---|---|---|---|---|
| 23-23 | 2,4,6-trimethylphenyl | CH2 | CH2 | — | H | compound No. 23-12, solvent: [DMSO], spectrometer: 399.95 MHz<br>8.1803 (0.4); 8.1644 (0.81); 8.1492 (0.41); 7.5252 (2.25); 7.5195 (2.43); 7.4713 (1.46); 7.4496 (2.2); 7.3726 (1.46); 7.3667 (1.39); 7.351 (0.97); 7.3452 (0.92); 7.1644 (5.38); 3.7449 (2.75); 3.729 (2.72); 3.3766 (0.59); 3.3352 (262.2); 2.6755 (0.4); 2.6711 (0.56); 2.6669 (0.41); 2.5415 (52.18); 2.5244 (1.83); 2.511 (32.18); 2.5067 (65.15); 2.5021 (86.34); 2.4976 (63.79); 2.4932 (31.7); 2.3334 (0.38); 2.3289 (0.52); 2.3244 (0.38); 2.0742 (0.36); 1.4397 (16); −0.0002 (3.1) |
| 23-24 | 3,4-bismethoxyphenyl | CH2 | CH2 | — | H | compound No. 23-13, solvent: [DMSO], spectrometer: 399.95 MHz<br>15.3304 (0.91); 14.7843 (0.89); 8.4566 (1.23); 8.4447 (1.06); 7.8866 (0.91); 7.442 (2.27); 7.4235 (2.45); 7.4186 (2.68); 7.3595 (1.83); 7.3415 (2.82); 7.3077 (1.14); 7.2929 (2.85); 7.2887 (2.2); 7.2751 (14.86); 7.2598 (2.02); 7.2538 (1.87); 3.9437 (0.86); 3.7152 (1.16); 3.7111 (1.12); 3.6657 (1.33); 3.6279 (0.97); 3.6084 (1.08); 3.5888 (1.4); 3.5481 (1.58); 3.5292 (1.71); 3.4739 (3.46); 3.4572 (4.98); 3.4396 (5.96); 3.4243 (5.58); 3.3369 (4888.75); 3.2607 (2.51); 3.2253 (1.62); 3.2208 (1.54); 3.2035 (1.25); 3.1766 (0.88); 3.1355 (1.06); 3.0607 (1.03); 2.9574 (2.89); 2.9401 (4.58); 2.9213 (2.47); 2.7494 (1.02); 2.7109 (1.79); 2.6756 (11.72); 2.6711 (16); 2.6665 (11.63); 2.6487 (1.41); 2.6168 (1.28); 2.5979 (1.95); 2.5922 (1.93); 2.5414 (434.46); 2.5245 (53.58); 2.5111 (966.23); 2.5067 (1928.89); 2.5021 (2522.35); 2.4975 (1818.19); 2.493 (878.69); 2.4235 (1.24); 2.3848 (0.93); 2.3676 (1.3); 2.3334 (11.4); 2.3289 (15.19); 2.3244 (11.05); 2.2907 (1.19); 2.0739 (8.74); 1.4393 (0.91); 1.258 (1.52); 1.2445 (1.31); 1.2354 (2.36); 0.0079 (1.5); −0.0002 (37.15); −3.2871 (0.87) |
| 23-25 | phenyl | CH2 | CH2 | — | H | compound No. 23-14, solvent: [DMSO], spectrometer: 399.95 MHz<br>8.4017 (1.01); 8.3886 (1.96); 8.3744 (1.08); 7.7614 (0.52); 7.5594 (5.74); 7.5492 (0.49); 7.5389 (6.81); 7.5281 (5.8); 7.5232 (5.72); 7.2553 (3.23); 7.2503 (3.09); 7.2382 (16); 7.2297 (2.73); 3.4901 (0.39); 3.4648 (2.16); 3.4478 (5.1); 3.4331 (5.43); 3.4161 (2.82); 3.3398 (844.78); 3.2759 (1.01); 3.2373 (0.37); 3.1759 (0.33); 2.8477 (0.4); 2.8323 (3.6); 2.8151 (7.12); 2.7978 (3.15); 2.7117 (1.08); 2.6761 (1.6); 2.6714 (2.17); 2.667 (1.53); 2.6622 (0.74); 2.5924 (0.4); 2.5873 (0.45); 2.5749 (0.5); 2.542 (235.81); 2.5245 (7.84); 2.5113 (134.34); 2.507 (263.42); 2.5025 (342.6); 2.498 (247.23); 2.4936 (119.52); 2.368 (1); 2.3335 (1.56); 2.3293 (2.16); 2.3248 (1.56); 2.0742 (0.7); 1.2346 (0.41); 0.0074 (0.4); −0.0002 (10.23); −0.0087 (0.32) |
| 23-26 | 4-chlorophenyl | C(CH2-CH2) | CH2 | — | H | |
| 23-27 | 2,4-dichlorophenyl | C(CH2-CH2) | CH2 | — | H | |
| 23-28 | 4-chlorophenyl | CH2 | C(CH2-CH2) | — | H | |
| 23-29 | 2,4-dichlorophenyl | CH2 | C(CH2-CH2) | — | H | |
| 23-30 | 4-chlorophenyl | O | CH2 | CH2 | H | |
| 23-31 | 2,4-dichlorophenyl | O | CH2 | CH2 | H | |
| 23-32 | 4-chlorophenyl | CH2 | CH2 | CH2 | H | |
| 23-33 | 4-chlorophenyl | NCH3 | CH2 | CH2 | H | |

TABLE 23-continued

Compounds of the formula I-23

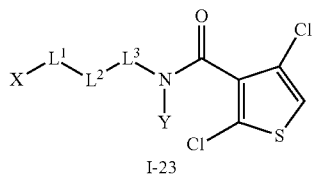

I-23

| Ex. No. | X | $L^1$ | $L^2$ | $L^3$ | Y | Physical data: $^1$H-NMR, δ [ppm] or CAS or patent No. |
|---|---|---|---|---|---|---|
| 23-34 | 2,4-dichlorophenyl | NCH3 | CH2 | CH2 | H | |
| 23-35 | 4-chlorophenyl | CH(OCH3) | CH2 | — | H | |
| 23-36 | 2,4-dichlorophenyl | CH(OCH3) | CH2 | — | H | |
| 23-37 | 2-thienyl | CH2 | CH2 | — | H | compound No. 23-37, solvent: [DMSO], spectrometer: 399.95 MHz 8.4975 (1.11); 8.4841 (1.96); 8.472 (1.09); 7.3549 (3.89); 7.3518 (3.79); 7.3421 (4.28); 7.3392 (3.91); 7.3007 (16); 6.9718 (2.98); 6.9632 (4.29); 6.9591 (2.89); 6.9505 (4); 6.9227 (4.15); 6.9144 (3); 3.4638 (2.26); 3.446 (5); 3.4315 (5.19); 3.4138 (2.67); 3.3944 (0.51); 3.3382 (270.42); 3.0456 (4.16); 3.0277 (7.37); 3.0099 (3.45); 2.7121 (0.82); 2.6758 (0.55); 2.6714 (0.73); 2.6673 (0.53); 2.5416 (179.54); 2.5249 (3.15); 2.5111 (46.29); 2.507 (88.09); 2.5025 (112.01); 2.4981 (80.99); 2.3682 (0.83); 2.3338 (0.53); 2.3293 (0.73); 2.325 (0.52); 2.074 (0.47); −0.0002 (5.87) |
| 23-38 | 3-thienyl | CH2 | CH2 | — | H | |
| 23-39 | 2-furyl | CH2 | CH2 | — | H | |
| 23-40 | 3-furyl | CH2 | CH2 | — | H | |
| 23-41 | phenyl | CH2 | CH2 | CH(CH3) | H | |
| 23-42 | phenyl | CH2 | CH2 | CH2 | H | |
| 23-43 | 2-Cl-phenyl | CH2 | CH2 | CH(CH3) | H | |
| 23-44 | 4-t-butylphenyl | CH2 | CH2 | CH2 | H | |
| 23-45 | 4-methylphenyl | CH2 | CH2 | CH2 | H | |
| 23-46 | phenyl | CH2 | CH2 | CH(CH2CH3) | H | |
| 23-47 | 2-methoxyphenyl | CH2 | CH2 | CH2 | H | |
| 23-48 | 2-methylphenyl | CH2 | CH2 | CH2 | H | |
| 23-49 | 3-methylphenyl | CH2 | CH2 | CH2 | H | |
| 23-50 | 3-chlorophenyl | CH2 | CH2 | CH2 | H | |
| 23-51 | 2,6-difluorophenyl | CH2 | CH2 | CH2 | H | |
| 23-52 | 4-chlorophenyl | CH2 | CH2 | CH2 | H | |
| 23-53 | 2,6-dichlorophenyl | CH2 | CH2 | CH(CH3) | H | |
| 23-54 | 3,5-dichlorophenyl | CH2 | CH2 | CH(CH3) | H | |
| 23-55 | 2,6-dimethylphenyl | CH2 | CH2 | CH2 | H | |
| 23-56 | 2,5-dichlorophenyl | CH2 | CH2 | CH2 | H | |
| 23-57 | 4-isopropoxyphenyl | CH2 | CH2 | CH2 | H | |
| 23-58 | 3-trifluoromethylphenyl | CH2 | CH2 | CH(CH3) | H | |
| 23-59 | 4-methylphenyl | CH2 | CH2 | CH(CH3) | H | |
| 23-60 | 2-methylphenyl | CH2 | CH2 | CH(CH3) | H | |
| 23-61 | 3,4-dichlorophenyl | CH2 | CH2 | CH(CH3) | H | |
| 23-62 | 3,5-dichlorophenyl | CH2 | CH2 | CH2 | H | |
| 23-63 | 2,6-dimethylphenyl | CH2 | CH2 | CH(CH3) | H | |
| 23-64 | 4-trifluoromethylphenyl | CH2 | CH2 | CH(CH3) | H | |
| 23-65 | 2,5-dichlorophenyl | CH2 | CH2 | CH(CH3) | H | |
| 23-66 | 4-phenoxyphenyl | CH2 | CH2 | CH2 | H | |
| 23-67 | 3-chlorophenyl | CH2 | CH2 | CH(CH3) | H | |
| 23-68 | 4-phenoxyphenyl | CH2 | CH2 | CH(CH3) | H | |
| 23-69 | 2,4-dichlorophenyl | CH2 | CH2 | CH(CH3) | H | |
| 23-70 | 2-difluoromethoxyphenyl | CH2 | CH2 | CH(CH3) | H | |
| 23-71 | 4-methoxyphenyl | CH2 | CH2 | CH2 | H | |
| 23-72 | 4-chlorophenyl | CH2 | CH2 | CH(CH3) | H | |
| 23-73 | 4-chlorophenyl | CH2 | CH2 | CH(i-propyl) | H | |
| 23-74 | 4-fluorophenyl | CH2 | CH2 | CH2 | H | |
| 23-75 | 4-chlorophenyl | CH2 | CH2 | CH(n-propyl) | H | |
| 23-76 | 4-chlorophenyl | CH2 | CH2 | CH(t-butyl) | H | |
| 23-77 | 2-chlorophenyl | CH2 | CH2 | CH2 | H | |
| 23-78 | 4-chlorophenyl | CH(CF3) | CH2 | — | H | compound No. 23-78, solvent: [DMSO], spectrometer: 399.95 MHz8.5276 (1.42); 8.5134 (2.6); 8.4994 (1.44); 7.4844 (5.04); 7.4793 (2.2); 7.4681 (3.4); 7.4628 (14.97); 7.4396 (11.51); 7.418 (4.25); 7.3903 (0.52); 7.1454 (16); 4.0563 (1.04); 4.0384 (3.55); 4.0207 (3.69); 4.0141 (1.46); 4.0026 (1.91); 3.9903 (1.1); 3.9757 (1.03); 3.9666 (0.39); |

TABLE 23-continued

Compounds of the formula I-23

I-23

| Ex. No. | X | L¹ | L² | L³ | Y | Physical data: $^1$H-NMR, δ [ppm] or CAS or patent No. |
|---|---|---|---|---|---|---|
| | | | | | | 3.8754 (1.03); 3.8618 (1.75); 3.8479 (1.12); 3.8413 (1.72); 3.8277 (2.63); 3.8139 (1.32); 3.7372 (1.46); 3.7211 (1.66); 3.7147 (1.44); 3.7029 (1.39); 3.6988 (1.57); 3.6872 (1.08); 3.6805 (0.98); 3.6645 (0.84); 3.3233 (20.51); 2.6714 (0.38); 2.5247 (1.29); 2.5111 (22.28); 2.5069 (43.47); 2.5024 (56.41); 2.4979 (41.12); 2.4936 (20.4); 2.3292 (0.35); 1.9894 (11.92); 1.3361 (0.65); 1.2491 (0.63); 1.1929 (3.24); 1.1751 (6.4); 1.1572 (3.15); 0.0079 (0.43); −0.0002 (11.12); −0.0085 (0.43) |

TABLE 24

Compounds of the formula I-24

I-24

| Ex. No. | X | L¹ | L² | L³ | Y | Physical data: $^1$H-NMR, δ [ppm] or CAS or patent No. |
|---|---|---|---|---|---|---|
| 24-1 | 4-chlorophenyl | CH2 | CH2 | — | H | compound No. 24-1, solvent: [DMSO], spectrometer: 399.95 MHz<br>8.6018 (1.23); 8.5881 (2.29); 8.5742 (1.19); 8.3155 (0.44); 7.802 (5.99); 7.789 (6.33); 7.4795 (2.37); 7.363 (1.02); 7.3567 (8.04); 7.3518 (3.4); 7.3466 (7.6); 7.3407 (8.93); 7.3354 (16); 7.2709 (1.7); 7.265 (10.87); 7.2603 (3.25); 7.2485 (2.58); 7.244 (6.87); 7.202 (2.52); 4.0379 (0.79); 4.0201 (0.82); 3.4588 (2.1); 3.4416 (4.42); 3.4268 (4.35); 3.4087 (2.3); 3.322 (68.28); 2.8414 (4.01); 2.8233 (7.02); 2.8055 (3.57); 2.6754 (0.49); 2.6708 (0.67); 2.6663 (0.49); 2.5241 (2.39); 2.5107 (38.3); 2.5063 (75.73); 2.5017 (98.94); 2.4972 (71.15); 2.4927 (34.13); 2.3328 (0.48); 2.3285 (0.66); 2.3239 (0.47); 1.9887 (3.59); 1.2494 (0.36); 1.1927 (0.97); 1.1749 (1.9); 1.1571 (0.94); 0.0079 (1.73); −0.0002 (46.38); −0.0085 (1.59) |
| 24-2 | 2,4-dichlorophenyl | CH2 | CH2 | — | H | compound No. 24-2, solvent: [DMSO], spectrometer: 399.95 MHz<br>8.6278 (1.72); 8.614 (3.26); 8.6001 (1.7); 7.8031 (6.94); 7.7901 (7.4); 7.5858 (6.65); 7.5818 (7.02); 7.4757 (2.83); 7.3787 (1.43); 7.3743 (1.11); 7.358 (9.35); 7.3502 (16); 7.3352 (11.46); 7.1982 (3); 6.5736 (1.09); 4.056 (0.95); 4.0383 (2.93); 4.0205 (2.96); 4.0027 (1); 3.4908 (2.48); 3.4738 (6.47); 3.4586 (6.59); 3.4419 (2.74); 3.3238 (55.1); 2.9641 (5.24); 2.9469 (10.17); 2.9296 (4.56); 2.6759 (0.35); 2.6714 (0.49); 2.6669 (0.37); 2.5068 (55.97); 2.5024 (72.04); 2.498 (53.39); 2.3334 (0.35); 2.3293 (0.47); 2.3246 (0.36); 1.9891 (12.66); 1.336 (1.08); 1.2494 (1.23); 1.2357 (0.52); 1.1932 (3.39); 1.1754 (6.64); 1.1576 (3.31); 0.007 (1.49); −0.0002 (29.67); −0.0083 (1.14) |

TABLE 24-continued

Compounds of the formula I-24

I-24

| Ex. No. | X | L¹ | L² | L³ | Y | Physical data: ¹H-NMR, δ [ppm] or CAS or patent No. |
|---|---|---|---|---|---|---|
| 24-3 | 4-chlorophenyl | CH(CH3) | CH2 | — | H | compound No. 24-3, solvent: [DMSO], spectrometer: 399.95 MHz<br>8.5559 (1.46); 8.5421 (2.72); 8.5282 (1.43); 8.3164 (0.36); 7.7816 (6.22); 7.7687 (6.55); 7.4071 (2.5); 7.361 (7.75); 7.3564 (3.12); 7.3447 (4.12); 7.3398 (13.66); 7.3338 (2.76); 7.3284 (7.16); 7.3154 (6.56); 7.2825 (12.61); 7.2679 (7.05); 7.2613 (7.73); 7.1296 (2.65); 6.5742 (1.02); 4.0563 (0.82); 4.0385 (2.48); 4.0207 (2.49); 4.0029 (0.84); 3.4041 (0.39); 3.3888 (0.49); 3.3844 (0.57); 3.371 (2.43); 3.3568 (3.62); 3.3517 (3.53); 3.3445 (3.48); 3.3413 (3.79); 3.3368 (3.64); 3.3242 (30.15); 3.309 (0.73); 3.2946 (0.45); 3.0927 (1.33); 3.0748 (2.53); 3.0568 (2.41); 3.0387 (1.15); 2.6715 (0.35); 2.5112 (21.26); 2.5069 (40.11); 2.5024 (51.39); 2.4979 (37.55); 2.4937 (18.75); 2.329 (0.33); 1.9891 (10.58); 1.3365 (0.37); 1.2494 (0.52); 1.2165 (16); 1.199 (15.75); 1.1933 (4.88); 1.1752 (5.71); 1.1574 (2.85); 0.0077 (1.13); −0.0002 (23.1); −0.0083 (0.95) |
| 24-4 | 2,4-dichlorophenyl | CH(CH3) | CH2 | — | H | compound No. 24-4, solvent: [DMSO], spectrometer: 399.95 MHz<br>8.7041 (2.05); 8.6909 (3.89); 8.6777 (2.01); 7.8323 (8.98); 7.8194 (9.47); 7.5715 (10.01); 7.5651 (10.66); 7.5505 (3.72); 7.4119 (7.89); 7.3842 (5.24); 7.3778 (5.14); 7.3672 (10.53); 7.3621 (7.84); 7.3549 (14.23); 7.2732 (3.88); 7.2404 (11.25); 7.2182 (8.36); 4.2266 (6.05); 4.212 (13.59); 4.1974 (6.57); 4.0559 (1.21); 4.0382 (3.71); 4.0203 (3.74); 4.0026 (1.25); 3.6341 (3.37); 3.6199 (9.51); 3.6057 (9.19); 3.5912 (3.13); 3.3231 (95.29); 2.6758 (0.64); 2.6712 (0.88); 2.6665 (0.65); 2.5243 (3.04); 2.511 (50.26); 2.5067 (98.59); 2.5022 (128.65); 2.4976 (93.43); 2.4932 (45.66); 2.3378 (0.32); 2.3333 (0.62); 2.3289 (0.86); 2.3244 (0.64); 1.989 (16); 1.3361 (0.39); 1.2495 (0.54); 1.1929 (4.3); 1.1751 (8.52); 1.1573 (4.17); 0.0079 (2.1); −0.0002 (54.16); −0.0085 (2.01) |
| 24-5 | 4-chlorophenyl | CH2 | CH(CH3) | — | H | compound No. 24-5, solvent: [DMSO], spectrometer: 399.95 MHz<br>8.4374 (2.62); 8.416 (2.65); 7.7917 (5.93); 7.7788 (6.24); 7.5632 (5.66); 7.5596 (5.45); 7.356 (0.94); 7.3351 (16); 7.3306 (8.14); 7.3206 (8.89); 7.3077 (6.33); 7.1817 (4.77); 7.0429 (2.38); 6.5736 (0.8); 4.3328 (0.51); 4.3112 (1.16); 4.2954 (1.47); 4.2803 (1.13); 4.2589 (0.54); 3.323 (43.65); 2.9677 (1.22); 2.954 (1.4); 2.9336 (3.47); 2.92 (3.2); 2.9025 (3.23); 2.8909 (0.69); 2.8803 (3.05); 2.8685 (1.27); 2.8463 (1.25); 2.6757 (0.32); 2.6714 (0.44); 2.6667 (0.34); 2.511 (26.45); 2.5068 (51.4); 2.5023 (66.93); 2.4978 (48.86); 2.4935 (24.19); 2.3333 (0.33); 2.3289 (0.44); 2.3246 (0.32); 1.989 (0.37); 1.2496 (0.43); 1.2182 (14.12); 1.2015 (13.92); 0.0079 (1.18); −0.0002 (28.35); −0.0085 (1.04) |
| 24-6 | 4-chlorophenyl | C(CH3)2 | CH2 | — | H | compound No. 24-6, solvent: [DMSO], spectrometer: 399.95 MHz<br>8.3673 (0.39); 8.3518 (0.77); 8.3362 (0.39); 7.7812 (1.95); 7.7682 (2.08); 7.4274 (2.01); 7.4223 (0.79); 7.411 (1.09); 7.4056 (4.35); 7.3995 (0.66); 7.372 (0.67); 7.3659 (4.47); 7.3605 (1.16); 7.3493 (0.84); 7.3441 (2.2); 7.317 (2.17); 7.3093 (0.93); 7.3042 (2.1); 7.1706 (1.64); 7.0318 (0.8); 6.5735 (0.4); 4.0558 (0.42); 4.038 (1.26); 4.0202 (1.28); 4.0024 (0.43); 3.4097 (2.7); 3.3939 (2.69); 3.3224 (17.03); 2.524 (0.59); 2.5107 (9.78); 2.5063 (19.27); 2.5018 (25.15); 2.4972 (18.14); 2.4928 (8.75); 1.9888 (5.57); 1.285 (16); 1.1928 (1.52); 1.175 (2.97); |

TABLE 24-continued

Compounds of the formula I-24

I-24

| Ex. No. | X | L¹ | L² | L³ | Y | Physical data: ¹H-NMR, δ [ppm] or CAS or patent No. |
|---|---|---|---|---|---|---|
| | | | | | | 1.1572 (1.55); 0.0079 (0.46); −0.0002 (11.85); −0.0085 (0.4) |
| 24-7 | 2,4-dichlorophenyl | C(CH3)2 | CH2 | — | H | compound No. 24-7, solvent: [DMSO], spectrometer: 399.95 MHz 8.6818 (2.47); 8.6684 (4.54); 8.6551 (2.47); 7.8185 (12.63); 7.8055 (13.48); 7.5222 (5.31); 7.3835 (11.22); 7.3606 (14.19); 7.3533 (9.67); 7.3499 (12.63); 7.3478 (14.63); 7.3406 (9.98); 7.3376 (9.68); 7.2448 (5.58); 6.9705 (7.5); 6.962 (10.13); 6.9578 (7.23); 6.9493 (9.69); 6.9132 (8.67); 6.9111 (8.98); 6.9049 (6.64); 6.9028 (6.39); 3.4816 (4.69); 3.4639 (10.68); 3.4495 (10.85); 3.4317 (5.5); 3.323 (63.7); 3.0708 (8.93); 3.053 (16); 3.0351 (7.52); 2.6751 (0.55); 2.6707 (0.75); 2.6662 (0.55); 2.524 (2.42); 2.5106 (44.14); 2.5062 (87.93); 2.5016 (115.1); 2.4971 (82.78); 2.4926 (39.78); 2.3329 (0.56); 2.3284 (0.78); 2.3239 (0.56); 1.9886 (0.37); 1.336 (0.78); 1.2495 (0.91); 0.0079 (1.91); −0.0002 (52.82); −0.0085 (1.77) |
| 24-8 | 3,4-dichlorophenyl | CH2 | CH2 | — | H | compound No. 24-8, solvent: [DMSO], spectrometer: 399.95 MHz 8.5603 (1.57); 8.5466 (2.85); 8.5332 (1.49); 7.8117 (7.45); 7.7988 (7.82); 7.5533 (3.12); 7.4145 (6.59); 7.383 (0.33); 7.3533 (8.98); 7.3443 (10.3); 7.3402 (11.18); 7.3284 (4.49); 7.3234 (16); 7.3174 (2.28); 7.2755 (3.63); 7.2625 (13.91); 7.2414 (8.3); 4.038 (0.69); 4.0202 (0.69); 3.3222 (73.2); 3.2429 (2.71); 3.2257 (5.62); 3.2107 (5.55); 3.1934 (2.74); 2.6754 (0.68); 2.6709 (0.87); 2.6663 (0.65); 2.6258 (4.78); 2.6071 (7.35); 2.5876 (5.16); 2.524 (3.12); 2.5107 (48.34); 2.5063 (94.42); 2.5018 (122.69); 2.4973 (88.21); 2.4928 (42.39); 2.333 (0.58); 2.3286 (0.78); 2.3239 (0.57); 2.0667 (0.33); 1.9888 (2.99); 1.8358 (1.44); 1.8169 (3.97); 1.7987 (5.37); 1.7803 (3.69); 1.7621 (1.23); 1.4369 (0.46); 1.3357 (0.39); 1.2492 (0.46); 1.1927 (0.84); 1.175 (1.59); 1.1571 (0.8); 0.0079 (2.04); −0.0002 (52.95); −0.0085 (1.83) |
| 24-9 | 2-thienyl | CH2 | CH2 | — | H | compound No. 24-9, solvent: [DMSO], spectrometer: 399.95 MHz 8.3776 (0.43); 8.3623 (0.86); 8.3468 (0.43); 7.7684 (2); 7.7554 (2.12); 7.5356 (2.22); 7.5299 (2.35); 7.458 (1.47); 7.4363 (2.41); 7.3765 (1.58); 7.3707 (1.47); 7.3549 (0.98); 7.3491 (0.92); 7.3056 (2.23); 7.2926 (2.88); 7.1534 (1.71); 7.0145 (0.83); 6.5739 (0.4); 4.0563 (0.37); 4.0385 (1.12); 4.0207 (1.13); 4.0029 (0.38); 3.7595 (2.82); 3.7437 (2.79); 3.323 (9.07); 2.5246 (0.44); 2.5113 (7.45); 2.5069 (14.54); 2.5024 (18.86); 2.4979 (13.64); 2.4936 (6.65); 1.9892 (4.77); 1.5663 (0.69); 1.4346 (16); 1.1932 (1.33); 1.1754 (2.52); 1.1576 (1.26); 0.0078 (0.35); −0.0002 (8.32) |
| 24-10 | 2-chlorophenyl | CH2 | CH2 | CH2 | H | compound No. 24-10, solvent: [DMSO], spectrometer: 399.95 MHz 8.5971 (2.38); 8.5836 (4.51); 8.5697 (2.35); 7.8061 (10.93); 7.7931 (11.58); 7.7602 (0.42); 7.5523 (12.57); 7.5418 (0.63); 7.5318 (14.42); 7.5155 (11.52); 7.5106 (11.72); 7.4655 (4.46); 7.3466 (12.14); 7.3336 (12.09); 7.3268 (9.98); 7.2402 (6.79); 7.2352 (6.52); 7.2196 (5.99); 7.2146 (5.76); 7.1879 (4.76); 4.0564 (1.19); 4.0386 (3.65); 4.0208 (3.7); 4.003 (1.25); 3.4818 (3.86); 3.4647 (9.81); 3.4501 (10.06); 3.4331 (4.21); 3.3242 (46.13); 2.8593 (7.42); 2.8421 (14.89); 2.8247 (6.67); 2.6767 (0.51); 2.6718 (0.63); 2.6674 (0.46); 2.5415 (0.36); 2.5251 (1.98); 2.5117 (35.85); 2.5073 (69.98); |

TABLE 24-continued

Compounds of the formula I-24

I-24

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | 2.5028 (90.41); 2.4982 (64.7); 2.4938 (30.93); 2.334 (0.42); 2.3295 (0.57); 2.3251 (0.42); 1.9894 (16); 1.3366 (0.65); 1.2497 (0.78); 1.1932 (4.36); 1.1754 (8.58); 1.576 (4.22); 0.0079 (1.68); −0.0002 (42.76); −0.0085 (1.37) |
| 24-11 | 2,4-dichlorophenyl | CH2 | CH2 | CH2 | H | compound No. 24-11, solvent: [DMSO], spectrometer: 399.95 MHz 8.6095 (2.34); 8.5955 (4.48); 8.582 (2.35); 8.3162 (0.49); 7.8169 (11.27); 7.8039 (11.94); 7.5563 (4.65); 7.4997 (11.61); 7.4932 (12.31); 7.4605 (11.84); 7.4391 (15.84); 7.4175 (10.11); 7.3586 (12.53); 7.3456 (11.93); 7.3355 (0.47); 7.322 (8.17); 7.3154 (7.79); 7.3006 (6.11); 7.2941 (5.8); 7.2787 (4.99); 6.5741 (1.68); 4.0563 (1.21); 4.0385 (3.67); 4.0207 (3.69); 4.0029 (1.25); 3.3231 (73.71); 3.2869 (3.83); 3.2699 (9.1); 3.255 (9.1); 3.238 (3.93); 2.7451 (7.06); 2.7264 (9.23); 2.7065 (7.58); 2.6807 (0.4); 2.6763 (0.71); 2.6716 (0.94); 2.6671 (0.69); 2.5419 (0.61); 2.5249 (2.86); 2.5115 (51.05); 2.5071 (101.32); 2.5026 (132.53); 2.498 (95.7); 2.4936 (46.22); 2.3338 (0.63); 2.3293 (0.84); 2.3249 (0.62); 1.9893 (16); 1.8444 (2.01); 1.8263 (5.62); 1.8075 (7.18); 1.7888 (5.26); 1.7709 (1.74); 1.3363 (0.79); 1.2495 (0.93); 1.1932 (4.29); 1.1878 (0.55); 1.1754 (8.44); 1.1576 (4.18); 0.0079 (2.2); −0.0002 (60.79); −0.0085 (2.02) |
| 24-12 | 2,4-dichlorophenyl | O | CH2 | CH2 | H | compound No. 24-12, solvent: [DMSO], spectrometer: 399.95 MHz 8.7049 (1.93); 8.6916 (3.77); 8.6782 (1.93); 8.3163 (0.55); 7.8328 (9.47); 7.8198 (10.06); 7.5718 (11.35); 7.5653 (12.08); 7.5587 (0.62); 7.551 (3.77); 7.4124 (8.13); 7.3844 (5.74); 7.378 (5.44); 7.3677 (10.83); 7.3623 (8.3); 7.3554 (15.58); 7.2738 (4); 7.2407 (11.98); 7.2184 (8.89); 4.2271 (6.07); 4.2124 (13.83); 4.1979 (6.63); 4.0561 (1.18); 4.0383 (3.64); 4.0205 (3.67); 4.0028 (1.23); 3.6346 (3.3); 3.6204 (9.39); 3.6062 (9.09); 3.5918 (3.08); 3.3238 (75.44); 2.676 (0.47); 2.6715 (0.66); 2.6669 (0.48); 2.5248 (2.05); 2.5199 (3.2); 2.5114 (38.35); 2.507 (76.68); 2.5024 (100.32); 2.4978 (71.87); 2.4933 (34.39); 2.3337 (0.49); 2.3292 (0.67); 2.3246 (0.49); 1.9893 (16); 1.3363 (0.46); 1.2495 (0.59); 1.193 (4.26); 1.1752 (8.46); 1.1574 (4.16); 0.0079 (1.73); −0.0002 (48.37); −0.0085 (1.56) |

TABLE 25

Compounds of the formula I-25

I-25

| Ex. No. | X | $L^1$ | $L^2$ | $L^3$ | Y | Physical data: $^1$H-NMR, δ [ppm] or CAS or patent No. |
|---|---|---|---|---|---|---|
| 25-1 | 4-chlorophenyl | CH2 | CH2 | — | H | compound No. 25-1, solvent: [DMSO], spectrometer: 399.95 MHz |

TABLE 25-continued
Compounds of the formula I-25
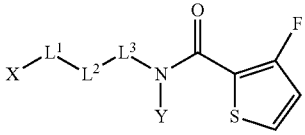
I-25
| Ex. No. | X | L¹ | L² | L³ | Y | Physical data: $^1$H-NMR, δ [ppm] or CAS or patent No. |
|---|---|---|---|---|---|---|
| | | | | | | 7.9396 (1.73); 7.9311 (1.73); 7.7686 (4.15); 7.7583 (4.54); 7.7548 (4.19); 7.7446 (3.91); 7.365 (1.08); 7.3586 (9.94); 7.3537 (3.55); 7.3426 (4.21); 7.3375 (16); 7.3314 (2.15); 7.2699 (2.33); 7.2639 (13.49); 7.2589 (3.78); 7.2476 (3.25); 7.2428 (8.57); 7.2365 (0.98); 7.0835 (9.5); 7.0697 (9.18); 6.5721 (0.36); 5.7547 (1.61); 3.5072 (0.68); 3.476 (2.67); 3.4593 (5.26); 3.4407 (5.18); 3.425 (2.98); 3.41 (0.77); 3.3553 (461.2); 3.2932 (0.55); 2.8362 (5.17); 2.8174 (7.81); 2.7996 (4.57); 2.6778 (0.41); 2.6732 (0.57); 2.6687 (0.41); 2.5263 (1.92); 2.5216 (2.98); 2.5132 (32.03); 2.5087 (63.88); 2.5041 (83.46); 2.4995 (59.25); 2.4949 (27.68); 2.4805 (0.37); 2.3353 (0.41); 2.3308 (0.55); 2.3262 (0.38); 1.3357 (0.55); 1.2491 (0.75); 1.2344 (0.65); 0.0079 (2.41); −0.0002 (65.23); −0.0086 (1.89) |
| 25-2 | 2,4-dichlorophenyl | CH2 | CH2 | — | H | compound No. 25-2, solvent: [DMSO], spectrometer: 399.95 MHz 8.0023 (2.51); 7.9943 (2.51); 7.7674 (5.03); 7.7572 (5.61); 7.7536 (5.21); 7.7434 (4.71); 7.5816 (8.7); 7.5771 (9.04); 7.3837 (2.16); 7.379 (1.59); 7.3631 (11.86); 7.3583 (13.1); 7.3537 (16); 7.3331 (2.5); 7.0815 (11.78); 7.0677 (11.39); 5.7565 (4.11); 3.5066 (3.17); 3.4897 (7.56); 3.4738 (7.79); 3.4568 (3.54); 3.3451 (371.93); 3.3111 (0.64); 3.298 (0.43); 2.9592 (7); 2.9415 (12.52); 2.9239 (6.12); 2.6778 (0.37); 2.6734 (0.5); 2.6689 (0.36); 2.5265 (1.86); 2.5132 (30.07); 2.5088 (58.71); 2.5043 (75.77); 2.4997 (53.82); 2.4952 (25.54); 2.3356 (0.35); 2.3311 (0.47); 2.3263 (0.33); 0.0079 (2.13); −0.0002 (51.9); −0.0085 (1.6) |
| 25-3 | 4-chlorophenyl | CH2 | CH2 | CH2 | H | compound No. 25-3, solvent: [DMSO], spectrometer: 399.95 MHz 7.9346 (2.57); 7.9275 (2.56); 7.7655 (6.73); 7.7552 (7.31); 7.7516 (6.79); 7.7414 (6.4); 7.2983 (5.13); 7.2944 (2.15); 7.2798 (13.24); 7.2661 (4.1); 7.2616 (12.84); 7.2272 (11.38); 7.2234 (16); 7.2182 (3.44); 7.2065 (8.26); 7.1937 (3.37); 7.1902 (4.43); 7.1867 (2.31); 7.177 (2.56); 7.1724 (6.78); 7.1671 (1.63); 7.1581 (1.5); 7.1545 (2.44); 7.1511 (1.21); 7.087 (14.65); 7.0798 (0.7); 7.0732 (14.16); 3.3639 (0.46); 3.334 (204.28); 3.3181 (0.97); 3.2764 (3.94); 3.2597 (7.93); 3.243 (7.99); 3.2262 (4.18); 2.6764 (0.38); 2.6719 (0.52); 2.6673 (0.38); 2.6238 (7.6); 2.605 (10.83); 2.5854 (8.23); 2.5253 (1.44); 2.5204 (2.26); 2.5119 (27.96); 2.5074 (56.26); 2.5028 (73.75); 2.4982 (52.42); 2.4936 (24.58); 2.3341 (0.34); 2.3296 (0.46); 2.3248 (0.34); 1.8486 (2.51); 1.8294 (5.98); 1.8112 (8.35); 1.7927 (5.49); 1.7743 (2.18); 1.2492 (0.35); 0.0079 (1.87); −0.0002 (54.32); −0.0086 (1.6) |
| 25-4 | 2,4-dichlorophenyl | CH2 | CH2 | CH2 | H | compound No. 25-4, solvent: [DMSO], spectrometer: 399.95 MHz 7.9777 (2.85); 7.97 (2.81); 7.7691 (6.85); 7.7588 (7.37); 7.7553 (6.95); 7.745 (6.32); 7.7385 (0.53); 7.7343 (0.34); 7.7259 (0.51); 7.5633 (12.59); 7.5581 (12.78); 7.4329 (0.66); 7.4243 (7.37); 7.4036 (16); 7.3885 (0.4); 7.3741 (11.44); 7.3687 (10.37); 7.3595 (0.65); 7.3534 (5.03); 7.348 (4.95); 7.3385 (0.64); 7.3173 (0.85); 7.2599 (0.75); 7.2385 (0.4); 7.1372 (0.36); 7.0892 (15.24); 7.0823 (0.7); 7.0754 (14.69); 5.7565 (2.13); 3.4518 (0.35); 3.4312 (0.46); 3.422 (0.45); 3.4075 (0.72); 3.3843 (1.64); 3.3486 (493.97); 3.3207 (0.96); 3.3158 (1.08); 3.2995 (3.77); 3.2827 (8.56); 3.2668 (8.42); 3.2499 (3.93); 3.2301 (0.36); 2.742 (0.58); 2.7267 (7.48); 2.7082 |

TABLE 25-continued

Compounds of the formula I-25

I-25

| Ex. No. | X | $L^1$ | $L^2$ | $L^3$ | Y | Physical data: $^1$H-NMR, δ [ppm] or CAS or patent No. |
|---|---|---|---|---|---|---|
| | | | | | | (9.17); 2.6882 (7.67); 2.674 (0.81); 2.6694 (0.55); 2.6004 (0.42); 2.5804 (0.33); 2.5443 (0.47); 2.5272 (2.35); 2.5225 (3.46); 2.514 (37.08); 2.5095 (74.41); 2.5049 (97.4); 2.5002 (69.34); 2.4957 (32.5); 2.3362 (0.43); 2.3315 (0.6); 2.3271 (0.43); 1.8267 (2.3); 1.808 (5.65); 1.7897 (7.33); 1.7714 (5.07); 1.753 (1.8); 1.3364 (0.47); 1.2584 (0.33); 1.2492 (0.69); 0.1459 (0.33); 0.0079 (2.84); −0.0002 (79.17); −0.0086 (2.31) |

TABLE 26

Compounds of the formula I-26

I-26

| Ex. No. | X | $L^1$ | $L^2$ | $L^3$ | Y | Physical data: $^1$H-NMR, δ [ppm] or CAS or patent No. |
|---|---|---|---|---|---|---|
| 26-1 | 2,4-dichlorophenyl | CH2 | CH2 | — | H | compound No. 26-1, solvent: [DMSO], spectrometer: 399.95 MHz 8.6356 (1.81); 8.6217 (3.48); 8.6076 (1.81); 8.0013 (8.12); 7.9979 (8.15); 7.5901 (8.38); 7.5858 (8.97); 7.3883 (2.12); 7.3837 (1.45); 7.3676 (13.18); 7.3629 (15.31); 7.3594 (16); 7.3463 (0.38); 7.3393 (2.12); 6.9491 (6.58); 6.9467 (8.59); 6.9444 (8.51); 6.9422 (6.61); 3.4761 (3.16); 3.459 (7.5); 3.4439 (7.54); 3.4265 (3.54); 3.3616 (0.46); 3.334 (191.59); 3.3173 (1.15); 2.9412 (6.66); 2.9235 (12.39); 2.906 (5.9); 2.6728 (0.45); 2.5262 (1.26); 2.5215 (1.88); 2.5128 (25.55); 2.5083 (52.22); 2.5037 (68.89); 2.4991 (49.05); 2.4945 (23.19); 2.335 (0.33); 2.3304 (0.46); 2.3259 (0.32); 1.3365 (0.41); 1.2495 (0.54); 0.008 (0.8); −0.0002 (26.28); −0.0085 (0.81) |
| 26-2 | 4-chlorophenyl | CH2 | CH2 | — | H | compound No. 26-2, solvent: [DMSO], spectrometer: 399.95 MHz 8.6089 (1.36); 8.5953 (2.55); 8.5815 (1.37); 8.0014 (6.37); 7.998 (6.33); 7.3655 (1.01); 7.3591 (9.75); 7.3542 (3.36); 7.3431 (4.14); 7.338 (16); 7.3319 (2.07); 7.2734 (1.83); 7.2673 (13.57); 7.2623 (3.77); 7.251 (3.01); 7.2462 (8.58); 7.2399 (0.95); 6.9496 (5.06); 6.9473 (6.6); 6.945 (6.59); 6.9428 (5.15); 3.4476 (2.67); 3.4303 (5.32); 3.4155 (5.19); 3.3971 (2.96); 3.3249 (40.22); 2.8185 (5.02); 2.8002 (8.42); 2.7823 (4.48); 2.6715 (0.41); 2.5249 (1.11); 2.5202 (1.7); 2.5115 (22.62); 2.507 (45.83); 2.5024 (60.3); 2.4978 (42.9); 2.4932 (20.22); 2.3291 (0.38); 0.008 (0.66); −0.0002 (20.61); −0.0085 (0.59) |
| 26-3 | 3,4-dichlorophenyl | CH2 | CH2 | — | H | compound No. 26-3, solvent: [DMSO], spectrometer: 399.95 MHz 8.5955 (2.06); 8.5818 (3.95); 8.5681 (2.09); 8.0021 (9.72); 7.9986 (9.6); 7.9976 (9.51); 7.5544 (13.94); 7.5442 (0.49); 7.5339 (16); 7.5233 (0.5); 7.5132 (11.75); 7.5082 (12.11); 7.2416 (6.86); 7.2365 (6.68); 7.221 (6.06); 7.2159 (5.93); 6.9274 (7.73); |

TABLE 26-continued

Compounds of the formula I-26

I-26

| Ex. No. | X | L¹ | L² | L³ | Y | Physical data: ¹H-NMR, δ [ppm] or CAS or patent No. |
|---|---|---|---|---|---|---|
| | | | | | | 6.925 (10.18); 6.9228 (10.16); 6.9205 (7.97); 5.7561 (2.11); 4.0387 (0.58); 4.0209 (0.58); 3.4721 (4.13); 3.4548 (10.04); 3.4401 (10.32); 3.4229 (4.64); 3.3479 (608.26); 3.3204 (1.46); 3.3026 (0.44); 3.2966 (0.34); 3.2852 (0.34); 2.834 (7.4); 2.8166 (14.78); 2.7992 (6.59); 2.6778 (0.54); 2.6732 (0.79); 2.6687 (0.58); 2.5434 (0.43); 2.5266 (2.49); 2.5218 (3.74); 2.5132 (41.84); 2.5087 (84.35); 2.5041 (110.41); 2.4995 (77.66); 2.4949 (35.75); 2.3355 (0.49); 2.3308 (0.68); 2.3262 (0.47); 1.9897 (2.48); 1.3361 (0.35); 1.2495 (0.47); 1.1932 (0.7); 1.1753 (1.37); 1.1576 (0.67); 0.008 (1.54); −0.0002 (43.91); −0.0086 (1.1) |
| 26-4 | 3,5-dichlorophenyl | CH2 | CH2 | — | H | compound No. 26-4, solvent: [DMSO], spectrometer: 399.95 MHz 8.5976 (1.31); 8.5838 (2.43); 8.5701 (1.28); 8.0077 (5.94); 8.0033 (6); 7.4448 (3.7); 7.44 (7.46); 7.4352 (4.21); 7.3247 (0.33); 7.3109 (16); 7.3062 (15.19); 6.9176 (4.53); 6.9154 (5.97); 6.9132 (6); 6.911 (4.73); 3.4838 (2.26); 3.4666 (6.04); 3.452 (6.26); 3.4351 (2.7); 3.3248 (23.55); 2.8469 (4.3); 2.8297 (8.79); 2.8125 (3.9); 2.6719 (0.37); 2.5252 (0.92); 2.5204 (1.42); 2.5119 (19.88); 2.5074 (40.56); 2.5028 (53.5); 2.4982 (38.14); 2.4936 (18.08); 2.3295 (0.34); 1.2495 (0.33); 0.008 (0.6); −0.0002 (19.31); −0.0085 (0.59) |
| 26-5 | 4-chlorophenyl | CH2 | CH(CH3) | — | H | compound No. 26-5, solvent: [DMSO], spectrometer: 399.95 MHz 8.4035 (2.3); 8.383 (2.29); 7.9889 (5.55); 7.9852 (5.61); 7.4624 (0.32); 7.3467 (0.88); 7.3405 (8.04); 7.3357 (2.76); 7.3244 (3.44); 7.3194 (13.07); 7.3134 (1.65); 7.2636 (0.54); 7.2573 (1.69); 7.2514 (11.57); 7.2465 (3.23); 7.2349 (2.61); 7.2303 (7.39); 6.9186 (5.51); 6.9165 (5.42); 4.1603 (0.65); 4.1435 (1.32); 4.1411 (1.35); 4.1242 (1.97); 4.1072 (1.44); 4.0882 (0.66); 3.3572 (252.39); 2.8167 (1.25); 2.7975 (1.19); 2.7831 (3.26); 2.7639 (3.28); 2.7494 (3.28); 2.7334 (3.32); 2.7158 (1.28); 2.6998 (1.15); 2.6739 (0.35); 2.5272 (0.99); 2.5224 (1.5); 2.514 (17.21); 2.5095 (34.45); 2.5049 (45.05); 2.5003 (32.11); 2.4958 (15.21); 1.9898 (0.39); 1.1307 (16); 1.114 (15.75); 1.1047 (1.19); 0.008 (0.56); −0.0002 (16.76); −0.0085 (0.5) |
| 26-6 | 4-chlorophenyl | CH(CH3) | CH2 | — | H | compound No. 26-6, solvent: [DMSO], spectrometer: 399.95 MHz 8.5641 (1.19); 8.5501 (2.3); 8.5357 (1.21); 7.9831 (5.35); 7.9793 (5.44); 7.3683 (0.77); 7.362 (7.64); 7.3572 (2.63); 7.3458 (3.37); 7.3408 (13.37); 7.3347 (1.79); 7.2877 (1.7); 7.2817 (12.3); 7.2766 (3.29); 7.2652 (2.54); 7.2604 (7.3); 7.2542 (0.82); 6.8923 (5.43); 6.8902 (5.39); 3.4008 (0.45); 3.39 (0.81); 3.3481 (342.01); 3.3232 (4.65); 3.3159 (3.57); 3.301 (0.89); 3.2867 (0.42); 3.2831 (0.5); 3.0364 (1.26); 3.0186 (2.51); 3.0008 (2.44); 2.983 (1.12); 2.6729 (0.43); 2.5261 (1.29); 2.5129 (25.33); 2.5084 (50.56); 2.5039 (66.04); 2.4993 (47.15); 2.4948 (22.49); 2.3306 (0.44); 1.2123 (16); 1.1948 (15.69); 0.0079 (0.74); −0.0002 (21.13); −0.0086 (0.65) |
| 26-7 | 2,4-dichlorophenyl | CH2 | CH(CH3) | — | H | compound No. 26-7, solvent: [DMSO], spectrometer: 399.95 MHz 8.4268 (2.05); 8.4054 (2.08); 7.9942 (4.7); 7.9907 (4.56); 7.9897 (4.56); 7.5685 (3.62); 7.5658 (6.64); 7.5628 (3.95); 7.3486 (16); 7.3455 (15.17); 6.9279 (3.66); 6.9256 (4.79); 6.9234 (4.82); 6.9211 (3.82); |

TABLE 26-continued

Compounds of the formula I-26

I-26

| Ex. No. | X | L¹ | L² | L³ | Y | Physical data: ¹H-NMR, δ [ppm] or CAS or patent No. |
|---|---|---|---|---|---|---|
| | | | | | | 5.7584 (2.25); 4.3007 (0.46); 4.28 (1.06); 4.2639 (1.41); 4.2481 (1.04); 4.2439 (0.82); 4.2271 (0.49); 3.3247 (22.34); 2.9385 (1.19); 2.9239 (1.34); 2.9043 (3.28); 2.8897 (3.03); 2.873 (3.14); 2.8521 (2.98); 2.8389 (1.19); 2.8179 (1.23); 2.5252 (0.91); 2.5204 (1.42); 2.5119 (17.27); 2.5074 (34.88); 2.5028 (45.79); 2.4982 (32.5); 2.4936 (15.27); 1.1769 (13.12); 1.1602 (12.99); 0.008 (0.5); −0.0002 (15.44); −0.0085 (0.44) |
| 26-8 | 2,4-dichlorophenyl | CH(CH3) | CH2 | — | H | compound No. 26-8, solvent: [DMSO], spectrometer: 399.95 MHz 8.5954 (1.56); 8.5809 (2.79); 8.5681 (1.33); 7.9821 (6.77); 7.9786 (6.71); 7.5619 (9.71); 7.5566 (10.19); 7.4648 (5.23); 7.4437 (12); 7.4164 (7.47); 7.411 (6.72); 7.3953 (3.13); 7.3899 (3.06); 6.903 (5.49); 6.9006 (7.06); 6.8984 (6.94); 6.8961 (5.32); 5.7569 (0.7); 4.0387 (0.47); 4.0209 (0.47); 3.5225 (1.18); 3.5056 (2.54); 3.4892 (3.95); 3.4812 (2.61); 3.4743 (2.68); 3.4651 (1.39); 3.4595 (3.14); 3.4445 (3.1); 3.4275 (1.6); 3.4021 (1.02); 3.3948 (1.27); 3.3789 (2.94); 3.364 (4.32); 3.3385 (331.19); 3.3212 (1.62); 3.3153 (0.82); 3.3007 (0.38); 2.6772 (0.36); 2.6727 (0.51); 2.6681 (0.35); 2.526 (1.63); 2.5213 (2.4); 2.5127 (28.94); 2.5082 (58.45); 2.5036 (76.65); 2.499 (54.08); 2.4944 (25.12); 2.3349 (0.36); 2.3304 (0.51); 2.3257 (0.34); 1.9896 (2.1); 1.4201 (0.47); 1.2493 (0.42); 1.2053 (15.95); 1.1967 (3.74); 1.1887 (16); 1.1753 (1.61); 1.1575 (0.67); 0.008 (0.93); −0.0002 (30.12); −0.0086 (0.87) |
| 26-9 | 2,6-difluorophenyl | CH2 | CH2 | — | H | compound No. 26-9, solvent: [DMSO], spectrometer: 399.95 MHz 8.7131 (2.65); 8.6985 (5.01); 8.6839 (2.65); 7.9991 (12.83); 7.9957 (12.64); 7.3654 (1.77); 7.3486 (3.86); 7.3444 (3.34); 7.3316 (2.64); 7.3276 (7.45); 7.3237 (2.99); 7.3104 (3.53); 7.3067 (4.8); 7.29 (2.26); 7.1033 (0.94); 7.0989 (1.33); 7.0869 (9.95); 7.0787 (1.84); 7.0669 (16); 7.0558 (1.94); 7.0468 (8.52); 7.0344 (1.18); 7.0311 (0.88); 6.9198 (10.15); 6.9174 (13.27); 6.9152 (13.21); 6.9129 (10.25); 3.4278 (4.8); 3.4111 (11.75); 3.3947 (11.69); 3.3777 (5.37); 3.3244 (43.4); 2.8847 (7.35); 2.867 (13.67); 2.8495 (6.6); 2.6765 (0.57); 2.6718 (0.76); 2.6672 (0.53); 2.5252 (2.1); 2.5205 (3.31); 2.5119 (43.26); 2.5074 (87.58); 2.5028 (114.99); 2.4981 (81.4); 2.4936 (38.07); 2.334 (0.54); 2.3295 (0.75); 2.325 (0.53); 1.3365 (0.65); 1.2498 (0.82); 0.008 (1.28); −0.0002 (40.16); −0.0085 (1.17) |
| 26-10 | 4-chlorophenyl | CH2 | CH2 | CH2 | H | compound No. 26-10, solvent: [DMSO], spectrometer: 399.95 MHz 8.56 (1.9); 8.5465 (3.39); 8.5334 (1.89); 8.0103 (9.73); 8.0068 (9.54); 8.0058 (9.4); 7.305 (5.4); 7.3011 (2.24); 7.2865 (13.19); 7.2728 (4.06); 7.2683 (12.59); 7.2269 (10.76); 7.2231 (16); 7.218 (3.55); 7.2061 (8.78); 7.197 (4.95); 7.1934 (2.47); 7.1837 (2.59); 7.179 (6.85); 7.1738 (1.68); 7.1645 (1.55); 7.161 (2.54); 7.1576 (1.31); 7.0007 (7.99); 6.9983 (10.42); 6.9961 (10.34); 6.9938 (8); 3.3236 (48.99); 3.2409 (4.43); 3.2233 (8.88); 3.2088 (8.84); 3.1912 (4.61); 2.6755 (0.59); 2.6709 (0.79); 2.6663 (0.58); 2.6306 (7.35); 2.6119 (10.08); 2.5921 (8.06); 2.5412 (0.37); 2.5244 (2.29); 2.5197 (3.47); 2.511 (42.44); 2.5065 (86); 2.5019 (112.99); 2.4973 (79.68); 2.4927 (36.96); 2.3333 (0.52); 2.3287 (0.74); 2.3241 (0.52); 1.8216 (2.43); 1.8026 (6); 1.7843 (8.01); 1.7661 |

TABLE 26-continued

Compounds of the formula I-26

I-26

| Ex. No. | X | L¹ | L² | L³ | Y | Physical data: ¹H-NMR, δ [ppm] or CAS or patent No. |
|---|---|---|---|---|---|---|
| 26-11 | 2,4-dichlorophenyl | CH2 | CH2 | CH2 | H | (5.51); 1.7476 (2.14); 1.3361 (0.52); 1.2493 (0.69); 0.0079 (1.24); −0.0002 (38.22); −0.0086 (1.09) compound No. 26-11, solvent: [DMSO], spectrometer: 399.95 MHz 8.6033 (1.98); 8.5896 (3.67); 8.5759 (1.96); 8.0134 (9.34); 8.0098 (9.31); 7.5714 (10.58); 7.5663 (10.83); 7.4191 (5.24); 7.3984 (16); 7.3837 (11.47); 7.3786 (10.33); 7.3631 (3.36); 7.3579 (3.54); 7.3482 (0.4); 7.327 (0.57); 7.2584 (0.5); 7.2376 (0.41); 6.997 (7.66); 6.9948 (9.64); 6.9926 (9.29); 6.9905 (6.99); 3.3697 (0.48); 3.3575 (0.88); 3.3347 (213.35); 3.3149 (0.73); 3.2704 (3.55); 3.2532 (8.1); 3.2382 (8.13); 3.2211 (3.66); 2.7359 (6.63); 2.7171 (7.91); 2.6972 (6.97); 2.6779 (0.46); 2.6733 (0.58); 2.6687 (0.42); 2.5266 (1.71); 2.5218 (2.64); 2.5133 (31.11); 2.5088 (62.1); 2.5043 (80.8); 2.4996 (56.99); 2.4951 (26.48); 2.3354 (0.36); 2.331 (0.51); 2.3264 (0.36); 1.8044 (1.96); 1.786 (4.98); 1.7673 (6.47); 1.7488 (4.67); 1.7306 (1.64); 1.3368 (0.41); 1.2495 (0.52); 0.008 (0.87); −0.0002 (27.33); −0.0085 (0.8) |
| 26-12 | 2,6-difluorophenyl | CH2 | CH2 | CH2 | H | compound No. 26-12, solvent: [DMSO], spectrometer: 399.95 MHz 8.5982 (2.65); 8.5846 (4.8); 8.5711 (2.62); 8.0104 (12.76); 8.0069 (12.58); 7.3503 (1.8); 7.3334 (3.92); 7.3292 (3.29); 7.3164 (2.73); 7.3125 (7.46); 7.3085 (2.99); 7.2952 (3.48); 7.2916 (4.87); 7.2748 (2.28); 7.1031 (1.07); 7.0986 (1.37); 7.0862 (9.78); 7.0784 (1.87); 7.0659 (16); 7.054 (1.96); 7.0457 (8.06); 7.0326 (1.09); 7.0292 (0.81); 6.9798 (10.33); 6.9775 (13.21); 6.9752 (12.93); 6.9729 (9.92); 6.514 (0.37); 3.328 (26.54); 3.2621 (4.91); 3.2446 (9.9); 3.2293 (9.86); 3.2118 (5.04); 2.6849 (6.61); 2.6657 (10.52); 2.6462 (7.04); 2.527 (1.7); 2.5222 (2.59); 2.5137 (30.04); 2.5092 (59.96); 2.5046 (78.2); 2.5 (55.19); 2.4954 (25.66); 2.336 (0.36); 2.3314 (0.5); 2.3266 (0.35); 1.7839 (2.64); 1.7649 (6.6); 1.7464 (9.32); 1.7277 (6.07); 1.7091 (2.29); 1.3377 (0.59); 1.2503 (0.76); 0.008 (0.96); −0.0002 (28.5); −0.0086 (0.8) |

Biological Experiments

Example A

Nippostrongylus brasiliensis test (NIPOBR)

Test Method for In Vitro Experiments with Nippostrongylus brasiliensis

Adult Nippostrongylus brasiliensis were isolated from the small intestine of female Wistar rats and transferred into 0.9% NaCl containing 20 g/ml sisomycin and 2 g/ml Canesten. The incubation of the worms (both sexes) was carried out in 1.0 ml of the medium also used for determining the acetylcholinesterase activity. The compounds were dissolved in DMSO and added to the incubation medium such that final concentrations of 100, 10 and 1 g/ml, respectively, were present. The controls contained only DMSO. Incubation and enzyme determination were described in the study by Rapson et al. (1987) Z. Parasitenkunde 73, 190-191.

Efficacy was classified using the categories 35 (0-35% inhibition), 60 (>35-60%), 84 (>60-84%) and 100 (>84-100%).

| Example number | Efficacy at 10 µg/ml |
|---|---|
| 1-2 | 100% |
| 1-7 | 100% |
| 1-14 | 100% |
| 1-20 | 100% |
| 1-22 | 100% |
| 2-3 | 100% |
| 2-7 | 100% |
| 2-8 | 100% |
| 2-9 | 100% |
| 2-11 | 100% |
| 2-12 | 100% |
| 2-16 | 100% |
| 2-19 | 100% |
| 2-20 | 100% |

-continued

| Example number | Efficacy at 10 μg/ml |
|---|---|
| 2-23 | 100% |
| 3-4 | 100% |
| 3-9 | 100% |
| 3-11 | 100% |
| 3-14 | 100% |
| 3-15 | 100% |
| 3-19 | 100% |
| 3-20 | 100% |
| 3-21 | 100% |
| 4-3 | 100% |
| 4-5 | 100% |
| 6-7 | 100% |
| 13-4 | 100% |
| 14-4 | 100% |
| 20-22 | 100% |

Example B

In Vivo Nematode Test

*Heligmosomoides polygyrus*/Mouse

Mice experimentally infected with *Heligmosomoides polyvgyrus* were treated after the prepatency time of the parasite had passed. The active compounds were administered orally in a Cremophor EL/water mixture.

The degree of activity was determined by counting the number of worms in the intestine during the dissection of the mice. The efficacy was determined via the number of worms compared to the number of worms in the intestine of untreated control animals.

Active compounds tested and effective dosages (Dosis effectiva) are shown in the table below.

| Substance | Efficacy at 100 mg/kg |
|---|---|
| 4-3 | 100% |
| 13-4 | 100% |
| 14-2 | 100% |
| 17-37 | 100% |

Example C

In Vivo Nematode Test

*Haemonchus contortus*/Sheep

Sheep experimentally infected with *Haemonchus contortus* were treated after the prepatency time of the parasite had passed. The active compounds were administered orally and/or intramuscularly as pure active compound.

The degree of activity was determined by counting the number of worms in the abomasum during the dissection of the sheep. The efficacy was determined via the number of worms compared to the number of worms in the abomasum of untreated control animals.

Active compounds tested and effective dosages (Dosis effectiva) are shown in the table below.

| Substance | Dosage | Efficacy |
|---|---|---|
| 13-4 | 20 mg/kg | 81% |
| 14-4 | 100 mg/kg | 100% |

Example D

*Haemonchus contortus* Test (HAEMCO)

Solvent: dimethyl sulfoxide

To produce a suitable preparation of active compound, 10 mg of active compound are mixed with 0.5 ml of dimethyl sulfoxide, and the concentrate is diluted with "Ringer solution" to the desired concentration. Vessels containing the active compound preparation of the desired concentration are populated with about 40 *Haemonchus contortus* larvae.

After 5 days, the kill in % is determined. 100% means that all larvae have been killed; 0% means that no larvae have been killed.

In this test, for example, the following compounds of the Preparation Examples show an effect of 100% at an application rate of 100 ppm: 20-26, 20-29

In this test, for example, the following compounds of the Preparation Examples show an effect of 90% at an application rate of 20 ppm: 13-4

In this test, for example, the following compounds of the Preparation Examples show an effect of 80% at an application rate of 20 ppm: 14-2, 14-4

*Cooperia curticei* Test (COOPCU)

Solvent: dimethyl sulfoxide

To produce a suitable preparation of active compound, 10 mg of active compound are mixed with 0.5 ml of dimethyl sulfoxide, and the concentrate is diluted with "Ringer solution" to the desired concentration. Vessels containing the active compound preparation of the desired concentration are populated with about 40 *Cooperia curticei* larvae.

After 5 days, the kill in % is determined. 100% means that all larvae have been killed; 0% means that no larvae have been killed.

In this test, for example, the following compounds of the Preparation Examples show an effect of 100% at an application rate of 100 ppm: 20-26

In this test, for example, the following compounds of the Preparation Examples show an effect of 80% at an application rate of 100 ppm: 17-37

In this test, for example, the following compounds of the Preparation Examples show an effect of 90% at an application rate of 20 ppm: 14-2, 14-4, 13-4

In this test, for example, the following compounds of the Preparation Examples show an effect of 80% at an application rate of 20 ppm: 20-29

The invention claimed is:

1. A method for controlling one or more endoparasites in an animal or human, comprising prophylactically and/or therapeutically administering to the animal or human a compound of the formula (I-b)

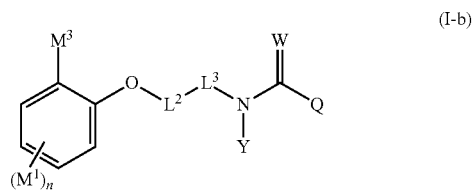

(I-b)

in which

Q represents mono- or poly-$M^1$-substituted pyridyl, thienyl, furanyl or isothiazolyl;

Y represents hydrogen or cyclopropyl;

W represents oxygen or sulfur;

$L^2$ represents —C($R^{21}$, $R^{22}$)—;

$L^3$ represents —C($R^{31}$, $R^{32}$)— or a direct bond;

$R^{21}$, $R^{22}$ each independently of one another represent hydrogen, fluorine or optionally mono- or poly-$M^2$-substituted ($C_1$-$C_4$)-alkyl, ($C_2$-$C_4$)-alkenyl, ($C_2$-$C_4$)-alkynyl, ($C_1$-$C_4$)-haloalkyl, ($C_1$-$C_6$)-alkoxy, ($C_2$-$C_4$)-alkenyloxy, ($C_3$-$C_4$)-alkynyloxy, ($C_3$-$C_4$)-cycloalkyl-($C_1$-$C_4$)-alkyl, or ($C_3$-$C_6$)-cycloalkyl;

$R^{31}$, $R^{32}$ each independently of one another represent hydrogen or ($C_1$-$C_4$)-alkyl;

$M^2$ each independently of one another represent chlorine, fluorine, formyl, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-haloalkylthio, ($C_1$-$C_4$)-alkylsulfonyl, ($C_1$-$C_4$)-haloalkylsulfonyl, ($C_1$-$C_4$)-alkylsulfanyl, ($C_1$-$C_4$)-haloalkylsulfanyl, ($C_1$-$C_4$)-alkylcarbonyl, ($C_1$-$C_4$)-haloalkylcarbonyl or ($C_3$-$C_6$)-cycloalkyl;

$M^1$ and $M^3$ independently of one another represent halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulfonyl, ($C_1$-$C_{10}$)-haloalkylsulfonyl, ($C_1$-$C_{10}$)-alkylsulfanyl, ($C_1$-$C_{10}$)-haloalkylsulfanyl, or (3- to 14-membered cyclic group)-O—;

n represents an integer from 0 to 4;

and/or a salt, N-oxide and/or tautomeric form thereof.

2. A method as claimed in claim 1 where

Q represents mono- or poly-$M^1$-substituted 2-thienyl, 3-thienyl, 2-furanyl, 5-isothiazolyl, 3-pyridyl or 2-pyridyl;

$M^1$ and $M^3$ independently of each other represents, halogen, cyano, nitro, OH, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-haloalkylthio, ($C_1$-$C_6$)-alkyl sulfonyl, ($C_1$-$C_6$)-haloalkylsulfonyl, ($C_1$-$C_6$)-alkyl sulfanyl, ($C_1$-$C_6$)-haloalkylsulfanyl, ($C_3$-$C_{14}$)-cycloalkyl-O—, ($C_3$-$C_{14}$)-cycloalkenyl-O—, ($C_6$-$C_{14}$)-aryl-O—, halogenated ($C_3$-$C_{14}$)-cycloalkyl-O—, halogenated ($C_3$-$C_{14}$)-cycloalkenyl-O—, halogenated ($C_6$-$C_4$)-aryl-O—;

and/or a salt, N-oxide and/or tautomeric form thereof.

3. The method as claimed in claim 1 where

Q represents mono- or di-$M^1$-substituted 2-thienyl, 3-thienyl, 2-furanyl, 5-isothiazolyl, 3-pyridyl or 2-pyridyl;

W represents oxygen;

$M^1$ and $M^3$ independently of each other represents, halogen, cyano, nitro, OH, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-haloalkylthio, ($C_1$-$C_4$)-alkylsulfonyl, ($C_1$-$C_4$)-haloalkylsulfonyl, ($C_1$-$C_4$)-alkylsulfanyl, ($C_1$-$C_6$)-haloalkylsulfanyl, ($C_3$-$C_{14}$)-cycloalkyl-O—, ($C_3$-$C_{14}$)-cycloalkenyl-O—, ($C_6$-$C_{14}$)-aryl-O—, halogenated ($C_3$-$C_{14}$)-cycloalkyl-O—, halogenated ($C_3$-$C_{14}$)-cycloalkenyl-O—, halogenated ($C_6$-$C_4$)-aryl-O—;

$R^{21}$, $R^{22}$ each independently of one another represent hydrogen, fluorine, (C1-C4)-alkyl, (C1-C4)-haloalkyl $M^2$ each independently of one another represent fluorine, chlorine, cyano, nitro, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methyl sulfonyl, ethyl sulfonyl, trifluoromethyl sulfonyl, 2,2,2-trifluoroethyl sulfonyl, methyl sulfanyl, ethyl sulfanyl, trifluoromethylsulfanyl, 2,2,2-trifluoroethylsulfanyl, cyclopropyl, cyclobutyl or cyclopentyl and/or a salt, N-oxide and/or tautomeric form thereof.

4. The method as claimed in claim 1 where

Q represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 4-chloro-5-isothiazolyl, 3,4-dichloro-5-isothiazolyl, 2-chloro-3-pyridyl, 3-chloro-2-pyridyl or 2-(trifluoromethyl)-3-pyridyl;

$M^1$ and $M^3$ independently of each other represents halogen, cyano, nitro, OH, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-haloalkylthio, ($C_1$-$C_4$)-alkylsulfonyl, ($C_1$-$C_4$)-haloalkylsulfonyl, ($C_1$-$C_4$)-alkyl sulfanyl, ($C_1$-$C_6$)-haloalkylsulfanyl, ($C_6$-$C_{14}$)-aryl-O—, halogenated ($C_6$-$C_{14}$)-aryl-O—;

$R^{21}$, $R^{22}$ each independently of one another represent hydrogen, fluorine, methyl, ethyl;

$R^{31}$, $R^{32}$ each independently of one another represent hydrogen or methyl, ethyl, n-propyl, isopropyl or tert-butyl;

and/or a salt, N-oxide and/or tautomeric form thereof.

5. A method as claimed in claim 1, wherein the compound is in the form of an endoparaiticidal composition.

6. A method as claimed in claim 1, wherein Y is hydrogen.

7. A method as claimed in claim 1, wherein Y is cyclopropyl.

8. A method as claimed in claim 1, wherein n is zero.

9. A method as claimed in claim 1, wherein Q represents mono- or poly-$M^1$-substituted pyridyl.

10. A method as claimed in claim 1, wherein Q represents mono- or poly-$M^1$-substituted thienyl.

11. A method as claimed in claim 1, wherein Q represents mono- or poly-$M^1$-substituted furanyl.

12. A method as claimed in claim 1, wherein Q represents mono- or poly-$M^1$-substituted or isothiazolyl.

13. A method as claimed in claim 1, wherein W is oxygen.

14. A method as claimed in claim 1, wherein W is sulfur.

15. A method as claimed in claim 1, wherein $R^{21}$, $R^{22}$ each independently of one another represent hydrogen, fluorine, ($C_1$-$C_4$)-alkyl, or ($C_1$-$C_4$)-haloalkyl.

16. A method as claimed in claim 1, wherein L3 is a direct bond.

\* \* \* \* \*